US012680132B2

(12) United States Patent
Tong et al.

(10) Patent No.: US 12,680,132 B2
(45) Date of Patent: Jul. 14, 2026

(54) NUCLEOTIDE CLEAVABLE LINKERS WITH RIGID SPACERS AND USES THEREOF

(71) Applicant: Singular Genomics Systems, Inc., San Diego, CA (US)

(72) Inventors: Ada Tong, San Diego, CA (US); Ronald Graham, Carlsbad, CA (US); Megha Cila, San Diego, CA (US); Eli N. Glezer, Del Mar, CA (US); Zachary Terranova, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 704 days.

(21) Appl. No.: 17/918,072

(22) PCT Filed: May 6, 2021

(86) PCT No.: PCT/US2021/031066
§ 371 (c)(1),
(2) Date: Oct. 10, 2022

(87) PCT Pub. No.: WO2021/226327
PCT Pub. Date: Nov. 11, 2021

(65) Prior Publication Data

US 2023/0160001 A1 May 25, 2023

Related U.S. Application Data

(60) Provisional application No. 63/022,089, filed on May 8, 2020.

(51) Int. Cl.

| | |
|---|---|
| ***C12Q 1/68*** | (2018.01) |
| ***C12Q 1/6869*** | (2018.01) |
| *C12Q 1/6818* | (2018.01) |

(52) U.S. Cl.
CPC ......... *C12Q 1/6869* (2013.01); *C12Q 1/6818* (2013.01)

(58) Field of Classification Search
CPC .... C12Q 1/6869; C12Q 1/6876; C07H 19/14; C07H 19/10
See application file for complete search history.

(56) References Cited

U.S. PATENT DOCUMENTS

| | | | |
|---|---|---|---|
| 5,034,506 | A | 7/1991 | Summerton et al. |
| 5,235,033 | A | 8/1993 | Summerton et al. |
| 6,664,079 | B2 | 12/2003 | Ju et al. |
| 7,574,306 | B1 | 8/2009 | Baker et al. |
| 2006/0003383 | A1 | 1/2006 | Graham |
| 2006/0016008 | A1 | 1/2006 | Choi et al. |

(Continued)

FOREIGN PATENT DOCUMENTS

| | | |
|---|---|---|
| WO | WO-2017/205336 A1 | 11/2017 |
| WO | WO-2020/086834 A1 | 11/2017 |

(Continued)

OTHER PUBLICATIONS

Bentley, D.R. et al. (Nov. 6, 2008). "Accurate whole human genome sequencing using reversible terminator chemistry," *Nature* 456(7218):53-59.

(Continued)

*Primary Examiner* — Jezia Riley
(74) *Attorney, Agent, or Firm* — Mintz, Levin, Cohn, Ferris, Glovsky and Popeo, P.C.; Zachary L. Terranova

(57) ABSTRACT

Disclosed herein, inter alia, are compounds, compositions, and methods of use thereof for sequencing a nucleic acid.

21 Claims, 10 Drawing Sheets

Specification includes a Sequence Listing.

(56) References Cited

U.S. PATENT DOCUMENTS

| | | | |
|---|---|---|---|
| 2007/0009980 | A1 | 1/2007 | Graham |
| 2007/0042407 | A1 | 2/2007 | Milton et al. |
| 2009/0047699 | A1 | 2/2009 | Graham |
| 2017/0313737 | A1 | 11/2017 | Ju et al. |
| 2018/0258472 | A1 | 9/2018 | Glezer |
| 2018/0274024 | A1 | 9/2018 | Ju et al. |
| 2018/0274025 | A1 | 9/2018 | Marma et al. |
| 2019/0077726 | A1 | 3/2019 | Graham et al. |
| 2019/0127790 | A1 | 5/2019 | Stupi et al. |

FOREIGN PATENT DOCUMENTS

| | | |
|---|---|---|
| WO | WO-2018/148723 A1 | 8/2018 |
| WO | WO-2020/056044 A1 | 3/2019 |

OTHER PUBLICATIONS

Bergen, K. et al. (Jun. 17, 2013, e-published Jun. 3, 2013). "Structures of KOD and 9° N DNA polymerases complexed with primer template duplex," *Chembiochem* 14(9):1058-1062.

Bergseid, M. et al. (Nov. 2000). "Small molecule-based chemical affinity system for the purification of proteins," *BioTechniques* 29(5):1126-1133.

Betzig, E. et al. (Sep. 15, 2006). "Imaging intracellular fluorescent proteins at nanometer resolution," *Science* 313(5793): 1642-1645.

Binauld, S. et al. (Mar. 14, 2013). "Acid-degradable polymers for drug delivery: a decade of innovation," *Chem Commun* 49(21):2082-2102.

Blackman, M.L. et al. (Oct. 15, 2008, e-published Sep. 18, 2008). "The Tetrazine ligation: fast bioconjugation based on inverse-electron-demand Diels-Alder reactivity," *J Am Chem Soc* 130(41):13518-13519.

Choi, H. et al. (Oct. 7, 2019). "Fabrication of rigidity and space variable protein oligomers with two peptide linkers," *Chemical Science*, 10(44), 10428-10435.

Chozinski, T.J. et al. (Oct. 1, 2014). "Twinkle, twinkle little star: Photoswitchable fluorophores for super-resolution imaging," *FEBS letters* 588(19): 3603-3612.

Debets, M.F. et al. (Oct. 14, 2013, e-published Aug. 23, 2013). "Bioorthogonal labelling of biomolecules: new functional handles and ligation methods," *Org Biomol Chem* 11(38):6439-6455.

Feeney, R. E. et al. (Apr. 1, 1982). "Chemical modification of proteins: An overview," *Advances in Chemistry Series* 182: 3-55.

Fuller, C.W. et al. (May 10, 2016, e-published Apr. 18, 2016). "Real-time single-molecule electronic DNA sequencing by synthesis using polymer-tagged nucleotides on a nanopore array," *PNAS USA* 113(19):5233-5238.

Guo, J. et al. (Jul. 8, 2008, e-published Jun. 30, 2008). "Four-color DNA sequencing with 3'-O-modified nucleotide reversible terminators and chemically cleavable fluorescent dideoxynucleotides," *PNAS USA* 105(27):9145-9150.

Haas, E. et al. (Jan. 15, 1975). "Distribution of end-to-end distances of oligopeptides in solution as estimated by energy transfer," *PNAS USA* 72(5): 1807-1811.

Heilemann, M. et al. (2008). "Subdiffraction-resolution fluorescence imaging with conventional fluorescent probes," *Angewandte Chemie International Edition* 47(33): 6172-6176.

Hutter, D. et al. (e-published Dec. 1, 2010). "Labeled nucleoside triphosphates with reversibly terminating aminoalkoxyl groups," *Nucleosides, Nucleotides and Nucleic Acids* 29(11-12): 879-895.

International Search Report mailed on Oct. 13, 2021, for PCT Application No. PCT/US2021/31066, filed May 6, 2021, 4 pages.

Jewett, J.C. et al. (Mar. 24, 2010). "Rapid Cu-free click chemistry with readily synthesized biarylazacyclooctynones," *J Am Chem Soc* 132(11): 3688-3690.

Ju, J. et al. (Dec. 26, 2006, e-published Dec. 14, 2006). "Four-color DNA sequencing by synthesis using cleavable fluorescent nucleotide reversible terminators," *PNAS USA* 103(52):19635-19640.

Klostermeier, D. et al. (2002). "Time-resolved fluorescence resonance energy transfer: A versatile tool for the analysis of nucleic acids." *Biopolymers: Original Research on Biomolecules* 61(3): 159-179.

Kumar, S. et al. (2012, e-published Sep. 21, 2012). "PEG-labeled nucleotides and nanopore detection for single molecule DNA sequencing by synthesis," *Sci Rep* 2:684.

Kurata, S. et al. (Mar. 15, 2001). "Fluorescent quenching-based quantitative detection of specific DNA/RNA using a BODIPY® FL-labeled probe or primer," *Nucleic acids research* 29(6): e34.

Lakowicz, J. R. et al. (Jan. 14, 1990). "Influence of oligopeptide flexibility on donor-acceptor distance distribution by frequency-domain fluorescence spectroscopy," *Proc Spie Time-Resolved Laser Spectroscopy in Biochemistry II* 1204:192-205. Los Angeles, CA.

Lee, H. et al. (Aug. 15, 2008). "Molecular dynamics studies of polyethylene oxide and polyethylene glycol: hydrodynamic radius and shape anisotropy." *Biophysical journal* 95(4):1590-1599.

Leriche, G. et al. (Jul. 2010). "Optimization of the Azobenzene Scaffold for Reductive Cleavage by Dithionite; Development of an Azobenzene Cleavable Linker for Proteomic Applications," *Eur J Org Chem* 2010(23):4360-4364.

Mag, M. et al. (1992). "Synthesis and selective cleavage of an oligodeoxynucleotide containing a bridged non-chiral internucleotide 3'-phosphoramidate linkage." *Tetrahedron Letters* 33(48): 7319-7322.

Meguro, Y. et al. (2020). "Efficient generation of thiolate sugars from glycosyl Bunte salts and its application to S-glycoside synthesis." *Tetrahedron Letters* 61(32): 152198.

Rathod, K.M. et al. (2013). "Synthesis and Antimicrobial Activity of Azo Compounds Containing m-Cresol Moiety," *Chem Sci Trans* 2(1):25-28.

Rosenblum, B.B. et al. (Nov. 15, 1997). "New dye-labeled terminators for improved DNA sequencing patterns," *Nucleic Acids Res* 25(22):4500-4504.

Ruparel, H. et al. (Apr. 26, 2005, e-published Apr. 13, 2005). "Design and synthesis of a 3'-O-allyl photocleavable fluorescent nucleotide as a reversible terminator for DNA sequencing by synthesis," *PNAS USA* 102(17):5932-5937.

Schröder, T. et al. (Jan. 25, 2019). "Interchromophoric interactions determine the maximum brightness density in DNA origami structures." *Nano letters* 19(2): 1275-1281.

Seio, K. et al. (Nov. 1, 2002). "A new protecting group for 5'-hydroxyl function of nucleotides in oligonucleotide synthesis without acid treatment utilizing unique properties of tritylthio group." *Nucleic acids symposium series* 2(1): 27-28. Oxford University Press.

Seliger, H. et al. (Dec. 1, 2003). "Arrays of immobilized oligonucleotides-contributions to nucleic acids technology," *Current pharmaceutical biotechnology* 4(6): 379-395.

Shenoi, R. A. et al. (Aug. 20, 2012). "Branched multifunctional polyether polyketals: variation of ketal group structure enables unprecedented control over polymer degradation in solution and within cells." *Journal of the American Chemical Society* 134(36): 14945-14957.

Southworth, M.W. et al. (May 28, 1996). "Cloning of thermostable DNA polymerases from hyperthermophilic marine Archaea with emphasis on *Thermococcus* sp. 9 degrees N-7 and mutations artectlnq a-s' exonuclease activity," *PNAS USA* 93(11):5281-5285.

Van Rosmalen et al. (Nov. 23, 2017). "Tuning the flexibility of glycine-serine linkers to allow rational design of multidomain proteins," *Biochemistry* 56(50): 6565-6574.

Walker, J. W. et al. (1988). "Photolabile 1-(2-nitrophenyl) ethyl phosphate esters of adenine nucleotide analogs. Synthesis and mechanism of photolysis," *Journal of the American Chemical Society* 110(21): 7170-7177.

Written Opinion mailed on Oct. 13, 2021 for PCT Application No. PCT/US2021/31066, filed May 6, 2021, 4 pages.

Wu, J. et al. (Oct. 16, 2007, e-published Oct. 8, 2007). "3'-O-modified nucleotides as reversible terminators for pyrosequencing," *PNAS USA* 104(42):16462-16467.

Zhu, Z. et al. (Aug. 25, 1994). "Directly labeled DNA probes using fluorescent nucleotides with different length linkers," *Nucleic Acids Res* 22(16):3418-3422.

SEQUENCE LISTING

```
<160> NUMBER OF SEQ ID NOS: 4

<210> SEQ ID NO 1
<211> LENGTH: 100
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (11)..(100)
<223> OTHER INFORMATION: These amino acids may be absent

<400> SEQUENCE: 1

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
            20                  25                  30

Ala Ala Lys Glu Ala Ala Ala Lys Glu Ala Ala Ala Lys Glu Ala Ala
        35                  40                  45

Ala Lys Glu Ala Ala Ala Lys Glu Ala Ala Ala Lys Glu Ala Ala Ala
    50                  55                  60

Lys Glu Ala Ala Ala Lys Glu Ala Ala Ala Lys Glu Ala Ala Ala Lys
65                  70                  75                  80

Glu Ala Ala Ala Lys Glu Ala Ala Ala Lys Glu Ala Ala Ala Lys Glu
                85                  90                  95

Ala Ala Ala Lys
            100
```

-continued

<210> SEQ ID NO 2
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 2

Gly Ser Ser Gly Ser Ser
1 5

<210> SEQ ID NO 3
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 3

Gly Ser Ser Ser Ser Ser
1 5

<210> SEQ ID NO 4
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 4

Ser Ser Ser Ser Ser Ser
1 5

NUCLEOTIDE CLEAVABLE LINKERS WITH RIGID SPACERS AND USES THEREOF

CROSS-REFERENCE TO RELATED APPLICATIONS

This application is the national stage filing under 35 U.S.C. § 371 of International Application No. PCT/US2021/031066 filed May 6, 2021, which claims the benefit of U.S. Provisional Application No. 63/022,089, filed May 8, 2020 which are incorporated herein by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 051385-527N01US_Sequence_Listing_ST25.txt, created Nov. 26, 2025, 4,368 bytes, machine format IBM-PC, MS Windows operating system, is hereby incorporated by reference.

BACKGROUND

DNA sequencing is a fundamental tool in biological and medical research; it is an essential technology for the paradigm of personalized precision medicine. Among various new DNA sequencing methods, sequencing by synthesis (SBS) is the leading method for realizing the goal of the $1,000 genome. Accordingly, there is a need for modified nucleotides and nucleosides that are effectively recognized as substrates by DNA polymerases, that are efficiently and accurately incorporated into growing DNA chains during SBS. Disclosed herein, inter alia, are solutions to these and other problems in the art.

BRIEF SUMMARY

In an aspect is provided a compound having the formula:

(I)

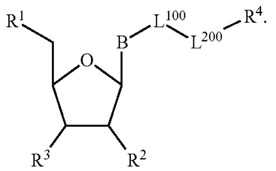

B is a divalent nucleobase. $L^{100}$ is a polymerase-compatible cleavable linker. $L^{200}$ is a rigid spacer. $R^1$ is independently a polyphosphate moiety, monophosphate moiety, 5'-O-nucleoside protecting group, nucleic acid moiety, hydrogen, or —OH. $R^2$ is independently hydrogen, —OH, —$OR^{2A}$, or a polymerase-compatible cleavable moiety. $R^3$ is independently an —O-polymerase-compatible cleavable moiety, a polymerase-compatible cleavable moiety, hydrogen, —OH, —$NH_3^+$, —$SO_3^-$, —$OPO_3H^-$, —SCN, —$ONO_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is an anchor moiety or a detectable moiety.

In an aspect is provided a composition including a first compound having the formula:

(I)

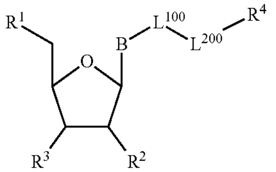

and a second compound having the formula $R^5$-$L^5$-$R^6$ (II). $R^1$, $R^2$, $R^3$, $L^{100}$, and $L^{200}$ are as described herein. $R^4$ is an anchor moiety. $R^5$ is a complementary anchor moiety to the $R^4$ anchor moiety of the first compound. $L^5$ is a covalent linker. $R^6$ is detectable moiety.

In an aspect is provided a method for sequencing a nucleic acid. In embodiments, the method includes (i) incorporating in series with a nucleic acid polymerase, within a reaction vessel, one of four different compounds into a primer to create an extension strand, wherein the primer is hybridized to the nucleic acid and wherein each of the four different compounds includes a unique detectable moiety or a unique anchor moiety; (ii) if the compound of step (i) above includes a unique anchor moiety, further adding to the reaction vessel a complementary anchor compound including a complementary anchor moiety to the unique anchor moiety bonded to a unique detectable moiety; and (iii) detecting the unique detectable moiety of each incorporated compound or incorporated compound-complementary anchor compound complex, so as to thereby identify each incorporated compound in the extension strand, thereby sequencing the nucleic acid; wherein each of the four different compounds is independently a compound as described herein, including embodiments. In embodiments, the complementary anchor compound is a composition as described herein, having formula (II): $R^5$-$L^5$-$R^6$, wherein $R^5$, $L^5$, and $R^6$ are as described herein.

In another aspect is provided a method of incorporating a compound into a primer, the method including combining a polymerase, a primer hybridized to nucleic acid template and the compound within a reaction vessel and allowing the polymerase to incorporate the compound into the primer thereby forming an extended primer, wherein the compound is a compound described herein, including embodiments.

In an aspect is a method for increasing the accuracy of a sequencing reaction, the method including (i) incorporating in series with a nucleic acid polymerase, within a reaction vessel, one of four different compounds into a primer to create an extension strand, wherein the primer is hybridized to the nucleic acid and wherein each of the four different compounds includes a unique detectable moiety or a unique anchor moiety; (ii) if the compound of step (i) above includes a unique anchor moiety, further adding to the reaction vessel a complementary anchor compound including a complementary anchor moiety to the unique anchor moiety bonded to a unique detectable moiety; and (iii) detecting the unique detectable moiety of each incorporated compound or incorporated compound-complementary anchor compound complex, so as to thereby identify each incorporated compound in the extension strand, thereby sequencing the nucleic acid; wherein each of the four different compounds is independently a compound as described herein.

In an aspect is provided a method of reducing photodamage to a biological component in a sequencing reaction, the method including (i) incorporating in series with a nucleic acid polymerase, within a reaction vessel, one of four different compounds into a primer to create an extension strand, wherein the primer is hybridized to the nucleic acid and wherein each of the four different compounds includes a unique detectable moiety or a unique anchor moiety; (ii) if the compound of step (i) above includes a unique anchor moiety, further adding to the reaction vessel a complementary anchor compound including a complementary anchor moiety to the unique anchor moiety bonded to a unique detectable moiety; and (iii) detecting the unique detectable moiety of each incorporated compound or incorporated compound-complementary anchor compound complex, so as to thereby identify each incorporated compound in the extension strand, thereby sequencing the nucleic acid; wherein each of the four different compounds is independently a compound as described herein.

DETAILED DESCRIPTION

I. Definitions

Figure 1:
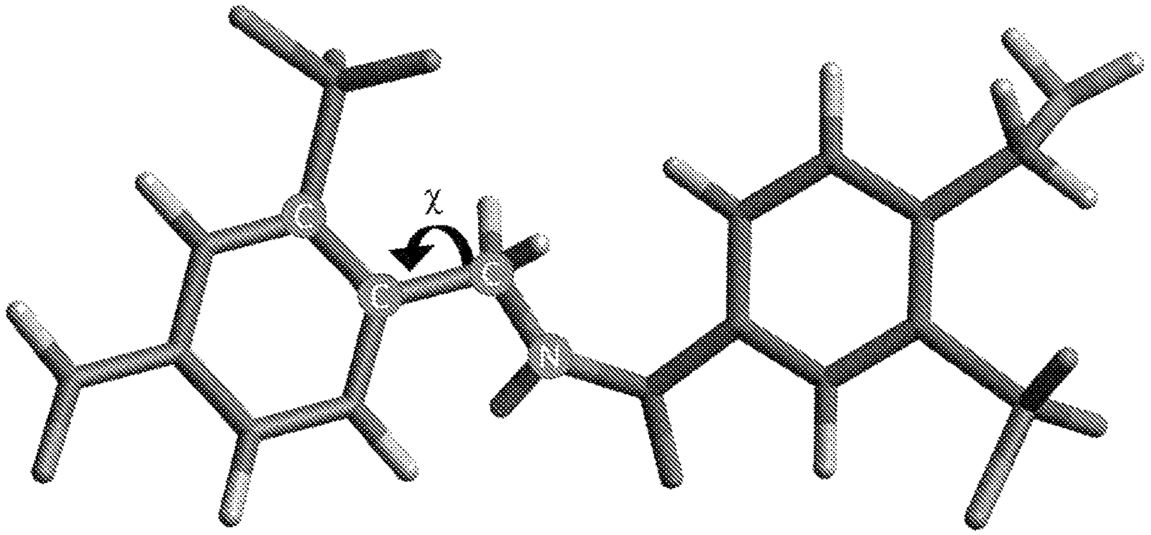
FIG. 1. A model dimer showing two sulfonated monomers linked together. The torsion angle χ(N—C—C—C) is formed by adjacent nitrogen, carbon (methylene), carbon (phenyl), and carbon (phenyl) atoms, which are depicted with circle overlays showing the atoms for clarity. A scan of this torsion angle found there is approximately a 7 kcal/mol barrier to rotation.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds. An alkenyl includes one or more double bonds. An alkynyl includes one or more triple bonds.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne. In embodiments, the alkylene is fully saturated. In embodiments, the alkylene is monounsaturated. In embodiments, the alkylene is polyunsaturated. An alkenylene includes one or more double bonds. An alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—S—CH_2$, $—S(O)—CH_3$, $—CH_2—CH_2—S(O)_2—CH_3$, $—CH{=}CHO—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. A heteroalkenylene includes one or more double bonds. A heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is monounsaturated. In embodiments, the heterocycloalkyl is polyunsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. In embodiments, a bicyclic or multicyclic cycloalkyl ring system refers to multiple rings fused together or multiple spirocyclic rings wherein at least one of the fused or spirocyclic rings is a cycloalkyl ring and wherein the multiple rings are attached to the parent molecular moiety through any carbon atom contained within a cycloalkyl ring of the multiple rings.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, a bicyclic or multicyclic cycloalkenyl ring system refers to multiple rings fused together or multiple spirocyclic rings wherein at least one of the fused or spirocyclic rings is a cycloalkenyl ring and wherein the multiple rings are attached to the parent molecular moiety through any carbon atom contained within a cycloalkenyl ring of the multiple rings.

In embodiments, the term "heterocycloalkyl" means a monocyclic, bicyclic, or a multicyclic heterocycloalkyl ring system. In embodiments, heterocycloalkyl groups are fully saturated. In embodiments, a bicyclic or multicyclic heterocycloalkyl ring system refers to multiple rings fused together or multiple spirocyclic rings wherein at least one of the fused or spirocyclic rings is a heterocycloalkyl ring and wherein the multiple rings are attached to the parent molecular moiety through any atom contained within a heterocycloalkyl ring of the multiple rings.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains one heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-S-yl, 1,2,3,4-tetrahydropyrido[4,3-g]isoquinolin-2-yl, 12H-benzo[b]phenoxazin-12-yl, and dodecahydro-1H-carbazol-9-yl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. In embodiments, a fused ring aryl refers to multiple rings fused together wherein at least one of the fused rings is an aryl ring and wherein the multiple rings are attached to the parent molecular moiety through any carbon atom contained within an aryl ring of the multiple rings. A fused ring aryl refers to multiple rings fused together wherein at least one of the fused rings is an aryl ring and wherein the multiple rings are attached to the parent molecular moiety through any carbon atom contained within an aryl ring of the multiple rings. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings). In embodiments, the term "heteroaryl" includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

The symbol "〰" denotes the point of attachment of a chemical moiety to the remainder of a molecule or chemical formula. The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

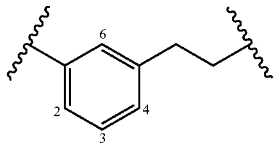

or

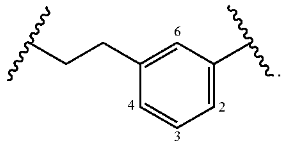

.

An alkylarylene moiety may be substituted (e.g., with a substituent group) on the alkylene moiety or the arylene linker (e.g., at carbons 2, 3, 4, or 6) with halogen, oxo, $—N_3$, $—CF_3$, $—CCl_3$, $—CBr_3$, $—Cl_3$, —CN, —CHO, —OH, $—NH_2$, —COOH, $—CONH_2$, $—NO_2$, —SH, $—SO_2CH_3$, $—SO_3H$, $—OSO_3H$, $—SO_2NH_2$, $—NHNH_2$, $—ONH_2$, —N HC(O)$NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., “alkyl,” “heteroalkyl,” “cycloalkyl,” “heterocycloalkyl,” “aryl,” and “heteroaryl”) includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', ═O, ═NR', ═N—OR', —NR'R", —SR', halogen, —SiR'R"R'", —OC(O)R', —C(O)R', $—CO_2R'$, —CONR'R", —OC(O)NR'R", —NR"C(O)R', —NR'—C (O)NR"R'", —NR"C(O)$_2$R', —NR—C(NR'R"R'")═NR"", —NR—C(NR'R")═NR'", —S(O)R', —S(O)$_2$R', —S(O)$_2$NR'R", $—NRSO_2R'$, —NR'NR"R'", —ONR'R", —NR'C(O)NR"NR'"R"", —CN, $—NO_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term “alkyl” is meant to include groups including carbon atoms bound to groups other than hydrogen groups, such as haloalkyl (e.g., $—CF_3$ and $—CH_2CF_3$) and acyl (e.g., $—C(O)CH_3$, $—C(O)CF_3$, $—C(O)CH_2OCH_3$, and the like).

Similar to the substituents described for the alkyl radical, substituents for the aryl and heteroaryl groups are varied and are selected from, for example: —OR', —NR'R", —SR', halogen, —SiR'R"R'", —OC(O)R', —C(O)R', $—CO_2R'$, —CONR'R", —OC(O)NR'R", —NR"C(O)R', —NR'—C (O)NR"R'", —NR"C(O)$_2$R', —NR—C(NR'R"R'")═NR"", —NR—C(NR'R")═NR'", —S(O)R', —S(O)$_2$R', —S(O)$_2$NR'R", $—NRSO_2R'$, —NR'NR"R'", —ONR'R", —NR'C(O)NR"NR'"R"", —CN, $—NO_2$, —R', $—N_3$, —CH $(Ph)_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —S(O)$_2$—, —S(O)$_2$NR'—, or a single bond, and r is an integer from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X'—$(C''R''R''')_d$—, where s and d are independently integers from 0 to 3, and X' is —O—, —NR'—, —S—, —S(O)—, —$S(O)_2$—, or —$S(O)_2NR'$—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_5$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_5$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_5$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_5$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and/or each substituted or unsubstituted heteroaryl is a substituted or unsubstituted 5 to 6 membered heteroaryl. In some embodiments, each substituted or unsubstituted alkylene is a substituted or unsubstituted $C_1$-$C_5$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene. In some embodiments, the compound (e.g., nucleotide analogue) is a chemical species set forth in the Examples section, claims, embodiments, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms. The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure. The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," "analogue" or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13.A}$, $R^{13.B}$, $R^{13.C}$, $R^{13.D}$ etc., wherein each of $R^{13.A}$, $R^{13.B}$, $R^{13.C}$, $R^{13.D}$, etc. is defined within the scope of the definition of $R^{13}$ and optionally differently.

A "detectable agent," "detectable compound," "detectable label," or "detectable moiety" is a substance, molecule, or composition detectable by spectroscopic, photochemical, biochemical, immunochemical, chemical, magnetic resonance imaging, or other physical means. For example, detectable agents include $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$ $^{90}Y$$^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}$, Pm, $^{153}Sm$, $^{154\text{-}1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, Tm, Yb, Lu, $^{32}P$, fluorophore (e.g., fluorescent dyes), modified oligonucleotides (e.g., moieties described in PCT/US2015/022063, which is incorporated herein by reference), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, radiolabeled glucose, radiolabeled water, radiolabeled ammonia, biocolloids, microbubbles (e.g., including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. In embodiments, a detectable moiety is a moiety (e.g., monovalent form) of a detectable agent.

Examples of detectable agents include imaging agents, including fluorescent and luminescent substances, molecules, or compositions, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescein isothiocyanate moiety, tetramethylrhodamine-5-(and 6)-isothiocyanate moiety, Cy2 moiety, Cy3 moiety, Cy5 moiety, Cy7 moiety, 4',6-diamidino-2-phenylindole moiety, Hoechst 33258 moiety, Hoechst 33342 moiety, Hoechst 34580 moiety, propidium-iodide moiety, or acridine orange moiety. In embodiments, the detectable moiety is a Indo-1, Ca saturated moiety, Indo-1 Ca2+ moiety, Cascade Blue BSA pH 7.0 moiety, Cascade Blue moiety, LysoTracker Blue moiety, Alexa 405 moiety, LysoSensor Blue pH 5.0 moiety, LysoSensor Blue moiety, DyLight 405 moiety, DyLight 350 moiety, BFP (Blue Fluorescent Protein) moiety, Alexa 350 moiety, 7-Amino-4-methylcoumarin pH 7.0 moiety, Amino Coumarin moiety, AMCA conjugate moiety, Coumarin moiety, 7-Hydroxy-4-methylcoumarin moiety, 7-Hydroxy-4-methylcoumarin pH 9.0 moiety, 6,8-Difluoro-7-hydroxy-4-methylcoumarin pH 9.0 moiety, Hoechst 33342 moiety, Pacific Blue moiety, Hoechst 33258 moiety, Hoechst 33258-DNA moiety, Pacific Blue antibody conjugate pH 8.0 moiety, PO-PRO-1 moiety, PO-PRO-1-DNA moiety, POPO-1 moiety, POPO-1-DNA moiety, DAPI-DNA moiety, DAPI moiety, Marina Blue moiety, SYTOX Blue-DNA moiety, CFP (Cyan Fluorescent Protein) moiety, eCFP (Enhanced Cyan Fluorescent Protein) moiety, 1-Anilinonaphthalene-8-sulfonic acid (1,8-ANS) moiety, Indo-1, Ca free moiety, 1,8-ANS (1-Anilinonaphthalene-8-sulfonic acid) moiety, BO-PRO-1-DNA moiety, BOPRO-1 moiety, BOBO-1-DNA moiety, SYTO 45-DNA moiety, evoglow-Pp1 moiety, evoglow-Bs1 moiety, evoglow-Bs2 moiety, Auramine O moiety, DiO moiety, LysoSensor Green pH 5.0 moiety, Cy 2 moiety, LysoSensor Green moiety, Fura-2, high Ca moiety, Fura-2 Ca2+sup> moiety, SYTO 13-DNA moiety, YO-PRO-1-DNA moiety, YOYO-1-DNA moiety, eGFP (Enhanced Green Fluorescent Protein) moiety, LysoTracker Green moiety, GFP (S65T) moiety, BODIPY FL, MeOH moiety, Sapphire moiety, BODIPY FL conjugate moiety, MitoTracker Green moiety, MitoTracker Green FM, MeOH moiety, Fluorescein 0.1 M NaOH moiety, Calcein pH 9.0 moiety, Fluorescein pH 9.0 moiety, Calcein moiety, Fura-2, no Ca moiety, Fluo-4 moiety, FDA moiety, DTAF moiety, Fluorescein moiety, CFDA moiety, FITC moiety, Alexa Fluor 488 hydrazide-water moiety, DyLight 488 moiety, 5-FAM pH 9.0 moiety, Alexa 488 moiety, Rhodamine 110 moiety, Rhodamine 110 pH 7.0 moiety, Acridine Orange moiety, BCECF pH 5.5 moiety, PicoGreendsDNA quantitation reagent moiety, SYBR Green I moiety, Rhodaminen Green pH 7.0 moiety, CyQUANT GR-DNA moiety, NeuroTrace 500/525, green fluorescent Nissl stain-RNA moiety, DansylCadaverine moiety, Fluoro-Emerald moiety, Nissl moiety, Fluorescein dextran pH 8.0 moiety, Rhodamine Green moiety, 5-(and-6)-Carboxy-2', 7'-dichlorofluorescein pH 9.0 moiety, DansylCadaverine, MeOH moiety, eYFP (Enhanced Yellow Fluorescent Protein) moiety, Oregon Green 488 moiety, Fluo-3 moiety, BCECF pH 9.0 moiety, SBFI-Na+ moiety, Fluo-3 Ca2+ moiety, Rhodamine 123 MeOH moiety, FlAsH moiety, Calcium Green-1 Ca2+ moiety, Magnesium Green moiety, DM-NERF pH 4.0 moiety, Calcium Green moiety, Citrine moiety, LysoSensor Yellow pH 9.0 moiety, TO-PRO-1-DNA moiety, Magnesium Green Mg2+ moiety, Sodium Green Na+ moiety, TOTO-1-DNA moiety, Oregon Green 514 moiety, Oregon Green 514 antibody conjugate pH 8.0 moiety, NBD-X moiety, DM-NERF pH 7.0 moiety, NBD-X, MeOH moiety, CI-NERF pH 6.0 moiety, Alexa 430 moiety, CI-NERF pH 2.5 moiety, Lucifer Yellow, CH moiety, LysoSensor Yellow pH 3.0 moiety, 6-TET, SE pH 9.0 moiety, Eosin antibody conjugate pH 8.0 moiety, Eosin moiety, 6-Carboxyrhodamine 6G pH 7.0 moiety, 6-Carboxyrhodamine 6G, hydrochloride moiety, Bodipy R6G SE moiety, BODIPY R6G MeOH moiety, 6 JOE moiety, Cascade Yellow moiety, mBanana moiety, Alexa 532 moiety, Erythrosin-5-isothiocyanate pH 9.0 moiety, 6-HEX, SE pH 9.0 moiety, mOrange moiety, mHoneydew moiety, Cy 3 moiety, Rhodamine B moiety, DiI moiety, 5-TAMRA-MeOH moiety, Alexa 555 moiety, DyLight 549 moiety, BODIPY TMR-X, SE moiety, BODIPY TMR-X MeOH moiety, PO-PRO-3-DNA moiety, PO-PRO-3 moiety, Rhodamine moiety, POPO-3 moiety, Alexa 546 moiety, Calcium Orange Ca2+ moiety, TRITC moiety, Calcium Orange moiety, Rhodaminephalloidin pH 7.0 moiety, MitoTracker Orange moiety, MitoTracker Orange MeOH moiety, Phycoerythrin moiety, Magnesium Orange moiety, R-Phycoerythrin pH 7.5 moiety, 5-TAMRA pH 7.0 moiety, 5-TAMRA moiety, Rhod-2 moiety, FM 1-43 moiety, Rhod-2 Ca2+ moiety, FM 1-43 lipid moiety, LOLO-1-DNA moiety, dTomato moiety, DsRed moiety, Dapoxyl (2-aminoethyl) sulfonamide moiety, Tetramethylrhodamine dextran pH 7.0 moiety, Fluor-Ruby moiety, Resorufin moiety, Resorufin pH 9.0 moiety, mTangerine moiety, LysoTracker Red moiety, Lissaminerhodamine moiety, Cy 3.5 moiety, Rhodamine Red-X antibody conjugate pH 8.0 moiety, Sulforhodamine 101 EtOH moiety, JC-1 pH 8.2 moiety, JC-1 moiety, mStrawberry moiety, MitoTracker Red moiety, MitoTracker Red, MeOH moiety, X-Rhod-1 Ca2+ moiety, Alexa 568 moiety, 5-ROX pH 7.0 moiety, 5-ROX (5-Carboxy-X-rhodamine, triethylammonium salt) moiety, BO-PRO-3-DNA moiety, BOPRO-3 moiety, BOBO-3-DNA moiety, Ethidium Bromide moiety, ReAsH moiety, Calcium Crimson moiety, Calcium Crimson Ca2+ moiety, mRFP moiety, mCherry moiety, HcRed moiety, DyLight 594 moiety, Ethidium homodimer-1-DNA moiety, Ethidiumhomodimer moiety, Propidium Iodide moiety, SYPRO Ruby moiety, Propidium Iodide-DNA moiety, Alexa 594 moiety, BODIPY TR-X, SE moiety, BODIPY TR-X, MeOH moiety, BODIPY TR-X phallacidin pH 7.0 moiety, Alexa Fluor 610 R-phycoerythrin streptavidin pH 7.2 moiety, YO-PRO-3-DNA moiety, Di-8 ANEPPS moiety, Di-8-ANEPPS-lipid moiety, YOYO-3-DNA moiety, Nile Red-lipid moiety, Nile Red moiety, DyLight 633 moiety, mPlum moiety, TO-PRO-3-DNA moiety, DDAO pH 9.0 moiety, Fura Red high Ca moiety, Allophycocyanin pH 7.5 moiety, APC (allophycocyanin) moiety, Nile Blue, EtOH moiety, TOTO-3-DNA moiety, Cy 5 moiety, BODIPY 650/665-X, MeOH moiety, Alexa Fluor 647 R-phycoerythrin streptavidin pH 7.2 moiety, DyLight 649 moiety, Alexa 647 moiety, Fura Red Ca2+ moiety, Atto 647 moiety, Fura Red, low Ca moiety, Carboxynaphthofluorescein pH 10.0 moiety, Alexa 660 moiety, Cy 5.5 moiety, Alexa 680 moiety, DyLight 680 moiety, Alexa 700 moiety, FM 4-64, 2% CHAPS moiety, or FM 4-64 moiety. In embodiments, the detectable moiety is a moiety of 1,1-Diethyl-4,4-carbocyanine iodide, 1,2-Diphenylacetylene, 1,4-Diphenylbutadiene, 1,4-Diphenylbutadiyne, 1,6-Diphenylhexatriene, 1,6-Diphenylhexatriene, 1-anilinonaphthalene-8-sulfonic acid, 2,7-Dichlorofluorescein, 2,5-DIPHENYLOXAZOLE, 2-Di-1-ASP, 2-dodecylresorufin, 2-Methylbenzoxazole, 3,3-Diethylthiadicarbocyanine iodide, 4-Dimethylamino-4-Nitrostilbene, 5(6)-Carboxyfluorescein, 5(6)-Carboxynaphtofluorescein, 5(6)-Carboxytetramethylrhodamine B, 5-(and-6)-carboxy-2',7'-dichlorofluorescein, 5-(and-6)-carboxy-2,7-dichlorofluorescein, 5-(N-hexadecanoyl)aminoeosin, 5-(N-hexadecanoyl)aminoeosin, 5-chloromethylfluorescein, 5-FAM, 5-ROX, 5-TAMRA, 5-TAMRA, 6,8-difluoro-7-hydroxy-4-methylcoumarin, 6,8-difluoro-7-hydroxy-4-methylcoumarin, 6-carboxyrhodamine 6G, 6-HEX, 6-JOE, 6-JOE, 6-TET, 7-aminoactinomycin D, 7-Benzylamino-4-Nitrobenz-2-Oxa-1,3-Diazole, 7-Methoxycoumarin-4-Acetic Acid, 8-Benzyloxy-5,7-diphenylquinoline, 8-Benzyloxy-5,7-diphenylquinoline, 9,10-Bis(Phenylethynyl) Anthracene, 9,10-Diphenylanthracene, 9-METHYLCARBAZOLE, (CS)2Ir(μ-Cl)2Ir(CS)2, AAA, Acridine Orange, Acridine Orange, Acridine Yellow, Acridine Yellow, Adams Apple Red 680, Adirondack Green 520, Alexa Fluor 350, Alexa Fluor 405, Alexa Fluor 430, Alexa Fluor 430, Alexa Fluor 480, Alexa Fluor 488, Alexa Fluor 488, Alexa Fluor 488 hydrazide, Alexa Fluor 500, Alexa Fluor 514, Alexa Fluor 532, Alexa Fluor 546, Alexa Fluor 546, Alexa Fluor 555, Alexa Fluor 555, Alexa Fluor 568, Alexa Fluor 594, Alexa Fluor 594, Alexa Fluor 594, Alexa Fluor 610, Alexa Fluor 610-R-PE, Alexa Fluor 633, Alexa Fluor 635, Alexa Fluor 647, Alexa Fluor 647, Alexa Fluor 647-R-PE, Alexa Fluor 660, Alexa Fluor 680, Alexa Fluor 680-APC, Alexa Fluor 680-R-PE, Alexa Fluor 700, Alexa Fluor 750, Alexa Fluor 790, Allophycocyanin, AmCyan1, Aminomethylcoumarin, Amplex Gold (product), Amplex Red Reagent, Amplex UltraRed, Anthracene, APC, APC-Seta-750, AsRed2, ATTO 390, ATTO 425, ATTO 430LS, ATTO 465, ATTO 488, ATTO 490LS, ATTO 495, ATTO 514, ATTO 520, ATTO 532, ATTO 550, ATTO 565, ATTO 590, ATTO 594, ATTO 610, ATTO 620, ATTO 633, ATTO 635, ATTO 647, ATTO 647N, ATTO 655, ATTO 665, ATTO 680, ATTO 700, ATTO 725, ATTO 740, ATTO Oxa12, ATTO Rho3B, ATTO Rho6G, ATTO Rho11, ATTO Rho12, ATTO Rho13, ATTO Rho14, ATTO Rho101, ATTO Thio12, Auramine O, Azami Green, Azami Green monomeric, B-phycoerythrin, BCECF, BCECF, Bex1, Biphenyl, Birch Yellow 580, Blue-green algae, BO-PRO-1, BO-PRO-3, BOBO-1, BOBO-3, BODIPY 630 650-X, BODIPY 650/665-X, BODIPY FL, BODIPY FL, BODIPY R6G, BODIPY TMR-X, BODIPY TR-X, BODIPY TR-X Ph 7.0, BODIPY TR-X phallacidin, BODIPY-DiMe, BODIPY-Phenyl, BODIPY-TMSCC, C3-Indocyanine, C3-Indocyanine, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, C545T, C-Phycocyanin, Calcein, Calcein red-orange, Calcium Crimson, Calcium Green-1, Calcium Orange, Calcofluor white 2MR, Carboxy SNARF-1 pH 6.0, Carboxy SNARF-1 pH 9.0, Carboxynaphthofluorescein, Cascade Blue, Cascade Yellow, Catskill Green 540, CBQCA, CellMask Orange, CellTrace BODIPY TR methyl ester, CellTrace calcein violet, CellTrace™ Far Red, CellTracker Blue, CellTracker Red CMTPX, CellTracker Violet BMQC, CF405M, CF405S, CF488A, CF543, CF555, CFP, CFSE, CF™ 350, CF™ 485, Chlorophyll A, Chlorophyll B, Chromeo 488, Chromeo 494, Chromeo 505, Chromeo 546, Chromeo 642, Citrine, Citrine, ClOH butoxy aza-BODIPY, ClOH C12 aza-BODIPY, CM-H2DCFDA, Coumarin 1, Coumarin 6, Coumarin 6, Coumarin 30, Coumarin 314, Coumarin 334, Coumarin 343, Coumarine 545T, Cresyl Violet Perchlorate, CryptoLight CF1, CryptoLight CF2, CryptoLight CF3, CryptoLight CF4, CryptoLight CF5, CryptoLight CF6, Crystal Violet, Cumarin153, Cy2, Cy3, Cy3, Cy3.5, Cy3B, Cy3B, Cy3Cy5 ET, Cy5, Cy5, Cy5.5, Cy7, Cyanine3 NHS ester, Cyanine5 carboxylic acid, Cyanine5 NHS ester, Cyclotella meneghiniana Kutzing, CypHer5, CypHer5 pH 9.15, CyQUANT GR, CyTrak Orange, Dabcyl SE, DAF-FM, DAMC (Weiss), dansyl cadaverine, Dansyl Glycine (Dioxane), DAPI, DAPI, DAPI, DAPI, DAPI (DMSO), DAPI (H2O), Dapoxyl (2-aminoethyl)sulfonamide, DCI, DCM, DCM, DCM (acetonitrile), DCM (MeOH), DDAO, Deep Purple, di-8-ANEPPS, DiA, Dichlorotris(1,10-phenanthroline) ruthenium(II), DiClOH $C_{12}$ aza-BODIPY, DiClOHbutoxy aza-BODIPY, DiD, DiI, DiIC18(3), DiO, DiR, Diversa Cyan-FP, Diversa Green-FP, DM-NERF pH 4.0, DOCI, Doxorubicin, DPP pH-Probe 590-7.5, DPP pH-Probe 590-9.0, DPP pH-Probe 590-11.0, DPP pH-Probe 590-11.0, Dragon Green, DRAQ5, DsRed, DsRed, DsRed, DsRed-Express, DsRed-Express2, DsRed-Express T1, dTomato, DY-350XL, DY-480, DY-480XL MegaStokes, DY-485, DY-485XL MegaStokes, DY-490, DY-490XL MegaStokes, DY-500, DY-500XL MegaStokes, DY-520, DY-520XL MegaStokes, DY-547, DY-549P1, DY-549P1, DY-554, DY-555, DY-557, DY-557, DY-590, DY-590, DY-615, DY-630, DY-631, DY-633, DY-635, DY-636, DY-647, DY-649P1, DY-649P1, DY-650, DY-651, DY-656, DY-673, DY-675, DY-676, DY-680, DY-681, DY-700, DY-701, DY-730, DY-731, DY-750, DY-751, DY-776, DY-782, Dye-28, Dye-33, Dye-45, Dye-304, Dye-1041, DyLight 488, DyLight 549, DyLight 594, DyLight 633, DyLight 649, DyLight 680, E2-Crimson, E2-Orange, E2-Red/Green, EBFP, ECF, ECFP, ECL Plus, eGFP, ELF 97, Emerald, Envy Green, Eosin, Eosin Y, epicocconone, EqFP611, Erythrosin-5-isothiocyanate, Ethidium bromide, ethidium homodimer-1, Ethyl Eosin, Ethyl Eosin, Ethyl Nile Blue A, Ethyl-p-Dimethylaminobenzoate, Ethyl-p-Dimethylaminobenzoate, Eu203 nanoparticles, Eu (Soini), Eu(tta) 3DEADIT, EvaGreen, EVOblue-30, EYFP, FAD, FITC, FITC, FlAsH (Adams), Flash Red EX, FlAsH-CCPGCC, FlAsH-CCXXCC, Fluo-3, Fluo-4, Fluo-5F, Fluorescein, Fluorescein 0.1 NaOH, Fluorescein-Dibase, fluoro-emerald, Fluorol 5G, FluoSpheres blue, FluoSpheres crimson, FluoSpheres dark red, FluoSpheres orange, FluoSpheres red, FluoSpheres yellow-green, FM4-64 in CTC, FM4-64 in SDS, FM 1-43, FM 4-64, Fort Orange 600, Fura Red, Fura Red Ca free, fura-2, Fura-2 Ca free, Gadodiamide, Gd-Dtpa-Bma, Gadodiamide, Gd-Dtpa-Bma, GelGreen™, GelRed™, H9-40, HcRed1, Hemo Red 720, HiLyte Fluor 488, HiLyte Fluor 555, HiLyte Fluor 647, HiLyte Fluor 680, HiLyte Fluor 750, HiLyte Plus 555, HiLyte Plus 647, HiLyte Plus 750, HmGFP, Hoechst 33258, Hoechst 33342, Hoechst-33258, Hoechst-33258, Hops Yellow 560, HPTS, HPTS, HPTS, HPTS, HPTS, indo-1, Indo-1 Ca free, Ir(Cn)2(acac), Ir(Cs)2(acac), IR-775 chloride, IR-806, Ir-OEP-CO-Cl, IRDye®650 Alkyne, IRDye® 650 Azide, IRDye®650 Carboxylate, IRDye® 650 DBCO, IRDye®650 Maleimide, IRDye®650 NHS Ester, IRDye®680LT Carboxylate, IRDye®680LT Maleimide, IRDye® 680LT NHS Ester, IRDye® 680RD Alkyne, IRDye® 680RD Azide, IRDye® 680RD Carboxylate, IRDye® 680RD DBCO, IRDye® 680RD Maleimide, IRDye® 680RD NHS Ester, IRDye® 700 phosphoramidite, IRDye® 700DX, IRDye® 700DX, IRDye® 700DX Carboxylate, IRDye® 700DX NHS Ester, IRDye® 750 Carboxylate, IRDye® 750 Maleimide, IRDye® 750 NHS Ester, IRDye® 800 phosphoramidite, IRDye® 800CW, IRDye® 800CW Alkyne, IRDye® 800CW Azide, IRDye® 800CW Carboxylate, IRDye® 800CW DBCO, IRDye® 800CW Maleimide, IRDye® 800CW NHS Ester, IRDye® 800RS, IRDye® 800RS Carboxylate, IRDye® 800RS NHS Ester, IRDye® QC-1 Carboxylate, IRDye® QC-1 NHS Ester, Isochrysis galbana—Parke, JC-1, JC-1, JOJO-1, Jonamac Red Evitag T2, Kaede Green, Kaede Red, kusabira orange, Lake Placid 490, LDS 751, Lissamine Rhodamine (Weiss), LOLO-1, lucifer yellow CH, Lucifer Yellow CH, lucifer yellow CH, Lucifer Yellow CH Dilitium salt, Lumio Green, Lumio Red, Lumogen F Orange, Lumogen Red F300, Lumogen Red F300, LysoSensor Blue DND-192, LysoSensor Green DND-153, LysoSensor Green DND-153, LysoSensor Yellow/Blue DND-160 pH 3, LysoSensor YellowBlue DND-160, LysoTracker Blue DND-22, LysoTracker Blue DND-22, LysoTracker Green DND-26, LysoTracker Red DND-99, LysoTracker Yellow HCK-123, Macoun Red Evitag T2, Macrolex Fluorescence Red G, Macrolex Fluorescence Yellow 10GN, Macrolex Fluorescence Yellow 10GN, Magnesium Green, Magnesium Octaethylporphyrin, Magnesium Orange, Magnesium Phthalocyanine, Magnesium Phthalocyanine, Magnesium Tetramesitylporphyrin, Magnesium Tetraphenylporphyrin, malachite green isothiocyanate, Maple Red-Orange 620, Marina Blue, mBanana, mBBr, mCherry, Merocyanine 540, Methyl green, Methyl green, Methyl green, Methylene Blue, Methylene Blue, mHoneyDew, MitoTracker Deep Red 633, MitoTracker Green FM, MitoTracker Orange CMTMRos, MitoTracker Red CMXRos, monobromobimane, Monochlorobimane, Monoraphidium, mOrange, mOrange2, mPlum, mRaspberry, mRFP, mRFP1, mRFP1.2 (Wang), mStrawberry (Shaner), mTangerine (Shaner), N,N-Bis(2,4,6-trimethylphenyl)-3, 4:9,10-perylenebis(dicarboximide), NADH, Naphthalene, Naphthalene, Naphthofluorescein, Naphthofluorescein, NBD-X, NeuroTrace 500525, Nilblau perchlorate, nile blue, Nile Blue, Nile Blue (EtOH), nile red, Nile Red, Nile Red, Nile red, Nileblue A, NIR1, NIR2, NIR3, NIR4, NIR820, Octaethylporphyrin, OH butoxy aza-BODIPY, OHC12 aza-BODIPY, Orange Fluorescent Protein, Oregon Green 488, Oregon Green 488 DUPE, Oregon Green 514, Oxazin1, Oxazin 750, Oxazine 1, Oxazine 170, P4-3, P-Quaterphenyl, P-Terphenyl, PA-GFP (post-activation), PA-GFP (pre-activation), Pacific Orange, Palladium (II) meso-tetraphenyl-tetrabenzoporphyrin, PdOEPK, PdTFPP, PerCP-Cy5.5, Perylene, Perylene, Perylene bisimide pH-Probe 550-5.0, Perylene bisimide pH-Probe 550-5.5, Perylene bisimide pH-Probe 550-6.5, Perylene Green pH-Probe 720-5.5, Perylene Green Tag pH-Probe 720-6.0, Perylene Orange pH-Probe 550-2.0, Perylene Orange Tag 550, Perylene Red pH-Probe 600-5.5, Perylenediimid, Perylne Green pH-Probe 740-5.5, Phenol, Phenylalanine, pHrodo, succinimidyl ester, Phthalocyanine, PicoGreen dsDNA quantitation reagent, Pinacyanol-Iodide, Piroxicam, Platinum(II) tetraphenyltetrabenzoporphyrin, Plum Purple, PO-PRO-1, PO-PRO-3, POPO-1, POPO-3, POPOP, Porphin, PPO, Proflavin, PromoFluor-350, PromoFluor-405, PromoFluor-415, PromoFluor-488, PromoFluor-488 Premium, PromoFluor-488LSS, PromoFluor-500LSS, PromoFluor-505, PromoFluor-510LSS, PromoFluor-514LSS, PromoFluor-520LSS, PromoFluor-532, PromoFluor-546, PromoFluor-555, PromoFluor-590, PromoFluor-610, PromoFluor-633, PromoFluor-647, PromoFluor-670, PromoFluor-680, PromoFluor-700, PromoFluor-750, PromoFluor-770, PromoFluor-780, PromoFluor-840, propidium iodide, Protoporphyrin IX, PTIR475/UF, PTIR545/UF, PtOEP, PtOEPK, PtTFPP, Pyrene, QD525, QD565, QD585, QD605, QD655, QD705, QD800, QD903, QD PbS 950, QDot 525, QDot 545, QDot 565, Qdot 585, Qdot 605, Qdot 625, Qdot 655, Qdot 705, Qdot 800, QpyMe2, QSY 7, QSY 7, QSY 9, QSY 21, QSY 35, quinine, Quinine Sulfate, Quinine sulfate, R-phycoerythrin, R-phycoerythrin, ReAsH-CCPGCC, ReAsH-CCXXCC, Red Beads (Weiss), Redmond Red, Resorufin, resorufin, rhod-2, Rhodamin 700 perchlorate, rhodamine, Rhodamine 6G, Rhodamine 6G, Rhodamine 101, rhodamine 110, Rhodamine 123, rhodamine 123, Rhodamine B, Rhodamine B, Rhodamine Green, Rhodamine pH-Probe 585-7.0, Rhodamine pH-Probe 585-7.5, Rhodamine phalloidin, Rhodamine Red-X, Rhodamine Red-X, Rhodamine Tag pH-Probe 585-7.0, Rhodol Green, Riboflavin, Rose Bengal, Sapphire, SBFI, SBFI Zero Na, *Scenedesmus* sp., SensiLight PBXL-1, SensiLight PBXL-3, Seta 633-NHS, Seta-633-NHS, SeTau-380-NHS, SeTau-647-NHS, Snake-Eye Red 900, SNIR1, SNIR2, SNIR3, SNIR4, Sodium Green, Solophenyl flavine 7GFE 500, Spectrum Aqua, Spectrum Blue, Spectrum FRed, Spectrum Gold, Spectrum Green, Spectrum Orange, Spectrum Red, Squarylium dye III, Stains All, Stilben derivate, Stilbene, Styry18 perchlorate, Sulfo-Cyanine3 carboxylic acid, Sulfo-Cyanine3 carboxylic acid, Sulfo-Cyanine3 NHS ester, Sulfo-Cyanine5 carboxylic acid, Sulforhodamine 101, sulforhodamine 101, Sulforhodamine B, Sulforhodamine G, Suncoast Yellow, SuperGlo BFP, SuperGlo GFP, Surf Green EX, SYBR Gold nucleic acid gel stain, SYBR Green I, SYPRO Ruby, SYTO 9, SYTO 11, SYTO 13, SYTO 16, SYTO 17, SYTO 45, SYTO 59, SYTO 60, SYTO 61, SYTO 62, SYTO 82, SYTO RNASelect, SYTO RNASelect, SYTOX Blue, SYTOX Green, SYTOX Orange, SYTOX Red, T-Sapphire, Tb (Soini), tCO, tdTomato, Terrylen, Terrylendiimid, testdye, Tetra-t-Butylazaporphine, Tetra-t-Butylnaphthalocyanine, Tetracen, Tetrakis(o-Aminophenyl)Porphyrin, Tetramesitylporphyrin, Tetramethylrhodamine, tetramethylrhodamine, Tetraphenylporphyrin, Tetraphenylporphyrin, Texas Red, Texas Red DUPE, Texas Red-X, ThiolTracker Violet, Thionin acetate, TMRE, TO-PRO-1, TO-PRO-3, Toluene, Topaz (Tsien1998), TOTO-1, TOTO-3, Tris(2,2-Bipyridyl)Ruthenium(II) chloride, Tris(4,4-diphenyl-2,2-bipyridine) ruthenium(II) chloride, Tris(4,7-diphenyl-1,10-phenanthroline) ruthenium(II) TMS, TRITC (Weiss), TRITC Dextran (Weiss), Tryptophan, Tyrosine, Vex1, Vybrant DyeCycle Green stain, Vybrant DyeCycle Orange stain, Vybrant DyeCycle Violet stain, WEGFP (post-activation), WellRED D2, WellRED D3, WellRED D4, WtGFP, WtGFP (Tsien1998), X-rhod-1, Yakima Yellow, YFP, YO-PRO-1, YO-PRO-3, YOYO-1, YoYo-1, YoYo-1 dsDNA, YoYo-1 ssDNA, YOYO-3, Zinc Octaethylporphyrin, Zinc Phthalocyanine, Zinc Tetramesitylporphyrin, Zinc Tetraphenylporphyrin, ZsGreenl, or ZsYellowl.

In embodiments, the detectable moiety is a moiety of a derivative of one of the detectable moieties described immediately above, wherein the derivative differs from one of the detectable moieties immediately above by a modification resulting from the conjugation of the detectable moiety to a compound described herein. In embodiments, the detectable label is a fluorescent dye. In embodiments, the detectable label is a fluorescent dye capable of exchanging energy with another fluorescent dye (e.g., fluorescence resonance energy transfer (FRET) chromophores).

The term "cyanine" or "cyanine moiety" as described herein refers to a detectable moiety containing two nitrogen groups separated by a polymethine chain. In embodiments, the cyanine moiety has 3 methine structures (i.e. cyanine 3 or Cy3). In embodiments, the cyanine moiety has 5 methine structures (i.e. cyanine 5 or Cy5). In embodiments, the cyanine moiety has 7 methine structures (i.e., cyanine 7 or Cy7).

Descriptions of compounds (e.g., nucleotide analogues) of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The compounds of the present invention may exist as salts. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art. The neutral forms of the compounds are preferably regenerated by contacting the salt with a base or acid and isolating the parent compound in the conventional manner. The parent form of the compound may differ from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Hybridize" shall mean the annealing of one single-stranded nucleic acid (such as a primer) to another nucleic acid based on the well-understood principle of sequence complementarity. In an embodiment the other nucleic acid is a single-stranded nucleic acid. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. Those skilled in the art understand how to estimate and adjust the stringency of hybridization conditions such that sequences having at least a desired level of complementarity will stably hybridize, while those having lower complementarity will not. As used herein, the term "stringent condition" refers to condition(s) under which a polynucleotide probe or primer will hybridize preferentially to its target sequence, and to a lesser extent to, or not at all to, other sequences. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex which comprises a double-stranded portion of nucleic acid.

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated, however, that the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The term "streptavidin" refers to a tetrameric protein (including homologs, isoforms, and functional fragments thereof) capable of binding biotin. The term includes any recombinant or naturally-occurring form of streptavidin variants thereof that maintain streptavidin activity (e.g., within at least 30%, 40%, 50%, 60%, 70%, 80%, 90%, 95%, or 100% activity compared to wildtype streptavidin).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Nucleic acid" refers to nucleotides (e.g., deoxyribonucleotides or ribonucleotides) and polymers thereof in either single-, double- or multiple-stranded form, or complements thereof, or nucleosides (e.g., deoxyribonucleosides or ribonucleosides). In embodiments, "nucleic acid" does not include nucleosides. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. Nucleic acids and polynucleotides are polymers of any length, including longer lengths, e.g., 200, 300, 500, 1000, 2000, 3000, 5000, 7000, 10,000, etc. In certain embodiments the nucleic acids herein contain phosphodiester bonds. In other embodiments, nucleic acid analogs are included that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. A residue of a nucleic acid, as referred to herein, is a monomer of the nucleic acid (e.g., a nucleotide). The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. Nucleosides may be modified at the base and/or the sugar. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g., polynucleotides contemplated herein include any types of RNA, e.g., mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like. In embodiments, when a nucleic acid is to be sequenced, it may be referred to as a template nucleic acid. A "nucleic acid moiety" as used herein is a monovalent form of a nucleic acid. In embodiments, the nucleic acid moiety is attached to the 3' or 5' position of a nucleotide or nucleoside.

"Nucleotide," as used herein, refers to a nucleoside-5'-phosphate (e.g., polyphosphate) compound, or a structural analog thereof, which can be incorporated (e.g., partially incorporated as a nucleoside-5'-monophosphate or derivative thereof) by a nucleic acid polymerase to extend a growing nucleic acid chain (such as a primer). Nucleotides may comprise bases such as A, C, G, T, U, or analogues thereof, and may comprise 2, 3, 4, 5, 6, 7, 8, or more phosphates in the phosphate group. Nucleotides may be modified at one or more of the base, sugar, or phosphate group. A nucleotide may have a label or tag attached (a "labeled nucleotide" or "tagged nucleotide").

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g., phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

In embodiments, "nucleotide analogue," "nucleotide analog," or "nucleotide derivative" shall mean an analogue of adenine (A), cytosine (C), guanine (G), thymine (T), or uracil (U) (that is, an analogue or derivative of a nucleotide comprising the base adenine (A), cytosine (C), guanine (G), thymine (T), or uracil (U)), comprising a phosphate group, which may be recognized by DNA or RNA polymerase (whichever is applicable) and may be incorporated into a strand of DNA or RNA (whichever is appropriate). Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the —OH group at the 3'-position of deoxyribose. Nucleotide analogues and DNA polymerase-based DNA sequencing are also described in U.S. Pat. No. 6,664,079, which is incorporated herein by reference in its entirety for all purposes.

A "nucleoside" is structurally similar to a nucleotide, but is missing the phosphate moieties. An example of a nucleoside analogue would be one in which the label is linked to the base and there is no phosphate group attached to the sugar molecule.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

As used herein, the term "template polynucleotide" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s). In the context of selective sequencing, "target polynucleotide(s)" refers to the subset of polynucleotide(s) to be sequenced from within a starting population of polynucleotides.

As used herein, the term "complementary" or "substantially complementary" refers to the hybridization, base pairing, or the formation of a duplex between nucleotides or nucleic acids. For example, complementarity exists between the two strands of a double-stranded DNA molecule or between an oligonucleotide primer and a primer binding site on a single-stranded nucleic acid when a nucleotide (e.g., RNA or DNA) or a sequence of nucleotides is capable of base pairing with a respective cognate nucleotide or cognate sequence of nucleotides. As described herein and commonly known in the art the complementary (matching) nucleotide of adenosine (A) is thymidine (T) and the complementary (matching) nucleotide of guanosine (G) is cytosine (C). Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. "Duplex" means at least two oligonucleotides and/or polynucleotides that are fully or partially complementary undergo Watson-Crick type base pairing among all or most of their nucleotides so that a stable complex is formed.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin or loop structure, with or without an overhang) or portions of separate polynucleotides. In embodiments, one or both sequences in a pair of complementary sequences form portions of longer polynucleotides, which may or may not include additional regions of complementarity.

The term "bioconjugate group" or "bioconjugate reactive moiety" or "bioconjugate reactive group" refers to a chemical moiety which participates in a reaction to form bioconjugate linker (e.g., covalent linker). Non-limiting examples of bioconjugate groups include $-NH_2$, —COOH, $-COOCH_3$, —N-hydroxysuccinimide, -maleimide,

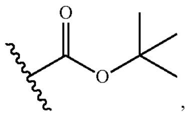

, or

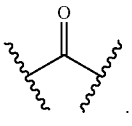

.

In embodiments, the bioconjugate reactive group may be protected (e.g., with a protecting group).

In embodiments, the bioconjugate reactive moiety is

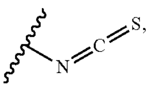

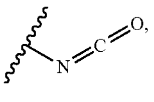

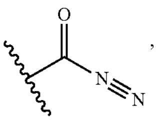

,

-continued

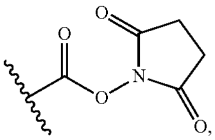

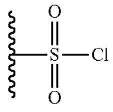

,

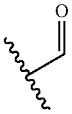

,

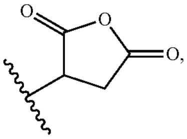

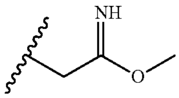

,

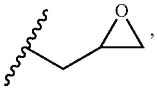

,

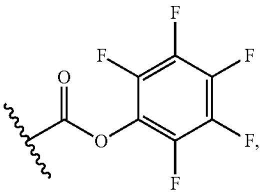

or $-NH_2$. Additional examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |

-continued

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g., —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine). In embodiments, the first bioconjugate reactive group (e.g., —COOH) is covalently attached to the second bioconjugate reactive group (e.g., 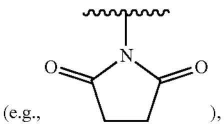 [SMILES: *N1C(=O)CCC1=O] ), thereby forming a bioconjugate (e.g., 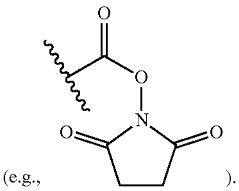 [SMILES: *C(=O)ON1C(=O)CCC1=O] ).

In embodiments, the first bioconjugate reactive group (e.g., —$NH_2$) is covalently attached to the second bioconjugate reactive group (e.g., 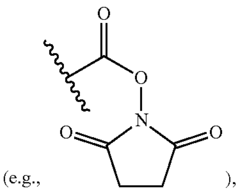 [SMILES: *C(=O)ON1C(=O)CCC1=O] ), thereby forming a bioconjugate (e.g., 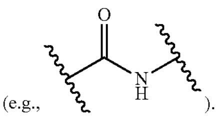 [SMILES: *NC(*)=O] ).

In embodiments, the first bioconjugate reactive group (e.g., a coupling reagent) is covalently attached to the second bioconjugate reactive group (e.g., 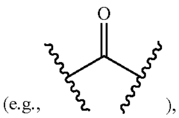 ), thereby forming a bioconjugate (e.g., 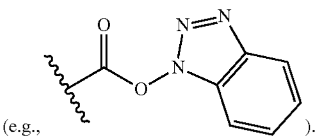 [SMILES: *C(=O)On1nnc2ccccc21] ).

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (1) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or streptavidin to form an avidin-biotin complex or streptavidin-biotin complex.

The term "monophosphate" is used in accordance with its ordinary meaning in the arts and refers to a moiety having the formula:

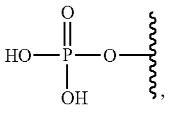

or ionized forms thereof. The term "polyphosphate" refers to at least two phosphate groups, having the formula:

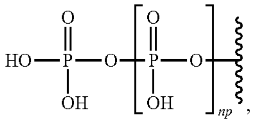

or ionized forms thereof, wherein np is an integer of 1 or greater. In embodiments, np is an integer from 1 to 5. In embodiments, np is an integer from 1 to 2. In embodiments, np is 2. The term "diphosphate" is used in accordance with its ordinary meaning in the arts and refers to a moiety having the formula:

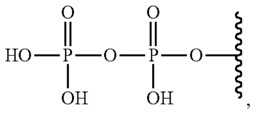

or ionized forms thereof. The term "triphosphate" is used in accordance with its ordinary meaning in the arts and refers to a moiety having the formula:

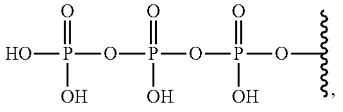 [SMILES: *OP(=O)(O)OP(=O)(O)OP(=O)(O)O]

or ionized forms thereof. In embodiments, a polyphosphate is a diphosphate. In embodiments, a polyphosphate is a triphosphate. In embodiments, a polyphosphate is a hexaphosphate.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In embodiments the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS)). In embodiments the protecting group is an amine protecting group. Non-limiting examples of amine protecting groups include carbobenzyloxy (Cbz), tert-butyloxycarbonyl (BOC), 9-Fluorenylmethyloxycarbonyl (FMOC), acetyl, benzoyl, benzyl, carbamate, p-methoxybenzyl ether (PMB), and tosyl (Ts). In embodiments, the protecting group is a nucleoside protecting group. In embodiments, the protecting group is a 5'-O-nucleoside protecting group.

The term "5'-nucleoside protecting group" as used herein refers to a moiety covalently bound to a heteroatom (e.g., O) on the 5' position of sugar to prevent reactivity of the heteroatom during one or more chemical reactions performed prior to removal of the protecting group. Typically a protecting group is bound to a heteroatom (e.g., O) during a part of a multipart synthesis wherein it is not desired to have the heteroatom react (e.g., during a chemical reduction) with the reagent. Following protection the protecting group may be removed by any appropriate means (e.g., by modulating the pH). Non-limiting examples of 5'-O-nucleoside protecting groups include silyl ethers (e.g., tert-butyl-diphenylsilyl (TBDPS), or primary and secondary tert-butyldimethylsilyl (TBDMS)) or trityl (e.g., 4,4'-dimethoxytrityl (DMT)). In embodiments, $R^1$ includes a protecting group found in *Green's Protective Groups in Organic Chemistry*, Wiley, Fourth edition, 2007, Peter G. M. Wuts and Theodora W. Greene, and *Current Protocols in Nucleic Acid Chemistry* (2000) 2.3.1-2.3.34, John Wiley & Sons, Inc. which is incorporated herein by reference in its entirety for all purposes.

The term "nucleobase" or "base" as used herein refers to a purine or pyrimidine compound, or a derivative thereof, that may be a constituent of nucleic acid (i.e., DNA or RNA, or a derivative thereof). In embodiments, the nucleobase is a divalent purine or pyrimidine, or derivative thereof. In embodiments, the nucleobase is a monovalent purine or pyrimidine, or derivative thereof. In embodiments, the base is a derivative of a naturally occurring DNA or RNA base (e.g., a base analogue). In embodiments the base is a hybridizing base. In embodiments the base hybridizes to a complementary base. In embodiments, the base is capable of forming at least one hydrogen bond with a complementary base (e.g., adenine hydrogen bonds with thymine, adenine hydrogen bonds with uracil, guanine pairs with cytosine). Non-limiting examples of a base includes cytosine or a derivative thereof (e.g., cytosine analogue), guanine or a derivative thereof (e.g., guanine analogue), adenine or a derivative thereof (e.g., adenine analogue), thymine or a derivative thereof (e.g., thymine analogue), uracil or a derivative thereof (e.g., uracil analogue), hypoxanthine or a derivative thereof (e.g., hypoxanthine analogue), xanthine or a derivative thereof (e.g., xanthine analogue), 7-methylguanine or a derivative thereof (e.g., 7-methylguanine analogue), deaza-adenine or a derivative thereof (e.g., deaza-adenine analogue), deaza-guanine or a derivative thereof (e.g., deaza-guanine), deaza-hypoxanthine or a derivative thereof, 5,6-dihydrouracil or a derivative thereof (e.g., 5,6-dihydrouracil analogue), 5-methylcytosine or a derivative thereof (e.g., 5-methylcytosine analogue), or 5-hydroxymethylcytosine or a derivative thereof (e.g., 5-hydroxymethylcytosine analogue) moieties. In embodiments, the base is adenine, guanine, hypoxanthine, xanthine, theobromine, caffeine, uric acid, or isoguanine, which may be optionally substituted or modified.

The term "non-covalent linker" is used in accordance with its ordinary meaning and refers to a divalent moiety which includes at least two molecules that are not covalently linked to each other but are capable of interacting with each other via a non-covalent bond (e.g., electrostatic interactions (e.g., ionic bond, hydrogen bond, halogen bond) or van der Waals interactions (e.g., dipole-dipole, dipole-induced dipole, London dispersion). In embodiments, the non-covalent linker is the result of two molecules that are not covalently linked to each other that interact with each other via a non-covalent bond.

The term "anchor moiety" as used herein refers to a chemical moiety capable of interacting (e.g., covalently or non-covalently) with a second, optionally different, chemical moiety (e.g., complementary anchor moiety binder). In embodiments, the anchor moiety is a bioconjugate reactive group capable of interacting (e.g., covalently) with a complementary bioconjugate reactive group (e.g., complementary anchor moiety reactive group, complementary anchor moiety binder). In embodiments, an anchor moiety is a click chemistry reactant moiety. In embodiments, the anchor moiety (an "affinity anchor moiety") is capable of non-covalently interacting with a second chemical moiety (e.g., complementary affinity anchor moiety binder). Non-limiting examples of an anchor moiety include biotin, azide, trans-cyclooctene (TCO) (Blackman, M. L., et al., *J. Am. Chem. Soc.,* 2008, 130, 13518-13519; Debets, M. F., et al. *Org. Biomol. Chem.,* 2013, 11, 6439-6455) and phenyl boric acid (PBA) (Bergseid M., et al., *BioTechniques,* 2000, 29, 1126-1133). In embodiments, an affinity anchor moiety (e.g., biotin moiety) interacts non-covalently with a complementary affinity anchor moiety binder (e.g., streptavidin moiety). In embodiments, an anchor moiety (e.g., azide moiety, trans-cyclooctene (TCO) moiety, phenyl boric acid (PBA) moiety) covalently binds a complementary anchor moiety binder (e.g., dibenzocyclooctyne (DBCO) moiety (Jewett J. C. and Bertozzi C. R. *J. Am. Chem. Soc.,* 2010, 132, 3688-3690), tetrazine (TZ) moiety, salicylhydroxamic acid (SHA) moiety).

The terms "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. In embodiments, a cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). In embodiments, a cleavable linker is a self-immolative linker, a trivalent linker, or a linker capable of dendritic amplication of signal, or a self-immolative dendrimer containing linker (e.g., all as described in US 2007/0009980, US 2006/0003383, and US 2009/0047699, which are incorporated by reference in their entirety for any purpose). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), hydrazine ($N_2H_4$)). A chemically cleavable linker is non-enzymatically cleavable. In embodiments, the cleavable linker is cleaved by contacting the cleavable linker with a cleaving agent (e.g., a reducing agent). In embodiments, the cleaving agent is sodium dithionite ($Na_2S_2O_4$), weak acid, hydrazine ($N_2H_4$), Pd(0), or light-irradiation (e.g., ultraviolet radiation). In embodiments, cleaving includes removing. A "cleavable site" or "scissile linkage" in the context of a polynucleotide is a site which allows controlled cleavage of the polynucleotide strand (e.g., the linker, the primer, or the polynucleotide) by chemical, enzymatic, or photochemical means known in the art and described herein. A scissile site may refer to the linkage of a nucleotide between two other nucleotides in a nucleotide strand (i.e., an internucleosidic linkage). In embodiments, the scissile linkage can be located at any position within the one or more nucleic acid molecules, including at or near a terminal end (e.g., the 3' end of an oligonucleotide) or in an interior portion of the one or more nucleic acid molecules. In embodiments, conditions suitable for separating a scissile linkage include a modulating the pH and/or the temperature. In embodiments, a scissile site can include at least one acid-labile linkage. For example, an acid-labile linkage may include a phosphoramidate linkage. In embodiments, a phosphoramidate linkage can be hydrolysable under acidic conditions, including mild acidic conditions such as trifluoroacetic acid and a suitable temperature (e.g., 30° C.), or other conditions known in the art, for example Matthias Mag, et al Tetrahedron Letters, Volume 33, Issue 48, 1992, 7319-7322. In embodiments, the scissile site can include at least one photolabile internucleosidic linkage (e.g., o-nitrobenzyl linkages, as described in Walker et al, J. Am. Chem. Soc. 1988, 110, 21, 7170-7177), such as o-nitrobenzyloxymethyl or p-nitrobenzyloxymethyl group (s). In embodiments, the scissile site includes at least one uracil nucleobase. In embodiments, a uracil nucleobase can be cleaved with a uracil DNA glycosylase (UDG) or Formamidopyrimidine DNA Glycosylase Fpg. In embodiments, the scissile linkage site includes a sequence-specific nicking site having a nucleotide sequence that is recognized and nicked by a nicking endonuclease enzyme or a uracil DNA glycosylase. The term "self-immolative" referring to a linker is used in accordance with its well understood meaning in Chemistry and Biology as used in US 2007/0009980, US 2006/0003383, and US 2009/0047699, which are incorporated by reference in their entirety for any purpose. In embodiments "self-immolative" referring to a linker refers to a linker that is capable of additional cleavage following initial cleavage by an external stimuli. The term dendrimer is used in accordance with its well understood meaning in Chemistry. In embodiments, the term "self-immolative dendrimer" is used as described in US 2007/0009980, US 2006/0003383, and US 2009/0047699, which are incorporated by reference in their entirety for any purpose and in embodiments refers to a dendrimer that is capable of releasing all of its tail units through a self-immolative fragmentation following initial cleavage by an external stimulus.

A photocleavable linker (e.g., including or consisting of an o-nitrobenzyl group) refers to a linker which is capable of being split in response to photo-irradiation (e.g., ultraviolet radiation). An acid-cleavable linker refers to a linker which is capable of being split in response to a change in the pH (e.g., increased acidity). A base-cleavable linker refers to a linker which is capable of being split in response to a change in the pH (e.g., decreased acidity). An oxidant-cleavable linker refers to a linker which is capable of being split in response to the presence of an oxidizing agent. A reductant-cleavable linker refers to a linker which is capable of being split in response to the presence of an reducing agent (e.g., tris(3-hydroxypropyl)phosphine). In embodiments, the cleavable linker is a dialkylketal linker (Binaulda S., et al., *Chem. Commun.,* 2013, 49, 2082-2102; Shenoi R. A., et al., *J Am. Chem. Soc.,* 2012, 134, 14945-14957), an azo linker (Rathod, K. M., et al., *Chem. Sci. Tran.,* 2013, 2, 25-28; Leriche G., et al., *Eur. J. Org. Chem.,* 2010, 23, 4360-64), an allyl linker, a cyanoethyl linker, a 1-(4,4-dimethyl-2,6-dioxocyclohex-1-ylidene)ethyl linker, or a nitrobenzyl linker.

The term "orthogonally cleavable linker" or "orthogonal cleavable linker" as used herein refer to a cleavable linker that is cleaved by a first cleaving agent (e.g., enzyme, nucleophilic/basic reagent, reducing agent, photo-irradiation, electrophilic/acidic reagent, organometallic and metal reagent, oxidizing reagent) in a mixture of two or more different cleaving agents and is not cleaved by any other different cleaving agent in the mixture of two or more cleaving agents. For example, two different cleavable linkers are both orthogonal cleavable linkers when a mixture of the two different cleavable linkers are reacted with two different cleaving agents and each cleavable linker is cleaved by only one of the cleaving agents and not the other cleaving agent and the agent that cleaves each cleavable linker is different. In embodiments, an orthogonally is a cleavable linker that following cleavage the two separated entities (e.g., fluorescent dye, bioconjugate reactive group) do not further react and form a new orthogonally cleavable linker.

The term "orthogonal detectable label" or "orthogonal detectable moiety" as used herein refer to a detectable label (e.g., fluorescent dye or detectable dye) that is capable of being detected and identified (e.g., by use of a detection means (e.g., emission wavelength, physical characteristic measurement)) in a mixture or a panel (collection of separate samples) of two or more different detectable labels. For example, two different detectable labels that are fluorescent dyes are both orthogonal detectable labels when a panel of the two different fluorescent dyes is subjected to a wavelength of light that is absorbed by one fluorescent dye but not the other and results in emission of light from the fluorescent dye that absorbed the light but not the other fluorescent dye. Orthogonal detectable labels may be separately identified by different absorbance or emission intensities of the orthogonal detectable labels compared to each other and not only be the absolute presence of absence of a signal. An example of a set of four orthogonal detectable labels is the set of Rox-Labeled Tetrazine, Alexa488-Labeled SHA, Cy5-Labeled Streptavidin, and R6G-Labeled Dibenzocyclooctyne.

The term "polymerase-compatible cleavable moiety" and "reversible terminator" and "polymerase-compatible cleavable linker" as used herein refers to a cleavable moiety or cleavable linker which does not interfere with the function of a polymerase (e.g., DNA polymerase or modified DNA polymerase, in incorporating the nucleotide, to which the polymerase-compatible cleavable moiety is attached, to the 3' end of the newly formed nucleotide strand). Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible cleavable moiety does not decrease the function of a polymerase relative to the absence of the polymerase-compatible cleavable moiety. In embodiments, the polymerase-compatible cleavable moiety does not negatively affect DNA polymerase recognition. In embodiments, the polymerase-compatible cleavable moiety does not negatively affect (e.g., limit) the read length of the DNA polymerase. Additional examples of a polymerase-compatible cleavable moiety may be found in U.S. Pat. No. 6,664,079, Ju J. et al. (2006) *Proc Natl Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218): 53-59; or Hutter D. et al. (2010) *Nucleosides Nucleotides & Nucleic Acids* 29:879-895, which are incorporated herein by reference in their entirety for all purposes. In embodiments, a polymerase-compatible cleavable moiety includes an azido moiety or a dithiol linking moiety. In embodiments, the polymerase-compatible cleavable moiety is independently —$NH_2$, —CN, —$CH_3$, $C_2$-$C_6$ allyl (e.g., —$CH_2$—CH═$CH_2$), methoxyalkyl (e.g., —$CH_2$—O—$CH_3$), or —$CH_2N_3$. In embodiments, the polymerase-compatible cleavable moiety comprises a disulfide moiety. In embodiments, a polymerase-compatible cleavable moiety is a cleavable moiety on a nucleotide, nucleobase, nucleoside, or nucleic acid that does not interfere with the function of a polymerase (e.g., DNA polymerase, modified DNA polymerase). In embodiments, a polymerase-compatible cleavable moiety is a moiety described herein.

In embodiments, the polymerase-compatible cleavable moiety may be referred to as a "reversible terminator". The terms "reversible terminator" and "reversible terminator moiety" are used in accordance with their plain and ordinary meanings and refers to a cleavable moiety on the 3' position of a nucleotide which does not interfere with the function of a polymerase (e.g., DNA polymerase, modified DNA polymerase). In embodiments, the reversible terminator moiety is

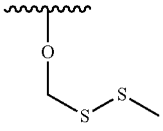,
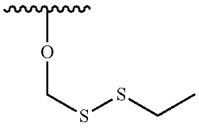,

-continued

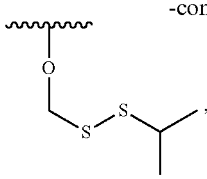, 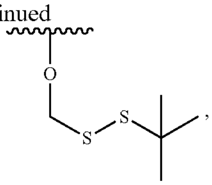,

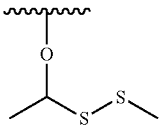, 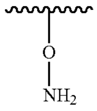, 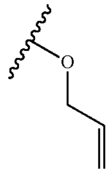,

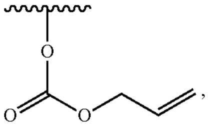, 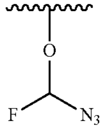, 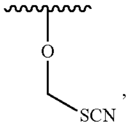,

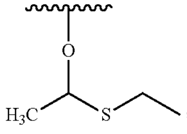, 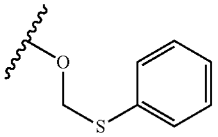,

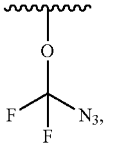 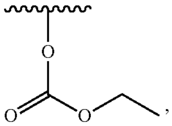, 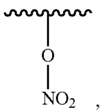,

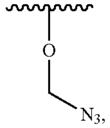 or 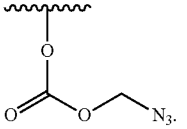

The term "allyl" as described herein refers to an unsubstituted methylene attached to a vinyl group (i.e., $-CH=CH_2$), having the formula

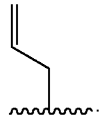 [SMILES: *CC=C]

An "allyl linker" refers to a divalent unsubstituted methylene attached to a vinyl group, having the formula

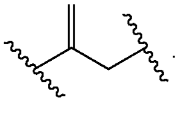 [SMILES: *CC(*)=C]

The term "polymer" refers to a molecule including repeating subunits (e.g., polymerized monomers). For example, polymeric molecules may be based upon polyethylene glycol (PEG), tetraethylene glycol (TEG), polyvinylpyrrolidone (PVP), poly(xylene), or poly(p-xylylene). The term "polymerizable monomer" is used in accordance with its meaning in the art of polymer chemistry and refers to a compound that may covalently bind chemically to other monomer molecules (such as other polymerizable monomers that are the same or different) to form a polymer.

The term "DNA polymerase" and "nucleic acid polymerase" are used in accordance with their plain ordinary meaning and refer to enzymes capable of synthesizing nucleic acid molecules from nucelotides (e.g., deoxyribonucleotides). Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g., Taq polymerase, Therminator 7, 9° N polymerase (exo-), Therminator II, Therminator III, or Therminator IX). In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044).

The term "thermophilic nucleic acid polymerase" as used herein refers to a family of DNA polymerases (e.g., 9°N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M. W., et al. *PNAS.* 1996; 93(11):5281-5285). A thermophilic nucleic acid polymerase is a member of the family B DNA polymerases. Site-directed mutagenesis of the 3'—5' exo motif I (Asp-Ile-Glu) to Asp-Ile-Asp resulted in reduction of 3'—5' exonuclease activity to <1% of wild-type, while maintaining other properties of the polymerase including its high strand displacement activity. Subsequent mutagenesis of key amino acids results in an increased ability of the enzyme to incorporate dideoxynucleotides, ribonucleotides and acyclonucleotides (e.g., Therminator II enzyme from New England Biolabs with D141A/E143A/Y409V/A485L mutations); 3'-amino-dNTPs, 3'-azido-dNTPs and other 3'-modified nucleotides (e.g., NEB Therminator III DNA Polymerase with D141A/E143A/L408S/Y409A/P410V mutations, NEB Therminator IX DNA polymerase), or γ-phosphate labeled nucleotides (e.g., Therminator γ: D141A/E143A/W355A/L408W/R460A/Q461S/K464E/D480V/R484W/A485L). Typically these enzymes do not have 5'—3' exonuclease activity. Additional information about thermophilic nucleic acid polymerases may be found in (Southworth M W, et al. *PNAS.* 1996; 93(11):5281-5285; Bergen K., et al. *ChemBioChem.* 2013; 14(9):1058-1062; Kumar S., et al. *Scientific Reports.* 2012; 2:684; Fuller C. W., et al. 2016; 113(19):5233-5238; Guo J., et al. *Proceedings of the National Academy of Sciences of the United States of America.* 2008; 105(27):9145-9150), which are incorporated herein in their entirety for all purposes.

As used herein, the terms "polynucleotide primer" and "primer" refer to any polynucleotide molecule that may hybridize to a polynucleotide template, be bound by a polymerase, and be extended in a template-directed process for nucleic acid synthesis. The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support. A primer can be of any length depending on the particular technique it will be used for. For example, PCR primers are generally between 10 and 40 nucleotides in length. The length and complexity of the nucleic acid fixed onto the nucleic acid template may vary. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The phrase "stringent hybridization conditions" refers to conditions under which a primer will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., *Current Protocols in Molecular Biology*, ed. Ausubel, et al., supra.

"Solid substrate" shall mean any suitable medium present in the solid phase to which a nucleic acid or an agent may be affixed. Non-limiting examples include chips, beads and columns. The solid substrate can be non-porous or porous. Exemplary solid substrates include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers. In embodiments, the solid substrate for have at least one surface located within a flow cell. The solid substrate, or regions thereof, can be substantially flat. The solid substrate can have surface features such as wells, pits, channels, ridges, raised regions, pegs, posts or the like. The term solid substrate is encompassing of a substrate (e.g., a flow cell) having a surface comprising a polymer coating covalently attached thereto. In embodiments, the solid substrate is a flow cell. The term "flowcell" or "flow cell" as used herein refers to a chamber including a solid surface across which one or more fluid reagents can be flowed. Examples of flowcells and related fluidic systems and detection platforms that can be readily used in the methods of the present disclosure are described, for example, in Bentley et al., Nature 456:53-59 (2008).

The term "thio-trigger moiety" refers to a substituent having the formula

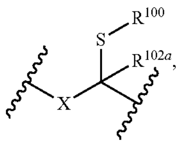

wherein X is —O—, —NH—, or —S—; $R^{100}$ is —$SO_3H$, —$SR^{102}$ or —CN; and $R^{102}$ and $R^{102a}$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, the thio-trigger moiety has the formula

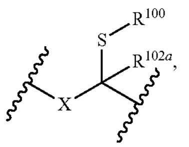

wherein X is —O—, —NH—, or —S—; $R^{100}$ is-$SR^{102}$ or —CN; and $R^{102}$ and $R^{102a}$ are independently hydrogen, halogen, —$CCl_3$, —$CBr_3$, —$CF_3$, —$Cl_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, the thio-trigger moiety has the formula:

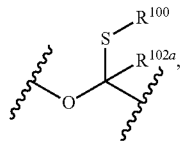

wherein $R^{100}$ and $R^{102a}$ are as described herein. In embodiments, the thio-trigger moiety has the formula:

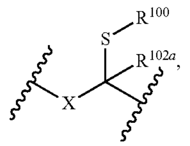

wherein X is —NH—, and $R^{100}$ and $R^{102a}$ are as described herein.

A "thio-trigger containing linker" refers to a covalent linker that includes a thio-trigger moiety. When a reducing agent (e.g., dithiothreitol, THPP, or TCEP) contacts a thio-trigger containing linker, the heteroatom represented by the symbol X (e.g., oxygen) of the thio-trigger moiety is reduced, and breaks the linker apart, according to the example mechanism:

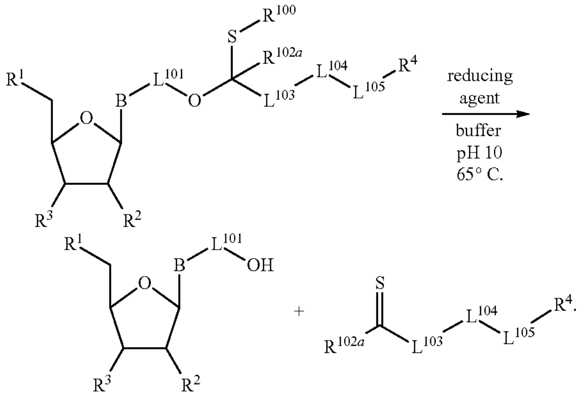

$R^2$, $R^3$, $R^4$, $R^{100}$, $R^{102a}$, $L^{101}$, $L^{103}$, $L^{104}$, and $L^{105}$ are as described herein, including in embodiments.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

As used herein, the term "salt" refers to acid or base salts of the compounds described herein. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. In embodiments, compounds may be presented with a positive charge, for example

and it is understood an appropriate counter-ion (e.g., chloride ion, fluoride ion, or acetate ion) may also be present, though not explicitly shown. Likewise, for compounds having a negative charge (e.g., 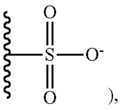 ), it is understood an appropriate counter-ion (e.g., a proton, sodium ion, potassium ion, or ammonium ion) may also be present, though not explicitly shown. The protonation state of the compound (e.g., a compound described herein) depends on the local environment (i.e., the pH of the environment), therefore, in embodiments, the compound may be described as having a moiety in a protonated state (e.g., 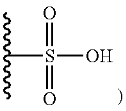 )

or an ionic state (e.g., 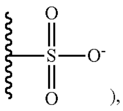 ), and it is understood these are interchangeable. In embodiments, the counter-ion is represented by the symbol M (e.g., $M^+$ or $M^-$).

As used herein, the terms "sequencing", "sequence determination", and "determining a nucleotide sequence", are used in accordance with their ordinary meaning in the art, and refer to determination of partial as well as full sequence information of the nucleic acid being sequenced, and particular physical processes for generating such sequence information. That is, the term includes sequence comparisons, fingerprinting, and like levels of information about a target nucleic acid, as well as the express identification and ordering of nucleotides in a target nucleic acid. The term also includes the determination of the identification, ordering, and locations of one, two, or three of the four types of nucleotides within a target nucleic acid. In some embodiments, a sequencing process described herein comprises contacting a template and an annealed primer with a suitable polymerase under conditions suitable for polymerase extension and/or sequencing. The sequencing methods are preferably carried out with the target polynucleotide arrayed on a solid substrate. Multiple target polynucleotides can be immobilized on the solid support through linker molecules, or can be attached to particles, e.g., microspheres, which can also be attached to a solid substrate. In embodiments, the solid substrate is in the form of a chip, a bead, a well, a capillary tube, a slide, a wafer, a filter, a fiber, a porous media, or a column. In embodiments, the solid substrate is gold, quartz, silica, plastic, glass, diamond, silver, metal, or polypropylene. In embodiments, the solid substrate is porous As used herein, the term "extension" or "elongation" is used in accordance with its plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) DNA strand.

As used herein, the term "sequencing cycle" is used in accordance with its plain and ordinary meaning and refers to incorporating one or more nucleotides (e.g., a compound described herein) to the 3' end of a polynucleotide with a polymerase, and detecting one or more labels that identify the one or more nucleotides incorporated. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes and other substances can be removed between steps by washing. Cycles may include repeating these steps, and the sequence of each cluster is read over the multiple repetitions. As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. In embodiments, a sequencing read includes reading a barcode sequence and a template nucleotide sequence. In embodiments, a sequencing read includes reading a template nucleotide sequence. In embodiments, a sequencing read includes reading a barcode and not a template nucleotide sequence.

The term "reaction vessel" is used in accordance with its ordinary meaning in chemistry or chemical engineering, and refers to a container having an inner volume in which a reaction takes place. In embodiments, the reaction vessel may be designed to provide suitable reaction conditions such as reaction volume, reaction temperature or pressure, and stirring or agitation, which may be adjusted to ensure that the reaction proceeds with a desired, sufficient or highest efficiency for producing a product from the chemical reaction. In embodiments, the reaction vessel is a container for liquid, gas or solid. In embodiments, the reaction vessel may include an inlet, an outlet, a reservoir and the like. In embodiments, the reaction vessel is connected to a pump (e.g., vacuum pump), a controller (e.g., CPU), or a monitoring device (e.g., UV detector or spectrophotometer). In embodiments, the reaction vessel is a flow cell. In embodiments, the reaction vessel is within a sequencing device.

As used herein, the term "rigid spacer" refers to a divalent linker moiety that prevents and/or minimizes a decrease in the detectability of the detectable label through interaction of the nucleobase (e.g., as described herein) within the compounds described herein (e.g., the compound of Formulae I, Ia, II, III, IV, IVa, IVb, IVc, V, Va, Vb, Vc, VI, or VII) relative to the detectability of the detectable label in the absence of nucleobase. In embodiments, the nucleobase is guanine. In embodiments, the decrease in detectability is due to quenching of the detectable linker through interaction with the nucleobase. In embodiments, the decrease in detectability is quenching and the detectable label is a fluorescent label. In embodiments, the rigid spacer prevents at least a 5% decrease in detectability (e.g., quenching) relative to the absence of the nucleobase. In embodiments, the rigid spacer prevents at least a 10% decrease in detectability (e.g., quenching) relative to the absence of the nucleobase. In embodiments, the rigid spacer prevents at least a 15% decrease in detectability (e.g., quenching) relative to the absence of the nucleobase. In embodiments, the rigid spacer prevents at least a 20% decrease in detectability (e.g., quenching) relative to the absence of the nucleobase. In embodiments, the rigid spacer prevents at least a 25% decrease in detectability (e.g., quenching) relative to the absence of the nucleobase. In embodiments, the rigid spacer prevents at least a 30% decrease in detectability (e.g., quenching) relative to the absence of the nucleobase. In embodiments, the rigid spacer prevents at least a 35% decrease in detectability (e.g., quenching) relative to the absence of the nucleobase. In embodiments, the rigid spacer prevents at least a 40% decrease in detectability (e.g., quenching) relative to the absence of the nucleobase. In embodiments, the rigid spacer prevents at least a 45% decrease in detectability (e.g., quenching) relative to the absence of the nucleobase. In embodiments, the rigid spacer prevents at least a 50% decrease in detectability (e.g., quenching) relative to the absence of the nucleobase. In embodiments, the rigid spacer prevents at least a 55% decrease in detectability (e.g., quenching) relative to the absence of the nucleobase. In embodiments, the rigid spacer prevents at least a 60% decrease in detectability (e.g., quenching) relative to the absence of the nucleobase. In embodiments, the rigid spacer prevents at least a 65% decrease in detectability (e.g., quenching) relative to the absence of the nucleobase. In embodiments, the rigid spacer prevents at least a 70% decrease in detectability (e.g., quenching) relative to the absence of the nucleobase. In embodiments, the rigid spacer prevents at least a 75% decrease in detectability (e.g., quenching) relative to the absence of the nucleobase. In embodiments, the rigid spacer prevents at least an 80% decrease in detectability (e.g., quenching) relative to the absence of the nucleobase. In embodiments, the rigid spacer prevents at least an 85% decrease in detectability (e.g., quenching) relative to the absence of the nucleobase. In embodiments, the rigid spacer prevents at least a 90% decrease in detectability (e.g., quenching) relative to the absence of the nucleobase. In embodiments, the rigid spacer prevents at least a 95% decrease in detectability (e.g., quenching) relative to the absence of the nucleobase. In embodiments, the rigid spacer prevents at least a 100% decrease in detectability (e.g., quenching) relative to the absence of the nucleobase. In embodiments, the rigid spacer includes at least one planar linker (e.g., an amide linker, an aromatic or heteroaromatic linker, a carbon-carbon double bond, or a carbon-carbon triple bond). In embodiments, the rigid spacer includes at least one degree of unsaturation (e.g., substituted or unsubstituted alkenylene, substituted or unsubstituted alkynylene, substituted or unsubstituted arylene, substituted or unsubstituted heteroarylene, —NHC(O)—, or —C(O)NH—). In embodiments, the rigid spacer maintains the detectable label from interacting with a nucleobase throughout the course of the reaction (e.g., during nucleotide incorporation). In embodiments, the rigid spacer is one or more consecutive monomeric subunits. In embodiments, the rigid spacer forms a linear linker. In embodiments, the rigid spacer is a divalent polymer, divalent double-stranded nucleic acid, or divalent polypeptide. In embodiments, the double-stranded nucleic acid is 50 bases or less in length. In embodiments, the double-stranded nucleic acid is 40 bases or less in length. In embodiments, the double-stranded nucleic acid is 30 bases or less in length. In embodiments, the double-stranded nucleic acid is 20 bases or less in length. In embodiments, the double-stranded nucleic acid is 10 bases or less in length. In embodiments, the rigid spacers as described herein do not substantially bend or flex and do not allow substantial rotation either along their length or at their attachments points. Due to differences in the relative flexibility of different linkers, distances are generally described as having operating or functional distances, e.g., the average maintained distance between a detectable label group and the nucleotide base. In embodiments, the rigid spacer is stiff (i.e., rigid) in solution, such that the rigid spacer is stiffer than a flexible linking moiety (e.g., a covalent linker without a rigid spacer). A flexible linking moiety is flexible in a manner similar to the hinge of tongs, or a slinky, such that it allows for movement of the covalent linker. Flexible, as used when describing a linking moiety, refers to the ability of a flexible linking moiety to change its bending or coiling conformation in solution. Known methods in the art to quantify rigidity, or degree of linearity may be used. The use of resonance energy transfer has been used to quantify flexible and rigid polypeptides by providing distance distributions separating a donor and acceptor pair (see for example Haas et al PNAS USA 72:1807-1811 (1975); and Lakowicz et al. Proc SPIE 1204:192-205 (1990), incorporated herein by reference for all uses. The FRET efficiency may then be converted to persistence length by comparing the FRET efficiency with calculated FRET efficiency based on models such as the worm-like chain model, or other known methods in the art. For the rigid spacers of the present disclosure, the rigid spacers increase the persistence length (lP) of the overall covalent linkage relative to an identical molecule absent the rigid spacer. The rigid spacer behaves like a rigid rod when the total end-to-end length is less than the (lP). It is estimated that the rigid spacers described herein, increase ($l_P$) approximately 8.6 Å per monomer. For example, a 5mer (i.e., a rigid spacer containing 5 monomers of Formula IV or Formula V) is estimated to have a persistence length of 4.3 nm and maintain rod-like, linear, character when the total length of the rigid spacer is less than 4.3 nm. In contrast, molecular dynamics simulations of 9, 18, 27, and 36-mers of polyethylene oxide (PEO) and 27-mers of polyethylene glycol (PEG) in solution have a persistence length $\lambda$=3.7 Å (Lee H, Venable RM, Mackerell AD Jr, Pastor R W. Molecular dynamics studies of polyethylene oxide and polyethylene glycol: hydrodynamic radius and shape anisotropy. Biophys J. 2008 August; 95(4):1590-9. Epub 2008 May 2).

As used herein, the term "FRET pair of detectable moieties" refers to a donor molecule (e.g., first detectable moiety) and an acceptor molecule (e.g., second detectable moiety) capable of undergoing fluorescence resonance energy transfer (FRET). In a FRET pair, a first detectable moiety is excited with an excitation wavelength and non-radiatively transfers the energy to a second detectable moiety, wherein the efficiency of the energy transfer correlates to the separation between the pair of detectable moieties. Changes in the efficiency of FRET are correlated to changes in the separation between the detectable moieties, which may be quantified by measuring the absorbance spectra of a FRET pair. The FRET donor molecule initially absorbs energy (and is thus excited) and then transfers energy, by way of emission, to the FRET acceptor molecule (resulting in excitation of the FRET acceptor molecule). The resonance energy transfer can occur over distances greater than interatomic distances, and without conversion to thermal energy nor any molecular collision. The FRET donor or the FRET acceptor can be selected based on a variety of factors such as stability, excitation, and emission wavelengths as well as signal intensity. For example, the FRET acceptor is generally selected such that it is capable of emitting light when excited by light of the wavelength emitted by the FRET donor. It is understood that FRET includes Time-Resolved FRET (or TR-FRET), which combines the use of long-lived fluorophores and time-resolved detection (a delay between excitation and emission detection) to minimize fluorescent interference due to any inherent fluorescence of, e.g., target molecules or target-selective binding agents (see, e.g., Klostermeier et al. (2001-2002) Biopolymers 61(3):159-79). In some embodiments, the first member of the FRET pair is a FRET donor and the second member of the FRET pair is a FRET acceptor. In some embodiments, the second member of the FRET pair is a FRET donor and the first member of the FRET pair is a FRET acceptor. In some embodiments, one or both of the first member of the FRET pair and the second member of the FRET pair is fluorescent.

As used herein, the term "triplet state quencher" refers to a photoprotective agent that can prevent the formation of triplet state fluorophores, which are often produced in illuminated reactions via photoionization. Triplet state fluorophores are desirably quenched in illuminated reactions because they typically generate highly reactive singlet oxygen species that can damage, e.g., oxidize, enzymes and other reagents in the reaction. Examples of triplet state quenchers include a monovalent ascorbic acid, monovalent cyclooctatetraene (COT), monovalent nitrobenzyl alcohol, monovalent methyl viologen, monovalent Trolox, or monovalent Trolox-quinone.

As used herein, the term "fluorescent dye moiety" refers to a fluorescent dye molecule or a plurality of fluorescent dye molecules, that is capable of emitting photons when simulated by a laser emitting light at the excitation wavelength of the moiety. A fluorescent dye moiety may be understood in the broadest sense as any dye moiety enabling fluorescence detection. Preferably, such fluorescence detection is in a range of from 400 to 1000 nm, i.e., in the visible spectrum and in the Near Infrared (NIR) spectrum, in particular in a range of from 400 to 800 nm, i.e. in the visible spectrum. Additionally, or alternatively, the dye moiety may also be chromatic, i.e., provoke a color perception when illuminated by any light. Such chromatic effect may be provoked by absorbing light of one or more particular wavelength range(s) in the visible range (i.e., in range(s) from approximately 400 nm to approximately 800 nm) and/or by emitting light of one or more particular wavelength range(s) in the visible range.

As used herein, the term "photodamage mitigating agent" refers to a composition that may prevent photodamage of one or more reagents, or it may mitigate the impact that a photodamaged reagent may have on a particular, limited reagent in the reaction of interest. By way of example, an agent that blocks a detrimental interaction between a photodamaged fluorescent compound and a critical enzyme component would still be referred to as a photodamage mitigating agent, regardless of the fact that it did not prevent the initial photodamage to the fluorescent reagent. In particular, photodamage mitigating agents are provided in the context of the analytical reaction to reduce the level of photodamage (and/or increase the photodamage threshold period), that would otherwise have occurred but for the presence of the photodamage mitigating agent. In general, the photodamage mitigating agents are present in the reaction mixture at levels sufficient to provide beneficial impact, e.g., reduced photodamage and/or extension of the photodamage threshold period, but are not present at such levels as to interfere with the reaction of interest, e.g., the sequencing reaction. Non-limiting examples of a photodamage mitigating agent include ascorbic acid, dithiothreitol (DTT), mercaptoethylamine (MEA), P-mercaptoethanol (BME), N-propyl gallate, p-phenylenediamene (PPD), hydroquinone, sodium azide ($NaN_3$), diazobicyclooctane (DABCO), cyclooctatetraene (COT), Trolox and its derivatives, butylated hydroxytoluene (BHT), ergothioneine, methionine, cysteine, beta-dimethyl cysteine, histidine, tryptophan, mercaptopropionylglycine, MESNA, glutathione, N-acetyl cysteine, captopril, lycopene, gamma-carotene, astazanthin, canthazanthin, alpha-carotene, beta-carotene, gamma-carotene, bixin, zeaxanthin, lutein, bilirubin, biliverdin, tocopherols, polyene dialdehydes, 32 melatonin, octocopheryl succinate and its analogs, pyridoxinel and its derivatives, hydrazine, sodium sulfite, and hydroxylamine. In embodiments, the photodamage mitigating agent is sodium pyruvate, N,N'-dimethylthiourea, mannitol, DMSO, carboxy-PTIO, 6-hydroxy-2,5,7,8-tetramethylchroman-2-carboxylic acid, alpha-tocopherol, 2-phenyl-1,2,benzisoselenazol-3 (2H)-one, uric acid, sodium azide, or manganese(III)-tetrakis(4-benzoic acid) porphyrin, 4,5-dihydroxybenzene-1,3-disulfonate. In embodiments, the photodamage mitigating agent is 3-carboxy-proxyl, N-propyl gallate, ascorbic acid, methyl viologen, Trolox, or Trolox-quinone.

As used herein, the term "photodamage" refers to any direct or indirect impact of illumination on one or more reagents in a desired reaction, such that it results in a negative impact upon that reaction. As such, photodamage would include a direct photoinduced change in a given reagent so as to reduce the reactivity of that reagent in the desired reaction, e.g., photobleaching of a fluorescent molecule, or otherwise reduce its usefulness in such reaction, e.g., by making the reagent less specific in the given reaction. Likewise, photodamage would include negative changes in a reagent that are caused by interaction of that reagent with a product of another photo-induced reaction, e.g., the generation of singlet oxygen during a fluorescence excitation event, which singlet oxygen may damage organic or other reagents, e.g., proteins.

II. Compounds, Compositions, and Kits

In an aspect is provided a compound having the formula:

(I)

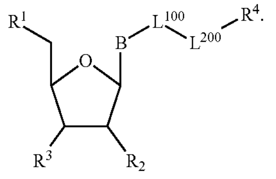

B is a divalent nucleobase. $L^{100}$ is a polymerase-compatible cleavable linker. $L^{200}$ is a rigid spacer. $R^1$ is independently a polyphosphate moiety, monophosphate moiety, 5'-nucleoside protecting group, nucleic acid moiety, hydrogen, or —OH. $R^2$ is independently hydrogen, —OH, —$OR^{2A}$, an —O-polymerase-compatible cleavable moiety, or a polymerase-compatible cleavable moiety. $R^3$ is independently an —O-polymerase-compatible cleavable moiety, a polymerase-compatible cleavable moiety, hydrogen, —OH, —$NH_3^+$, —$SO_3^-$, —$OPO_3H^-$, —SCN, —$ONO_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is an anchor moiety or a detectable moiety. As disclosed herein, the term "5'-nucleoside protecting group" can be used interchangeably with "5'-O-nucleoside protecting group". In embodiments, the compounds described herein are considered modified nucleotides or modified nucleosides.

In an aspect is provided a compound having the formula:

(I)

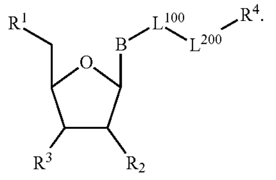

B is a divalent nucleobase. $L^{100}$ is a polymerase-compatible cleavable linker. $L^{200}$ is a rigid spacer. $R^1$ is independently a polyphosphate moiety, monophosphate moiety, 5'-O-nucleoside protecting group, nucleic acid moiety, hydrogen, or —OH. $R^2$ is independently hydrogen, —OH, —$OR^{2A}$, or a polymerase-compatible cleavable moiety. $R^3$ is independently a polymerase-compatible cleavable moiety, hydrogen, —OH, —$NH_3^+$, —$SO_3^-$, —$OPO_3H^-$, —SCN, —$ONO_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is an anchor moiety or a detectable moiety.

In an aspect is provided a composition including a first compound having the formula:

(I)

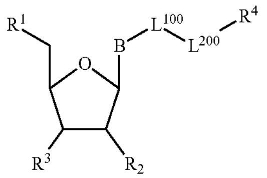

and a second compound having the formula $R^5$-$L^5$-$R^6$ (II). $R^1$, $R^2$, $R^3$, $L^{100}$, and $L^{200}$ are as described herein. $R^4$ is an anchor moiety. $R^5$ is a complementary anchor moiety to the $R^4$ anchor moiety of the first compound. $L^5$ is a covalent linker. $R^6$ is detectable moiety. In embodiments, the composition has the formula:

(III)

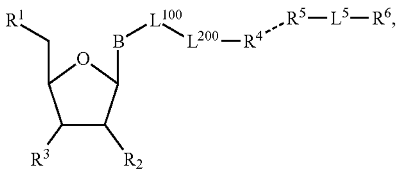

wherein the symbol "----" is a non-covalent bond. In embodiments, the composition further includes a photodamage mitigating agent.

In embodiments, the compound of Formula I and composition of Formula III are referred to as nucleotides. In embodiments, the compound of Formula I and composition of Formula III include a nucleotide portion and a 3'-O-reversible terminator. For example, the nucleotide portion is

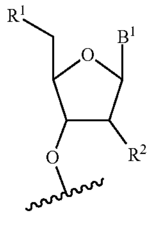

and the 3'-O-reversible terminator portion is $R^{3A}$ as described herein.

In embodiments, B is

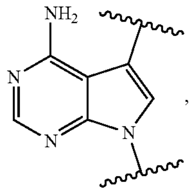
,
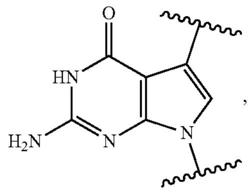
,
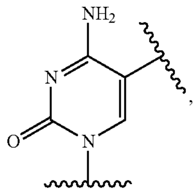
, or
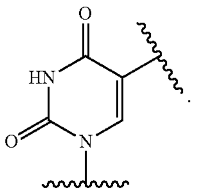
.

embodiments, B is

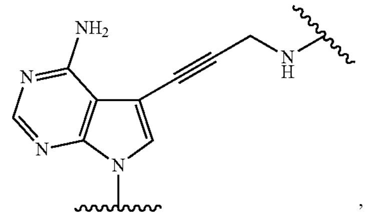
,
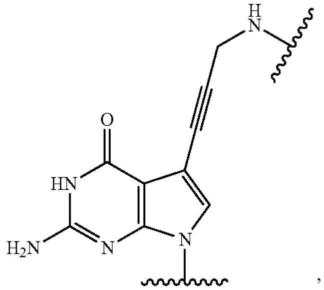
,
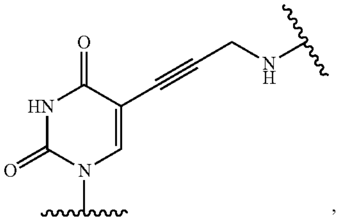
,
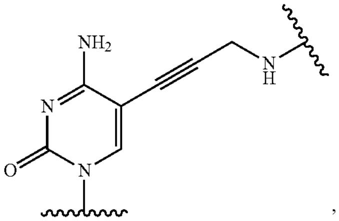
,
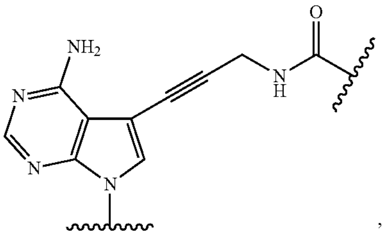
,

-continued

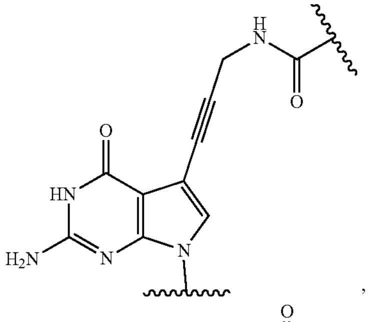

,

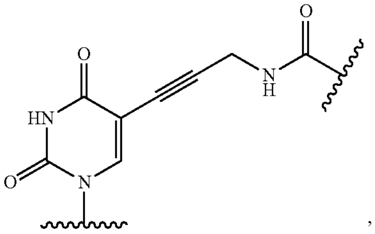

, or

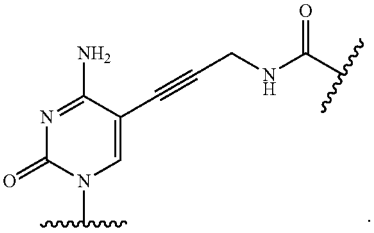

.

In embodiments, B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof. In embodiments, B is a divalent cytosine or a derivative thereof. In embodiments, B is a divalent guanine or a derivative thereof. In embodiments, B is a divalent adenine or a derivative thereof. In embodiments, B is a divalent thymine or a derivative thereof. In embodiments, B is a divalent uracil or a derivative thereof. In embodiments, B is a divalent hypoxanthine or a derivative thereof. In embodiments, B is a divalent xanthine or a derivative thereof. In embodiments, B is a divalent 7-methylguanine or a derivative thereof. In embodiments, B is a divalent 5,6-dihydrouracil or a derivative thereof. In embodiments, B is a divalent 5-methylcytosine or a derivative thereof. In embodiments, B is a divalent 5-hydroxymethylcytosine or a derivative thereof. In embodiments, B is a divalent cytosine. In embodiments, B is a divalent guanine. In embodiments, B is a divalent adenine. In embodiments, B is a divalent thymine. In embodiments, B is a divalent uracil. In embodiments, B is a divalent hypoxanthine. In embodiments, B is a divalent xanthine. In embodiments, B is a divalent 7-methylguanine. In embodiments, B is a divalent 5,6-dihydrouracil. In embodiments, B is a divalent 5-methylcytosine. In embodiments, B is a divalent 5-hydroxymethylcytosine.

In embodiments, $R^1$ is —OH, a 5'-nucleoside protecting group, monophosphate moiety, polyphosphate moiety, or nucleic acid moiety. In embodiments, $R^1$ is a triphosphate moiety. In embodiments, $R^1$ is —OH. In embodiments, $R^1$ is a 5'-nucleoside protecting group. In embodiments, $R^1$ is a nucleic acid moiety. In embodiments, $R^1$ is independently a monophosphate moiety or a derivative thereof (e.g., including a phosphoramidate moiety, phosphorothioate moiety, phosphorodithioate moiety, or O-methylphosphoroamidite moiety), polyphosphate moiety or derivative thereof (e.g., including a phosphoramidate, phosphorothioate, phosphorodithioate, or O-methylphosphoroamidite), or nucleic acid moiety or derivative thereof (e.g., including a phosphoramidate, phosphorothioate, phosphorodithioate, or O-methylphosphoroamidite). As indicated above, a person having ordinary skill in the art would understand that a 5'-nucleoside protecting group is equivalent to a 5'-O-nucleoside protecting group.

In embodiments, $R^1$ is independently a monophosphate moiety including a phosphodiester derivative. In embodiments, $R^1$ is independently a polyphosphate moiety including a phosphodiester derivative. In embodiments, $R^1$ is independently a nucleic acid moiety including a phosphodiester derivative. In embodiments, $R^1$ is independently a phosphoramidate moiety. In embodiments, $R^1$ is independently a polyphosphate moiety including a phosphoramidate. In embodiments, $R^1$ is independently a nucleic acid moiety including a phosphoramidate. In embodiments, $R^1$ is independently a phosphorothioate moiety. In embodiments, $R^1$ is independently a polyphosphate moiety including a phosphorothioate. In embodiments, $R^1$ is independently a nucleic acid moiety including a phosphorothioate. In embodiments, $R^1$ is independently a phosphorodithioate moiety. In embodiments, $R^1$ is independently a polyphosphate moiety including a phosphorodithioate. In embodiments, $R^1$ is independently a nucleic acid moiety including a phosphorodithioate. In embodiments, $R^1$ is independently an O-methylphosphoroamidite moiety. In embodiments, $R^1$ is independently a polyphosphate moiety including an O-methylphosphoroamidite. In embodiments, $R^1$ is independently a nucleic acid moiety including an O-methylphosphoroamidite. In embodiments, $R^1$ is independently a nucleic acid moiety including a nucleotide analog. In embodiments, $R^1$ is independently a nucleic acid moiety including a plurality of optionally different nucleotide analogs.

In embodiments, $R^1$ is independently a monophosphate moiety. In embodiments, $R^1$ is independently a polyphosphate moiety. In embodiments, $R^1$ is independently a nucleic acid moiety. In embodiments, $R^1$ has the formula:

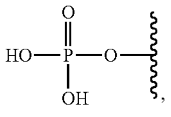

or ionized forms thereof. In embodiments, $R^1$ has the formula

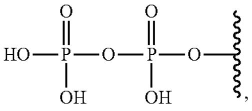 [SMILES: *OP(=O)(O)OP(=O)(O)O]

or ionized forms thereof. In embodiments, $R^1$ has the formula

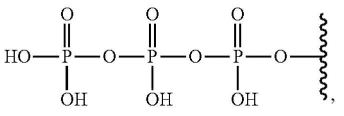 [SMILES: *OP(=O)(O)OP(=O)(O)OP(=O)(O)O]

or ionized forms thereof.

In embodiments, $R^1$ has the formula:

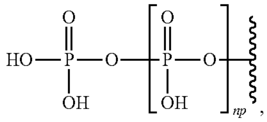

or ionized forms thereof, wherein np is an integer of 1 or greater. In embodiments, np is an integer from 1 to 5. In embodiments, np is 2. In embodiments, np is 1. In embodiments, np is 2.

In embodiments, $R^1$ is independently a 5'-nucleoside protecting group, for example a 5'-nucleoside protecting group known in the art include those described in Seliger H. Curr. Protoc Nucleic Acid Chem. 2001; Chapter 2 or K. Seio et al, Nucleic Acids Research Supplement 2, 27-28 (2002); both of which are incorporated by reference for all purposes. Non-limiting examples of 5'-nucleoside protecting groups include 2,2,2-Trichloroethyl carbonate (Troc), 2-Methoxyethoxymethyl ether (MEM), 2-Naphthylmethyl ether (Nap), 4-Methoxybenzyl ether (PMB), Acetate (Ac), Benzoate (Bz), Benzyl ether (Bn), Benzyloxymethyl acetal (BOM), Ethoxyethyl acetal (EE), Methoxymethyl acetal (MOM), Methoxypropyl acetal (MOP), Methyl ether, Tetrahydropyranyl acetal (THP), Triethylsilyl ether (TES), Triisopropylsilyl ether (TIPS), Trimethylsilyl ether (TMS), tert-Butyldimethylsilyl ether (TBS, TBDMS), or tert-butyldiphenylsilyl ether (TBDPS).

In embodiments, $R^1$ is

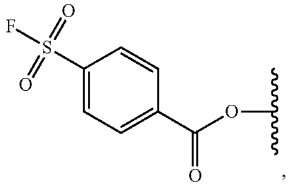
,
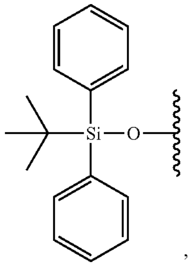
,

-continued

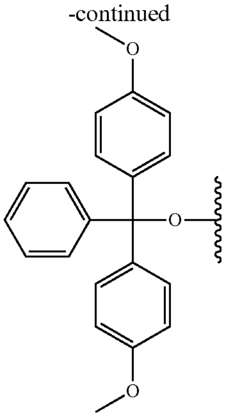
,
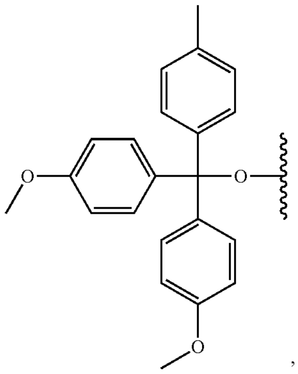
, or
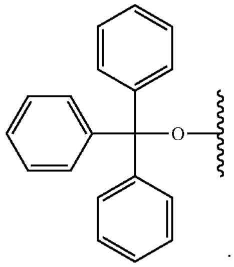
.

In embodiments, $R^2$ is independently hydrogen or —OH. In embodiments, $R^2$ is independently hydrogen. In embodiments, $R^2$ is independently —OH. In embodiments, $R^2$ is independently an —O-polymerase-compatible cleavable moiety. In embodiments, $R^2$ is independently a polymerase-compatible cleavable moiety.

In embodiments, $R^2$ is independently hydrogen, —OH, a polymerase-compatible cleavable moiety, or an —O-polymerase-compatible cleavable moiety. In embodiments, $R^2$ is hydrogen. In embodiments, $R^2$ is —OH. In embodiments, $R^2$ is an —O-polymerase-compatible cleavable moiety. In embodiments, $R^2$ is independently —$OR^{2A}$.

In embodiments, $R^2$ is independently hydrogen, —OH, a polymerase-compatible cleavable moiety, or an —O-polymerase-compatible cleavable moiety. In embodiments, $R^2$ is hydrogen. In embodiments, $R^2$ is —OH. In embodiments, $R^2$ is an —O-polymerase-compatible cleavable moiety, wherein the —O— is attached to the 2' position of the ribose sugar of a nucleotide and a polymerase-compatible cleavable moiety is as described herein. In embodiments, $R^2$ is independently —$OR^{2A}$.

$R^{2A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H$—, —SCN, —$ONO_2$, $R^{2B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2B}$-substituted or unsubstituted heteroalkyl (e.g., 2 to 20, 8 to 20, 2 to 10, 2 to 8, 2 to 6, or 2 to 4 membered), $R^{2B}$-substituted or unsubstituted cycloalkyl (e.g., $C_3$-$C_8$, $C_3$-$C_6$, or $C_5$-$C_6$), $R^{2B}$-substituted or unsubstituted heterocycloalkyl (e.g., 3 to 8, 3 to 6, or 5 to 6 membered), $R^{2B}$-substituted or unsubstituted aryl (e.g., $C_6$-$C_{10}$, $C_{10}$, or phenyl), or $R^{2B}$-substituted or unsubstituted heteroaryl (e.g., 5 to 10, 5 to 9, or 5 to 6 membered), or a polymerase-compatible cleavable moiety. In embodiments, $R^{2A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{2B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2B}$-substituted or unsubstituted heteroalkyl (e.g., 2 to 20, 8 to 20, 2 to 10, 2 to 8, 2 to 6, or 2 to 4 membered), $R^{2B}$-substituted or unsubstituted cycloalkyl (e.g., $C_3$-$C_8$, $C_3$-$C_6$, or $C_5$-$C_6$), $R^{2B}$-substituted or unsubstituted heterocycloalkyl (e.g., 3 to 8, 3 to 6, or 5 to 6 membered), $R^{2B}$-substituted or unsubstituted aryl (e.g., $C_6$-$C_{10}$, $C_{10}$, or phenyl), or $R^{2B}$-substituted or unsubstituted heteroaryl (e.g., 5 to 10, 5 to 9, or 5 to 6 membered). In embodiments, $R^{2A}$ is independently a polymerase-compatible cleavable moiety.

$R^{2B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H$—, —SCN, —$ONO_2$, $R^{2C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2C}$-substituted or unsubstituted heteroalkyl (e.g., 2 to 20, 8 to 20, 2 to 10, 2 to 8, 2 to 6, or 2 to 4 membered), $R^{2C}$-substituted or unsubstituted cycloalkyl (e.g., $C_3$-$C_8$, $C_3$-$C_6$, or $C_5$-$C_6$), $R^{2C}$-substituted or unsubstituted heterocycloalkyl (e.g., 3 to 8, 3 to 6, or 5 to 6 membered), $R^{2C}$-substituted or unsubstituted aryl (e.g., $C_6$-$C_{10}$, $C_{10}$, or phenyl), or $R^{2C}$-substituted or unsubstituted heteroaryl (e.g., 5 to 10, 5 to 9, or 5 to 6 membered).

$R^{2C}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H$—, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^2$ is a polymerase-compatible cleavable moiety or an —O-polymerase-compatible cleavable moiety; and the polymerase-compatible cleavable moiety is

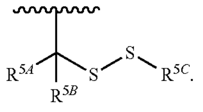

$R^{5A}$ is independently hydrogen, halogen, —$CX^{5A}_3$, —$CHX^{5A}_2$, —$CH_2X^{5A}$, —$OCX^{5A}_3$, —$OCH_2X^{5A}$, —$OCHX^{5A}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8, 2 to 6, 4 to 6, 2 to 3, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8, 3 to 6, 4 to 6, 4 to 5, or 5 to 6 membered), substituted or unsubstituted aryl (e.g., $C_6$-$C_{10}$ or phenyl), or substituted or unsubstituted heteroaryl (e.g., 5 to 10, 5 to 9, or 5 to 6 membered). $R^{5B}$ is independently hydrogen, halogen, —$CX^{5B}_3$, —$CHX^{5B}_2$, —$CH_2X^{5B}$, —$OCX^{5B}_3$, —$OCH_2X^{5B}$, —$OCHX^{5B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8, 2 to 6, 4 to 6, 2 to 3, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8, 3 to 6, 4 to 6, 4 to 5, or 5 to 6 membered), substituted or unsubstituted aryl (e.g., $C_6$-$C_{10}$ or phenyl), or substituted or unsubstituted heteroaryl (e.g., 5 to 10, 5 to 9, or 5 to 6 membered). In embodiments, $R^{5A}$ and $R^{5B}$ are combined to form an oxo. $R^{5C}$ is hydrogen, halogen, —$CX^{5C}_3$, —$CHX^{5C}_2$, —$CH_2X^{5C}$, —$OCX^{5C}_3$, —$OCH_2X^{5C}$, —$OCHX^{5C}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, substituted or unsubstituted alkyl (e.g., $C_1$-$C_5$, $C_1$-$C_6$, $C_1$-$C_4$, or $C_1$-$C_2$), substituted or unsubstituted heteroalkyl (e.g., 2 to 8, 2 to 6, 4 to 6, 2 to 3, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8, 3 to 6, 4 to 6, 4 to 5, or 5 to 6 membered), substituted or unsubstituted aryl (e.g., $C_6$-$C_{10}$ or phenyl), or substituted or unsubstituted heteroaryl (e.g., 5 to 10, 5 to 9, or 5 to 6 membered). In embodiments, $R^{5C}$ is unsubstituted $C_1$-$C_4$ alkyl. In embodiments, $R^{5C}$ is unsubstituted methyl. In embodiments, $R^{5C}$ is unsubstituted tert-butyl. The symbols $X^{5A}$, $X^{5B}$, and $X^{5C}$ are independently —F, —Cl, —Br, or —I.

In embodiments, $R^{2A}$ is a polymerase-compatible cleavable moiety; and the polymerase-compatible cleavable moiety is

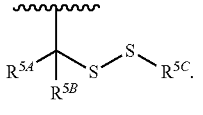

$R^{5B}$, $R^{5A}$, $R^{5B}$, and $R^{5C}$ are as described herein, including in embodiments. In embodiments, $R^2$ is an —O-polymerase-compatible cleavable moiety; and the polymerase-compatible cleavable moiety is

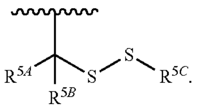

In embodiments, $R^2$ is a polymerase-compatible cleavable moiety or an —O-polymerase-compatible cleavable moiety; and the polymerase-compatible cleavable moiety is

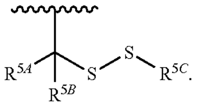

In embodiments, $R^{5A}$ is independently hydrogen, halogen, $—CX^{5A}_3$, $—CHX^{5A}_2$, $—CH_2X^{5A}$, $—OCX^{5A}_3$, $—OCH_2X^{5A}$, $—OCHX^{5A}_2$, —CN, —OH, —SH, $—NH_2$, —COOH, $—CONH_2$, $—NO_2$, $—SO_3H$, $—SO_4H$, $—SO_2NH_2$, $—NHNI_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3$, $—SO_3^-$, $—OPO_3H—$, —SCN, $—ONO_2$, $R^{5D}$-substituted or unsubstituted alkyl, $R^{5D}$-substituted or unsubstituted heteroalkyl, $R^{5D}$-substituted or unsubstituted cycloalkyl, $R^{5D}$-substituted or unsubstituted heterocycloalkyl, $R^{5D}$-substituted or unsubstituted aryl, or $R^{5D}$-substituted or unsubstituted heteroaryl. $R^{5D}$ is independently halogen, oxo, $—CX^{5D}_3$, $—CHX^{5D}_2$, $—CH_2X^{5D}$, $—OCX^{5D}_3$, $—OCH_2X^{5D}$, $—OCHX^{5D}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, $—ONO_2$, $R^{5E}$-substituted or unsubstituted alkyl, $R^{5E}$-substituted or unsubstituted heteroalkyl, $R^{5E}$-substituted or unsubstituted cycloalkyl, $R^{5E}$-substituted or unsubstituted heterocycloalkyl, $R^{5E}$-substituted or unsubstituted aryl, or $R^{5E}$-substituted or unsubstituted heteroaryl. $R^{5E}$ is independently halogen, oxo, $—CX^{5E}_3$, $—CHX^{5E}_2$, $—CH_2X^{5E}$, $—OCX^{5E}_3$, $—OCH_2X^{5E}$, $—OCHX^{5E}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, $—ONO_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{5B}$ is independently hydrogen, halogen, $—CX^{5B}_3$, $—CHX^{5B}_2$, $—CH_2X^{5B}$, $—OCX^{5B}_3$, $—OCH_2X^{5B}$, $—OCHX^{5B}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H—$, —SCN, $—ONO_2$, $R^{5F}$-substituted or unsubstituted alkyl, $R^{5F}$-substituted or unsubstituted heteroalkyl, $R^{5F}$-substituted or unsubstituted cycloalkyl, $R^{5F}$-substituted or unsubstituted heterocycloalkyl, $R^{5F}$-substituted or unsubstituted aryl, or $R^{5F}$-substituted or unsubstituted heteroaryl. $R^{5F}$ is independently halogen, oxo, $—CX^{5F}_3$, $—CHX^{5F}_2$, $—CH_2X^{5F}$, $—OCX^{5F}_3$, $—OCH_2X^{5F}$, $—OCHX^{5F}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, $—ONO_2$, $R^{5G}$-substituted or unsubstituted alkyl, $R^{5G}$-substituted or unsubstituted heteroalkyl, $R^{5G}$-substituted or unsubstituted cycloalkyl, $R^{5G}$-substituted or unsubstituted heterocycloalkyl, $R^{5G}$-substituted or unsubstituted aryl, or $R^{5G}$-substituted or unsubstituted heteroaryl. $R^{5G}$ is independently halogen, oxo, $—CX^{5G}_3$, $—CHX^{5G}_2$, $—CH_2X^{5G}$, $—OCX^{5G}_3$, $—OCH_2X^{5G}$, $—OCHX^{5G}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, $—ONO_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{5A}$ and $R^{5B}$ are combined to form an oxo. In embodiments, $R^{5C}$ is independently hydrogen, halogen, $—CX^{5C}_3$, $—CHX^{5C}_2$, $—CH_2X^{5C}$, $—OCX^{5C}_3$, $—OCH_2X^{5C}$, $—OCHX^{5C}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, $—ONO_2$, $R^{5H}$-substituted or unsubstituted alkyl, $R^{5H}$-substituted or unsubstituted heteroalkyl, $R^{5H}$-substituted or unsubstituted cycloalkyl, $R^{5H}$-substituted or unsubstituted heterocycloalkyl, $R^{5H}$-substituted or unsubstituted aryl, or $R^{5H}$-substituted or unsubstituted heteroaryl. $R^{5H}$ is independently halogen, oxo, $—CX^{5H}_3$, $—CHX^{5H}_2$, $—CH_2X^{5H}$, $—OCX^{5H}_3$, $—OCH_2X^{5H}$, $—OCHX^{5H}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, $—ONO_2$, $R^{5I}$-substituted or unsubstituted alkyl, $R^{5I}$-substituted or unsubstituted heteroalkyl, $R^{5I}$-substituted or unsubstituted cycloalkyl, $R^{5I}$-substituted or unsubstituted heterocycloalkyl, $R^{5I}$-substituted or unsubstituted aryl, or $R^{5I}$-substituted or unsubstituted heteroaryl. $R^{5I}$ is independently halogen, oxo, $—CX^{5I}_3$, $—CHX^{5I}_2$, $—CH_2X^{5I}$, $—OCX^{5I}_3$, $—OCH_2X^{5I}$, $—OCHX^{5I}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, $—ONO_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{5C}$ is unsubstituted $C_1$-$C_4$ alkyl. In embodiments, $R^{5C}$ is unsubstituted methyl. In embodiments, $R^{5C}$ is unsubstituted tert-butyl. The symbols $X^{5A}$, $X^{5B}$, $X^{5C}$, $X^{5D}$, $X^{5E}$, $X^{5F}$, $X^{5G}$, $X^{5H}$, and $X^{5I}$ are independently —F, —Cl, —Br, or —I.

In embodiments, $R^2$ is a polymerase-compatible cleavable moiety or an —O-polymerase-compatible cleavable moiety; and the polymerase-compatible cleavable moiety is

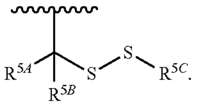

In embodiments, $R^{5A}$ is independently hydrogen, halogen, —$CX^{5A}_3$, —$CHX^{5A}_2$, —$CH_2X^{5A}$, —$OCX^{5A}_3$, —$OCH_2X^{5A}$, —$OCHX^{5A}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H$—, —SCN, —$ONO_2$, $R^{5D}$-substituted or unsubstituted alkyl (e.g., $C_1$-$C_8$, $C_1$-$C_6$, $C_1$-$C_4$, or $C_1$-$C_2$), $R^{5D}$-substituted or unsubstituted heteroalkyl (e.g., 2 to 8, 2 to 6, 4 to 6, 2 to 3, or 4 to 5 membered), $R^{5D}$-substituted or unsubstituted cycloalkyl (e.g., $C_3$-$C_8$, $C_3$-$C_6$, $C_4$-$C_6$, or $C_5$-$C_6$), $R^{5D}$-substituted or unsubstituted heterocycloalkyl (e.g., 3 to 8, 3 to 6, 4 to 6, 4 to 5, or 5 to 6 membered), $R^{5D}$-substituted or unsubstituted aryl (e.g., $C_6$-$C_{10}$ or phenyl), or $R^{5D}$-substituted or unsubstituted heteroaryl (e.g., 5 to 10, 5 to 9, or 5 to 6 membered). In embodiments, $R^{5D}$ is independently halogen, oxo, —$CX^{5D}_3$, —$CHX^{5D}_2$, —$CH_2X^{5D}$, —$OCX^{5D}_3$, —$OCH_2X^{5D}$, —$OCHX^{5D}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5E}$-substituted or unsubstituted alkyl (e.g., $C_1$-$C_8$, $C_1$-$C_6$, $C_1$-$C_4$, or $C_1$-$C_2$), $R^{5E}$-substituted or unsubstituted heteroalkyl (e.g., 2 to 8, 2 to 6, 4 to 6, 2 to 3, or 4 to 5 membered), $R^{5E}$-substituted or unsubstituted cycloalkyl (e.g., $C_3$-$C_8$, $C_3$-$C_6$, $C_4$-$C_6$, or $C_5$-$C_6$), $R^{5E}$-substituted or unsubstituted heterocycloalkyl (e.g., 3 to 8, 3 to 6, 4 to 6, 4 to 5, or 5 to 6 membered), $R^{5E}$-substituted or unsubstituted aryl (e.g., $C_6$-$C_{10}$ or phenyl), or $R^{5E}$-substituted or unsubstituted heteroaryl (e.g., 5 to 10, 5 to 9, or 5 to 6 membered). In embodiments, $R^{5E}$ is independently halogen, oxo, —$CX^{5E}_3$, —$CHX^{5E}_2$, —$CH_2X^{5E}$, -$OCX^{5E}_3$, —$OCH_2X^{5E}$, —$OCHX^{5E}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8, 2 to 6, 4 to 6, 2 to 3, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8, 3 to 6, 4 to 6, 4 to 5, or 5 to 6 membered), unsubstituted aryl (e.g., $C_6$-$C_{10}$ or phenyl), or unsubstituted heteroaryl (e.g., 5 to 10, 5 to 9, or 5 to 6 membered). In embodiments, $R^{5B}$ is independently hydrogen, halogen, —$CX^{5B}_3$, —$CHX^{5B}_2$, —$CH_2X^{5B}$, —$OCX^{5B}_3$, —$OCH_2X^{5B}$, —$OCHX^{5B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5F}$-substituted or unsubstituted alkyl (e.g., $C_1$-$C_8$, $C_1$-$C_6$, $C_1$-$C_4$, or $C_1$-$C_2$), $R^{5F}$-substituted or unsubstituted heteroalkyl (e.g., 2 to 8, 2 to 6, 4 to 6, 2 to 3, or 4 to 5 membered), $R^{5F}$-substituted or unsubstituted cycloalkyl (e.g., $C_3$-$C_8$, $C_3$-$C_6$, $C_4$-$C_6$, or $C_5$-$C_6$), $R^{5F}$-substituted or unsubstituted heterocycloalkyl (e.g., 3 to 8, 3 to 6, 4 to 6, 4 to 5, or 5 to 6 membered), $R^{5F}$-substituted or unsubstituted aryl (e.g., $C_6$-$C_{10}$ or phenyl), or $R^{5F}$-substituted or unsubstituted heteroaryl (e.g., 5 to 10, 5 to 9, or 5 to 6 membered). In embodiments, $R^{5F}$ is independently halogen, oxo, —$CX^{5F}_3$, —$CHX^{5F}_2$, —$CH_2X^{5F}$, —$OCX^{5F}_3$, —$OCH_2X^{5F}$, —$OCHX^{5F}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5G}$-substituted or unsubstituted alkyl (e.g., $C_1$-$C_8$, $C_1$-$C_6$, $C_1$-$C_4$, or $C_1$-$C_2$), $R^{5G}$-substituted or unsubstituted heteroalkyl (e.g., 2 to 8, 2 to 6, 4 to 6, 2 to 3, or 4 to 5 membered), $R^{5G}$-substituted or unsubstituted cycloalkyl (e.g., $C_3$-$C_8$, $C_3$-$C_6$, $C_4$-$C_6$, or $C_5$-$C_6$), $R^{5G}$-substituted or unsubstituted heterocycloalkyl (e.g., 3 to 8, 3 to 6, 4 to 6, 4 to 5, or 5 to 6 membered), $R^{5G}$-substituted or unsubstituted aryl (e.g., $C_6$-$C_{10}$ or phenyl), or $R^{5G}$-substituted or unsubstituted heteroaryl (e.g., 5 to 10, 5 to 9, or 5 to 6 membered). In embodiments, $R^{5G}$ is independently halogen, oxo, —$CX^{5G}_3$, —$CHX^{5G}_2$, —$CH_2X^{5G}$, —$OCX^{5G}_3$, —$OCH_2X^{5G}$, —$OCHX^{5G}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O) $NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8, 2 to 6, 4 to 6, 2 to 3, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8, 3 to 6, 4 to 6, 4 to 5, or 5 to 6 membered), unsubstituted aryl (e.g., $C_6$-$C_{10}$ or phenyl), or unsubstituted heteroaryl (e.g., 5 to 10, 5 to 9, or 5 to 6 membered). In embodiments, $R^{5A}$ and $R^{5B}$ are combined to form an oxo. In embodiments, $R^{5C}$ is independently hydrogen, halogen, —$CX^{5C}_3$, —$CHX^{5C}_2$, —$CH_2X^{5C}$, —$OCX^{5C}_3$, —$OCH_2X^{5C}$, —$OCHX^{5C}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)OH, —NHOH, —$N_3$, —$SF_5$, —$NH_3^+$, —$SO_3^-$, —$OPO_3H^-$, —SCN, —$ONO_2$, $R^{5H}$-substituted or unsubstituted alkyl (e.g., $C_1$-$C_8$, $C_1$-$C_6$, $C_1$-$C_4$, or $C_1$-$C_2$), $R^{5H}$-substituted or unsubstituted heteroalkyl (e.g., 2 to 8, 2 to 6, 4 to 6, 2 to 3, or 4 to 5 membered), $R^{5H}$-substituted or unsubstituted cycloalkyl (e.g., $C_3$-$C_8$, $C_3$-$C_6$, $C_4$-$C_6$, or $C_5$-$C_6$), $R^{5H}$-substituted or unsubstituted heterocycloalkyl (e.g., 3 to 8, 3 to 6, 4 to 6, 4 to 5, or 5 to 6 membered), $R^{5H}$-substituted or unsubstituted aryl (e.g., $C_6$-$C_{10}$ or phenyl), or $R^{5H}$-substituted or unsubstituted heteroaryl (e.g., 5 to 10, 5 to 9, or 5 to 6 membered). In embodiments, $R^{5H}$ is independently halogen, oxo, —$CX^{5H}_3$, —$CHX^{5H}_2$, —$CH_2X^{5H}$, —$OCX^{5H}_3$, —$OCH_2X^{5H}$, —$OCHX^{5H}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)OH, —NHOH, —$N_3$, —$SF_5$, —$NH_3^+$, —$SO_3^-$, —$OPO_3H^-$, —SCN, —$ONO_2$, $R^{5I}$-substituted or unsubstituted alkyl (e.g., $C_1$-$C_8$, $C_1$-$C_6$, $C_1$-$C_4$, or $C_1$-$C_2$), $R^{5I}$-substituted or unsubstituted heteroalkyl (e.g., 2 to 8, 2 to 6, 4 to 6, 2 to 3, or 4 to 5 membered), $R^{5I}$-substituted or unsubstituted cycloalkyl (e.g., $C_3$-$C_8$, $C_3$-$C_6$, $C_4$-$C_6$, or $C_5$-$C_6$), $R^{5I}$-substituted or unsubstituted heterocycloalkyl (e.g., 3 to 8, 3 to 6, 4 to 6, 4 to 5, or 5 to 6 membered), $R^{5I}$-substituted or unsubstituted aryl (e.g., $C_6$-$C_{10}$ or phenyl), or $R^{5I}$-substituted or unsubstituted heteroaryl (e.g., 5 to 10, 5 to 9, or 5 to 6 membered). In embodiments, $R^{5I}$ is independently halogen, oxo, —$CX^{5I}_3$, —$CHX^{5I}_2$, —$CH_2X^{5I}$, —$OCX^{5I}_3$, —$OCH_2X^{5I}$, —$OCHX^{5I}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8, 2 to 6, 4 to 6, 2 to 3, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8, 3 to 6, 4 to 6, 4 to 5, or 5 to 6 membered), unsubstituted aryl (e.g., $C_6$-$C_{10}$ or phenyl), or unsubstituted heteroaryl (e.g., 5 to 10, 5 to 9, or 5 to 6 membered). In embodiments, $R^{5C}$ is unsubstituted $C_1$-$C_4$ alkyl. In embodiments, $R^{5C}$ is unsubstituted methyl. In embodiments, $R^{5C}$ is unsubstituted tert-butyl. The symbols $X^{5A}$, $X^{5B}$, $X^{5C}$, $X^{5D}$, $X^{5E}$, $X^{5F}$, $X^{5G}$, $X^{5H}$, and $X^{5I}$ are independently —F, —Cl, —Br, or —I.

In embodiments, $R^{5A}$ is independently hydrogen, halogen, $—CX^{5A}_3$, $—CHX^{5A}_2$, $—CH_2X^{5A}$, $—OCX^{5A}_3$, $—OCH_2X^{5A}$, $—OCHX^{5A}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, $—ONO_2$, $R^{5D}$-substituted $C_1$-$C_4$ alkyl (e.g., $R^{5D}$-substituted $C_1$-$C_3$ alkyl, $R^{5D}$-substituted $C_1$-$C_2$ alkyl, or $R^{5D}$-substituted methyl) or $R^{5D}$-substituted 2 to 8 membered heteroalkyl (e.g., $R^{5D}$-substituted 2 to 6 membered heteroalkyl, $R^{5D}$-substituted 2 to 5 membered heteroalkyl, or $R^{5D}$-substituted 2 to 4 membered heteroalkyl). In embodiments, $R^{5D}$ is independently halogen, oxo, $—CX^{5D}_3$, $—CHX^{5D}_2$, $—CH_2X^{5D}$, $—OCX^{5D}_3$, $—OCH_2X^{5D}$, $—OCHX^{5D}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC (O)H, —NHC(O)OH, —NHOH, $—N_3$, $—SF_5$, $—NH_3^+$, $—SO_3^-$, $—OPO_3H—$, —SCN, or $—ONO_2$. In embodiments, $R^{5B}$ is independently hydrogen, halogen, $—CX^{5B}_3$, $—CHX^{5B}_2$, $—CH_2X^{5B}$, $—OCX^{5B}_3$, $—OCH_2X^{5B}$, $—OCHX^{5B}_2$, —CN, —OH, —SH, $—NH_2$, —COOH, $—CONH_2$, $—NO_2$, $—SO_3H$, $—SO_4H$, $—SO_2NH_2$, $—NHNI_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H$, —SCN, $—ONO_2$, $R^{5F}$-substituted $C_1$-$C_4$ alkyl, (e.g., $R^{5F}$-substituted $C_1$-$C_3$ alkyl, $R^{5F}$-substituted $C_1$-$C_2$ alkyl, or $R^{5F}$-substituted methyl) or $R^{5F}$-substituted 2 to 8 membered heteroalkyl (e.g., $R^{5F}$-substituted 2 to 6 membered heteroalkyl, $R^{5F}$-substituted 2 to 5 membered heteroalkyl, or $R^{5F}$-substituted 2 to 4 membered heteroalkyl). In embodiments, $R^{5F}$ is independently halogen, oxo, $—CX^{5F}_3$, $—CHX^{5F}_2$, $—CH_2X^{5F}$, $—OCX^{5F}_3$, $—OCH_2X^{5F}$, $—OCHX^{5F}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC (O)H, —NHC(O)OH, —NHOH, $—N_3$, $—SF_5$, $—NH_3^+$, $—SO_3^-$, $—OPO_3H^-$, —SCN, or $—ONO_2$. In embodiments, $R^{5A}$ and $R^{5B}$ are be combined to form an oxo. The symbols $X^{5A}$, $X^{5B}$, $X^{5D}$, and $X^{5F}$ are independently —F, —Cl, —Br, or —I.

In embodiments, the -polymerase-compatible cleavable moiety is:

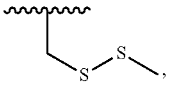,
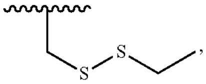,
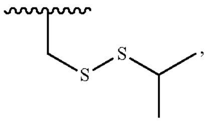,
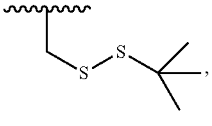,

-continued

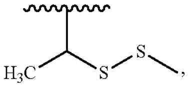, 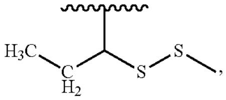,
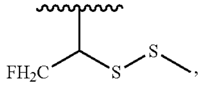, 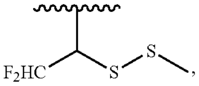,
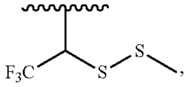, 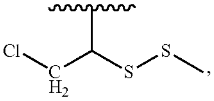,
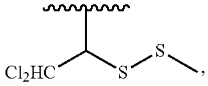, 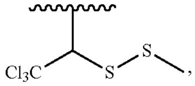,
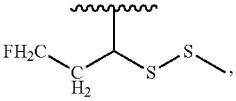, 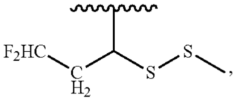,
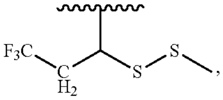, 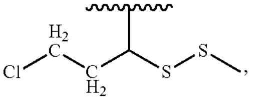,
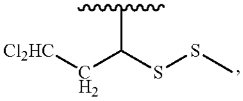, 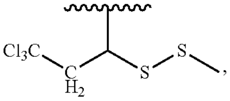,
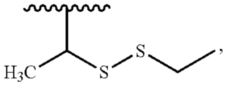, 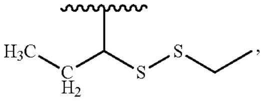,
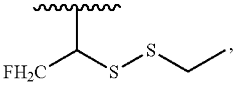, 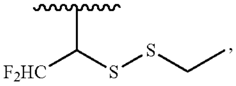,
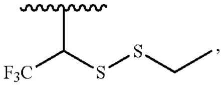, 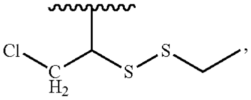,
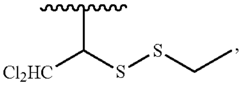, 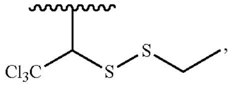,
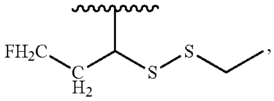, 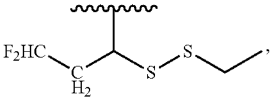,
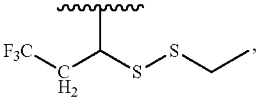, 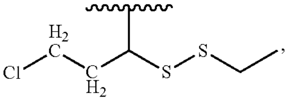,
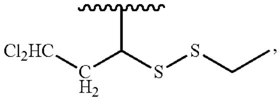, 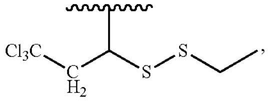,
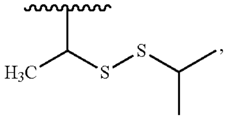, 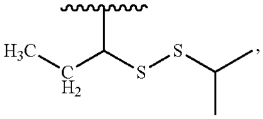,
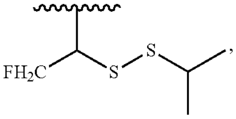, 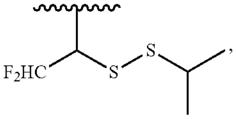,
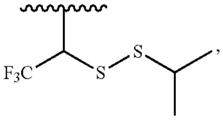, 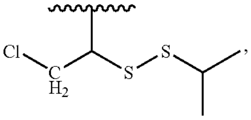, -continued
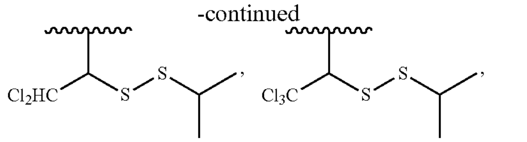
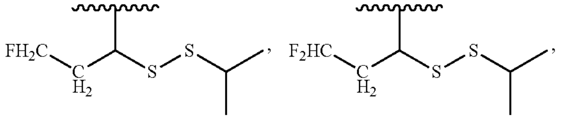
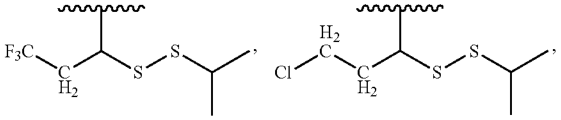
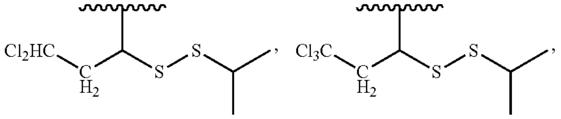
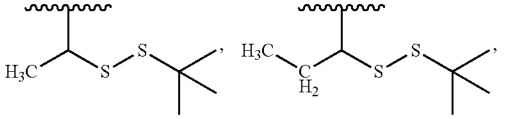
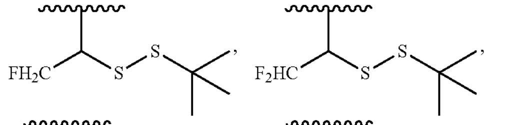
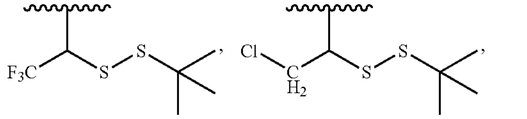
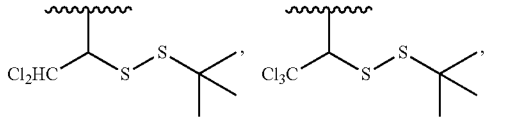
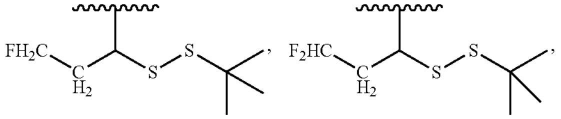
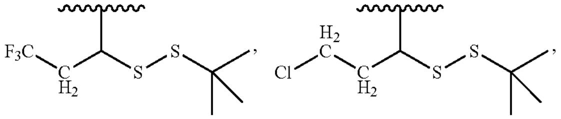
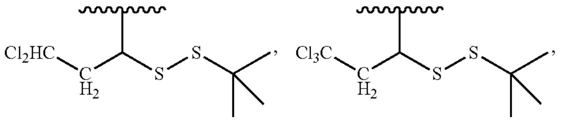
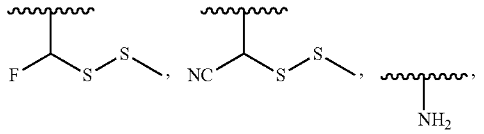
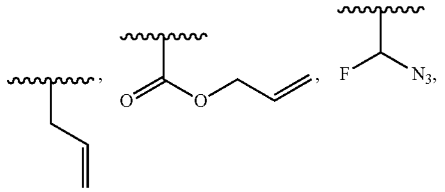
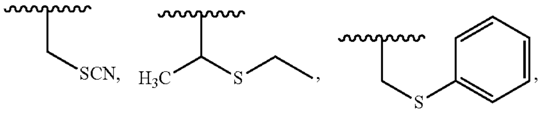
-continued
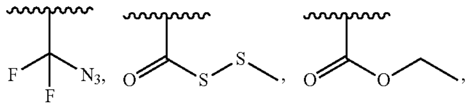
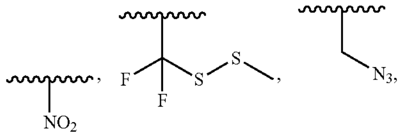
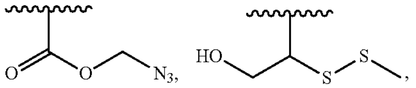
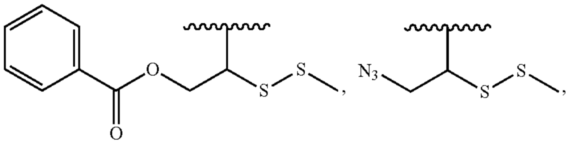
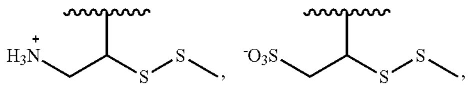
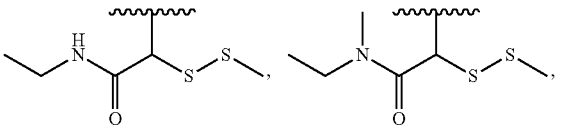
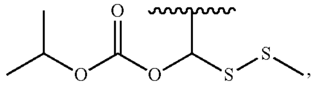
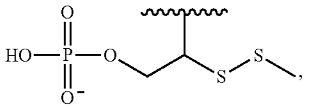
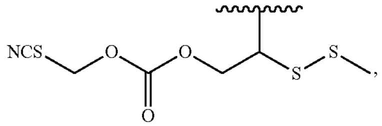
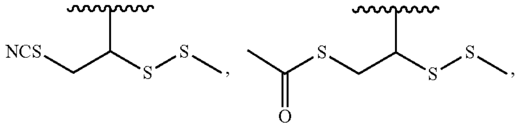
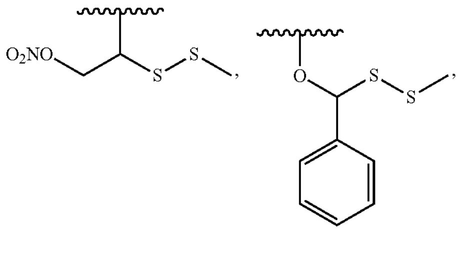
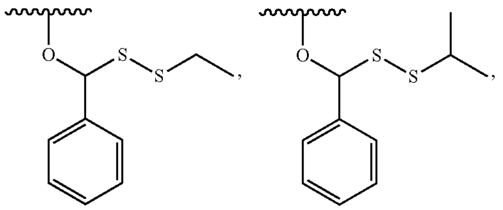

-continued
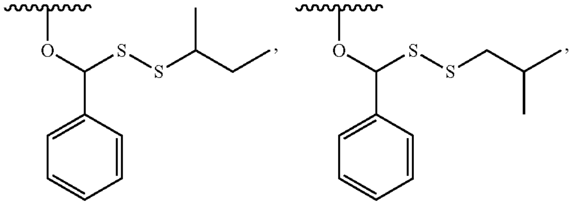
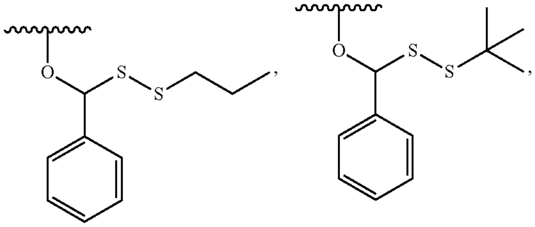
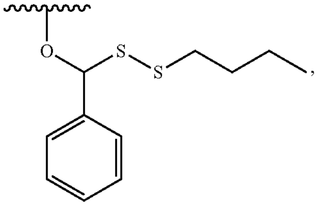
or
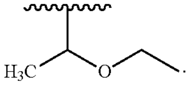
In embodiments, $R^2$ is —$OR^{2A}$. In embodiments, $R^{2A}$ is independently:
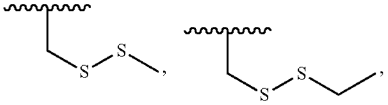
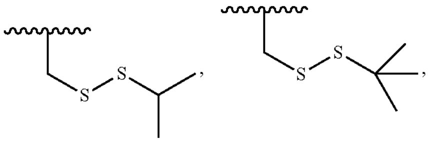
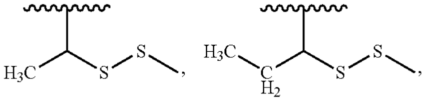
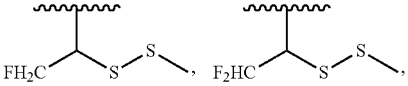
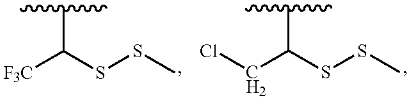
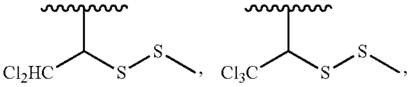
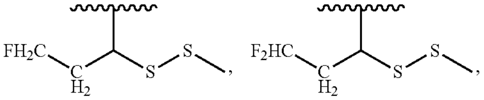
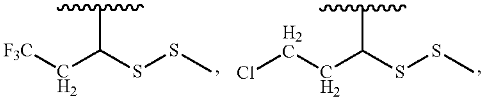
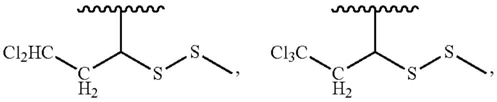
-continued
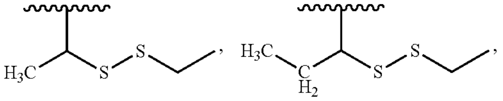
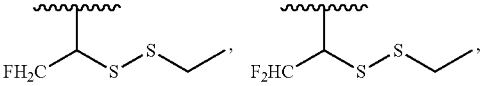
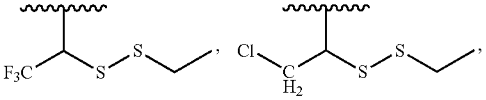
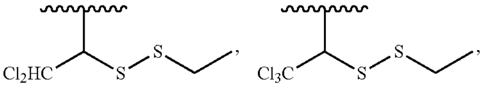
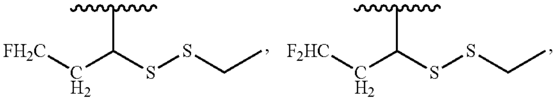
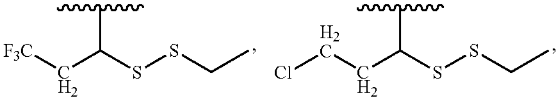
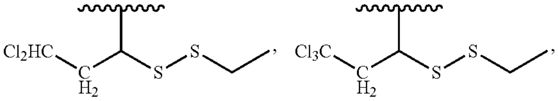
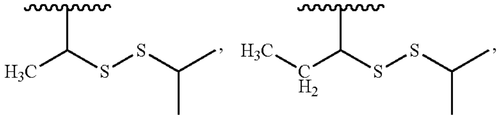
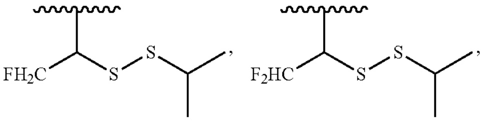
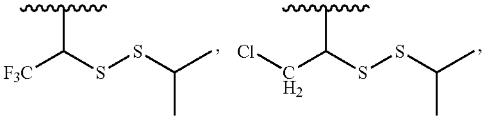
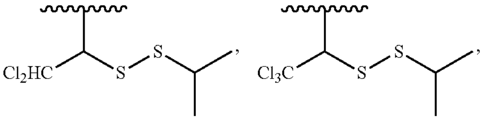
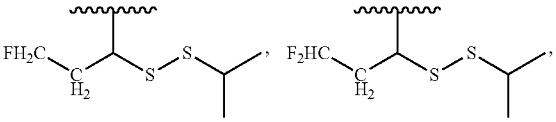
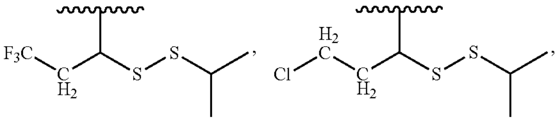
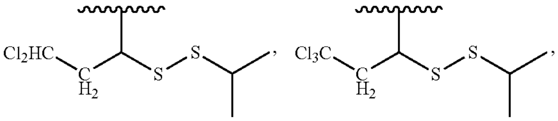
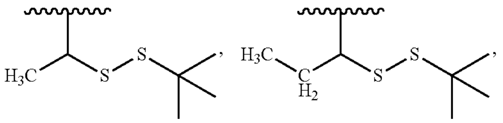

-continued
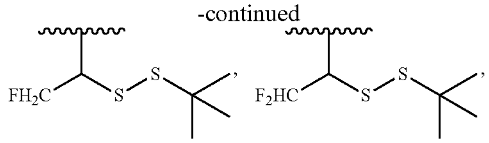
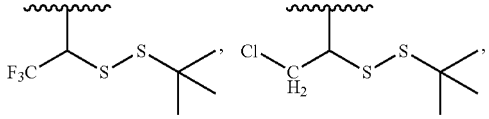
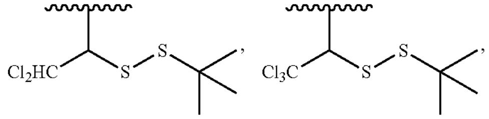
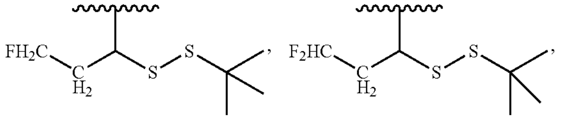
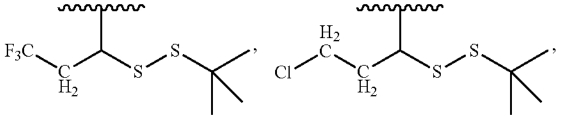
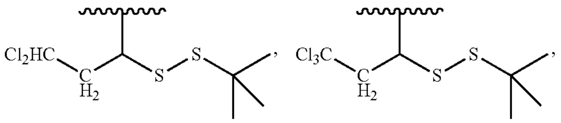
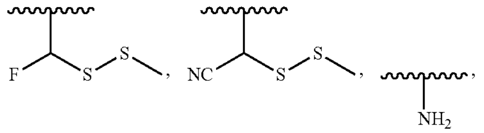
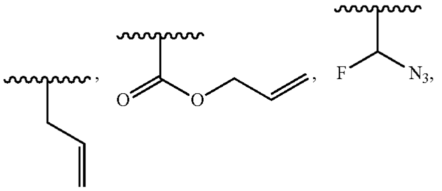
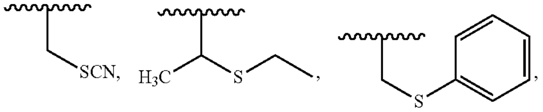
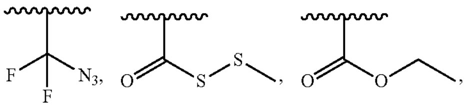
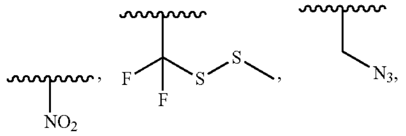
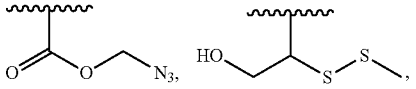
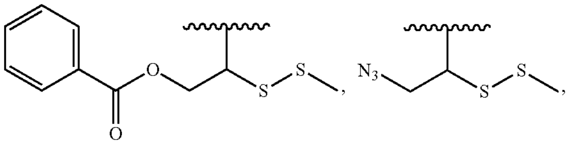
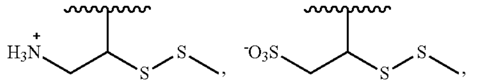
-continued
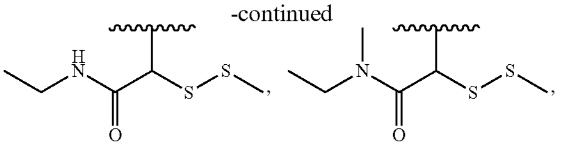
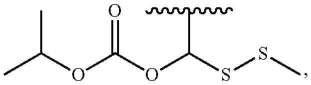
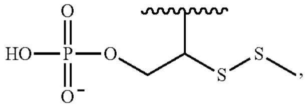
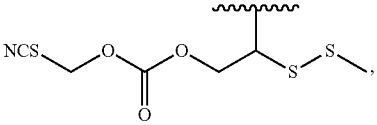
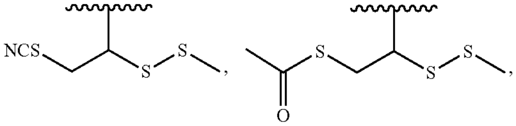
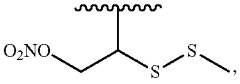
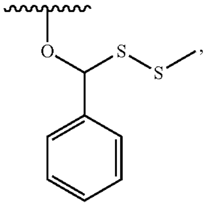
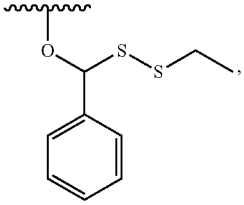
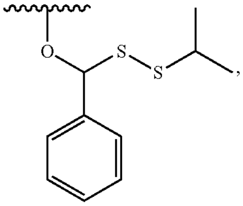
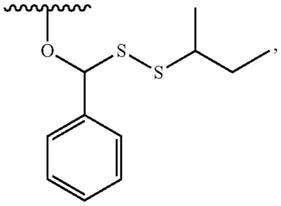
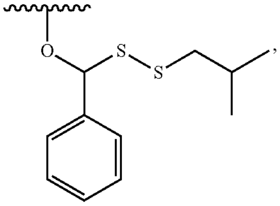
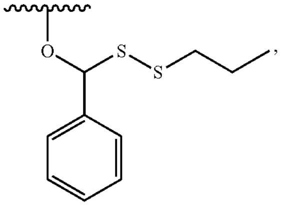
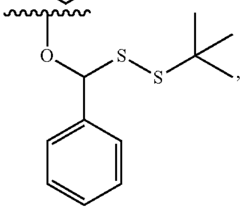
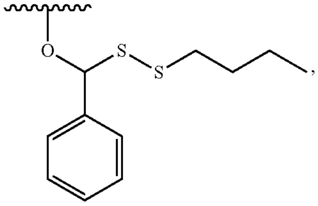
or
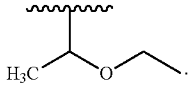
In embodiments, $R^3$ is independently an —O-polymerase-compatible cleavable moiety, a polymerase-compatible cleavable moiety, hydrogen, —OH, $—NH_3^+$, $—SO_3^-$, —$OPO_3H^-$, —SCN, —$ONO_2$, substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), or substituted or unsubstituted heteroaryl (e.g., 5 to 10, 5 to 9, or 5 to 6 membered).

In embodiments, a substituted $R^3$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. In embodiments, when $R^3$ is substituted, it is substituted with at least one substituent group. In embodiments, when $R^3$ is substituted, it is substituted with at least one size-limited substituent group. In embodiments, when $R^3$ is substituted, it is substituted with at least one lower substituent group.

In embodiments, $R^3$ is independently an —O-polymerase-compatible cleavable moiety, a polymerase-compatible cleavable moiety, hydrogen, or —OH. In embodiments, $R^3$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is independently —$NH_3^+$, —$SO_3^-$, —$OPO_3H^-$, —SCN, or —$ONO_2$.

In embodiments, $R^3$ is a polymerase-compatible cleavable moiety or an —O-polymerase-compatible cleavable moiety; and the polymerase-compatible cleavable moiety is independently

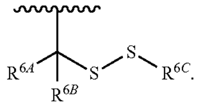

It is understood the —O— moiety of the —O-polymerase-compatible cleavable moiety refers to the 3' oxygen atom of a nucleotide sugar. In embodiments, $R^{6A}$ is independently hydrogen, halogen, —$CX^{6A}_3$, —$CHX^{6A}_2$, —$CH_2X^{6A}$, —$OCX^{6A}_3$, —$OCH_2X^{6A}$, —$OCHX^{6A}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{6D}$-substituted or unsubstituted alkyl, $R^{6D}$-substituted or unsubstituted heteroalkyl, $R^{6D}$-substituted or unsubstituted cycloalkyl, $R^{6D}$-substituted or unsubstituted heterocycloalkyl, $R^{6D}$-substituted or unsubstituted aryl, or $R^{6D}$-substituted or unsubstituted heteroaryl. $R^{6D}$ is independently halogen, oxo, —$CX^{6D}_3$, —$CHX^{6D}_2$, —$CH_2X^{6D}$, —$OCX^{6D}_3$, —$OCH_2X^{6D}$, —$OCHX^{6D}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{6E}$-substituted or unsubstituted alkyl, $R^{6E}$-substituted or unsubstituted heteroalkyl, $R^{6E}$-substituted or unsubstituted cycloalkyl, $R^{6E}$-substituted or unsubstituted heterocycloalkyl, $R^{6E}$-substituted or unsubstituted aryl, or $R^{6E}$-substituted or unsubstituted heteroaryl. $R^{6E}$ is independently halogen, oxo, —$CX^{6E}_3$, —$CHX^{6E}_2$, —$CH_2X^{6E}$, —$OCX^{6E}_3$, —$OCH_2X^{6E}$, —$OCHX^{6E}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H$—, —SCN, —$ONO_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{6B}$ is independently hydrogen, halogen, —$CX^{6B}_3$, —$CHX^{6B}_2$, —$CH_2X^{6B}$, —$OCX^{6B}_3$, —$OCH_2X^{6B}$, —$OCHX^{6B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{6F}$-substituted or unsubstituted alkyl, $R^{6F}$-substituted or unsubstituted heteroalkyl, $R^{6F}$-substituted or unsubstituted cycloalkyl, $R^{6F}$-substituted or unsubstituted heterocycloalkyl, $R^{6F}$-substituted or unsubstituted aryl, or $R^{6F}$-substituted or unsubstituted heteroaryl. $R^{6F}$ is independently halogen, oxo, —$CX^{6F}_3$, —$CHX^{6F}_2$, —$CH_2X^{6F}$, —$OCX^{6F}_3$, —$OCH_2X^{6F}$, —$OCHX^{6F}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3$, —$OPO_3H$—, —SCN, —$ONO_2$, $R^{6G}$-substituted or unsubstituted alkyl, $R^{6G}$-substituted or unsubstituted heteroalkyl, $R^{6G}$-substituted or unsubstituted cycloalkyl, $R^{6G}$-substituted or unsubstituted heterocycloalkyl, $R^{6G}$-substituted or unsubstituted aryl, or $R^{6G}$-substituted or unsubstituted heteroaryl. $R^{6G}$ is independently halogen, oxo, —$CX^{6G}_3$, —$CHX^{6G}_2$, —$CH_2X^{6G}$, —$OCX^{6G}_3$, —$OCH_2X^{6G}$, —$OCHX^{6G}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{6A}$ and $R^{6B}$ are combined to form an oxo. In embodiments, $R^{6C}$ is independently hydrogen, halogen, —$CX^{6C}_3$, —$CHX^{6C}_2$, —$CH_2X^{6C}$, —$OCX^{6C}_3$, —$OCH_2X^{6C}$, —$OCHX^{6C}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{6H}$-substituted or unsubstituted alkyl, $R^{6H}$-substituted or unsubstituted heteroalkyl, $R^{6H}$-substituted or unsubstituted cycloalkyl, $R^{6H}$-substituted or unsubstituted heterocycloalkyl, $R^{6H}$-substituted or unsubstituted aryl, or $R^{6H}$-substituted or unsubstituted heteroaryl. $R^{6H}$ is independently halogen, oxo, —$CX^{6H}_3$, —$CHX^{6H}_2$, —$CH_2X^{6H}$—$OCX^{6H}_3$, —$OCH_2X^{6H}$, —$OCHX^{6H}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{6I}$-substituted or unsubstituted alkyl, $R^{6I}$-substituted or unsubstituted heteroalkyl, $R^{6I}$-substituted or unsubstituted cycloalkyl, $R^{6I}$- substituted or unsubstituted heterocycloalkyl, $R^{6I}$-substituted or unsubstituted aryl, or $R^{6I}$-substituted or unsubstituted heteroaryl. $R^{6I}$ is independently halogen, oxo, —$CX^{6I}_3$, —$CHX^{6I}_2$, —$CH_2X^{6I}$, —$OCX^{6I}_3$, —$OCH_2X^{6I}$, —$OCHX^{6I}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{6C}$ is unsubstituted $C_1$-$C_4$ alkyl. In embodiments, $R^{6C}$ is unsubstituted methyl. In embodiments, $R^{6C}$ is unsubstituted tert-butyl. The symbols $X^{6A}$, $X^{6B}$, $X^{6C}$, $X^{6D}$, $X^{6E}$, $X^6F$, $X^{6G}$, $X^6H$, and $X^{6I}$ are independently —F, —Cl, —Br, or —I.

In embodiments, $R^3$ is a polymerase-compatible cleavable moiety or an —O-polymerase-compatible cleavable moiety; and the polymerase-compatible cleavable moiety is independently

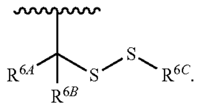

In embodiments, $R^{6A}$ is independently hydrogen, halogen, —$CX^{6A}_3$, —$CHX^{6A}_2$, —$CH_2X^{6A}$, —$OCX^{6A}_3$, —$OCH_2X^{6A}$, —$OCHX^{6A}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{6D}$-substituted or unsubstituted alkyl (e.g., $C_1$-$C_8$, $C_1$-$C_6$, $C_1$-$C_4$, or $C_1$-$C_2$), $R^{6D}$-substituted or unsubstituted heteroalkyl (e.g., 2 to 8 membered, 2 to 6 membered, 4 to 6 membered, 2 to 3 membered, or 4 to 5 membered), $R^{6D}$-substituted or unsubstituted cycloalkyl (e.g., $C_3$-$C_5$, $C_3$-$C_6$, $C_4$-$C_6$, or $C_5$-$C_6$), $R^{6D}$-substituted or unsubstituted heterocycloalkyl (e.g., 3 to 8 membered, 3 to 6 membered, 4 to 6 membered, 4 to 5 membered, or 5 to 6 membered), $R^{6D}$-substituted or unsubstituted aryl (e.g., $C_6$-$C_{10}$ or phenyl), or $R^{6D}$-substituted or unsubstituted heteroaryl (e.g., 5 to 10 membered, 5 to 9 membered, or 5 to 6 membered). $R^{6D}$ is independently halogen, oxo, —$CX^{6D}_3$, —$CHX^{6D}_2$, —$CH_2X^{6D}$, —$OCX^{6D}_3$, —$OCH_2X^{6D}$, —$OCHX^{6D}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC (O)H, —NHC(O)OH, —NHOH, —$N_3$, —$SF_5$, —$NH_3^+$, —$SO_3^-$, —$OPO_3H^-$, —SCN, —$ONO_2$, $R^{6E}$-substituted or unsubstituted alkyl (e.g., $C_1$-$C_8$, $C_1$-$C_6$, $C_1$-$C_4$, or $C_1$-$C_2$), $R^{6E}$-substituted or unsubstituted heteroalkyl (e.g., 2 to 8 membered, 2 to 6 membered, 4 to 6 membered, 2 to 3 membered, or 4 to 5 membered), $R^{6E}$-substituted or unsubstituted cycloalkyl (e.g., $C_3$-$C_8$, $C_3$-$C_6$, $C_4$-$C_6$, or $C_5$-$C_6$), $R^{6E}$-substituted or unsubstituted heterocycloalkyl (e.g., 3 to 8 membered, 3 to 6 membered, 4 to 6 membered, 4 to 5 membered, or 5 to 6 membered), $R^{6E}$-substituted or unsubstituted aryl (e.g., $C_6$-$C_{10}$ or phenyl), or $R^{6E}$-substituted or unsubstituted heteroaryl (e.g., 5 to 10 membered, 5 to 9 membered, or 5 to 6 membered). $R^{6E}$ is independently halogen, oxo, —$CX^{6E}_3$, —$CHX^{6E}_2$, —$CH_2X^{6E}$, —$OCX^{6E}_3$, —$OCH_2X^{6E}$, —$OCHX^{6E}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)—$NHNH_2$, —$NHC(O)NH_2$, —$NHSO_2H$, —NHC(O)H, —NHC(O)OH, —NHOH, —$N_3$, —$SF_5$, —$NH_{31}$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{6B}$ is independently hydrogen, halogen, —$CX^{6B}_3$, —$CHX^{6B}_2$, —$CH_2X^{6B}$, —$OCX^{6B}_3$, —$OCH_2X^{6B}$, —$OCHX^{6B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{6F}$-substituted or unsubstituted alkyl (e.g., $C_1$-$C_8$, $C_1$-$C_6$, $C_1$-$C_4$, or $C_1$-$C_2$), $R^{6F}$-substituted or unsubstituted heteroalkyl (e.g., 2 to 8 membered, 2 to 6 membered, 4 to 6 membered, 2 to 3 membered, or 4 to 5 membered), $R^{6F}$-substituted or unsubstituted cycloalkyl (e.g., $C_3$-$C_8$, $C_3$-$C_6$, $C_4$-$C_6$, or $C_5$-$C_6$), $R^{6F}$-substituted or unsubstituted heterocycloalkyl (e.g., 3 to 8 membered, 3 to 6 membered, 4 to 6 membered, 4 to 5 membered, or 5 to 6 membered), $R^{6F}$-substituted or unsubstituted aryl (e.g., $C_6$-$C_{10}$ or phenyl), or $R^{6F}$-substituted or unsubstituted heteroaryl (e.g., 5 to 10 membered, 5 to 9 membered, or 5 to 6 membered). $R^{6F}$ is independently halogen, oxo, —$CX^{6F}_3$, —$CHX^{6F}_2$, —$CH_2X^{6F}$, —$OCX^{6F}_3$, —$OCH_2X^{6F}$, —$OCHX^{6F}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{6G}$-substituted or unsubstituted alkyl (e.g., $C_1$-$C_8$, $C_1$-$C_6$, $C_1$-$C_4$, or $C_1$-$C_2$), $R^{6G}$-substituted or unsubstituted heteroalkyl (e.g., 2 to 8 membered, 2 to 6 membered, 4 to 6 membered, 2 to 3 membered, or 4 to 5 membered), $R^{6G}$-substituted or unsubstituted cycloalkyl (e.g., $C_3$-$C_8$, $C_3$-$C_6$, $C_4$-$C_6$, or $C_5$-$C_6$), $R^{6G}$-substituted or unsubstituted heterocycloalkyl (e.g., 3 to 8 membered, 3 to 6 membered, 4 to 6 membered, 4 to 5 membered, or 5 to 6 membered), $R^{6G}$-substituted or unsubstituted aryl (e.g., $C_6$-$C_{10}$ or phenyl), or $R^{6G}$-substituted or unsubstituted heteroaryl (e.g., 5 to 10 membered, 5 to 9 membered, or 5 to 6 membered). $R^{6G}$ is independently halogen, oxo, —$CX^{6G}_3$, —$CHX^{6G}_2$, —$CH_2X^{6G}$, —$OCX^{6G}_3$, —$OCH_2X^{6G}$, —$OCHX^{6G}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC (O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{6A}$ and $R^{6B}$ are combined to form an oxo. In embodiments, $R^{6C}$ is independently hydrogen, halogen, —$CX^{6C}_3$, —$CHX^{6C}_2$, $—CH_2X^{6C}$, $—OCX^6C_3$, $—OCH_2X^{6C}$, $—OCHX^{6C}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H—$, —SCN, $—ONO_2$, $R^{6H}$-substituted or unsubstituted alkyl (e.g., $C_1$-$C_8$, $C_1$-$C_6$, $C_1$-$C_4$, or $C_1$-$C_2$), $R^{6H}$-substituted or unsubstituted heteroalkyl (e.g., 2 to 8 membered, 2 to 6 membered, 4 to 6 membered, 2 to 3 membered, or 4 to 5 membered), $R^{6H}$-substituted or unsubstituted cycloalkyl (e.g., $C_3$-$C_8$, $C_3$-$C_6$, $C_4$-$C_6$, or $C_5$-$C_6$), $R^{6H}$-substituted or unsubstituted heterocycloalkyl (e.g., 3 to 8 membered, 3 to 6 membered, 4 to 6 membered, 4 to 5 membered, or 5 to 6 membered), $R^{6H}$-substituted or unsubstituted aryl (e.g., $C_6$-$C_{10}$ or phenyl), or $R^{6H}$-substituted or unsubstituted heteroaryl (e.g., 5 to 10 membered, 5 to 9 membered, or 5 to 6 membered). $R^{6H}$ is independently halogen, oxo, $—CX^{6H}_3$, $—CHX^{6H}_2$, $—CH_2X^{6H}$, $—OCX^{6H}_3$, $—OCH_2X^{6H}$, $—OCHX^{6H}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, $—ONO_2$, $R^{6I}$-substituted or unsubstituted alkyl (e.g., $C_1$-$C_8$, $C_1$-$C_6$, $C_1$-$C_4$, or $C_1$-$C_2$), $R^{6I}$-substituted or unsubstituted heteroalkyl (e.g., 2 to 8 membered, 2 to 6 membered, 4 to 6 membered, 2 to 3 membered, or 4 to 5 membered), $R^{6I}$-substituted or unsubstituted cycloalkyl (e.g., $C_3$-$C_8$, $C_3$-$C_6$, $C_4$-$C_6$, or $C_5$-$C_6$), $R^{6'}$-substituted or unsubstituted heterocycloalkyl (e.g., 3 to 8 membered, 3 to 6 membered, 4 to 6 membered, 4 to 5 membered, or 5 to 6 membered), $R^{6I}$-substituted or unsubstituted aryl (e.g., $C_6$-$C_{10}$ or phenyl), or $R^{6I}$-substituted or unsubstituted heteroaryl (e.g., 5 to 10 membered, 5 to 9 membered, or 5 to 6 membered). $R^{6I}$ is independently halogen, oxo, $—CX^{6I}_3$, $—CHX^{6I}_2$, $—CH_2X^{6I}$, $—OCX^{6I}_3$, $—OCH_2X^{6I}$, $—OCHX^{6I}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3$, $—SO_3^-$, $—OPO_3H—$, —SCN, $—ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{6C}$ is unsubstituted $C_1$-$C_4$ alkyl. In embodiments, $R^{6C}$ is unsubstituted methyl. In embodiments, $R^{6C}$ is unsubstituted tert-butyl. The symbols $X^{6A}$, $X^{6B}$, $X^{6C}$, $X^{6D}$, $X^{6E}$, $X^{6F}$, $X^{6G}$, $X^6H$, and $X^{6I}$ are independently —F, —Cl, —Br, or —I.

In embodiments, $R^{6A}$ is independently hydrogen, halogen, $—CX^{6A}_3$, $—CHX^{6A}_2$, $—CH_2X^{6A}$, $—OCX^{6A}_3$, $—OCH_2X^{6A}$, $—OCHX^{6A}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, $—ONO_2$, $R^{6D}$-substituted $C_1$-$C_4$ alkyl (e.g., $R^{6D}$-substituted $C_1$-$C_3$ alkyl, $R^{6D}$-substituted $C_1$-$C_2$ alkyl, or $R^{6D}$-substituted methyl) or $R^{6D}$-substituted 2 to 8 membered heteroalkyl (e.g., $R^{6D}$-substituted 2 to 6 membered heteroalkyl, $R^{6D}$-substituted 2 to 5 membered heteroalkyl, or $R^{6D}$-substituted 2 to 4 membered heteroalkyl). In embodiments, $R^{6D}$ is independently halogen, oxo, $—CX^{6D}_3$, $—CHX^{6D}_2$, $—CH_2X^{6D}$, $—OCX^{6D}_3$, $—OCH_2X^{6D}$, $—OCHX^{6D}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3$, $—SO_3^-$, $—OPO_3H—$, —SCN, or $—ONO_2$. In embodiments, $R^{6B}$ is independently hydrogen, halogen, $—CX^{6B}_3$, $—CHX^{6B}_2$, $—CH_2X^{6B}$, $—OCX^{6B}_3$, $—OCH_2X^{6B}$, $—OCHX^{6B}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3$, $—SO_3^-$, $—OPO_3H—$, —SCN, $—ONO_2$, $R^{6F}$-substituted $C_1$-$C_4$ alkyl, (e.g., $R^{6F}$-substituted $C_1$-$C_3$ alkyl, $R^{6F}$-substituted $C_1$-$C_2$ alkyl, or $R^{6F}$-substituted methyl) or $R^{6F}$-substituted 2 to 8 membered heteroalkyl (e.g., $R^{6F}$-substituted 2 to 6 membered heteroalkyl, $R^{6F}$-substituted 2 to 5 membered heteroalkyl, or $R^{6F}$-substituted 2 to 4 membered heteroalkyl). In embodiments, $R^{6F}$ is independently halogen, oxo, $—CX^{6F}_3$, $—CHX^{6F}_2$, $—CH_2X^{6F}$, $—OCX^{6F}_3$, $—OCH_2X^{6F}—OCHX^{6F}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, or $—ONO_2$. In embodiments, $R^{6A}$ and $R^{6B}$ are combined to form an oxo. The symbols $X^{6A}$, $X^{6B}$, $X^{6D}$, and $X^{6F}$ are independently —F, —Cl, —Br, or —I.

In embodiments, $R^3$ is independently $—OR^{3A}$. In embodiments, $R^3$ is independently a reversible terminator moiety.

$R^{3A}$ is independently oxo, halogen, $—CCl_3$, $—CBr_3$, $—CF_3$, $—Cl_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCl_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, $—NH_3^+$, $—SO_3^-$, $—OPO_3H—$, —SCN, $—ONO_2$, $R^{3B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{3B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{3B}$-substituted or unsubstituted cycloalkyl (e.g., $C_3$-$C_8$, $C_3$-$C_6$, or $C_5$-$C_6$), $R^{3B}$-substituted or unsubstituted heterocycloalkyl (e.g., 3 to 8 membered, 3 to 6 membered, or 5 to 6 membered), $R^{3B}$-substituted or unsubstituted aryl (e.g., $C_6$-$C_{10}$, $C_{10}$, or phenyl), $R^{3B}$-substituted or unsubstituted heteroaryl (e.g., 5 to 10 membered, 5 to 9 membered, or 5 to 6 membered), or a polymerase-compatible cleavable moiety. In embodiments, $R^{3A}$ is independently oxo, halogen, $—CCl_3$, $—CBr_3$, $—CF_3$, $—Cl_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCl_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, $—NH_3^+$, $—SO_3^-$, $—OPO_3H^-$, —SC N, $—ONO_2$, $R^{3B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{3B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{3B}$-substituted or unsubstituted cycloalkyl (e.g., $C_3$-$C_8$, $C_3$-$C_6$, or $C_5$-$C_6$), $R^{3B}$-substituted or unsubstituted heterocycloalkyl (e.g., 3 to 8 membered, 3 to 6 membered, or 5 to 6 membered), $R^{3B}$-substituted or unsubstituted aryl (e.g., $C_6$-$C_{10}$, $C_{10}$, or phenyl), or $R^{3B}$-substituted or unsubstituted heteroaryl (e.g., 5 to 10 membered, 5 to 9 membered, or 5 to 6 membered). In embodiments, $R^{3A}$ is independently a polymerase-compatible cleavable moiety.

$R^{3B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H$—, —SCN, —$ONO_2$, $R^{3C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{3C}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{3C}$-substituted or unsubstituted cycloalkyl (e.g., $C_3$-$C_8$, $C_3$-$C_6$, or $C_5$-$C_6$), $R^{3C}$-substituted or unsubstituted heterocycloalkyl (e.g., 3 to 8 membered, 3 to 6 membered, or 5 to 6 membered), $R^{3C}$-substituted or unsubstituted aryl (e.g., $C_6$-$C_{10}$, $C_{10}$, or phenyl), or $R^{3C}$-substituted or unsubstituted heteroaryl (e.g., 5 to 10 membered, 5 to 9 membered, or 5 to 6 membered).

$R^{3C}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H$—, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, $R^3$ is an —O-polymerase-compatible cleavable moiety. In embodiments, the -polymerase-compatible cleavable moiety is independently -(substituted or unsubstituted alkylene)-SS-(unsubstituted alkyl). In embodiments, the -polymerase-compatible cleavable moiety is independently -(halo-substituted or unsubstituted $C_1$-$C_3$ alkylene)-SS-(unsubstituted $C_1$-$C_4$ alkyl).

In embodiments, $R^3$ is —$OR^{3A}$. In embodiments, $R^3$ is —OH. In embodiments, $R^{3A}$ is hydrogen. In embodiments, $R^{3A}$ is a polymerase-compatible cleavable moiety. In embodiments, $R^{3A}$ is a polymerase-compatible cleavable moiety including an azido moiety. In embodiments, $R^{3A}$ is a polymerase-compatible cleavable moiety including a dithiol linker. In embodiments, $R^{3A}$ is a polymerase-compatible cleavable moiety; and the polymerase-compatible cleavable moiety is independently —$CH_2N_3$.

In embodiments, the polymerase-compatible cleavable moiety is independently —$NH_2$, —$NO_2$, —CN, —$CH_3$, $C_2$-$C_6$ allyl (e.g., —$CH_2$—CH═$CH_2$), methoxyalkyl (e.g., —$CH_2$—O—$CH_3$), or —$CH_2N_3$. In embodiments, the polymerase-compatible cleavable moiety is independently —$NH_2$. In embodiments, the polymerase-compatible cleavable moiety is independently —CN. In embodiments, the polymerase-compatible cleavable moiety is independently —$CH_3$. In embodiments, the polymerase-compatible cleavable moiety is independently $C_2$-$C_6$ allyl (e.g., —$CH_2$—CH═$CH_2$). In embodiments, the polymerase-compatible cleavable moiety is independently methoxyalkyl (e.g., —$CH_2$—O—$CH_3$). In embodiments, the polymerase-compatible cleavable moiety is independently —$CH_2N_3$. In embodiments, the polymerase-compatible cleavable moiety is independently —$NH_2$. In embodiments, the polymerase-compatible cleavable moiety is independently —$NO_2$. In embodiments, the polymerase-compatible cleavable moiety is independently —$CH_2N_3$. In embodiments, the polymerase-compatible cleavable moiety is independently

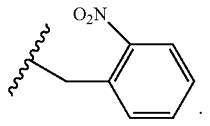 [SMILES: *Cc1ccccc1[N+](=O)[O-]]

In embodiments, the polymerase-compatible cleavable moiety is independently

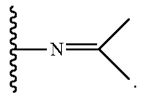

In embodiments, the polymerase-compatible cleavable moiety is independently

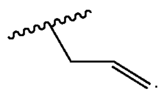

In embodiments, the polymerase-compatible cleavable moiety is independently

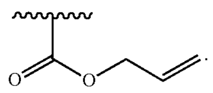 [SMILES: *C(=O)OCC=C]

In embodiments, the polymerase-compatible cleavable moiety is independently

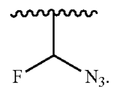

In embodiments, the polymerase-compatible cleavable moiety is independently

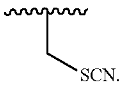

In embodiments, the polymerase-compatible cleavable moiety is independently

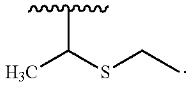

In embodiments, the polymerase-compatible cleavable moiety is independently

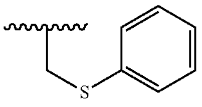 [SMILES: *CSc1ccccc1]

In embodiments, the polymerase-compatible cleavable moiety is independently

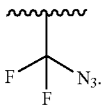

In embodiments, the polymerase-compatible cleavable moiety is independently

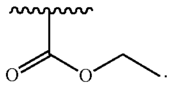

In embodiments, the polymerase-compatible cleavable moiety is independently

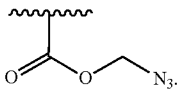

In embodiments, the polymerase-compatible cleavable moiety is independently $-CH_2-O-CH_3$. In embodiments, the polymerase-compatible cleavable moiety is independently $-NH_2$, $-CH_2N_3$,

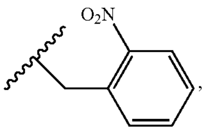, 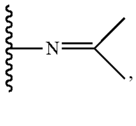, 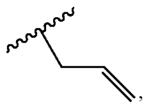,

-continued

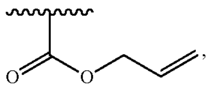, 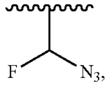, 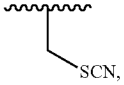

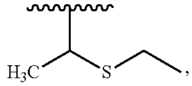, 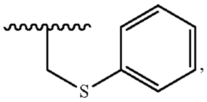,

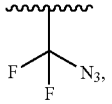, 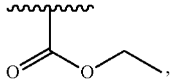, 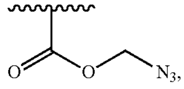

or $-CH_2-O-CH_3$.

In embodiments, $R^{3A}$ is independently $-NH_2$, $-CN$, $-CH_3$, $C_2$-$C_6$ allyl (e.g., $-CH_2-CH=CH_2$), methoxyalkyl (e.g., $-CH_2-O-CH_3$), or $-CH_2N_3$. In embodiments, $R^{3A}$ independently is $-NH_2$. In embodiments, $R^{3A}$ is independently $-CN$. In embodiments, $R^{3A}$ is independently $-CH_3$. In embodiments, $R^{3A}$ is independently $C_2$-$C_6$ allyl (e.g., $-CH_2-CH=CH_2$). In embodiments, $R^{3A}$ independently is methoxyalkyl (e.g., $-CH_2-O-CH_3$). In embodiments, $R^{3A}$ is independently $-CH_2N_3$. In embodiments, $R^{3A}$ is independently

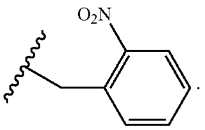 [SMILES: *Cc1ccccc1[N+](=O)[O-]]

In embodiments, $R^{3A}$ is independently

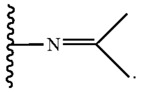 [SMILES: *N=C(C)C]

In embodiments, $R^{3A}$ is independently

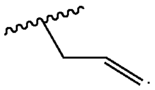 [SMILES: *CC=C]

In embodiments, $R^{3A}$ is

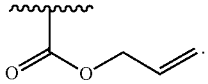 [SMILES: *C(=O)OCC=C]

In embodiments $R^{3A}$ is

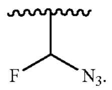

In embodiments, $R^{3A}$ is independently

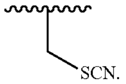

In embodiments, $R^{3A}$ is independently

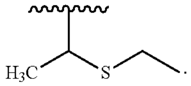

In embodiments, $R^{3A}$ is independently

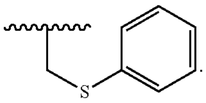 [SMILES: *CSc1ccccc1]

In embodiments, $R^{3A}$ is independently

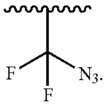

In embodiments, $R^{3A}$ is independently

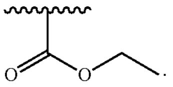

In embodiments, $R^{3A}$ is independently

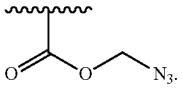

In embodiments, $R^{3A}$ is independently $—CH_2—O—CH_3$. In embodiments, $R^{3A}$ is independently $—NH_2$, $—CH_2N_3$,

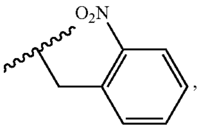, 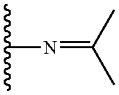, 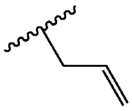,

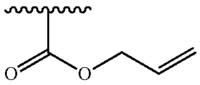, 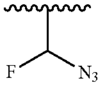, 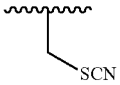,

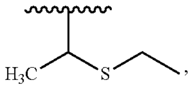, 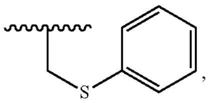, 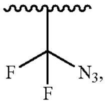

-continued

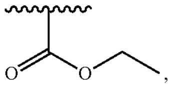, 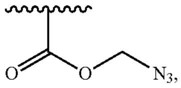

or $—CH_2—O—CH_3$.

In embodiments, $R^{3A}$ is a polymerase-compatible cleavable moiety; and the polymerase-compatible cleavable moiety is independently

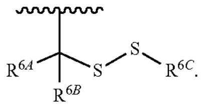

$R^{6B}$. $R^{6A}$, $R^{6B}$, and $R^{6C}$ are as described herein, including in embodiments.

In embodiments, $R^{3A}$ is independently:

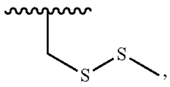, 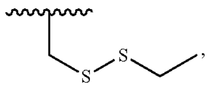,

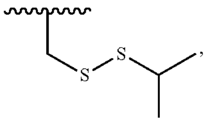, 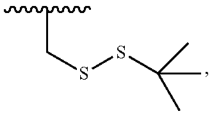,

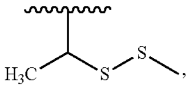, 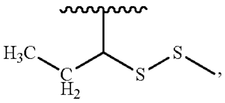,

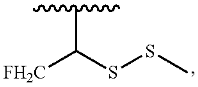, 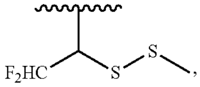,

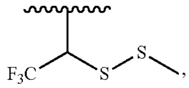, 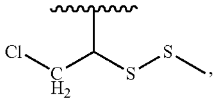,

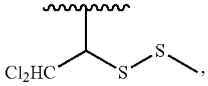, 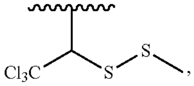,

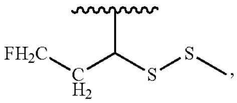, 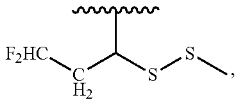,

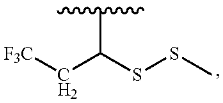, 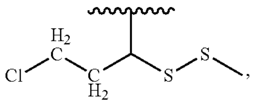,

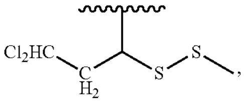, 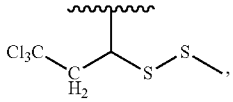,

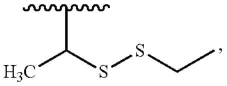, 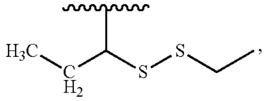,

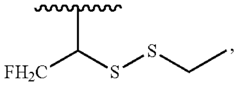, 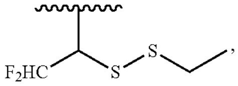,

-continued
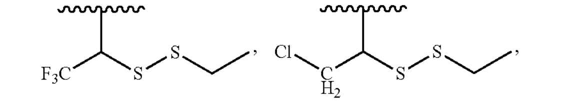
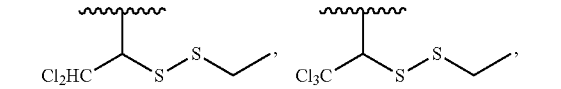
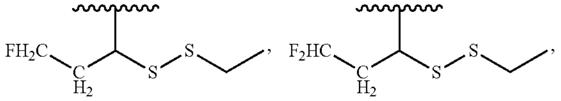
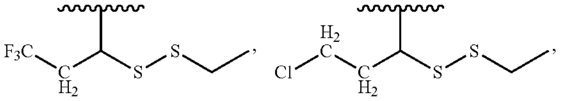
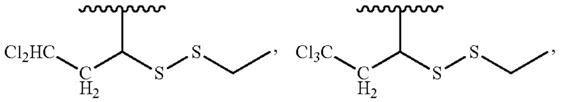
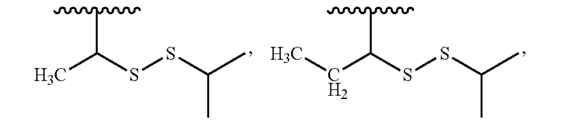
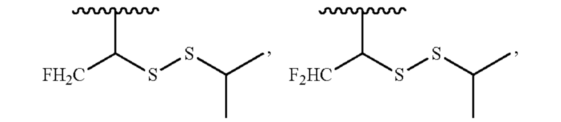
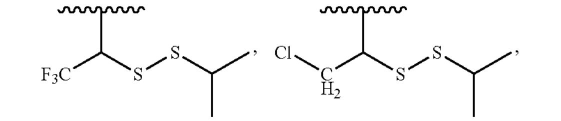
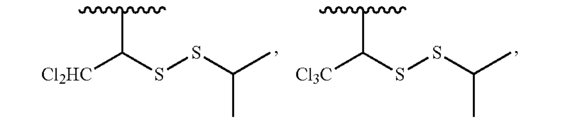
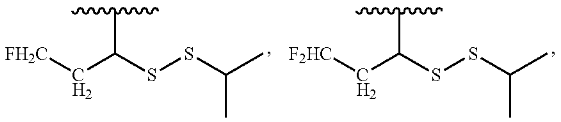
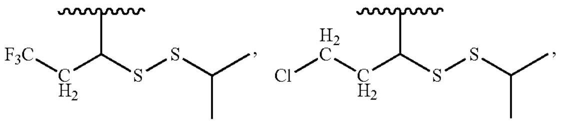
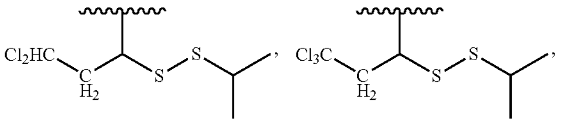
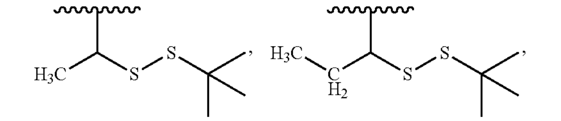
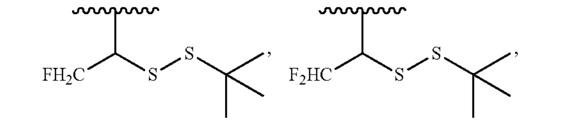
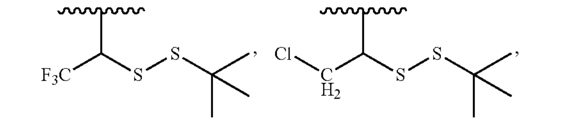
-continued
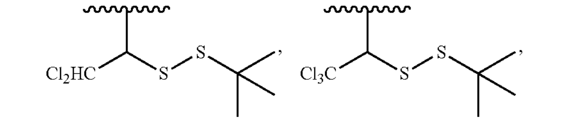
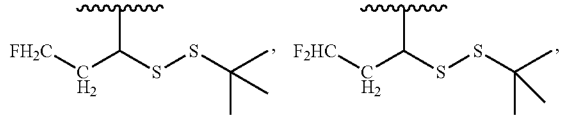
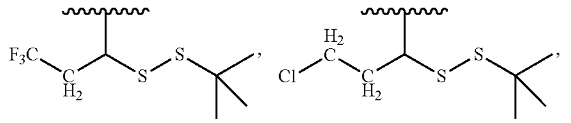
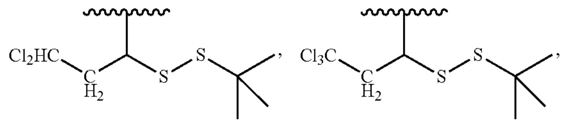
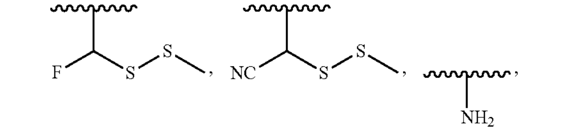
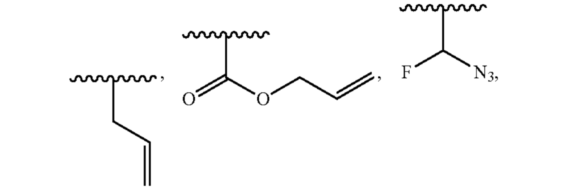
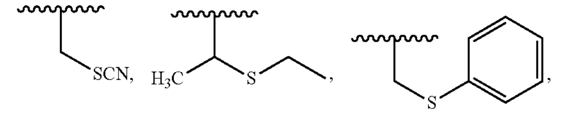
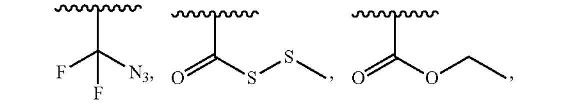
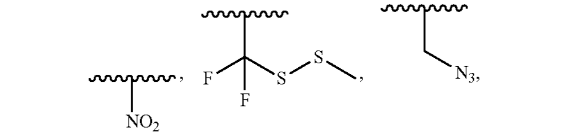
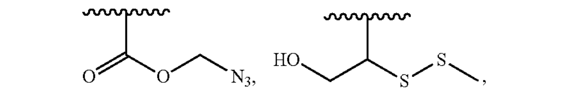
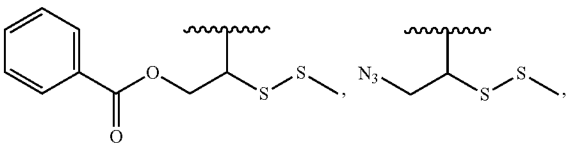
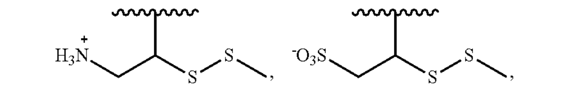
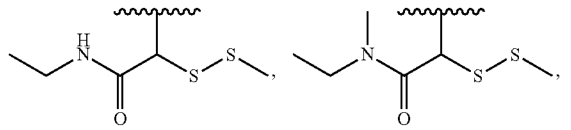
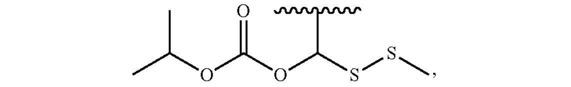

-continued
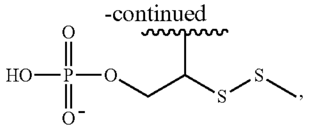,
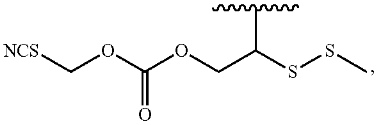,
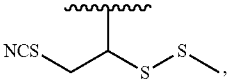, 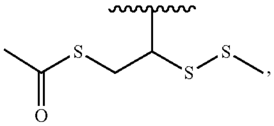,
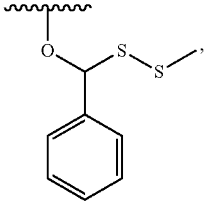,
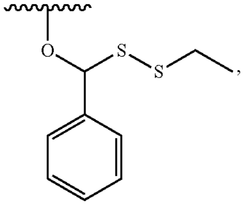, 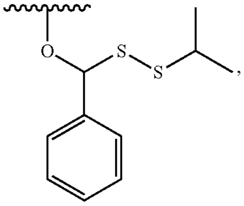,
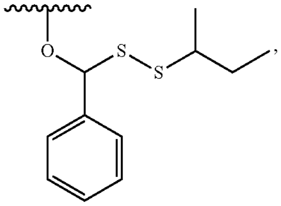, 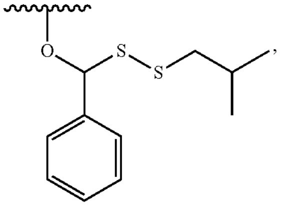,
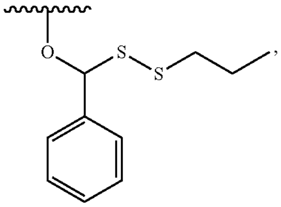, 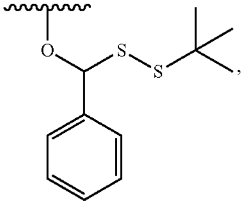,
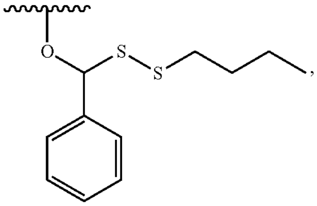,
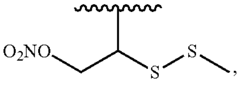, or 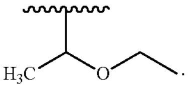.
In embodiments, $R^{3A}$ is independently:
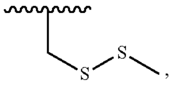, 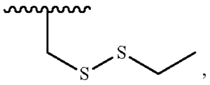,
-continued
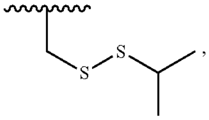, 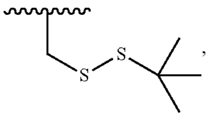,
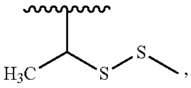, 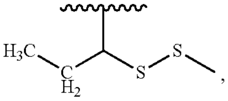,
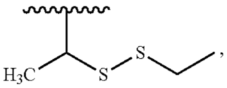, 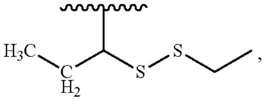,
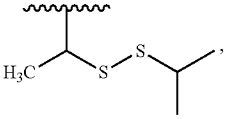, 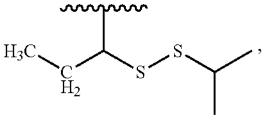,
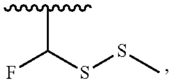, 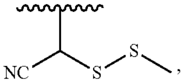, 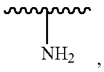,
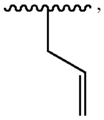, 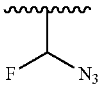, 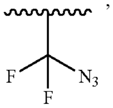, 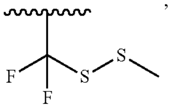,
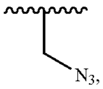 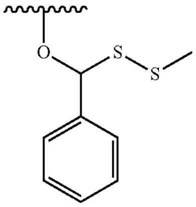,
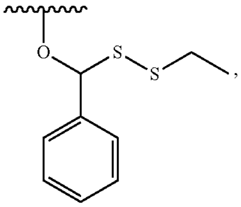, 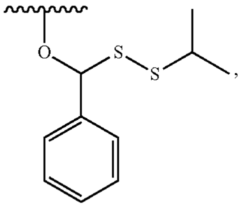,
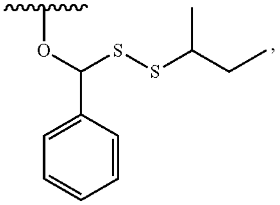,
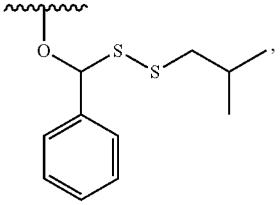,
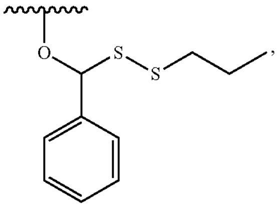, 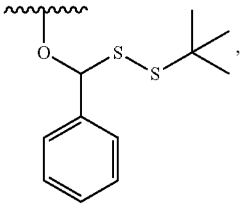, or -continued

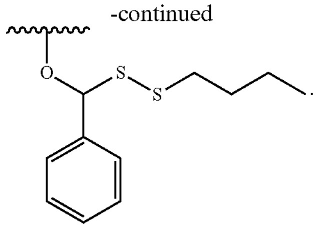

In embodiments, $R^3$ is hydrogen. In embodiments, $R^3$ is a polymerase-compatible cleavable moiety. In embodiments, $R^3$ is a polymerase-compatible cleavable moiety including an azido moiety. In embodiments, $R^3$ is a polymerase-compatible cleavable moiety including a dithiol linker. In embodiments, $R^3$ is an —O-polymerase-compatible cleavable moiety; and the polymerase-compatible cleavable moiety is —$CH_2N_3$. In embodiments, $R^3$ is an —O-polymerase-compatible cleavable moiety. In embodiments, the polymerase-compatible cleavable moiety is independently —$NH_2$, —$NO_2$, —CN, —$CH_3$, $C_2$-$C_6$ allyl (e.g., —$CH_2$—CH═$CH_2$), methoxyalkyl (e.g., —$CH_2$—O—$CH_3$), or —$CH_2N_3$. In embodiments, the polymerase-compatible cleavable moiety is independently —$NH_2$. In embodiments, the polymerase-compatible cleavable moiety is independently —CN. In embodiments, the polymerase-compatible cleavable moiety is independently —$CH_3$. In embodiments, the polymerase-compatible cleavable moiety is independently $C_2$-$C_6$ allyl (e.g., —$CH_2$—CH═$CH_2$). In embodiments, the polymerase-compatible cleavable moiety is independently methoxyalkyl (e.g., —$CH_2$—O—$CH_3$). In embodiments, the polymerase-compatible cleavable moiety is independently

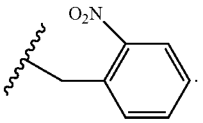 [SMILES: *Cc1ccccc1[N+](=O)[O-]]

In embodiments, the polymerase-compatible cleavable moiety is independently

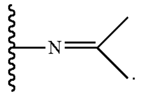 [SMILES: *N=C(C)C]

In embodiments, the polymerase-compatible cleavable moiety is independently

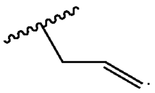 [SMILES: *CC=C]

In embodiments, the polymerase-compatible cleavable moiety is independently

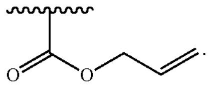

In embodiments, the polymerase-compatible cleavable moiety is independently

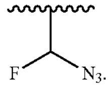

In embodiments, the polymerase-compatible cleavable moiety is independently

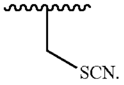

In embodiments, the polymerase-compatible cleavable moiety is independently

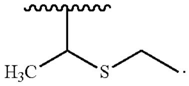

In embodiments, the polymerase-compatible cleavable moiety is independently

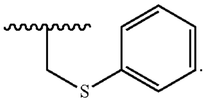 [SMILES: *CSc1ccccc1]

In embodiments, the polymerase-compatible cleavable moiety is independently

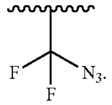

In embodiments, the polymerase-compatible cleavable moiety is independently

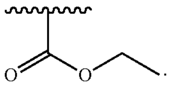 [SMILES: *C(=O)OCC]

In embodiments, the polymerase-compatible cleavable moiety is independently

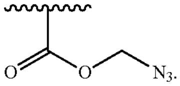

In embodiments, the polymerase-compatible cleavable moiety is independently —$CH_2$—O—$CH_3$. In embodiments, the polymerase-compatible cleavable moiety is independently —$NH_2$, —$CH_2N_3$,

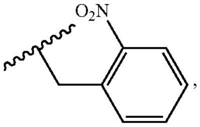, 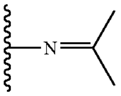, 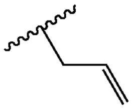, 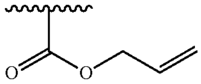, 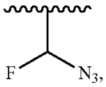 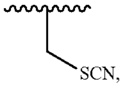 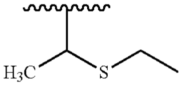 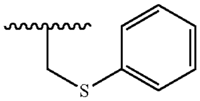, 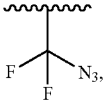 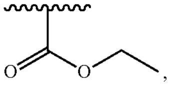, 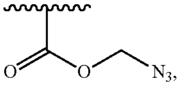

or $—CH_2—O—CH_3$.

In embodiments, the polymerase-compatible cleavable moiety is

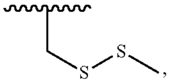 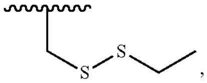, 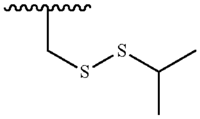, 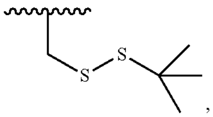, 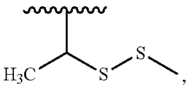, 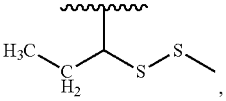, or 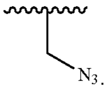

In embodiments, the polymerase-compatible cleavable moiety is

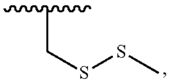 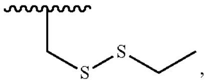, 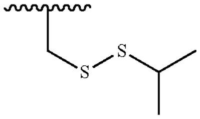, 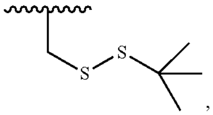, 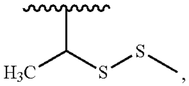, 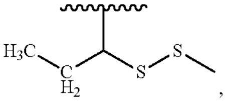, 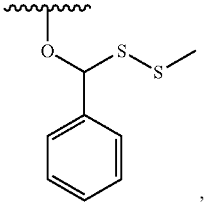, or 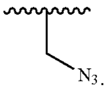

In embodiments, the polymerase-compatible cleavable moiety is

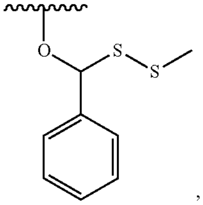, 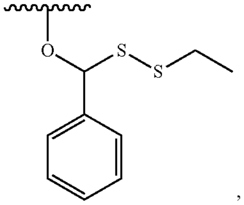, 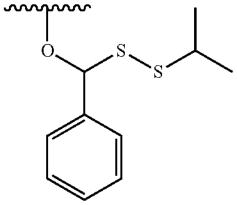, 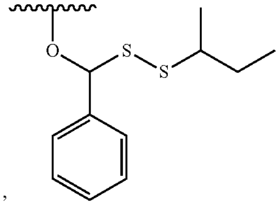, 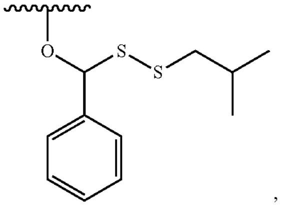, 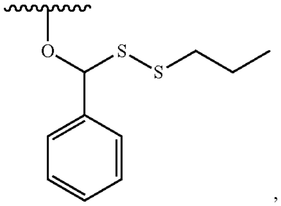, 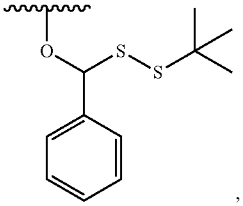, or 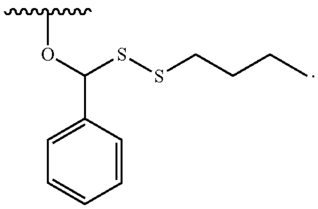.

In embodiments, $L^{100}$ is a thio-trigger containing linker. In embodiments, the thio-trigger moiety has the formula:

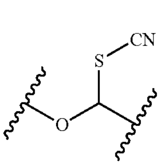 or 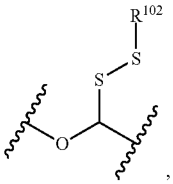, wherein $R^{102}$ is as described herein, including in embodiments. In embodiments, $L^{100}$ is an azido containing linker (e.g., an azido containing linker as described in US 2006/016008, which is incorporated herein by reference for all purposes). In embodiments, the azido containing linker has the formula:

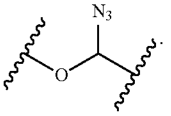 [SMILES: *OC(*)N=[N+]=[N-]]

In embodiments, $L^{100}$ includes

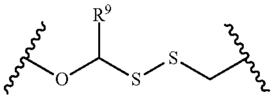
or
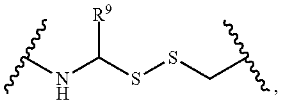
, wherein $R^9$ is independently hydrogen, halogen, —$CCl_3$, —$CBr_3$, —$CF_3$, —$Cl_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^9$ is a moiety represented by $R^7$. In embodiments, $L^{100}$ includes

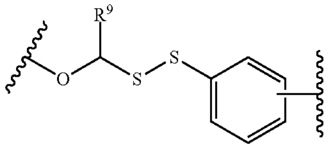
or
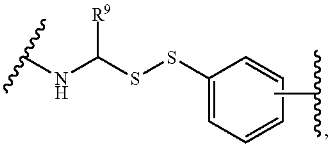
, wherein $R^9$ is as described herein. In embodiments, $L^{100}$ includes

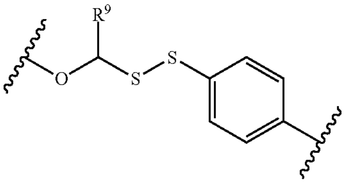
or

-continued

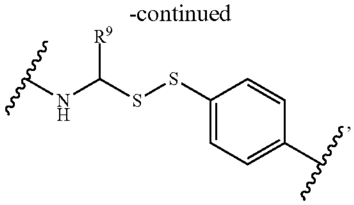
, wherein $R^9$ is as described herein.

In embodiments, $L^{100}$ includes a thio-trigger moiety. In embodiments, $L^{100}$ includes

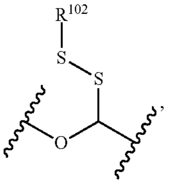
, wherein $R^{102}$ is as described herein. In embodiments, $L^{100}$ includes

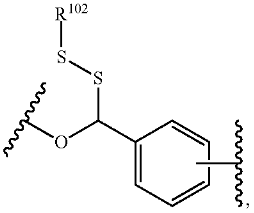
, wherein $R^{102}$ is as described herein. In embodiments, $L^{100}$ includes

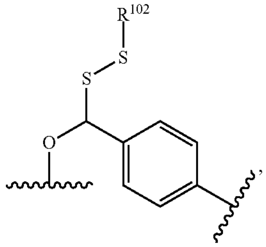
, wherein $R^{102}$ is as described herein. In embodiments, $R^{102}$ is unsubstituted $C_1$-$C_4$ alkyl. In embodiments, $R^{102}$ is unsubstituted $C_1$ alkyl. In embodiments, $R^{102}$ is unsubstituted $C_2$ alkyl. In embodiments, $R^{102}$ is unsubstituted $C_3$ alkyl. In embodiments, $R^{102}$ is unsubstituted $C_4$ alkyl. In embodiments, $L^{100}$ includes

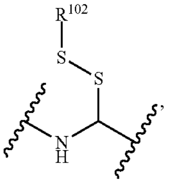
, wherein $R^{102}$ is as described herein. In embodiments, $L^{100}$ includes

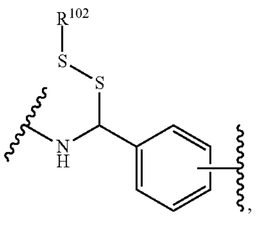

wherein $R^{102}$ is as described herein. In embodiments, $L^{100}$ includes

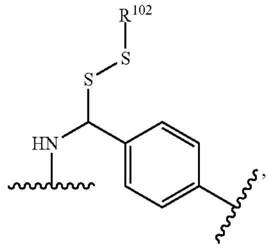

wherein $R^{102}$ is as described herein. In embodiments, $R^{102}$ is unsubstituted $C_1$-$C_4$ alkyl. In embodiments, $R^{102}$ is unsubstituted $C_1$ alkyl. In embodiments, $R^{102}$ is unsubstituted $C_2$ alkyl. In embodiments, $R^{102}$ is unsubstituted $C_3$ alkyl. In embodiments, $R^{102}$ is unsubstituted $C_4$ alkyl.

In embodiments, $L^{100}$ is a polymerase-compatible cleavable linker, having the formula $-L^{101}-L^{102}-L^{103}-L^{104}-L^{105}-$. $L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, —SS—, thio-trigger moiety, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, wherein at least one of $L^{101}$, $L^{102}$, $L^{103}$, $L^{104}$, and $L^{105}$ is not a bond. In embodiments, $L^{101}$, $L^{102}$, $L^{103}$, $L^{104}$, and $L^{105}$ independently includes PEG. In embodiments, $L^{101}$, $L^{102}$, $L^{103}$, $L^{104}$, and $L^{105}$ independently includes

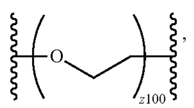

wherein z100 is independently 1 to 8. In embodiments, z100 is 1. In embodiments, z100 is 2. In embodiments, z100 is 3. In embodiments, z100 is 4. In embodiments, z100 is 5. In embodiments, z100 is 6. In embodiments, z100 is 7. In embodiments, z100 is 8. In embodiments, z100 is 2 to 8. In embodiments, z100 is 4 to 6.

In embodiments, at least one of $L^{101}$, $L^{102}$, $L^{103}$, $L^{104}$, and $L^{105}$ independently includes

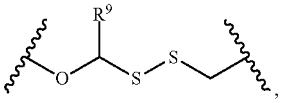

wherein $R^9$ is as described herein. In embodiments, at least one of $L^{101}$, $L^{102}$, $L^{103}$, $L^{104}$, and $L^{105}$ independently includes

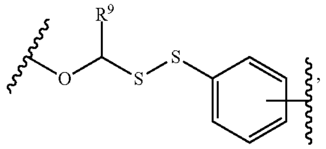

wherein $R^9$ is as described herein. In embodiments, at least one of $L^{101}$, $L^{102}$, $L^{103}$, $L^{104}$, and $L^{105}$ independently includes

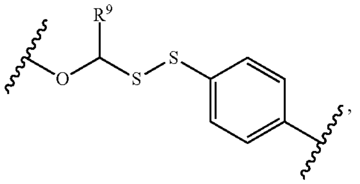

wherein $R^9$ is as described herein. In embodiments, at least one of $L^{101}$, $L^{102}$, $L^{103}$, $L^{104}$, and $L^{105}$ independently includes

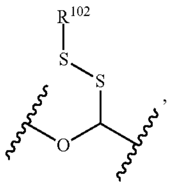

wherein $R^{102}$ is as described herein. In embodiments, at least one of $L^{101}$, $L^{102}$, $L^{103}$, $L^{104}$, and $L^{105}$ independently includes

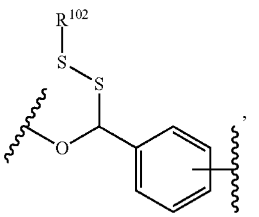

wherein $R^{102}$ is as described herein. In embodiments, at least one of $L^{101}$, $L^{102}$, $L^{103}$, $L^{104}$, and $L^{105}$ independently includes

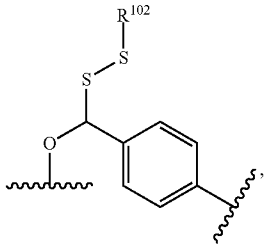

wherein $R^{102}$ is as described herein. In embodiments, at least one of $L^{101}$, $L^{102}$, $L^{103}$, $L^{104}$, and $L^{105}$ independently includes

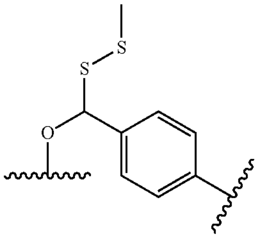

or

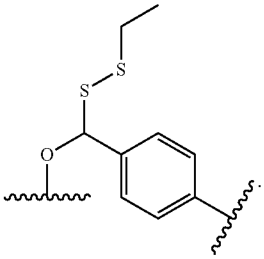

In embodiments, at least one of $L^{11}$, $L^{102}$, $L^{103}$, $L^{104}$, and $L^{105}$ independently includes

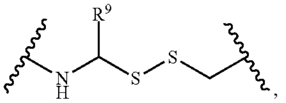

wherein $R^9$ is as described herein. In embodiments, at least one of $L^{101}$, $L^{102}$, $L^{103}$, $L^{104}$, and $L^{105}$ independently includes

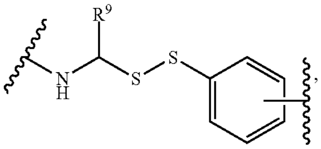

wherein $R^9$ is as described herein. In embodiments, at least one of $L^{101}$, $L^{102}$, $L^{103}$, $L^{104}$ and $L^{105}$ independently includes

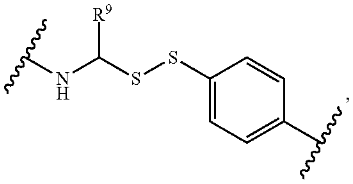

wherein $R^9$ is as described herein. In embodiments, at least one of $L^{101}$, $L^{102}$, $L^{103}$, $L^{104}$, and $L^{105}$ independently includes

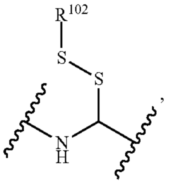

wherein $R^{102}$ is as described herein. In embodiments, at least one of $L^{101}$, $L^{102}$, $L^{103}$, $L^{104}$, and $L^{105}$ independently includes

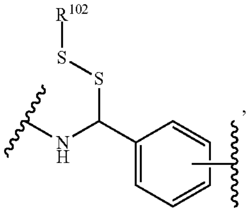

wherein $R^{102}$ is as described herein. In embodiments, at least one of $L^{101}$, $L^{102}$, $L^{103}$, $L^{104}$, and $L^{105}$ independently includes

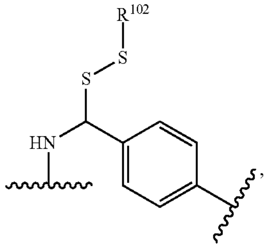

wherein $R^{102}$ is as described herein. In embodiments, at least one of $L^{101}$, $L^{102}$, $L^{103}$, $L^{104}$, and $L^{105}$ independently includes

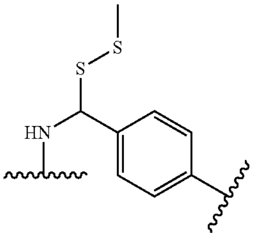

or

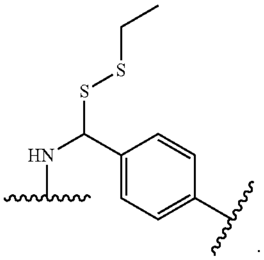

In embodiments, $L^{101}$ is a bond, —NH—, —O—, —C(O)—, —C(O)NH—, —NHC(O)—, —NHC(O)NH—, —C(O)O—, —OC(O)—, —SS—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{101}$ is a bond, —NH—, —O—, —C(O)—, —C(O)NH—, —NHC(O)—, —NHC(O)NH—, —C(O)O—, —OC(O)—, —SS—, $R^{101}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{101}$-substituted or unsubstituted heteroalkylene (e.g., 2 to 20, 8 to 20, 2 to 10, 2 to 8, 2 to 6, or 2 to 4 membered), $R^{101}$-substituted or unsubstituted cycloalkylene (e.g., $C_3$-$C_8$, $C_3$-$C_6$, or $C_5$-$C_6$), $R^{101}$-substituted or unsubstituted heterocycloalkylene (e.g., 3 to 8, 3 to 6, or 5 to 6 membered), $R^{101}$-substituted or unsubstituted arylene (e.g., $C_6$-$C_{10}$, $C_{10}$, or phenylene), or $R^{101}$-substituted or unsubstituted heteroarylene (e.g., 5 to 10, 5 to 9, or 5 to 6 membered). In embodiments, $L^{101}$ is $R^{101}$-substituted or unsubstituted $C_1$-$C_{20}$ alkylene. In embodiments, $L^{101}$ is $R^{101}$-substituted or unsubstituted 2 to 20 membered heteroalkylene. In embodiments, $L^{101}$ is $R^{101}$-substituted or unsubstituted $C_3$-$C_8$ cycloalkylene. In embodiments, $L^{101}$ is $R^{101}$-substituted or unsubstituted 3 to 8 membered heterocycloalkylene. In embodiments, $L^{101}$ is $R^{101}$-substituted or unsubstituted $C_6$-$C_{10}$ arylene. In embodiments, $L^{101}$ is $R^{101}$-substituted or unsubstituted 5 to 10 membered heteroarylene.

In embodiments, $L^{101}$ is $—(CH_2CH_2O)_b—$. In embodiments, $L^{101}$ is $—CCCH_2(OCH_2CH_2)_a—NHC(O)—(CH_2)_c(OCH_2CH_2)_b—$. In embodiments, $L^{101}$ is $—CHCHCH_2—NHC(O)—(CH_2)_c(OCH_2CH_2)_b—$. In embodiments, $L^{101}$ is $—CCCH_2—NHC(O)—(CH_2)_c(OCH_2CH_2)_b—$. In embodiments, $L^{101}$ is $—CCCH_2—$. The symbol a is an integer from 0 to 8. In embodiments, a is 1. In embodiments, a is 0. The symbol b is an integer from 0 to 8. In embodiments, b is 1 or 2. In embodiments, b is an integer from 2 to 8. In embodiments, b is 1. The symbol c is an integer from 0 to 8. In embodiments, c is 3. In embodiments, c is 1. In embodiments, c is 2. In embodiments, $L^{101}$ is independently a substituted or unsubstituted $C_1$-$C_4$ alkylene or substituted or unsubstituted 8 to 20 membered heteroalkylene.

$R^{101}$ is independently oxo, halogen, $—CCl_3$, $—CBr_3$, $—CF_3$, $—CI_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—N_3$, $R^{101A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{101A}$-substituted or unsubstituted heteroalkyl (e.g., 2 to 20, 8 to 20, 2 to 10, 2 to 8, 2 to 6, or 2 to 4 membered), $R^{101A}$-substituted or unsubstituted cycloalkyl (e.g., $C_3$-$C_8$, $C_3$-$C_6$, or $C_5$-$C_6$), $R^{101A}$-substituted or unsubstituted heterocycloalkyl (e.g., 3 to 8, 3 to 6, or 5 to 6 membered), $R^{101A}$-substituted or unsubstituted aryl (e.g., $C_6$-$C_{10}$, $C_{10}$, or phenyl), or $R^{101A}$-substituted or unsubstituted heteroaryl (e.g., 5 to 10, 5 to 9, or 5 to 6 membered). $R^{101A}$ is independently oxo, halogen, $—CCl_3$, $—CBr_3$, $—CF_3$, $—CI_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{101}$ is

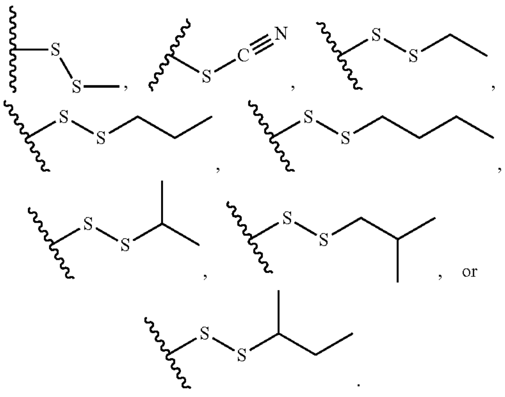

In embodiments, $R^{101}$-$R^{101A}$ is

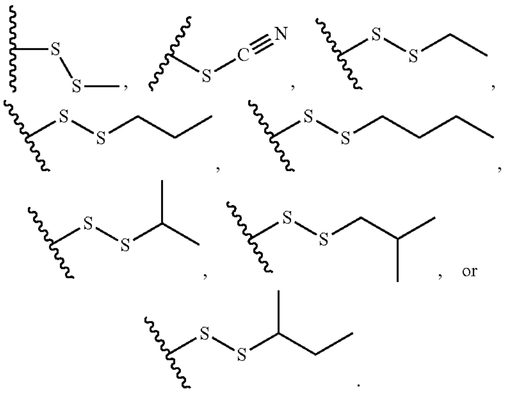

In embodiments, $L^{102}$ is a bond, —NH—, —O—, —C(O)—, —C(O)NH—, —NHC(O)—, —NHC(O)NH—, —C(O)O—, —OC(O)—, —SS—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{102}$ is a bond, —NH—, —O—, —C(O)—, —C(O)NH—, —NHC(O)—, —NHC(O)NH—, —C(O)O—, —OC(O)—, —SS—, $R^{106}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{106}$-substituted or unsubstituted heteroalkylene (e.g., 2 to 20, 8 to 20, 2 to 10, 2 to 8, 2 to 6, or 2 to 4 membered), $R^{106}$-substituted or unsubstituted cycloalkylene (e.g., $C_3$-$C_8$, $C_3$-$C_6$, or $C_5$-$C_6$), $R^{106}$-substituted or unsubstituted heterocycloalkylene (e.g., 3 to 8, 3 to 6, or 5 to 6 membered), $R^{106}$-substituted or unsubstituted arylene (e.g., $C_6$-$C_{10}$, $C_{10}$, or phenylene), or $R^{106}$-substituted or unsubstituted heteroarylene (e.g., 5 to 10, 5 to 9, or 5 to 6 membered). In embodiments, $L^{106}$ is $R^{106}$-substituted or unsubstituted $C_1$-$C_{20}$ alkylene. In embodiments, $L^{106}$ is $R^{106}$-substituted or unsubstituted 2 to 20 membered heteroalkylene. In embodiments, $L^{106}$ is $R^{106}$-substituted or unsubstituted $C_3$-$C_8$ cycloalkylene. In embodiments, $L^{106}$ is $R^{106}$-substituted or unsubstituted 3 to 8 membered heterocycloalkylene. In embodiments, $L^{106}$ is $R^{106}$-substituted or unsubstituted $C_6$-$C_{10}$ arylene. In embodiments, $L^{106}$ is $R^{106}$-substituted or unsubstituted 5 to 10 membered heteroarylene.

In embodiments, $L^{102}$ is independently a bond or substituted or unsubstituted 2 to 10 membered heteroalkylene.

$R^{106}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{106A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{106A}$-substituted or unsubstituted heteroalkyl (e.g., 2 to 20, 8 to 20, 2 to 10, 2 to 8, 2 to 6, or 2 to 4 membered), $R^{106A}$-substituted or unsubstituted cycloalkyl (e.g., $C_3$-$C_8$, $C_3$-$C_6$, or $C_5$-$C_6$), $R^{106A}$-substituted or unsubstituted heterocycloalkyl (e.g., 3 to 8, 3 to 6, or 5 to 6 membered), $R^{106A}$-substituted or unsubstituted aryl (e.g., $C_6$-$C_{10}$, $C_{10}$, or phenyl), or $R^{106A}$-substituted or unsubstituted heteroaryl (e.g., 5 to 10, 5 to 9, or 5 to 6 membered). $R^{106A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl

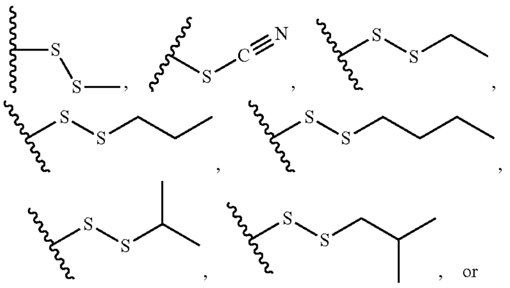

or

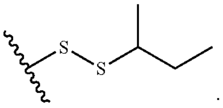

In embodiments,

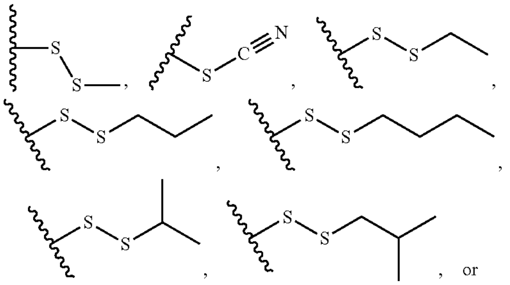

, or

-continued

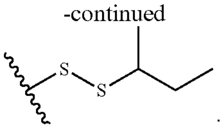

In embodiments, $L^{103}$ is a bond, —NH—, —O—, —C(O)—, —C(O)NH—, —NHC(O)—, —NHC(O)NH—, —C(O)O—, —OC(O)—, —SS—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{103}$ is a bond, —NH—, —O—, —C(O)—, —C(O)NH—, —NHC(O)—, —NHC(O)NH—, —C(O)O—, —OC(O)—, —SS—, $R^{103}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{103}$-substituted or unsubstituted heteroalkylene (e.g., 2 to 20, 8 to 20, 2 to 10, 2 to 8, 2 to 6, or 2 to 4 membered), $R^{103}$-substituted or unsubstituted cycloalkylene (e.g., $C_3$-$C_8$, $C_3$-$C_6$, or $C_5$-$C_6$), $R^{103}$-substituted or unsubstituted heterocycloalkylene (e.g., 3 to 8, 3 to 6, or 5 to 6 membered), $R^{103}$-substituted or unsubstituted arylene (e.g., $C_6$-$C_{10}$, $C_{10}$, or phenylene), or $R^{103}$-substituted or unsubstituted heteroarylene (e.g., 5 to 10, 5 to 9, or 5 to 6 membered). In embodiments, $L^{103}$ is $R^{103}$-substituted or unsubstituted $C_1$-$C_{20}$ alkylene. In embodiments, $L^{103}$ is $R^{103}$-substituted or unsubstituted 2 to 20 membered heteroalkylene. In embodiments, $L^{103}$ is $R^{103}$-substituted or unsubstituted $C_3$-$C_8$ cycloalkylene. In embodiments, $L^{103}$ is $R^{103}$-substituted or unsubstituted 3 to 8 membered heterocycloalkylene. In embodiments, $L^{103}$ is $R^{103}$-substituted or unsubstituted $C_6$-$C_{10}$ arylene. In embodiments, $L^{103}$ is $R^{103}$-substituted or unsubstituted 5 to 10 membered heteroarylene.

In embodiments, $L^{103}$ is —$(CH_2CH_2O)_d$—. In embodiments, $L^{103}$ is —$(CH_2O)_d$—. In embodiments, $L^{103}$ is —$(CH_2)_d$—. In embodiments, $L^{103}$ is —$(CH_2)_d$—NH—. In embodiments, $L^{103}$ is -(unsubstituted phenylene)-. In embodiments, $L^{103}$ is

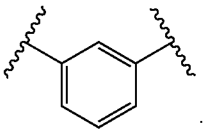 [SMILES: *c1cccc(*)c1]

In embodiments, $L^{103}$ is -(unsubstituted phenylene)-C(O)NH—. In embodiments, $L^{103}$ is

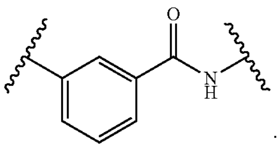 [SMILES: *NC(=O)c1cccc(*)c1]

In embodiments, $L^{103}$ is -(unsubstituted phenylene)-NHC(O)—. In embodiments, $L^{103}$ is

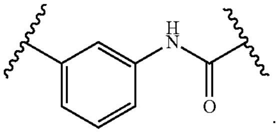 [SMILES: *C(=O)Nc1cccc(*)c1]
.

The symbol d is an integer from 0 to 8. In embodiments, d is 3. In embodiments, d is 2. In embodiments, d is 1. In embodiments, d is 0.

In embodiments, $L^{103}$ is independently a bond or substituted or unsubstituted 2 to 10 membered heteroalkylene.

$R^{103}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{103A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{103A}$-substituted or unsubstituted heteroalkyl (e.g., 2 to 20, 8 to 20, 2 to 10, 2 to 8, 2 to 6, or 2 to 4 membered), $R^{103A}$-substituted or unsubstituted cycloalkyl (e.g., $C_3$-$C_8$, $C_3$-$C_6$, or $C_5$-$C_6$), $R^{103A}$ substituted or unsubstituted heterocycloalkyl (e.g., 3 to 8, 3 to 6, or 5 to 6 membered), $R^{103A}$-substituted or unsubstituted aryl (e.g., $C_6$-$C_{10}$, $C_{10}$, or phenyl), or $R^{103A}$-substituted or unsubstituted heteroaryl (e.g., 5 to 10, 5 to 9, or 5 to 6 membered).

$R^{103A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{103}$ is

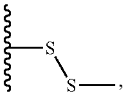
,
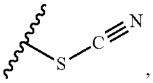
,
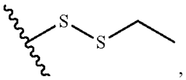
,
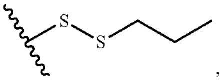
,
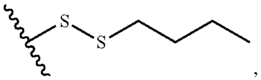
,
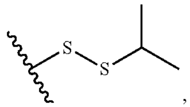
,
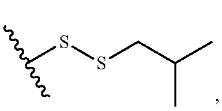
, or
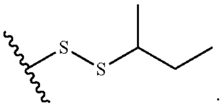
.

In embodiments, $R^{103}$-$R^{103A}$ is

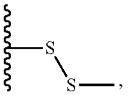
,
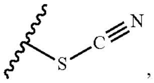
,
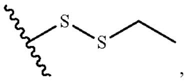
,
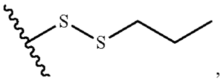
,
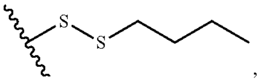
,
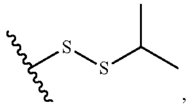
,
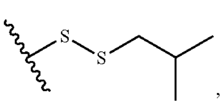
, or
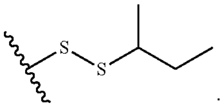
.

In embodiments, $L^{104}$ is a bond, —NH—, —O—, —C(O)—, —C(O)NH—, —NHC(O)—, —NHC(O)NH—, —C(O)O—, —OC(O)—, —SS—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{104}$ is a bond, —NH—, —O—, —C(O)—, —C(O)NH—, —NHC(O)—, —NHC(O)NH—, —C(O)O—, —OC(O)—, —SS—, $R^{104}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{104}$-substituted or unsubstituted heteroalkylene (e.g., 2 to 20, 8 to 20, 2 to 10, 2 to 8, 2 to 6, or 2 to 4 membered), $R^{104}$-substituted or unsubstituted cycloalkylene (e.g., $C_3$-$C_8$, $C_3$-$C_6$, or $C_5$-$C_6$), $R^{104}$-substituted or unsubstituted heterocycloalkylene (e.g., 3 to 8, 3 to 6, or 5 to 6 membered), $R^{104}$-substituted or unsubstituted arylene (e.g., $C_6$-$C_{10}$, $C_{10}$, or phenylene), or $R^{104}$-substituted or unsubstituted heteroarylene (e.g., 5 to 10, 5 to 9, or 5 to 6 membered). In embodiments, $L^{104}$ is $R^{104}$-substituted or unsubstituted $C_1$-$C_{20}$ alkylene. In embodiments, $L^{104}$ is $R^{104}$-substituted or unsubstituted 2 to 20 membered heteroalkylene. In embodiments, $L^{104}$ is $R^{104}$-substituted or unsubstituted $C_3$-$C_8$ cycloalkylene. In embodiments, $L^{104}$ is $R^{104}$-substituted or unsubstituted 3 to 8 membered heterocycloalkylene. In embodiments, $L^{104}$ is $R^{104}$-substituted or unsubstituted $C_6$-$C_{10}$ arylene. In embodiments, $L^{104}$ is $R^{104}$-substituted or unsubstituted 5 to 10 membered heteroarylene.

In embodiments, $L^{104}$ is —$(CH_2CH_2O)_e$—. In embodiments, $L^{104}$ is —$(CH_2O)_e$—. In embodiments, $L^{104}$ is —$(CH_2)_e$—. In embodiments, $L^{104}$ is —$(CH_2)_e$—NH—. In embodiments, $L^{104}$ is -(unsubstituted phenylene)-. In embodiments, $L^{104}$ is

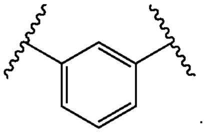 [SMILES: *c1cccc(*)c1]
.

In embodiments, $L^{104}$ is -(unsubstituted phenylene)-C(O)NH—. In embodiments, $L^{104}$ is

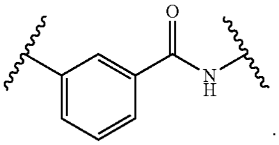 [SMILES: *NC(=O)c1cccc(*)c1]

.

In embodiments, $L^{104}$ is -(unsubstituted phenylene)-NHC(O)—. In embodiments, $L^{104}$ is

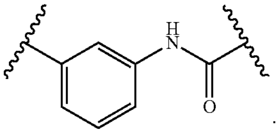 [SMILES: *C(=O)Nc1cccc(*)c1]

.

The symbol e is an integer from 0 to 8. In embodiments, e is 3. In embodiments, e is 1. In embodiments, e is 2. In embodiments, $L^{104}$ is unsubstituted phenylene. In embodiments, $L^{104}$ is independently a bond, substituted or unsubstituted 4 to 18 membered heteroalkylene, or substituted or unsubstituted phenylene.

$R^{104}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{104A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{104A}$-substituted or unsubstituted heteroalkyl (e.g., 2 to 20, 8 to 20, 2 to 10, 2 to 8, 2 to 6, or 2 to 4 membered), $R^{104A}$-substituted or unsubstituted cycloalkyl (e.g., $C_3$-$C_8$, $C_3$-$C_6$, or $C_5$-$C_6$), $R^{104A}$-substituted or unsubstituted heterocycloalkyl (e.g., 3 to 8, 3 to 6, or 5 to 6 membered), $R^{104A}$-substituted or unsubstituted aryl (e.g., $C_6$-$C_{10}$, $C_{10}$, or phenyl), or $R^{104A}$-substituted or unsubstituted heteroaryl (e.g., 5 to 10, 5 to 9, or 5 to 6 membered). $R^{104A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{104}$ is

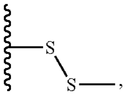
,
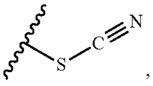
,
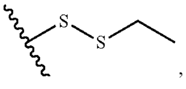
,
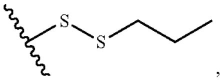
,
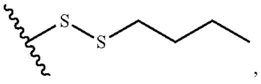
,

-continued

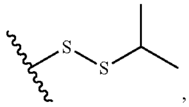
,
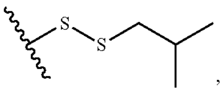
, or
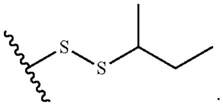
.

In embodiments, $R^{104}$-$R^{104A}$ is

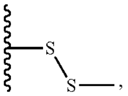
,
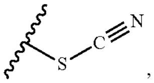
,
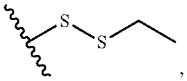
,
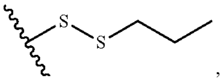
,
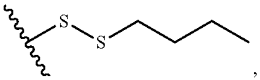
,
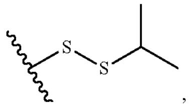
,
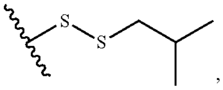
, or
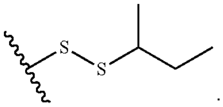
.

In embodiments, $L^{105}$ is a bond, —NH—, —O—, —C(O)—, —C(O)NH—, —NHC(O)—, —NHC(O)NH—, —C(O)O—, —OC(O)—, —SS—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{105}$ is a bond, —NH—, —O—, —C(O)—, —C(O)NH—, —NHC(O)—, —NHC(O)NH—, —C(O)O—, —OC(O)—, —SS—, $R^{105}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{105}$-substituted or unsubstituted heteroalkylene (e.g., 2 to 20, 8 to 20, 2 to 10, 2 to 8, 2 to 6, or 2 to 4 membered), $R^{105}$-substituted or unsubstituted cycloalkylene (e.g., $C_3$-$C_8$, $C_3$-$C_6$, or $C_5$-$C_6$), $R^{105}$-substituted or unsubstituted heterocycloalkylene (e.g., 3 to 8, 3 to 6, or 5 to 6 membered), $R^{105}$-substituted or unsubstituted arylene (e.g., $C_6$-$C_{10}$, $C_{10}$, or phenylene), or $R^{105}$-substituted or unsubstituted heteroarylene (e.g., 5 to 10, 5 to 9, or 5 to 6 membered). In embodiments, $L^{105}$ is $R^{105}$-substituted or unsubstituted $C_1$-$C_{20}$ alkylene. In embodiments, $L^{105}$ is $R^{105}$-substituted or unsubstituted 2 to 20 membered heteroalkylene. In embodiments, $L^{105}$ is $R^{105}$-substituted or unsubstituted $C_3$-$C_8$ cycloalkylene. In embodiments, $L^{105}$ is $R^{105}$-substituted or unsubstituted 3 to 8 membered heterocycloalkylene. In embodiments, $L^{105}$ is $R^{105}$-substituted or unsubstituted $C_6$-$C_{10}$ arylene. In embodiments, $L^{105}$ is $R^{105}$-substituted or unsubstituted 5 to 10 membered heteroarylene.

In embodiments, $L^{105}$ is —$(CH_2CH_2O)_f$—. In embodiments, $L^{105}$ is —$(CH_2O)_f$—. In embodiments, $L^{105}$ is —$(CH_2)_f$—. In embodiments, $L^{105}$ is —$(CH_2)_f$—NH—. In embodiments, $L^{105}$ is —C(O)NH$(CH_2)_f$—NH—. In embodiments, $L^{105}$ is —$(CH_2CH_2O)_f$—, —$(CH_2)_g$—NH—. In embodiments, $L^{105}$ is —$(CH_2)_g$—. In embodiments, $L^{105}$ is —$(CH_2)_g$—NH—. In embodiments, $L^{105}$ is —NHC(O)—$(CH_2)_f$—NH—. In embodiments, $L^{105}$ is —NHC(O)—$(CH_2)_f$—NH—. In embodiments, $L^{105}$ is —NHC(O)—$(CH_2CH_2O)_f$—$(CH_2)_g$—NH—. In embodiments, $L^{105}$ is —NHC(O)—$(CH_2)_g$—. In embodiments, $L^{105}$ is —NHC(O)—$(CH_2)_g$—NH—. In embodiments, $L^{105}$ is —C(O)NH$(CH_2)_f$—NH—. In embodiments, $L^{105}$ is —C(O)NH—$(CH_2CH_2O)_f$—, —$(CH_2)_g$—NH—. In embodiments, $L^{105}$ is —C(O)NH—$(CH_2)_g$—. In embodiments, $L^{105}$ is —C(O)NH—$(CH_2)_g$—NH—. The symbol f is an integer from 0 to 8. In embodiments, f is 3. In embodiments, f is 1. In embodiments, f is 2. In embodiments, f is 0. The symbol g is an integer from 0 to 8. In embodiments, g is 3. In embodiments, g is 1. In embodiments, g is 2. In embodiments, g is 0.

In embodiments, $L^{105}$ is independently bond or substituted or unsubstituted 4 to 18 membered heteroalkylene.

$R^{105}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{105A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{105A}$-substituted or unsubstituted heteroalkyl (e.g., 2 to 20, 8 to 20, 2 to 10, 2 to 8, 2 to 6, or 2 to 4 membered), $R^{105A}$-substituted or unsubstituted cycloalkyl (e.g., $C_3$-$C_8$, $C_3$-$C_6$, or $C_5$-$C_6$), $R^{105A}$-substituted or unsubstituted heterocycloalkyl (e.g., 3 to 8, 3 to 6, or 5 to 6 membered), $R^{105A}$-substituted or unsubstituted aryl (e.g., $C_6$-$C_{10}$, $C_{10}$, or phenyl), or $R^{105A}$-substituted or unsubstituted heteroaryl (e.g., 5 to 10, 5 to 9, or 5 to 6 membered). $R^{105A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{105}$ is

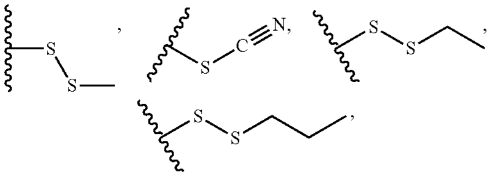

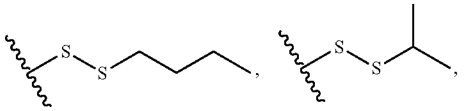

-continued

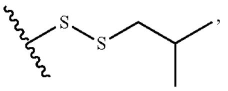

or

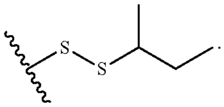

In embodiments, $R^{105}$-$R^{105A}$ is

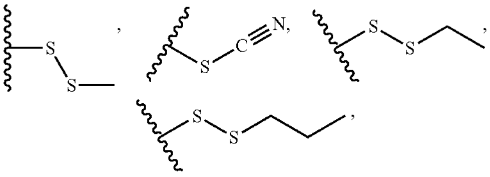

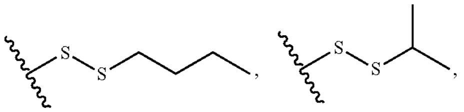

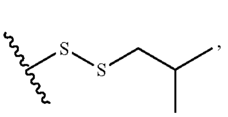

or

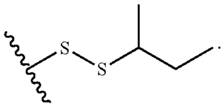

In embodiments, $L^{101}$ is independently a substituted or unsubstituted $C_1$-$C_4$ alkylene or substituted or unsubstituted 8 to 20 membered heteroalkylene; In embodiments, $L^{102}$ is independently a substituted or unsubstituted $C_1$-$C_4$ alkylene or substituted or unsubstituted 8 to 20 membered heteroalkylene; $L^{103}$ is independently a bond or substituted or unsubstituted 2 to 10 membered heteroalkylene; $L^{104}$ is independently a bond, substituted or unsubstituted 4 to 18 membered heteroalkylene, or substituted or unsubstituted phenylene; $L^{105}$ is independently bond or substituted or unsubstituted 4 to 18 membered heteroalkylene.

In embodiments, $L^{101}$, $L^{102}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$ is

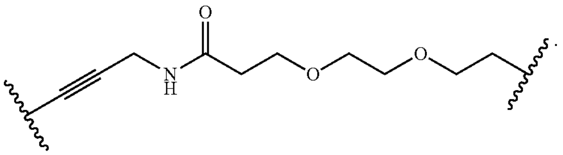 [SMILES: *C#CCNC(=O)CCOCCOCC*]

In embodiments, $L^{101}$ is

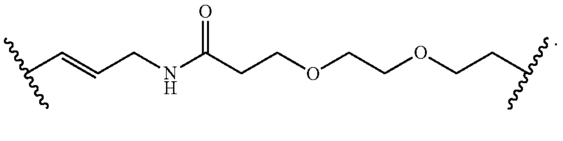 [SMILES: */C=C/CNC(=O)CCOCCOCC*]

In embodiments $L^{101}$ is $—CCCH_2—$. In embodiments, $L^{101}$ is
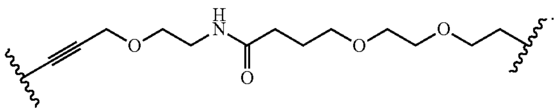 [SMILES: *C#CCOCCNC(=O)CCCOCCOCC*]
In embodiments, $L^{101}$ is
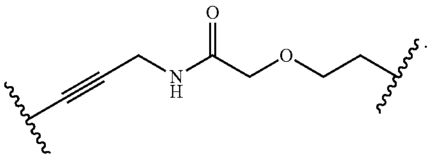 [SMILES: *C#CCNC(=O)COCC*]
In embodiments, $L^{101}$ is
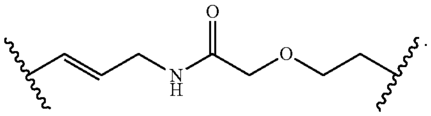 [SMILES: */C=C/CNC(=O)COCC*]
In embodiments, $L^{102}$ is
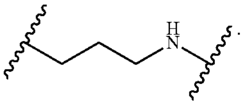 [SMILES: *CCCN*]
In embodiments, $L^{102}$ is
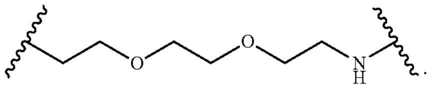 [SMILES: *CCOCCOCCN*]
In embodiments, $L^{102}$ is
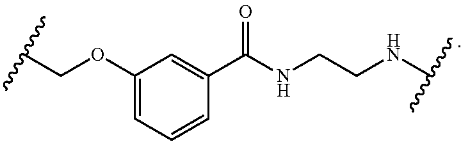 [SMILES: *COc1cccc(C(=O)NCCN*)c1]
In embodiments, $L^{102}$ is
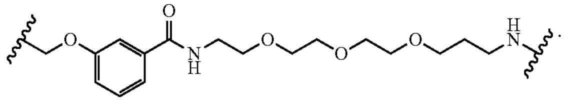 [SMILES: *COc1cccc(C(=O)NCCOCCOCCOCCCN*)c1]
In embodiments, $L^{102}$ is
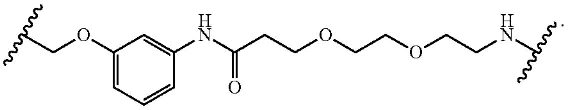 [SMILES: *COc1cccc(NC(=O)CCOCCOCCN*)c1]
In embodiments, $L^{102}$ is a bond. In embodiments, $L^{103}$ is
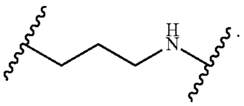 [SMILES: *CCCN*]
In embodiments, $L^{103}$ is
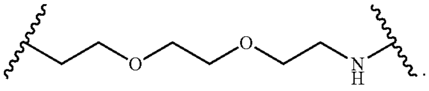 [SMILES: *CCOCCOCCN*]
In embodiments, $L^{103}$ is
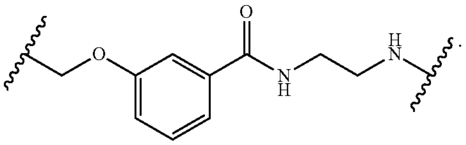 [SMILES: *COc1cccc(C(=O)NCCN*)c1]
In embodiments, $L^{103}$ is
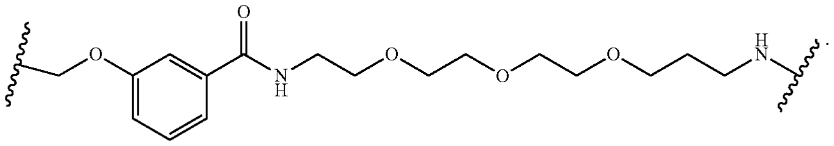 [SMILES: *COc1cccc(C(=O)NCCOCCOCCOCCCN*)c1]

In embodiments, $L^{103}$ is
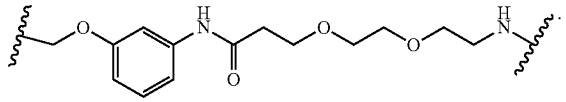 [SMILES: *COc1cccc(NC(=O)CCOCCOCCN*)c1]
In embodiments, $L^{103}$ is a bond. In embodiments, $L^{104}$ is
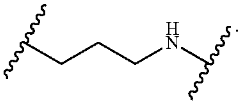 [SMILES: *CCCN*]
In embodiments, $L^{104}$ is
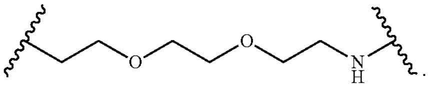 [SMILES: *CCOCCOCCN*]
In embodiments, $L^{104}$ is
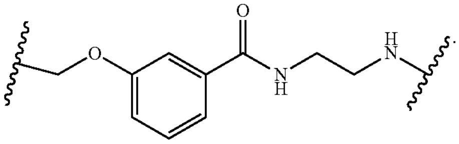 [SMILES: *COc1cccc(C(=O)NCCN*)c1]
In embodiments, $L^{104}$ is
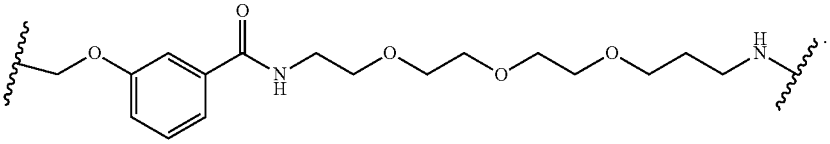 [SMILES: *COc1cccc(C(=O)NCCOCCOCCOCCCN*)c1]
In embodiments, $L^{104}$ is
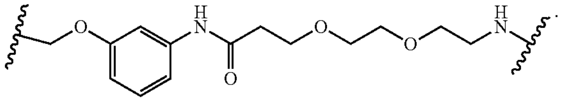 [SMILES: *COc1cccc(NC(=O)CCOCCOCCN*)c1]
In embodiments, $L^{104}$ is a bond. In embodiments, $L^{105}$ is
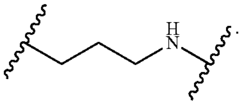 [SMILES: *CCCN*]

In embodiments, $L^{105}$ is
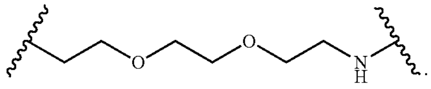 [SMILES: *CCOCCOCCN*]
In embodiments, $L^{105}$ is
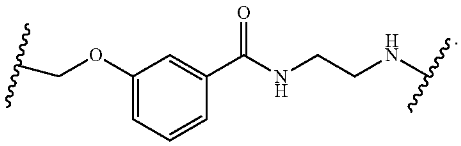 [SMILES: *COc1cccc(C(=O)NCCN*)c1]
In embodiments, $L^{105}$ is
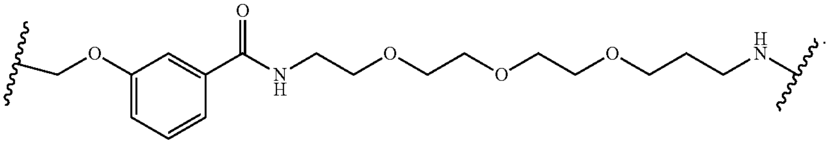 [SMILES: *COc1cccc(C(=O)NCCOCCOCCOCCCN*)c1]
In embodiments, $L^{105}$ is
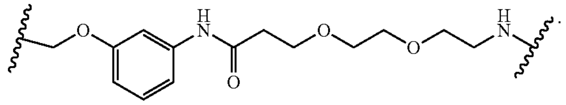 [SMILES: *COc1cccc(NC(=O)CCOCCOCCN*)c1]
In embodiments, $L^{105}$ is a bond. In embodiments, $L^{103}$-$L^{104}$-$L^{105}$- is
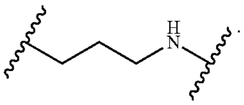
In embodiments, $L^{103}$-$L^{104}$-$L^{105}$- is
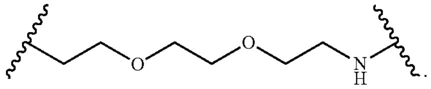 [SMILES: *CCOCCOCCN*]
In embodiments, $L^{103}$-$L^{104}$-$L^{105}$- is
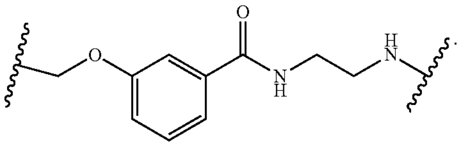 [SMILES: *COc1cccc(C(=O)NCCN*)c1]
In embodiments, $L^{103}$-$L^{104}$-$L^{105}$- is
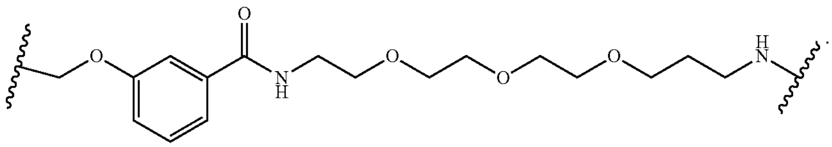 [SMILES: *COc1cccc(C(=O)NCCOCCOCCOCCCN*)c1]

In embodiments, $L^{103}$-$L^{104}$-$L^{105}$- is

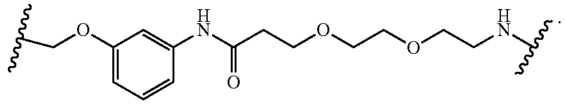 [SMILES: *COc1cccc(NC(=O)CCOCCOCCN*)c1]

In embodiments, $L^{100}$ is -$L^{101}$-O—CH(—$SR^{100}$)-$L^{103}$-$L^{104}$-$L^{105}$-, -$L^{101}$-O—C($CH_3$)(—$SR^{100}$)-$L^{103}$-$L^{104}$-$L^{105}$-, -$L^{101}$-O—CH($N_3$)-$L^{103}$-$L^{104}$-$L^{105}$-, or -$L^{101}$-SS-$L^{103}$-$L^{104}$-$L^{105}$-, wherein $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^{100}$ is —$SO_3H$, —$SR^{102}$, or —CN. In embodiments, $R^{100}$ is —$SR^{102}$ or —CN. In embodiments, $R^{102}$ is unsubstituted $C_1$-$C_4$ alkyl. In embodiments, $R^{100}$ is —$SR^{102}$. In embodiments, $R^{100}$ is —CN. In embodiments, $R^{100}$ is

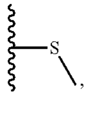, 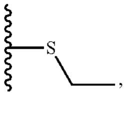, 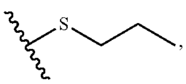, 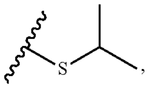, 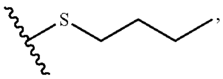, 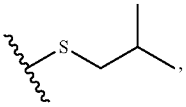, or 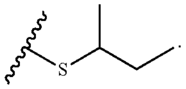.

In embodiments, $R^{100}$ is

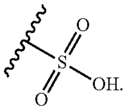 [SMILES: *S(=O)(=O)O]

In embodiments, $L^{100}$ is -$L^{101}$-O—CH(—$SR^{100}$)-$L^{103}$-$L^{104}$-$L^{105}$-, -$L^{101}$-O—C($CH_3$)(—$SR^{100}$)-$L^{103}$-$L^{104}$-$L^{105}$-, -$L^{101}$-O—CH($N_3$)-$L^{103}$-$L^{104}$-$L^{105}$-, or -$L^{101}$-SS-$L^{103}$-$L^{104}$-$L^{105}$-, wherein $L^{101}$ is independently a substituted or unsubstituted $C_1$-$C_4$ alkylene or substituted or unsubstituted 8 to 20 membered heteroalkylene, $L^{103}$ is independently a bond or substituted or unsubstituted 2 to 10 membered heteroalkylene; $L^{104}$ is independently a bond, substituted or unsubstituted 4 to 18 membered heteroalkylene, or substituted or unsubstituted phenylene, $L^{105}$ is independently bond or substituted or unsubstituted 4 to 18 membered heteroalkylene, and $R^{100}$ is as described herein. In embodiments, $R^{100}$ is —$SO_3H$.

In embodiments, $L^{100}$ is -$L^{101}$-O—CH(—$SR^{100}$)-$L^{103}$-$L^{104}$-$L^{105}$-, -$L^{101}$-O—C($CH_3$)(—$SR^{100}$)-$L^{103}$-$L^{104}$-$L^{105}$-, or -$L^{101}$-O—CH($N_3$)—$CH_2$—O-$L^{104}$-$L^{105}$-, wherein $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, $L^{104}$ is unsubstituted phenylene, and $R^{100}$ is as described herein. In embodiments, $R^{100}$ is —$SO_3H$.

In embodiments, $L^{100}$ is

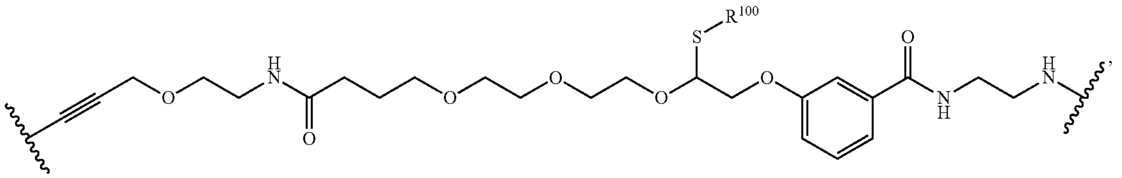,

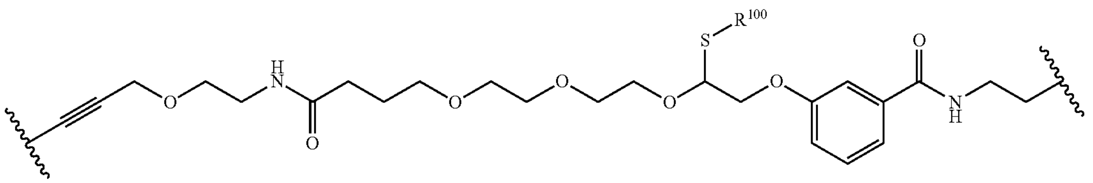

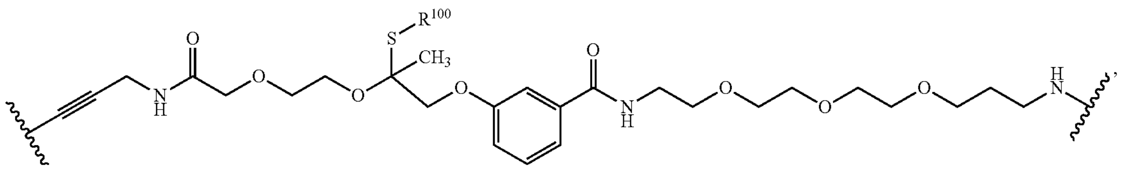,

-continued
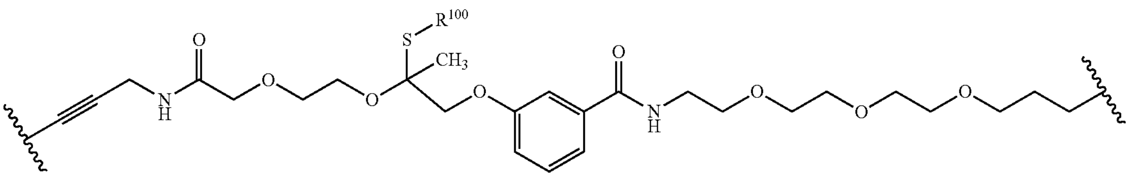
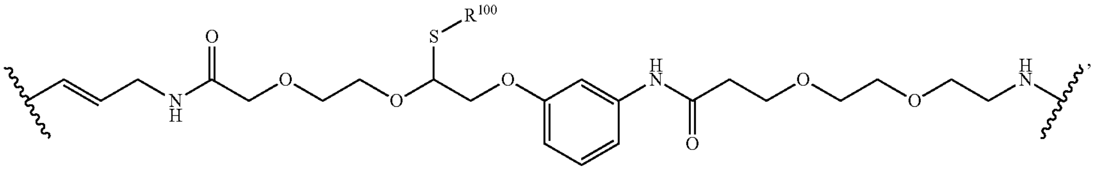
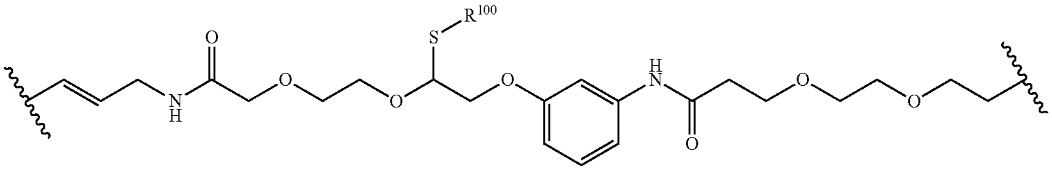
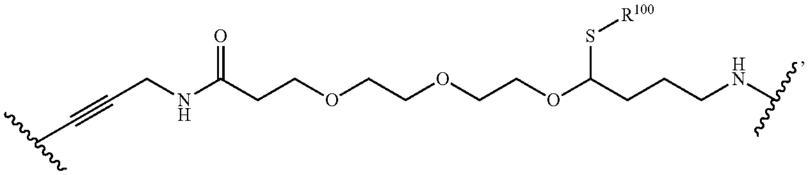
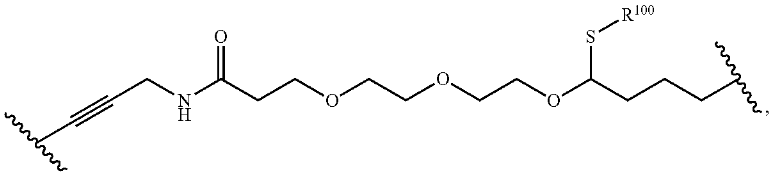
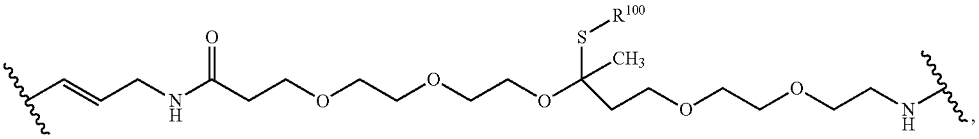
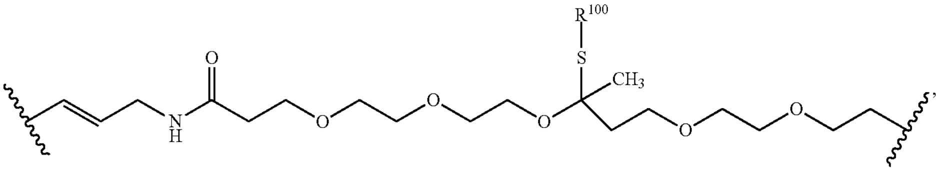
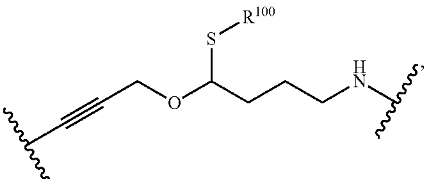
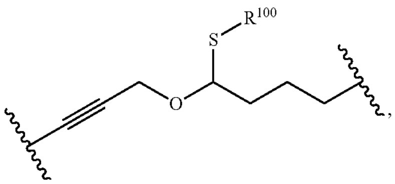
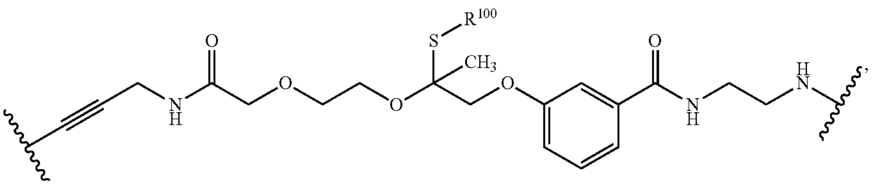

-continued

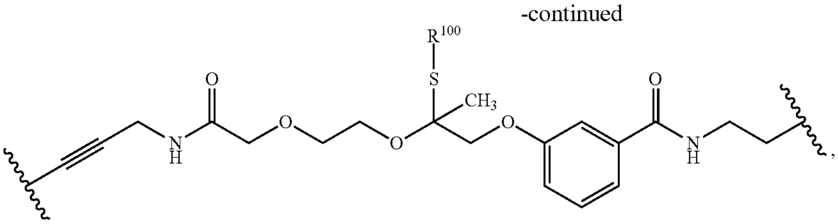

,

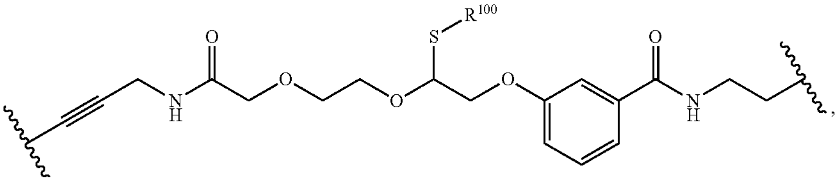

, or

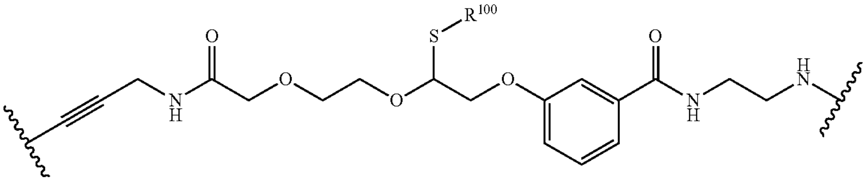

, wherein $R^{100}$ is

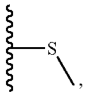
,
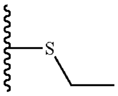
,
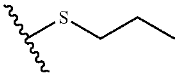
,
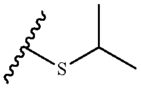
,
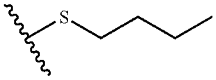
,
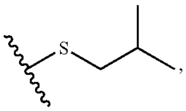
,
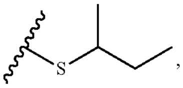
, or —CN. In embodiments, $L^{100}$ is

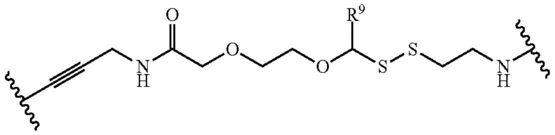

, wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^9$ is substituted or unsubstituted alkyl. In embodiments, $R^9$ is substituted or unsubstituted aryl, or substituted or unsubstituted heteroaryl. In embodiments, $L^{100}$

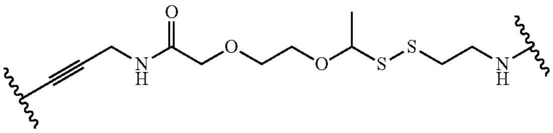

,

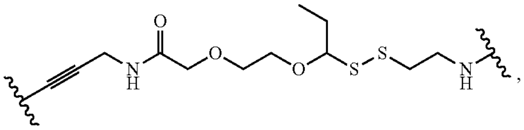

, or

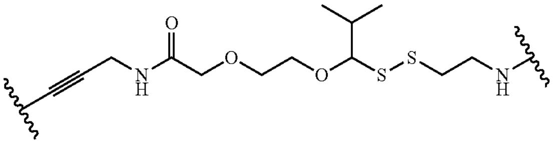

.

In embodiments, $L^{100}$ is

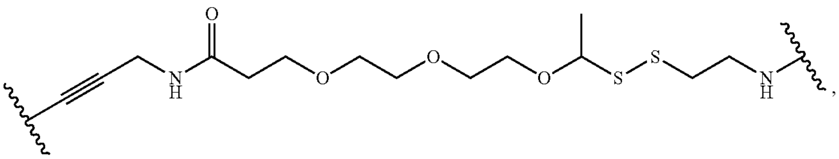

,

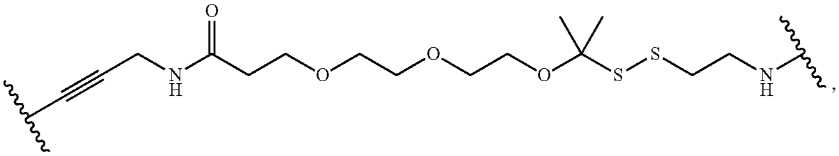

, or

-continued
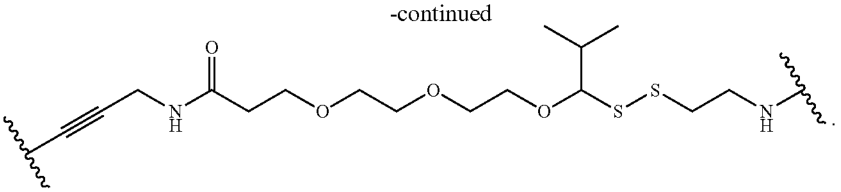
In embodiments, $L^{100}$ is
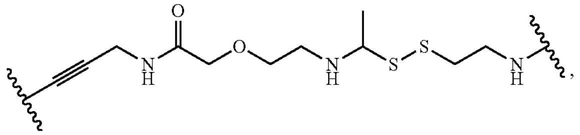
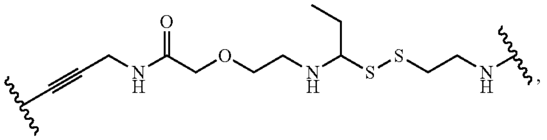
, or
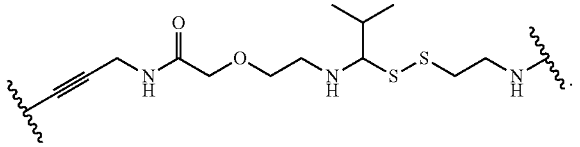
In embodiments, $L^{100}$ is
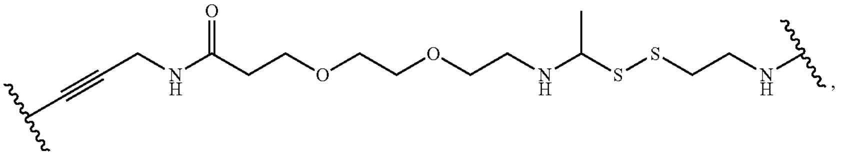
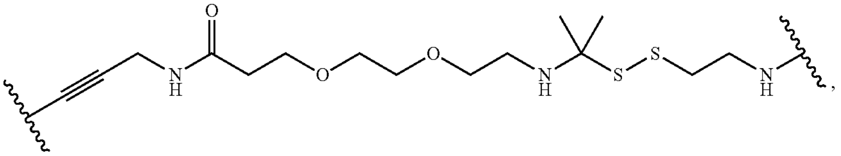
, or
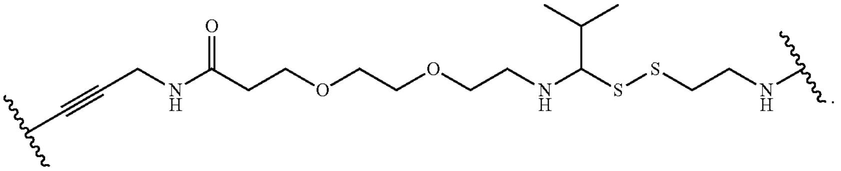

In embodiments, $L^{100}$ is

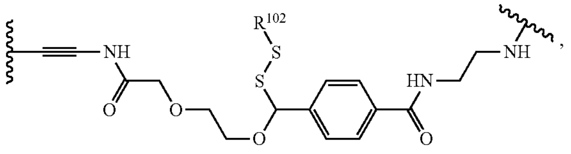

wherein $R^{102}$ is as described herein. In embodiments, $L^{100}$ is

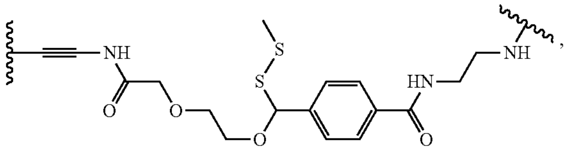

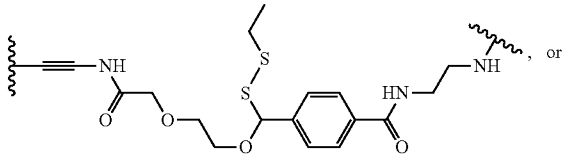

or

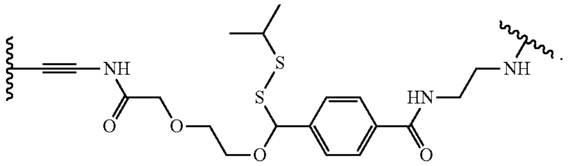

In embodiments, $L^{100}$ is

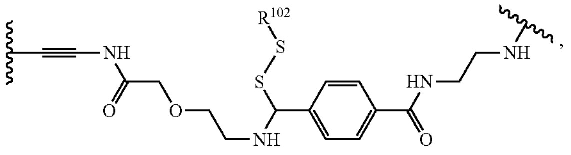

wherein $R^{102}$ is as described herein. In embodiments, $L^{100}$ is

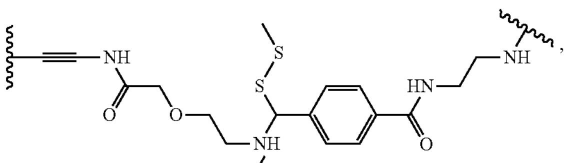

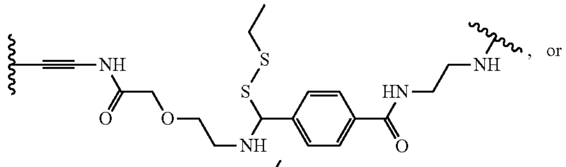

or

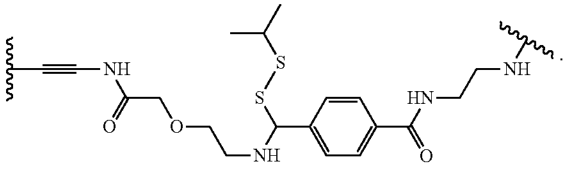

In embodiments, $L^{100}$ is

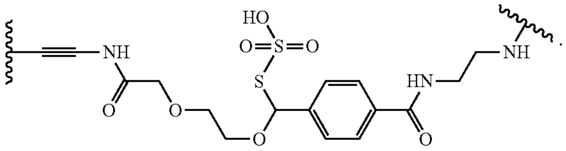 [SMILES: *C#CNC(=O)COCCOC(SS(=O)(=O)O)c1ccc(C(=O)NCCN*)cc1]

In embodiments, $L^{100}$ is

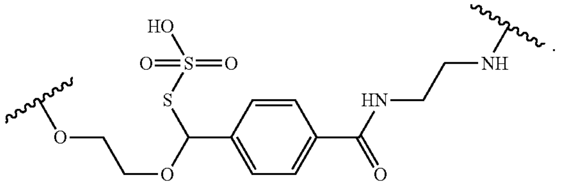 [SMILES: *NCCNC(=O)c1ccc(C(OCCO*)SS(=O)(=O)O)cc1]

Methods for cleaving the disulfide bond of —S—$SO_3H$ bonds are known in the art, see for example Meguro et al. Tetrahedron Letters 61 (2020) 152198, which is incorporated herein by reference in its entirety. In embodiments, the cleaving agent is aqueous sodium sulfide ($Na_2S$). In embodiments, the cleaving agent is TCEP or THPP.

In embodiments, -$L^{101}$-$L^{102}$-$L^{103}$-$L^{104}$-$L^{105}$- has the formula:

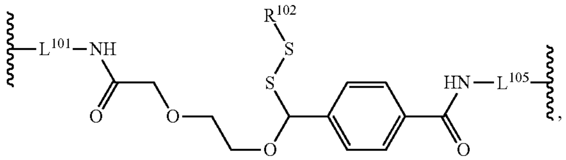

wherein $L^{101}$, $R^{102}$, and $L^{105}$ are as described herein. In embodiments, $R^{102}$ is unsubstituted $C_1$-$C_6$ alkyl. In embodiments, $R^{102}$ is unsubstituted aryl. In embodiments, $R^{102}$ is unsubstituted heteroaryl. In embodiments, -$L^{101}$-$L^{102}$-$L^{103}$-$L^{104}$-$L^{105}$- has the formula:

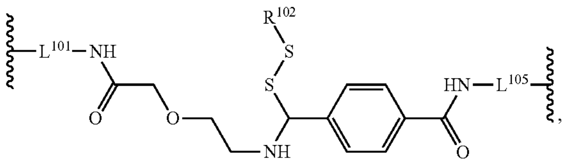

wherein $L^{101}$, $R^{102}$, and $L^{105}$ are as described herein. In embodiments, $R^{102}$ is unsubstituted $C_1$-$C_6$ alkyl. In embodiments, $R^{102}$ is unsubstituted aryl. In embodiments, $R^{102}$ is unsubstituted heteroaryl.

In embodiments, $L^{100}$ is

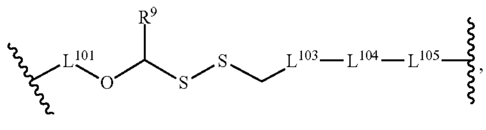

wherein $L^{101}$, $L^{103}$, $L^{104}$, $L^{105}$, and $R^9$ are as described herein. In embodiments, $L^{100}$ is

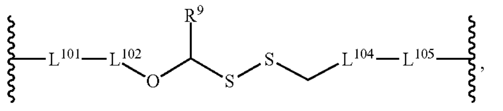

wherein $L^{101}$, $L^{102}$, $L^{104}$, $L^{105}$, and $R^9$ are as described herein. In embodiments, $L^{100}$ is

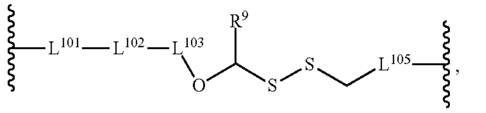

wherein $L^{101}$, $L^{102}$, $L^{103}$, $L^{105}$, and $R^9$ are as described herein. In embodiments, $L^{100}$ is

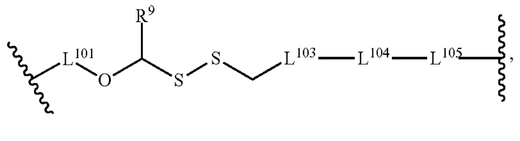

wherein $L^{101}$, $L^{103}$, $L^{104}$, $L^{105}$, and $R^9$ are as described herein. In embodiments, $L^{100}$ is

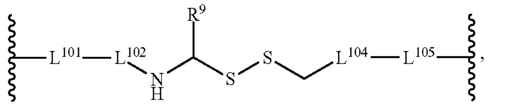

wherein $L^{101}$, $L^{102}$, $L^{104}$, $L^{105}$, and $R^9$ are as described herein. In embodiments, $L^{100}$ is

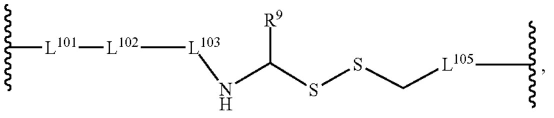

wherein $L^{101}$, $L^{102}$, $L^{103}$, $L^{105}$, and $R^9$ are as described herein.

In embodiments, $L^{102}$ is

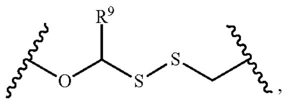

wherein $R^9$ is as described herein. In embodiments, $L^{103}$ is

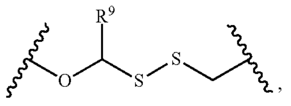

wherein $R^9$ is as described herein. In embodiments, $L^{104}$ is

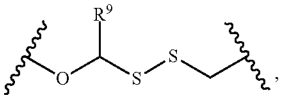

wherein $R^9$ is as described herein. In embodiments, $L^{102}$ is

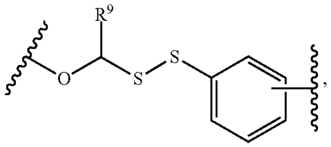

wherein $R^9$ is as described herein. In embodiments, $L^{103}$ is

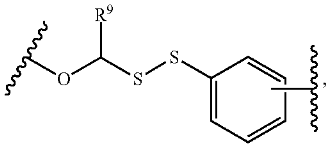

wherein $R^9$ is as described herein. In embodiments, $L^{104}$ is

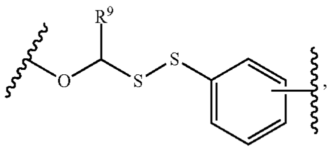

wherein $R^9$ is as described herein. In embodiments, $L^{102}$ is

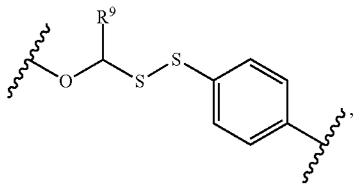

wherein $R^9$ is as described herein. In embodiments, $L^{103}$ is

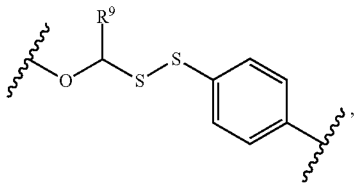

wherein $R^9$ is as described herein. In embodiments, $L^{104}$ is

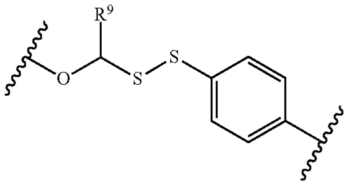, wherein $R^9$ is as described herein.

In embodiments, $L^{102}$ is

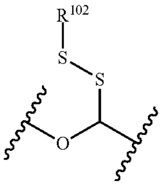, wherein $R^{102}$ is as described herein. In embodiments, $L^{103}$ is

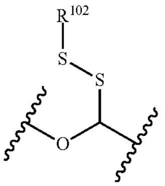, wherein $R^{102}$ is as described herein. In embodiments, $L^{104}$ is

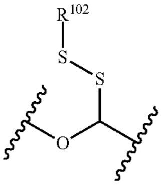, wherein $R^{102}$ is as described herein. In embodiments, $L^{102}$ is

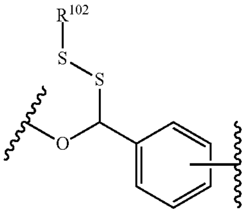, wherein $R^{102}$ is as described herein. In embodiments, $L^{103}$ is

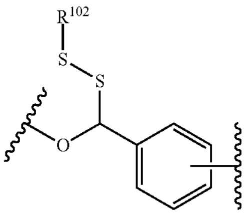, wherein $R^{102}$ is as described herein. In embodiments, $L^{104}$ is

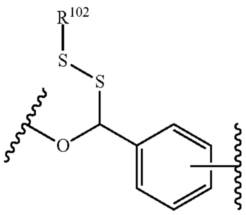, wherein $R^{102}$ is as described herein. In embodiments, $L^{102}$ is

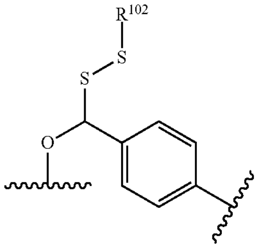, wherein $R^{102}$ is as described herein. In embodiments, $L^{103}$ is

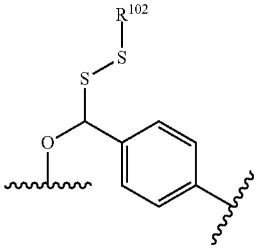, wherein $R^{102}$ is as described herein. In embodiments, $L^{104}$ is

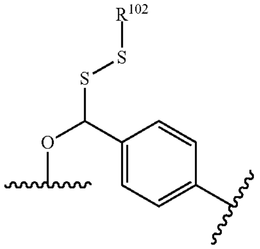, wherein $R^{102}$ is as described herein.

In embodiments, $R^9$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), or substituted or unsubstituted heteroaryl (e.g., 5 to 10, 5 to 9, or 5 to 6 membered).

In embodiments, $R^9$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{10}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{10}$-substituted or unsubstituted heteroalkyl (e.g., 2 to 20, 8 to 20, 2 to 10, 2 to 8, 2 to 6, or 2 to 4 membered), $R^{10}$-substituted or unsubstituted cycloalkyl (e.g., $C_3$-$C_8$, $C_3$-$C_6$, or $C_5$-$C_6$), $R^{10}$-substituted or unsubstituted heterocycloalkyl (e.g., 3 to 8, 3 to 6, or 5 to 6 membered), $R^{10}$-substituted or unsubstituted aryl (e.g., $C_6$-$C_{10}$, $C_{10}$, or phenyl), or $R^{10}$-substituted or unsubstituted heteroaryl (e.g., 5 to 10, 5 to 9, or 5 to 6 membered). In embodiments, $R^9$ is $R^{10}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{10}$-substituted or unsubstituted heteroalkyl (e.g., 2 to 20, 8 to 20, 2 to 10, 2 to 8, 2 to 6, or 2 to 4 membered), $R^{10}$-substituted or unsubstituted cycloalkyl (e.g., $C_3$-$C_8$, $C_3$-$C_6$, or $C_5$-$C_6$), $R^{10}$-substituted or unsubstituted heterocycloalkyl (e.g., 3 to 8, 3 to 6, or 5 to 6 membered), $R^{10}$-substituted or unsubstituted aryl (e.g., $C_6$-$C_{10}$, $C_{10}$, or phenyl), or $R^{10}$-substituted or unsubstituted heteroaryl (e.g., 5 to 10, 5 to 9, or 5 to 6 membered). In embodiments, $R^9$ is unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^9$ is independently unsubstituted alkyl (e.g., $C_1$-$C_{20}$, $C_{10}$-$C_{20}$, $C_1$-$C_5$, $C_1$-$C_6$, or $C_1$-$C_4$). In embodiments, $R^9$ is independently unsubstituted $C_1$-$C_6$ alkyl. In embodiments, $R^9$ is independently unsubstituted $C_1$-$C_4$ alkyl. In embodiments, $R^9$ is independently unsubstituted methyl. In embodiments, $R^9$ is independently unsubstituted ethyl. In embodiments, $R^9$ is independently unsubstituted propyl. In embodiments, $R^9$ is independently unsubstituted tert-butyl.

In embodiments, $R^9$ is independently unsubstituted $C_3$-$C_8$ cycloalkyl. In embodiments, $R^9$ is independently unsubstituted $C_3$-$C_6$ cycloalkyl. In embodiments, $R^9$ is independently unsubstituted $C_5$-$C_6$ cycloalkyl. In embodiments, $R^9$ is independently unsubstituted 3 to 8 membered heterocycloalkyl. In embodiments, $R^9$ is independently unsubstituted 3 to 6 membered heterocycloalkyl. In embodiments, $R^9$ is independently unsubstituted 5 to 6 membered heterocycloalkyl. In embodiments, $R^9$ is independently unsubstituted phenyl. In embodiments, $R^9$ is independently unsubstituted 5 to 6 membered heteroaryl. In embodiments, $R^9$ is independently unsubstituted 5 membered heteroaryl. In embodiments, $R^9$ is independently unsubstituted 6 membered heteroaryl.

$R^{10}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{100}$ is

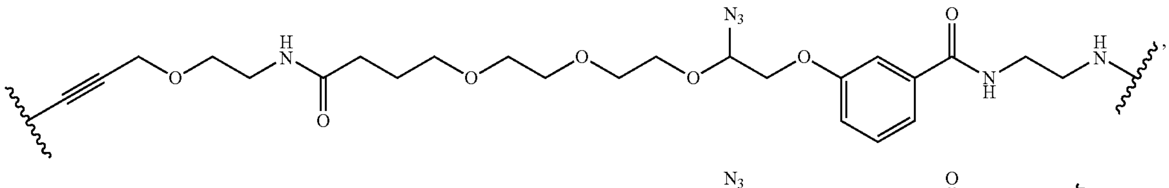

,

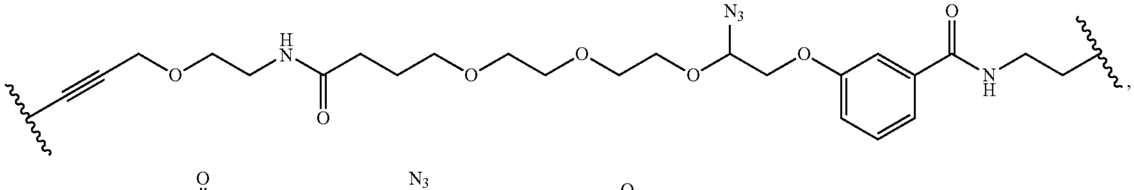

,

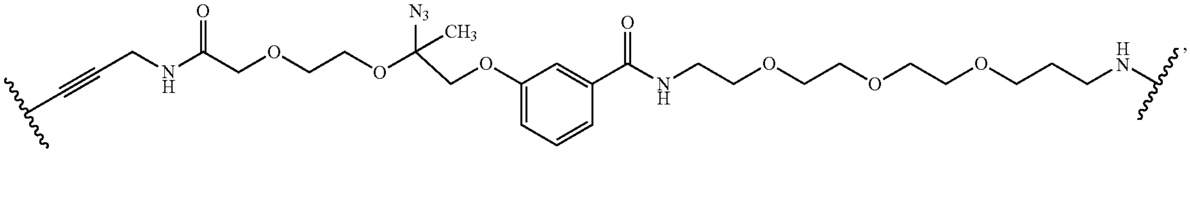

,

-continued
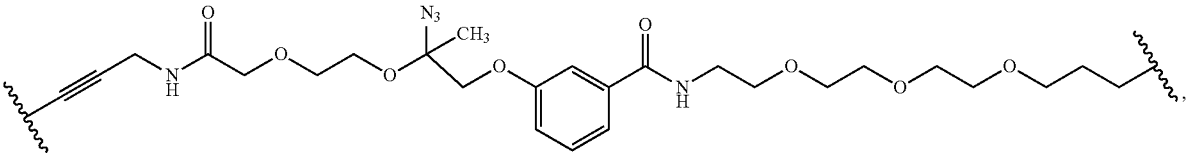,
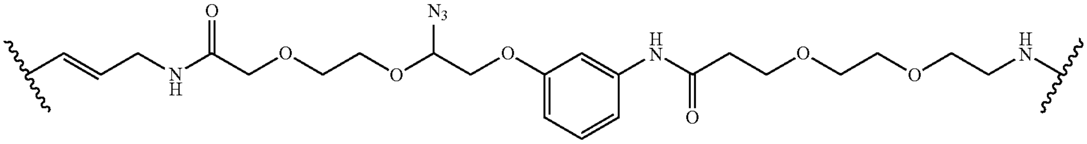,
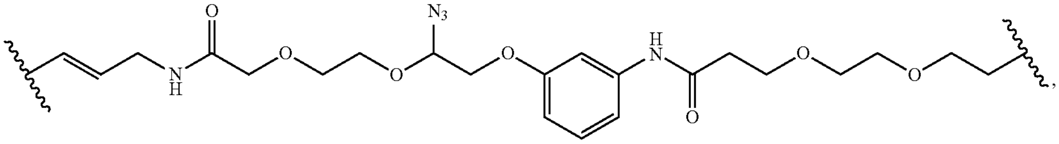,
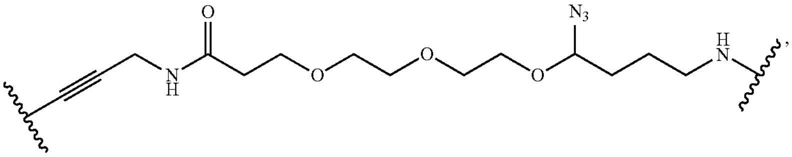,
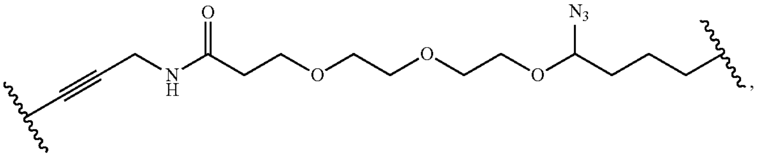,
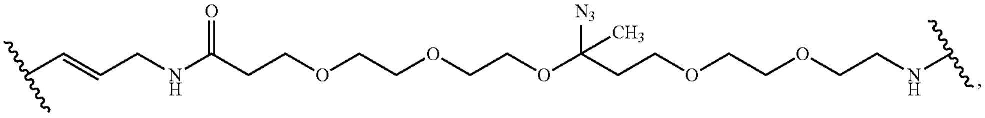,
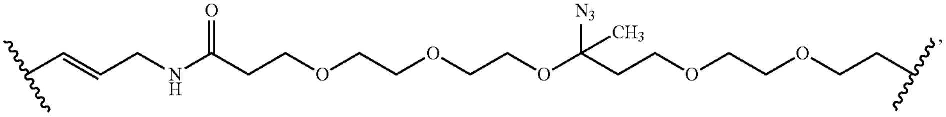,
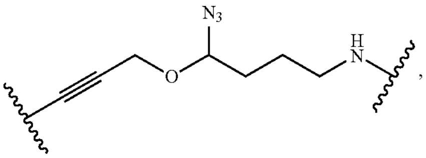, 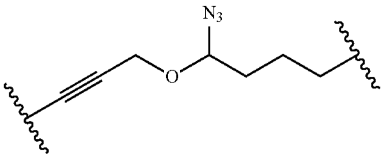,
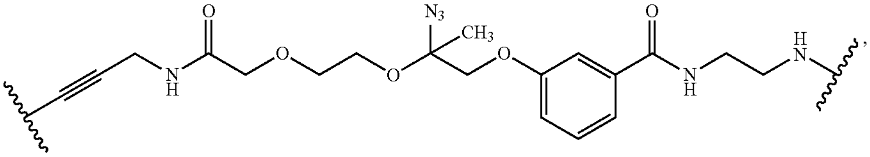,
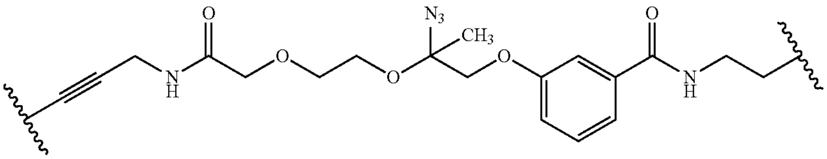,
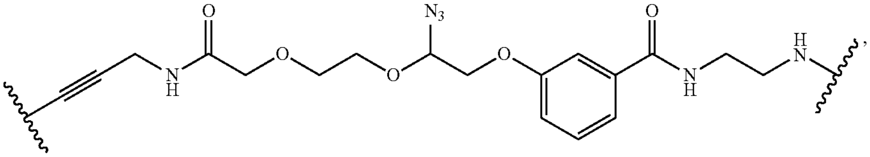, -continued
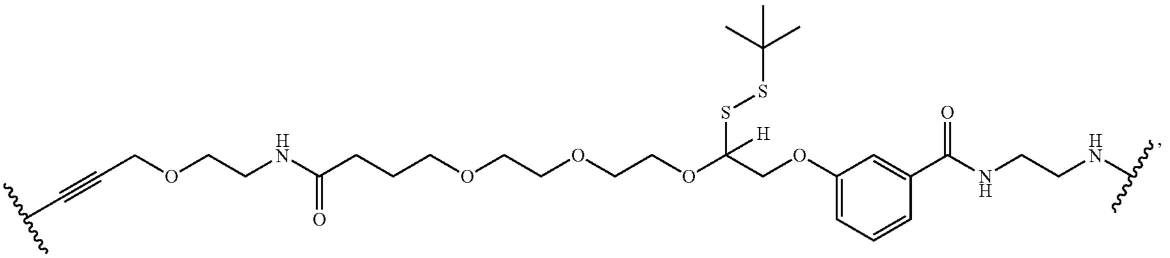
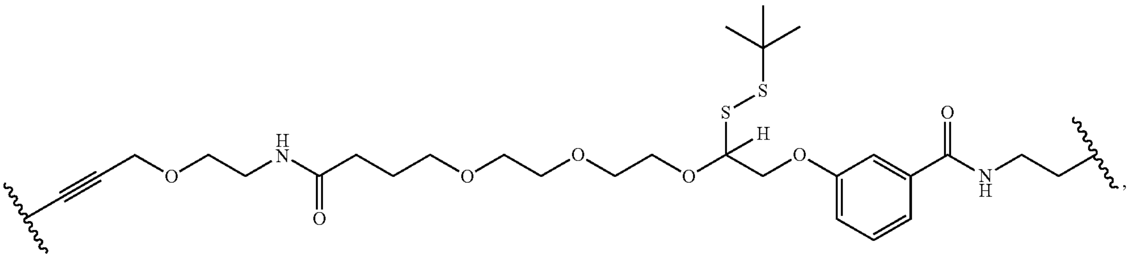
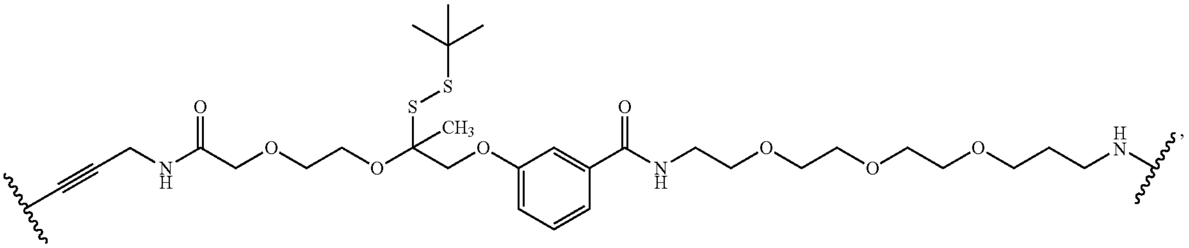
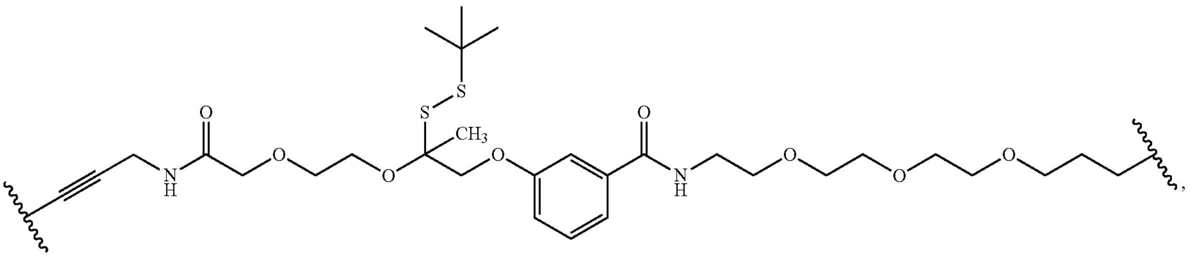
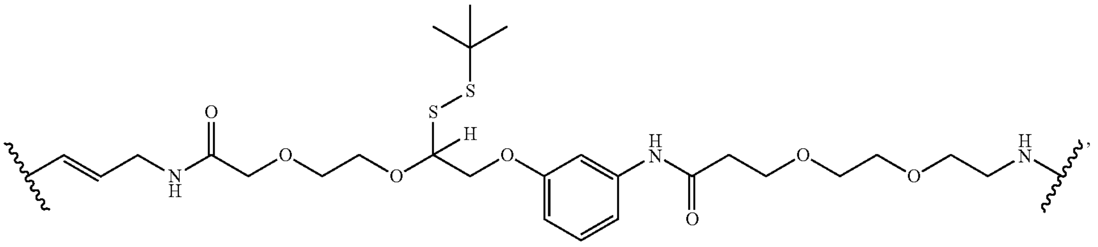
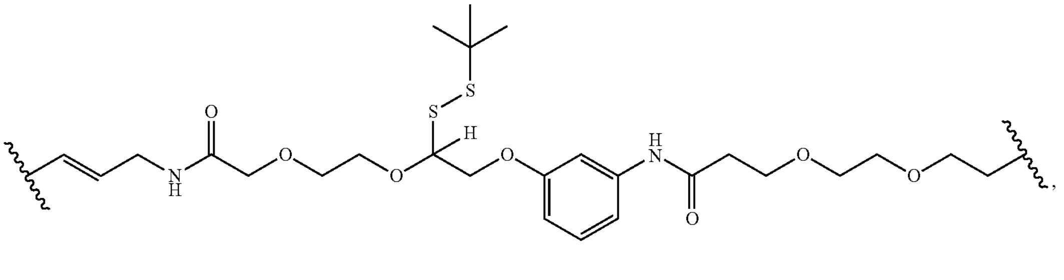

-continued
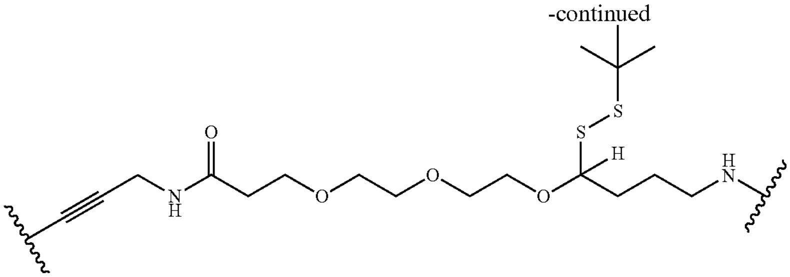,
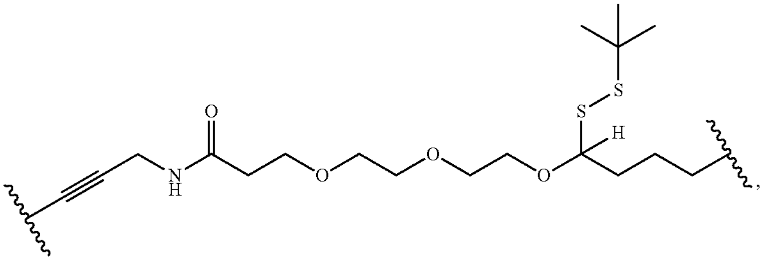,
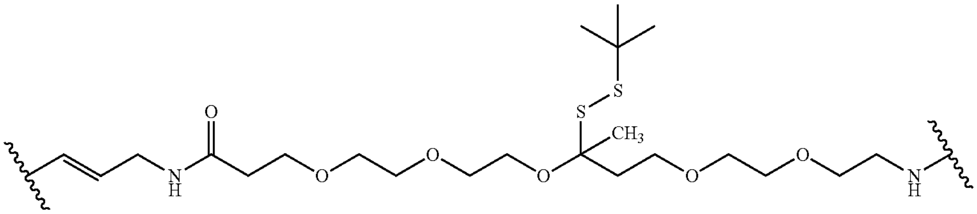,
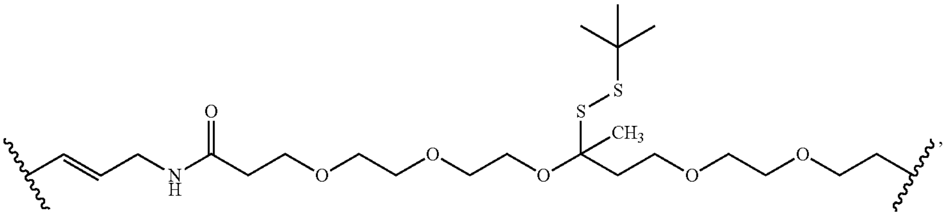,
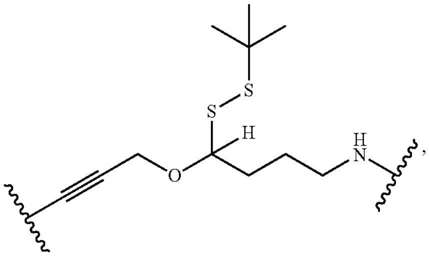, 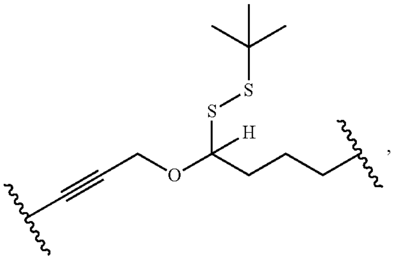,
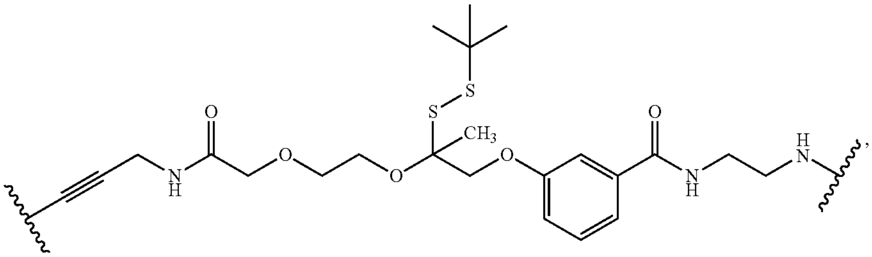,
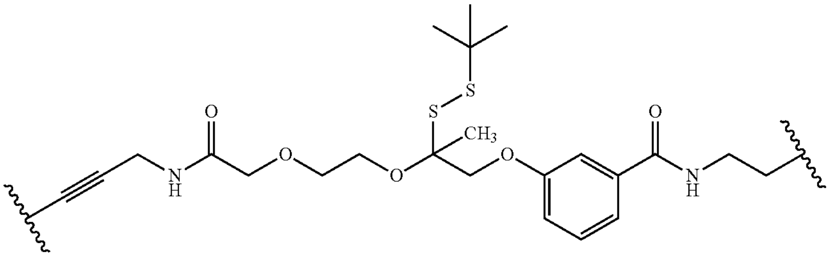, -continued
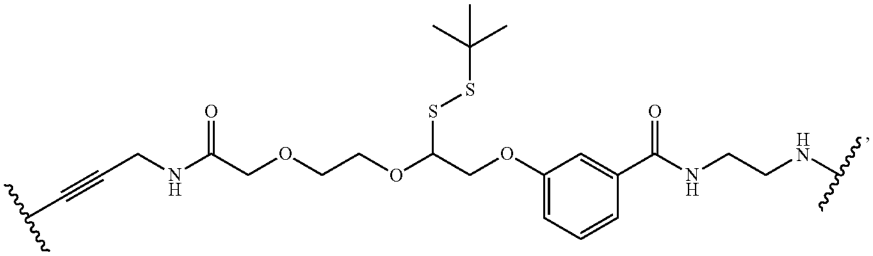,
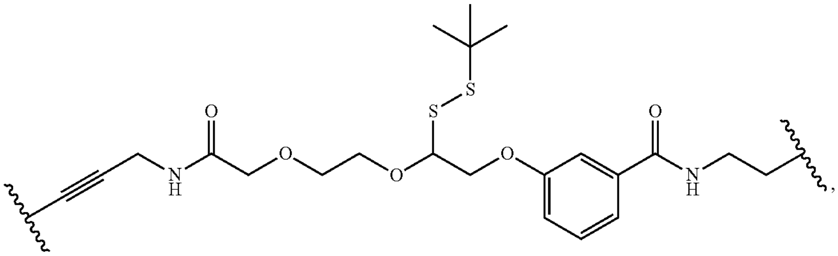,
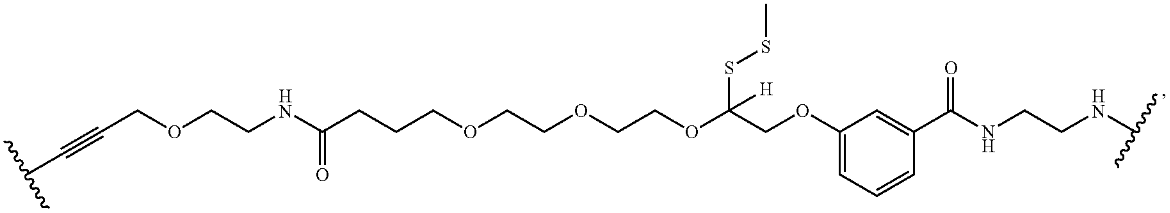,
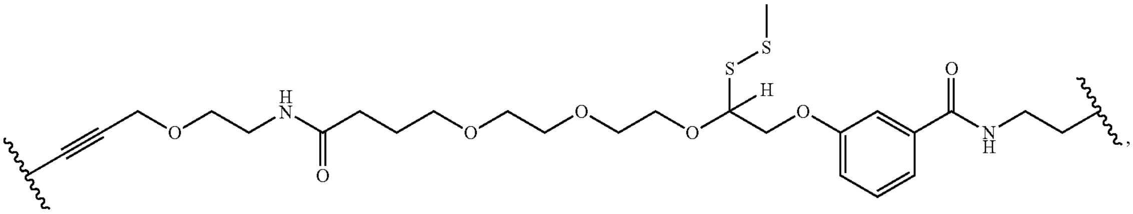,
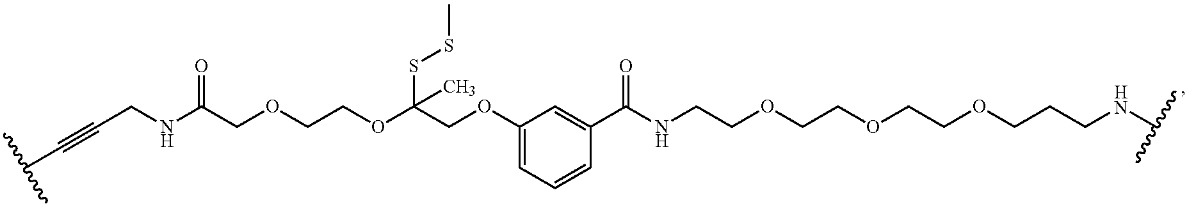,
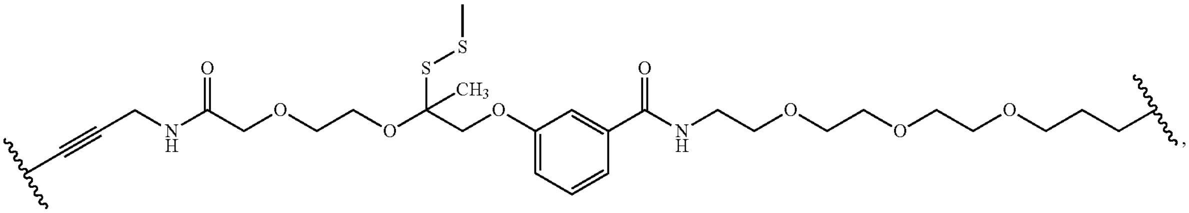,
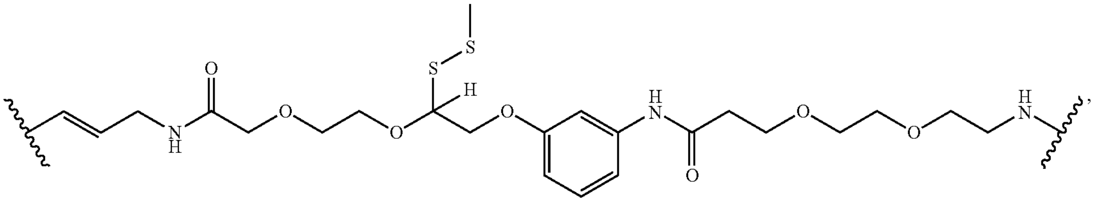, -continued
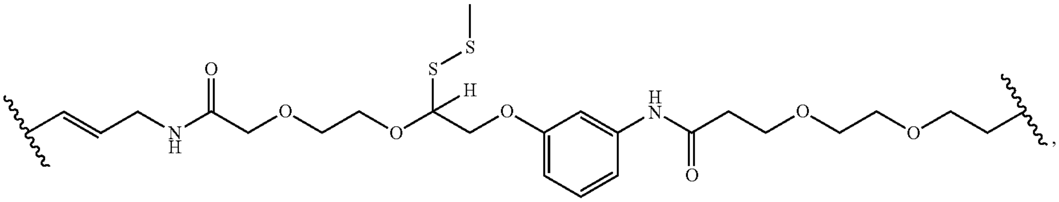,
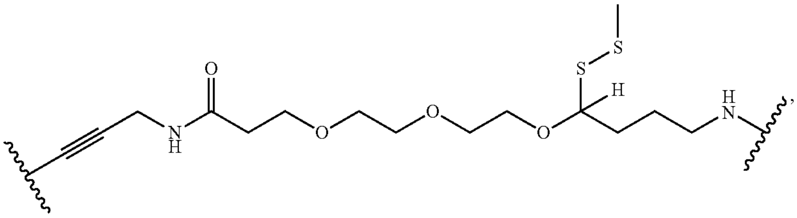,
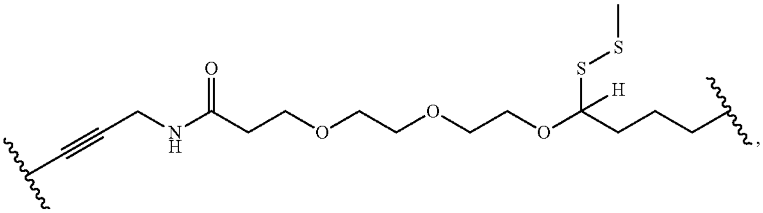,
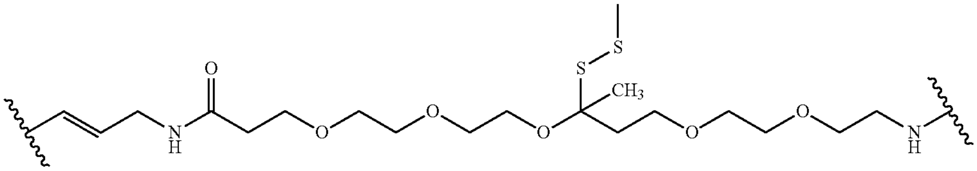,
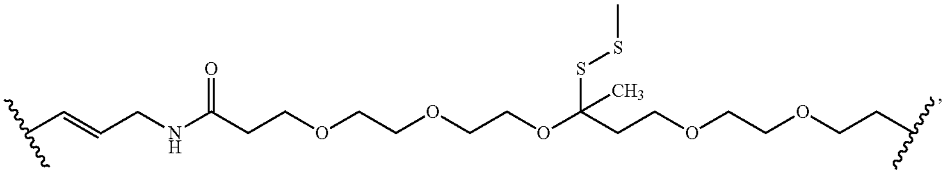,
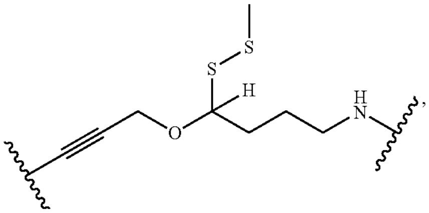, 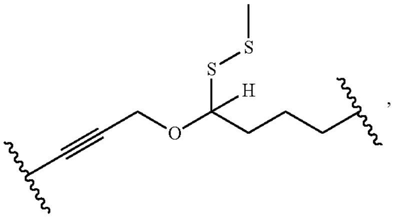,
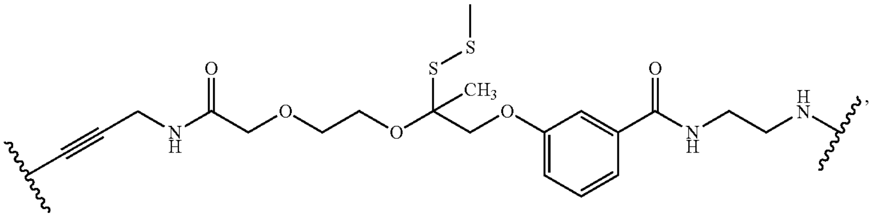,
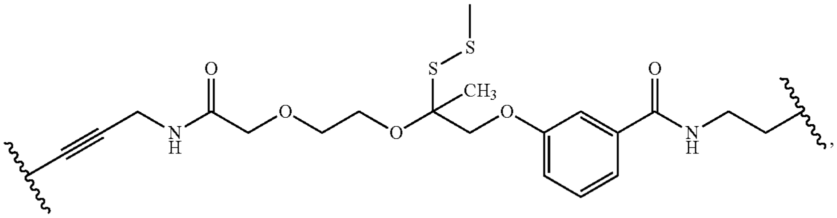, -continued
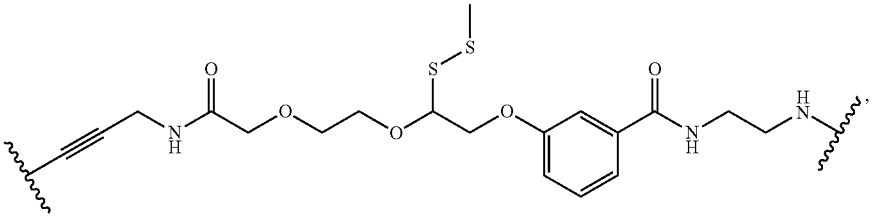
,
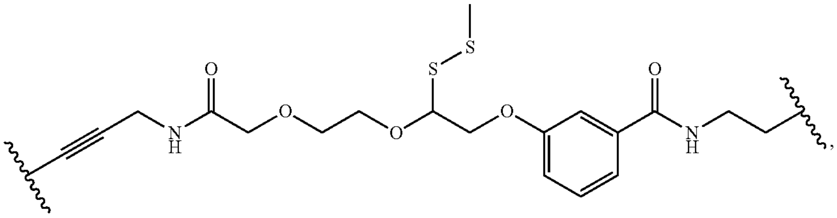
,
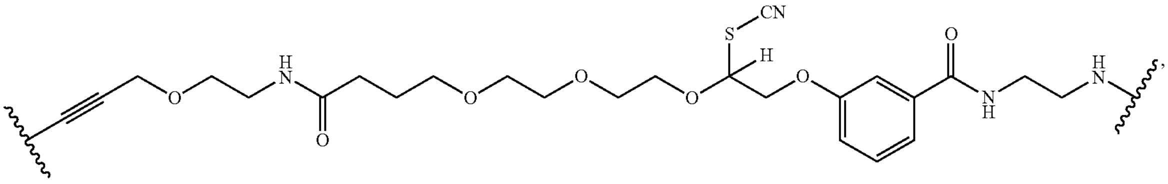
,
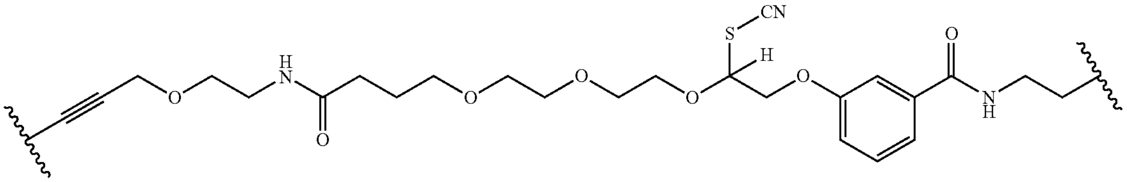
,
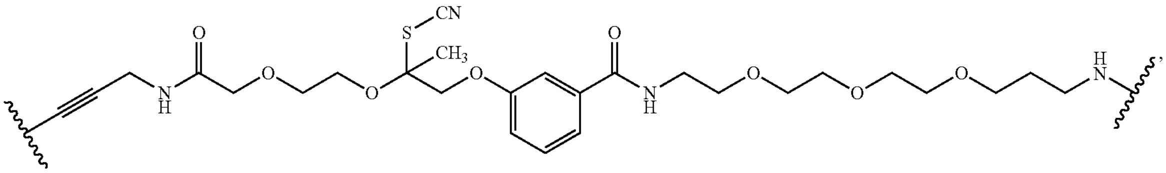
,
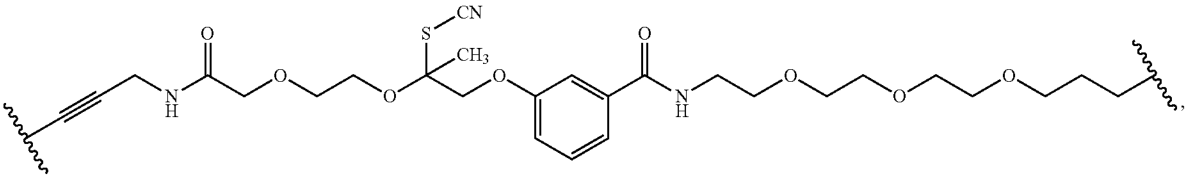
,
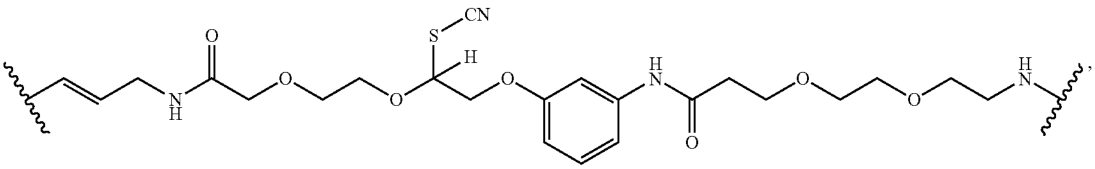
,
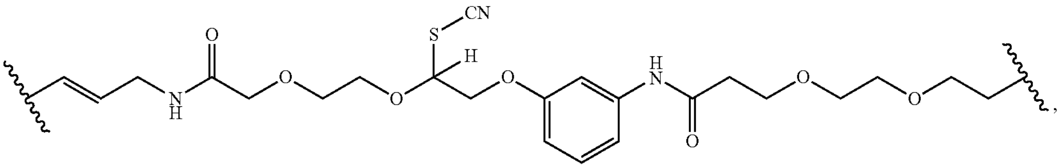
,
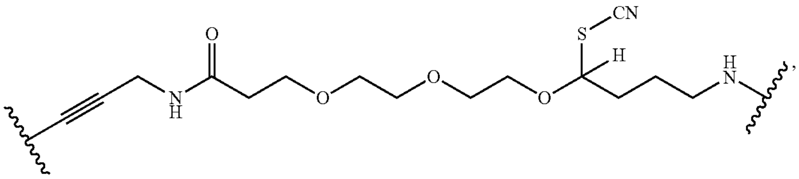
, -continued
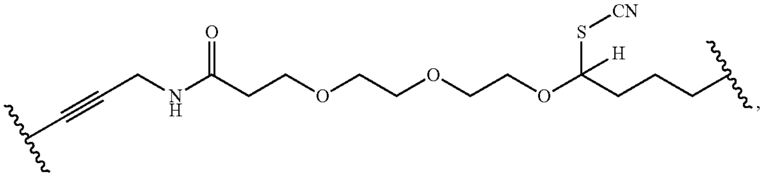
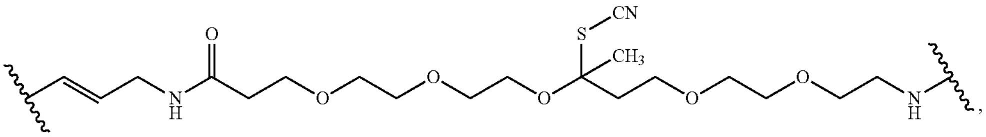
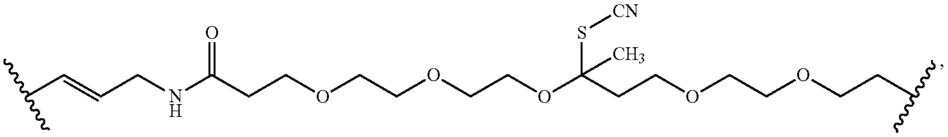
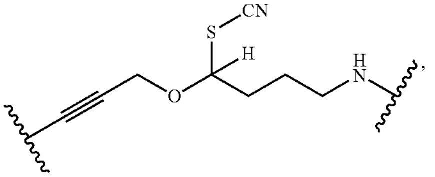
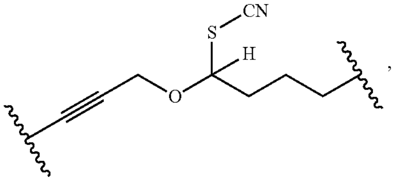
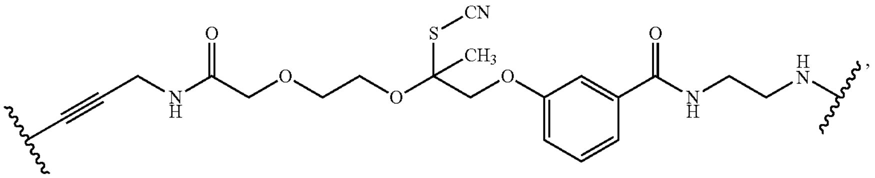
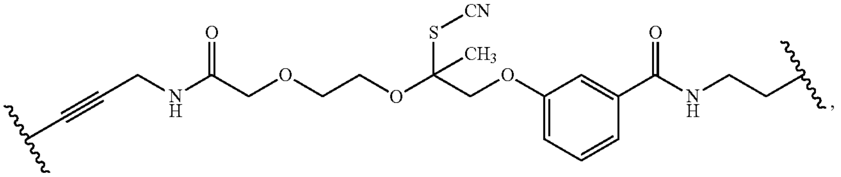
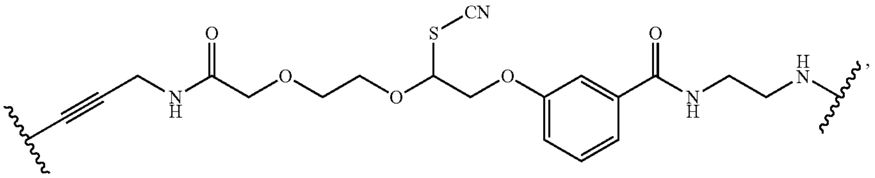
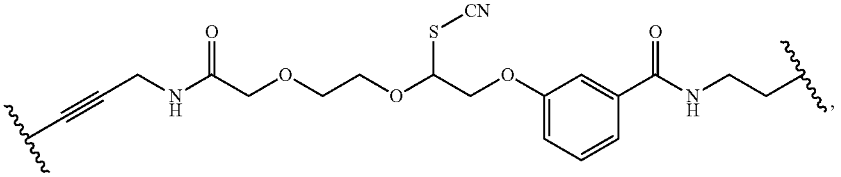
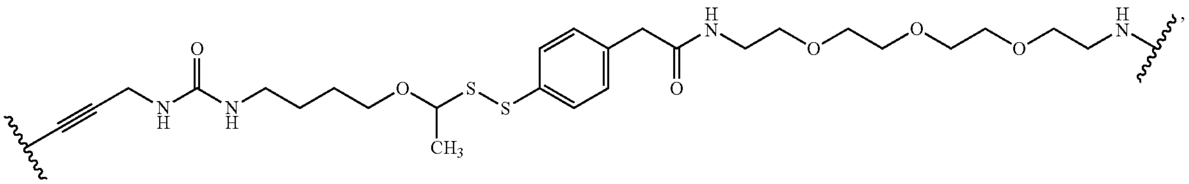

-continued
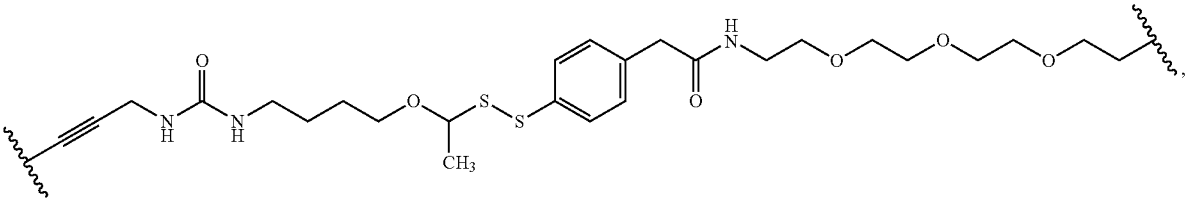
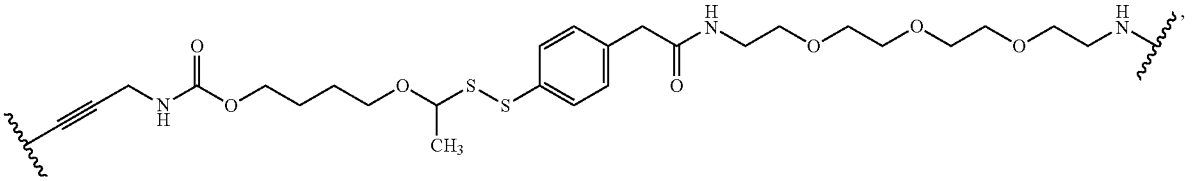
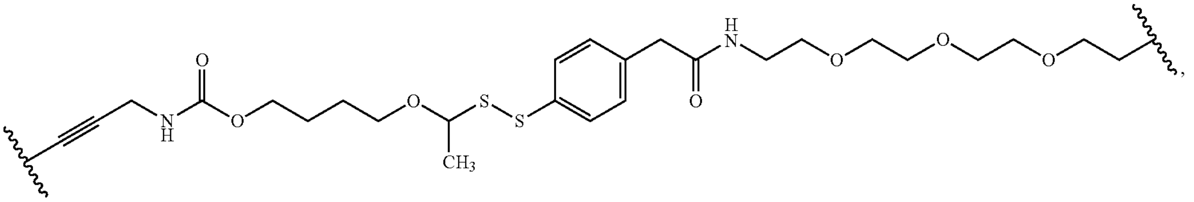
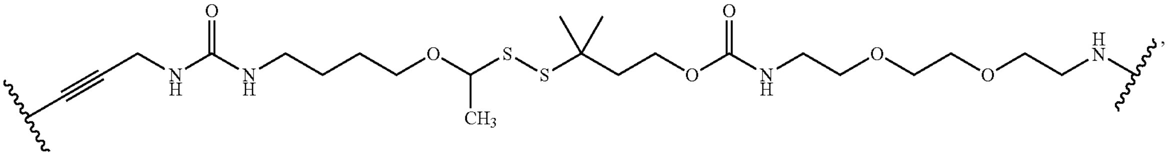
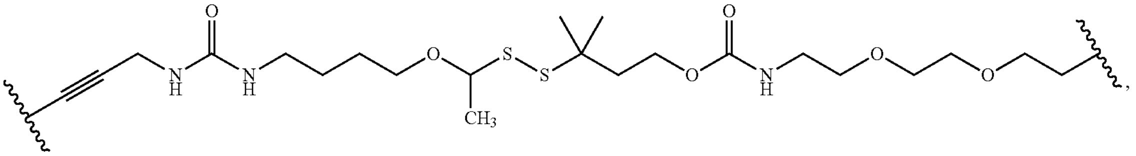
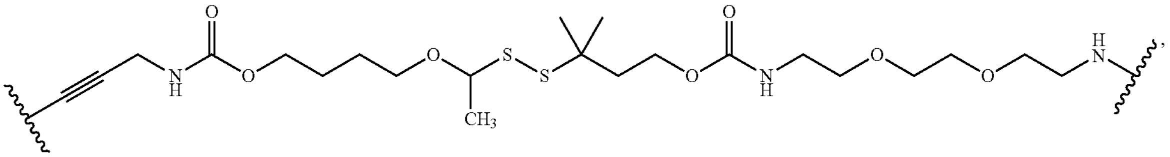
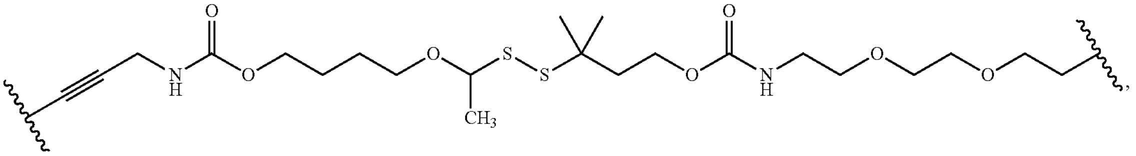
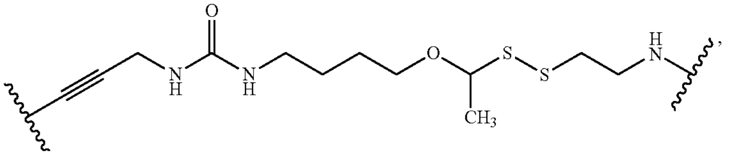
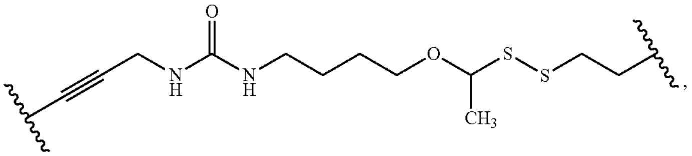
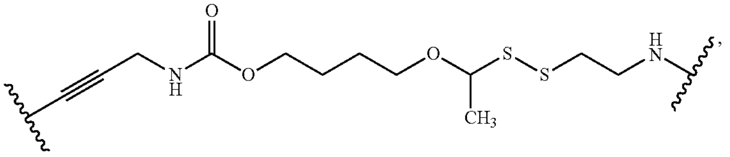

-continued
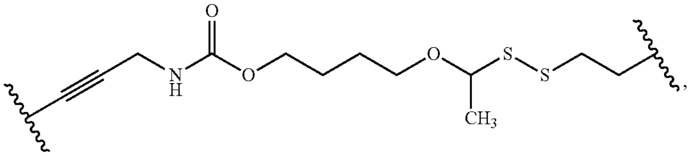,
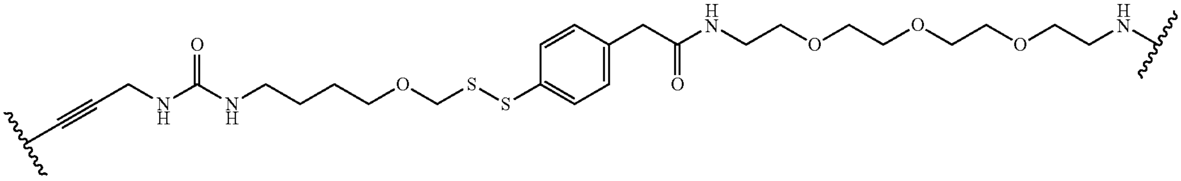,
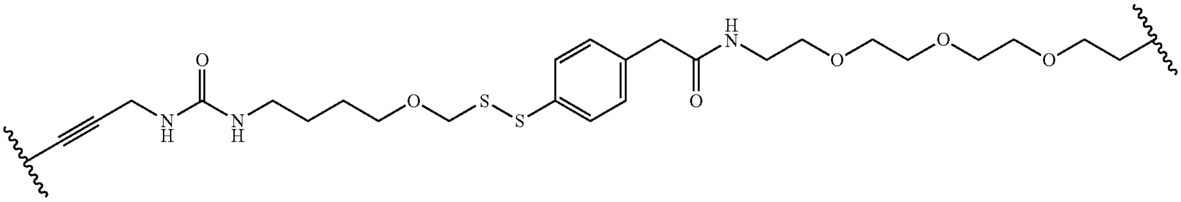,
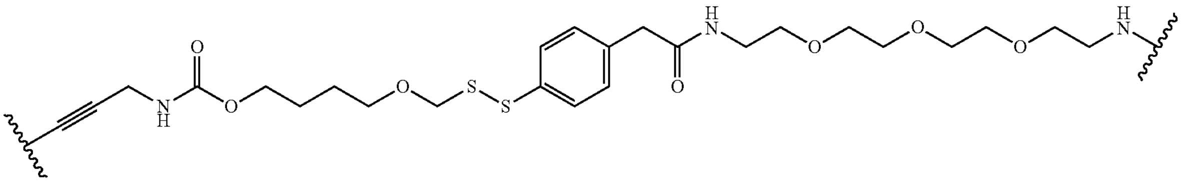,
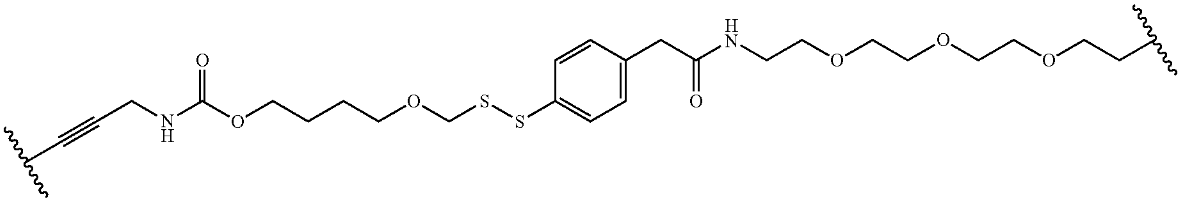,
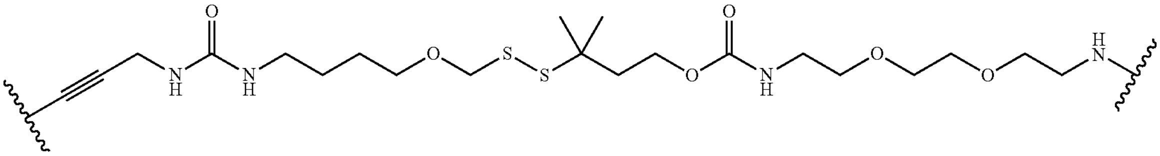,
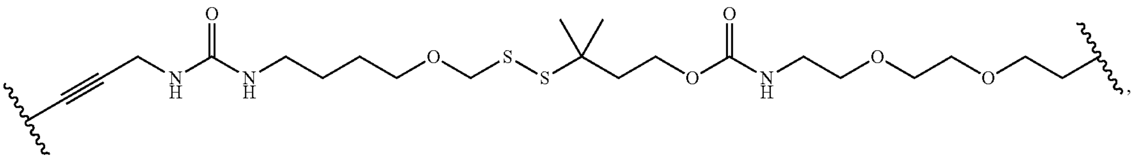,
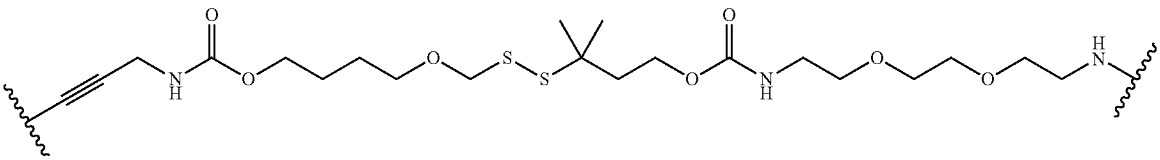,
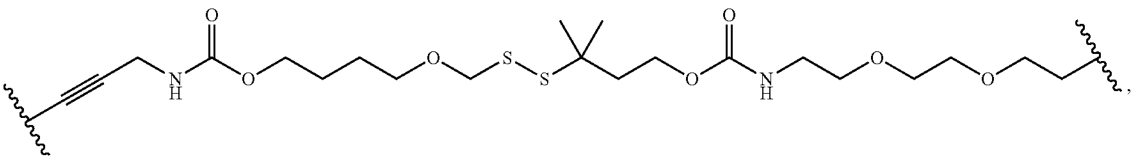, -continued
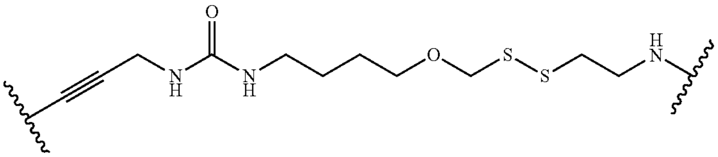
,
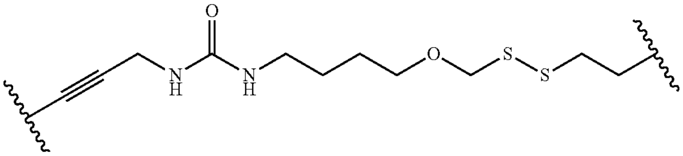
,
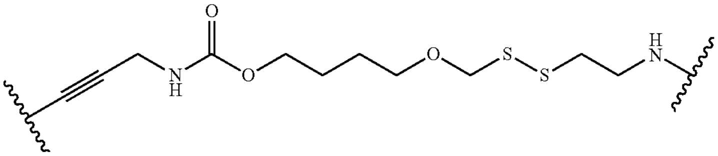
,
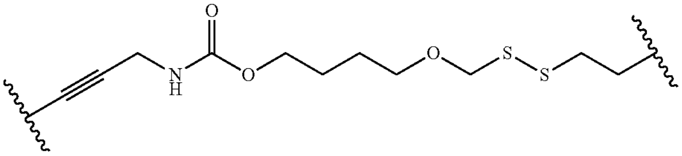
,
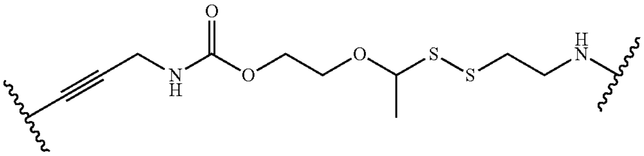
,
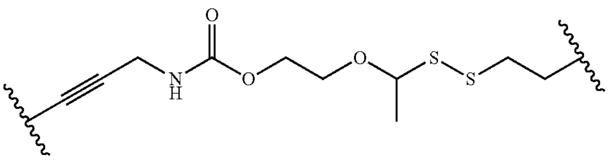
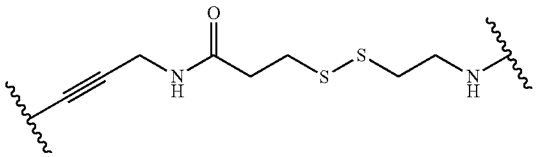
,
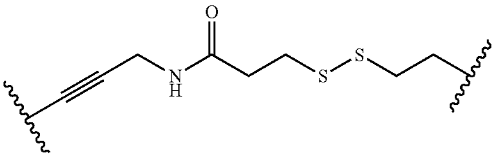
,
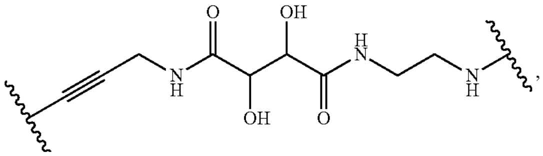
,
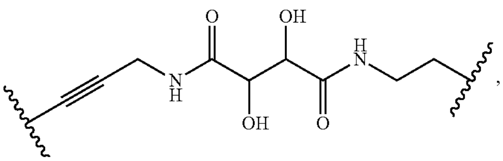
,
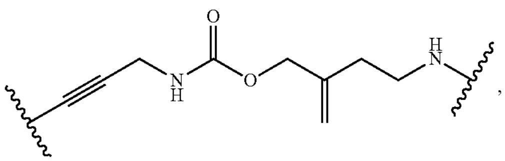
,
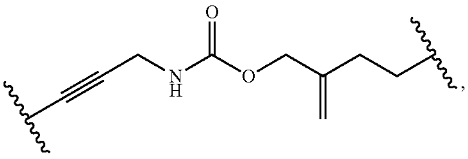
, -continued
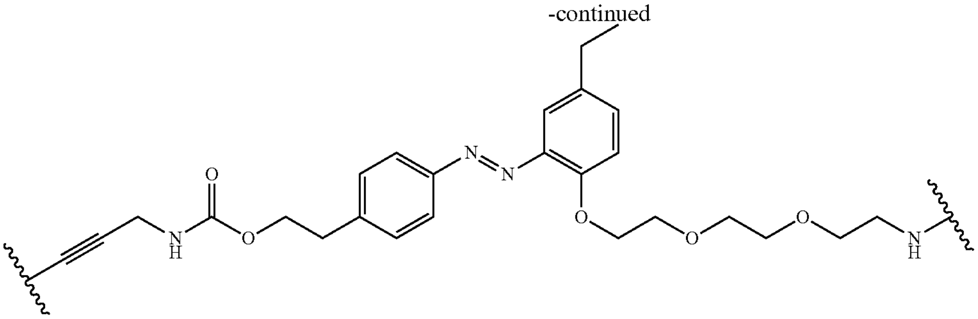,
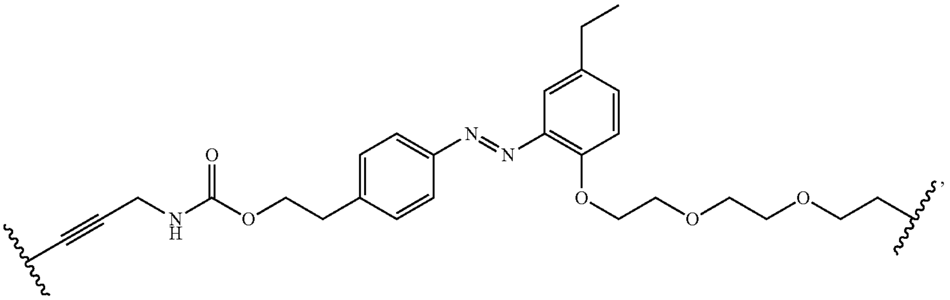,
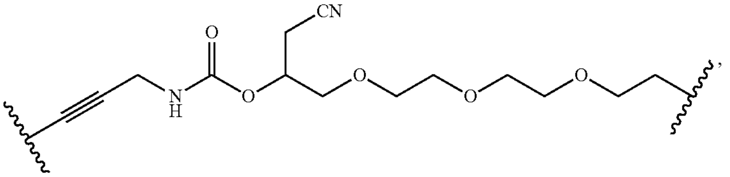, or
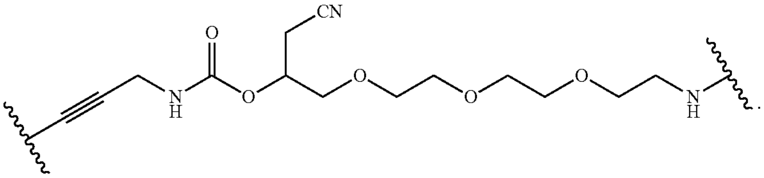.
In embodiments, $L^{100}$ is
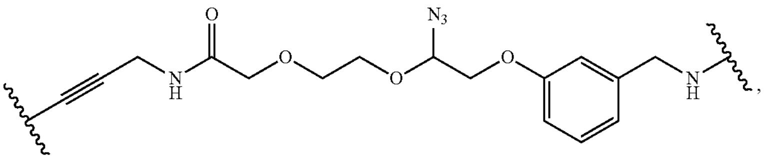,
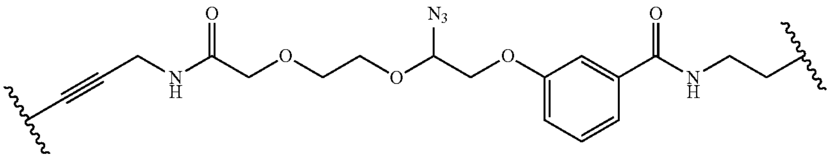,
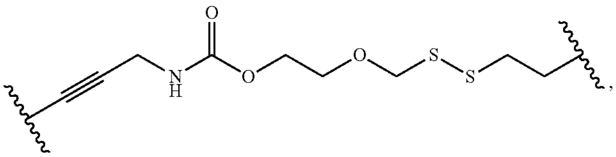,
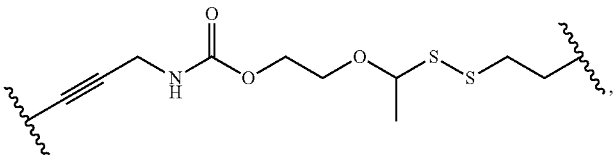, or -continued
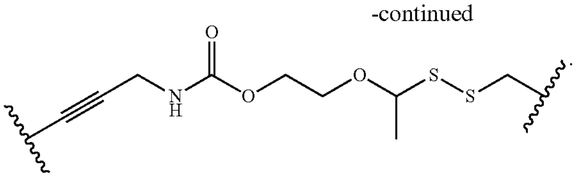
In embodiments, $L^{100}$ is $-(L^{101})-(L^{102})-SS-(L^{104})-(L^{105})-$. $L^{101}$, $L^{102}$, $L^{104}$, and $L^{105}$ are as described herein. In embodiments, $L^{100}$ is $-(L^{101})—OCH(R^{102})-SS-(L^{1O4})-(L^{105})-$. $L^{101}$, $L^{104}$, and $L^{105}$ are as described herein.
In embodiments, $-(L^{101})-(L^{102})-SS-(L^{104})-(L^{105})-$ is
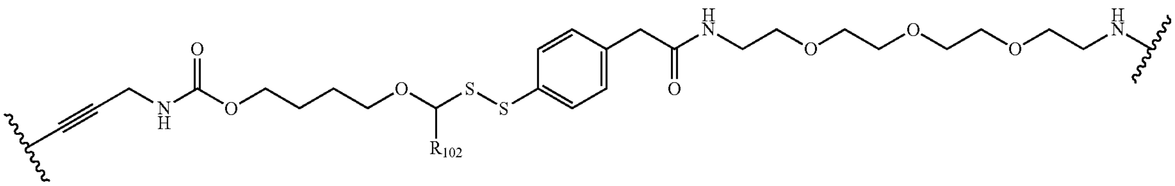
,
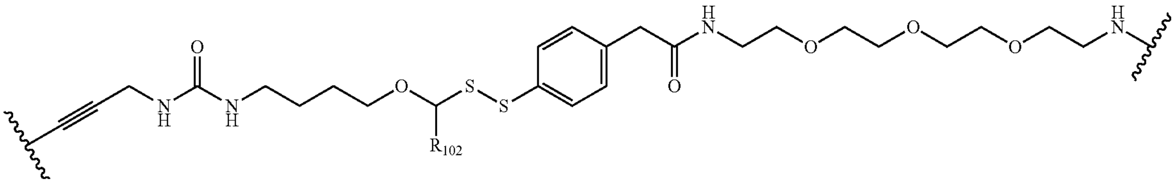
,
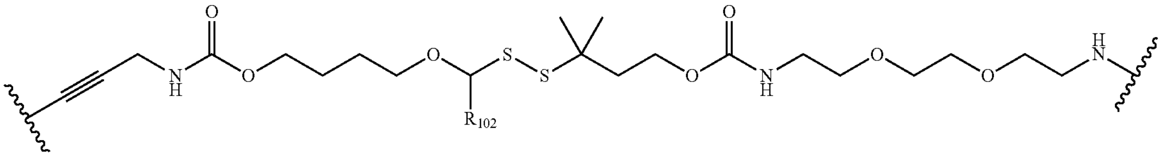
,
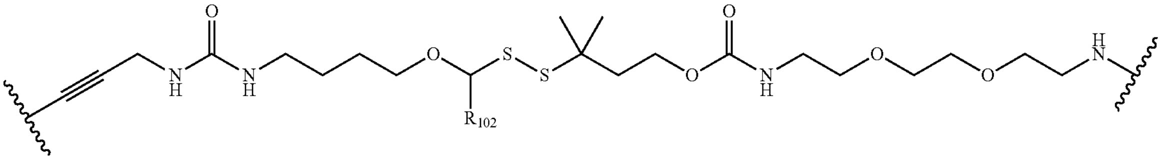
,
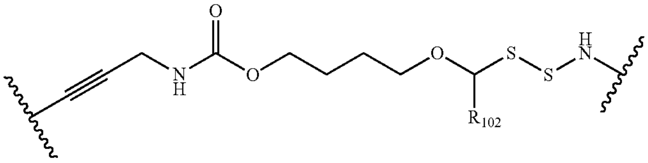
,
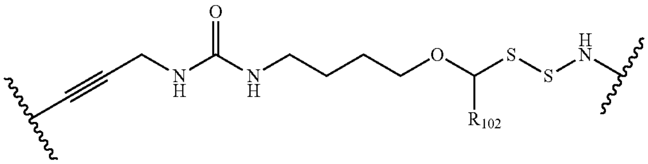
, or
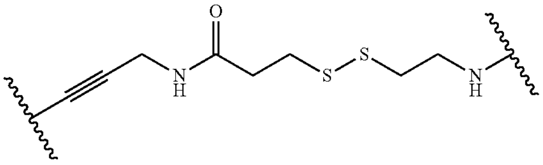
.

In embodiments, -($L^{101}$)-($L^{102}$)-SS-($L^{104}$)-($L^{105}$)- is
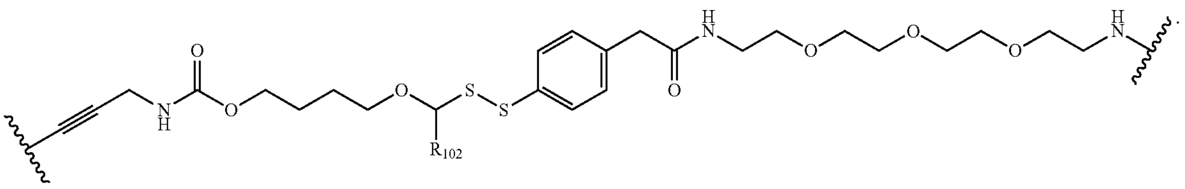
In embodiments, -($L^{101}$)-($L^{102}$)-SS-($L^{104}$)-($L^{105}$)- is
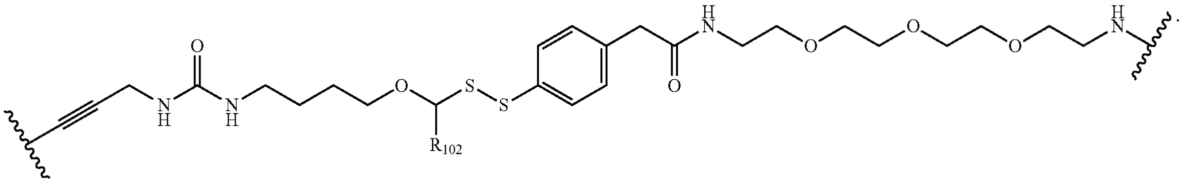
In embodiments, -($L^{101}$)-($L^{102}$)-SS-($L^{104}$)-($L^{105}$)- is
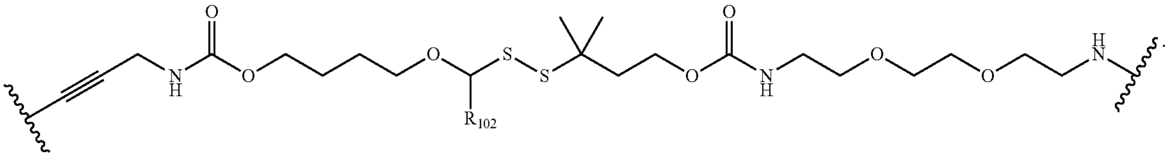
In embodiments, -($L^{101}$)-($L^{102}$)-SS-($L^{104}$)-($L^{105}$)- is
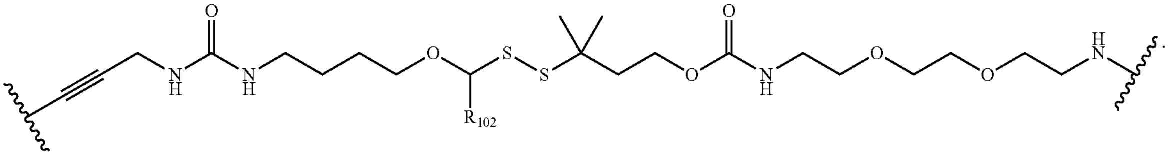
In embodiments, -($L^{101}$)-($L^{102}$)-SS-($L^{104}$)-($L^{105}$)- is
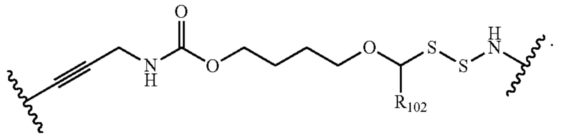
In embodiments, -($L^{101}$)-($L^{102}$)-SS-($L^{104}$)-($L^{105}$)- is
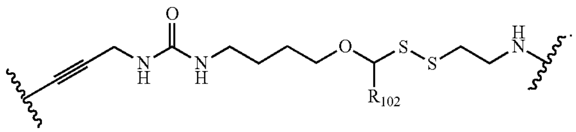

In embodiments, $-(L^{101})-(L^{102})-SS-(L^{104})-(L^{105})-$ is
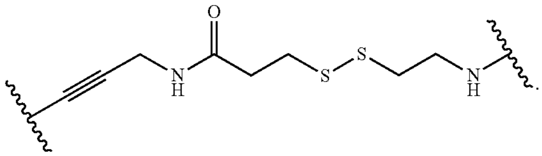 [SMILES: *C#CCNC(=O)CCSSCCN*]
$R^{102}$ is as described herein, including in embodiments.
In embodiments, $-(L^{10})-(L^{102})-SS-(L^{104})-(L^{105})-$ is
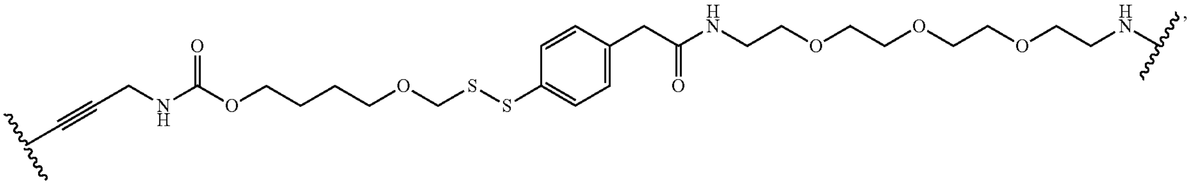
,
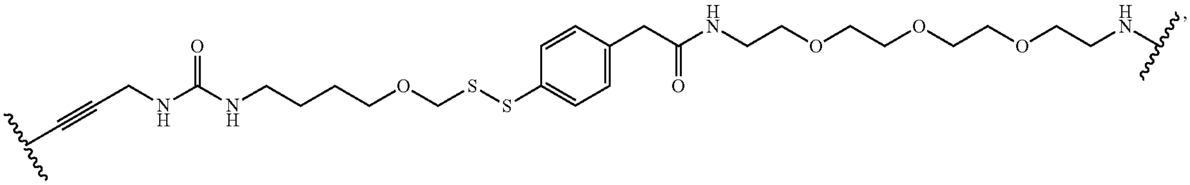
,
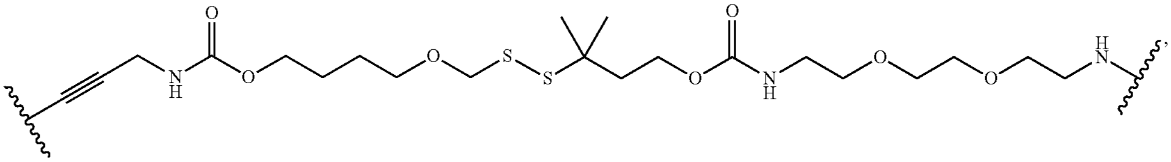
,
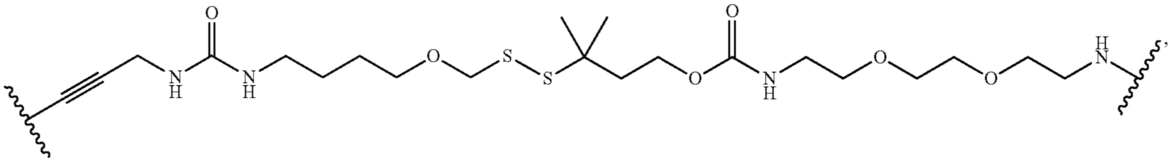
,
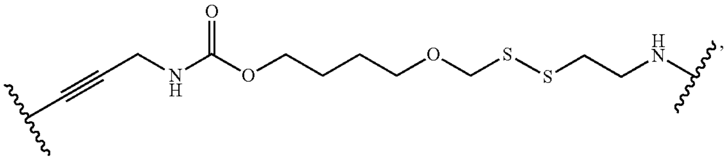
,
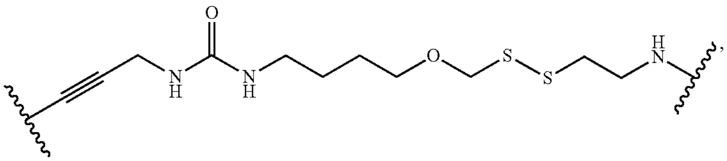
, or
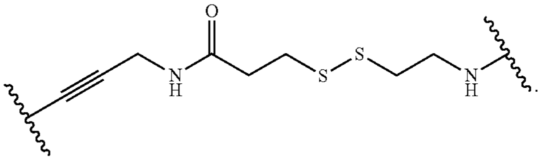
.

In embodiments, $-(L^{101})-(L^{102})-SS-(L^{104})-(L^{105})-$ is
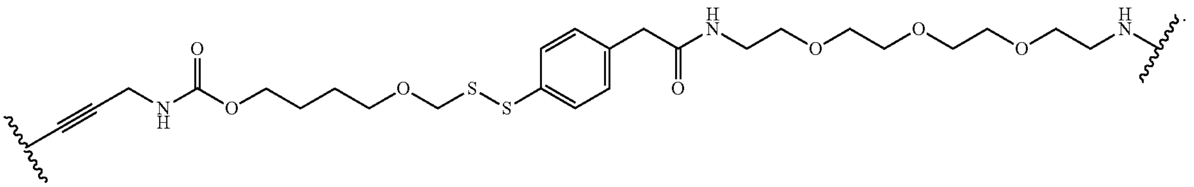 [SMILES: *C#CCNC(=O)OCCCCOCSSc1ccc(CC(=O)NCCOCCOCCOCCN*)cc1]
In embodiments, $-(L^{101})-(L^{102})-SS-(L^{104})-(L^{105})-$ is
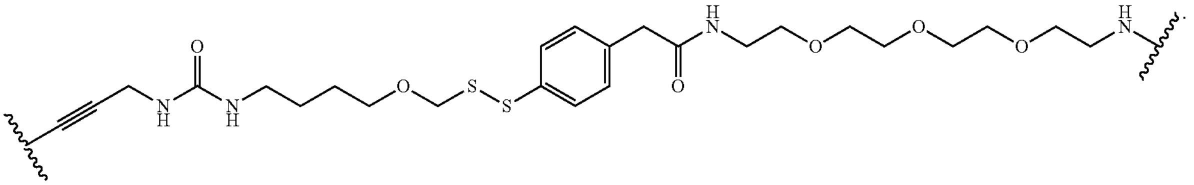 [SMILES: *C#CCNC(=O)NCCCCOCSSc1ccc(CC(=O)NCCOCCOCCOCCN*)cc1]
In embodiments, $-(L^{101})-(L^{102})-SS-(L^{104})-(L^{105})-$ is
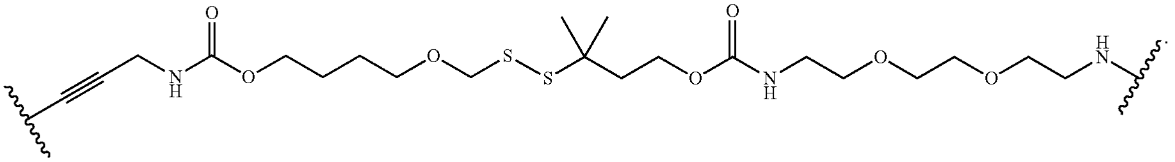 [SMILES: *C#CCNC(=O)OCCCCOCSSC(C)(C)CCOC(=O)NCCOCCOCCN*]
In embodiments, $-(L^{101})-(L^{102})-SS-(L^{104})-(L^{105})-$ is
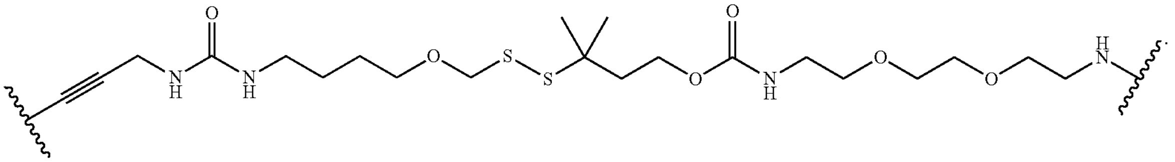 [SMILES: *C#CCNC(=O)NCCCCOCSSC(C)(C)CCOC(=O)NCCOCCOCCN*]
In embodiments, $-(L^{14})-(L^{102})-SS-(L^{104})-(L^{105})-$ is
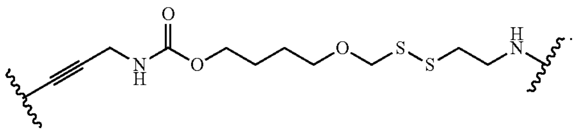 [SMILES: *C#CCNC(=O)OCCCCOCSSCCN*]
In embodiments $-(L^{101})-(L^{102})-SS-(L^{104})-(L^{105})-$ is
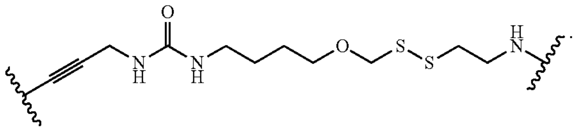 [SMILES: *C#CCNC(=O)NCCCCOCSSCCN*]

In embodiments, $-(L^{101})-(L^{102})-SS-(L^{104})-(L^{105})-$ is
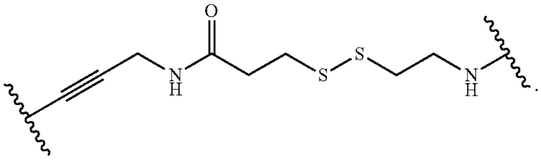 [SMILES: *C#CCNC(=O)CCSSCCN*]
.
In embodiments, $-(L^{101})-(L^{102})-SS-(L^{104})-(L^{105})-$ is
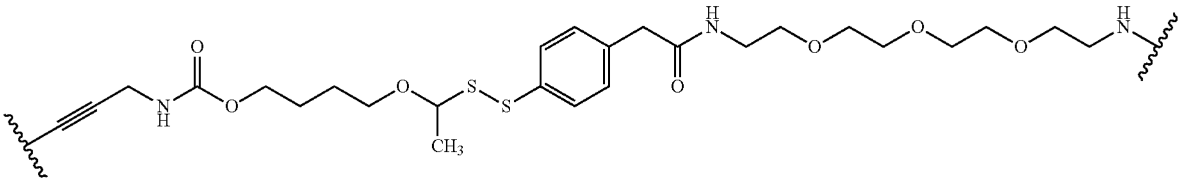
,
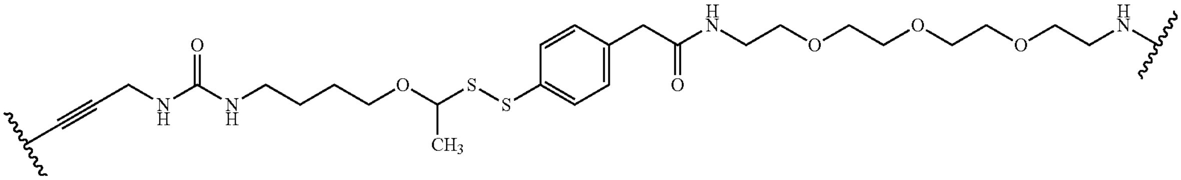
,
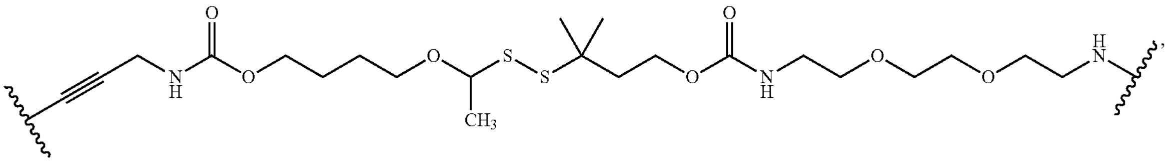
,
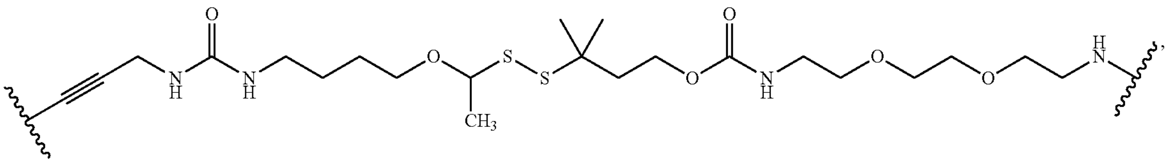
,
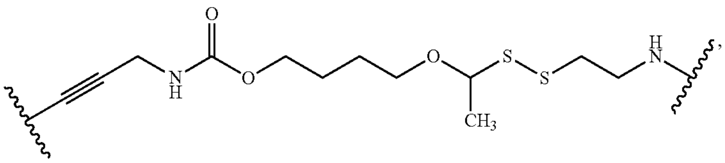
,
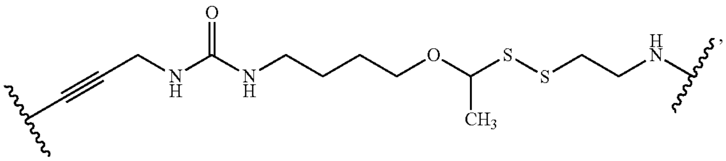
, or
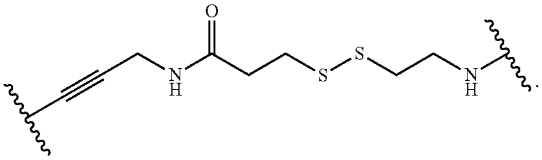
.

In embodiments, -($L^{101}$)-($L^{102}$)-SS-($L^{104}$)-($L^{105}$)- is
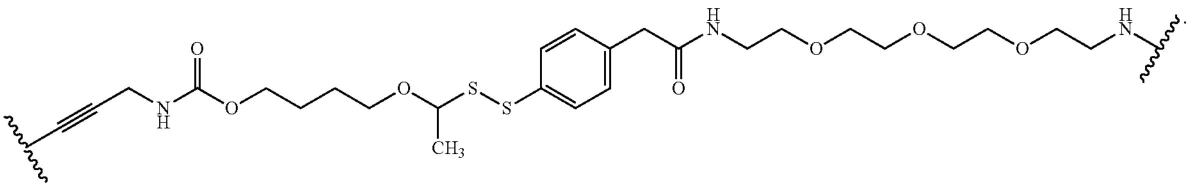 [SMILES: *C#CCNC(=O)OCCCCOC(C)SSc1ccc(CC(=O)NCCOCCOCCOCCN*)cc1]
In embodiments, -($L^{1}$)-($L^{102}$)-SS-($L^{104}$)-($L^{105}$)- is
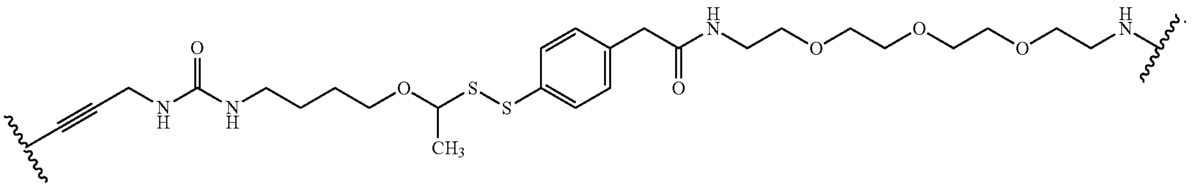 [SMILES: *C#CCNC(=O)NCCCCOC(C)SSc1ccc(CC(=O)NCCOCCOCCOCCN*)cc1]
In embodiments, -($L^{101}$)-($L^{102}$)-SS-($L^{104}$)-($L^{105}$)- is
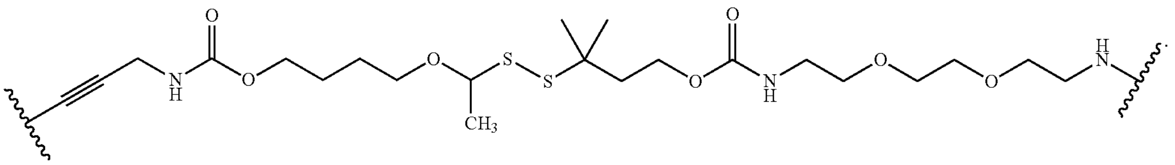 [SMILES: *C#CCNC(=O)OCCCCOC(C)SSC(C)(C)CCOC(=O)NCCOCCOCCN*]
In embodiments, -($L^{101}$)-($L^{102}$)-SS-($L^{104}$)-($L^{105}$)- is
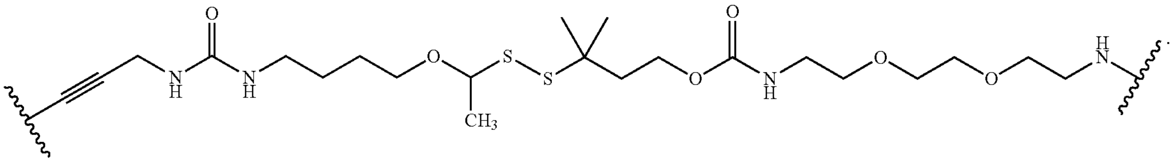 [SMILES: *C#CCNC(=O)NCCCCOC(C)SSC(C)(C)CCOC(=O)NCCOCCOCCN*]
In embodiments, -($L^{101}$)-($L^{102}$)-SS-($L^{104}$)-($L^{105}$)- is
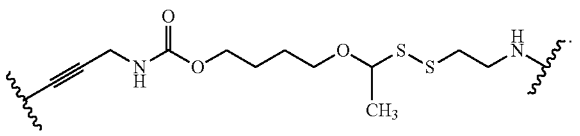 [SMILES: *C#CCNC(=O)OCCCCOC(C)SSCCN*]
In embodiments,
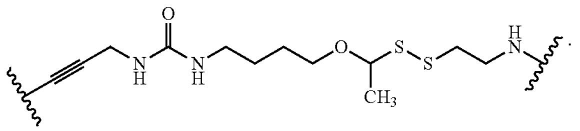 [SMILES: *C#CCNC(=O)NCCCCOC(C)SSCCN*]

In embodiments, $-(L^{101})-(L^{102})-SS-(L^{104})-(L^{105})-$ is
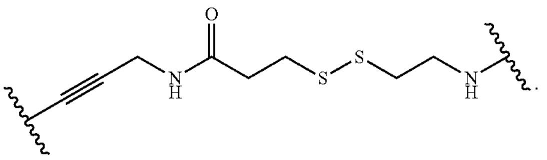 [SMILES: *C#CCNC(=O)CCSSCCN*]
In embodiments, $L^{101}$ is
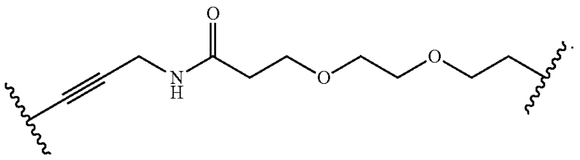 [SMILES: *C#CCNC(=O)CCOCCOCC*]
In embodiments, $L^{101}$ is
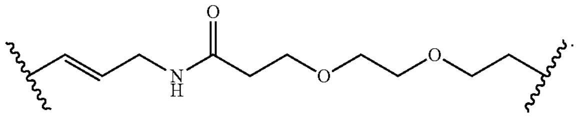 [SMILES: */C=C/CNC(=O)CCOCCOCC*]
In embodiments, $L^{101}$ is $-CCCH_2-$. In embodiments, $L^{101}$ is
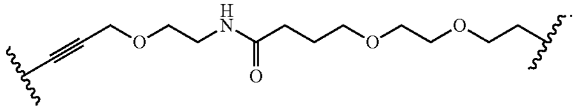 [SMILES: *C#CCOCCNC(=O)CCCOCCOCC*]
In embodiments, $L^{101}$ is
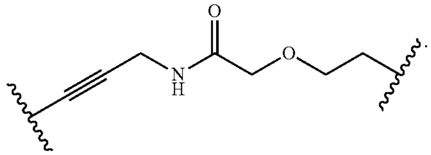 [SMILES: *C#CCNC(=O)COCC*]
In embodiments, $L^{101}$ is
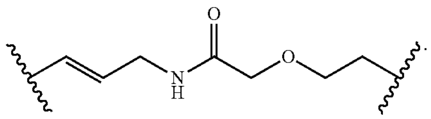 [SMILES: */C=C/CNC(=O)COCC*]
In embodiments, $L^{103}$ is
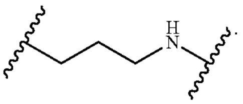 [SMILES: *CCCN*]
In embodiments, $L^{103}$ is
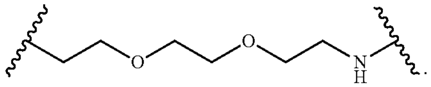 [SMILES: *CCOCCOCCN*]
In embodiments, $L^{103}$ is
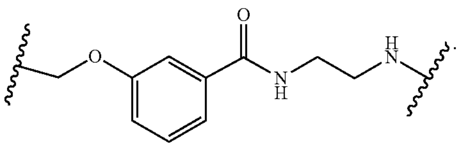 [SMILES: *COc1cccc(C(=O)NCCN*)c1]
In embodiments, $L^{103}$ is
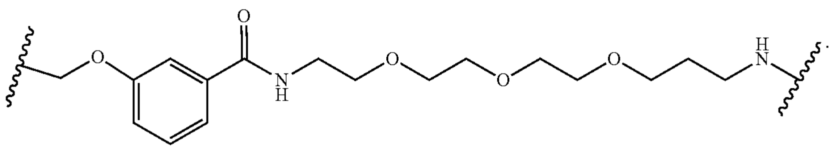 [SMILES: *COc1cccc(C(=O)NCCOCCOCCOCCCN*)c1]

In embodiments, $L^{103}$ is a bond.
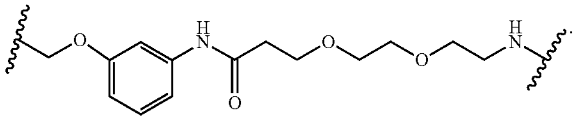 [SMILES: *COc1cccc(NC(=O)CCOCCOCCN*)c1]
In embodiments, $L^{104}$ is
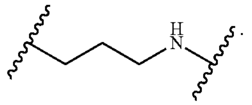 [SMILES: *CCCN*]
In embodiments, $L^{104}$ is
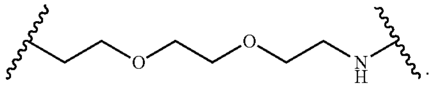 [SMILES: *CCOCCOCCN*]
In embodiments, $L^{104}$ is
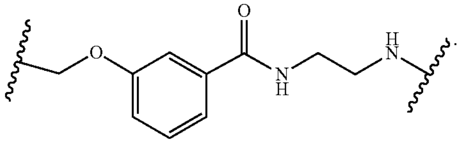 [SMILES: *COc1cccc(C(=O)NCCN*)c1]
In embodiments, $L^{104}$ is
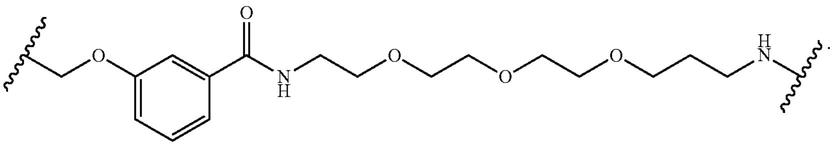 [SMILES: *COc1cccc(C(=O)NCCOCCOCCOCCCN*)c1]
In embodiments, $L^{104}$ is a bond.
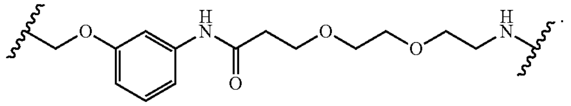 [SMILES: *COc1cccc(NC(=O)CCOCCOCCN*)c1]
In embodiments, $L^{105}$ is
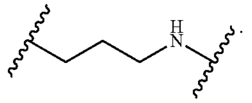 [SMILES: *CCCN*]

In embodiments, $L^{105}$ is
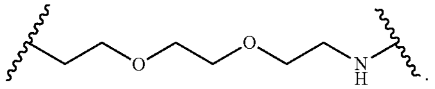 [SMILES: *CCOCCOCCN*]
In embodiments, $L^{105}$ is
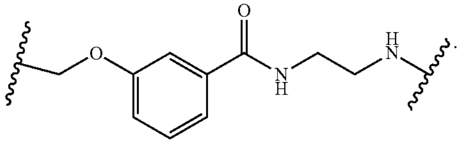 [SMILES: *COc1cccc(C(=O)NCCN*)c1]
In embodiments, $L^{105}$ is
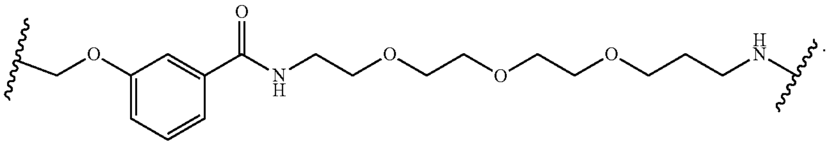 [SMILES: *COc1cccc(C(=O)NCCOCCOCCOCCCN*)c1]
In embodiments, $L^{105}$ is
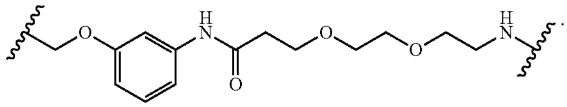 [SMILES: *COc1cccc(NC(=O)CCOCCOCCN*)c1]
In embodiments, $L^{105}$ is a bond.
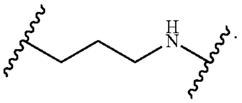 [SMILES: *CCCN*]
In embodiments, $L^{103}$-$L^{104}$-$L^{105}$- is
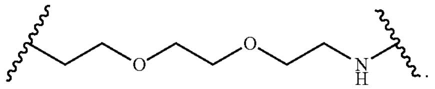 [SMILES: *CCOCCOCCN*]
In embodiments, $L^{103}$-$L^{104}$-$L^{105}$- is
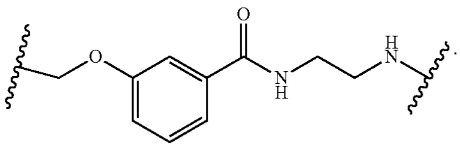 [SMILES: *COc1cccc(C(=O)NCCN*)c1]

In embodiments, $L^{103}$-$L^{104}$-$L^{105}$- is
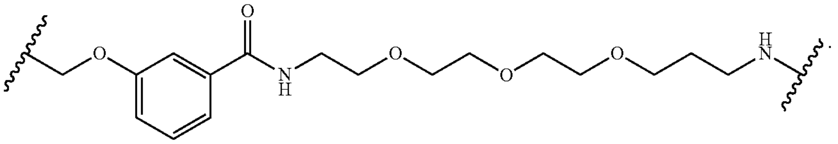 [SMILES: *COc1cccc(C(=O)NCCOCCOCCOCCCN*)c1]
In embodiments, $L^{103}$-$L^{104}$-$L^{105}$- is
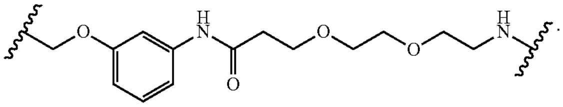 [SMILES: *COc1cccc(NC(=O)CCOCCOCCN*)c1]
In embodiments, $L^{100}$ is
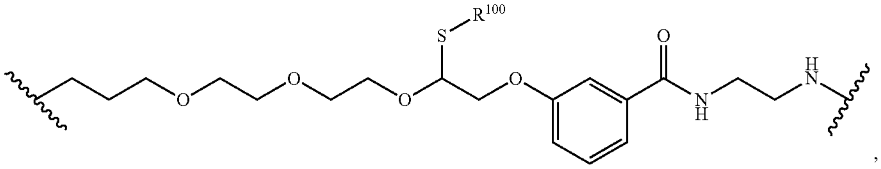
,
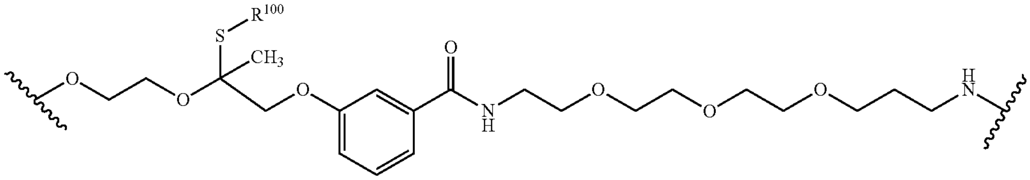
,
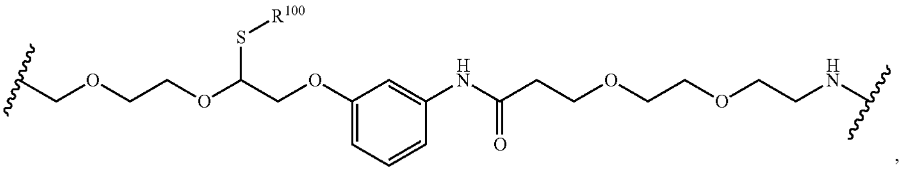
,
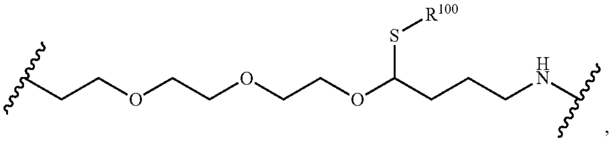
,
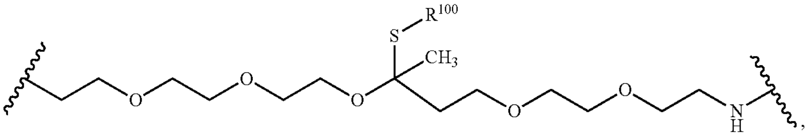
,
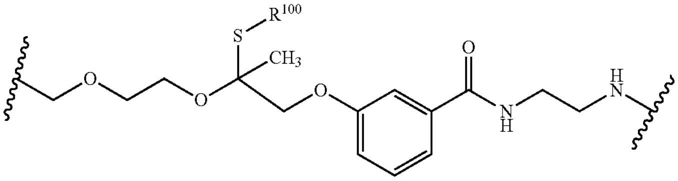
, or -continued
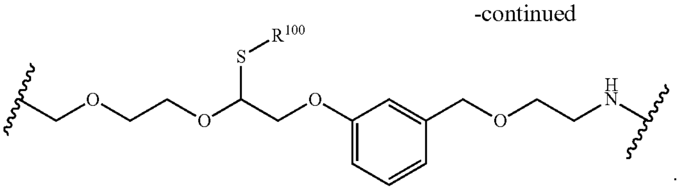
$R^{100}$ is as described herein, including in embodiments.
In embodiments, B is
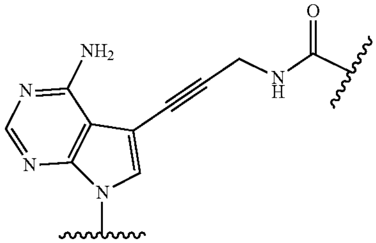
,
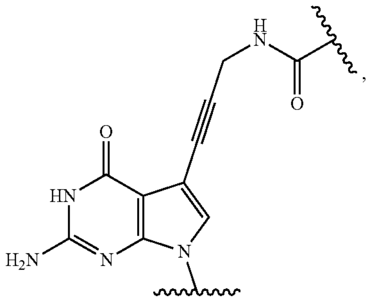
,
-continued
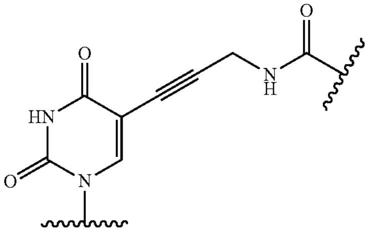
, or
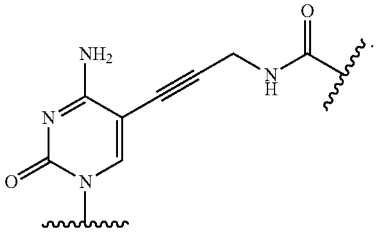
.
In embodiments, $L^{100}$ is
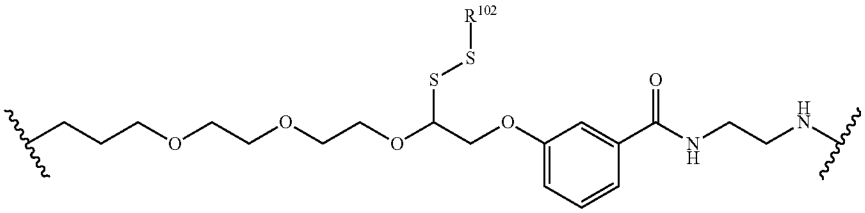
,
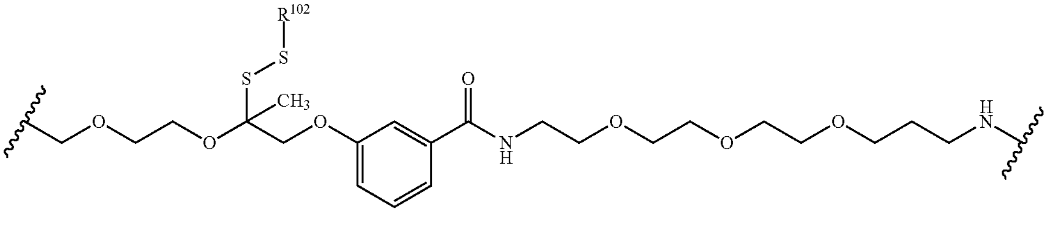
,
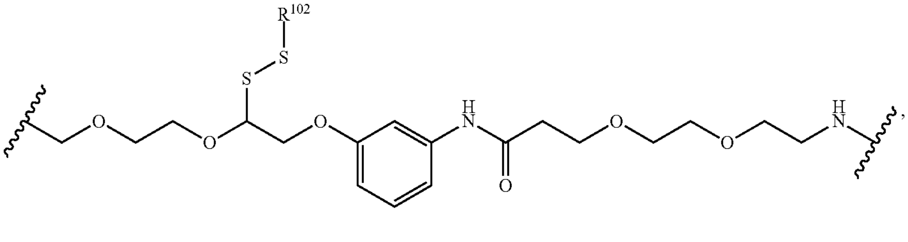
, -continued
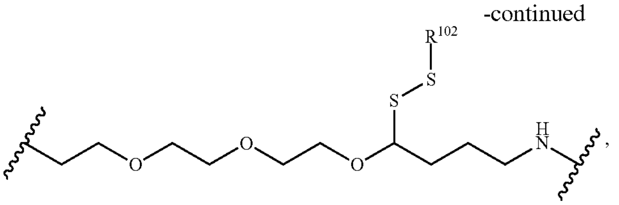
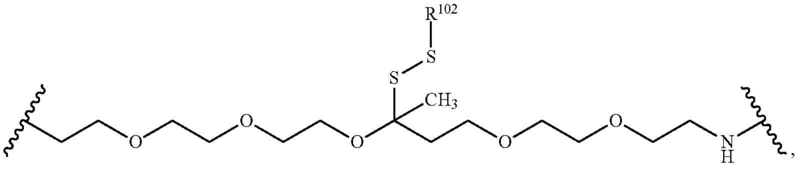
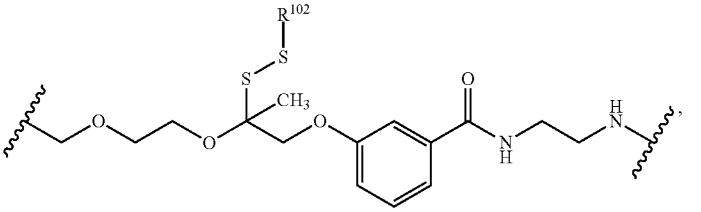
or
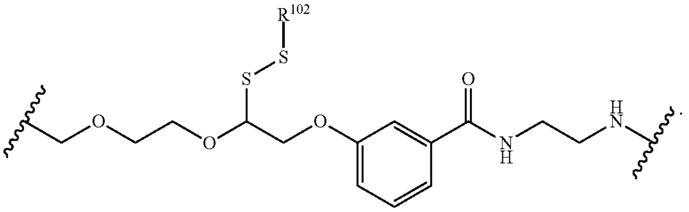
$R^{102}$ is as described herein, including in embodiments.
In embodiments, B is
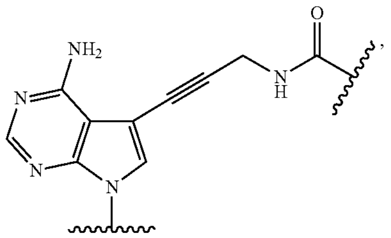
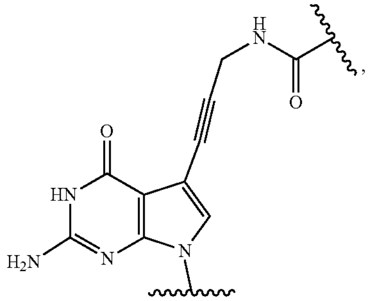
-continued
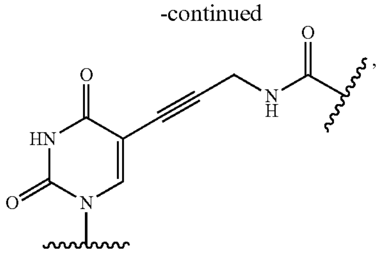
or
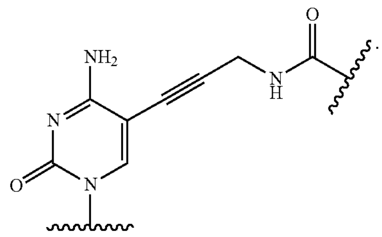

In embodiments, $L^{100}$ is
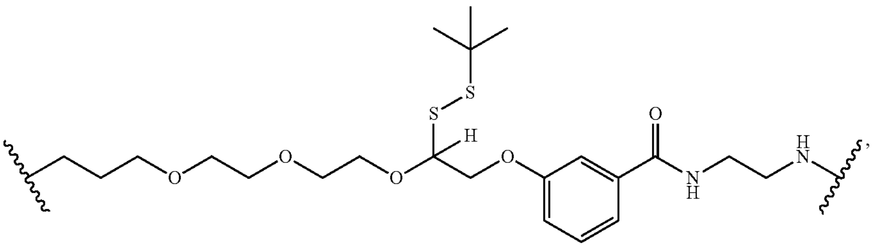
,
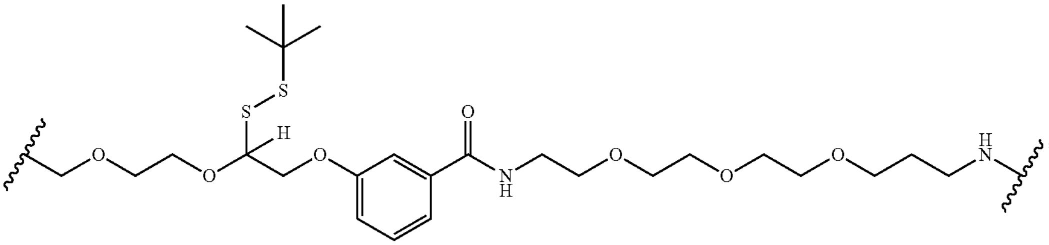
,
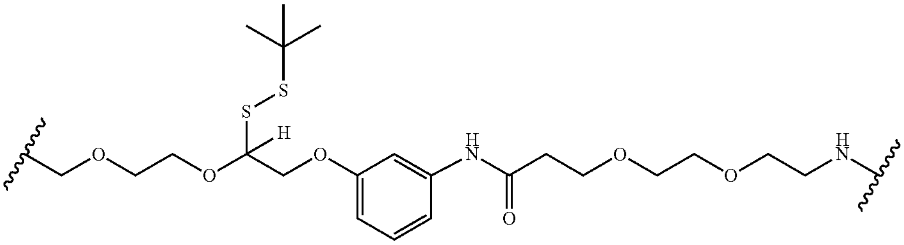
,
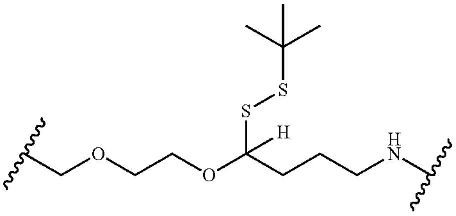
,
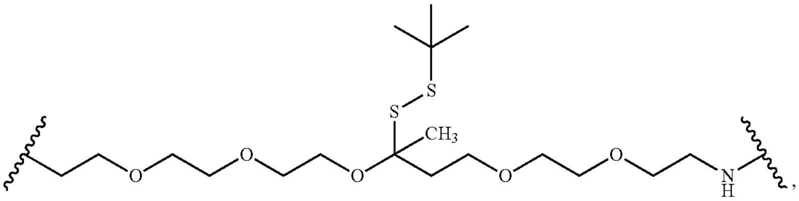
,
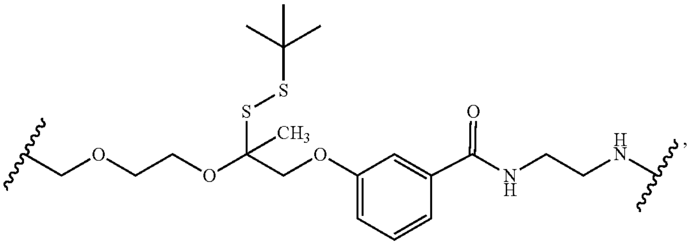
, or
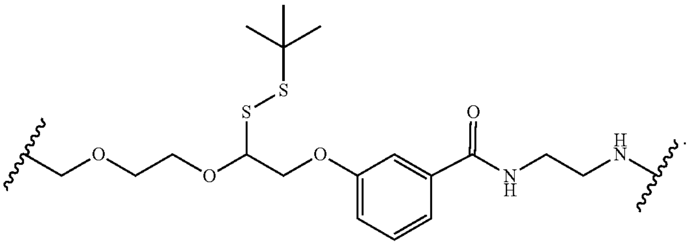
.

In embodiments, B is
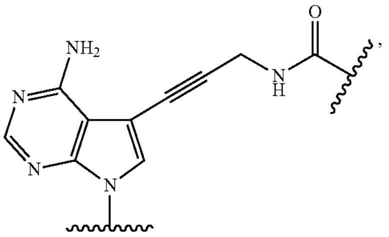
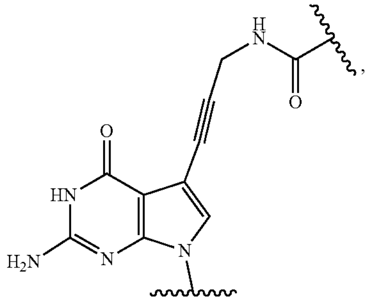
-continued
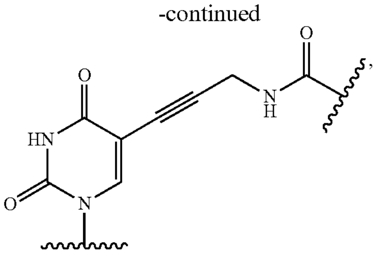
or
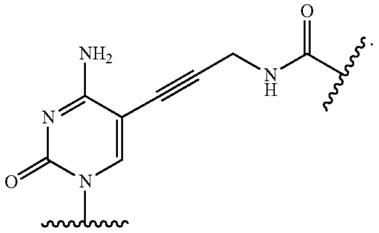
In embodiments,
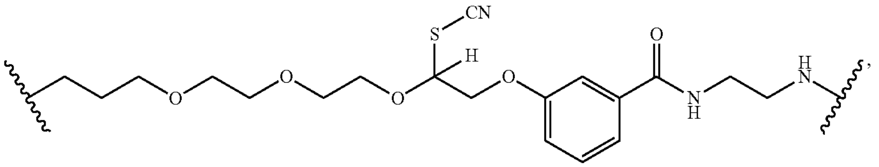
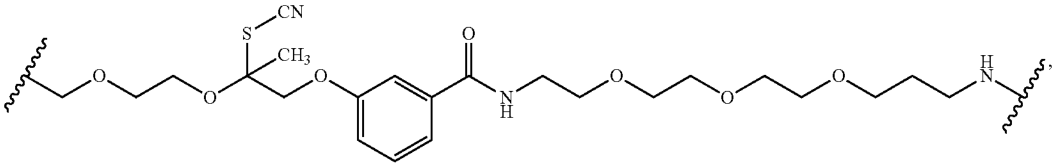
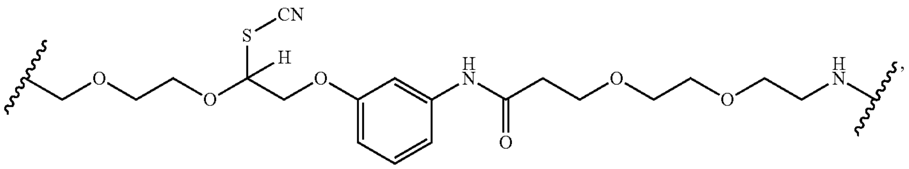
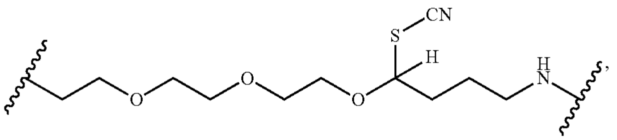
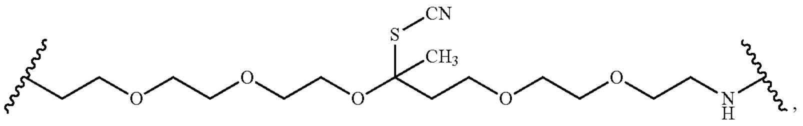
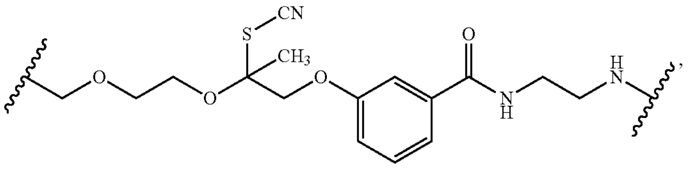
or -continued
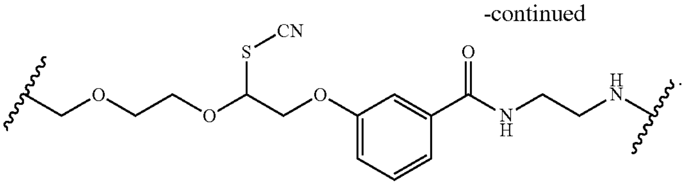
In embodiments, B is
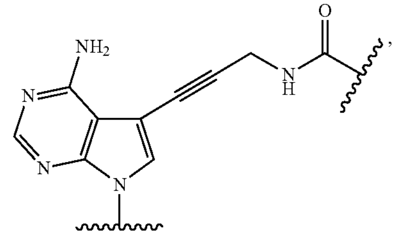
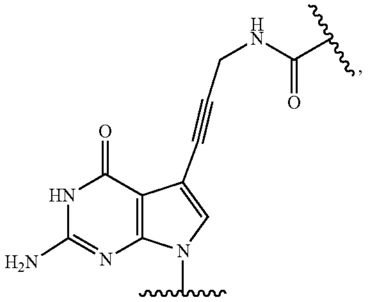
-continued
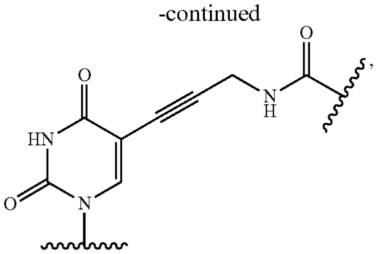
, or
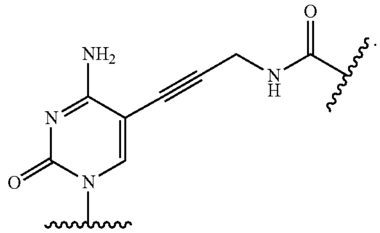
In embodiments, $L^{100}$ is
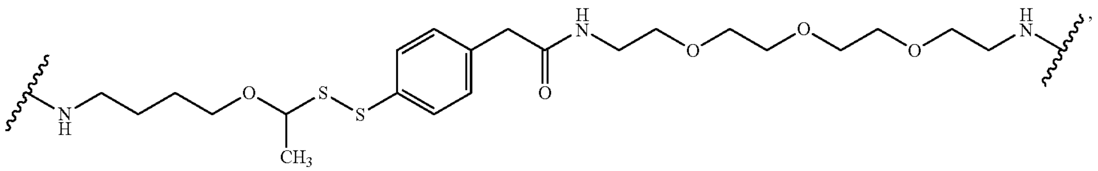
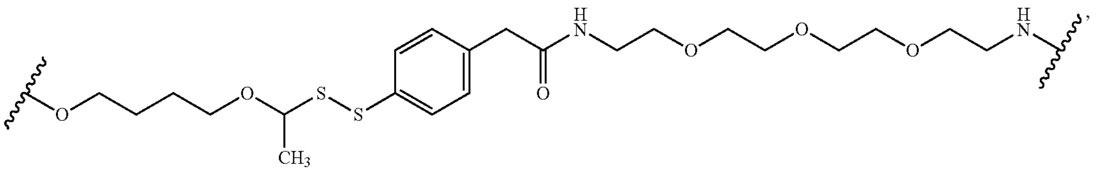
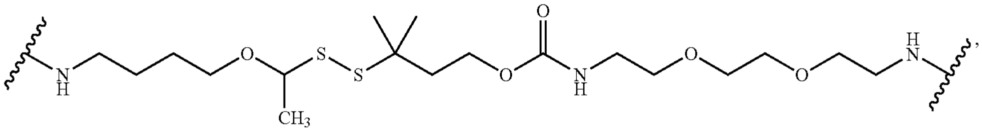
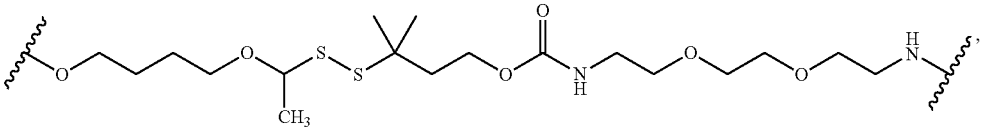
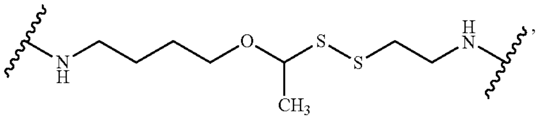
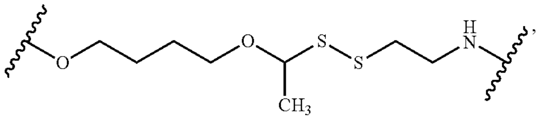

-continued
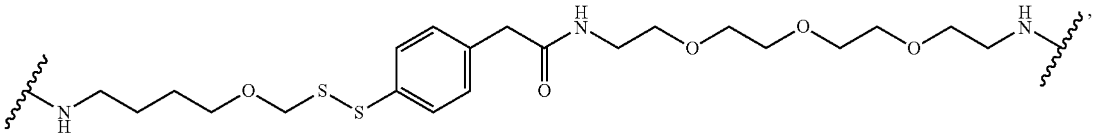
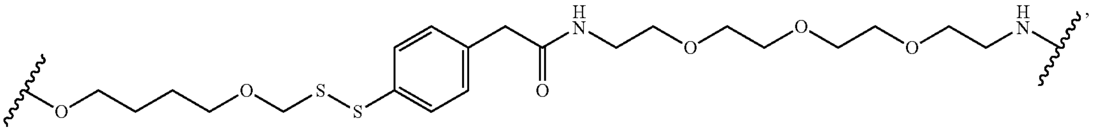
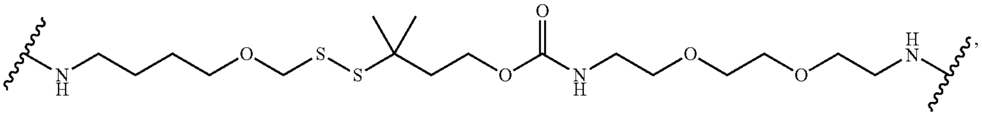
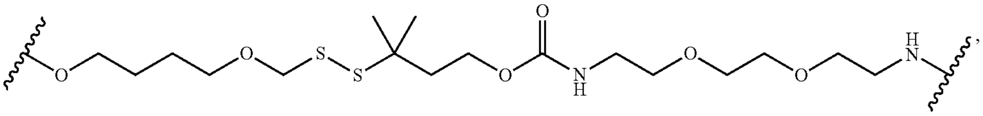
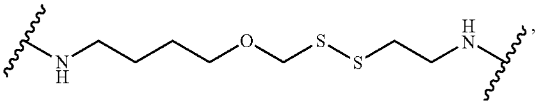
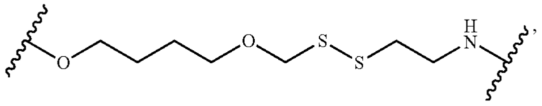
or
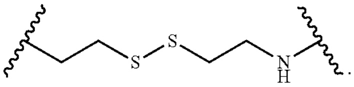
In embodiments, B is
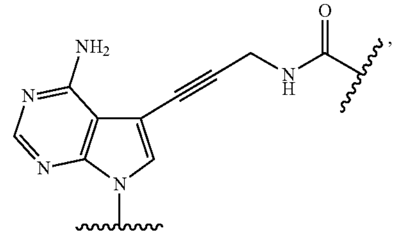
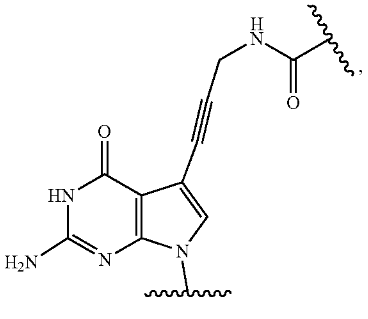
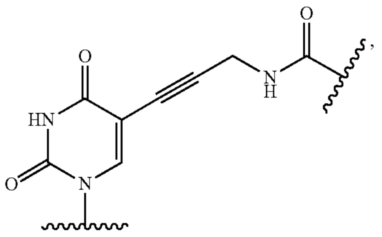
or
-continued
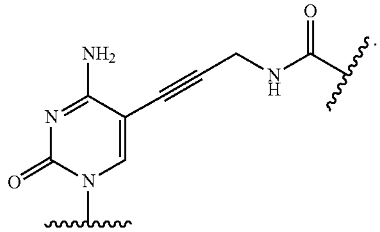
In embodiments, $L^{100}$ is
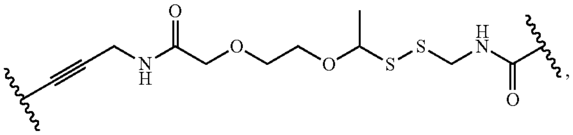
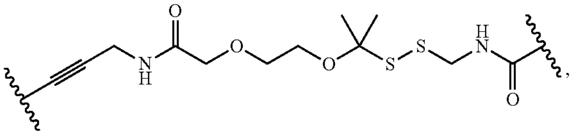
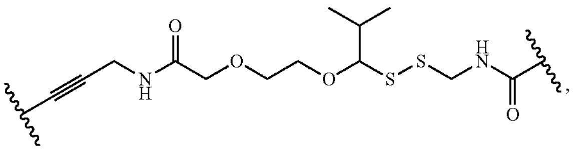
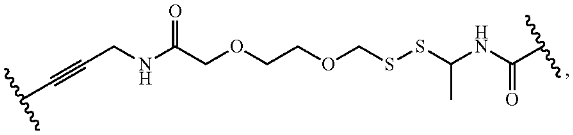

-continued
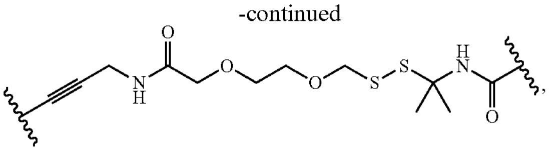
, or
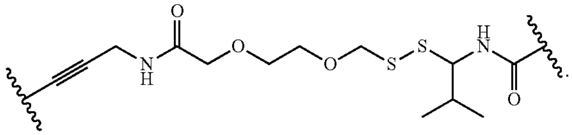
.
In embodiments, $L^{100}$ is
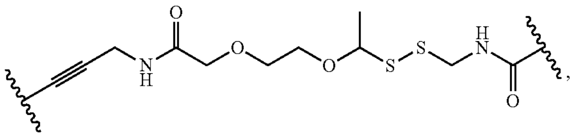
,
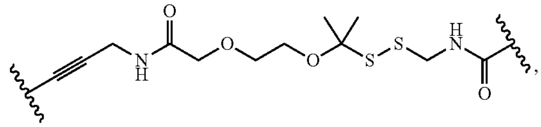
, or
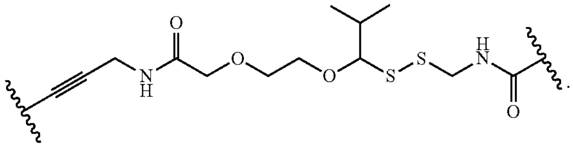
.
In embodiments, $L^{100}$ is
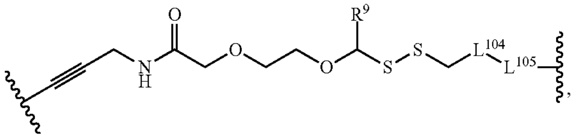
,
-continued
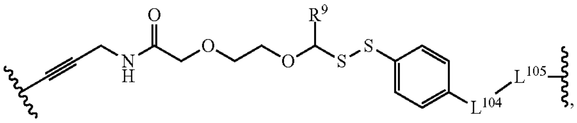
,
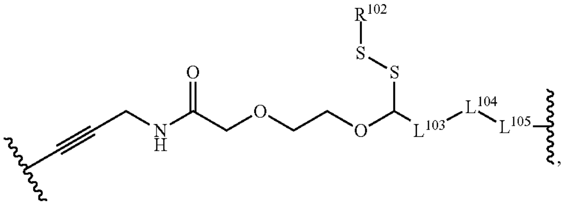
,
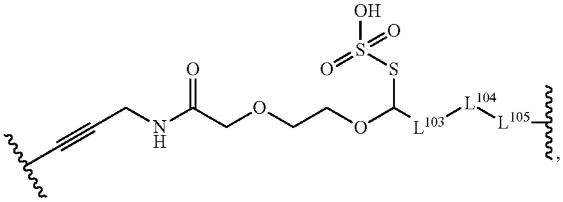
,
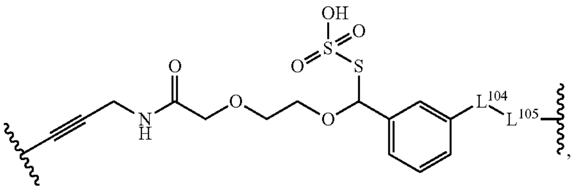
,
or
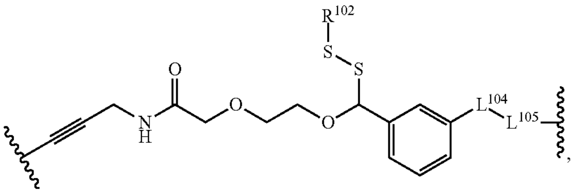
,
wherein $R^9$, $L^{104}$, $L^{105}$, and $R^{102}$ are as described herein. In embodiments, $L^{100}$ is
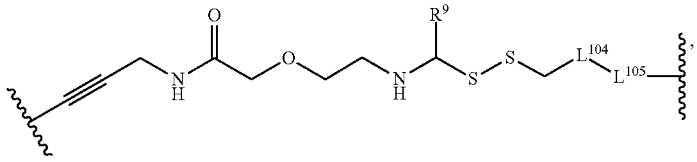
,
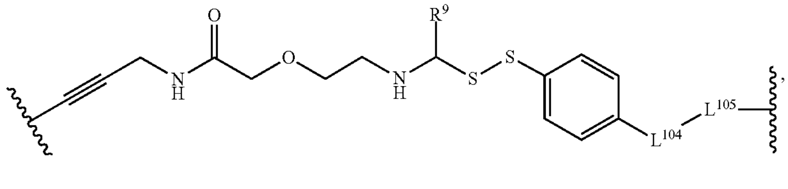
,
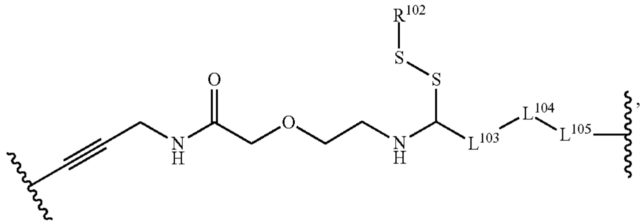
, -continued
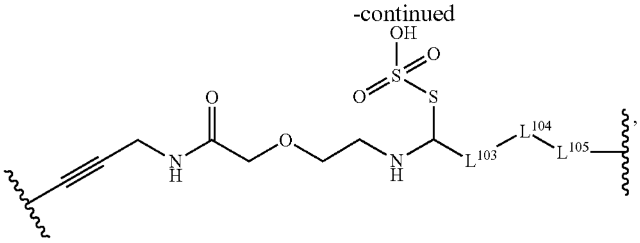
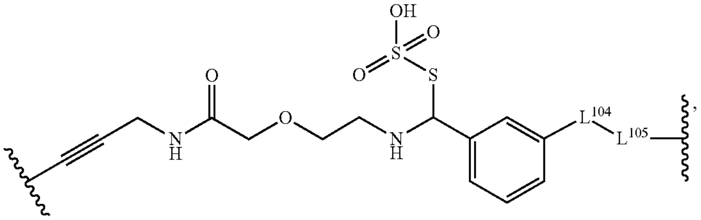
or
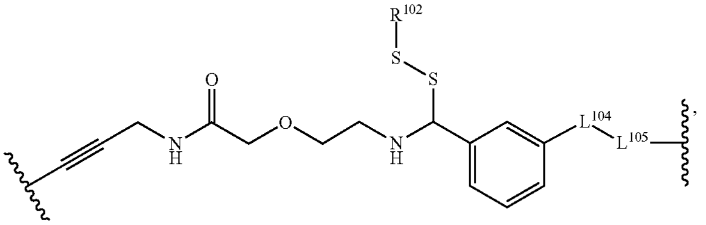
wherein $R^9$, $L^{104}$, $L^{05}$, and $R^{102}$ are as described herein. In embodiments, $L^{100}$ is
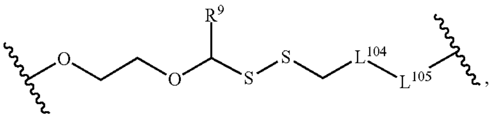
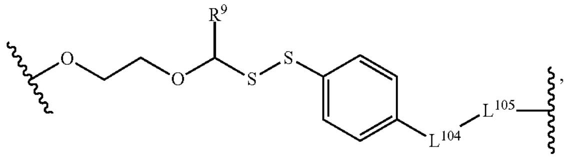
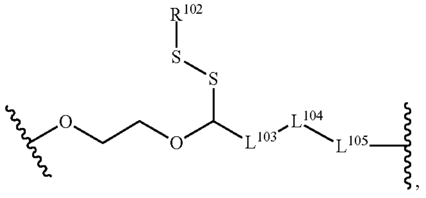
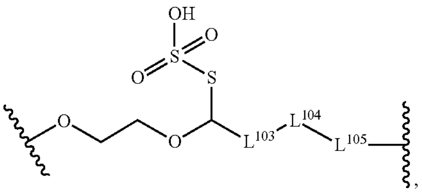
or
-continued
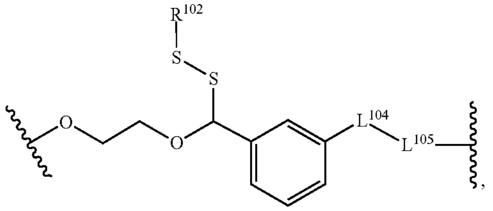
wherein $R^9$, $L^{104}$, $L^{105}$, and $R^{102}$ are as described herein. In embodiments, $L^{100}$ is
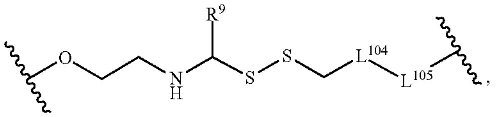
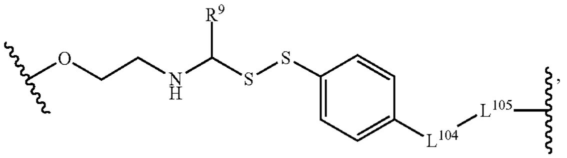
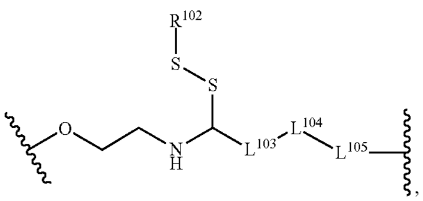

-continued
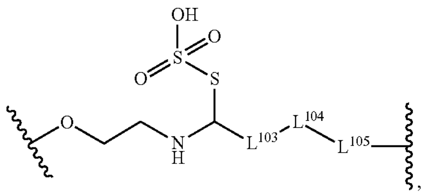
, or
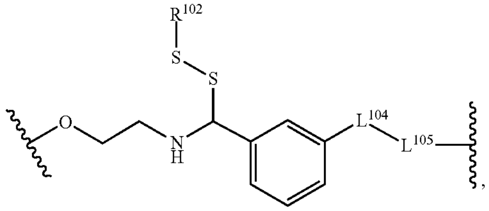
,
wherein $R^9$, $L^{104}$, $L^{105}$, and $R^{102}$ are as described herein.
In embodiments, $L^{100}$ is
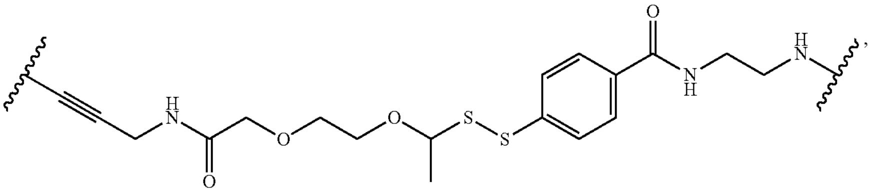
,
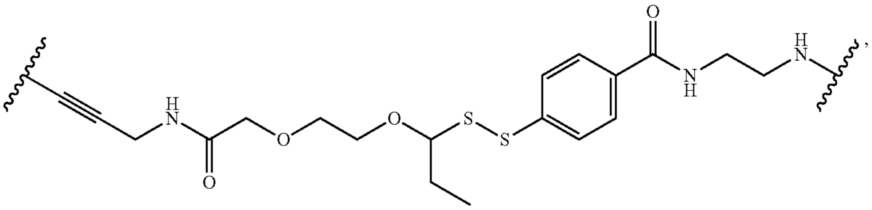
, or
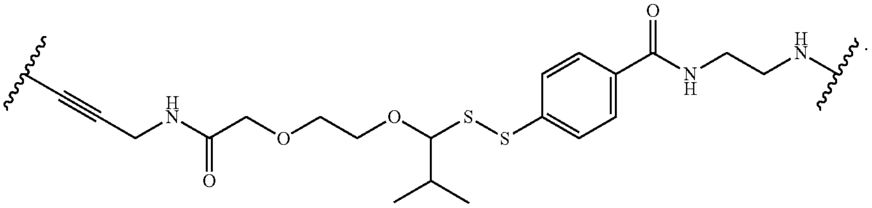
.
In embodiments, $L^{100}$ is
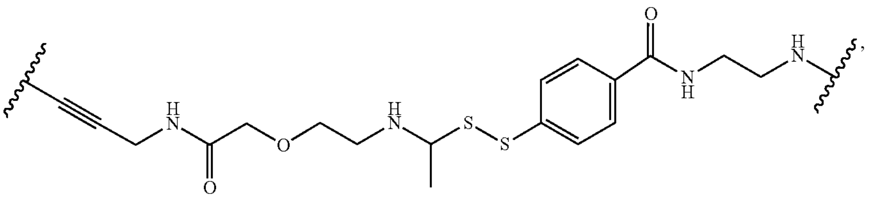
,
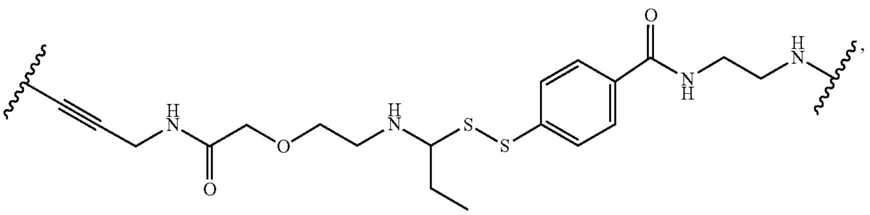
, or -continued
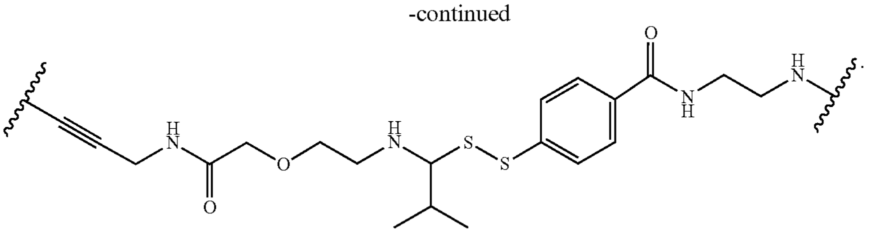
In embodiments, $L^{100}$ is
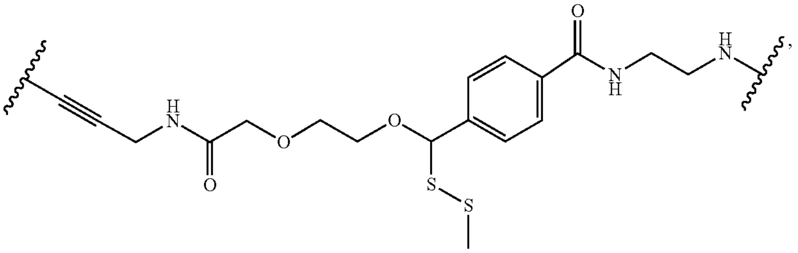
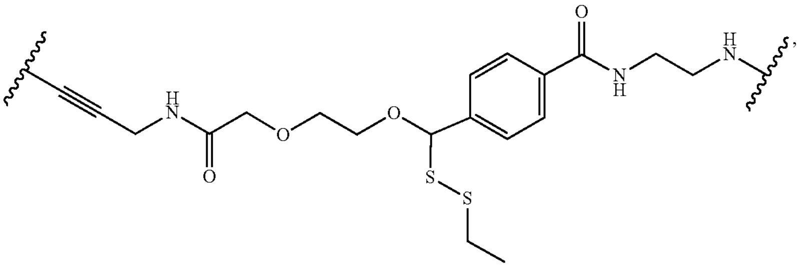
or
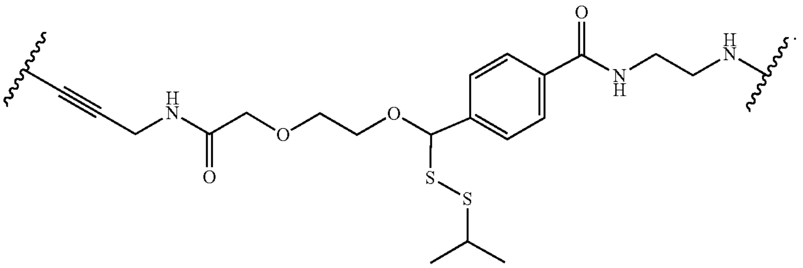
In embodiments, $L^{100}$ is
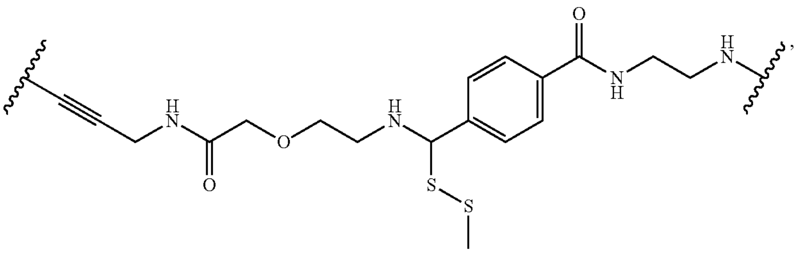

-continued

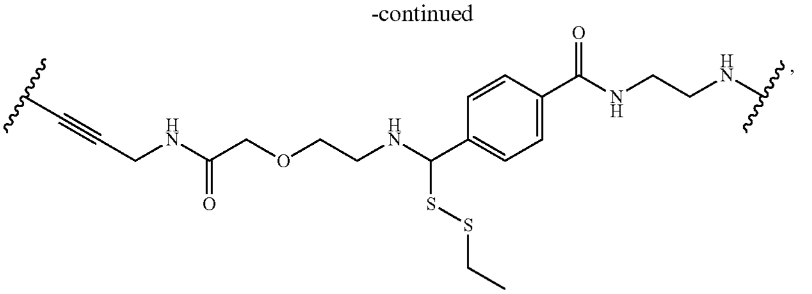

or

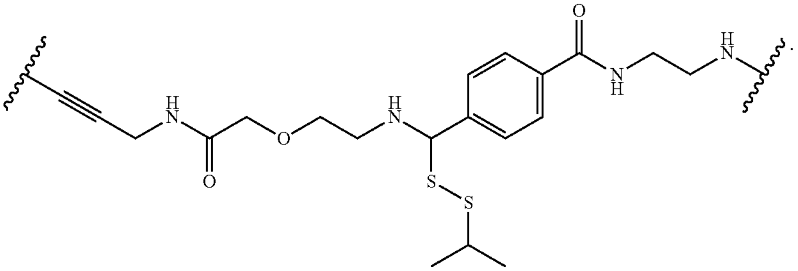

In embodiments, $L^{100}$ is

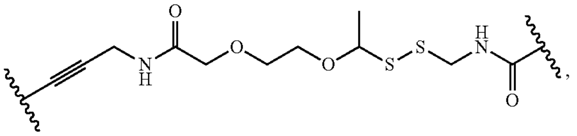

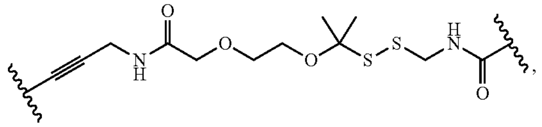

or

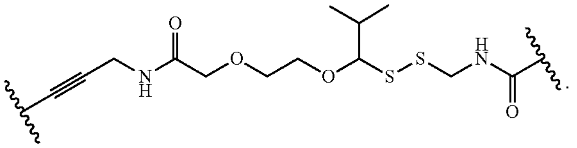

In embodiments, $L^{100}$ is

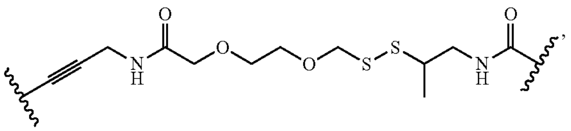

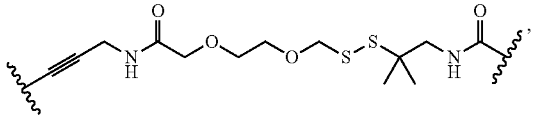

or

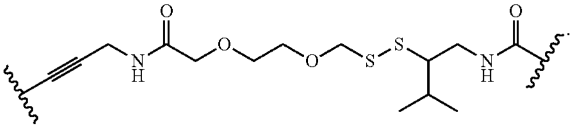

In embodiments, $R^4$ is a detectable moiety. In embodiments, $R^4$ is a fluorescent dye moiety. In embodiments, $R^4$ is a detectable moiety described herein (e.g., Table 1). In embodiments, $R^4$ is a detectable moiety described in Table 1.

TABLE 1

Detectable moieties to be used in selected embodiments.

| Nucleoside/nucleotide abbreviation | Dye name | λmax (nm) |
|---|---|---|
| dC | Atto 532 | 532 |
| dC | Atto Rho 6G | 535 |
| dC | R6G | 534 |
| dC | Tet | 521 |
| dT | Atto Rho 11 | 572 |
| dT | Atto 565 | 564 |
| dT | Alexa Fluor 568 | 578 |
| dT | dTamra | 578 |
| dA | Alexa Fluor 647 | 650 |
| dA | Atto 647N | 644 |
| dA | Janelia Fluor 646 | 646 |
| dG | Alexa Fluor 680 | 682 |
| dG | Alexa Fluor 700 | 696 |
| dG | CF680R | 680 |

In embodiments, $R^4$ is

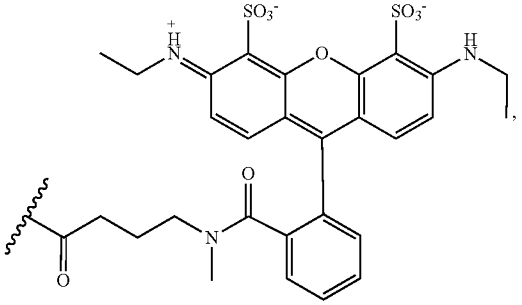

-continued

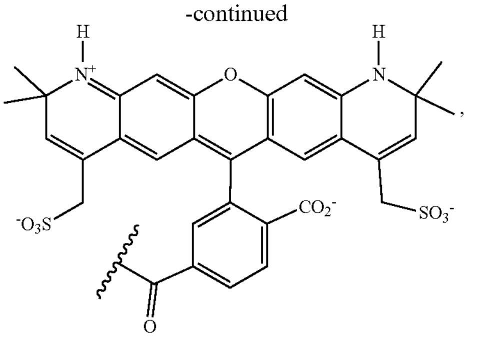

,

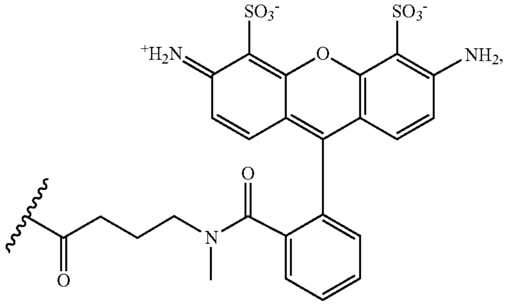

or

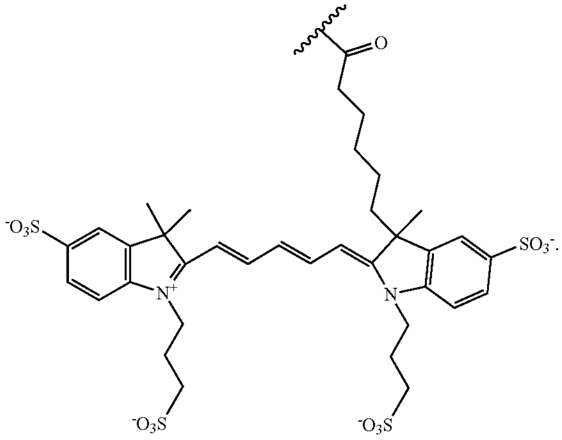

.

In embodiments, $R^4$ is an anchor moiety. In embodiments, the anchor moiety (e.g., biotin moiety) interacts non-covalently with a complementary anchor moiety binder (e.g., streptavidin moiety). In embodiments, the anchor moiety (e.g., azide moiety, trans-cyclooctene (TCO) moiety, phenyl boric acid (PBA) moiety) covalently binds a complementary anchor moiety binder (e.g., dibenzocyclooctyne (DBCO) moiety (Jewett J. C. and Bertozzi C. R. *J. Am. Chem. Soc.*, 2010, 132, 3688-3690), tetrazine (TZ) moiety, salicylhydroxamic acid (SHA) moiety), thereby forming a covalent linker (e.g., azide-TZ linker; TCO-DBCO linker; PBA-SHA linker). In embodiments, the anchor moiety is biotin, azide, transcyclooctene (TCO), or phenyl boric acid (PBA). In embodiments, the anchor moiety is a biotin moiety.

In embodiments, $R^4$ has the formula $L^4$-$R^{4D}$; wherein $L^4$ is a covalent linker and $R^{4D}$ is a anchor moiety or a detectable moiety, as described herein. In embodiments, $R^{4D}$ is a detectable moiety. In embodiments, $R^{4D}$ is a fluorescent dye moiety. In embodiments, $R^{4D}$ is a detectable moiety described herein (e.g., Table 1). In embodiments, $R^{4D}$ is a detectable moiety described in Table 1.

In embodiments, $L^4$ is a bond, —NH—, —O—, —C(O)—, —C(O)NH—, —NHC(O)—, —NHC(O)NH—, —C(O)O—, —OC(O)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^4$ is a bond, —NH—, —O—, —C(O)—, —C(O)NH—, —NHC(O)—, —NHC(O)NH—, —C(O)O—, —OC(O)—, $R^{4A}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{4A}$-substituted or unsubstituted heteroalkylene (e.g., 2 to 20, 8 to 20, 2 to 10, 2 to 8, 2 to 6, or 2 to 4 membered), $R^{4A}$-substituted or unsubstituted cycloalkylene (e.g., $C_3$-$C_8$, $C_3$-$C_6$, or $C_5$-$C_6$), $R^{4A}$-substituted or unsubstituted heterocycloalkylene (e.g., 3 to 8, 3 to 6, or 5 to 6 membered), $R^{4A}$-substituted or unsubstituted arylene (e.g., $C_6$-$C_{10}$, $C_{10}$, or phenylene), or $R^{4A}$-substituted or unsubstituted heteroarylene (e.g., 5 to 10, 5 to 9, or 5 to 6 membered). In embodiments, $L^{4A}$ is $R^{4A}$-substituted or unsubstituted $C_1$-$C_{20}$ alkylene. In embodiments, $L^{4A}$ is $R^{4A}$-substituted or unsubstituted 2 to 20 membered heteroalkylene. In embodiments, $L^{4A}$ is $R^{4A}$-substituted or unsubstituted $C_3$-$C_8$ cycloalkylene. In embodiments, $L^{4A}$ is $R^{4A}$-substituted or unsubstituted 3 to 8 membered heterocycloalkylene. In embodiments, $L^{4A}$ is $R^{4A}$-substituted or unsubstituted $C_6$-$C_{10}$ arylene. In embodiments, $L^{4A}$ is $R^{4A}$-substituted or unsubstituted 5 to 10 membered heteroarylene. In embodiments, $L^{4A}$ is independently a bond or substituted or unsubstituted 2 to 10 membered heteroalkylene.

$R^{4A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^4$ is

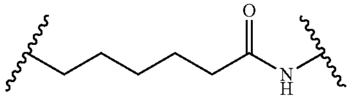

,

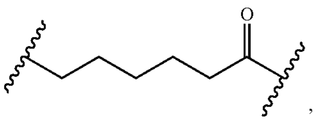

,

-continued
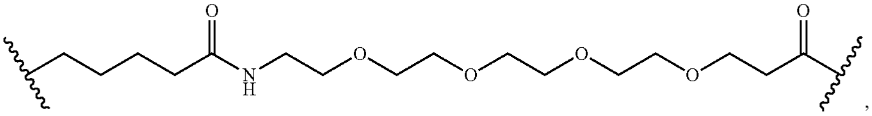
,
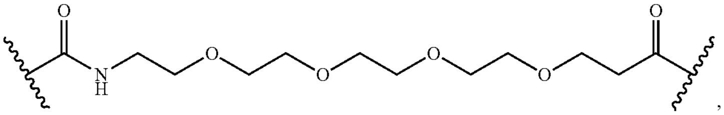
, or
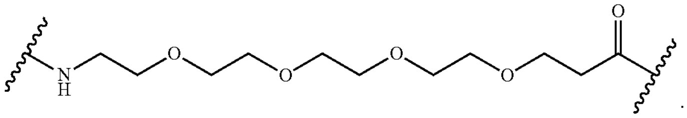
.
In embodiments, $L^4$ is
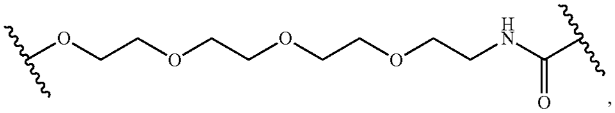
,
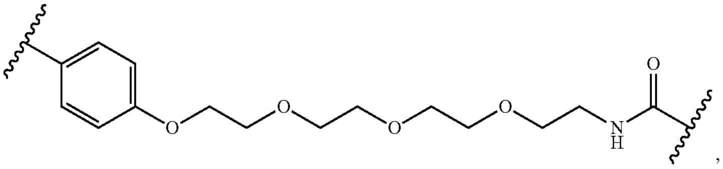
,
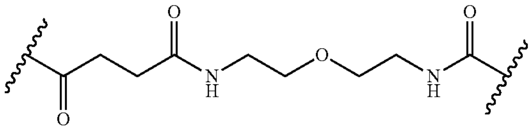
,
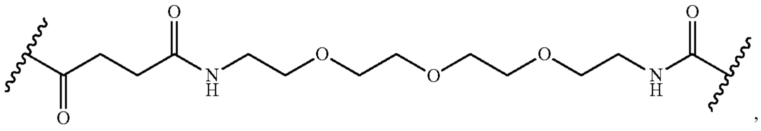
, or
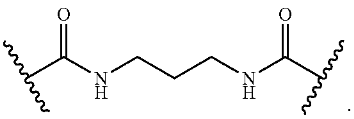
.
In embodiments, the compound has the formula:
(Ia)
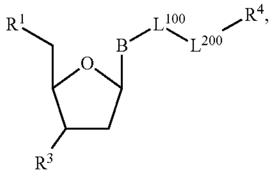

wherein $R^1$, $R^3$, $L^{100}$, $L^{200}$, and $R^4$ are as described herein, including embodiments. In embodiments, the compound has the formula:
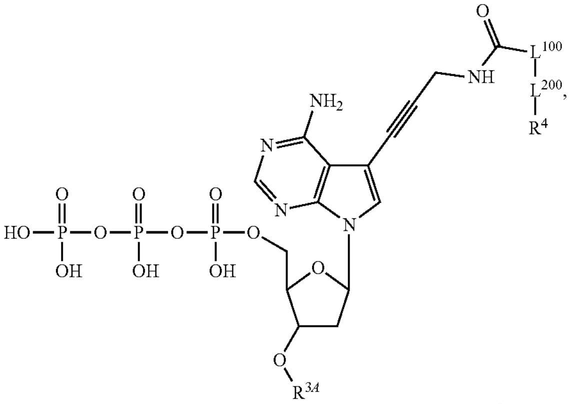
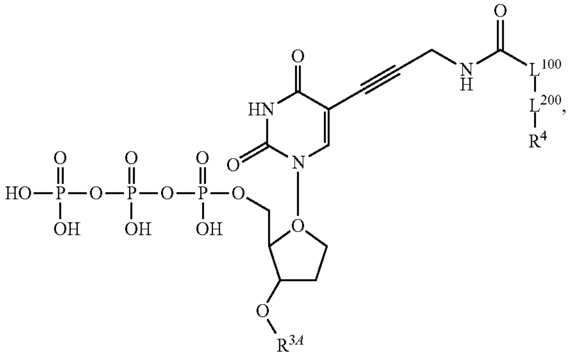
-continued
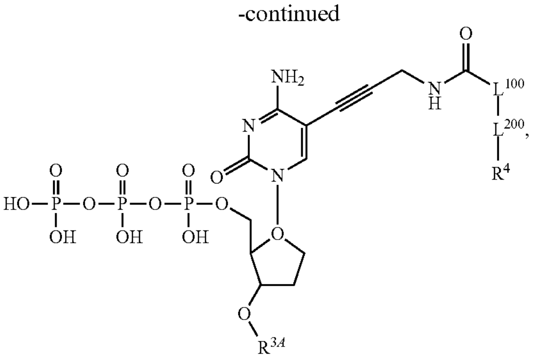
or
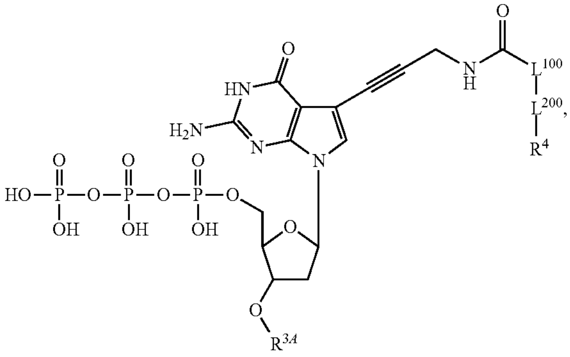
wherein $L^{100}$, $L^{200}$, $R^3$, and $R^4$ are as described herein. In embodiments, the compound has the formula:
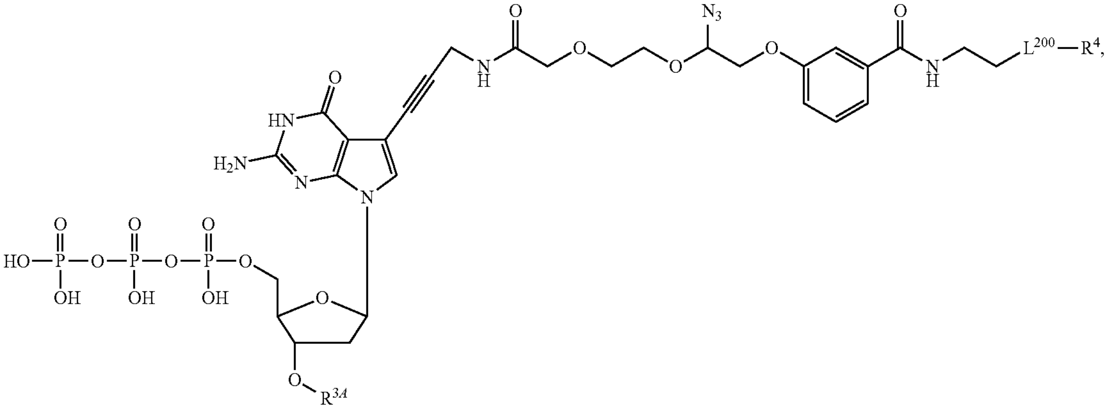

-continued
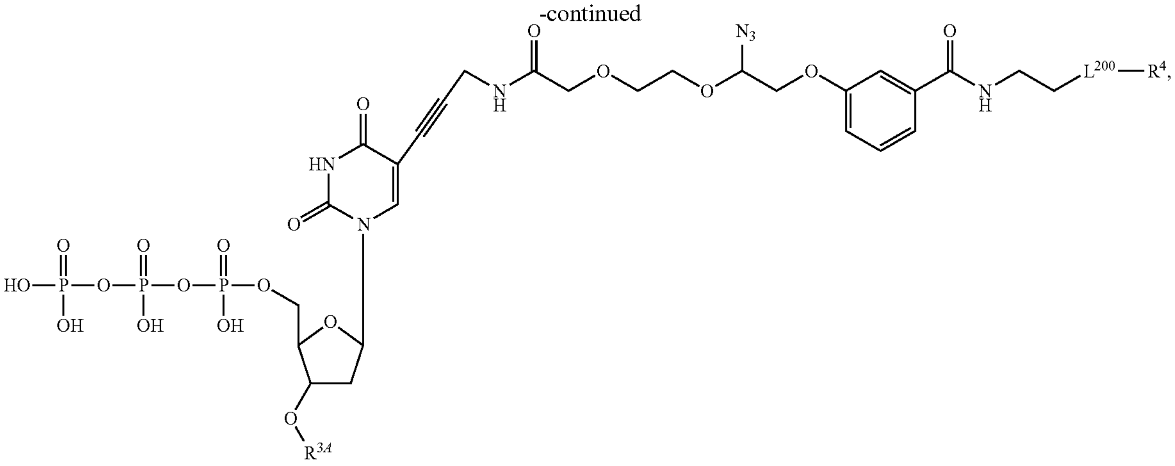
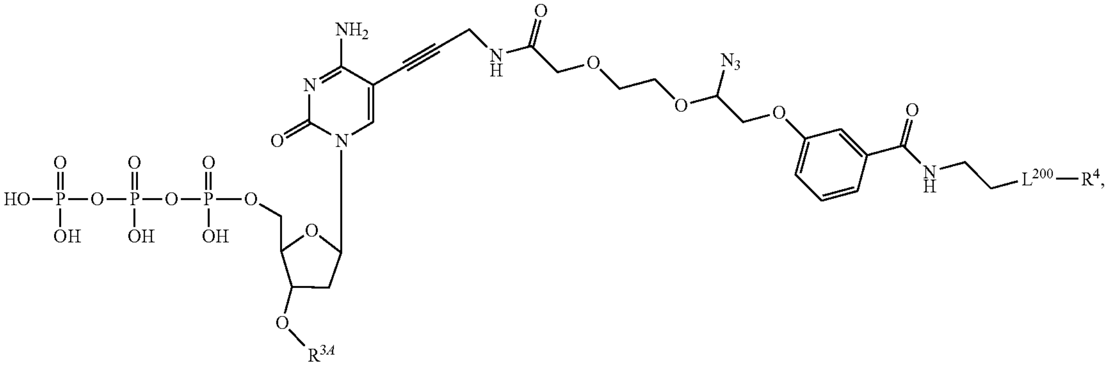
, or
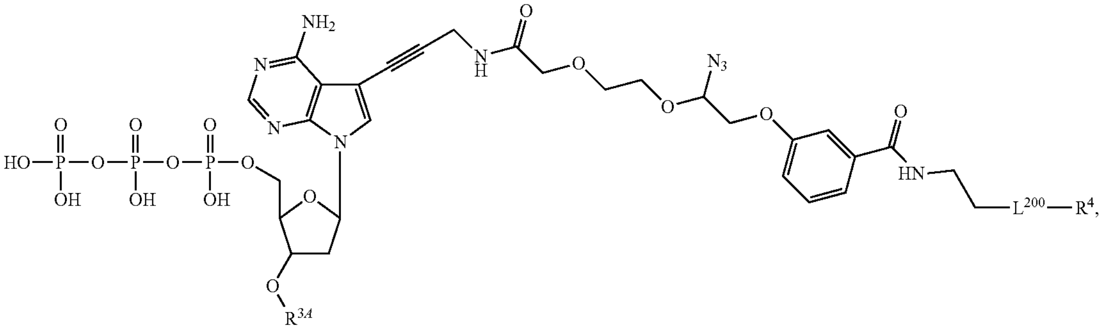
wherein $L^{200}$, $R^{3A}$, and $R^4$ are as described herein. In embodiments, the compound has the formula:
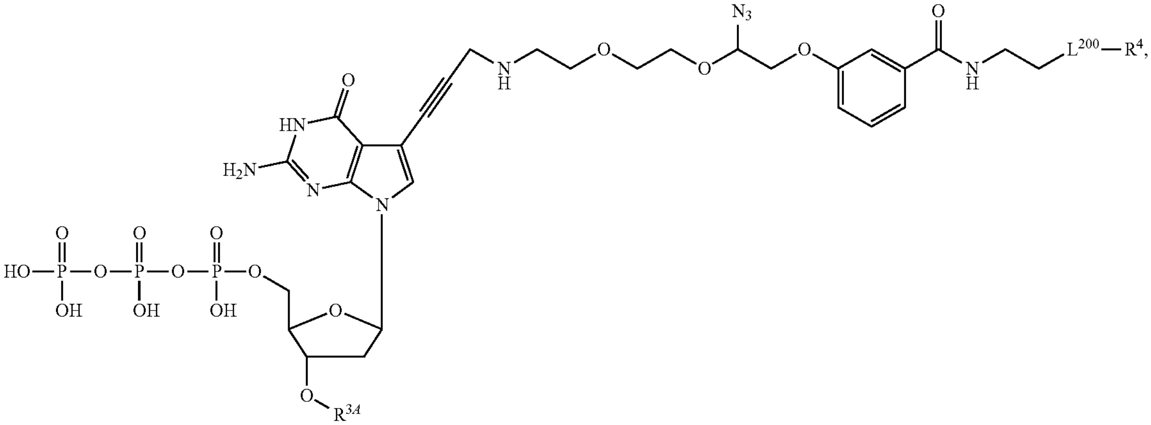

-continued
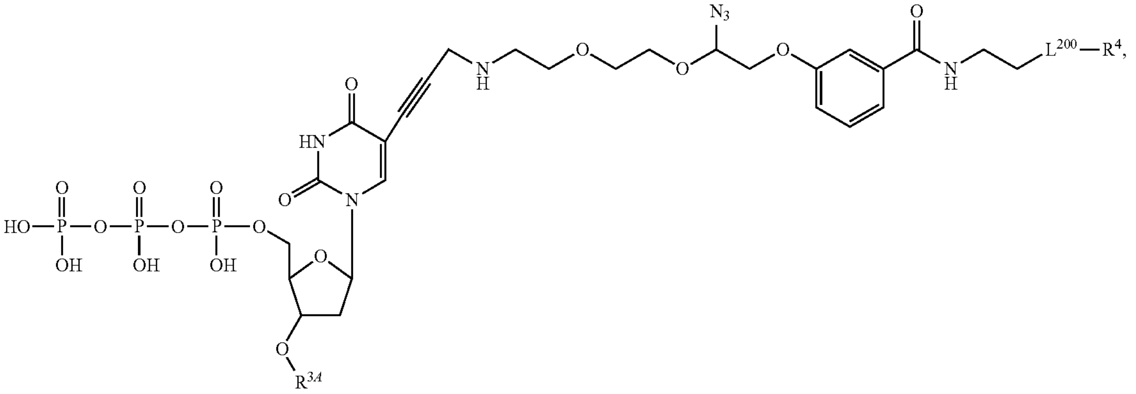
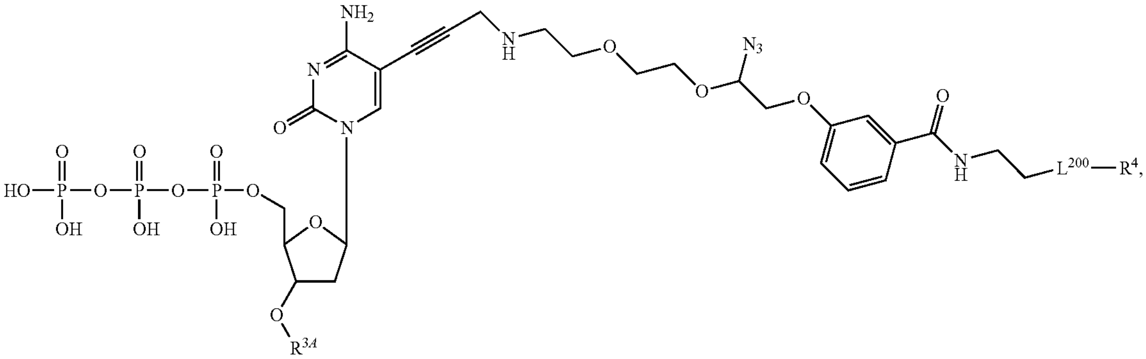
or
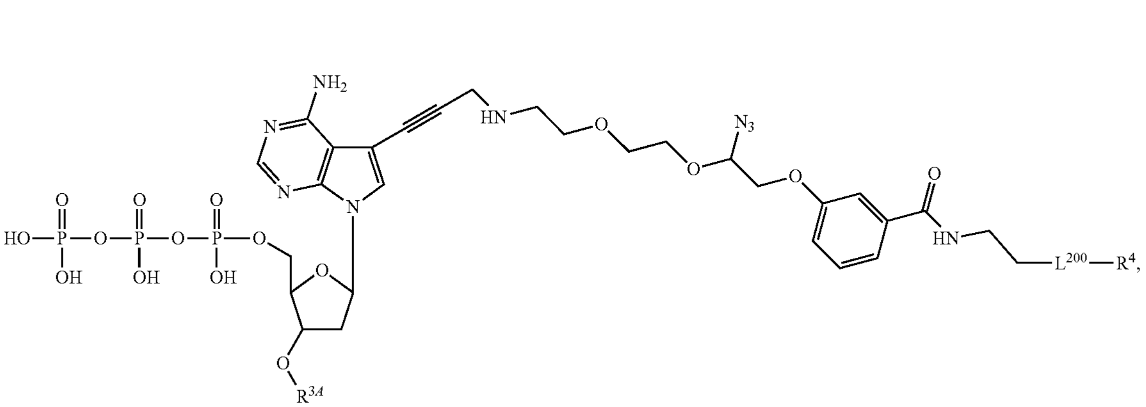

wherein $L^{200}$, $R^{3A}$, and $R^4$ are as described herein.
In embodiments, the compound has the formula:
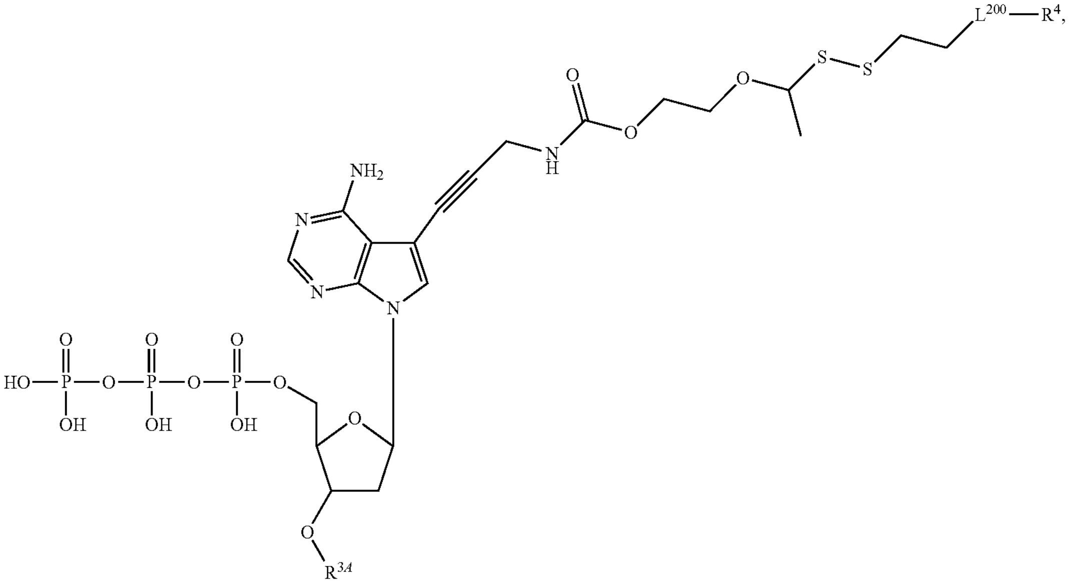
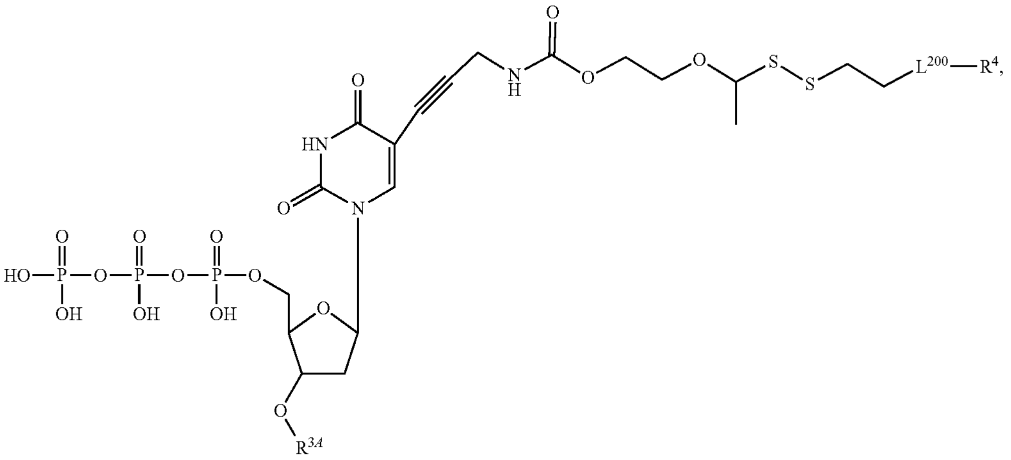
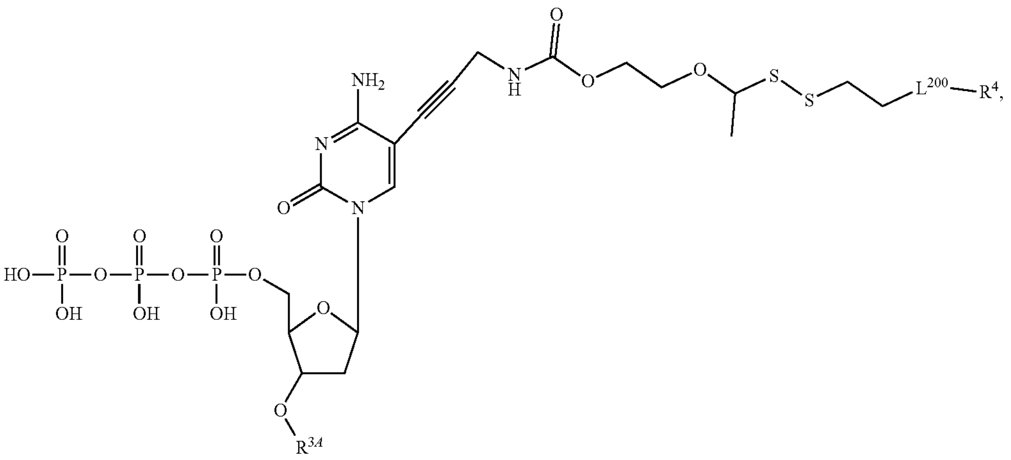
or -continued
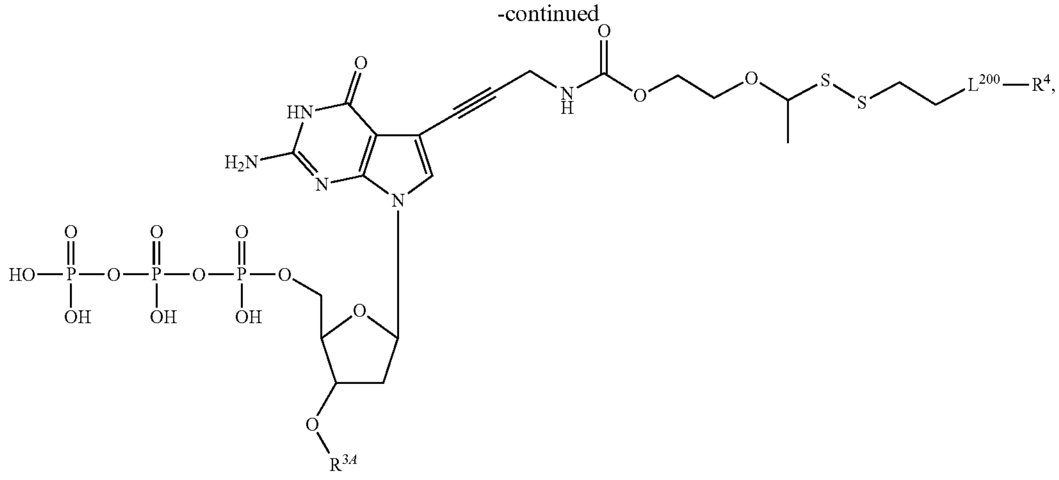
wherein $L^{200}$, $R^{3A}$, and $R^4$ are as described herein.
In embodiments, the compound has the formula:
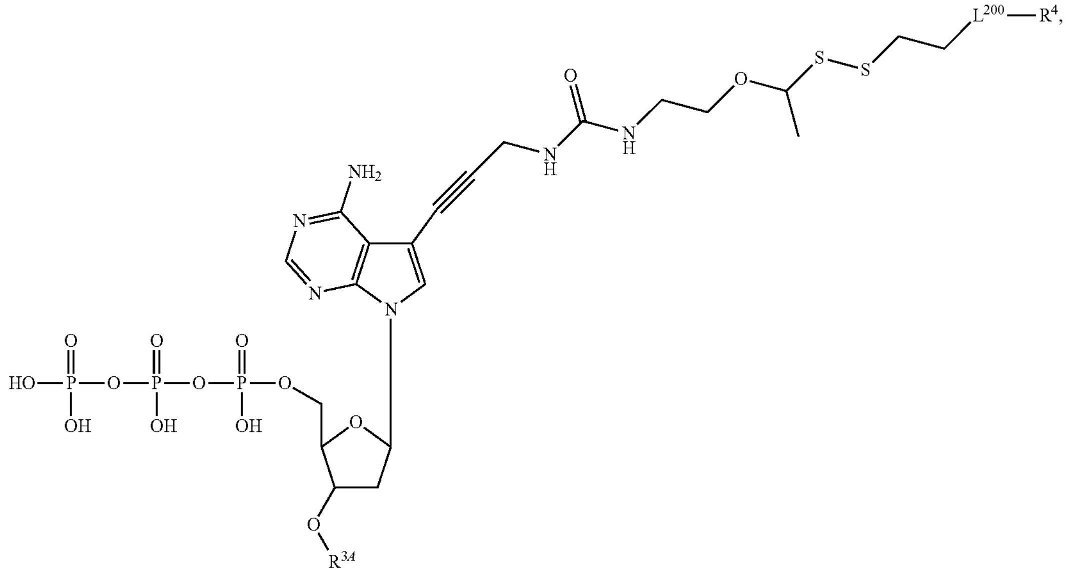
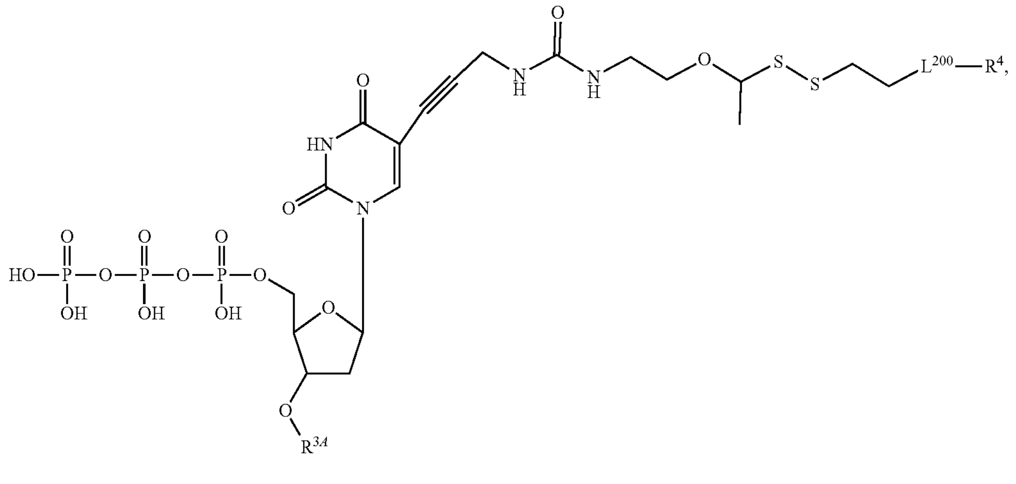

-continued
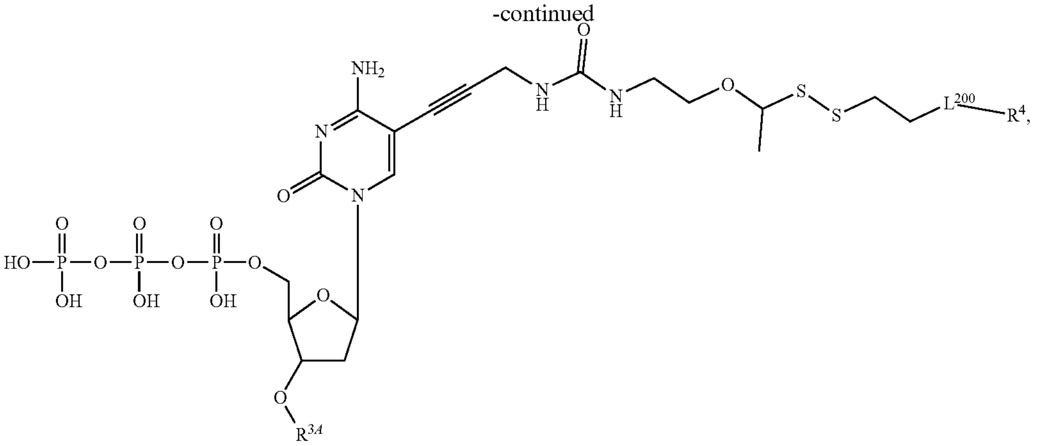
or
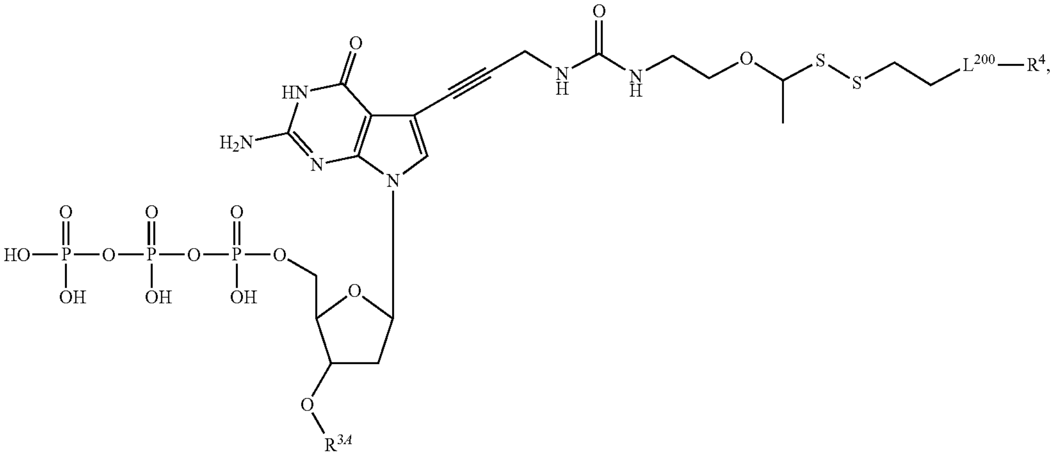
wherein $L^{200}$, $R^{3A}$ and $R^4$ are as described herein.
In embodiments, the compound has the formula:
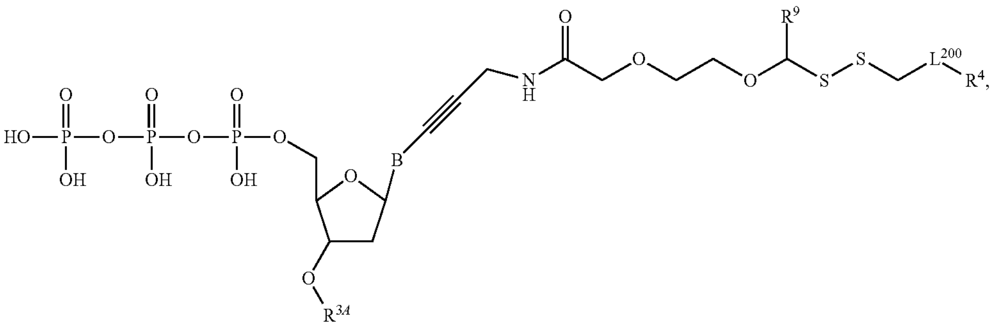

$L^{200}$, and $R^4$ are as described herein, including in embodiments. In embodiments, the compound has the formula:

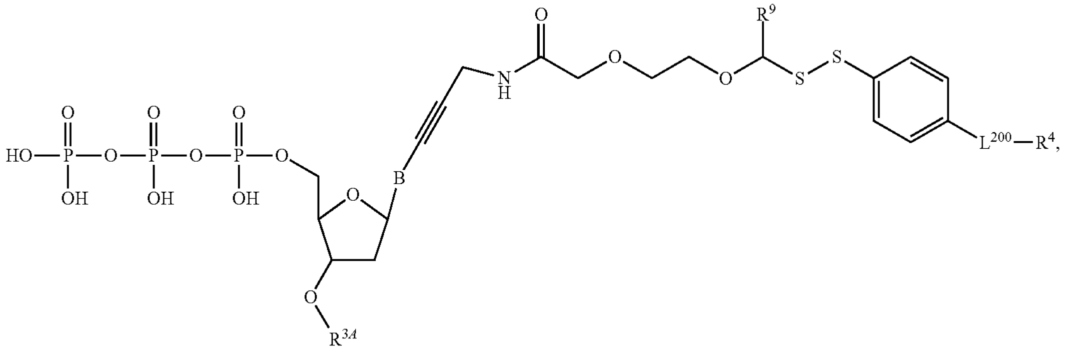

wherein B, $R^{3A}$, $R^9$, $L^{200}$, and $R^4$ are as described herein, including in embodiments. In embodiments, the compound has the formula:

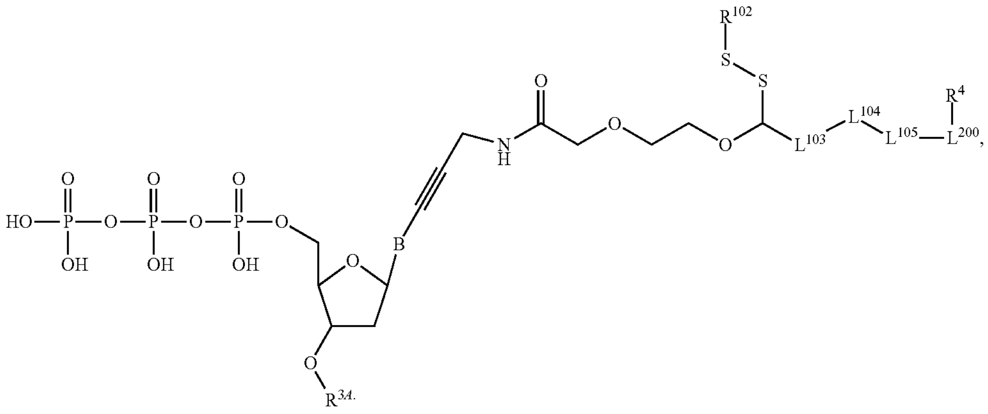

wherein B, $R^{3A}$, $R^{102}$, $L^{103}$, $L^{104}$, $L^{105}$, $L^{200}$, and $R^4$ are as described herein, including in embodiments. In embodiments, the compound has the formula:

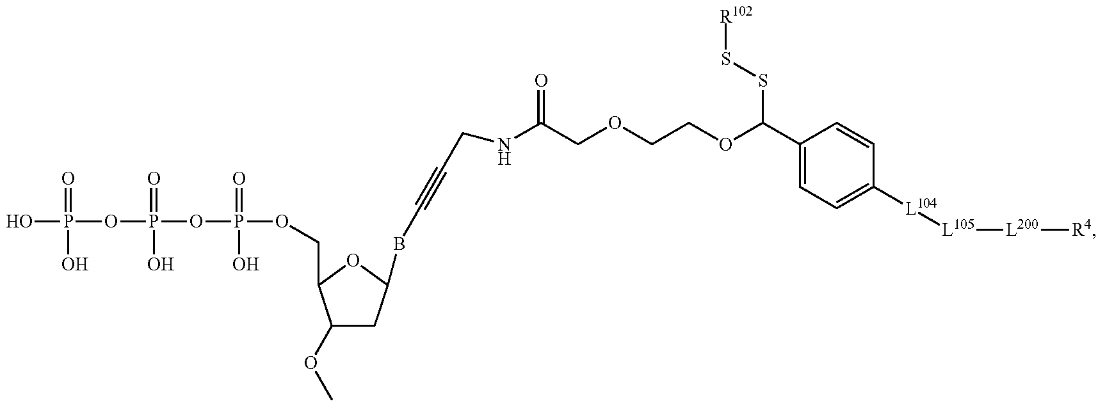

wherein B, $R^3$, $R^{102}$, $L^{103}$, $L^{104}$, $L^{105}$, $L^{200}$, and $R^4$ are as described herein, including in embodiments. In embodiments, $R^8$ is an unsubstituted $C_1$-$C_2$ alkyl.

In embodiments, $L^{200}$ is a rigid spacer. One function of the rigid spacer is to maintain the detectable label (e.g., $R^4$ or $R^6$) a fixed length away from the nucleobase. In embodiments, the rigid spacer is a plurality of monomeric subunits (e.g., of formula IV) that prevents the detectable label from interacting with a nucleobase (e.g., the nucleobase to which the detectable label is covalently linked). In embodiments, the rigid spacer forms a linear linker. In embodiments, the rigid spacers as described herein do not substantially bend or flex and do not allow substantial rotation either along their length or at their attachments points. Due to differences in the relative flexibility of different linkers, distances are generally described as having operating or functional distances, e.g., the average maintained distance between a detectable label group and the nucleotide base.

In embodiments, the rigid spacer is stiff (i.e., rigid) in solution, such that the rigid spacer is stiffer than a flexible linking moiety (e.g., a covalent linker without a rigid spacer). A flexible linking moiety is flexible in a manner similar to the hinge of tongs, or a slinky, such that it allows for movement of the covalent linker. Flexible, as used when describing a linking moiety, refers to the ability of a flexible linking moiety to change its bending or coiling conformation in solution. Known methods in the art to quantify rigidity, or degree of linearity may be used. The use of resonance energy transfer has been used to quantify flexible and rigid polypeptides by providing distance distributions separating a donor and acceptor pair (see for example Haas et al PNAS USA 72:1807-1811 (1975); and Lakowicz et al. Proc SPIE 1204:192-205 (1990), incorporated herein by reference for all uses. The FRET efficiency may then be converted to persistence length by comparing the FRET efficiency with calculated FRET efficiency based on models such as the worm-like chain model, or other known methods in the art. For the rigid spacers of the present disclosure, the rigid spacers increase the persistence length ($l_P$) of the overall covalent linkage relative to an identical molecule absent the rigid spacer. The rigid spacer behaves like a rigid rod when the total end-to-end length is less than the ($l_P$). Experimental and theoretical data suggests polyphenylene linkers have surprisingly large persistence length values, and found a phenylene monomer ($l_P$) of 0.86 nm/phenylene (Forero-Martinez, N. C., et al. (2019). Macromolecules, 52(14), 5307-5316), incorporated herein by reference for all uses, and extract a monomer persistence length of 0.86 nm/phenylene). Therefore, it is estimated that the rigid spacers described herein, such as the rigid spacers formed using Formula IV or Formula V, increase ($l_P$) approximately 8.6 Å per monomer. For example, a 5mer (i.e., a rigid spacer containing 5 monomers of Formula IV or Formula V) is estimated to have a persistence length of 4.3 nm and maintain rod-like, linear, character when the total length of the rigid spacer is less than 4.3 nm.

A simple method for quantifying the rigidity of a nucleotide containing a rigid spacer, is to measure the absorbance spectra of a FRET pair (i.e., a donor dye and acceptor dye) separated by a rigid spacer as further described in Example 5. In this sense, the efficiency of Fluorescence Resonance Energy Transfer (FRET) between a donor and an acceptor molecule attached to opposite ends of a linker containing a rigid spacer is used as a proxy for the nucleobase covalently linked to a detectable label. Briefly, in an organic solvent, (e.g., ethanol) the donor and acceptor moieties are solvated by the organic molecules and prevented from aggregating. In water, the donor and acceptor moieties come into contact, stack, or aggregate in water and thus their absorbance spectra is altered. Similarly, if the linker is too flexible, it permits the donor and acceptor moieties to come into contact, stack, or aggregate, modifying the absorbance spectra. Ideally, a rigid linker (i.e., a linker described herein containing rigid spacers) limits the contact between the FRET pair and, for example, will have an absorbance spectra similar to the FRET pair in EtOH. Further, a FRET ratio may be calculated. In embodiments, a rigid spacer prevents the detectable label from interacting with the nucleobase. This may be inferred from measuring the absorbance spectra of a FRET pair (i.e., a donor dye and acceptor dye) separated by a rigid spacer as further described in Example 5. Non-limiting examples of flexible linking moieties include aliphatic moieties, PEG moieties, single-stranded DNA oligonucleotide moieties, single-stranded RNA moieties, single-stranded PNA moieties, sugar phosphate moieties (i.e., a DNA backbone without the nucleobases), and peptide moieties.

In embodiments, the rigid spacer minimally change their conformation solution. In embodiments, the rigid spacer has a persistence length, which is the length at which the rigid spacer retains stiffness (i.e., rigidity) in solution. In embodiments, the length of the rigid spacer may be determined based on the persistence length.

In embodiments, $L^{200}$ is a divalent polymer, divalent double-stranded nucleic acid, or divalent polypeptide. In embodiments, $L^{200}$ is a divalent polymer. In embodiments, $L^{200}$ is a divalent double-stranded nucleic acid. In embodiments, the double-stranded nucleic acid is 50 bases or less in length. In embodiments, the double-stranded nucleic acid is 40 bases or less in length. In embodiments, the double-stranded nucleic acid is 30 bases or less in length. In embodiments, the double-stranded nucleic acid is 20 bases or less in length. In embodiments, the double-stranded nucleic acid is 10 bases or less in length.

Typically, non-peptide rigid spacers may include laterally rigid chemical groups, such as having ring structures (e.g., aromatic moieties), or higher order chemical bonds between adjacent groups (e.g., double or triple bonds), in order to prevent rotation of groups relative to each other. Preventing bending and/or rotation limits the flexibility of the overall covalent linker. Polypeptides rigid linkers may be comprised of rigid monomers. Polypeptide rigid linkers may derive rigidity both from secondary structures, or may be comprised of other amino acids or amino acid combinations or sequences that impart rigid secondary or tertiary structures (e.g., helices, fibrils, sheets). For example a rigid linker may be comprised of fragments of structured rigid proteins, such as fibrin, collagen, or tubulin. In embodiments, the polypeptide rigid spacer is described in Choi et al Chem. Sci., 2019, 10, 10428-10435, which is incorporated herein by reference for all purposes.

In embodiments, $L^{200}$ is a divalent polypeptide. In embodiments, the divalent polypeptide is divalent polyproline. In embodiments, the divalent polypeptide includes the amino acid sequences $(EAAAK)_{n1}$ (SEQ ID NO:1), $(EP)_{n2}$ (SEQ ID NO:5), $(KP)_{n3}$ (SEQ ID NO:6), $(AP)_{n4}$ (SEQ ID NO:7), or $(TPR)_{n5}$ (SEQ ID NO:8), wherein n1, n2, n3, n4, and n5 are each independently an integer from 2 to 20. In embodiments, the divalent polypeptide comprises the amino acid sequences $(EAAAK)_{n1}$ (SEQ ID NO:1), $(EP)_{n2}$ (SEQ ID NO:5), $(KP)_{n3}$ (SEQ ID NO:6), wherein n1, n2, and n3 are each independently an integer from 2 to 6.

In embodiments, the rigid spacer maintains the detectable label at least 1, 1.5, 2, 2.5, 3, 3.5, 4, 4.5, or 5 nm from the nucleobase. In embodiments, the covalent linker (e.g., $L^5$) and the rigid spacer (e.g., $L^{200}$) collectively maintain the detectable label (e.g., $R^4$ or $R^6$) at least 1, 1.5, 2, 2.5, 3, 3.5, 4, 4.5, or 5 nm from the nucleobase (e.g., B). In embodiments, the detectable label is at least 1, 1.5, 2, 2.5, 3, 3.5, 4, 4.5, or 5 nm from the nucleobase. In embodiments, the rigid spacer maintains the detectable label 1, 1.5, 2, 2.5, 3, 3.5, 4, 4.5, or 5 nm from the nucleobase. In embodiments, the covalent linker and the rigid spacer collectively maintain the detectable label 1, 1.5, 2, 2.5, 3, 3.5, 4, 4.5, or 5 nm from the nucleobase. In embodiments, the detectable label is 1, 1.5, 2, 2.5, 3, 3.5, 4, 4.5, or 5 nm from the nucleobase. In embodiments, the rigid spacer maintains the detectable label at least 1 nm from the nucleobase. In embodiments, the covalent linker and the rigid spacer collectively maintain the detectable label at least 1 nm from the nucleobase. In embodiments, the detectable label is 1 nm from the nucleobase. In embodiments, the rigid spacer maintains the detectable label 1 nm from the nucleobase. In embodiments, the covalent linker and the rigid spacer collectively maintain the detectable label 1 nm from the nucleobase. In embodiments, the detectable label is 1 nm from the nucleobase. In embodiments, the rigid spacer maintains the detectable label at least 1, 2, 3, 4, 5, 6, 7, 8, 9, or 10 nm from the nucleobase. In embodiments, the covalent linker and the rigid spacer collectively maintain the detectable label at least 1, 2, 3, 4, 5, 6, 7, 8, 9, or 10 nm from the nucleobase. In embodiments, the detectable label is at least 1, 2, 3, 4, 5, 6, 7, 8, 9, or 10 nm from the nucleobase. In embodiments, the rigid spacer maintains the detectable label 1, 2, 3, 4, 5, 6, 7, 8, 9, or 10 nm from the nucleobase. In embodiments, the covalent linker and the rigid spacer collectively maintain the detectable label 1, 2, 3, 4, 5, 6, 7, 8, 9, or 10 nm from the nucleobase. In embodiments, the detectable label is 1, 2, 3, 4, 5, 6, 7, 8, 9, or 10 nm from the nucleobase. In embodiments, the rigid spacer maintains the detectable label 1 to 2 nm from the nucleobase. In embodiments, the rigid spacer maintains the detectable label 1 to 3 nm from the nucleobase. In embodiments, the rigid spacer maintains the detectable label 2 to 3 nm from the nucleobase. In embodiments, the rigid spacer maintains the detectable label 2 to 4 nm from the nucleobase. In embodiments, the rigid spacer maintains the detectable label 2 to 5 nm from the nucleobase. In embodiments, the covalent linker and the rigid spacer collectively maintain the detectable label 1 to 2 nm from the nucleobase. In embodiments, the covalent linker and the rigid spacer collectively maintain the detectable label 1 to 3 nm from the nucleobase. In embodiments, the covalent linker and the rigid spacer collectively maintain the detectable label 2 to 3 nm from the nucleobase. In embodiments, the covalent linker and the rigid spacer collectively maintain the detectable label 2 to 4 nm from the nucleobase. In embodiments, the covalent linker and the rigid spacer collectively maintain the detectable label 2 to 5 nm from the nucleobase. In embodiments, the detectable label is 1 to 2 nm from the nucleobase. In embodiments, the detectable label is 1 to 3 nm from the nucleobase. In embodiments, the detectable label is 2 to 3 nm from the nucleobase. In embodiments, the detectable label is 2 to 4 nm from the nucleobase. In embodiments, the detectable label is 2 to 5 nm from the nucleobase.

In embodiments, $L^{200}$ has the formula:

(IV)

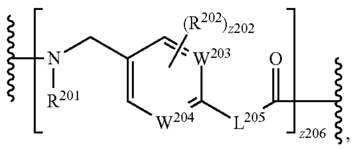

-continued (V)

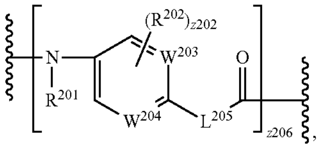

(VI)

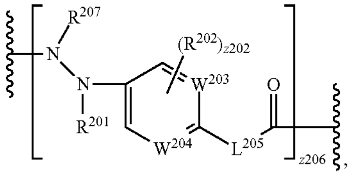

or (VII)

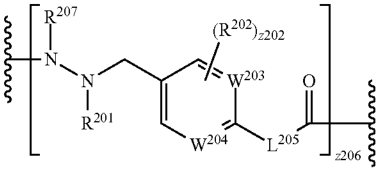

$W^{203}$ and $W^{204}$ are independently CH, N, or $C(R^{202})$. $R^{201}$ and $R^{207}$ are independently hydrogen, $-CCl_3$, $-CBr_3$, $-CF_3$, $-Cl_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-COOH$, $-CONH_2$, $-OCCl_3$, $-OCF_3$, $-OCBr_3$, $-OCl_3$, $-OCHCl_2$, $-OCHBr_2$, $-OCHI_2$, $-OCHF_2$, $-OCH_2Cl$, $-OCH_2Br$, $-O\ CH_2I$, $-OCH_2F$, substituted or unsubstituted alkyl, or substituted or unsubstituted heteroalkyl. $R^{202}$ is independently halogen, $-CCl_3$, $-CBr_3$, $-CF_3$, $-Cl_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCl_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, $-PO_3H$, $-PO_4H$, $-SO_2Cl$, substituted or unsubstituted alkyl, substituted or unsubstituted heteroalkyl, or $L^{202}$-$R^{202A}$. $L^{202}$ is independently a covalent linker. $R^{202A}$ is independently a detectable moiety, photoswitchable moiety, anchor moiety, triplet quencher moiety, or protein moiety. $R^{201}$ and $R^{202}$ may optionally be joined to form a substituted or unsubstituted heterocycloalkyl. $L^{205}$ is independently a bond or $-CH_2NH-$. The symbol z202 is independently an integer from 0 to 2. The symbol z206 is an integer from 1 to 100. In embodiments, $R^{202A}$ is independently a detectable moiety. In embodiments, $R^{202A}$ is independently a photoswitchable moiety. In embodiments, $R^{202A}$ is independently an anchor moiety. In embodiments, $R^{202A}$ is independently a triplet quencher moiety. In embodiments, $R^{202A}$ is independently a protein moiety.

In embodiments, $L^{200}$ has the formula:

(IV)

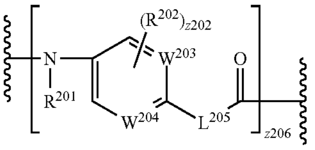

or

-continued (V)

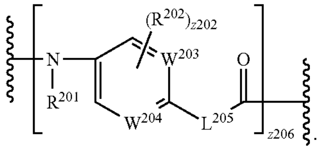

$W^{203}$ and $W^{204}$ are independently CH, N, or C($R^{202}$). $R^{201}$ is independently hydrogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, or substituted or unsubstituted heteroalkyl. $R^{202}$ is independently halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$PO_3H$, —$PO_4H$, —$SO_2Cl$, substituted or unsubstituted alkyl, substituted or unsubstituted heteroalkyl, or $L^{202}$-$R^{202A}$. $L^{202}$ is independently a covalent linker. $R^{202A}$ is independently a detectable moiety, anchor moiety, triplet quencher moiety, or protein moiety. $R^{201}$ and $R^{202}$ may optionally be joined to form a substituted or unsubstituted heterocycloalkyl. $L^{205}$ is independently a bond or —$CH_2NH$—. The symbol z202 is independently an integer from 0 to 2. The symbol z206 is an integer from 1 to 100.

In embodiments, $R^{102}$ and $R^{102a}$ are independently hydrogen, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), or substituted or unsubstituted heteroaryl (e.g., 5 to 10, 5 to 9, or 5 to 6 membered).

In embodiments, a substituted $R^{102}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{102}$ is substituted with a plurality of groups selected from substituent groups, size-limited substituent groups, and lower substituent groups; each substituent group, size-limited substituent group, and/or lower substituent group may optionally be different. In embodiments, when $R^{102}$ is substituted, it is substituted with at least one substituent group. In embodiments, when $R^{102}$ is substituted, it is substituted with at least one size-limited substituent group. In embodiments, when $R^{102}$ is substituted, it is substituted with at least one lower substituent group.

In embodiments, a substituted $R^{102a}$(e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{102a}$ is substituted with a plurality of groups selected from substituent groups, size-limited substituent groups, and lower substituent groups; each substituent group, size-limited substituent group, and/or lower substituent group may optionally be different. In embodiments, when $R^{102a}$ is substituted, it is substituted with at least one substituent group. In embodiments, when $R^{102a}$ is substituted, it is substituted with at least one size-limited substituent group. In embodiments, when $R^{102a}$ is substituted, it is substituted with at least one lower substituent group.

In embodiments, $R^{102a}$ is independently hydrogen, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{102a}$ is independently hydrogen or unsubstituted alkyl (e.g., $C_1$-$C_{20}$, $C_{10}$-$C_{20}$, $C_1$-$C_8$, $C_1$-$C_6$, or $C_1$-$C_4$). In embodiments, $R^{102a}$ is independently unsubstituted alkyl (e.g., $C_1$-$C_{20}$, $C_{10}$-$C_{20}$, $C_1$-$C_8$, $C_1$-$C_6$, or $C_1$-$C_4$). In embodiments, $R^{102a}$ is independently unsubstituted $C_1$-$C_6$ alkyl. In embodiments, $R^{102a}$ is independently unsubstituted $C_1$-$C_4$ alkyl. In embodiments, $R^{102a}$ is independently unsubstituted methyl. In embodiments, $R^{102a}$ is independently unsubstituted tert-butyl. In embodiments, $R^{102a}$ is independently hydrogen.

In embodiments, $W^{203}$ is CH, N, or C($R^{202}$). In embodiments, $W^{203}$ is CH. In embodiments, $W^{203}$ is N. In embodiments, $W^{203}$ is C($R^{202}$). In embodiments, $W^{204}$ is CH, N, or C($R^{202}$). In embodiments, $W^{204}$ is CH. In embodiments, $W^{204}$ is N. In embodiments, $W^{204}$ is C($R^{202}$). In embodiments, $W^{203}$ is CH and $W^{204}$ is CH. In embodiments, $W^{203}$ is CH and $W^{204}$ is N. In embodiments, $W^{203}$ is CH and $W^{204}$ is C($R^{202}$). In embodiments, $W^{203}$ is N and $W^{204}$ is CH. In embodiments, $W^{203}$ is N and $W^{204}$ is N. In embodiments, $W^{203}$ is N and $W^{204}$ is C($R^{202}$). In embodiments, $W^{203}$ is C($R^{202}$) and $W^{204}$ is CH. In embodiments, $W^{203}$ is C($R^{202}$) and $W^{204}$ is N. In embodiments, $W^{203}$ is C($R^{202}$) and $W^{204}$ is C($R^{202}$).

In embodiments, $L^{205}$ is independently a bond. In embodiments, $L^{205}$ is independently —$CH_2NH$—.

In embodiments, $R^{201}$ is independently hydrogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, or —$OCH_2F$. In embodiments, $R^{201}$ is independently hydrogen. In embodiments, $R^{201}$ is unsubstituted alkyl (e.g., $C_1$-$C_8$, $C_1$-$C_6$, $C_1$-$C_4$, or $C_1$-$C_2$). In embodiments, $R^{201}$ is unsubstituted $C_1$-$C_4$, or $C_1$-$C_2$ alkyl.

In embodiments, $R^{201}$ is independently hydrogen, substituted or unsubstituted alkyl, or substituted or unsubstituted heteroalkyl. In embodiments, $R^{201}$ is independently hydrogen, $R^{201A}$-substituted or unsubstituted alkyl, or $R^{201A}$-substituted or unsubstituted heteroalkyl. In embodiments, $R^{201}$ is independently hydrogen. In embodiments, $R^{201}$ is independently unsubstituted alkyl. In embodiments, $R^{201}$ is independently unsubstituted $C_1$-$C_4$ alkyl. In embodiments, $R^{201}$ is independently unsubstituted $C_1$-$C_2$ alkyl. In embodiments, $R^{201}$ is independently unsubstituted $C_2$ alkyl.

In embodiments, $R^{202}$ is independently halogen, —$CCl_3$, —$CBr_3$, —$CF_3$, —$Cl_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$PO_3H$, —$PO_4H$, —$SO_2Cl$, substituted or unsubstituted alkyl, substituted or unsubstituted heteroalkyl. In embodiments, $R^{202}$ is independently substituted or unsubstituted alkyl, substituted or unsubstituted heteroalkyl. In embodiments, $R^{202}$ is independently —$SO_3H$, —$SO_4H$, —$SO_2NH_2$, —$PO_3H$, —$PO_4H$, or —$SO_2Cl$. In embodiments, $R^{202}$ is independently —$SO_3H$. In embodiments, $R^{202}$ is independently —$SO_4H$. In embodiments, $R^{202}$ is independently —$SO_2NH_2$. In embodiments, $R^{202}$ is independently —$PO_3H$. In embodiments, $R^{202}$ is independently —$PO_4H$. In embodiments, $R^{202}$ is independently —$SO_2Cl$. In embodiments, $R^{202}$ is independently —OH.

In embodiments, $R^{202}$ is independently halogen, —$CCl_3$, —$CBr_3$, —$CF_3$, —$Cl_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$PO_3H$, —$PO_4H$, —$SO_2Cl$, $R^{203}$-substituted or unsubstituted alkyl, or $R^{203}$-substituted or unsubstituted heteroalkyl.

$R^{203}$ is independently halogen, —$CF_3$, —$CCl_3$, —$Cl_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCl_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, $R^{204}$-substituted or unsubstituted alkyl (e.g., $C_1$-$C_8$, $C_1$-$C_6$, $C_1$-$C_4$, or $C_1$-$C_2$), $R^{204}$-substituted or unsubstituted heteroalkyl (e.g., 2 to 8, 2 to 6, 4 to 6, 2 to 3, or 4 to 5 membered), $R^{204}$-substituted or unsubstituted cycloalkyl (e.g., $C_3$-$C_8$, $C_3$-$C_6$, $C_4$-$C_6$, or $C_5$-$C_6$), $R^{204}$-substituted or unsubstituted heterocycloalkyl e.g., 3 to 8, 3 to 6, 4 to 6, 4 to 5, or 5 to 6 membered), $R^{204}$-substituted or unsubstituted aryl (e.g., $C_6$-$C_{10}$ or phenyl), or $R^{204}$-substituted or unsubstituted heteroaryl(e.g., 5 to 10, 5 to 9, or 5 to 6 membered).

$R^{204}$ is independently halogen, —$CF_3$, —$CCl_3$, —$Cl_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCl_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, $R^{205}$-substituted or unsubstituted alkyl (e.g., $C_1$-$C_8$, $C_1$-$C_6$, $C_1$-$C_4$, or $C_1$-$C_2$), $R^{205}$-substituted or unsubstituted heteroalkyl (e.g., 2 to 8, 2 to 6, 4 to 6, 2 to 3, or 4 to 5 membered), $R^{205}$-substituted or unsubstituted cycloalkyl (e.g., $C_3$-$C_8$, $C_3$-$C_6$, $C_4$-$C_6$, or $C_5$-$C_6$), $R^{205}$-substituted or unsubstituted heterocycloalkyl e.g., 3 to 8, 3 to 6, 4 to 6, 4 to 5, or 5 to 6 membered), $R^{205}$-substituted or unsubstituted aryl (e.g., $C_6$-$C_{10}$ or phenyl), or $R^{205}$-substituted or unsubstituted heteroaryl(e.g., 5 to 10, 5 to 9, or 5 to 6 membered).

In embodiments, $R^{207}$ is independently hydrogen, —$CCl_3$, —$CBr_3$, —$CF_3$, —$Cl_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —COOH, —$CONH_2$, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, or —$OCH_2F$. In embodiments, $R^{207}$ is independently hydrogen. In embodiments, $R^{207}$ is unsubstituted alkyl (e.g., $C_1$-$C_8$, $C_1$-$C_6$, $C_1$-$C_4$, or $C_1$-$C_2$). In embodiments, $R^{207}$ is unsubstituted $C_1$-$C_4$, or $C_1$-$C_2$ alkyl. In embodiments, $R^{207}$ is independently hydrogen, substituted or unsubstituted alkyl, or substituted or unsubstituted heteroalkyl. In embodiments, $R^{207}$ is independently hydrogen, $R^{207A}$-substituted or unsubstituted alkyl, or $R^{207A}$-substituted or unsubstituted heteroalkyl.

$R^{201A}$ and $R^{205}$ are each independently oxo, halogen, —$CF_3$, —$CCl_3$, —$Cl_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCl_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8, 2 to 6, 4 to 6, 2 to 3, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8, 3 to 6, 4 to 6, 4 to 5, or 5 to 6 membered), unsubstituted aryl (e.g., $C_6$-$C_{10}$ or phenyl), or unsubstituted heteroaryl (e.g., 5 to 10, 5 to 9, or 5 to 6 membered).

$R^{207A}$ is independently oxo, halogen, —$CF_3$, —$CCl_3$, —$Cl_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCl_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8, 2 to 6, 4 to 6, 2 to 3, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8, 3 to 6, 4 to 6, 4 to 5, or 5 to 6 membered), unsubstituted aryl (e.g., $C_6$-$C_{10}$ or phenyl), or unsubstituted heteroaryl (e.g., 5 to 10, 5 to 9, or 5 to 6 membered).

In embodiments, $R^{201}$ and $R^{202}$ may optionally be joined to form a substituted or unsubstituted heterocycloalkyl. In embodiments, $R^{201}$ and $R^{202}$ may optionally be joined to form a $R^{203}$-substituted or unsubstituted heterocycloalkyl. In embodiments, $R^{201}$ and $R^{202}$ may optionally be joined to form a $R^{203}$-substituted or unsubstituted heterocycloalkyl (e.g., 3 to 8, 3 to 6, 4 to 6, 4 to 5, or 5 to 6 membered). In embodiments, $R^{201}$ and $R^{202}$ may optionally be joined to form a $R^{203}$-substituted or unsubstituted 5 to 6 membered heterocycloalkyl.

In embodiments, $R^{202}$ is $L^{202}$-$R^{202A}$. In embodiments, $L^{202}$ is independently a covalent linker. In embodiments, $L^{202}$ is -$L^{202A}$-$L^{202B}$-$L^{202C}$-. $L^{202A}$, $L^{202B}$, and $L^{202C}$ are independently a bond, —NH—, —O—, —C(O)—, —C(O)NH—, —NHC(O)—, —NHC(O)NH—, —C(O)O—, —OC(O)—, —SS—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{202A}$ is a bond, —NH—, —O—, —C(O)—, —C(O)NH—, —NHC(O)—, —NHC(O)NH—, —C(O)O—, —OC(O)—, —SS—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{202A}$ is a bond, —NH—, —O—, —C(O)—, —C(O)NH—, —NHC(O)—, —NHC(O)NH—, —C(O)O—, —OC(O)—, —SS—, $R^{203A}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{203A}$-substituted or unsubstituted heteroalkylene (e.g., 2 to 20, 8 to 20, 2 to 10, 2 to 8, 2 to 6, or 2 to 4 membered), $R^{203A}$-substituted or unsubstituted cycloalkylene (e.g., $C_3$-$C_8$, $C_3$-$C_6$, or $C_5$-$C_6$), $R^{203A}$-substituted or unsubstituted heterocycloalkylene (e.g., 3 to 8, 3 to 6, or 5 to 6 membered), $R^{203A}$-substituted or unsubstituted arylene (e.g., $C_6$-$C_{10}$, $C_{10}$, or phenylene), or $R^{203A}$-substituted or unsubstituted heteroarylene (e.g., 5 to 10, 5 to 9, or 5 to 6 membered). In embodiments, $L^{203A}$ is $R^{203A}$-substituted or unsubstituted $C_1$-$C_{20}$ alkylene. In embodiments, $L^{203A}$ is $R^{203A}$-substituted or unsubstituted 2 to 20 membered heteroalkylene. In embodiments, $L^{203A}$ is $R^{203A}$-substituted or unsubstituted $C_3$-$C_8$ cycloalkylene. In embodiments, $L^{203A}$ is $R^{203A}$-substituted or unsubstituted 3 to 8 membered heterocycloalkylene. In embodiments, $L^{203A}$ is $R^{203A}$-substituted or unsubstituted $C_6$-$C_{10}$ arylene. In embodiments, $L^{203A}$ is $R^{203A}$-substituted or unsubstituted 5 to 10 membered heteroarylene. In embodiments, $L^{203A}$ is independently a bond or substituted or unsubstituted 2 to 10 membered heteroalkylene.

$R^{203A}$ is independently oxo, halogen, —$CCl_3$, —$CBr_3$, —$CF_3$, —$Cl_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$N_3$, $R^{204A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{204A}$-substituted or unsubstituted heteroalkyl (e.g., 2 to 20, 8 to 20, 2 to 10, 2 to 8, 2 to 6, or 2 to 4 membered), $R^{204A}$-substituted or unsubstituted cycloalkyl (e.g., $C_3$-$C_8$, $C_3$-$C_6$, or $C_5$-$C_6$), $R^{204A}$-substituted or unsubstituted heterocycloalkyl (e.g., 3 to 8, 3 to 6, or 5 to 6 membered), $R^{204A}$-substituted or unsubstituted aryl (e.g., $C_6$-$C_{10}$, $C_{10}$, or phenyl), or $R^{204A}$-substituted or unsubstituted heteroaryl (e.g., 5 to 10, 5 to 9, or 5 to 6 membered).

$R^{204A}$ is independently oxo, halogen, —$CCl_3$, —$CBr_3$, —$CF_3$, —$Cl_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{202B}$ is a bond, —NH—, —O—, —C(O)—, —C(O)NH—, —NHC(O)—, —NHC(O)NH—, —C(O)O—, —OC(O)—, —SS—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{202B}$ is a bond, —NH—, —O—, —C(O)—, —C(O)NH—, —NHC(O)—, —NHC(O)NH—, —C(O)O—, —OC(O)—, —SS—, $R^{203B}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{203B}$-substituted or unsubstituted heteroalkylene (e.g., 2 to 20, 8 to 20, 2 to 10, 2 to 8, 2 to 6, or 2 to 4 membered), $R^{203B}$-substituted or unsubstituted cycloalkylene (e.g., $C_3$-$C_8$, $C_3$-$C_6$, or $C_5$-$C_6$), $R^{203B}$-substituted or unsubstituted heterocycloalkylene (e.g., 3 to 8, 3 to 6, or 5 to 6 membered), $R^{203B}$-substituted or unsubstituted arylene (e.g., $C_6$-$C_{10}$, $C_{10}$, or phenylene), or $R^{203B}$-substituted or unsubstituted heteroarylene (e.g., 5 to 10, 5 to 9, or 5 to 6 membered). In embodiments, $L^{203}$B is $R^{203B}$-substituted or unsubstituted $C_1$-$C_{20}$ alkylene. In embodiments, $L^{203}$B is $R^{203B}$-substituted or unsubstituted 2 to 20 membered heteroalkylene. In embodiments, $L^{203}$B is $R^{203B}$-substituted or unsubstituted $C_3$-$C_8$ cycloalkylene. In embodiments, $L^{203B}$ is $R^{203B}$-substituted or unsubstituted 3 to 8 membered heterocycloalkylene. In embodiments, $L^{203B}$ is $R^{203B}$-substituted or unsubstituted $C_6$-$C_{10}$ arylene. In embodiments, $L^{203B}$ is $R^{203B}$-substituted or unsubstituted 5 to 10 membered heteroarylene. In embodiments, $L^{203B}$ is independently a bond or substituted or unsubstituted 2 to 10 membered heteroalkylene.

$R^{203B}$ is independently oxo, halogen, —$CCl_3$, —$CBr_3$, —$CF_3$, —$Cl_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$N_3$, $R^{204B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{204B}$-substituted or unsubstituted heteroalkyl (e.g., 2 to 20, 8 to 20, 2 to 10, 2 to 8, 2 to 6, or 2 to 4 membered), $R^{204B}$-substituted or unsubstituted cycloalkyl (e.g., $C_3$-$C_8$, $C_3$-$C_6$, or $C_5$-$C_6$), $R^{204B}$-substituted or unsubstituted heterocycloalkyl (e.g., 3 to 8, 3 to 6, or 5 to 6 membered), $R^{204B}$-substituted or unsubstituted aryl (e.g., $C_6$-$C_{10}$, $C_{10}$, or phenyl), or $R^{204B}$-substituted or unsubstituted heteroaryl (e.g., 5 to 10, 5 to 9, or 5 to 6 membered). $R^{204B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{202C}$ is a bond, —NH—, —O—, —C(O)—, —C(O)NH—, —NHC(O)—, —NHC(O)NH—, —C(O)O—, —OC(O)—, —SS—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{202C}$ is a bond, —NH—, —O—, —C(O)—, —C(O)NH—, —NHC(O)—, —NHC(O)NH—, —C(O)O—, —OC(O)—, —SS—, $R^{203C}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{203C}$-substituted or unsubstituted heteroalkylene (e.g., 2 to 20, 8 to 20, 2 to 10, 2 to 8, 2 to 6, or 2 to 4 membered), $R^{203C}$-substituted or unsubstituted cycloalkylene (e.g., $C_3$-$C_8$, $C_3$-$C_6$, or $C_5$-$C_6$), $R^{203C}$-substituted or unsubstituted heterocycloalkylene (e.g., 3 to 8, 3 to 6, or 5 to 6 membered), $R^{203C}$-substituted or unsubstituted arylene (e.g., $C_6$-$C_{10}$, $C_{10}$, or phenylene), or $R^{203C}$-substituted or unsubstituted heteroarylene (e.g., 5 to 10, 5 to 9, or 5 to 6 membered). In embodiments, $L^{203C}$ is $R^{203C}$-substituted or unsubstituted $C_1$-$C_{20}$ alkylene. In embodiments, $L^{203C}$ is $R^{203C}$-substituted or unsubstituted 2 to 20 membered heteroalkylene. In embodiments, $L^{203C}$ is $R^{203C}$-substituted or unsubstituted $C_3$-$C_8$ cycloalkylene. In embodiments, $L^{203C}$ is $R^{203C}$-substituted or unsubstituted 3 to 8 membered heterocycloalkylene. In embodiments, $L^{203C}$ is $R^{203C}$-substituted or unsubstituted $C_6$-$C_{10}$ arylene. In embodiments, $L^{203C}$ is $R^{203C}$-substituted or unsubstituted 5 to 10 membered heteroarylene. In embodiments, $L^{203C}$ is independently a bond or substituted or unsubstituted 2 to 10 membered heteroalkylene.

$R^{203C}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{204C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{204C}$-substituted or unsubstituted heteroalkyl (e.g., 2 to 20, 8 to 20, 2 to 10, 2 to 8, 2 to 6, or 2 to 4 membered), $R^{204C}$-substituted or unsubstituted cycloalkyl (e.g., $C_3$-$C_8$, $C_3$-$C_6$, or $C_5$-$C_6$), $R^{204C}$-substituted or unsubstituted heterocycloalkyl (e.g., 3 to 8, 3 to 6, or 5 to 6 membered), $R^{204C}$-substituted or unsubstituted aryl (e.g., $C_6$-$C_{10}$, $C_{10}$, or phenyl), or $R^{204C}$-substituted or unsubstituted heteroaryl (e.g., 5 to 10, 5 to 9, or 5 to 6 membered). $R^{204C}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{202}$ is

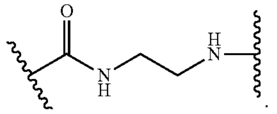 [SMILES: *NCCNC(*)=O]

In embodiments, $L^{202}$ is

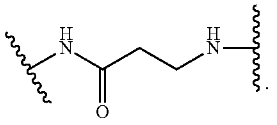 [SMILES: *NCCC(=O)N*]

In embodiments, $L^{202}$ is

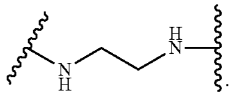 [SMILES: *NCCN*]

In embodiments, $L^{202}$-$R^{202A}$ is

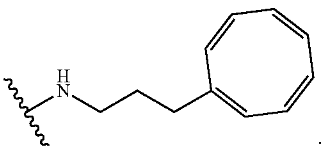 [SMILES: *NCCCC1=C/C=C\C=C/C=C\1]

In embodiments, $L^{202}$-$R^{202A}$ is

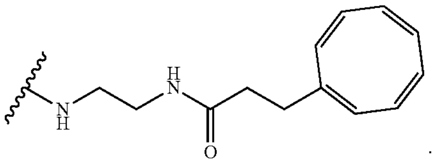 [SMILES: *NCCNC(=O)CCC1=C/C=C\C=C/C=C\1]

In embodiments, $L^{202}$-$R^{202A}$ is

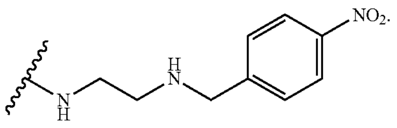 [SMILES: *NCCNCc1ccc([N+](=O)[O-])cc1]

In embodiments, $L^{202}$-$R^{202A}$ is

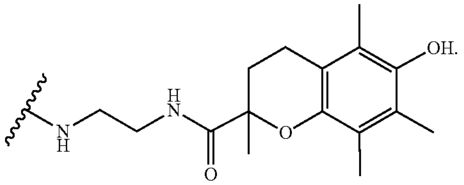 [SMILES: *NCCNC(=O)C1(C)CCc2c(C)c(O)c(C)c(C)c2O1]

In embodiments, $L^{202}$-$R^{202A}$ is

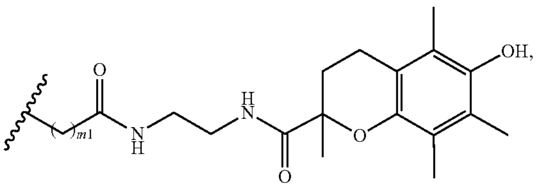

wherein m1 is an integer from 1 to 12. In embodiments, $L^{202}$-$R^{202A}$ is

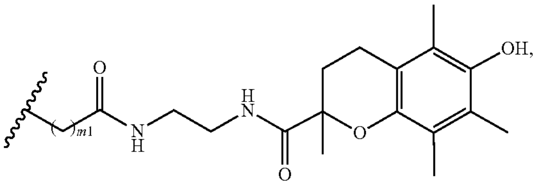

wherein m1 is 5. In embodiments, $L^{202}$-$R^{202A}$ is

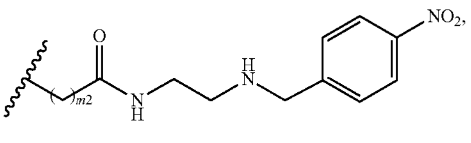

wherein m2 is an integer from 1 to 12. In embodiments, $L^{202}$-$R^{202A}$ is

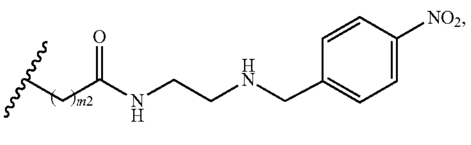

wherein m2 is 5. In embodiments, $L^{202}$-$R^{202A}$ is

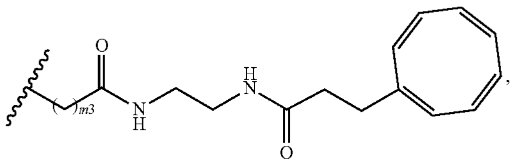

wherein m3 is an integer from 1 to 12. In embodiments, $L^{202}$-$R^{202A}$ is

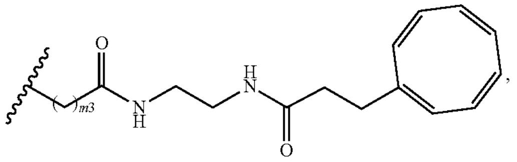

wherein m3 is 3.

In embodiments, $L^{202}$-$R^{202A}$ is

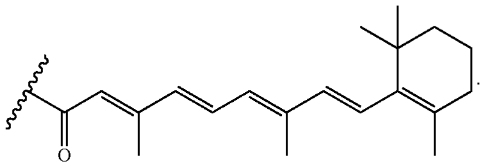 [SMILES: *C(=O)/C=C(C)/C=C/C=C(C)/C=C/C1=C(C)CCCC1(C)C]

In embodiments, $L^{202}$-$R^{202A}$ is

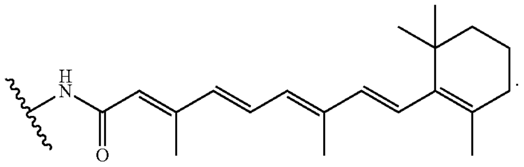 [SMILES: *NC(=O)/C=C(C)/C=C/C=C(C)/C=C/C1=C(C)CCCC1(C)C]

In embodiments, $L^{202}$-$R^{202A}$ is

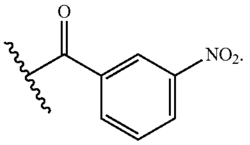 [SMILES: *C(=O)c1cccc([N+](=O)[O-])c1]

In embodiments, $L^{202}$-$R^{202A}$ is

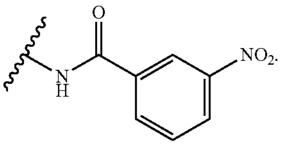 [SMILES: *NC(=O)c1cccc([N+](=O)[O-])c1]

In embodiments, $L^{202}$-$R^{202A}$ is

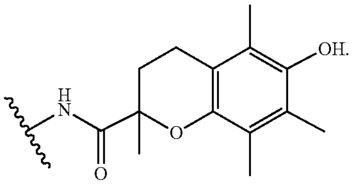 [SMILES: *NC(=O)C1(C)CCc2c(C)c(O)c(C)c(C)c2O1]

In embodiments, $L^{202}$-$R^{202A}$ is

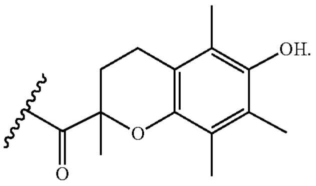 [SMILES: *C(=O)C1(C)CCc2c(C)c(O)c(C)c(C)c2O1]

In embodiments, $L^{202}$-$R^{202A}$ is

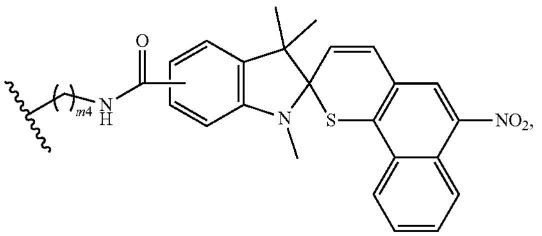

wherein m4 is an integer from 0 to 5. In embodiments, $L^{202}$-$R^{202A}$ is

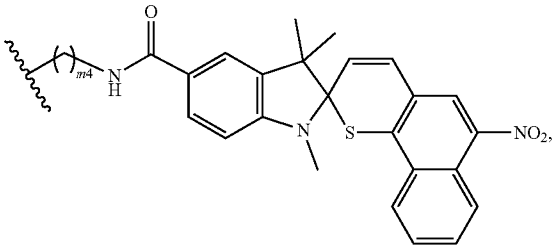

wherein m4 is an integer from 0 to 5. In embodiments, m4 is 1 to 4. In embodiments, $L^{202}$-$R^{202A}$ is

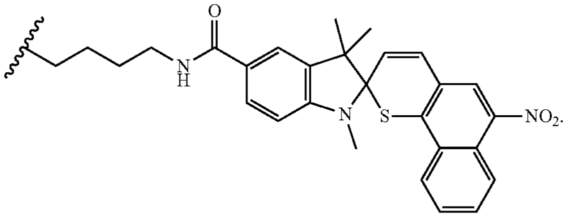 [SMILES: *CCCCNC(=O)c1ccc2c(c1)C(C)(C)C1(C=Cc3cc([N+](=O)[O-])c4ccccc4c3S1)N2C]

$R^{202A}$ is independently a detectable moiety, photoswitchable moiety, anchor moiety, triplet quencher moiety, or protein moiety. In embodiments, $R^{202A}$ is independently an anchor moiety. In embodiments, $R^{202A}$ is an anchor moiety. In embodiments, $R^{202A}$ is a bioconjugate reactive moiety. In embodiments, $R^{202A}$ is a trans-cyclooctene moiety or azide moiety. In embodiments, $R^{202A}$ is an affinity anchor moiety. In embodiments, $R^{202A}$ is a biotin moiety. In embodiments, $R^{202A}$ is a reactant for a bioconjugate reaction that forms a covalent bond between $R^{202A}$ and a second bioconjugate reaction reactant (i.e., $R^5$). In embodiments, $R^{202A}$ is a biotin moiety. In embodiments, $R^{202A}$ is a biotin moiety and $R^5$ is a streptavidin moiety.

In embodiments, $R^{202A}$ is

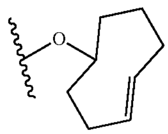

,

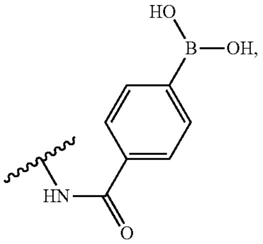

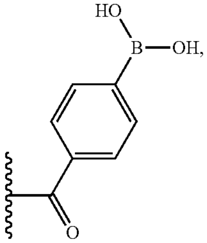

$—N_3$,

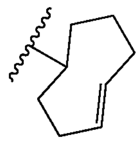

, or

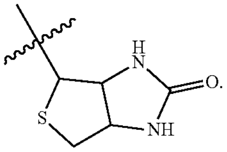

In embodiments, $R^{202A}$ is independently a protein moiety. The reactive groups (e.g., bioconjugate reactive moieties) on various amino acids can be used to provide specific sites of attachment to the rigid spacer. Reactive groups for the attachment of moieties to the protein include amine groups on lysine or arginine, the thiol group on cysteine, the acid group on aspartic acid or glutamic acid, and the hydroxyl group on serene or threonine. In embodiments, the protein moiety will have appropriate residues for connection to the rigid spacer. In embodiments, the protein moiety includes one or more modifications to allow for connection to the rigid spacers. There are many types of chemical reactions that can be used to react with specific amino acid residues on proteins. For example, coupling through the cysteine thiol can be accomplished using a reaction with maleimide. Cysteine groups can also be coupled with allylic halides, phenylmethyl halides, alkyl halides, or alpha-halo carbonyl groups. Amine groups can be coupled to activated carboxylates or activated sulfonic acids. Amine or carboxylate functionality on the protein can be used to produce amide linkages. Linkages containing nitrogen double bonds such as oxime or hydrazones can be used.

In embodiments, the protein moiety is ubiquitin. Ubiquitin is a small regulatory protein that has been found in almost all tissues of eukaryotic organisms. The ubiquitin protein has about 76 amino acids and has a molecular mass of about 8.5 kDa. Any suitable ubiquitin protein can be used as protein moiety. In embodiments, human ubiquitin (1UBQ) is the protein moiety. In embodiments, the protein moiety is TOP7. The protein TOP7 is an artificial 93-residue protein, which was was designed to have a unique fold not found in nature. (See for example U.S. Pat. No. 7,574,306). In embodiments, the protein moiety is papain. Papain, also known as *papaya* proteinase I, is a cysteine protease enzyme present in *papaya*. In embodiments, the protein moiety is avidin, streptavidin, tamavidin, traptavidin, xenavidin, bradavidin, AVR2, AVR4, and homologs thereof.

In embodiments, $R^{202A}$ is a detectable moiety. In embodiments, $R^{212A}$ is a fluorescent dye moiety. In embodiments, $R^{212A}$ is a detectable moiety described herein (e.g., Table 1). In embodiments, $R^{212A}$ is a detectable moiety described in Table 1.

In embodiments, $R^{212A}$ is independently a triplet quencher moiety. In embodiments, the triplet state quencher is a monovalent ascorbic acid, monovalent cyclooctatetraene (COT), monovalent nitrobenzyl alcohol, monovalent methyl viologen, monovalent Trolox, or monovalent Trolox-quinone. In embodiments, $R^{202A}$ is

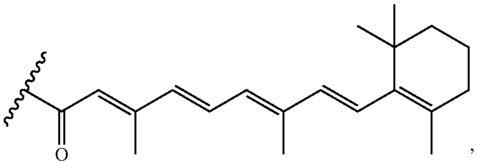
,
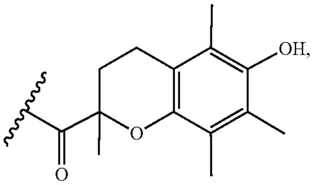
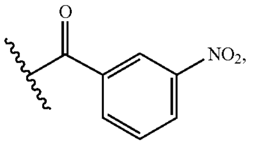
or
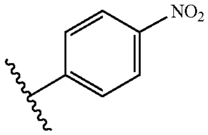
.

In embodiments, $R^{202A}$ is

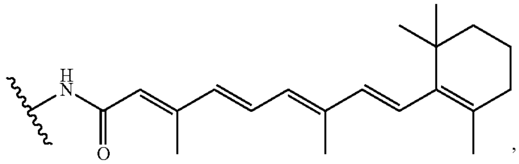
,
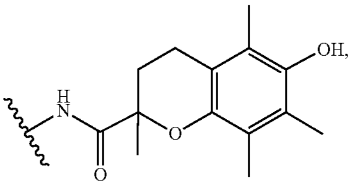
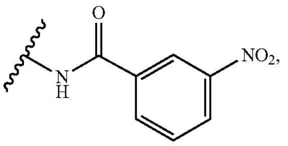
or
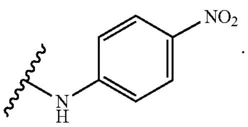
.

In embodiments, $R^{202A}$ is a chelating agent and Ni(II). In embodiments, $R^{202A}$ is tris N-nitrilotriacetic acid nickel (trisNTA-Ni(II)).

In embodiments, $R^{202A}$ is a photoswitchable moiety. Non-limiting examples of photoswitchable moieties include diarylethenes (e.g., bisthienylethene derivatives), azines (e.g., azobenzenes), photochromic quinones (e.g., phenoxynaphthacene quinone), spirooxazine, spirothiazines, mesoaldehyde 1-allyl-1-phenyl-2-phenylosazone, tetrachloro-1,2-ketonaphthalenone, thioindigoides, dinitrobenzylpyridine, and chromenes. In embodiments, $R^{202A}$ is

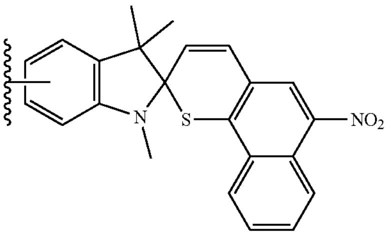
or
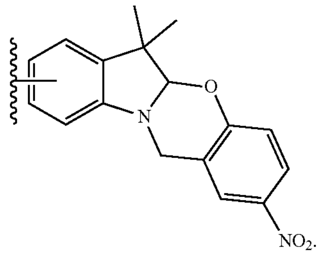

In embodiments, $L^{200}$ has the formula:

(IVa)

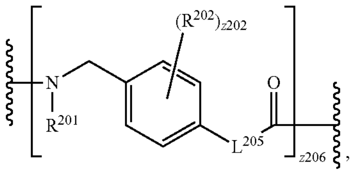

(IVb)

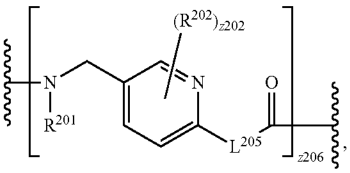
or (IVc)

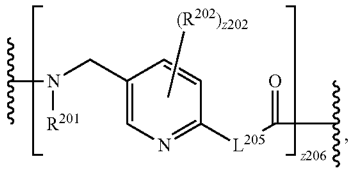

wherein $R^{201}$, $R^{202}$, $L^{205}$ and z206 are as described herein. In embodiments, $L^{200}$ has the formula:

(Va)

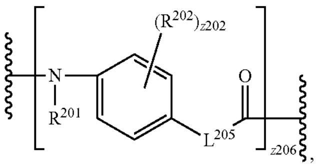

(Vb)

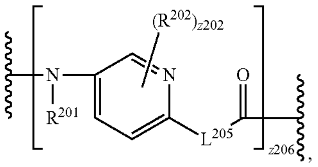

or (Vc)

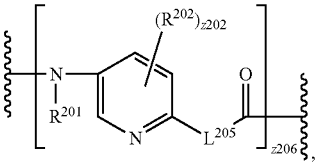

wherein $R^{201}$, $R^{202}$, $L^{205}$, and z206 are as described herein.

In embodiments, $L^{200}$ has the formula

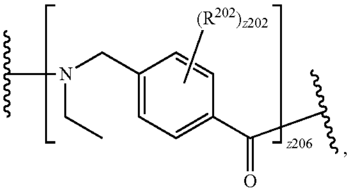

wherein $R^{202}$ and z206 are as described herein. In embodiments, $L^{200}$ has the formula

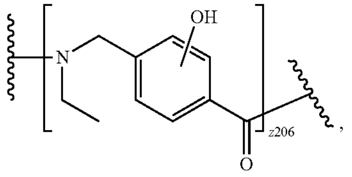

wherein z206 are as described herein. In embodiments, $L^{200}$ has the formula

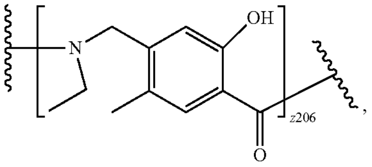

wherein z206 is as described herein. In embodiments, $L^{200}$ has the formula

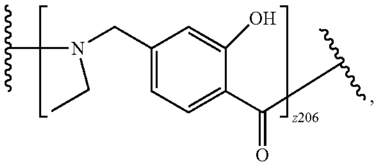

wherein z206 is as described herein.

In embodiments, $L^{200}$ has the formula:

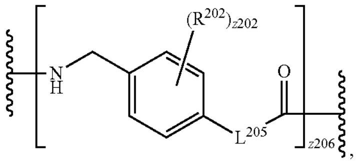

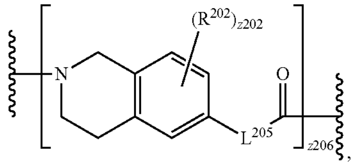

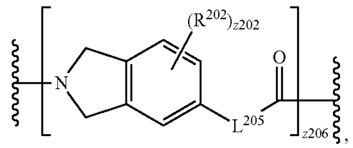

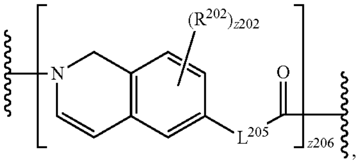

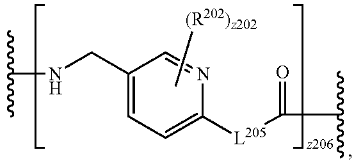

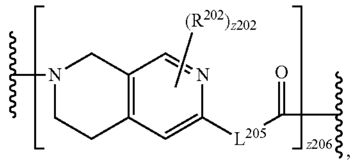

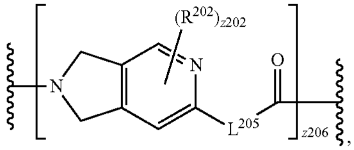

or

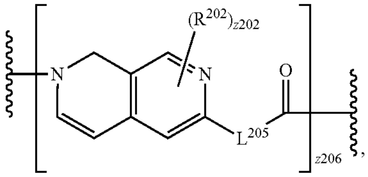

wherein $R^{202}$, $L^{205}$, z202, and z206 are as described herein.

In embodiments, $L^{200}$ has the formula:
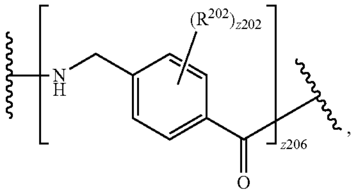
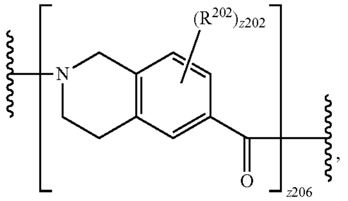
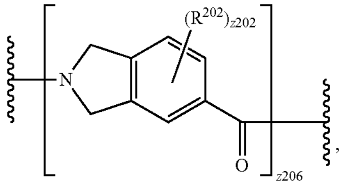
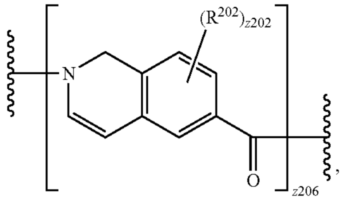
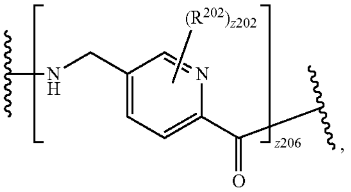
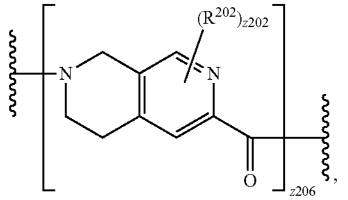
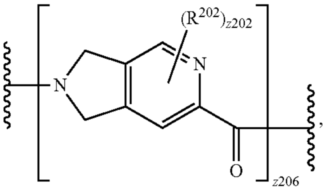
or
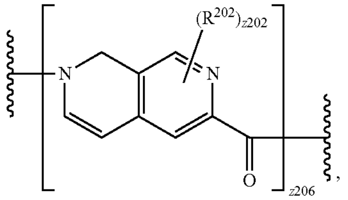
wherein $R^{202}$, z202, and z206 are as described herein. In embodiments, $L^{200}$ has the formula:
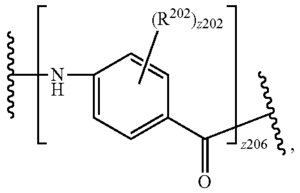
wherein $R^{202}$, z202, and z206 are as described herein. In embodiments, $L^{200}$ has the formula:
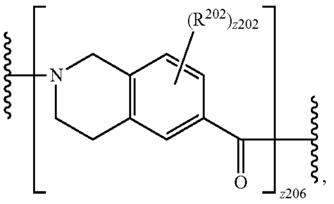
wherein $R^{202}$, z202, and z206 are as described herein. In embodiments, $L^{200}$ has the formula:
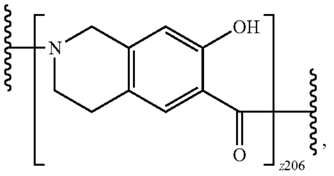
wherein z206 is as described herein.
In embodiments, $L^{200}$ has the formula:
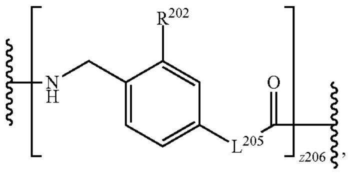
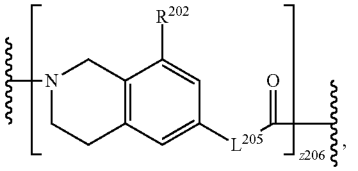
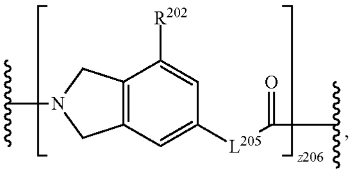
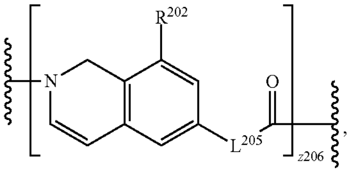

-continued

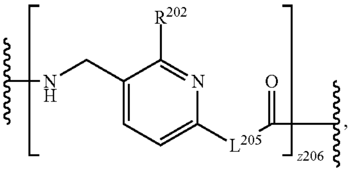

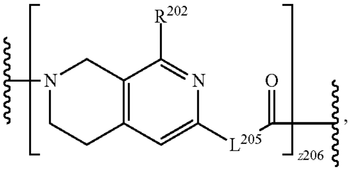

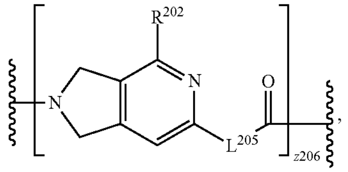

or

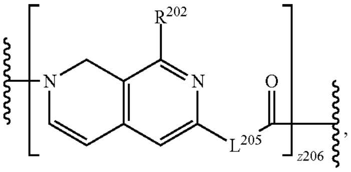

wherein $R^{202}$, $L^{205}$, and z206 are as described herein. In embodiments, $R^{202}$ is independently —$SO_3H$, —$SO_4H$, —$SO_2NH_2$, —$PO_3H$, —$PO_4H$, or —$SO_2Cl$. In embodiments, $R^{202}$ is independently —$SO_3H$. In embodiments, $R^{202}$ is independently —$SO_4H$. In embodiments, $R^{202}$ is independently —$SO_2NH_2$. In embodiments, $R^{202}$ is independently —$PO_3H$. In embodiments, $R^{202}$ is independently —$PO_4H$. In embodiments, $R^{202}$ is independently —OH. In embodiments, $R^{202}$ is independently —$CH_3$.

In embodiments, $L^{200}$ has the formula:

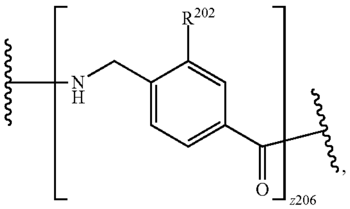

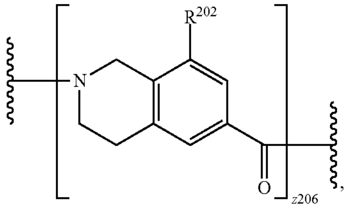

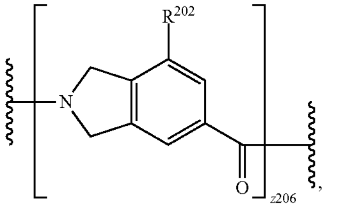

-continued

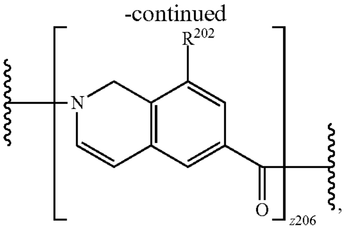

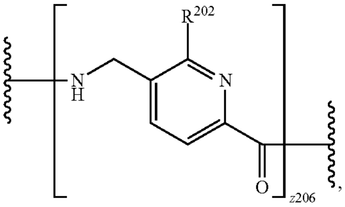

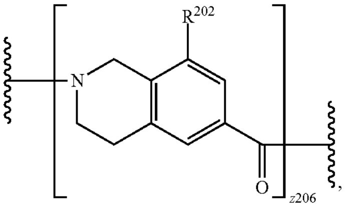

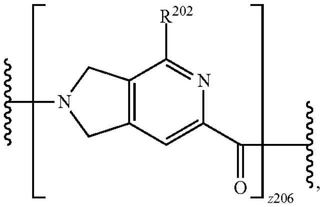

or

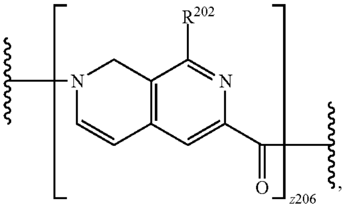

wherein $R^{202}$ and z206 are as described herein. In embodiments, $L^{200}$ has the formula:

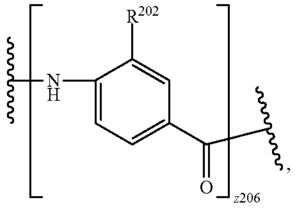

wherein $R^{202}$ and z206 are as described herein.

In embodiments, $L^{200}$ has the formula:

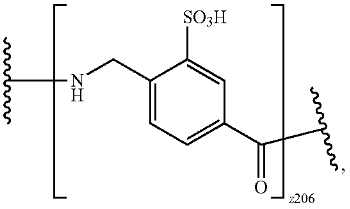

-continued
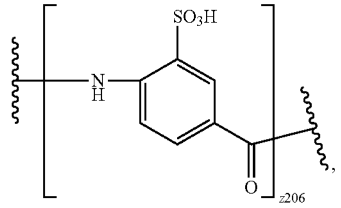
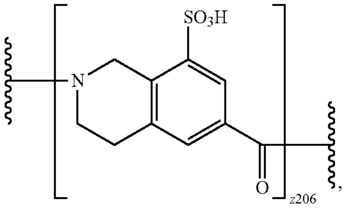
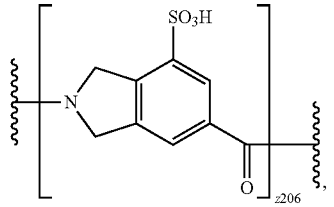
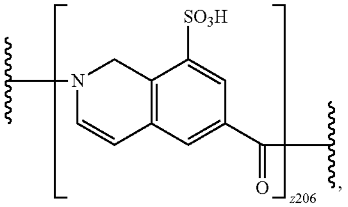
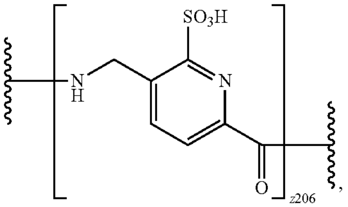
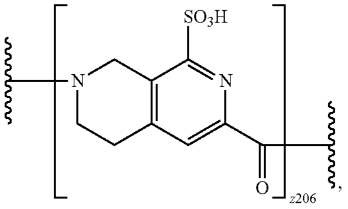
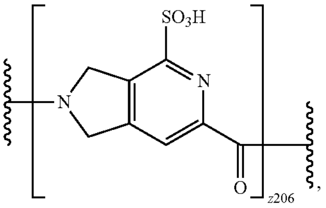
or
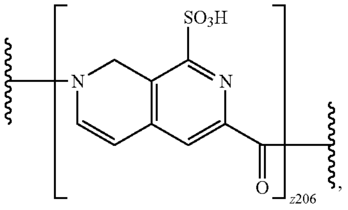
wherein z206 is 1 to 10.
In embodiments, $L^{200}$ has the formula:
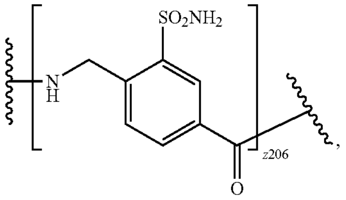
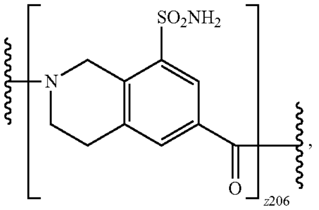
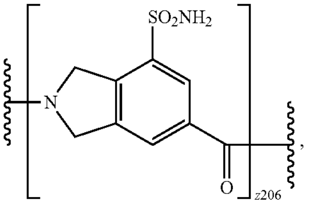
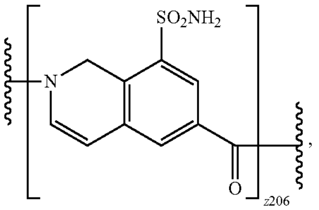
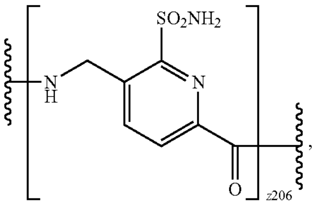
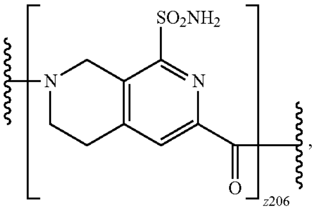
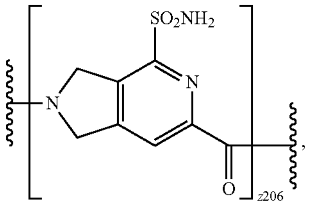
or -continued
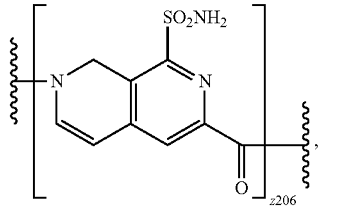
wherein z206 is 1 to 10.
In embodiments, $L^{200}$ has the formula:
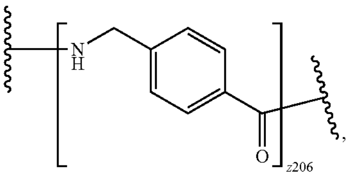
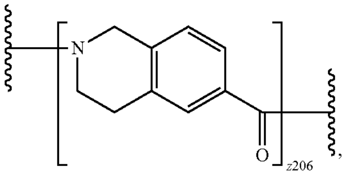
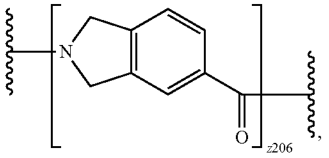
-continued
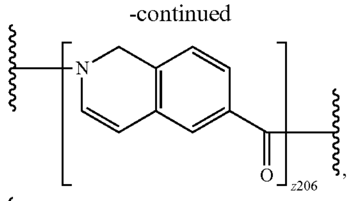
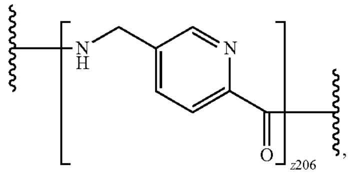
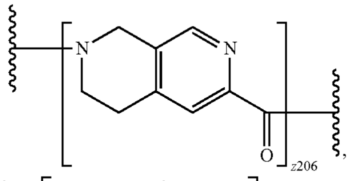
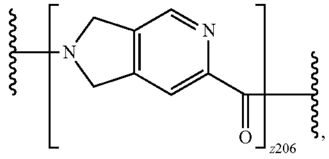
or
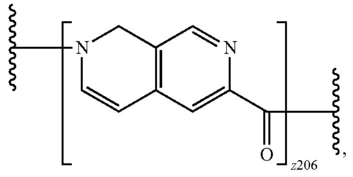
wherein z206 is as described herein.
In embodiments, $L^{200}$ has the formula:
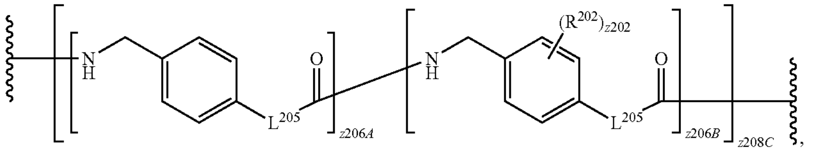

wherein z206A is an integer from 1 to 50; z206B is an integer from 1 to 50; and z206C is an integer from 1 to 50.
In embodiments, $L^{200}$ has the formula:
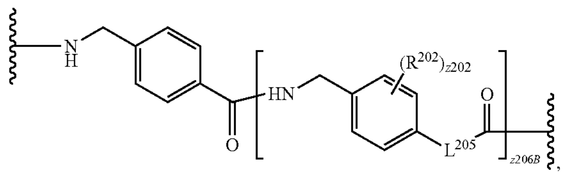
wherein z206B is an integer from 1 to 20. In embodiments, $L^{200}$ has the formula:
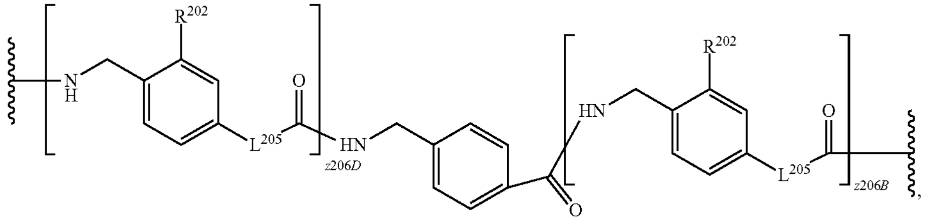
wherein z206B is an integer from 1 to 50 and z206D is an integer from 1 to 50.
In embodiments, $L^{200}$ has the formula:
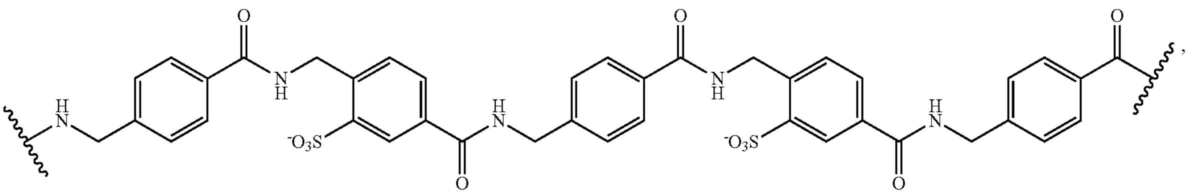
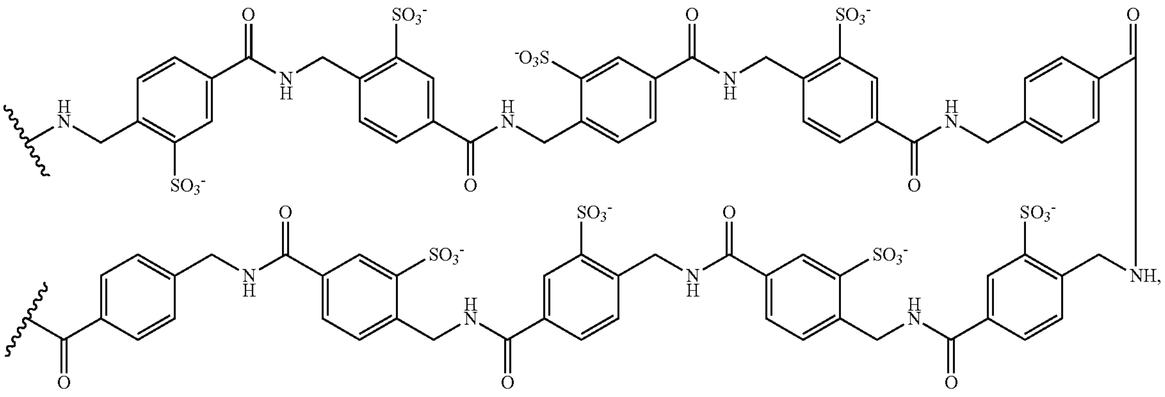

-continued
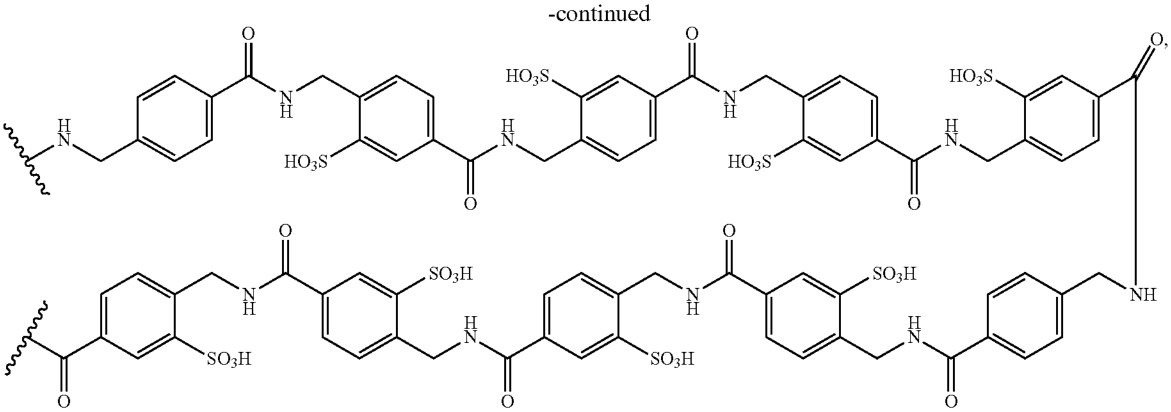
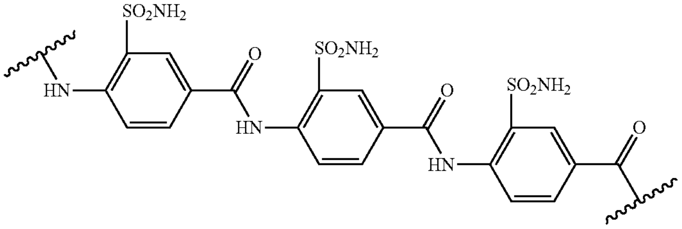
,
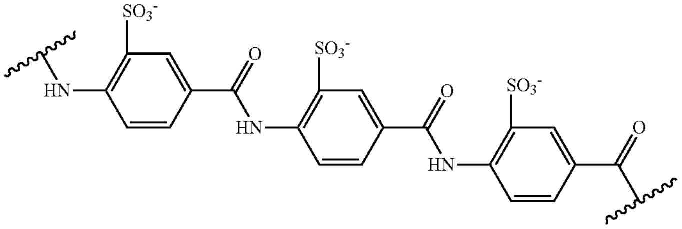
, or
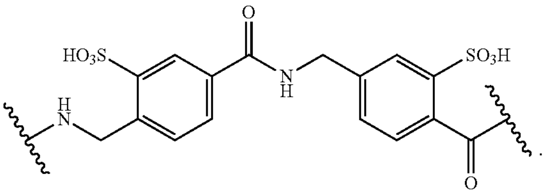
.
In embodiments, $L^{200}$ has the formula:
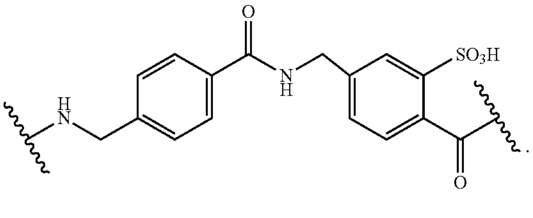 [SMILES: *NCc1ccc(C(=O)NCc2ccc(C(*)=O)c(S(=O)(=O)O)c2)cc1]
.
In embodiments, $L^{200}$ has the formula:
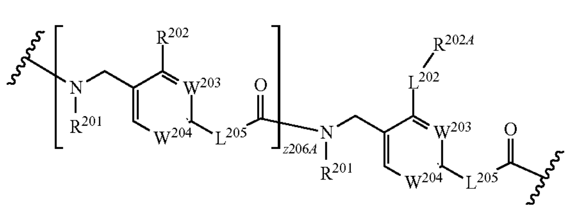
or
-continued
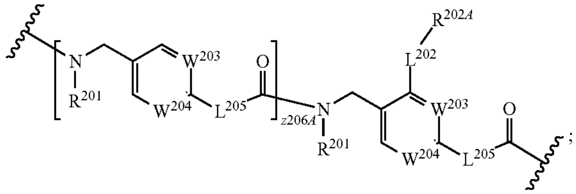
;
wherein z206A is an integer from 1 to 50. In embodiments, $L^{200}$ has the formula:
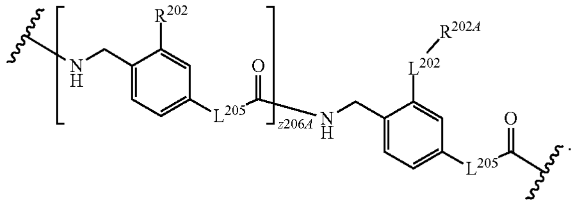
.

In embodiments, $L^{200}$ has the formula:

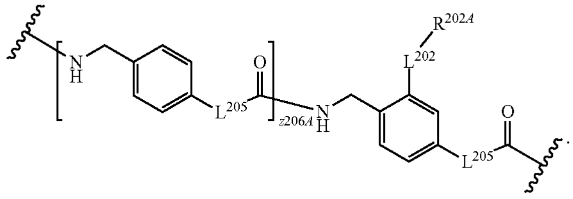

In embodiments, z206A is an integer from 1 to 10. In embodiments, $R^4$ and $R^{202A}$ are independently detectable moieties. In embodiments, $R^4$ and $R^{202A}$ are a FRET pair of detectable moieties. In embodiments, $R^4$ and $R^{202A}$ includes a fluorescence resonance energy transfer donor and acceptor fluorescent dye pair separated by about 0.1 nm to 10 nm. Changes in the efficiency of FRET energy transfer is correlated to changes in the separation between $R^4$ and $R^{202A}$ In embodiments, $R^4$ and $R^{202A}$ are detectable labels or derivatives thereof exhibit a change in their fluorescence properties as a spatial separation occurs between the detectable labels or derivatives thereof (e.g., FRET, quenching, and the like). Non-limiting examples of fluorescence properties that change include intensity, absorption, emission, and the like. Examples of detectable labels or derivatives include Cy3 (e.g., a detectable label derived from Cy3) and Cy5 (e.g., a detectable label derived from Cy5), fluorescein (e.g., a detectable label derived from fluorescein) and tetramethylrhodamine (e.g., a detectable label derived from tetramethylrhodamine), 5-((2-acetamidoethyl)amino)naphthalene-1-sulfonic acid (e.g., a detectable label derived from 5-((2-acetamidoethyl)amino)naphthalene-1-sulfonic acid) or 5-((2-Aminoethyl)amino)naphthalene-1-sulfonic acid (e.g., a detectable label derived from 5-((2-Aminoethyl)amino)naphthalene-1-sulfonic acid) and fluorescein (e.g., a detectable label derived from fluorescein), 5-((2-acetamidoethyl)amino)naphthalene-1-sulfonic acid (e.g., a detectable label derived from 5-((2-acetamidoethyl)amino)naphthalene-1-sulfonic acid) or 5-((2-Aminoethyl)amino)naphthalene-1-sulfonic acid (e.g., a detectable label derived from 5-((2-Aminoethyl)amino)naphthalene-1-sulfonic acid) and (E)-4-((4-(dimethylamino)phenyl)diazenyl)benzoic acid (e.g., a detectable label derived from (E)-4-((4-(dimethylamino)phenyl)diazenyl)benzoic acid), fluorescein (e.g., a detectable label derived from fluorescein) and fluorescein (e.g., a detectable label derived from fluorescein), BODIPY (e.g., a detectable label derived from BODIPY) and BODIPY (e.g., a detectable label derived from BODIPY), fluorescein (e.g., a detectable label derived from fluorescein) and QSY7 (e.g., a detectable label derived from QSY7) and QSY9 (e.g., a detectable label derived from QSY9), various combinations of Alexa Fluor dyes (e.g., Alexa 488—Alexa 555, and detectable labels derived therefrom), or various combinations of ATTO dyes (e.g., Atto 488—Atto 532, and detectable labels derived therefrom).

In embodiments, $R^4$ is a detectable moiety and $R^{212A}$ is a triplet state quencher.

In embodiments, z206 is an integer from 1 to 20. In embodiments, z206 is an integer from 1 to 10. In embodiments, z206 is an integer from 1 to 5. In embodiments, z206 is an integer from 2 to 10. In embodiments, z206 is an integer from 2 to 5. In embodiments, z206 is an integer from 2 to 4. In embodiments, z206 is an integer from 3 to 5. In embodiments, z206 is an integer from 5 to 8. In embodiments, z206 is 1, 2, 3, 4, 5, 6, 7, 8, 9, or 10. In embodiments, z206 is 1. In embodiments, z206 is 2. In embodiments, z206 is 3.

In embodiments, z206A is an integer from 1 to 20. In embodiments, z206A is an integer from 1 to 10. In embodiments, z206A is an integer from 1 to 5. In embodiments, z206A is an integer from 2 to 10. In embodiments, z206A is an integer from 2 to 5. In embodiments, z206A is an integer from 2 to 4. In embodiments, z206A is an integer from 3 to 5. In embodiments, z206A is an integer from 5 to 8. In embodiments, z206A is 1, 2, 3, 4, 5, 6, 7, 8, 9, or 10. In embodiments, z206B is an integer from 1 to 20. In embodiments, z206B is an integer from 1 to 10. In embodiments, z206B is an integer from 1 to 5. In embodiments, z206B is an integer from 2 to 10. In embodiments, z206B is an integer from 2 to 5. In embodiments, z206B is an integer from 2 to 4. In embodiments, z206B is an integer from 3 to 5. In embodiments, z206B is an integer from 5 to 8. In embodiments, z206B is 1, 2, 3, 4, 5, 6, 7, 8, 9, or 10. In embodiments, z206C is an integer from 1 to 20. In embodiments, z206C is an integer from 1 to 10. In embodiments, z206C is an integer from 1 to 5. In embodiments, z206C is an integer from 2 to 10. In embodiments, z206C is an integer from 2 to 5. In embodiments, z206C is an integer from 2 to 4. In embodiments, z206C is an integer from 3 to 5. In embodiments, z206C is an integer from 5 to 8. In embodiments, z206C is 1, 2, 3, 4, 5, 6, 7, 8, 9, or 10. In embodiments, z206D is an integer from 1 to 20. In embodiments, z206D is an integer from 1 to 10. In embodiments, z206D is an integer from 1 to 5. In embodiments, z206D is an integer from 2 to 10. In embodiments, z206D is an integer from 2 to 5. In embodiments, z206D is an integer from 2 to 4. In embodiments, z206D is an integer from 3 to 5. In embodiments, z206D is an integer from 5 to 8. In embodiments, z206D is 1, 2, 3, 4, 5, 6, 7, 8, 9, or 10.

In embodiments, z206 is 1. In embodiments, z206 is 2. In embodiments, z206 is 3. In embodiments, z206 is 4. In embodiments, z206 is 5. In embodiments, z206A is 1. In embodiments, z206A is 2. In embodiments, z206A is 3. In embodiments, z206A is 4. In embodiments, z206A is 5. In embodiments, z206B is 1. In embodiments, z206B is 2. In embodiments, z206B is 3. In embodiments, z206B is 4. In embodiments, z206B is 5. In embodiments, z206C is 1. In embodiments, z206C is 2. In embodiments, z206C is 3. In embodiments, z206C is 4. In embodiments, z206C is 5. In embodiments, z206D is 1. In embodiments, z206D is 2. In embodiments, z206D is 3. In embodiments, z206D is 4. In embodiments, z206D is 5.

In embodiments, z206A is an integer from 1 to 10; z206B is an integer from 1 to 10; and z206C is an integer from 1 to 5. In embodiments, z206A is an integer from 1 to 3; z206B is an integer from 1 to 3; and z206C is an integer from 1 to 5. In embodiments, z206A is 2; z206B is an integer from 2; and z206C is an integer from 1 to 5. In embodiments, z206B and z206D are each independently an integer from 1 to 10.

In embodiments, $L^{200}$ has the formula:

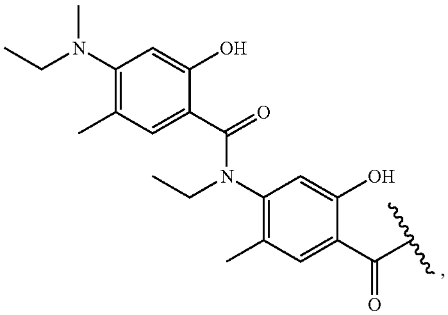
,

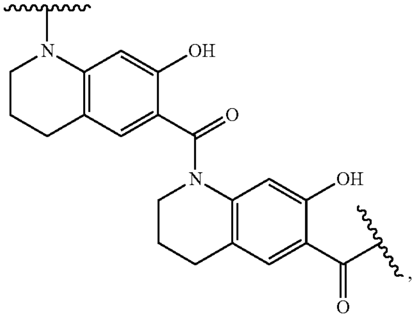
, or

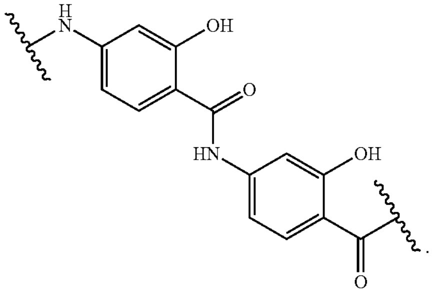
.

Described herein is a composition that includes a first compound having the formula (I) and a second compound having the formula $R^5$-$L^5$-$R^6$ (II), wherein $R^5$ is a complementary anchor moiety to the $R^4$ anchor moiety of the first compound. In embodiments, $R^5$ is a streptavidin moiety.

In embodiments, $R^5$ is

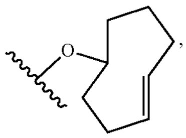
,
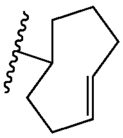
,
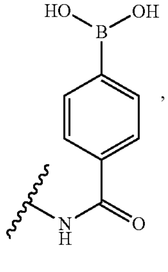
,
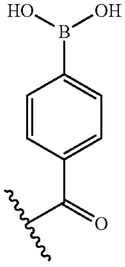
,
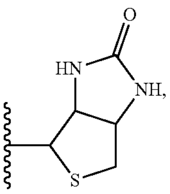
,
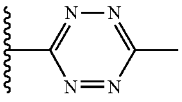
, -continued

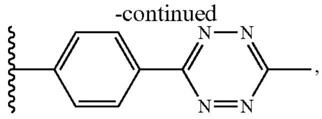
,
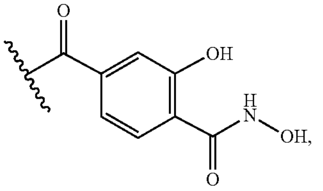
or
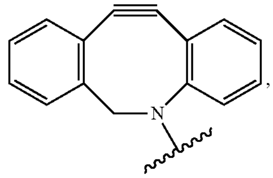 [SMILES: *N1Cc2ccccc2C#Cc2ccccc21]
, or a streptavidin moiety. In embodiments, $R^5$ is a bioconjugate reactive moiety. In embodiments, $R^4$ and $R^5$ are bioconjugate reactive moieties described in the Bioconjugate Table which react to form a bioconjugate linker.

In embodiments, $R^6$ is a detectable moiety. In embodiments, $R^6$ is a fluorescent dye moiety. In embodiments, $R^6$ is a detectable moiety described herein (e.g., Table 1). In embodiments, $R^6$ is a detectable moiety described in Table 1.

In embodiments, $L^5$ is a covalent linker. In embodiments, $L^5$ is -$L^{505A}$-$L^{505B}$-$L^{505C}$-$L^{505A}$, $L^{505B}$, and $L^{505C}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{505A}$ is a bond, —NH—, —O—, —C(O)—, —C(O)NH—, —NHC(O)—, —NHC(O)NH—, —C(O)O—, —OC(O)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{505A}$ is a bond, —NH—, —O—, —C(O)—, —C(O)NH—, —NHC(O)—, —NHC(O)NH—, —C(O)O—, —OC(O)—, $R^{506A}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{506A}$-substituted or unsubstituted heteroalkylene (e.g., 2 to 20, 8 to 20, 2 to 10, 2 to 8, 2 to 6, or 2 to 4 membered), $R^{506A}$-substituted or unsubstituted cycloalkylene (e.g., $C_3$-$C_8$, $C_3$-$C_6$, or $C_5$-$C_6$), $R^{506A}$-substituted or unsubstituted heterocycloalkylene (e.g., 3 to 8, 3 to 6, or 5 to 6 membered), $R^{506A}$-substituted or unsubstituted arylene (e.g., $C_6$-$C_{10}$, $C_{10}$, or phenylene), or $R^{506A}$-substituted or unsubstituted heteroarylene (e.g., 5 to 10, 5 to 9, or 5 to 6 membered). In embodiments, $L^{506A}$ is $R^{506A}$-substituted or unsubstituted $C_1$-$C_{20}$ alkylene. In embodiments, $L^{506A}$ is $R^{506A}$-substituted or unsubstituted 2 to 20 membered heteroalkylene. In embodiments, $L^{506A}$ is $R^{506A}$-substituted or unsubstituted $C_3$-$C_8$ cycloalkylene. In embodiments, $L^{506A}$ is $R^{506A}$-substituted or unsubstituted 3 to 8 membered heterocycloalkylene. In embodiments, $L^{506A}$ is $R^{506A}$-substituted or unsubstituted $C_6$-$C_{10}$ arylene. In embodiments, $L^{506A}$ is $R^{506A}$-substituted or unsubstituted 5 to 10 membered heteroarylene. In embodiments, $L^{506A}$ is independently a bond or substituted or unsubstituted 2 to 10 membered heteroalkylene.

$R^{506A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{507a}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{507A}$-substituted or unsubstituted heteroalkyl (e.g., 2 to 20, 8 to 20, 2 to 10, 2 to 8, 2 to 6, or 2 to 4 membered), $R^{507A}$-substituted or unsubstituted cycloalkyl (e.g., $C_3$-$C_8$, $C_3$-$C_6$, or $C_5$-$C_6$), $R^{507A}$-substituted or unsubstituted heterocycloalkyl (e.g., 3 to 8, 3 to 6, or 5 to 6 membered), $R^{507A}$-substituted or unsubstituted aryl (e.g., $C_6$-$C_{10}$, $C_{10}$, or phenyl), or $R^{507A}$-substituted or unsubstituted heteroaryl (e.g., 5 to 10, 5 to 9, or 5 to 6 membered). $R^{507A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{505B}$ is a bond, —NH—, —O—, —C(O)—, —C(O)NH—, —NHC(O)—, —NHC(O)NH—, —C(O)O—, —OC(O)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{505B}$ is a bond, —NH—, —O—, —C(O)—, —C(O)NH—, —NHC(O)—, —NHC(O)NH—, —C(O)O—, —OC(O)—, $R^{506B}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{506B}$-substituted or unsubstituted heteroalkylene (e.g., 2 to 20, 8 to 20, 2 to 10, 2 to 8, 2 to 6, or 2 to 4 membered), $R^{506B}$-substituted or unsubstituted cycloalkylene (e.g., $C_3$-$C_8$, $C_3$-$C_6$, or $C_5$-$C_6$), $R^{506B}$-substituted or unsubstituted heterocycloalkylene (e.g., 3 to 8, 3 to 6, or 5 to 6 membered), $R^{506B}$-substituted or unsubstituted arylene (e.g., $C_6$-$C_{10}$, $C_{10}$, or phenylene), or $R^{506B}$-substituted or unsubstituted heteroarylene (e.g., 5 to 10, 5 to 9, or 5 to 6 membered). In embodiments, $L^{506}$B is $R^{506B}$-substituted or unsubstituted $C_1$-$C_{20}$ alkylene. In embodiments, $L^{506}$B is $R^{506B}$-substituted or unsubstituted 2 to 20 membered heteroalkylene. In embodiments, $L^{506}$B is $R^{506B}$-substituted or unsubstituted $C_3$-$C_8$ cycloalkylene. In embodiments, $L^{506}$B is $R^{506B}$-substituted or unsubstituted 3 to 8 membered heterocycloalkylene. In embodiments, $L^{506}$B is $R^{506B}$-substituted or unsubstituted $C_6$-$C_{10}$ arylene. In embodiments, $L^{506}$B is $R^{506B}$-substituted or unsubstituted 5 to 10 membered heteroarylene. In embodiments, $L^{506B}$ is independently a bond or substituted or unsubstituted 2 to 10 membered heteroalkylene.

$R^{506B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{507B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{507B}$-substituted or unsubstituted heteroalkyl (e.g., 2 to 20, 8 to 20, 2 to 10, 2 to 8, 2 to 6, or 2 to 4 membered), $R^{507B}$-substituted or unsubstituted cycloalkyl (e.g., $C_3$-$C_8$, $C_3$-$C_6$, or $C_5$-$C_6$), $R^{507B}$-substituted or unsubstituted heterocycloalkyl (e.g., 3 to 8, 3 to 6, or 5 to 6 membered), $R^{507B}$-substituted or unsubstituted aryl (e.g., $C_6$-$C_{10}$, $C_{10}$, or phenyl), or $R^{507B}$-substituted or unsubstituted heteroaryl (e.g., 5 to 10, 5 to 9, or 5 to 6 membered). $R^{507B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{505}$ is a bond, —NH—, —O—, —C(O)—, —C(O)NH—, —NHC(O)—, —NHC(O)NH—, —C(O)O—, —OC(O)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{505}$ is a bond, —NH—, —O—, —C(O)—, —C(O)NH—, —NHC(O)—, —NHC(O)NH—, —C(O)O—, —OC(O)—, $R^{506C}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{506C}$-substituted or unsubstituted heteroalkylene (e.g., 2 to 20, 8 to 20, 2 to 10, 2 to 8, 2 to 6, or 2 to 4 membered), $R^{506C}$-substituted or unsubstituted cycloalkylene (e.g., $C_3$-$C_8$, $C_3$-$C_6$, or $C_5$-$C_6$), $R^{506C}$-substituted or unsubstituted heterocycloalkylene (e.g., 3 to 8, 3 to 6, or 5 to 6 membered), $R^{506C}$-substituted or unsubstituted arylene (e.g., $C_6$-$C_{10}$, $C_{10}$, or phenylene), or $R^{506C}$-substituted or unsubstituted heteroarylene (e.g., 5 to 10, 5 to 9, or 5 to 6 membered). In embodiments, $L^{506C}$ is $R^{506C}$-substituted or unsubstituted $C_1$-$C_{20}$ alkylene. In embodiments, $L^{506C}$ is $R^{506C}$-substituted or unsubstituted 2 to 20 membered heteroalkylene. In embodiments, $L^{506C}$ is $R^{506C}$-substituted or unsubstituted $C_3$-$C_8$ cycloalkylene. In embodiments, $L^{506C}$ is $R^{506C}$-substituted or unsubstituted 3 to 8 membered heterocycloalkylene. In embodiments, $L^{506C}$ is $R^{506C}$-substituted or unsubstituted $C_6$-$C_{10}$ arylene. In embodiments, $L^{506C}$ is $R^{506C}$-substituted or unsubstituted 5 to 10 membered heteroarylene. In embodiments, $L^{506C}$ is independently a bond or substituted or unsubstituted 2 to 10 membered heteroalkylene.

$R^{506C}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-N_3$, $R^{507C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{507C}$-substituted or unsubstituted heteroalkyl (e.g., 2 to 20, 8 to 20, 2 to 10, 2 to 8, 2 to 6, or 2 to 4 membered), $R^{507C}$-substituted or unsubstituted cycloalkyl (e.g., $C_3$-$C_8$, $C_3$-$C_6$, or $C_5$-$C_6$), $R^{507C}$-substituted or unsubstituted heterocycloalkyl (e.g., 3 to 8, 3 to 6, or 5 to 6 membered), $R^{507C}$-substituted or unsubstituted aryl (e.g., $C_6$-$C_{10}$, $C_{10}$, or phenyl), or $R^{507C}$-substituted or unsubstituted heteroaryl (e.g., 5 to 10, 5 to 9, or 5 to 6 membered).

$R^{507C}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^5$ is

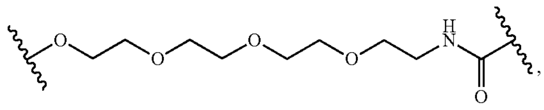
,
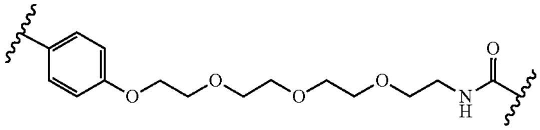
,
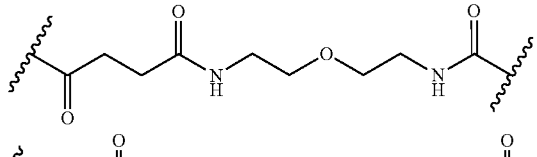
,
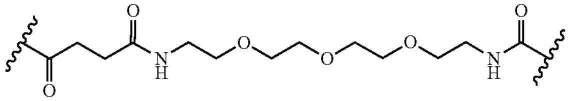
,
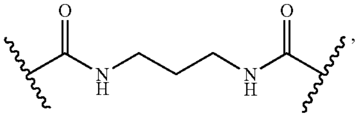
, or
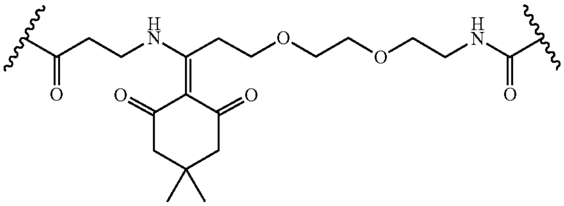
.

In embodiments, $R^5$-$L^5$-$R^6$ have the formula:

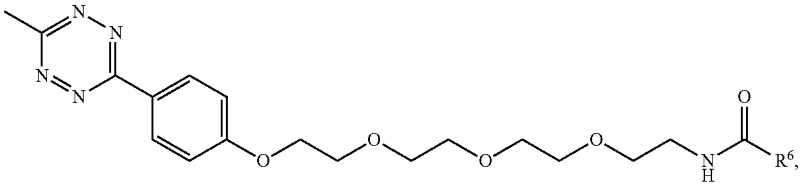
,
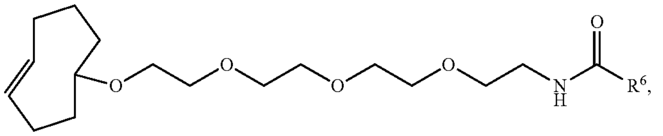
,
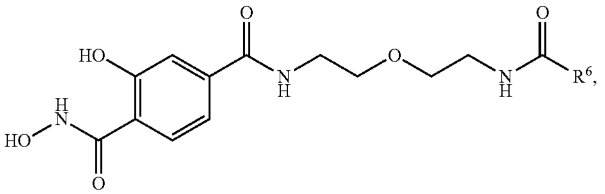
,
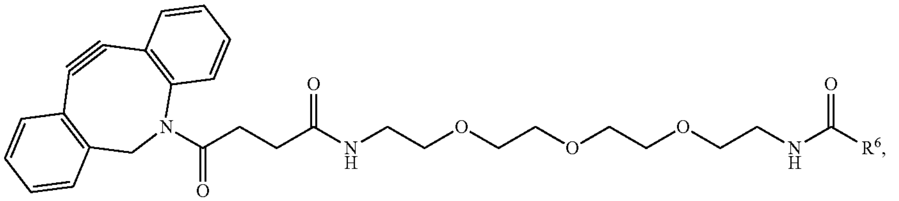
, or

-continued

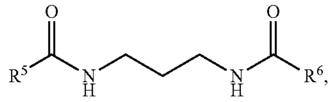

wherein $R^5$ is streptavidin, or

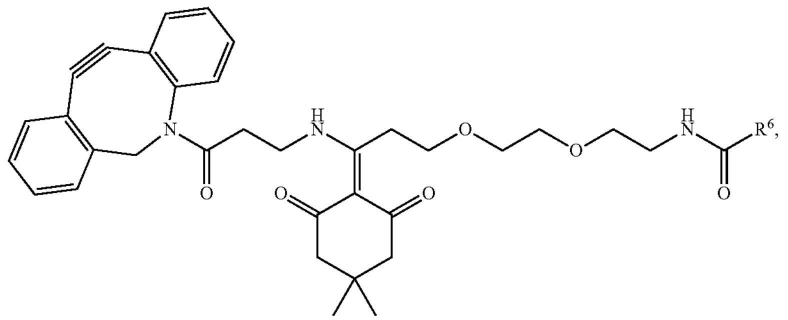

wherein $R^6$ is as described herein.

In embodiments, the composition includes a photodamage mitigating agent. Non-limiting examples of a photodamage mitigating agent include ascorbic acid, dithiothreitol (DTT), mercaptoethylamine (MEA), P-mercaptoethanol (BME), N-propyl gallate, p-phenylenediamene (PPD), hydroquinone, sodium azide ($NaN_3$), diazobicyclooctane (DABCO), cyclooctatetraene (COT), Trolox and its derivatives, butylated hydroxytoluene (BHT), ergothioneine, methionine, cysteine, beta-dimethyl cysteine, histidine, tryptophan, mercaptopropionylglycine, MESNA, glutathione, N-acetyl cysteine, captopril, lycopene, gamma-carotene, astazanthin, canthazanthin, alpha-carotene, beta-carotene, gamma-carotene, bixin, zeaxanthin, lutein, bilirubin, biliverdin, tocopherols, polyene dialdehydes, 32 melatonin, octocopheryl succinate and its analogs, pyridoxinel and its derivatives, hydrazine, sodium sulfite, and hydroxylamine. In embodiments, the photodamage mitigating agent is sodium pyruvate, N,N'-dimethylthiourea, mannitol, DMSO, carboxy-PTIO, 6-hydroxy-2,5,7,8-tetramethylchroman-2-carboxylic acid, alpha-tocopherol, 2-phenyl-1,2,benzisoselenazol-3 (2H)-one, uric acid, sodium azide, or manganese(III)-tetrakis(4-benzoic acid) porphyrin, 4,5-dihydroxybenzene-1,3-disulfonate. In embodiments, the photodamage mitigating agent is 3-carboxy-proxyl, N-propyl gallate, ascorbic acid, methyl viologen, Trolox, or Trolox-quinone.

In an aspect is provided a nucleic acid polymerase complex including a nucleic acid polymerase, wherein the nucleic acid polymerase is bound to a compound as described herein.

In an aspect is a composition including four fluorescently labeled nucleotides, wherein the first nucleotide has the formula

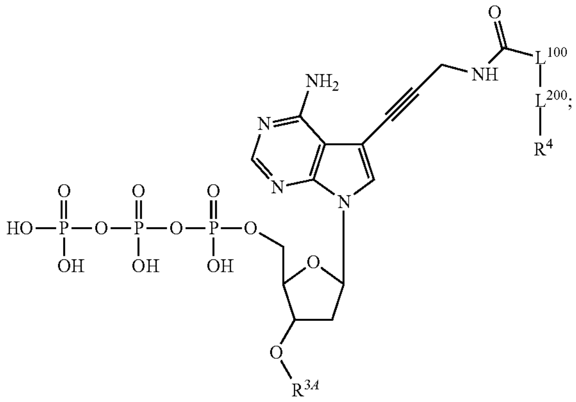

the second nucleotide has the formula:

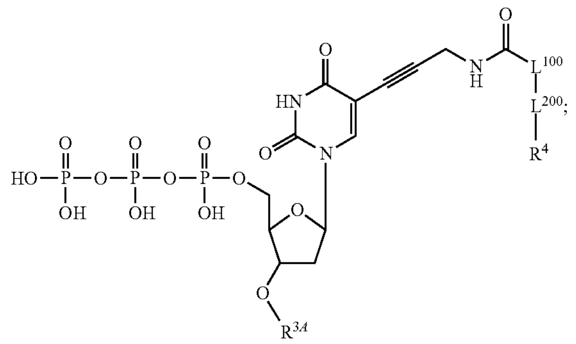

the third nucleotide has the formula:

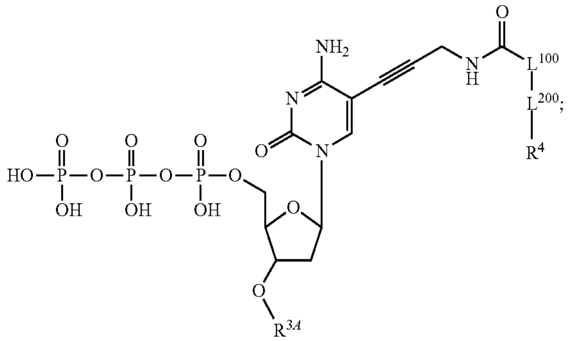

and the fourth nucleotide has the formula:

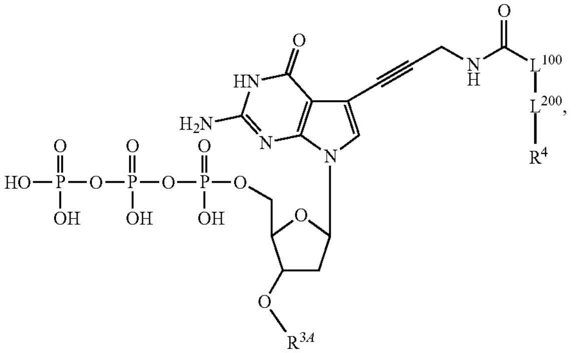

wherein each $L^{100}$ is independently a polymerase-compatible cleavable linker; each $L^{200}$ is independently a rigid spacer; each $R^{3A}$ is independently a polymerase-compatible cleavable moiety; and each $R^4$ is independently a fluorescent label. In embodiments, the fluorescent intensity (i.e., brightness) for each fluorescent label is substantially similar. In embodiments, $L^{100}$ and $R^{3A}$ are the same for all four nucleotides. In embodiments, the first nucleotide is:

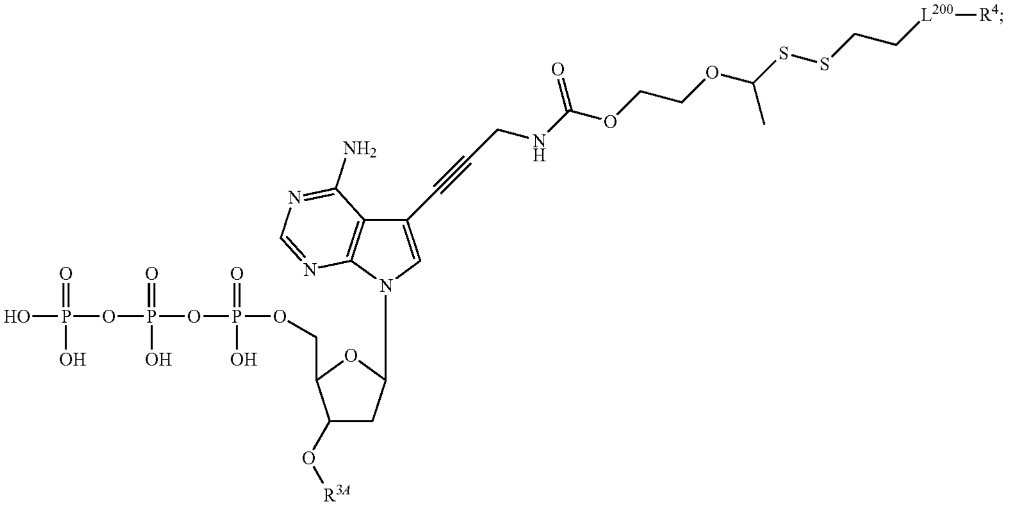

the second nucleotide is
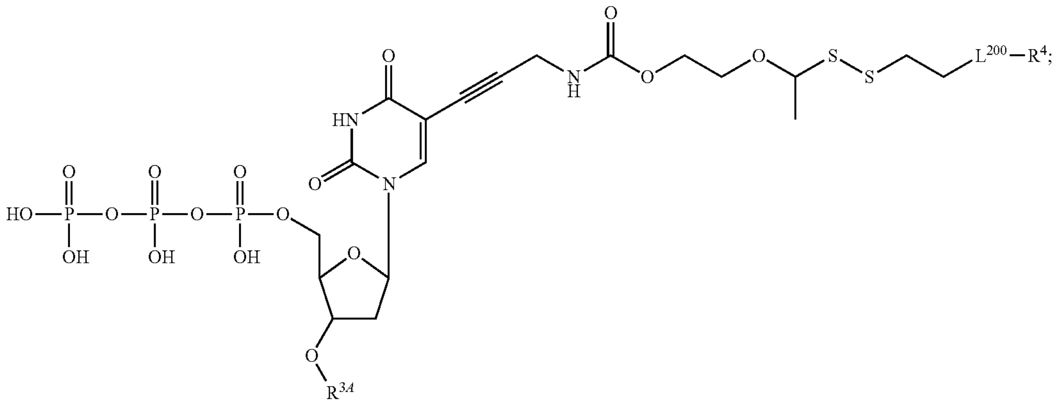
the third nucleotide is
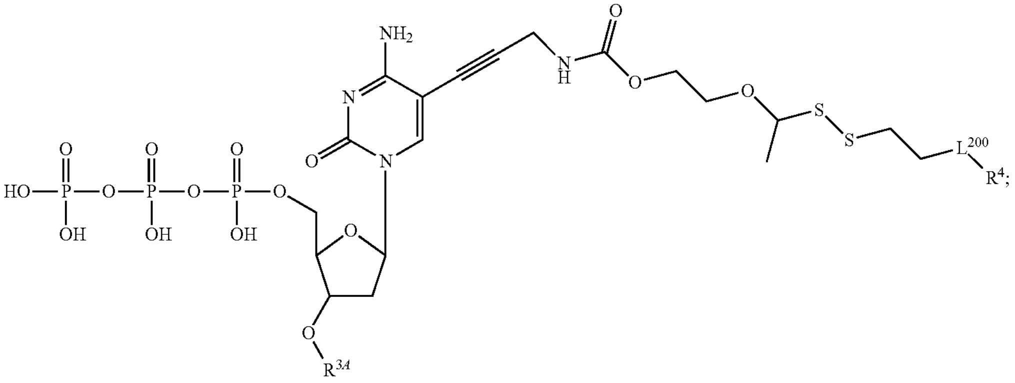
and the fourth nucleotide is
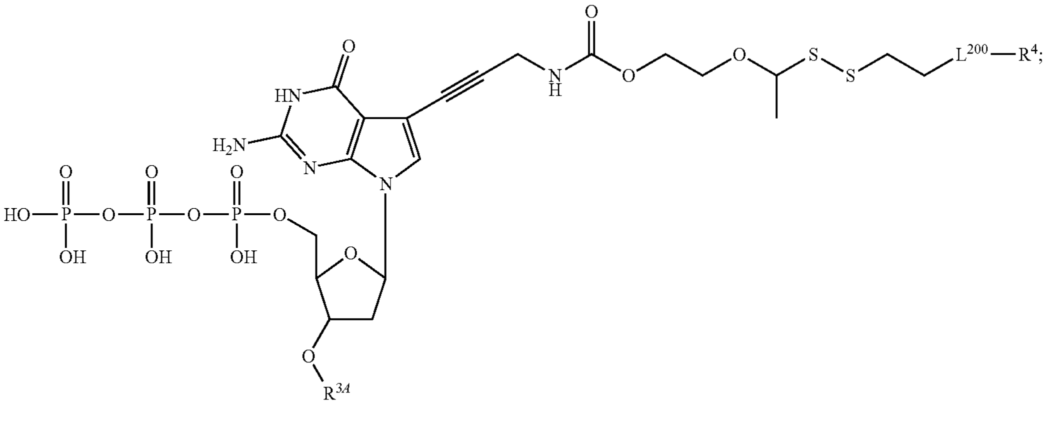

wherein $L^{200}$, $R^{3A}$, and $R^4$ are as described herein. In embodiments, the first nucleotide is
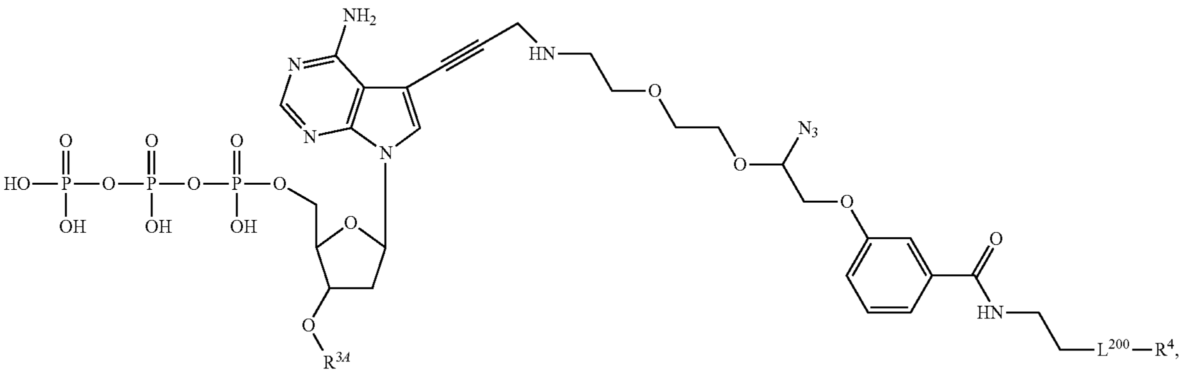
the second nucleotide is
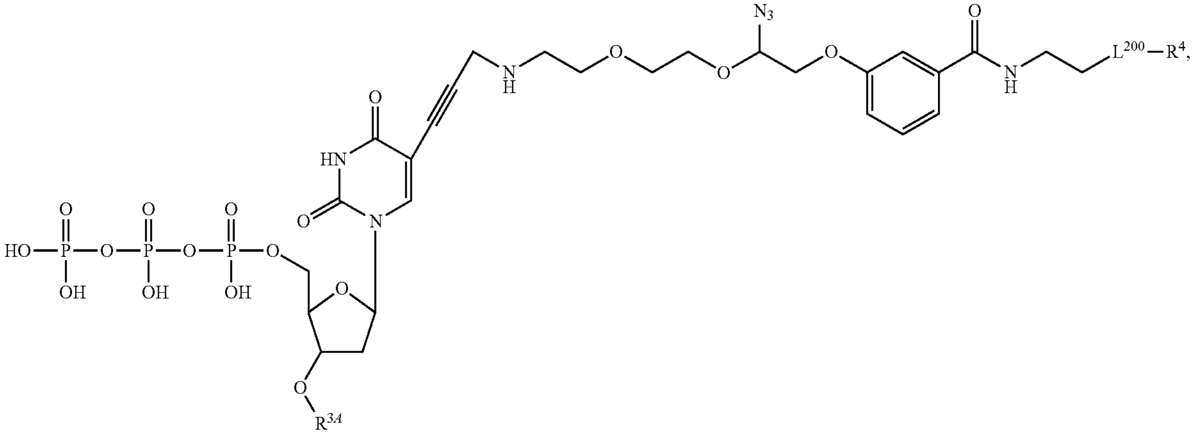
the third nucleotide is
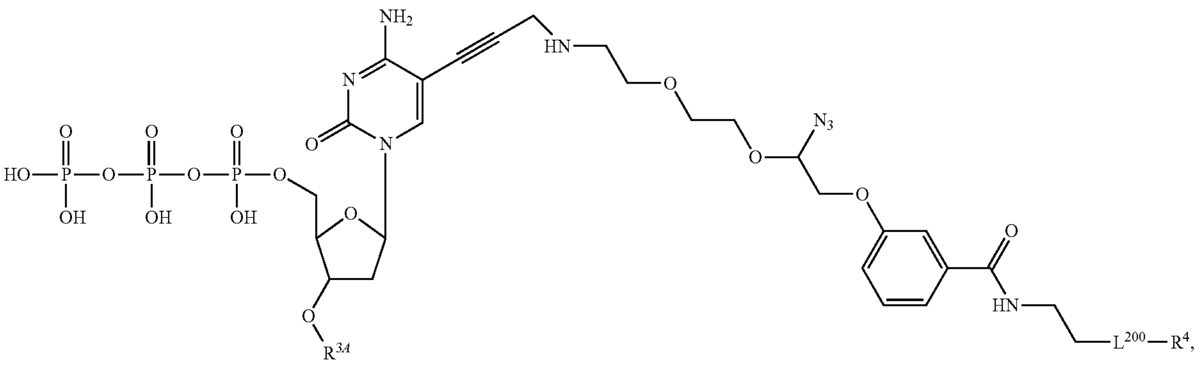

and the fourth nucleotide is

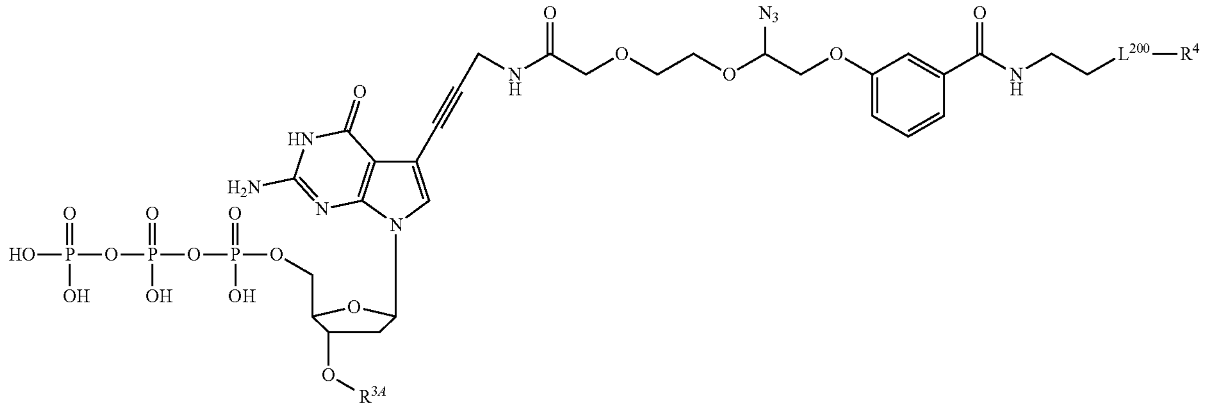

wherein $L^{200}$, $R^{3A}$, and $R^4$ are as described herein. In embodiments, $R^{3A}$ is independently:

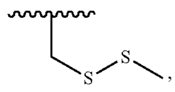,
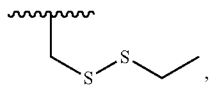,
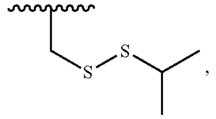,
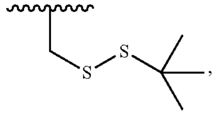,
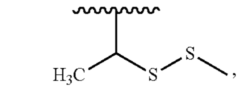,
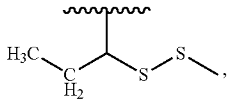,
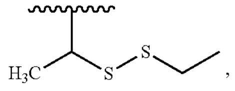,
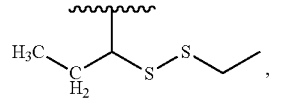,
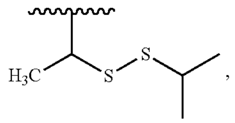,
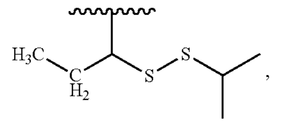,
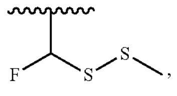,
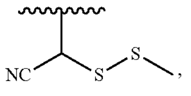,
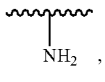,
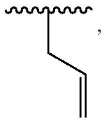,
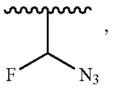,
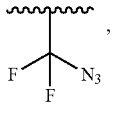,
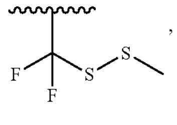,
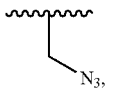,
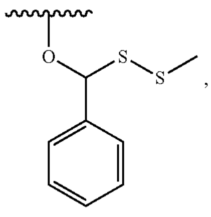,
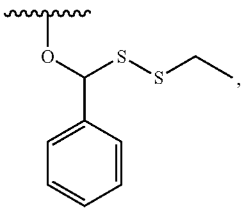, -continued

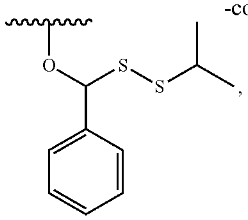,
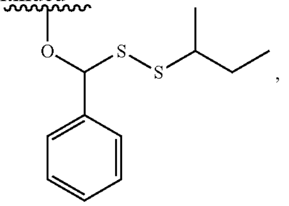,
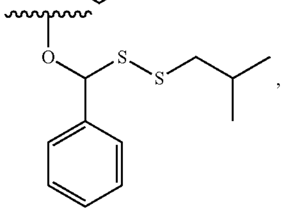,
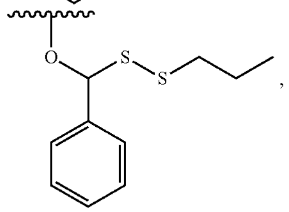,
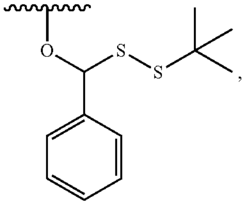, or
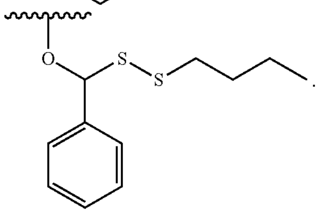.

Some embodiments disclosed herein relate to kits including a labeled nucleoside or nucleotide including a linker between the fluorophore and the nucleoside or nucleotide, wherein the linker includes a rigid spacer as described herein.

In an aspect, provided herein are kits for use in accordance with any of the compounds, compositions, or methods disclosed herein, and including one or more elements thereof. In embodiments, a kit includes labeled nucleotides including differently labeled nucleotides (e.g., compounds described herein). In embodiments, the kit further includes instructions for use thereof. In embodiments, kits described herein include a polymerase. In embodiments, the polymerase is a DNA polymerase. In embodiments, the DNA polymerase is a thermophilic nucleic acid polymerase. In embodiments, the DNA polymerase is a modified archaeal DNA polymerase. In embodiments, the kit includes a sequencing solution. In embodiments, the sequencing solution include labeled nucleotides including differently labeled nucleotides, wherein the label (or lack thereof) identifies the type of nucleotide. For example, each adenine nucleotide, or analog thereof, a thymine nucleotide; a cytosine nucleotide, or analog thereof, and a guanine nucleotide, or analog thereof may be labeled with a different fluorescent label.

In embodiments, the kit include sat least one labeled nucleotide or nucleoside together with labeled or unlabeled nucleotides or nucleosides. For example, nucleotides labeled with detectable labeles may be supplied in combination with unlabeled or native nucleotides, and/or with fluorescently labeled nucleotides or any combination thereof. Combinations of nucleotides may be provided as separate individual components (e.g., one nucleotide type per vessel or tube) or as nucleotide mixtures (e.g., two or more nucleotides mixed in the same vessel or tube).

In embodiments, the sequencing solution includes a buffer solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, Tricine, bicine, HEPES, TES, MOPS, MOPSO and PIPES. Additionally, other buffer agents that can be used in enzyme reactions, hybridization reactions, and detection reactions are well known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can comprise one or more divalent cations. Examples of divalent cations can include, but are not limited to, Mg2+, Mn2+, $Zn^{2+}$, and Ca2+. In embodiments, the buffered solution can contain one or more divalent cations at a concentration sufficient to permit hybridization of a nucleic acid. In some embodiments, a concentration can be more than about 1 M, more than about 2 M, more than about 5 M, more than about 10 M, more than about 25 M, more than about 50 M, more than about 75 M, more than about 100 M, more than about 200 M, more than about 300 M, more than about 400 M, more than about 500 M, more than about 750 M, more than about 1 mM, more than about 2 mM, more than about 5 mM, more than about 10 mM, more than about 20 mM, more than about 30 mM, more than about 40 mM, more than about 50 mM, more than about 60 mM, more than about 70 mM, more than about 80 mM, more than about 90 mM, more than about 100 mM, more than about 150 mM, more than about 200 mM, more than about 250 mM, more than about 300 mM, more than about 350 mM, more than about 400 mM, more than about 450 mM, more than about 500 mM, more than about 550 mM, more than about 600 mM, more than about 650 mM, more than about 700 mM, more than about 750 mM, more than about 800 mM, more than about 850 mM, more than about 900 mM, more than about 950 mM or more than about 1 M.

III. Methods of use

In an aspect is provided a method for sequencing a nucleic acid. In embodiments, the method includes (i) incorporating in series with a nucleic acid polymerase, within a reaction vessel, one of four different compounds into a primer to create an extension strand, wherein the primer is hybridized to the nucleic acid and wherein each of the four different compounds includes a unique detectable moiety or a unique anchor moiety; (ii) if the compound of step (i) above includes a unique anchor moiety, further adding to the reaction vessel a complementary anchor compound including a complementary anchor moiety to the unique anchor moiety bonded to a unique detectable moiety; and (iii) detecting the unique detectable moiety of each incorporated compound or incorporated compound-complementary anchor compound complex, so as to thereby identify each incorporated compound in the extension strand, thereby sequencing the nucleic acid; wherein each of the four different compounds is independently a compound as described herein, including embodiments. In embodiments, the complementary anchor compound is a composition as described herein, having formula (II): $R^5$-$L^5$-$R^6$, wherein $R^5$, $L^5$, and $R^6$ are as described herein. In some further embodiments, the one of four different compounds include nucleotide types selected from the group consisting of modified dATP, modified dTTP, modified dUTP, modified dCTP, modified dGTP, and non-natural nucleotide analogs thereof.

In embodiments, the compound includes at least one of the following: cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, 7-methylguanine or a derivative thereof, 5,6-dihydrouracil or a derivative thereof, 5-methylcytosine or a derivative thereof, and 5-hydroxymethylcytosine or a derivative thereof. In embodiments, the compound includes at least one of the following: cytosine or a derivative thereof, guanine or a derivative thereof, adenine or a derivative thereof, thymine or a derivative thereof, and uracil or a derivative thereof. In embodiments, the compound includes at least one of the following: cytosine or a derivative thereof, guanine or a derivative thereof, adenine or a derivative thereof, and thymine or a derivative thereof. In embodiments, the compound includes at least one of the following: cytosine or a derivative thereof, guanine or a derivative thereof, adenine or a derivative thereof, and uracil or a derivative thereof. In embodiments, the method further includes, after incorporating, contacting the compound with a cleaving agent. In embodiments, the method includes generating one or more sequencing reads.

In embodiments, the nucleic acid to be sequenced is DNA or RNA, or a hybrid molecule comprised of deoxynucleotides and ribonucleotides. In embodiments, the nucleic acid to be sequenced is attached to a solid substrate via any suitable linkage method known in the art, e.g., using covalent linkage. In embodiments, the nucleic acid is attached directly to a solid substrate. In embodiments, the surface of the solid support includes a polymer that provides the attachment points for the nucleic acid.

In embodiments, the nucleic acid is within a cluster. The terms "cluster" and "colony" are used interchangeably throughout this application and refer to a discrete site on a solid support comprised of a plurality of immobilized nucleic acid strands. The term "clustered array" refers to an array formed from such clusters or colonies. In this context the term "array" is not to be understood as requiring an ordered arrangement of clusters. The term "array" is used in accordance with its ordinary meaning in the art, and refers to a population of different molecules that are attached to one or more solid-phase substrates such that the different molecules can be differentiated from each other according to their relative location. An array can include different molecules that are each located at different addressable features on a solid-phase substrate. The molecules of the array can be nucleic acid primers, nucleic acid probes, nucleic acid templates or nucleic acid enzymes such as polymerases or ligases. Arrays useful in the invention can have densities that ranges from about 2 different features to many millions, billions or higher. The density of an array can be from 2 to as many as a billion or more different features per square cm. For example an array can have at least about 100 features/$cm^2$, at least about 1,000 features/$cm^2$, at least about 10,000 features/$cm^2$, at least about 100,000 features/$cm^2$, at least about 10,000,000 features/$cm^2$, at least about 100,000,000 features/$cm^2$, at least about 1,000,000,000 features/$cm^2$, at least about 2,000,000,000 features/$cm^2$ or higher. In embodiments, the arrays have features at any of a variety of densities including, for example, at least about 10 features/$cm^2$, 100 features/$cm^2$, 500 features/$cm^2$, 1,000 features/$cm^2$, 5,000 features/$cm^2$, 10,000 features/$cm^2$, 50,000 features/$cm^2$, 100,000 features/$cm^2$, 1,000,000 features/$cm^2$, 5,000,000 features/$cm^2$, or higher.

In embodiments, the method further includes adding to the reaction vessel a photodamage mitigating agent. In embodiments, the the photodamage mitigating agent is sodium pyruvate, N,N'-dimethylthiourea, mannitol, DMSO, carboxy-PTIO, 6-hydroxy-2,5,7,8-tetramethylchroman-2-carboxylic acid, alpha-tocopherol, 2-phenyl-1,2,benzisoselenazol-3(2H)-one, uric acid, sodium azide, or manganese(III)-tetrakis(4-benzoic acid) porphyrin, or 4,5-dihydroxybenzene-1,3-disulfonate.

In embodiments, the method further including, after each of the incorporating steps, adding to the reaction vessel four different unlabeled nucleotide analogues. In embodiments, the unlabeled nucleotide analogues have the structure

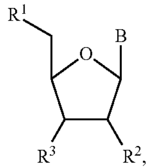

, wherein B is a monovalent nucleobase (e.g., B is

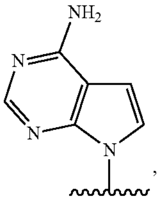

,

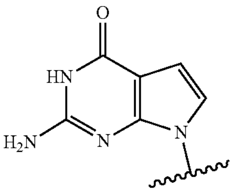

,

-continued

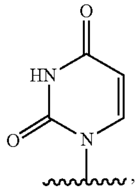

,

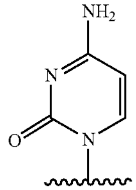

), and $R^1$, $R^2$, and $R^3$ are as described herein. In embodiments, the first of the four different unlabeled nucleotide analogues, B is a thymidine or uridine hybridizing base; in the second of the four different unlabeled nucleotide analogues, B is an adenosine hybridizing base; in the third of the four different unlabeled nucleotide analogues, B is a guanosine hybridizing base; and in the fourth of the four different unlabeled nucleotide analogues, B is a cytosine hybridizing base.

In embodiments, the primer is immobilized on a substrate. In embodiments, the nucleic acid is immobilized on a substrate. In embodiments, the sequencing methods are performed with the primer arrayed on a solid substrate. Multiple nucleic acids can be immobilized on the solid support through linker molecules, or can be attached to particles, e.g., microspheres, which can also be attached to a solid substrate. The solid substrate is in the form of a chip, a bead, a well, a capillary tube, a slide, a wafer, a filter, a fiber, a porous media, or a column. This invention also provides the instant method, wherein the solid substrate is gold, quartz, silica, plastic, glass, diamond, silver, metal, or polypropylene. This invention also provides the instant method, wherein the solid substrate is porous. In embodiments, the primer is covalently attached to the solid support. In embodiments, the 5' end of the primer contains a functional group that is tethered to the solid support. Non-limiting examples of covalent attachment include amine-modified polynucleotides reacting with epoxy or isothiocyanate groups on the solid support, succinylated polynucleotides reacting with aminophenyl or aminopropyl functional groups on the solid support, dibenzocyclooctyne-modified polynucleotides reacting with azide functional groups on the solid support (or vice versa), trans-cyclooctyne-modified polynucleotides reacting with tetrazine or methyl tetrazine groups on the solid support (or vice versa), disulfide modified polynucleotides reacting with mercapto-functional groups on the solid support, amine-functionalized polynucleotides reacting with carboxylic acid groups on the core via 1-ethyl-3-(3-dimethylaminopropyl)-carbodiimide hydrochloride (EDC) chemistry, thiol-modified polynucleotides attaching to a solid support via a disulphide bond or maleimide linkage, alkyne-modified polynucleotides attaching to a solid support via copper-catalyzed click reactions to azide functional groups on the solid support, and acrydite-modified polynucleotides polymerizing with free acrylic acid monomers on the solid support to form polyacrylamide or reacting with thiol groups on the solid support. In embodiments, the primer is attached to the solid support polymer through electrostatic binding. For example, the negatively charged phosphate backbone of the primer may be bound electrostatically to positively charged monomers in the solid support.

Flow cells provide a convenient format for housing an array of clusters produced by the methods described herein, in particular when subjected to an SBS or other detection technique that involves repeated delivery of reagents in cycles. For example, to initiate a first SBS cycle, one or more labeled nucleotides and a DNA polymerase in a buffer, can be flowed into/through a flow cell that houses an array of clusters. The clusters of an array where primer extension causes a labeled nucleotide (e.g., a compound as described herein) to be incorporated can then be detected. A deblocking reagent (e.g., a reducing agent) can be delivered to the flow cell (before, during, or after detection occurs). Washes can be carried out between the various delivery steps as needed. The cycle can then be repeated N times to extend the primer by N nucleotides, thereby detecting a sequence of length N. Example SBS procedures, fluidic systems and detection platforms that can be readily adapted for use with an array produced by the methods of the present disclosure are described, for example, in Bentley et al., *Nature* 456: 53-59 (2008), US 2018/0274024, WO 2017/205336, US 2018/0258472, each of which are incorporated herein in their entirety for all purposes.

In embodiments, the method includes performing a plurality of sequencing cycles. In embodiments, the methods of sequencing a template nucleic acid include a total number of sequencing cycles of about 1 to about 100, or about 20 to about 50. In embodiments, the total number of sequencing cycles is about 1, 2, 5, 10, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 cycles. In embodiments, the total number of sequencing cycles is about 50 cycles. In embodiments, the total number of sequencing cycles is about 100 cycles. In embodiments, the total number of sequencing cycles is about 150 cycles. In embodiments, the total number of sequencing cycles is about 200 cycles. In embodiments, the total number of sequencing cycle is greater than 50 cycles. In embodiments, the total number of sequencing cycle is greater than 100 cycles. In embodiments, the total number of sequencing cycle is greater than 150 cycles. In embodiments, the total number of sequencing cycle is greater than 200 cycles. In embodiments, the total number of sequencing cycles is 50 to 250 cycles. In embodiments, the total number of sequencing cycles is 50 to 150 cycles. In embodiments, the total number of sequencing cycles is 50 to 100 cycles. In embodiments, the total number of sequencing cycles is 100 to 250 cycles. In embodiments, the total number of sequencing cycles is 100 to 150 cycles.

In embodiments, the method includes simultaneously sequencing a plurality of different nucleic acids, including: a) extending a plurality of primer DNA strands hybridized to template DNAs, each of which includes one of the primer DNA strands, by incorporating a labeled nucleotide (i.e., a compound as described herein); and b) identifying each labeled nucleotide, so as to simultaneously sequence the plurality of different nucleic acids. In embodiments, the labeled nucleotide is a compound described herein.

In embodiments, the cleaving reagent cleaves both the linker and the polymerase-compatible cleavable moiety simultaneously.

In embodiments, the nucleic acid can include any nucleic acid of interest. The nucleic acid can include DNA, RNA, peptide nucleic acid, morpholino nucleic acid, locked nucleic acid, glycol nucleic acid, threose nucleic acid, mixtures thereof, and hybrids thereof. In embodiments, the nucleic acid is obtained from one or more source organisms. As used herein the term "organism" is not necessarily limited to a particular species of organism but can be used to refer to the living or self replicating particle at any level of classification, which includes the template nucleic acid. For example, the term "organism" can be used to refer collectively to all of the species within the genus *Salmonella* or all of the bacteria within the kingdom Eubacteria. In some embodiments, the nucleic acid can include a selected sequence or a portion of a larger sequence. In embodiments, sequencing a portion of a nucleic acid or a fragment thereof can be used to identify the source of the nucleic acid. With reference to nucleic acids, polynucleotides and/or nucleotide sequences a "portion," "fragment" or "region" can be at least 5 consecutive nucleotides, at least 10 consecutive nucleotides, at least 15 consecutive nucleotides, at least 20 consecutive nucleotides, at least 25 consecutive nucleotides, at least 50 consecutive nucleotides, at least 100 consecutive nucleotides, or at least 150 consecutive nucleotides.

In embodiments, the methods of sequencing a nucleic acid include extending a polynucleotide by using a polymerase. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol ε DNA polymerase, Pol α DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g., Therminator γ, 9° N polymerase (exo-), Therminator II, Therminator III, or Therminator IX). In embodiments, the DNA polymerase is a thermophilic nucleic acid polymerase. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes).

In embodiments, the methods of sequencing a nucleic acid include extending a complementary polynucleotide (e.g., a primer) that is hybridized to the nucleic acid by incorporating a first nucleotide. In embodiments, the method includes a buffer exchange or wash step. In embodiments, the methods of sequencing a nucleic acid include a sequencing solution. The sequencing solution includes (a) an adenine nucleotide, or analog thereof, (b) (i) a thymine nucleotide, or analog thereof, or (ii) a uracil nucleotide, or analog thereof, (c) a cytosine nucleotide, or analog thereof, and (d) a guanine nucleotide, or analog thereof.

In another aspect is provided a method of incorporating a compound into a primer, the method including combining a polymerase, a primer hybridized to nucleic acid template and the compound within a reaction vessel and allowing the polymerase to incorporate the compound into the primer thereby forming an extended primer, wherein the compound is a compound described herein, including embodiments.

In an aspect is provided a method for sequencing a nucleic acid, including: incorporating in series with a nucleic acid polymerase, within a reaction vessel, one of four different compounds into a primer to create an extension strand, wherein the primer is hybridized to the nucleic acid and wherein each of the four different compounds includes a unique detectable label; detecting the unique detectable label of each incorporated compound, so as to thereby identify each incorporated compound in the extension strand, thereby sequencing the nucleic acid; wherein each of the four different compounds is independently a compound described herein, including in embodiments.

In an aspect is a method for increasing the accuracy of a sequencing reaction, the method including (i) incorporating in series with a nucleic acid polymerase, within a reaction vessel, one of four different compounds into a primer to create an extension strand, wherein the primer is hybridized to the nucleic acid and wherein each of the four different compounds includes a unique detectable moiety or a unique anchor moiety; (ii) if the compound of step (i) above includes a unique anchor moiety, further adding to the reaction vessel a complementary anchor compound including a complementary anchor moiety to the unique anchor moiety bonded to a unique detectable moiety; and (iii) detecting the unique detectable moiety of each incorporated compound or incorporated compound-complementary anchor compound complex, so as to thereby identify each incorporated compound in the extension strand, thereby sequencing the nucleic acid; wherein each of the four different compounds is independently a compound as described herein. In embodiments, the method increases the accuracy of a sequencing reaction relative to a sequencing reaction (or plurality of sequencing reactions) wherein the compounds are otherwise identical to Formula (I) without a rigid spacer (i.e., without $L^{200}$ in Formula I).

In an aspect is provided a method of modulating the fluorescent intensity ratio of at least two different fluorescently-labeled compounds, the method including (i) providing a reaction mixture including two different fluorescently-labeled compounds, wherein each of two different compounds is independently a compound as described herein; (ii) measuring the fluorescence intensity of the two different fluorescently-labeled compounds under excitation illumination to determine the first fluorescent intensity ratio; (iii) modulating the functional distance of the rigid spacer of at least one of the two different fluorescently-labeled compounds; and (iv) measuring the fluorescence intensity of the two different fluorescently-labeled compounds under excitation illumination to determine the second fluorescent intensity ratio, thereby modulating the fluorescent intensity ratio of at least two different fluorescently-labeled compounds. In embodiments, the modulating the functional distance of the rigid spacer includes increasing the number of rigid spacer monomers.

In an aspect is provided a method of reducing photodamage to a biological component in a sequencing reaction, the method including (i) incorporating in series with a nucleic acid polymerase, within a reaction vessel, one of four different compounds into a primer to create an extension strand, wherein the primer is hybridized to the nucleic acid and wherein each of the four different compounds includes a unique detectable moiety or a unique anchor moiety; (ii) if the compound of step (i) above includes a unique anchor moiety, further adding to the reaction vessel a complementary anchor compound including a complementary anchor moiety to the unique anchor moiety bonded to a unique detectable moiety; and (iii) detecting the unique detectable moiety of each incorporated compound or incorporated compound-complementary anchor compound complex, so as to thereby identify each incorporated compound in the extension strand, thereby sequencing the nucleic acid; wherein each of the four different compounds is independently a compound as described herein. In embodiments, the method reduces photodamage to a biological component in a sequencing reaction (or plurality of sequencing reactions) wherein the compounds are otherwise identical to Formula (I) without a rigid spacer (i.e., without $L^{200}$ in Formula I).

In embodiments, the method further including, after the incorporating, cleaving the cleavable linker (e.g., $L^{100}$) with a cleaving reagent (e.g., a water-soluble phosphine, such as tris(hydroxypropyl)phosphine (THPP)). In embodiments, the cleaving reagent is a reducing agent. In embodiments, the cleaving agent is a phosphine containing agent. In embodiments, the cleaving agent is a thiol containing agent. In embodiments, the cleaving agent is di-mercaptopropane sulfonate (DMPS). In embodiments, the cleaving agent is aqueous sodium sulfide ($Na_2S$). In embodiments, the cleaving reagent is Tris-(2-carboxyethyl)phosphines trisodium salt (TCEP), tris(hydroxypropyl)phosphine (THPP), guanidine, urea, cysteine, 2-mercaptoethylamine, or dithiothreitol (DTT). In embodiments, the cleaving reagent is an acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$). In embodiments, the method includes contacting the compound (e.g., a compound described herein) with a reducing agent. In embodiments, the method further including, after the incorporating, cleaving the linker at about 55° C. In embodiments, the method further including, after the incorporating, cleaving the linker at about 45° C. to about 60° C. In embodiments, the method further including, after the incorporating, cleaving the linker at about 55° C. to about 80° C. In embodiments, the method further including, after the incorporating, cleaving the linker at about 60° C. to about 70° C. In embodiments, the method further including, after the incorporating, cleaving the linker at about 50° C. to about 60° C. In embodiments, the method further including, after the incorporating, cleaving the linker at about 65° C. to about 75° C. In embodiments, the method further including, after the incorporating, cleaving the linker at about 65° C. In embodiments, the method further including, after the incorporating, cleaving the linker at about 55° C. In embodiments, the method further including, after the incorporating, cleaving the linker at about 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or about 80° C. In embodiments, the method further including, after the incorporating, cleaving the linker at a pH at about 8.0 to 11.0. In embodiments, the pH is 9.0 to 11.0. In embodiments, the pH is 9.5. In embodiments, the pH is 10.0. In embodiments, the pH is 8.0, 8.5, 9.0, 9.5, 10.0, 10.5, or 11.0. In embodiments, the pH is from 9.0 to 11.0, and the temperature is about 60° C. to about 70° C. In embodiments, the pH is from 9.0 to 11.0, and the temperature is about 50° C. to about 60° C.

In embodiments the biological component includes a nucleotide, DNA, or RNA. In embodiments, the biological component is a nucleotide, DNA, or RNA. In embodiments, the biological is an enzyme. In embodiments, the enzyme is a polymerase, nuclease, or ligase enzyme. In embodiments, the enzyme is a DNA polymerase.

The methods and kits of the present disclosure may be applied, mutatis mutandis, to the sequencing of RNA, or to determining the identity of a ribonucleotide.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1. Nucleotide Cleavable Linkers with Rigid Spacers

Described herein are linkers having predictable length and rigidity to address two problems in detection technologies:

minimizing photodamage and normalizing fluorescent signal intensities. Fluorescence is an inherently inefficient process; the emission is orders of magnitude weaker than the intensity of excitation light. There is an incentive to increase the intensity of the excitation light, however increasing the excitation light to generate a sufficiently strong signal from typical fluorophores is damaging to many components in biological systems. Even at modest intensities, common deleterious effects arise due to generation of chemically reactive spices such as free radicals and singlet and triplet forms of oxygen, which may render biological molecules (e.g., enzymes) non-functional.

Additionally, within the context of nucleic acid sequencing, guanine (G) is efficient at quenching fluorophores, meaning that a fluorophore covalently linked to G-nucleotide is harder to detect than the equivalent fluorophore attached to adenine (A), thymine (T), or cytosine (C) (Kurata at al., Nucleic Acids Res., 29(6) e34 (2001)). In next generation sequencing technology based on detection of fluorescent labeled nucleotides, this in turn means that the fluorescent signal detected from labeled guanine nucleotides incorporated during the sequencing reaction will generally be of a lower intensity than that detected from labeled nucleotides bearing the same fluorophore attached to adenine, thymine or cytosine containing nucleotides. Thus, in certain circumstances the presence of a G nucleotide may be harder to call with certainty than the presence of A, T or C under the same reaction and detection conditions. Accordingly, it would be desirable to be able to increase the intensity of the fluorescent signal from fluorescently labeled G nucleotides so that the intensity of the signal is normalized relative to the intensity of the other fluorescently labeled nucleotides (i.e., the signal from a labeled G compares more favorably with a signal which can be obtained from fluorescently labeled A, T or C nucleotides under the same reaction and detection conditions).

Previous attempts to lengthen the linker between the fluorophore and a guanine base relied on a polyethylene glycol spacer (PEG) linker (see for example US 2007/0042407). The PEG linkers attempt to position the fluorescent label away from the guanine base to reduce the quenching effects, however PEG is notoriously flexible and is capable of folding back to be in close proximity to guanine. Furthermore, the PEG linkers described in the '407 application potentially address the fluorescent intensity of only one single nucleotide (i.e., G), whereas the remaining nucleotide fluorescent intensities are still variable. In embodiments, the compounds described herein normalizes the intensity for all nucleotides (e.g., A, T, C, and G) to be sequenced, such that the fluorescent intensities are substantially similar (i.e., within 10% of each other).

The rigid spacer containing linkers described herein allow for customization of the polarity and charge by controlling the amount and type of substituents; for example some potential rigid spacer monomers with differing substituents are listed in Table 2 and Table 3. Synthesizing the linkers is highly controlled such that the resulting polymer may have alternating monomers similar to a copolymer (e.g., an alternating copolymer). For example, the resulting rigid spacer may be comprised of varying blocks of monomers bearing one type of substituent (e.g., a phenylene bearing a —$SO_3H$ moiety) followed by a series of monomers bearing a different monomer (e.g., an unsubstituted phenylene), having the general formula -AAA-BBB—, wherein A represents one type of monomer, and B represents a different (i.e. different from A) monomer; see for example some synthesized rigid spacer linkers with their respective abbreviations in Table 3.

In embodiments, the rigid spacers as described herein are hydrophilic. The hydrophilicity may be governed by the substituent (i.e. $R^{202}$ of Formula (IV)), the quantity of substitutions (i.e., z202 of Formula (IV)), or the type of aromatic ring (e.g., phenylene or pyridine). For example, the rigid spacer may include charged (e.g., sulfonate) substituents to enhance solubility in sequencing reactions. Alternatively, the rigid spacer may include pyridine rings or include uncharged substitutents (e.g., sulfonamide) to enhance solubility in sequencing reactions without modulating the charge of the rigid spacer.

TABLE 2

Rigid spacer monomers with differing substituents.

| Abbreviation | Charge | Monomer Structure |
|---|---|---|
| A | 0 | 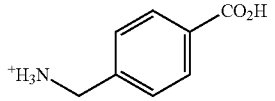 [SMILES: [NH3+]Cc1ccc(C(=O)O)cc1] |
| B | −1 | 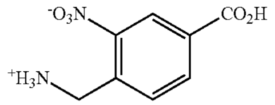 |
| C | 0 | 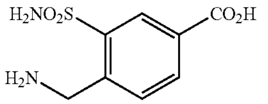 |

TABLE 3

Nucleotides of Formula I, A, T, C, and G, containing a cleavable linker, abbreviated N3 for an azido containing linker or SS for a linker containing a disulfide, and a rigid spacer. The abbreviations for the rigid spacer monomers (i.e., A, B, C) are described in Table 2.

| Nucleotide-linker-spacer-dye | Quantity of monomers | Formal charge of total spacer | Abbreviated spacer nomenclature |
|---|---|---|---|
| G-N3-$(AB_4)_2$-dye1 | 10 | −8 | ABBBBABBBB |
| C-N3-$(AB_4)_2$-dye2 | 10 | −8 | ABBBBABBBB |
| T-N3-$(AB_4)_2$-dye3 | 10 | −8 | ABBBBABBBB |
| A-N3-$(AB_4)_2$-dye4 | 10 | −8 | ABBBBABBBB |
| T-N3-$(AB_4)_2$-biotinPEG$_4$-streptavidin-dye3 | 10 | −8 | ABBBBABBBB |
| G-N3-$(ABABA)_3$-dye1 | 15 | −6 | ABABAABABAABABA |
| T-N3-(ABABA)-dye3 | 5 | −2 | ABABA |
| G-SS-$B_5$-dye1 | 5 | −5 | BBBBB |
| C-SS-$B_5$-dye2 | 5 | −5 | BBBBB |
| T-SS-$B_5$-dye3 | 5 | −5 | BBBBB |
| A-SS-$B_5$-dye4 | 5 | −5 | BBBBB |
| G-SS-$B_1$-dye1 | 1 | −1 | B |
| G-SS-$B_2$-dye1 | 2 | −2 | BB |
| G-SS-$B_3$-dye1 | 3 | −3 | BBB |
| G-SS-$B_4$-dye1 | 4 | −4 | BBBB |
| G-N3-$C_5$-dye1 | 5 | 0 | CCCCC |

The rigid spacers as described herein are do not substantially bend or flex and do not allow substantial rotation either along their length or at their attachments points. For example, an energy minimization calculation using the MMFF94 force field on a model dimer estimates a 7 kcal/mol barrier preventing rotation about the χ(N—C—

C—C) angle (see FIG. 1), implying the linkers with rigid spacers maintain their linear nature.

As such, these rigid spacers maintain a persistent length throughout the course of the reaction. Persistence length can be measured or calculated using methods known in the art. This is in contrast to flexible linkers. Flexible linkers include, but are not limited to, those comprising a single-stranded oligonucleotide, a short carbon spacer (e.g. alkanes), a non-cyclic containing polypeptide (e.g., polyhistidine, polylysine), polysaccharide or combinations thereof. Flexible linkers typically also allow rotation. Flexible linkers may permit rotation in at least one axis.

Figure 2:
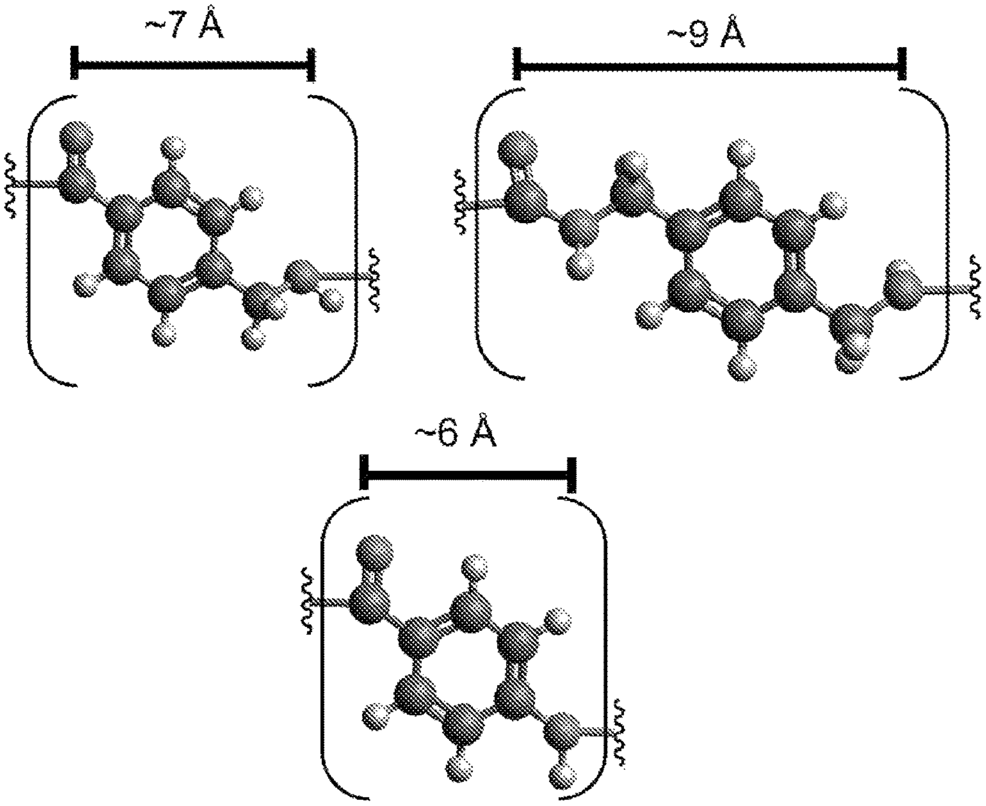
FIG. 2. A ball-and-stick rendering of a monomer of Formula (IV) showing the measured distance between the carbonyl carbon and the nitrogen atom of an unsubstituted rigid linker monomer.
Figure 3:
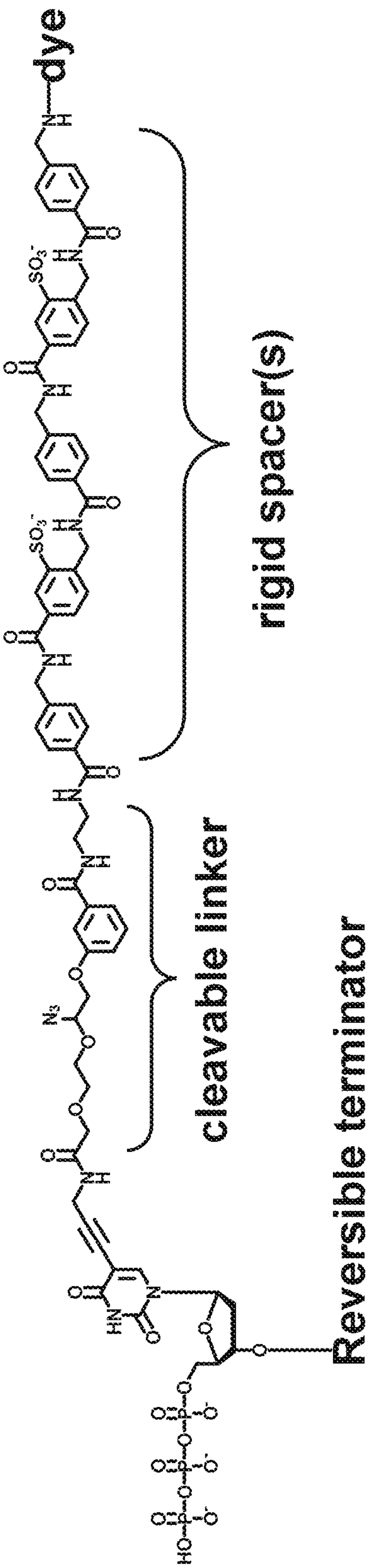
FIG. 3. An illustration of a non-limiting example of a nucleotide comprising a reversible terminator, cleavable linker, rigid spacer(s), and a detectable moiety.
Figure 4A:
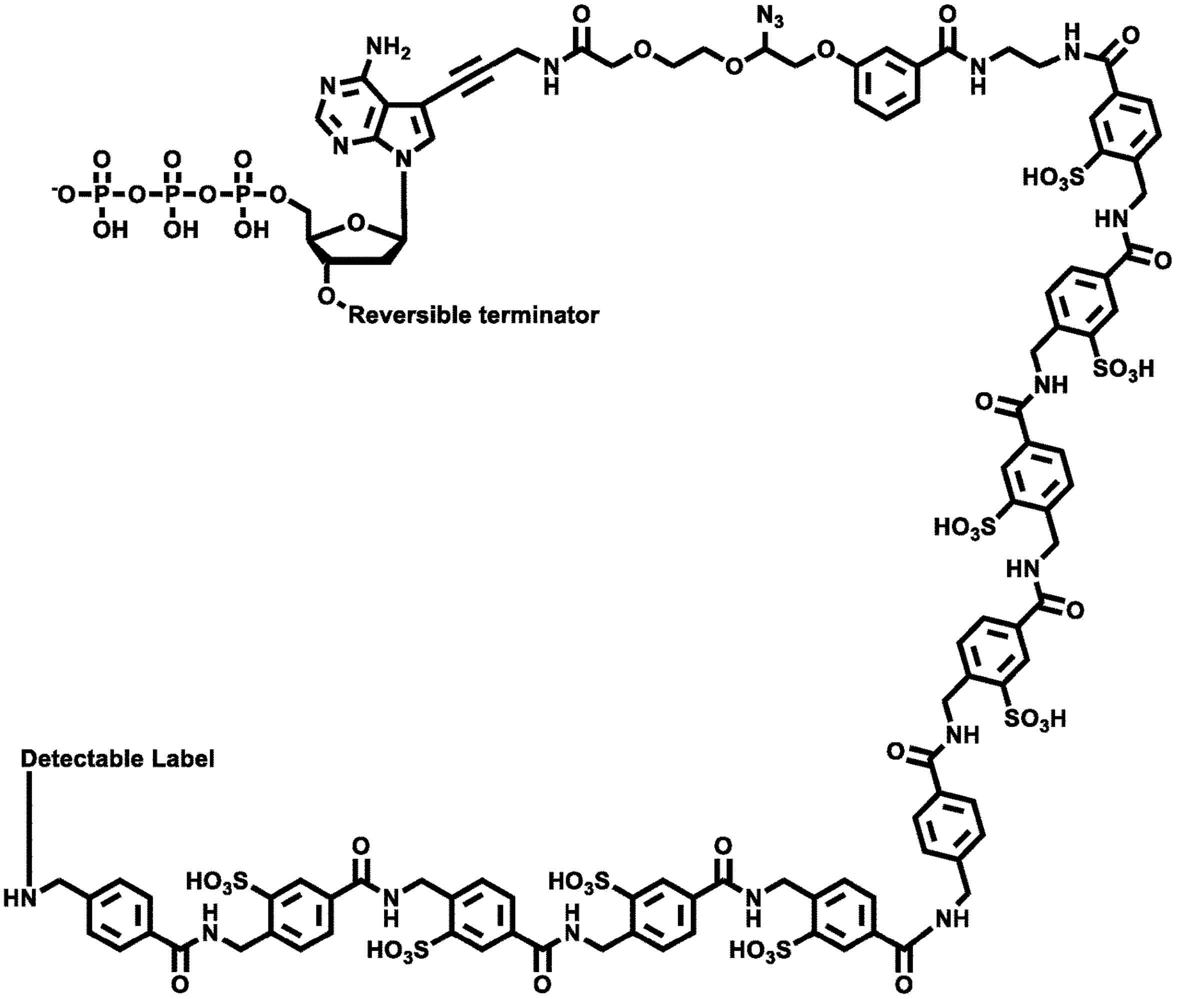
FIGS. 4A-4D. A non-limiting example of a synthesized set of nucleotides containing 10 rigid spacer monomers (10mer) and a detectable label.
Figure 4B:
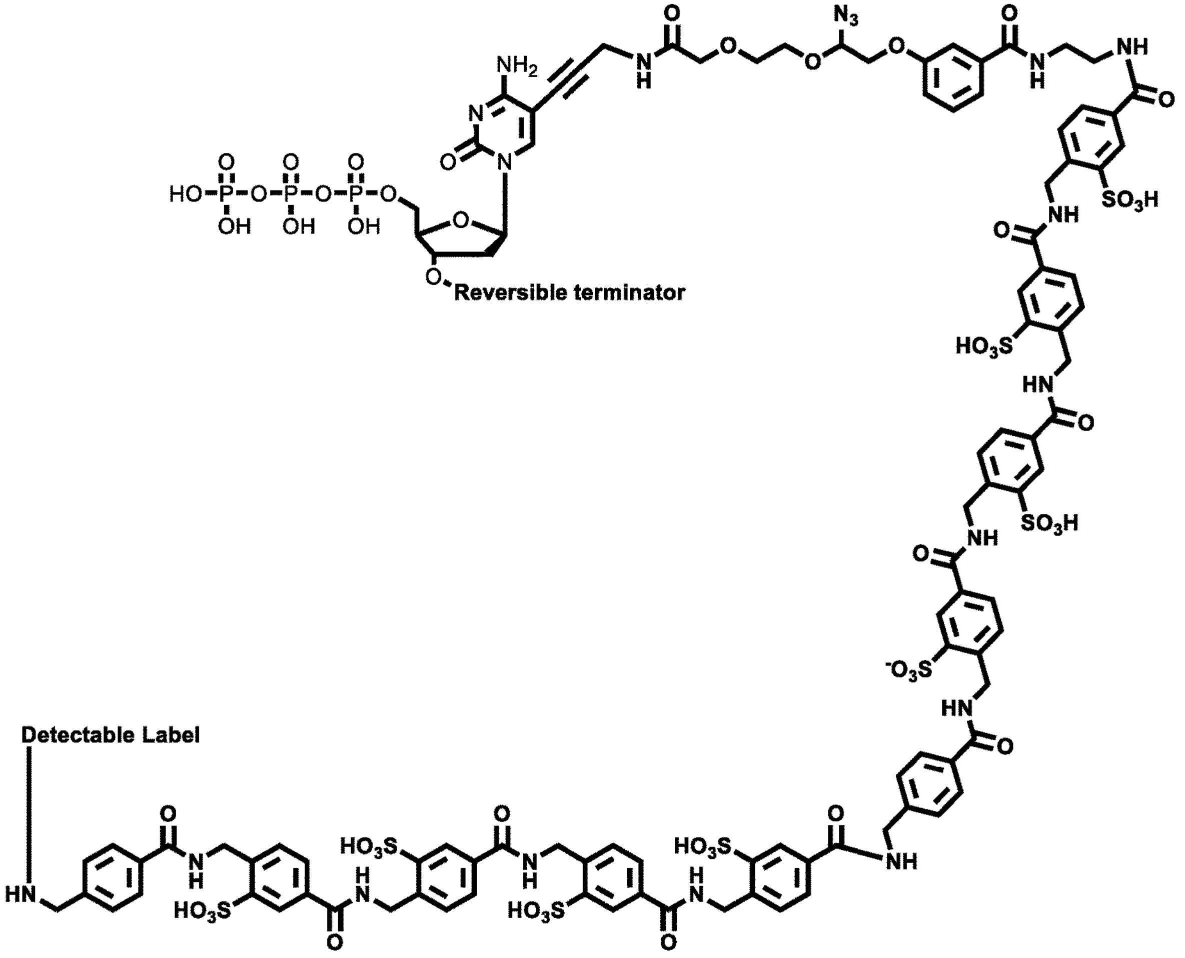
Figure 4C:
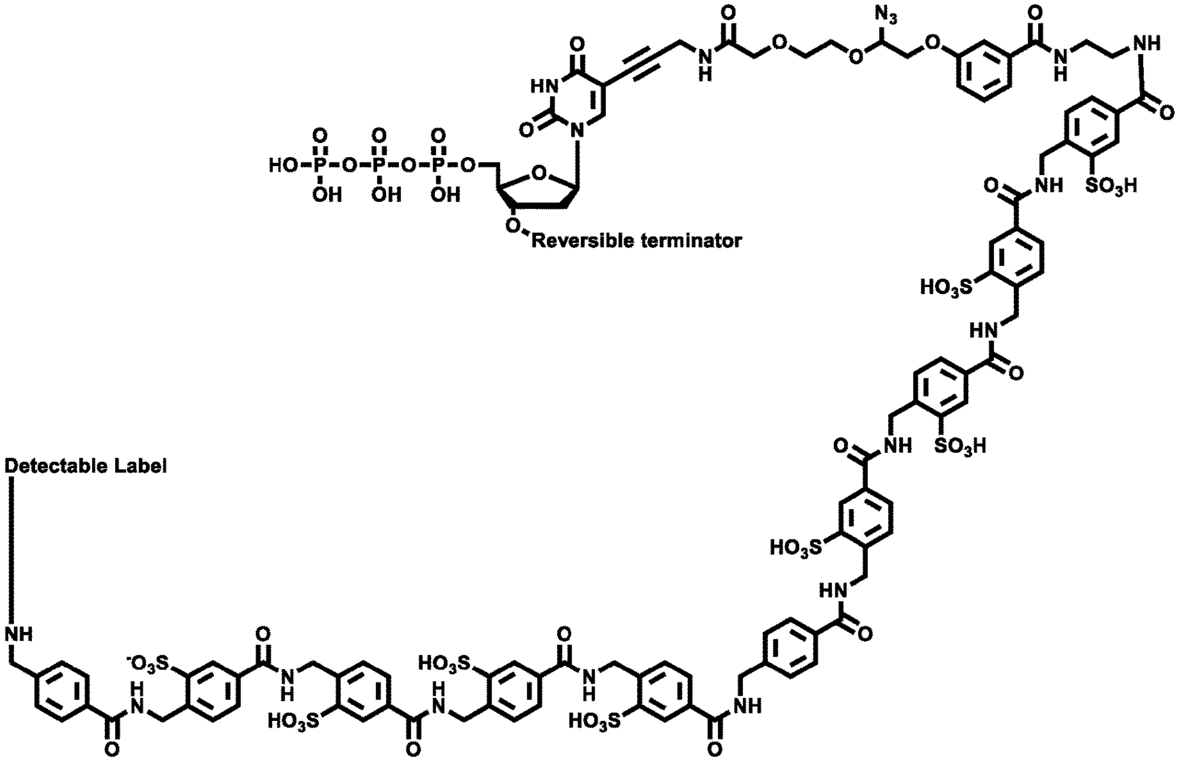
Figure 4D:
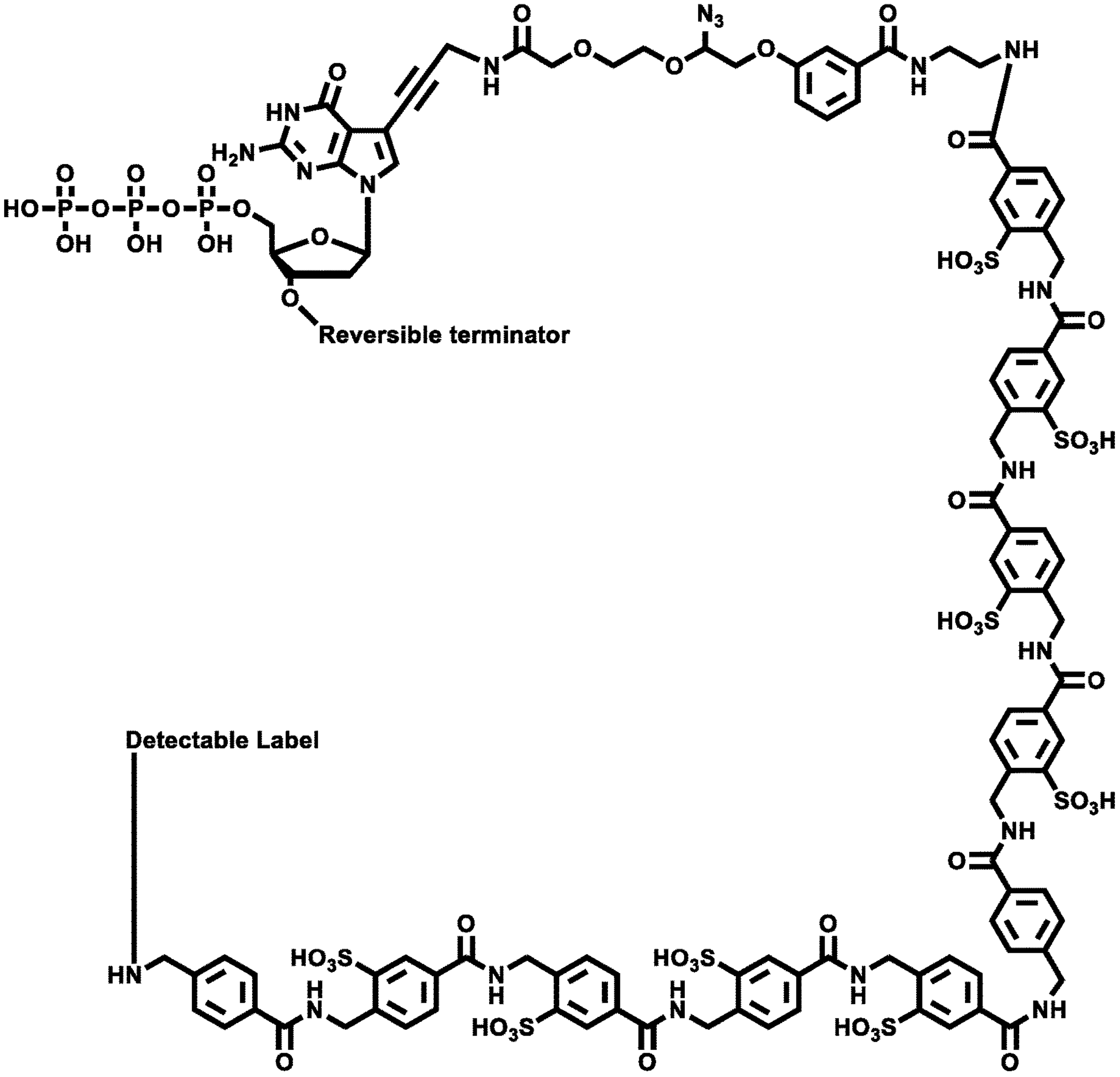
Figure 5:
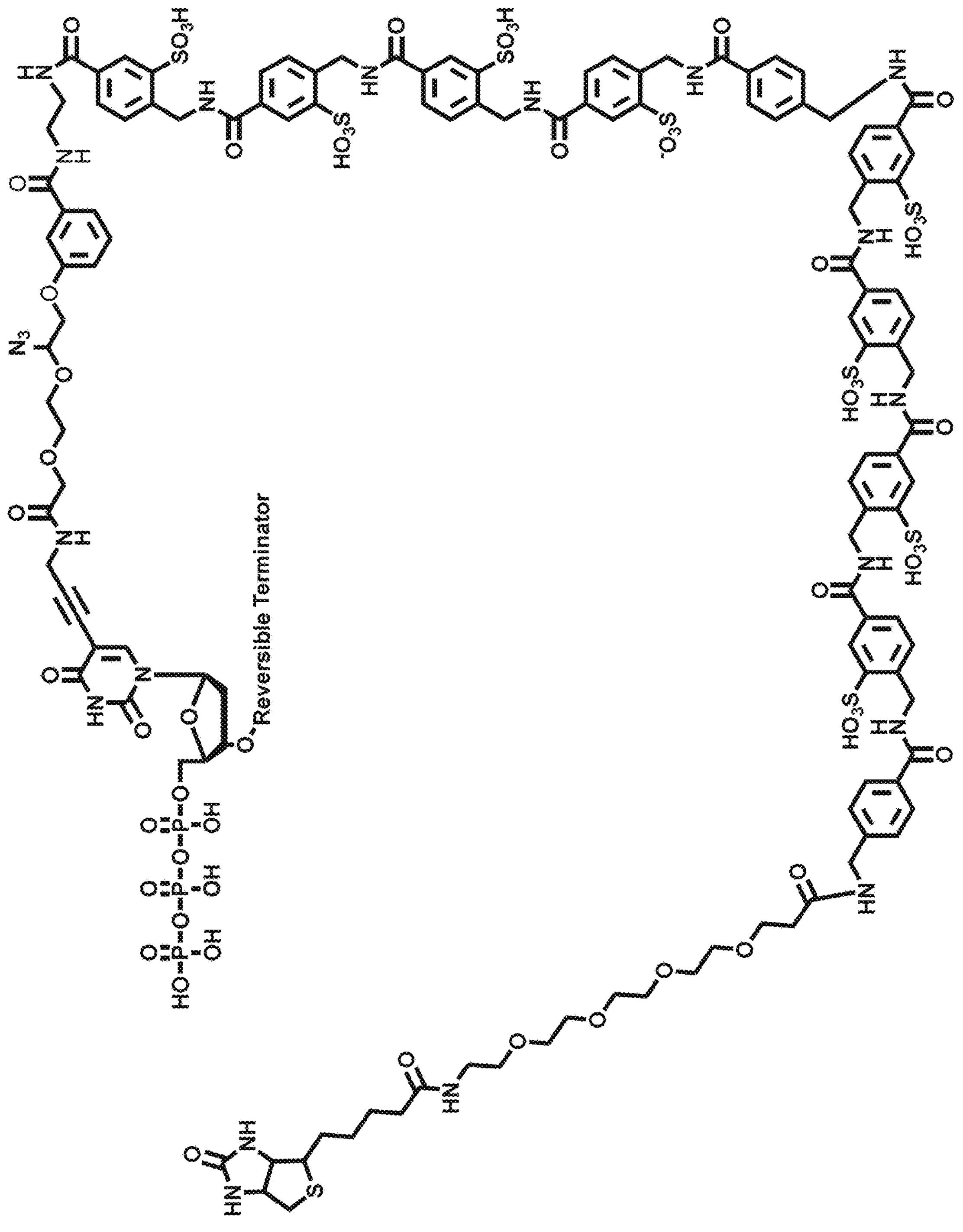
FIG. 5. A non-limiting example of a synthesized nucleotide containing 10 rigid spacer monomers (10mer) and a biotin anchor moiety.
Figure 6:
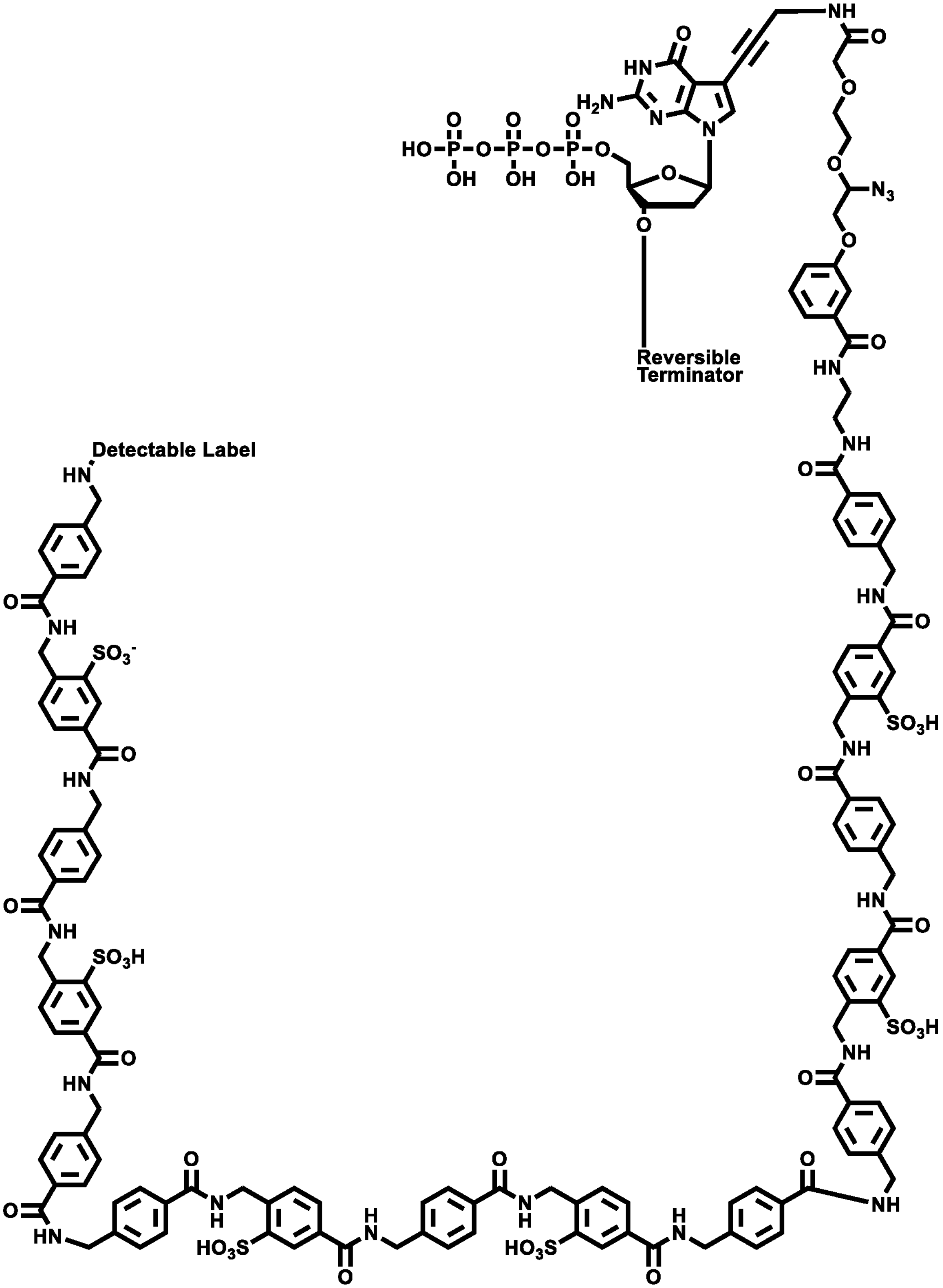
FIG. 6. A non-limiting example of a synthesized nucleotide containing 15 rigid spacer monomers (15mer) and a detectable label. The rigid spacer monomers alternate with sulfonate-substituted and unsubstituted monomers, similar to a copolymer (ABABA-ABABA-ABABA) repetition pattern.
Figure 7:
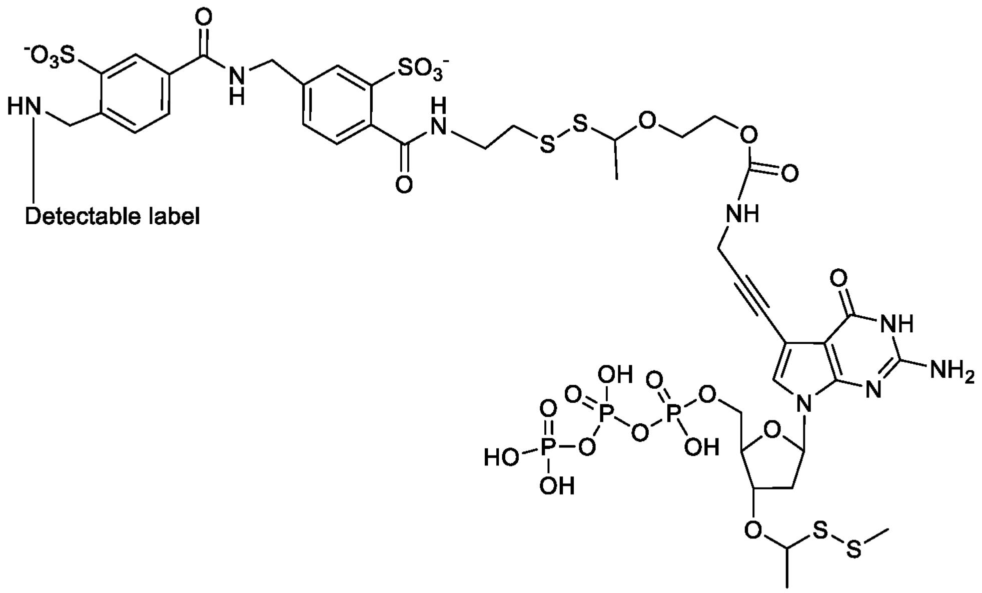
FIG. 7. A non-limiting example of a synthesized nucleotide containing 2 rigid spacer monomers (2mer) and a detectable label.

Additionally, utilizing the synthetic protocols described herein, the precise distance can be tailored to suit any application. For example, the approximate distance between the exocyclic carbonyl and the nitrogen atom (for example, see FIG. 2) is about 7 Å or about 9 Å when $L^{205}$ is a bond or $—CH_2NH—$ in Formula (IV), respectively for the rigid spacer monomers. Due to the rigidity afforded by the aromatic ring, this distance remains relatively invariant in situ. When incorporated into a nucleotide, the location of the dye relative to the base can be controlled systematically (e.g., 4 monomers corresponds to approximately 28 Å of spacing from the cleavable linking moiety; 10 monomers corresponds to approximately 70 Å of spacing from the cleavable linking moiety). Allowing for a rigid customizable spacer separating the nucleobase from the fluorescent dye aids in minimizing photodamage and normalizing fluorescent signal intensities in SBS technologies.

Example 2. Synthetic Protocols to Produce Modified Nucleotides Containing Rigid Spacers Rigid spacer synthesis can begin with fuming sulfuric acid.

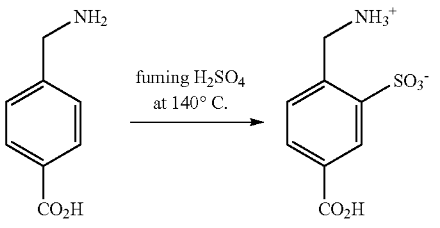

1 2

Scheme 1: Synthesis of compound 2. 10 g of compound 1 was dissolved in 25 ml of 20% fuming sulfuric acid at 140° C. for 5 hours. Mixture was poured over 400 ml of ice, and resultant milky slush was vacuum filtered. Crude compound 2 was dissolved in TEA and $H_2O$ in a ratio of 50 mg:50 μl:90 μl compound 2:TEA:$H_2O$, and then purified by reverse phase HPLC eluting with 50 mM TEAB isocratic. Product fractions were dried down, desalted with MeOH, and compound 2 was scraped off the flask walls. Product formation was confirmed by LCMS (calculated and observed m/z=231) and by 1H and C18 NMR. $^1H$ NMR (500 MHz, $D_2O$) δ 8.37 (s, 1H), 8.03 (d, J=7.8 Hz, 1H), 7.63 (d, J=7.9 Hz, 1H), 4.55 (s, 2H), 3.19 (q, J=7.3 Hz, 6H), 1.27 (t, J=7.3 Hz, 9H). $^{13}C$ NMR (125 MHz, $D_2O$) δ 173.50, 142.17, 138.12, 132.41, 132.14, 131.74, 127.76, 46.74, 41.12, 8.28.

Note, that the schemes are shown for one embodiment, however these schemes may equally be applied to structures of Formula IV. For example, the same synthetic procudes may be used to generate the pyridyl analog (la and 3a) as shown in the scheme below.

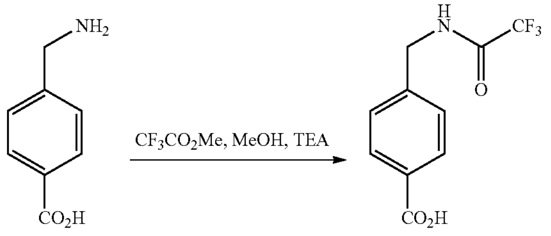

1 3

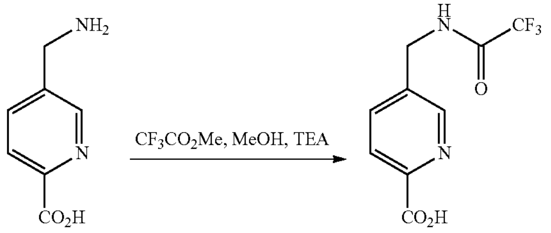

1a 3a

Scheme 2: Synthesis of compound 3. 1.5 g of compound 1 was dissolved in 10 ml $CF_3CO_2Me$, 10 ml MeOH, and 1 equivalent TEA. Reaction was vacuum filtered and rinsed with MeOH. Product in flow-through was pumped down to remove $CF_3CO_2Me$ and TEA. Next, product was dissolved in water and ether in separatory funnel for aqueous workup. After three extractions, 1M HCl was added dropwise until product precipitated out at ~pH<4. Resultant white slush was vacuum filtered and air dried over vacuum for 1 hour to give an ivory powder. Compound 3 was confirmed by LCMS: observed m/z 247=calculated m/z 247.

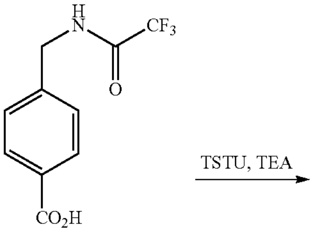

3

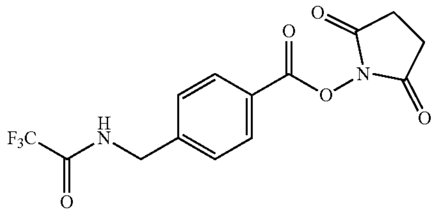

4

+

-continued

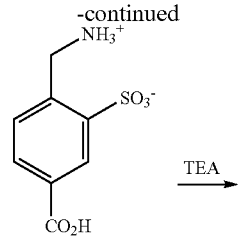

2

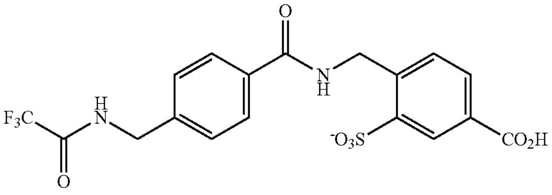

5

Scheme 3: Synthesis of compound 5. Compound 3 was dissolved in minimal volume anhydrous DMF and treated with 1.2 equivalents TSTU and 2 equivalents TEA. Formation of compound 4 was confirmed by LCMS (expected and observed NHS-butylamide m/z=302). 1 equivalent of compound 2 was added to reaction mixture to form compound 5, which was purified by reverse phase HPLC eluting with acetonitrile and 50 mM TEAB. Product fractions were dried down, desalted with MeOH, and dried by vacuum pump. Compound 5 was confirmed by LCMS: calculated and observed m/z 459.

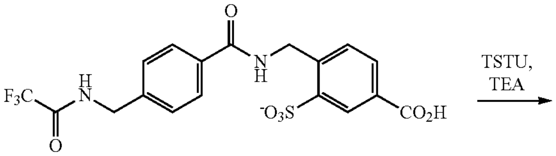

5

-continued

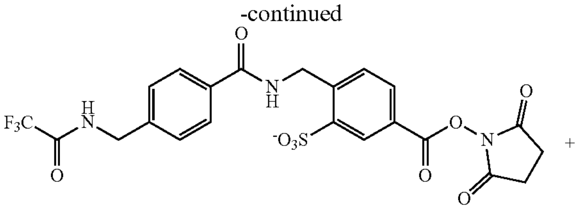

6

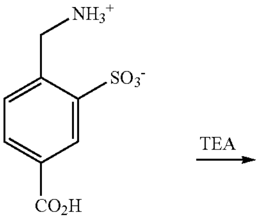

2

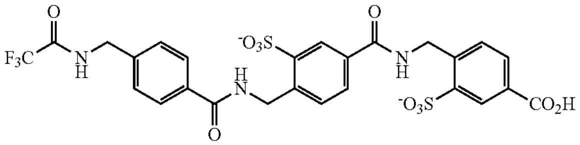

7

Scheme 4: Synthesis of compound 7. Compound 5 was dissolved in minimal volume anhydrous DMF and treated with 1.2 equivalents TSTU and 2 equivalents TEA. Formation of compound 6 was confirmed by LCMS of butylamide product (expected and observed m/z=514). 1 equivalent of compound 2 was added to reaction mixture to form compound 7, which was purified by reverse phase HPLC eluting with acetonitrile and 50 mM TEAB. Product fractions were dried down, desalted with MeOH, and dried by vacuum pump. Compound 7 was confirmed by LCMS: calculated and observed m/z=671.

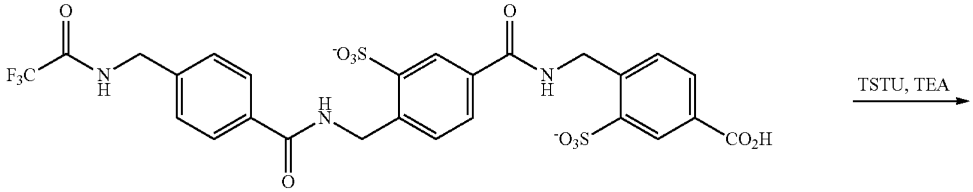

7

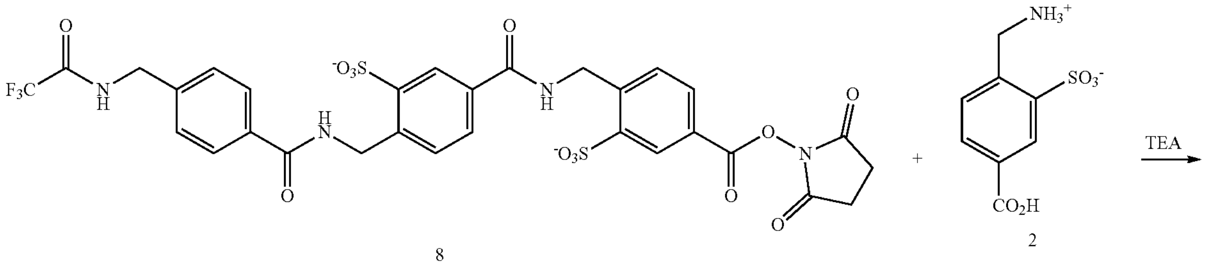

8

2

-continued

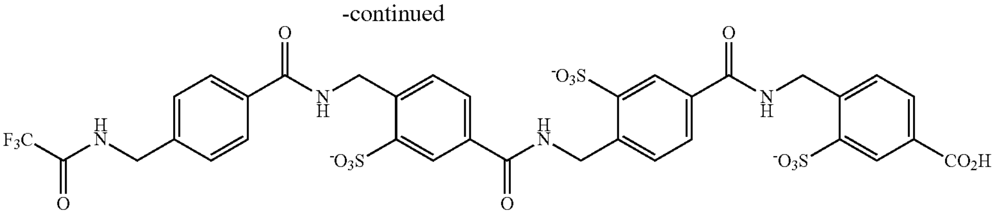

9

Scheme 5: Synthesis of compound 9. Compound 7 was dissolved in minimal volume anhydrous DMF and treated with 1.2 equivalents TSTU and 2 equivalents TEA. Formation of compound 8 was confirmed by LCMS of butylamide product (expected and observed m/z=726). 1 equivalent of compound 2 was added to reaction mixture to form compound 9, which was purified by reverse phase HPLC eluting with acetonitrile and 50 mM TEAB. Product fractions were dried down, desalted with MeOH, and dried by vacuum pump. Compound 9 was confirmed by LCMS: calculated and observed m/z=883.

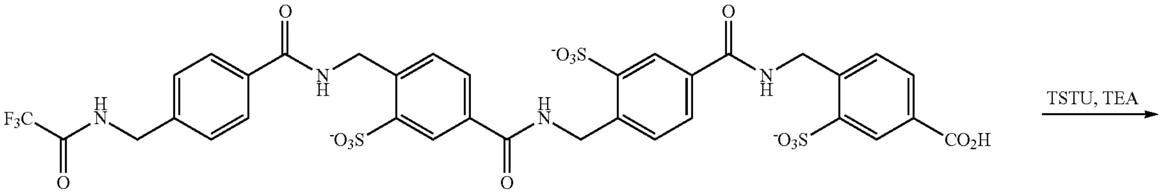

9

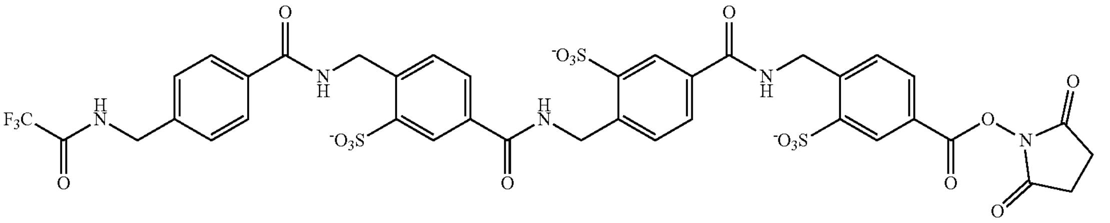

10

+

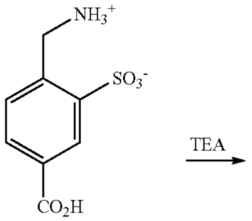

2

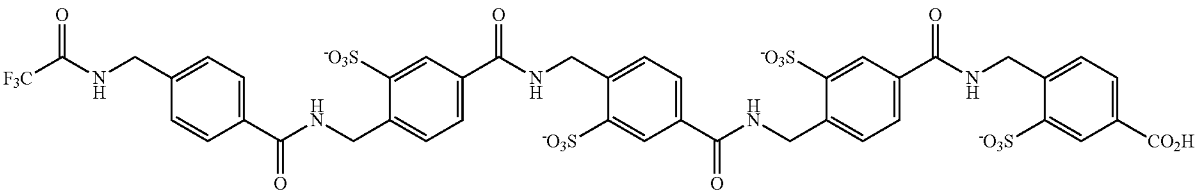

11

Scheme 6: Synthesis of compound 11. Compound 9 was dissolved in minimal volume anhydrous DMF and treated with 1.2 equivalents TSTU and 2 equivalents TEA. Formation of compound 8 was confirmed by LCMS of butylamide product (expected and observed m/z=940). 1 equivalent of compound 2 was added to reaction mixture to form compound 9, which was purified by reverse phase HPLC eluting with acetonitrile and 50 mM TEAB. Product fractions were dried down, desalted with MeOH, and dried by vacuum pump. Compound 9 was confirmed by LCMS: calculated and observed m/z=1099.

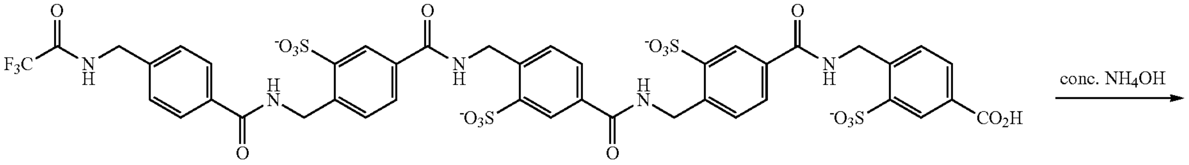

11

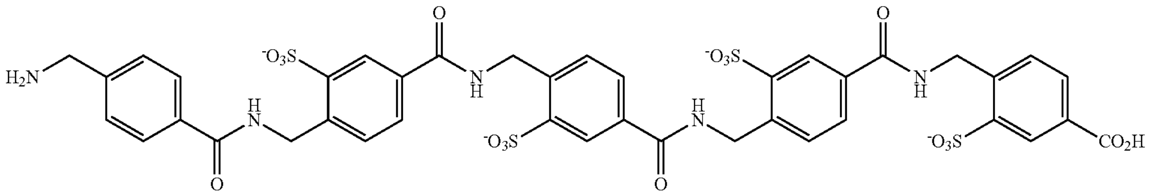

12

Scheme 7: Synthesis of compound 12. Compound 11 was dissolved in concentrated $NH_4OH$ for 2 hours until the tfa protecting group was cleaved. In order to exchange counterions, compound 12 was purified by reverse phase HPLC eluting with acetonitrile and 50 mM TEAB. Product fractions were dried down, desalted with MeOH, and dried by vacuum pump. Compound 12 was confirmed by LCMS: calculated and observed m/z=1103.

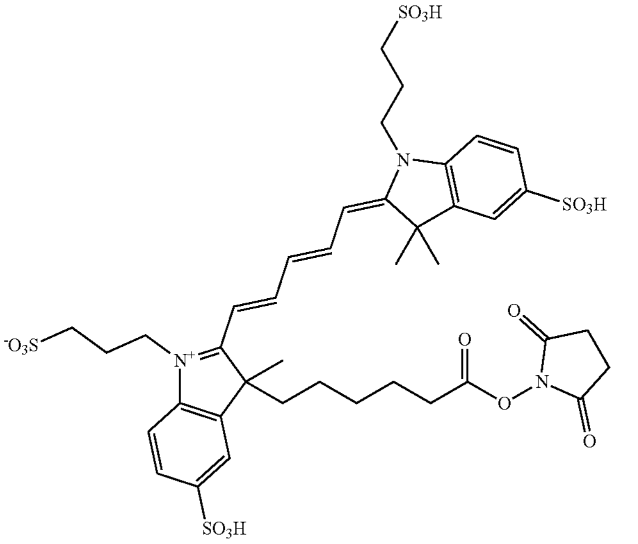

+

13

-continued

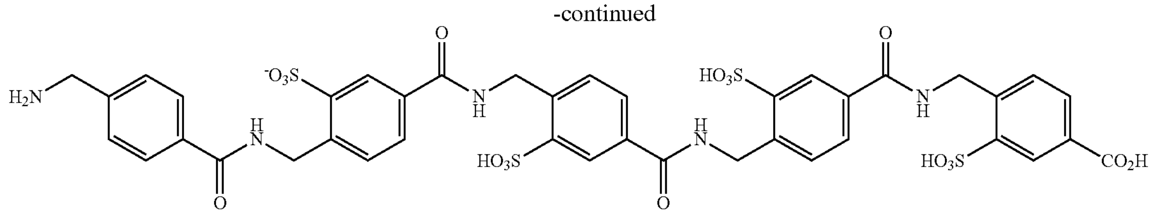

12

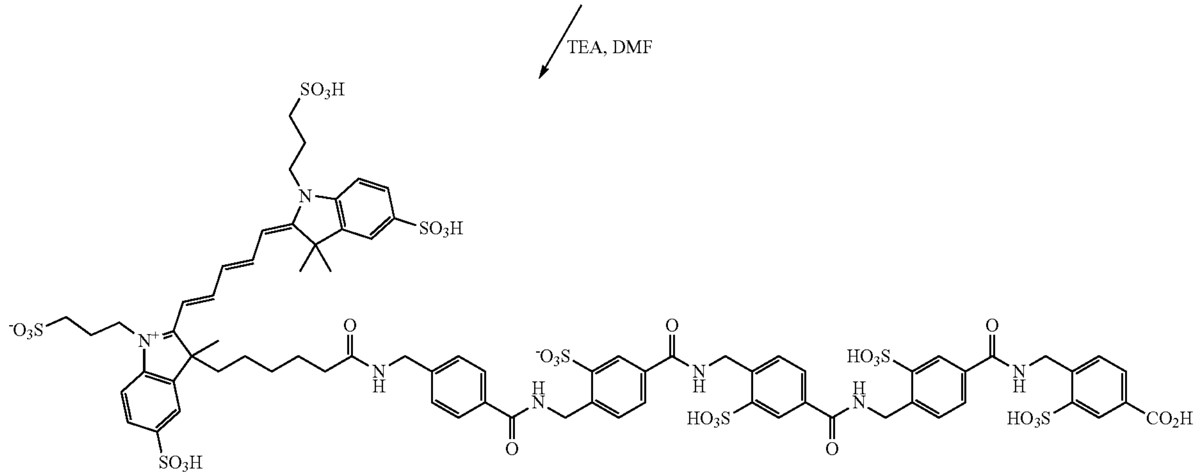

14

Scheme 8: Synthesis of compound 14. Compound 13 (a detectable label with $a_{max}$≈647) was dissolved in minimal volume of anhydrous DMF. 1 equivalent compound 12 and 5 equivalents TEA were added to reaction, which was purified by reverse phase HPLC eluting with acetonitrile and 50 mM TEAB. Product fractions were dried down, desalted with MeOH, and dried by vacuum pump. Compound 14 was confirmed by LCMS: calculated and observed m/2z=921.

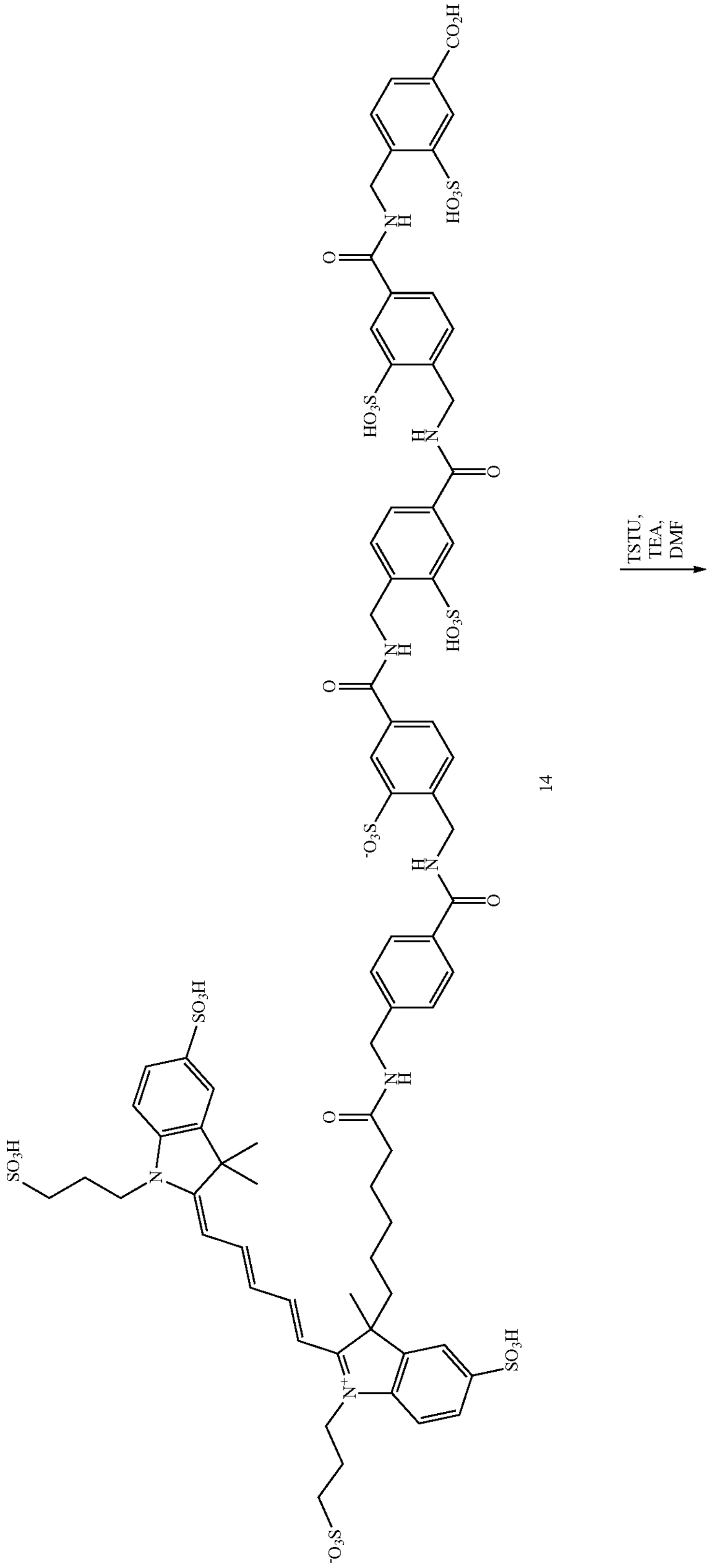
14

-continued
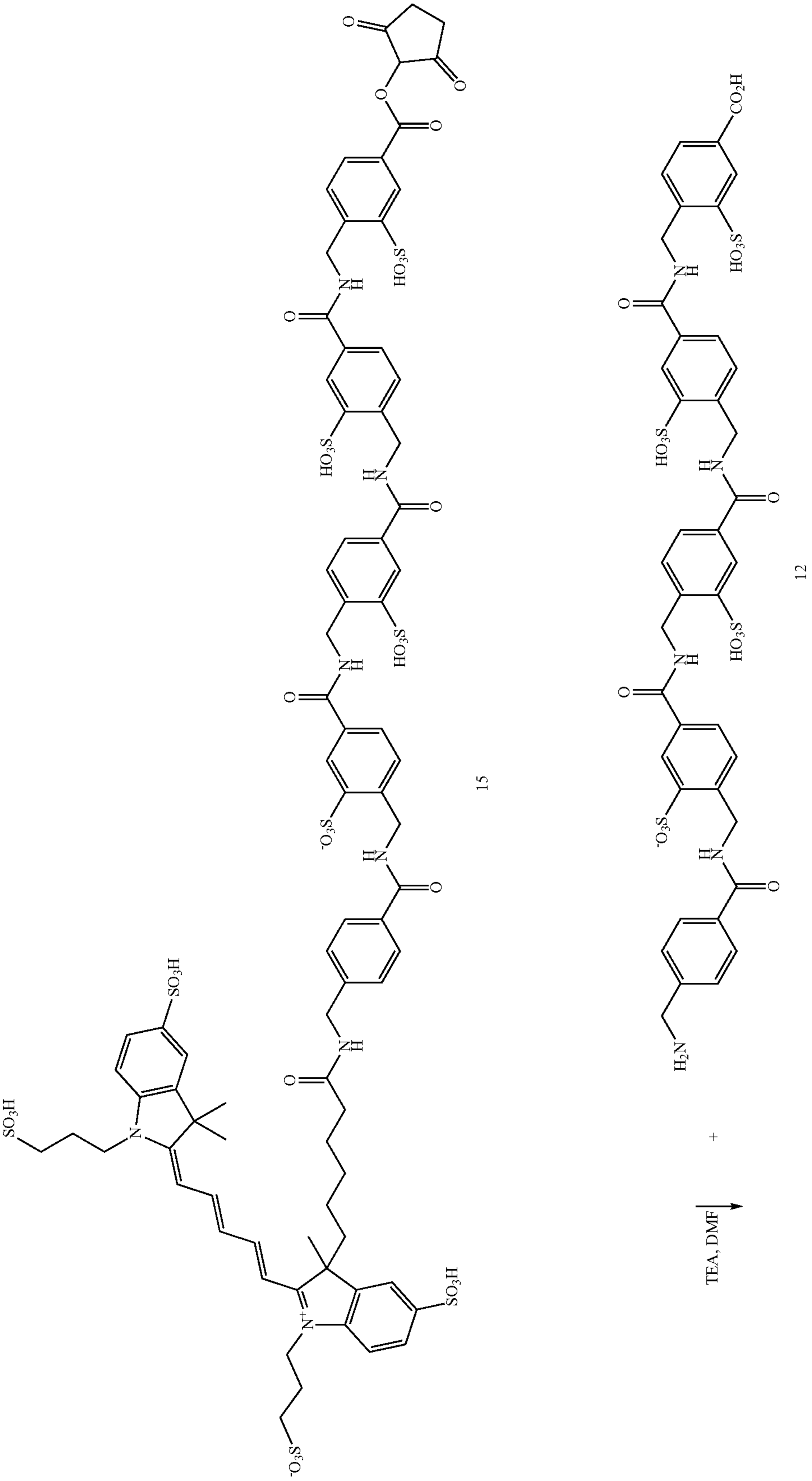
15
12

-continued
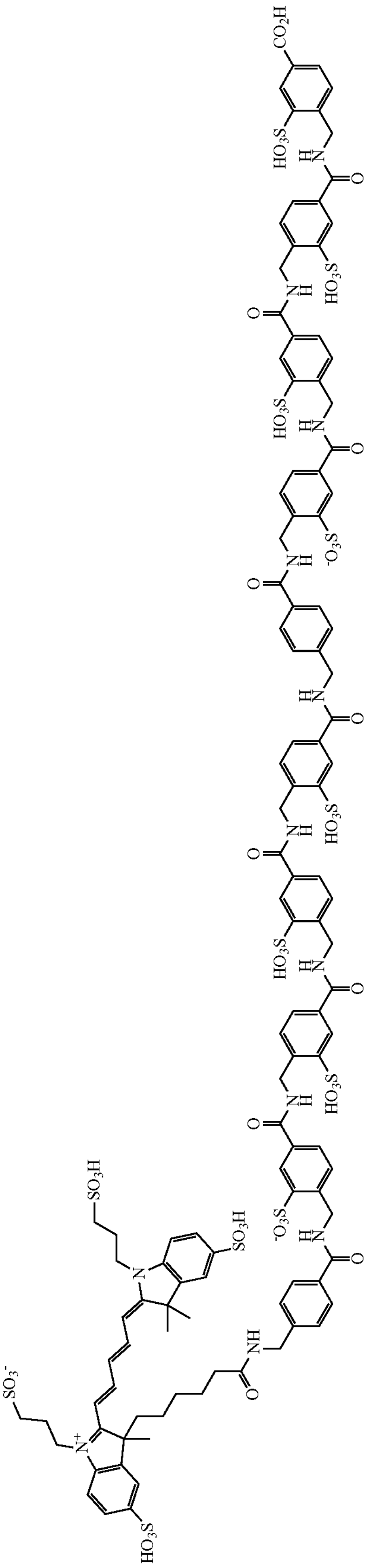
16

Scheme 9: Synthesis of compound 16. Compound 14 was dissolved in minimal volume anhydrous DMF and treated with 1.2 equivalents TSTU and 2 equivalents TEA. Formation of compound 15 was confirmed by LCMS of butylamide product (expected and observed m/2z=948). 1 equivalent of compound 12 was added to reaction mixture to form compound 16, which was purified by reverse phase HPLC eluting with acetonitrile and 50 mM TEAB. Product fractions were dried down, desalted with MeOH, and dried by vacuum pump. Compound 16 was confirmed by LCMS: calculated and observed m/2z, m/3z for product+3×TEA counterions=1566, 1043.

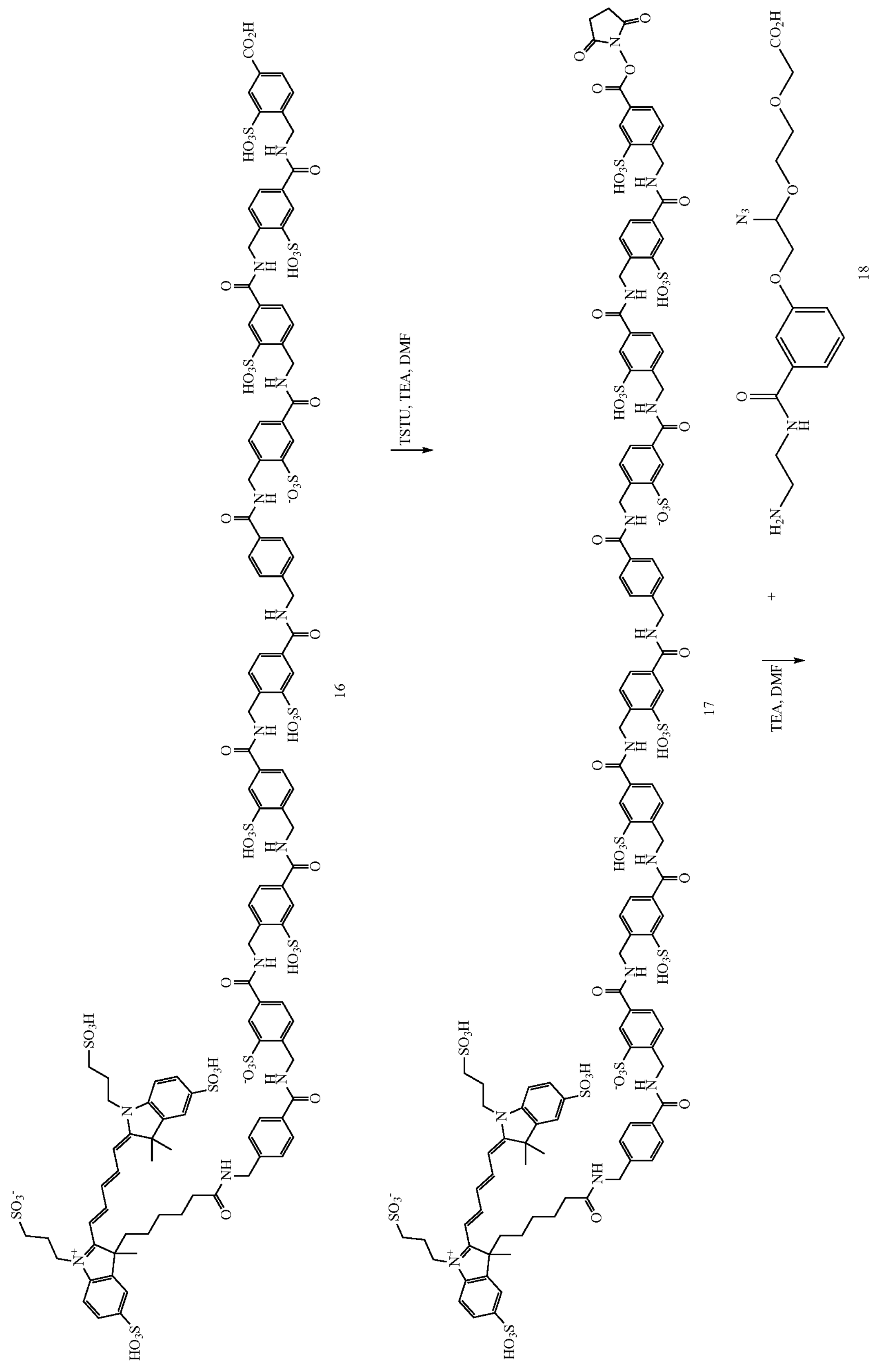
16
17
18

-continued
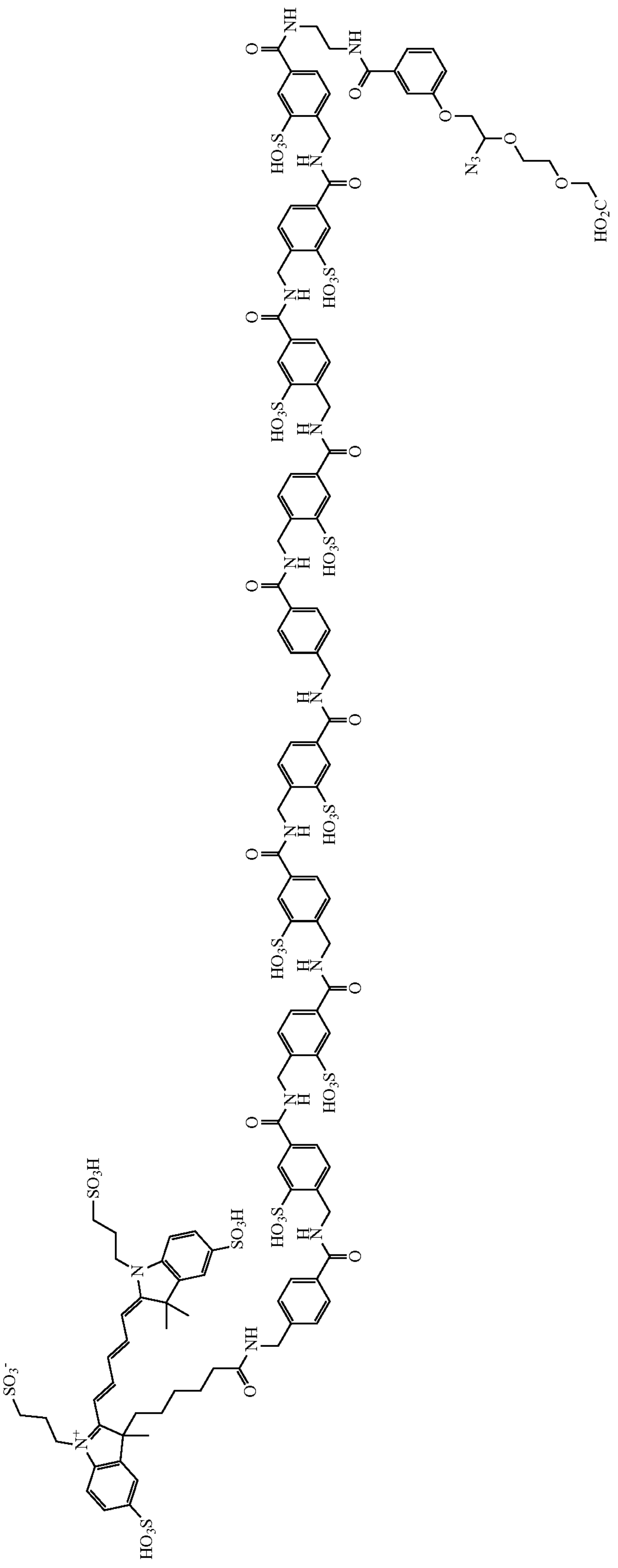
19

Scheme 10: Synthesis of compound 19. Compound 16 was dissolved in minimal volume anhydrous DMF and treated with 1.2 equivalents TSTU and 2 equivalents TEA. Formation of compound 17 was confirmed by LCMS of butylamide product (expected and observed m/2z for product+3×TEA counterions=1593). 1 equivalent of compound 18 (i.e., a cleavable linker) was added to reaction mixture to form compound 19, which was purified by reverse phase HPLC eluting with acetonitrile and 50 mM TEAB. Product fractions were dried down, desalted with MeOH, and dried by vacuum pump. Compound 19 was confirmed by LCMS: calculated and observed m/2z, m/3z for product+3×TEA counterions=1740, 1160.

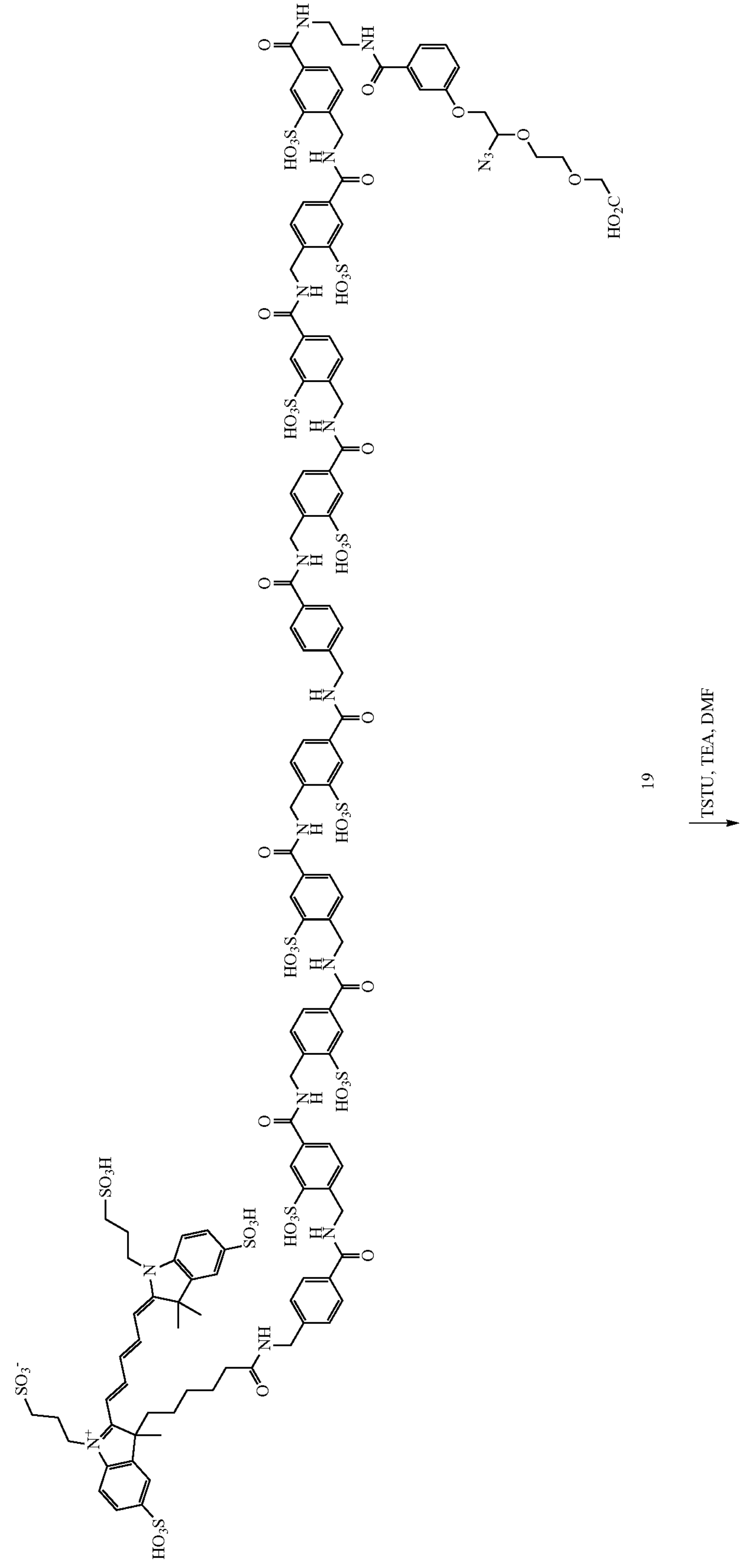
19
TSTU, TEA, DMF

-continued
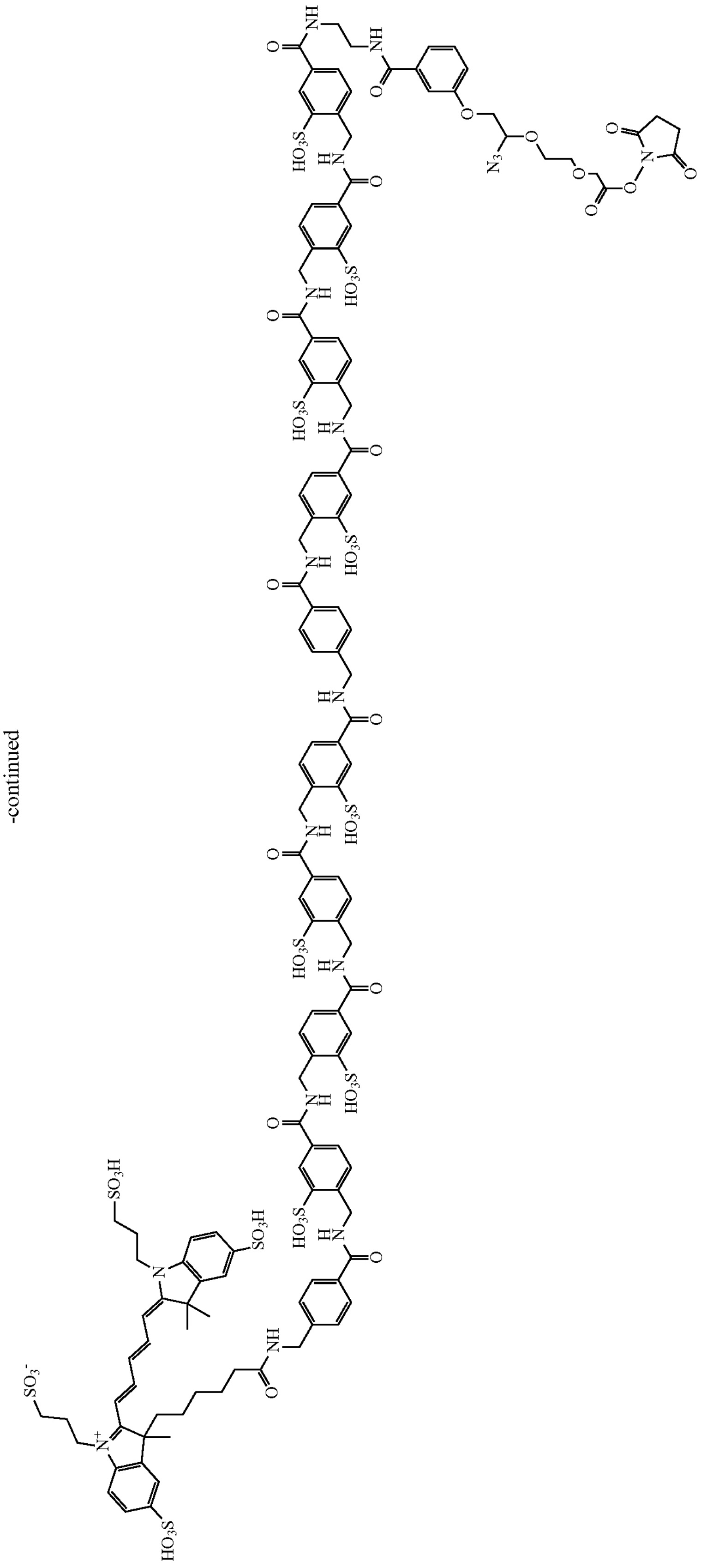

-continued
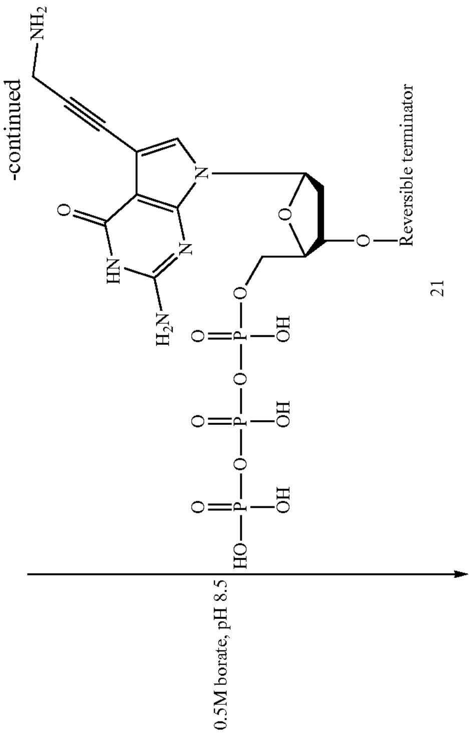
21

-continued
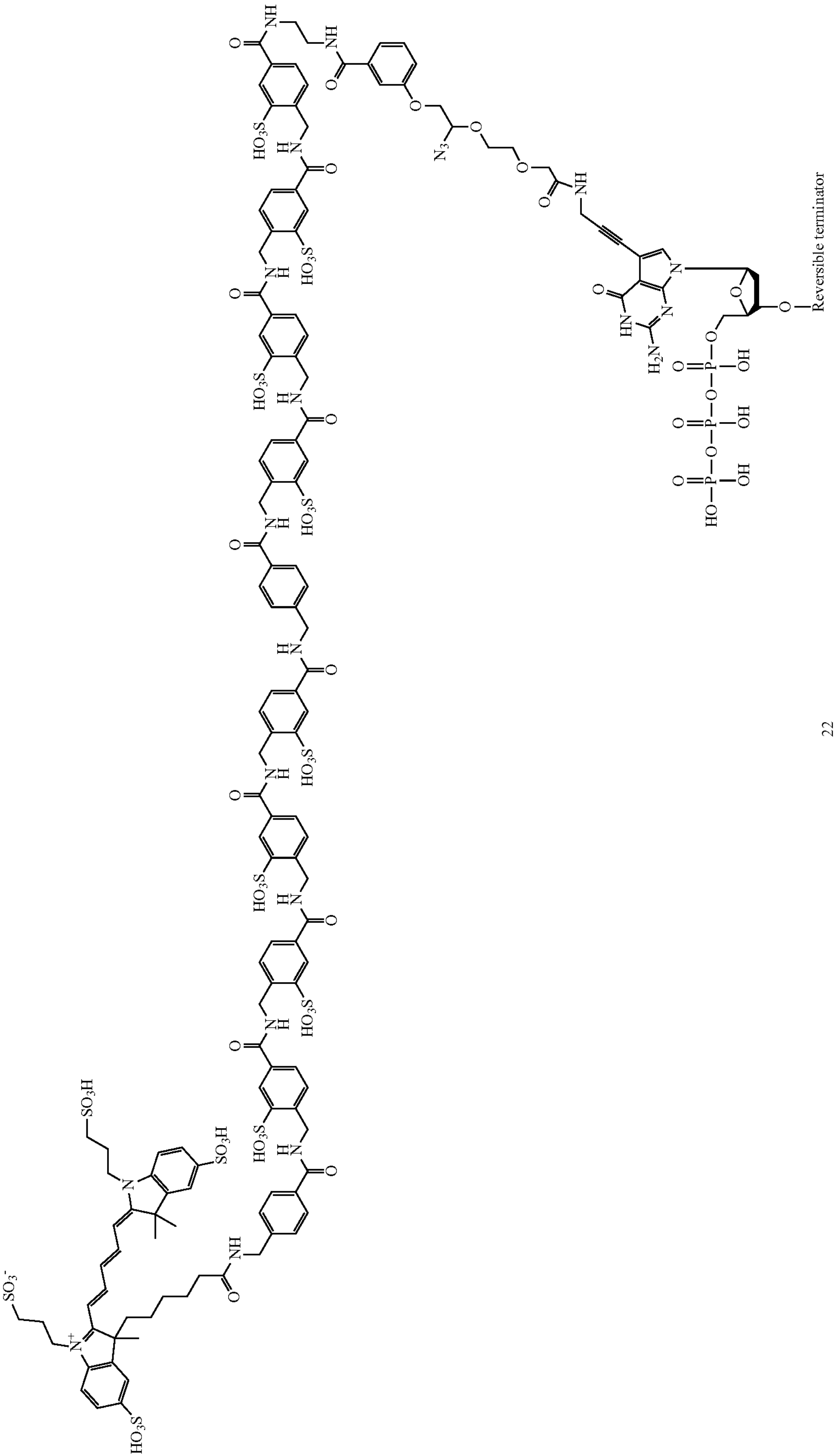
22

Scheme 11: Synthesis of compound 22. Compound 19 was dissolved in minimal volume anhydrous DMF and treated with 1.2 equivalents TSTU and 2 equivalents TEA. Formation of compound 20 was confirmed by LCMS of butylamide product (expected and observed m/2z for product+3×TEA counterions=1767). 1 equivalent of compound 21 (dGTP nucleotide) was added to reaction mixture to form compound 22, which was purified by reverse phase HPLC eluting with acetonitrile and 50 mM TEAB. Product fractions were dried down, desalted with MeOH, and resuspended in $H_2O$ for sequencing use. Compound 22 was confirmed by LCMS.

Synthesis of remaining dye-spacer-dNTPs. An analogous synthesis method was used for all four dye-labeled nucleotides. Compound 13 (detectable label with $\lambda_{max}$≈647 nm) was substituted for another dye with different $\lambda_{max}$ (e.g., $\lambda_{max}$ 449 nm or 520 nm or 680 nm) and compound 21 (dGTP) was substituted for d(C, T, A)TP, respectively.

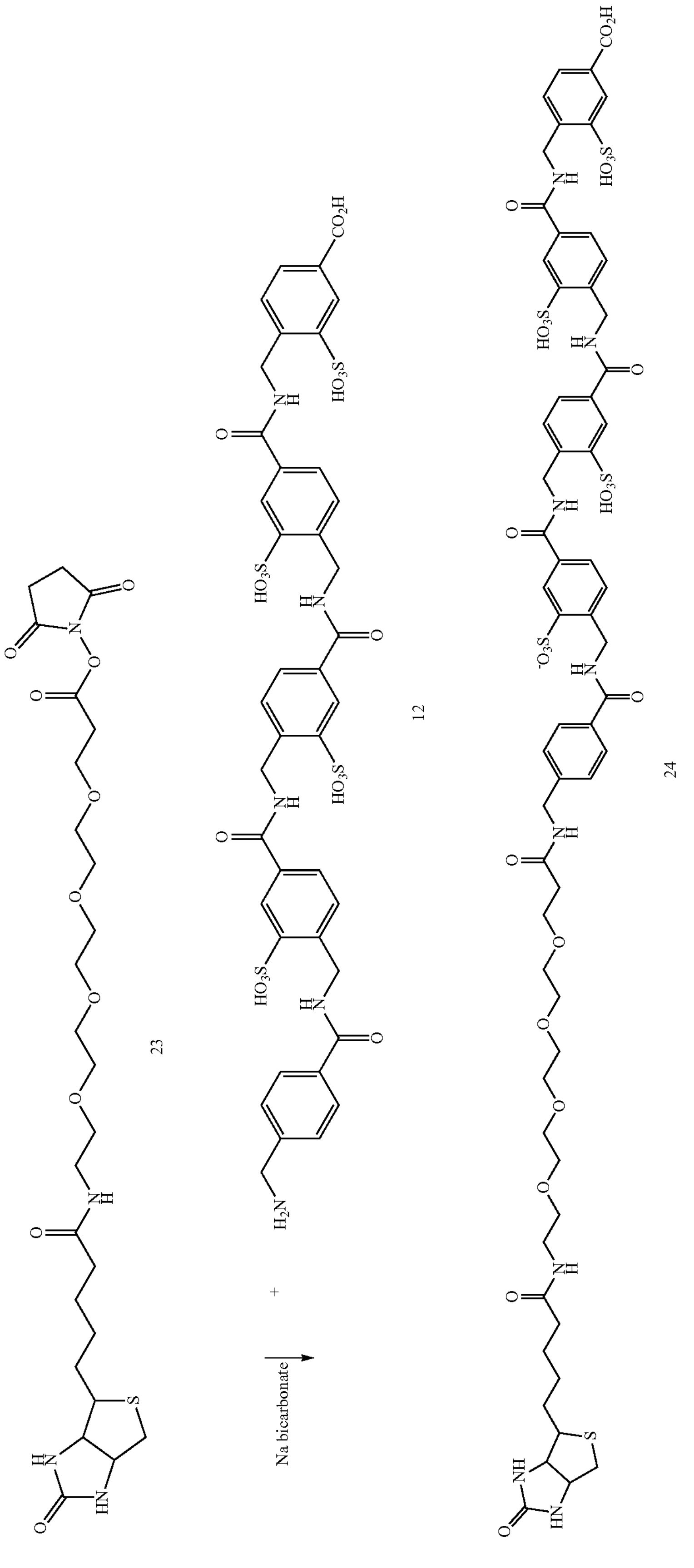
23
12
24

Scheme 12: Synthesis of compound 24. Compound 23 was added to compound 12 in minimal volume sodium bicarbonate, and 0.5M borate pH 8.5 was added until reaction was pH neutral. Reaction mixture was purified by reverse phase HPLC eluting with acetonitrile and 50 mM TEAB. Compound 24 was confirmed by LCMS: calculated and observed m/2z for product+1×TEA counterions=787. Product fractions were dried down and desalted with MeOH.

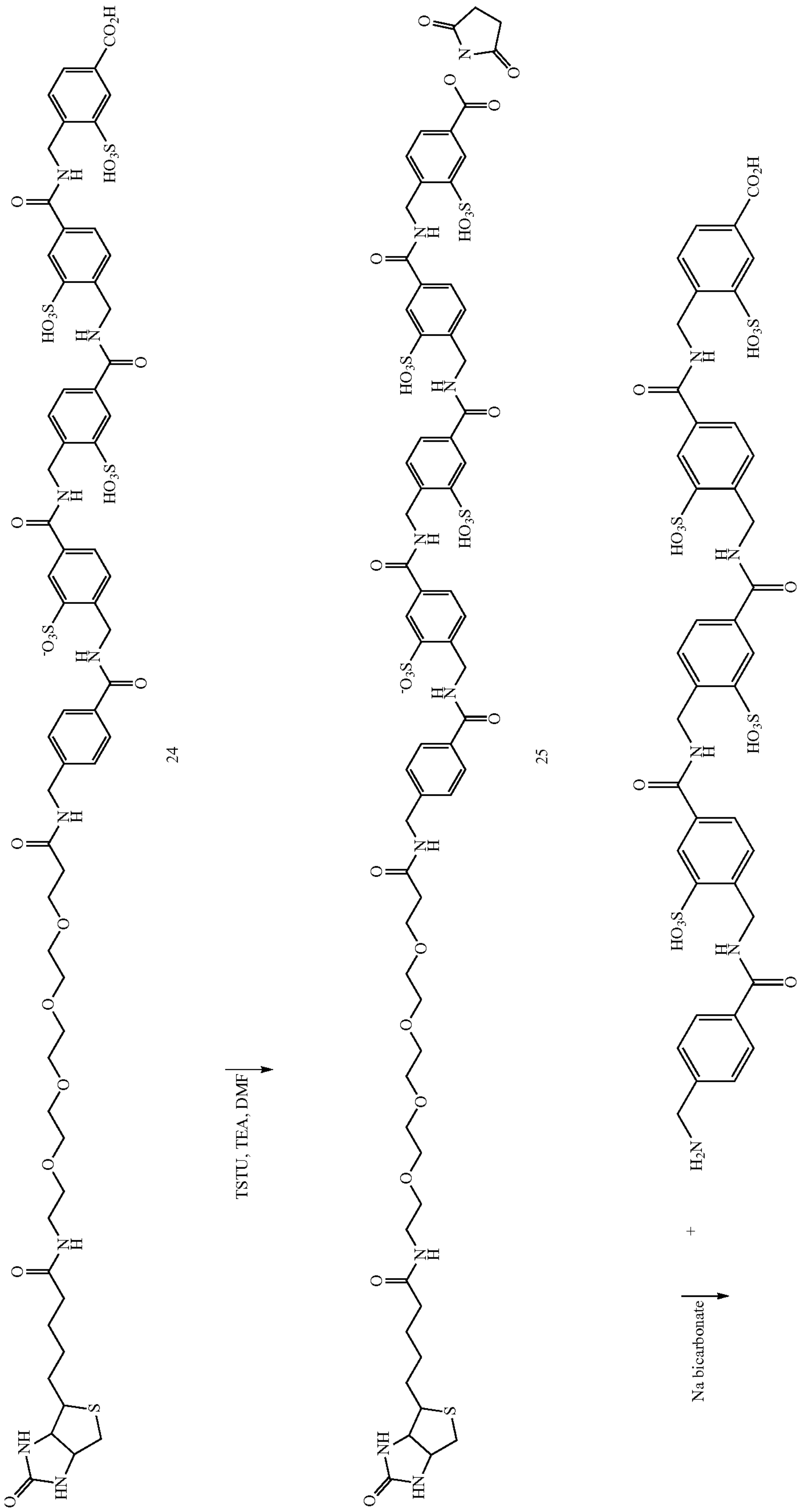
24
25
12

-continued
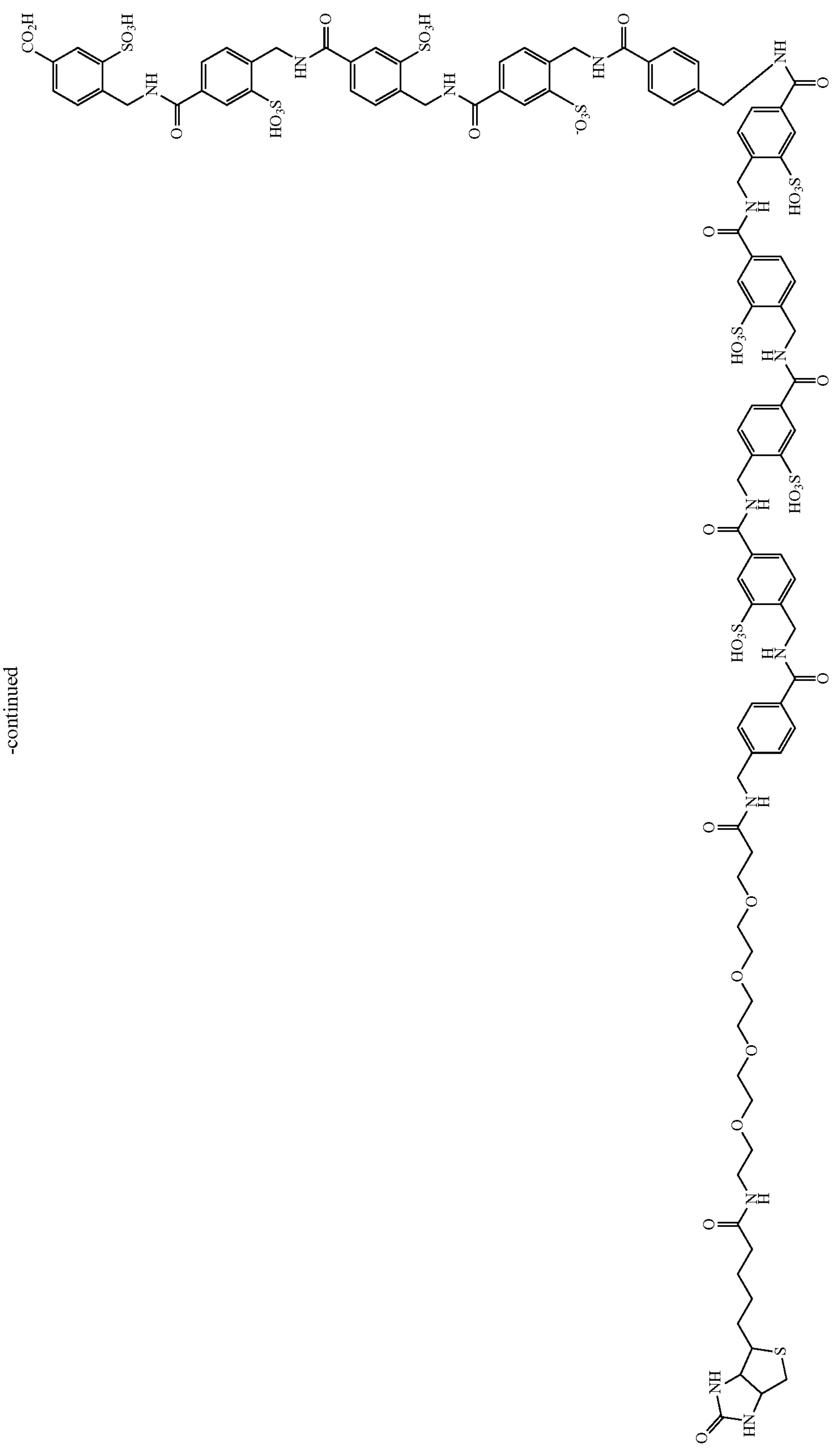
26

Scheme 13: Synthesis of compound 26. Compound 24 was dissolved in minimal volume anhydrous DMF and treated with 1.2 equivalents TSTU and 2 equivalents TEA. Formation of compound 25 was confirmed by LCMS of butylamide product (expected and observed m/2z for product+1×TEA counterions=815). 1 equivalent of compound 12 was added to reaction mixture to form compound 26, which was purified by reverse phase HPLC eluting with acetonitrile and 50 mM TEAB. Compound 22 was confirmed by LCMS: calculated and observed m/2z for product +5×TEA counterions=1482. Product fractions were dried down and desalted with MeOH.

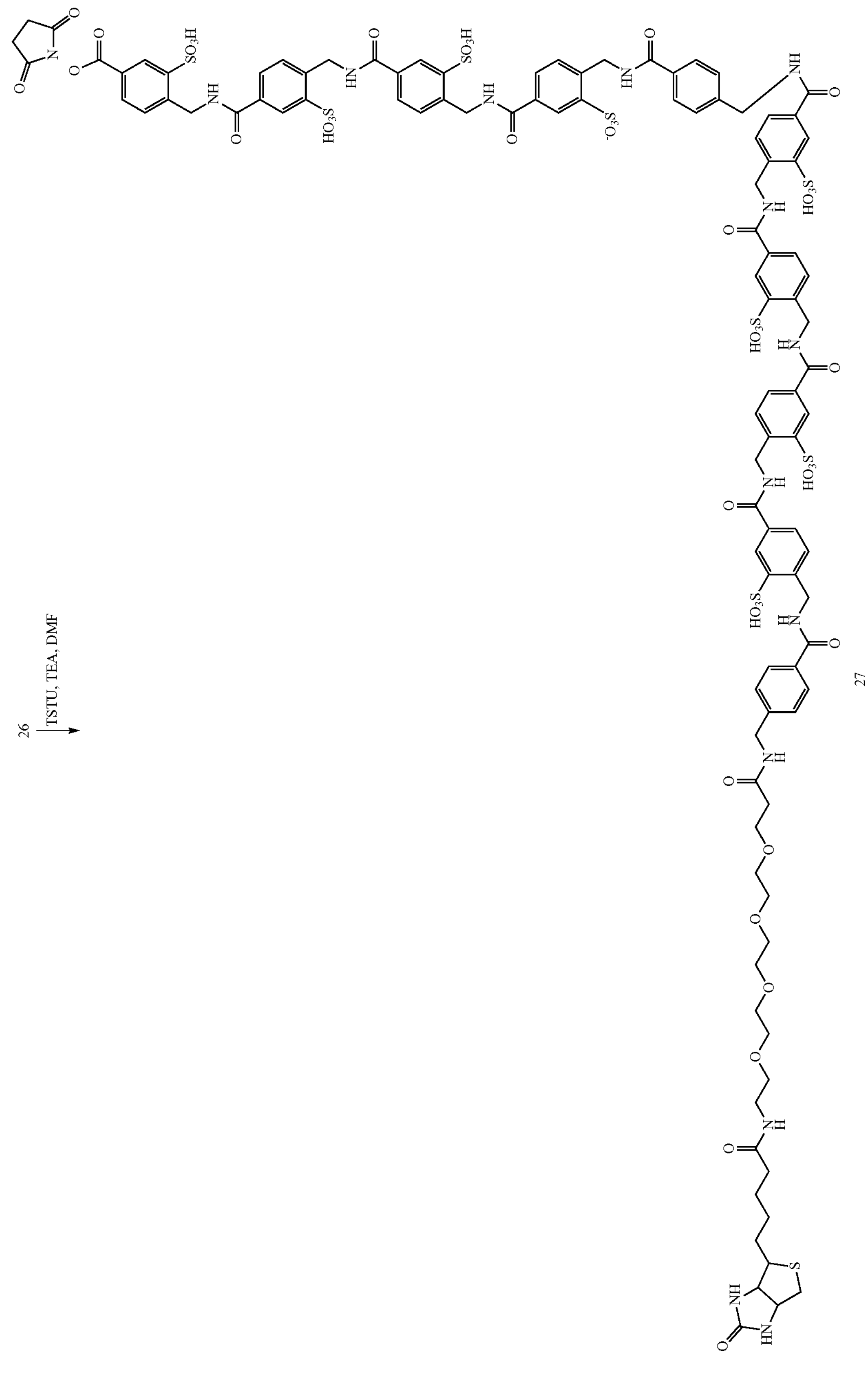
26
TSTU, TEA, DMF
27

-continued
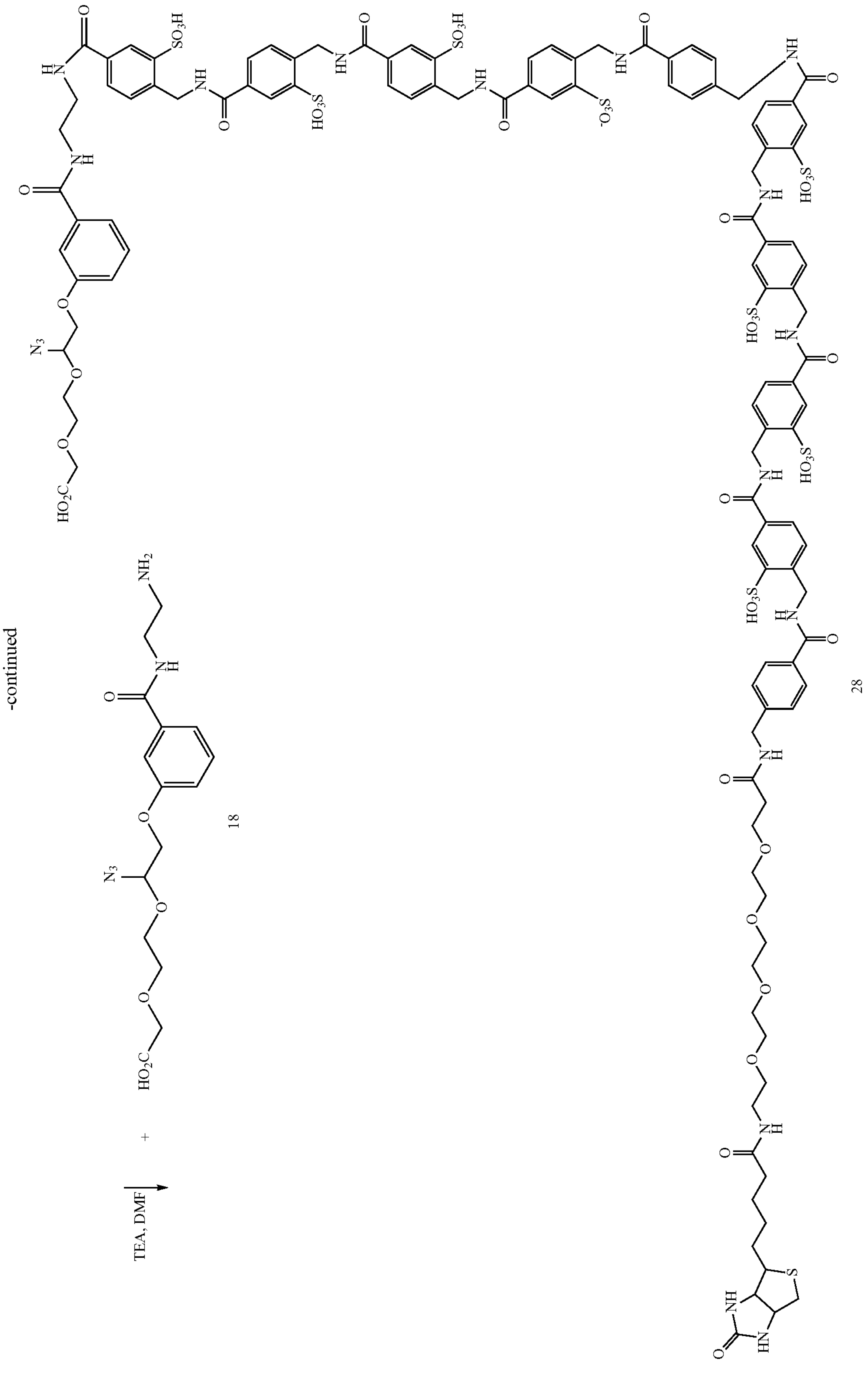
18
28

Scheme 14: Synthesis of compound 28. Compound 26 was dissolved in minimal volume anhydrous DMF and treated with 1.2 equivalents TSTU and 2 equivalents TEA. Formation of compound 27 was confirmed by LCMS of butylamide product (expected and observed m/2z for product+5×TEA counterions=1509). 1 equivalent of compound 18 was added to reaction mixture to form compound 28, which was purified by reverse phase HPLC eluting with acetonitrile and 50 mM TEAB. Compound 28 was confirmed by LCMS: calculated and observed m/2z for product+5×TEA counterions=1657. Product fractions were dried down and desalted with MeOH.

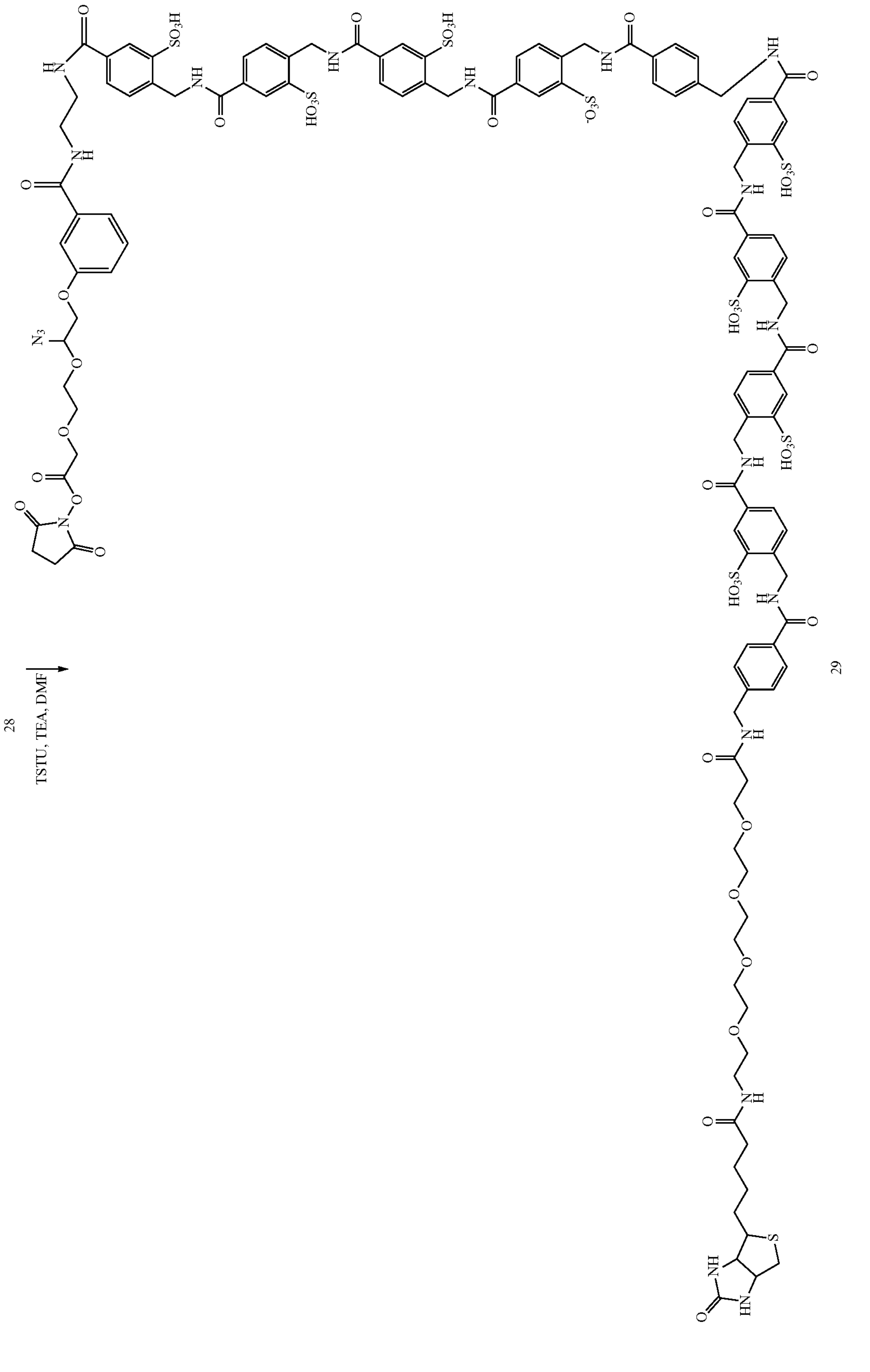
28
29

-continued
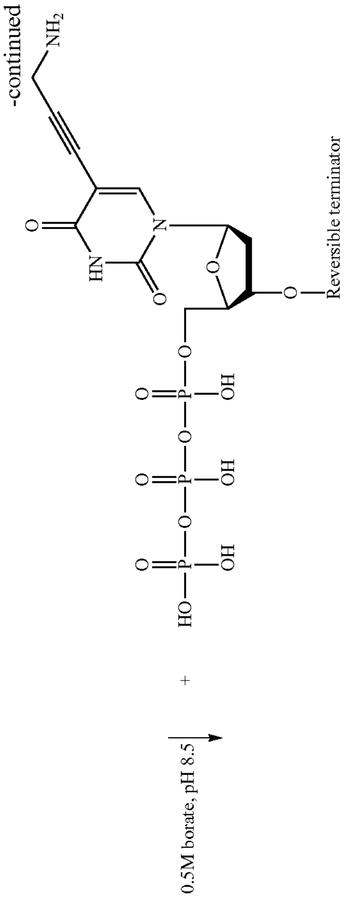
30

-continued
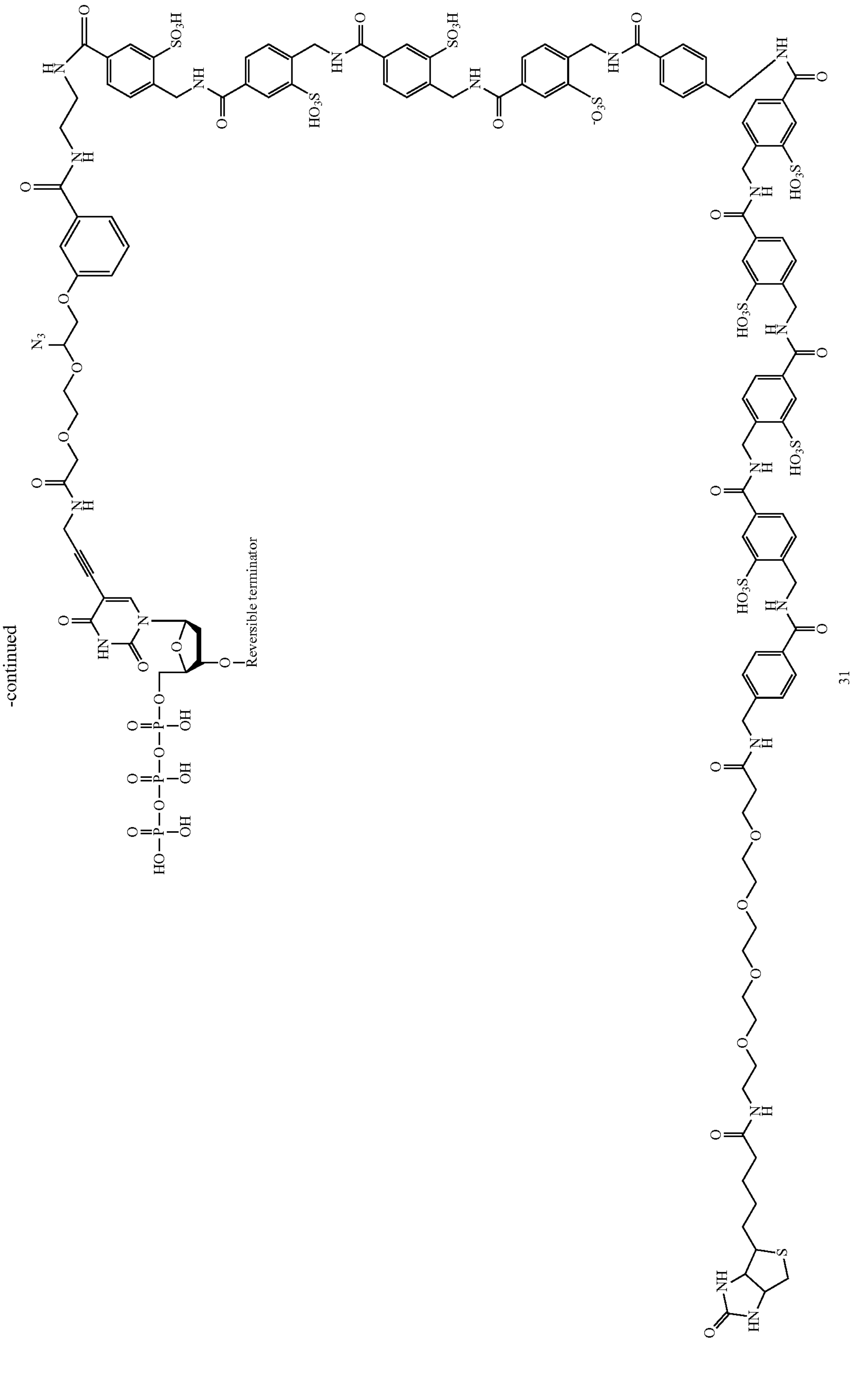
31

Scheme 15: Synthesis of compound 31. Compound 28 was dissolved in minimal volume anhydrous DMF and treated with 1.2 equivalents TSTU and 2 equivalents TEA. Formation of compound 29 was confirmed by LCMS of butylamide product (expected and observed m/2z for product+5×TEA counterions=1684). 1 equivalent of compound 30 was added to reaction mixture to form compound 31, which was purified by reverse phase HPLC eluting with acetonitrile and 50 mM TEAB. Compound 31 was confirmed by LCMS. Product fractions were dried down and desalted with MeOH, then resuspended in $H_2O$.

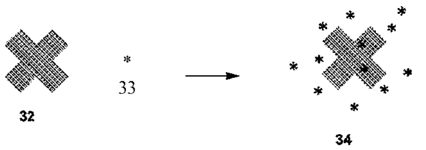

32 33 34

Scheme 16: Synthesis of compound 34. Compound 32, represented as an 'X' in Schemes 16 and 17 (commercially available streptavidin) was dissolved in minimal volume 50 mM borate pH 8. 12 equivalents of compound 33 (dye-NHS) dissolved in minimal volume anhydrous DMF were added to the compound 32 mixture. This reaction was filtered by size exclusion using Sephadex G-25, and then dialyzed overnight to yield compound 34.

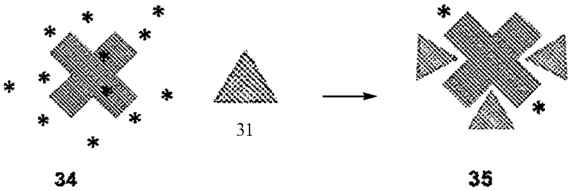

34 31 35

Scheme 17: Synthesis of compound 35. To compound 34, 8 equivalents of compound 31, represented as a triangle in this scheme, were added. This mixture was dialyzed overnight and then filtered by size exclusion using Sephadex G-25 to yield compound 35.

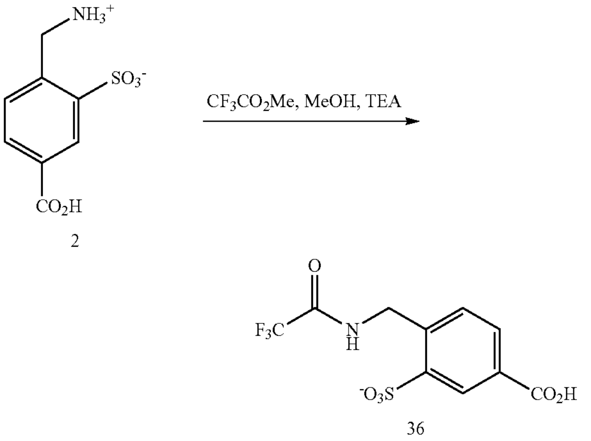

2

36

Scheme 18: Synthesis of compound 36. 1 g of compound 2 was dissolved in MeOH with 10 equivalents $CF_3CO_2Me$ and 4 equivalents TEA. Reaction was vacuum filtered and product in flow-through was pumped down to remove $CF_3CO_2Me$ and TEA. Next, product was dissolved in water and purified by reverse phase HPLC eluting with acetonitrile and 50 mM TEAB. Product fractions were dried down, desalted with MeOH, and dried by vacuum pump. Compound 36 was confirmed by LCMS, $^1H$ NMR, and $^{13}C$ NMR. LCMS: calculated and observed m/z=326. $^1H$ NMR (500 MHz, $D_2O$) δ 8.38 (d, J=1.5 Hz, 1H), 8.00 (dd, J=8.0, 1.6 Hz, 1H), 7.52 (d, J=8.0 Hz, 1H), 4.96 (s, 2H), 3.12 (q, J=7.3 Hz, 12H), 1.21 (t, J=7.4 Hz, 18H). $^{13}C$ NMR (125 MHz, $D_2O$) δ 173.26, 158.92, 140.90, 136.29, 136.02, 131.96, 128.79, 127.79, 115.98, 46.71, 40.82, 8.27.

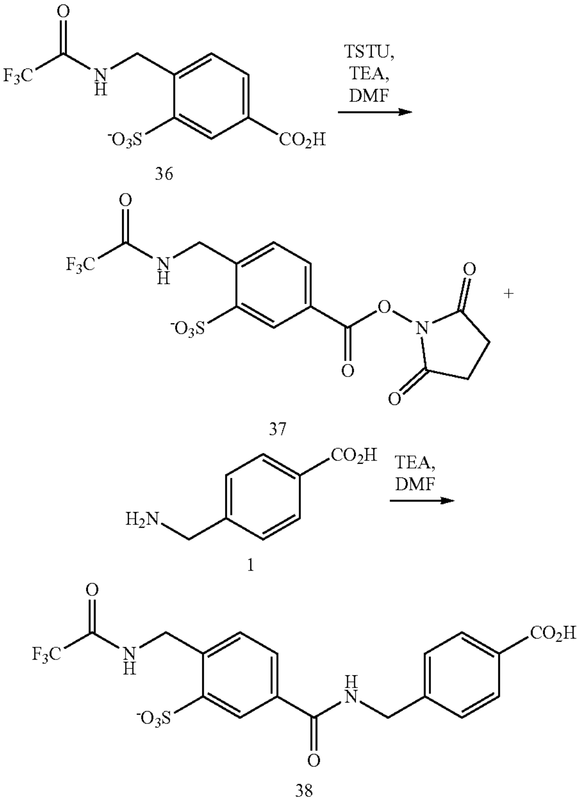

36

37

1

38

Scheme 19: Synthesis of compound 38. Compound 36 was dissolved in minimal volume anhydrous DMF and treated with 1.2 equivalents TSTU and 2 equivalents TEA. Formation of compound 37 was confirmed by LCMS of butylamide product (expected and observed m/z=423). 1 equivalent of compound 1 was added to reaction mixture to form compound 38, which was purified by reverse phase HPLC eluting with acetonitrile and 50 mM TEAB. Product fractions were dried down, desalted with MeOH, and compound 38 was confirmed by LCMS: calculated and observed m/z=459.

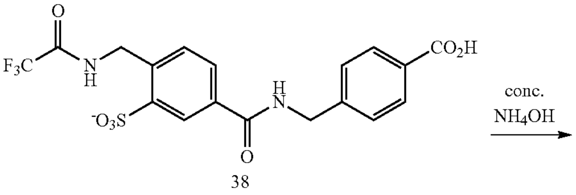

38

-continued

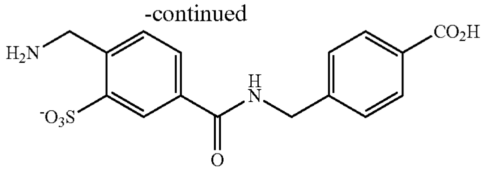

39

Scheme 20. Synthesis of compound 39. Compound 38 was treated with concentrated $NH_{40}H$ for 2 hours to yield compound 39. $NH_4OH$ was pumped off and in order to exchange for TEA counterions, reaction was purified by reverse phase HPLC eluting with acetonitrile and 50 mM TEAB. Product fractions were dried down, desalted with MeOH, and compound 39 was confirmed by LCMS: calculated and observed m/z=363.

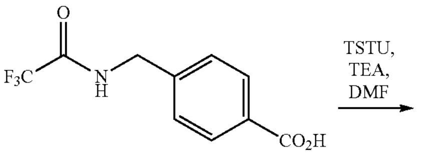

3

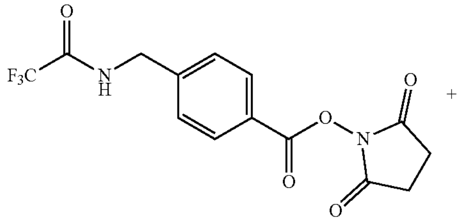

40

-continued

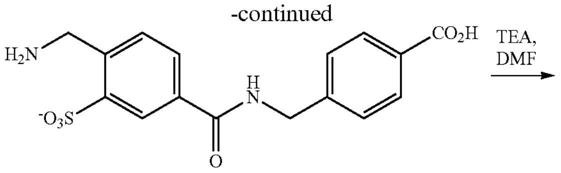

39

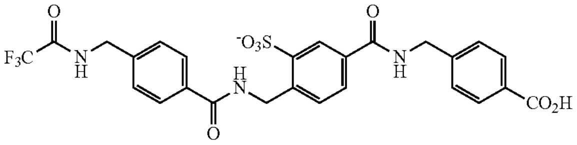

41

Scheme 21: Synthesis of compound 41. Compound 3 was dissolved in minimal volume anhydrous DMF and treated with 1.2 equivalents TSTU and 2 equivalents TEA. Formation of compound 40 was confirmed by LCMS of butylamide product. 1 equivalent of compound 39 was added to reaction mixture to form compound 41, which was purified by reverse phase HPLC eluting with acetonitrile and 50 mM TEAB. Product fractions were dried down, desalted with MeOH, and compound 41 was confirmed by LCMS: calculated and observed m/z=592.

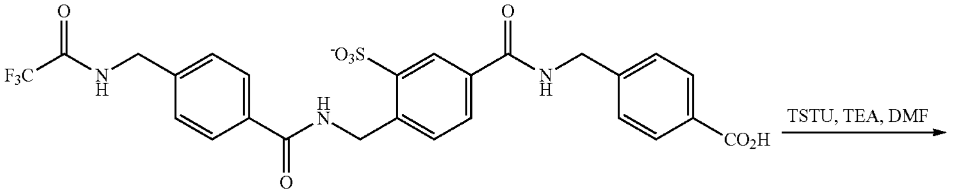

41

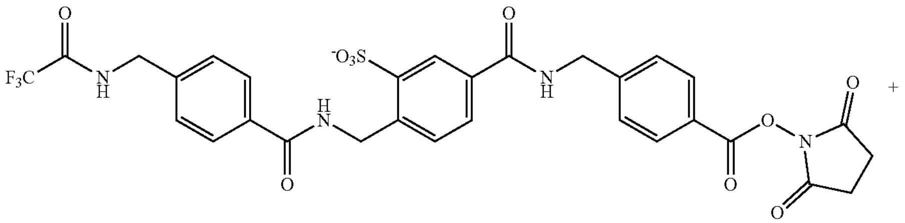

42

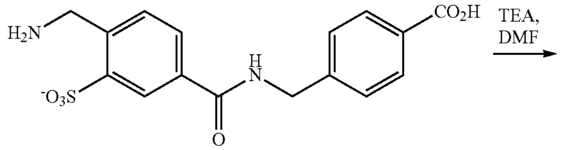

39

-continued

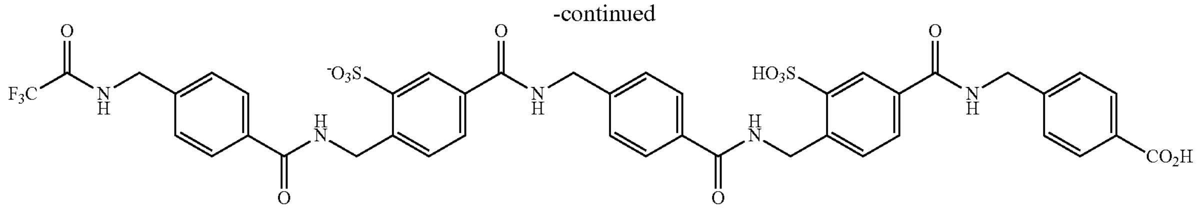

43

Scheme 22: Synthesis of compound 43. Compound 41 was dissolved in minimal volume anhydrous DMF and treated with 1.2 equivalents TSTU and 2 equivalents TEA. Formation of compound 42 was confirmed by LCMS of butylamide product. 1 equivalent of compound 39 was added to reaction mixture to form compound 43, which was purified by reverse phase HPLC eluting with acetonitrile and 50 mM TEAB. Product fractions were dried down, desalted with MeOH, and compound 43 was confirmed by LCMS: calculated and observed m/z=938.

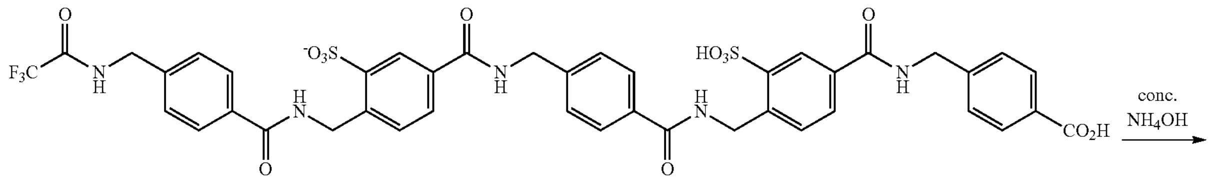

43

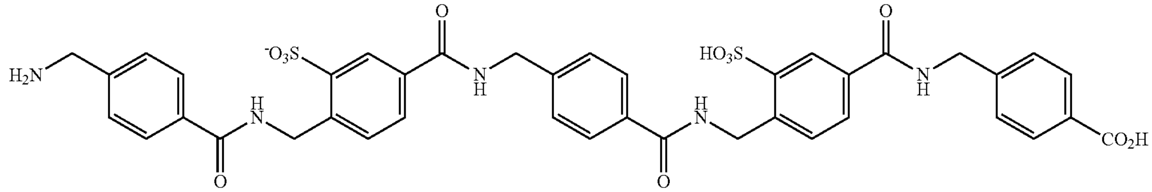

44

Scheme 23: Synthesis of compound 44. Compound 43 was treated with concentrated $NH_4OH$ for 2 hours to yield compound 44. $NH_4OH$ was pumped off and in order to exchange for TEA counterions, reaction was purified by reverse phase HPLC eluting with acetonitrile and 50 mM TEAB. Product fractions were dried down, desalted with MeOH, and compound 44 was confirmed by LCMS: calculated and observed m/z=842.

AF647 NHS

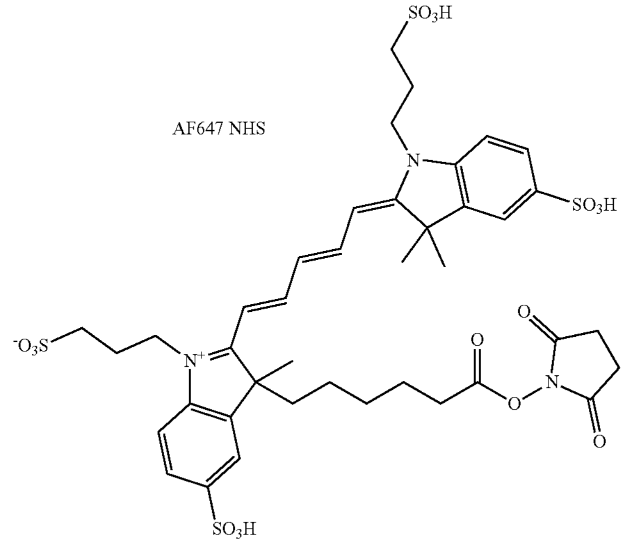

13

+

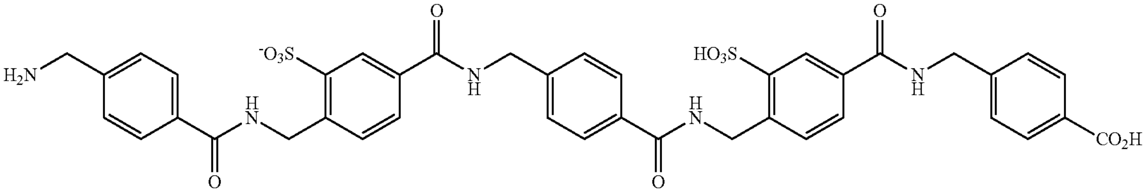

44

DMF,
TEA

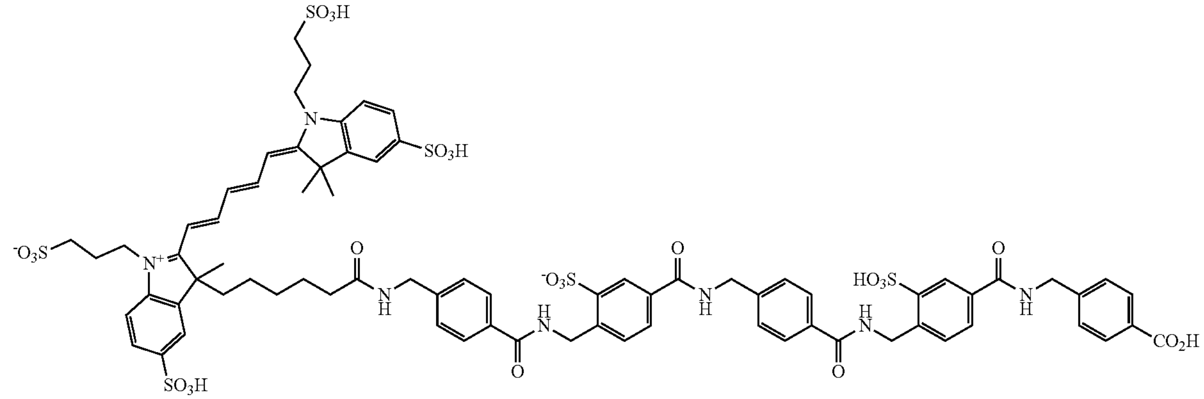

45

Scheme 24: Synthesis of compound 45. Compound 13 (a detectable label with $\lambda_{max}\approx 647$) was dissolved in minimal volume of anhydrous DMF. 1 equivalent compound 44 and 5 equivalents TEA were added to reaction, which was purified by reverse phase HPLC eluting with acetonitrile and 50 mM TEAB. Product fractions were dried down, desalted with MeOH, and compound 45 was confirmed by LCMS: calculated and observed m/2z=840.

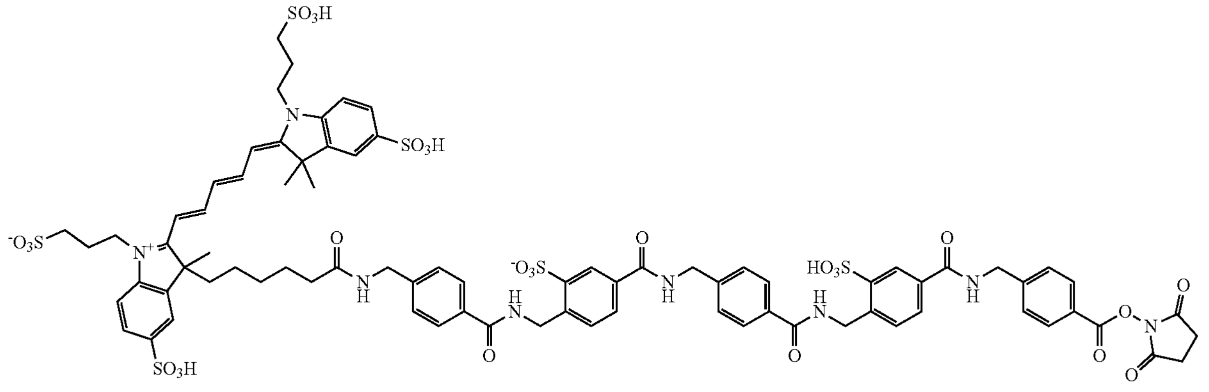

46

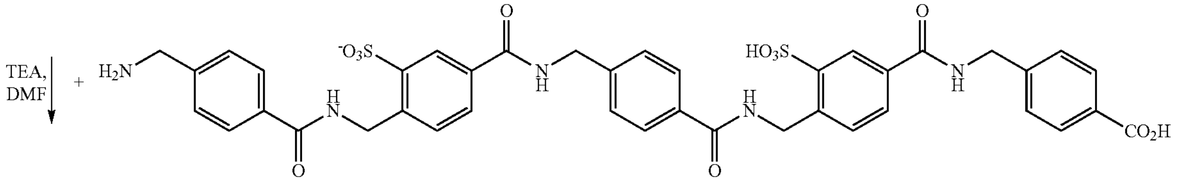

44

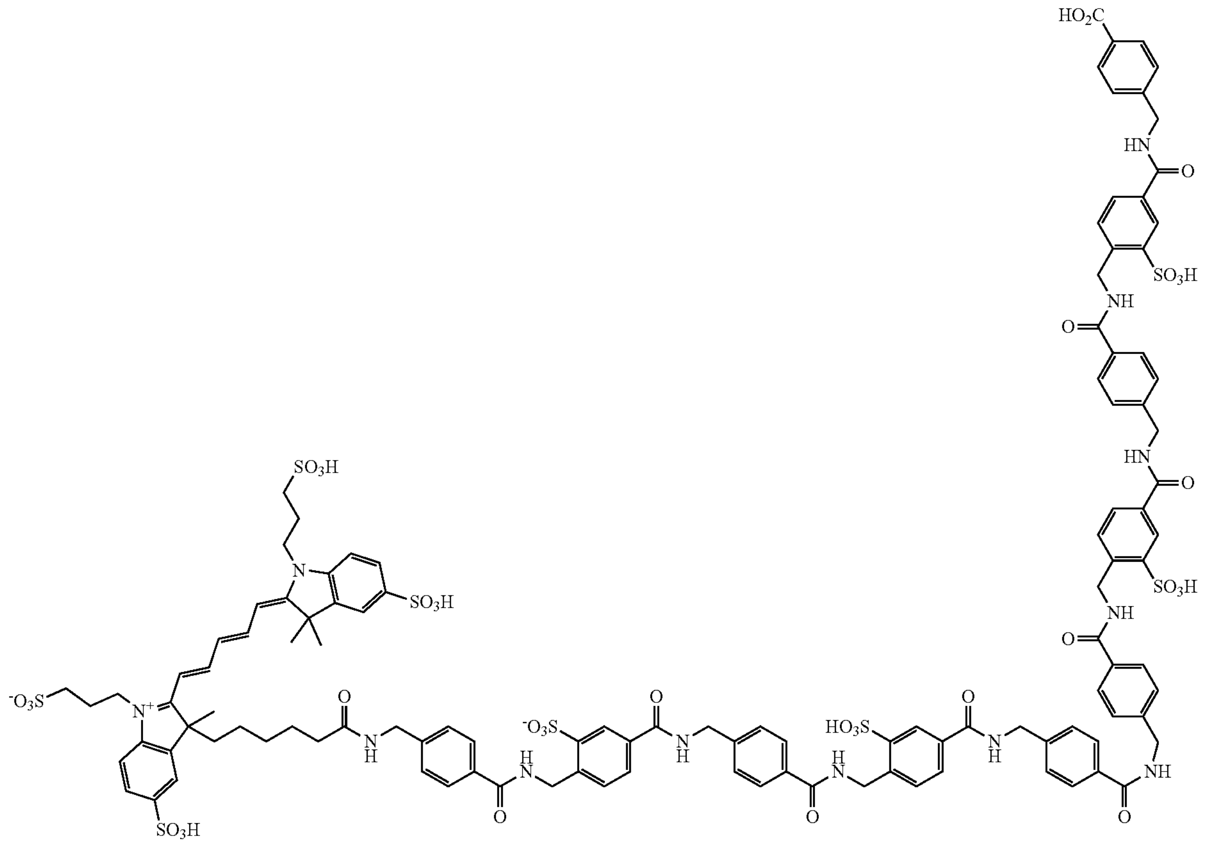

47

Scheme 25: Synthesis of compound 47. Compound 45 was dissolved in minimal volume anhydrous DMF and treated with 1.2 equivalents TSTU and 2 equivalents TEA. Formation of compound 46 was confirmed by LCMS of butylamide product. 1 equivalent of compound 44 was added to reaction mixture to form compound 47, which was purified by reverse phase HPLC eluting with acetonitrile and 50 mM TEAB. Product fractions were dried down, desalted with MeOH, and compound 47 was confirmed by LCMS: calculated and observed m/2z=1253.

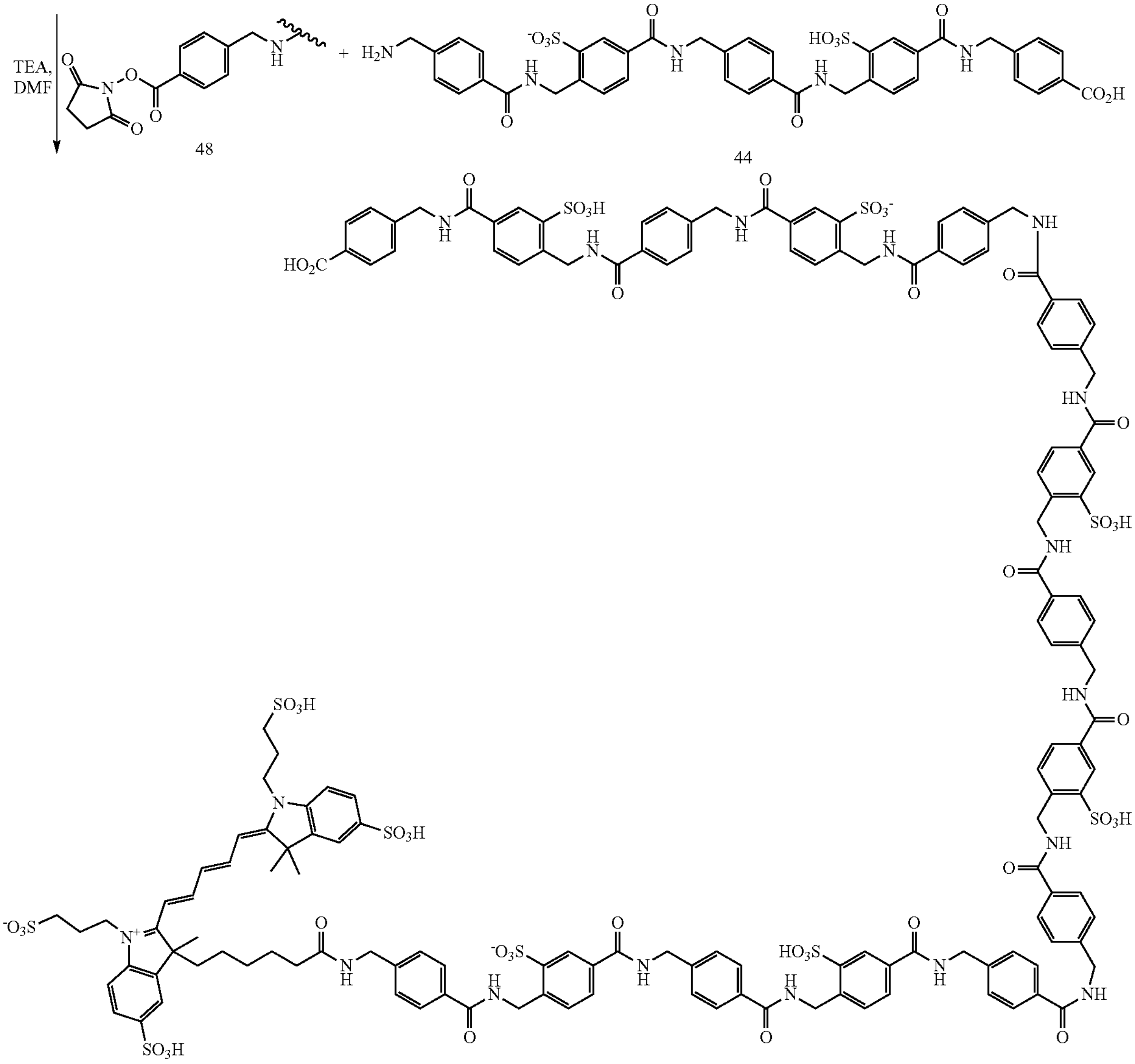

48

44

49

Scheme 26: Synthesis of compound 49. Compound 47 was dissolved in minimal volume anhydrous DMF and treated with 1.2 equivalents TSTU and 2 equivalents TEA. Formation of compound 48 (the NHS ester) was confirmed by LCMS of butylamide product. 1 equivalent of compound 44 was added to reaction mixture to form compound 49 which was purified by reverse phase HPLC eluting with acetonitrile and 50 mM TEAB. Product fractions were dried down, desalted with MeOH, and compound 49 was confirmed by LCMS: calculated and observed m/2z for product+1×TEA counterion=1716.

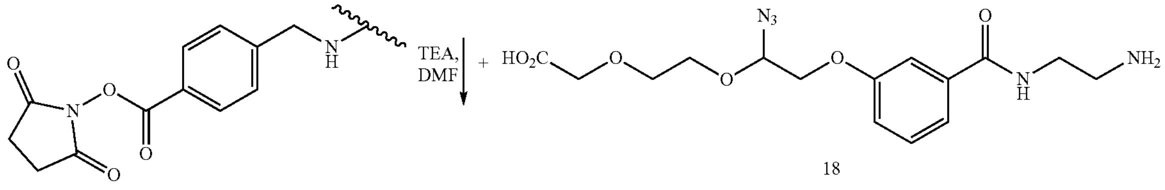

50

18

-continued

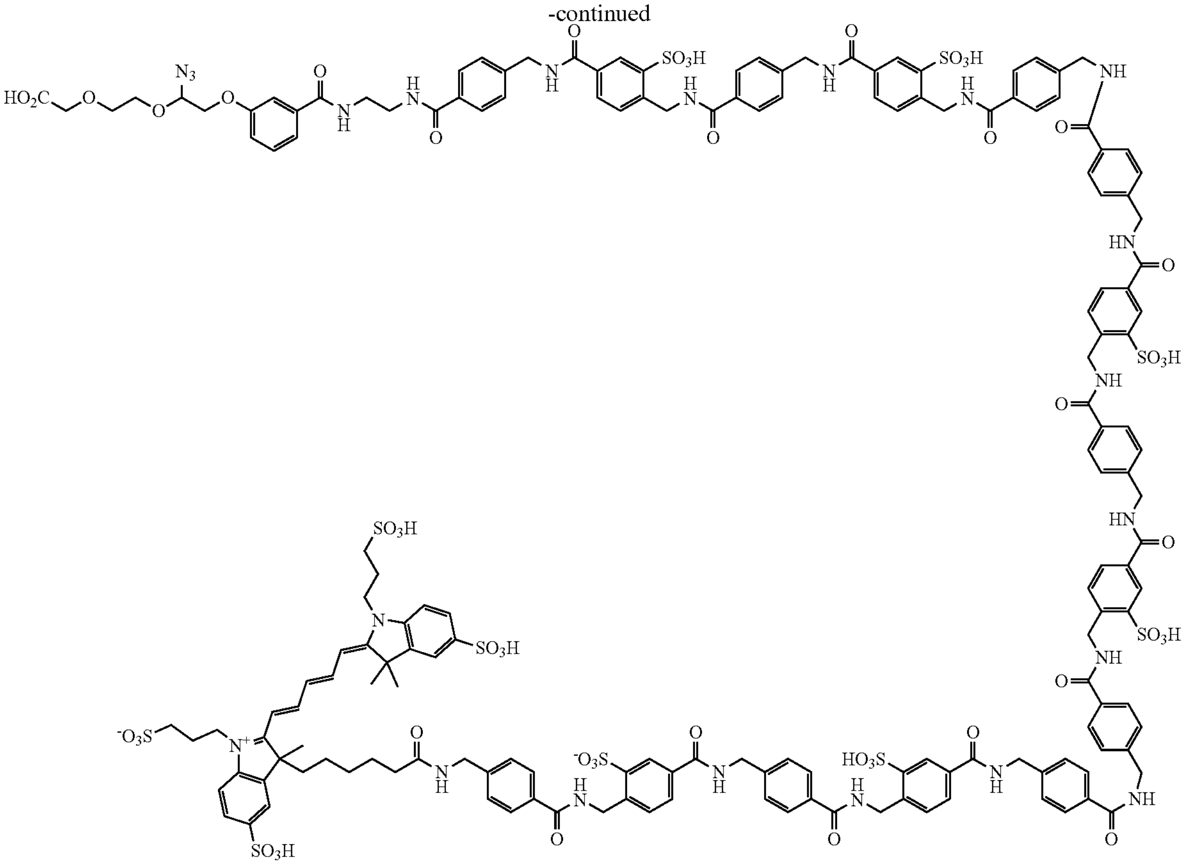

51

Scheme 27: Synthesis of compound 51. Compound 49 was dissolved in minimal volume anhydrous DMF and treated with 1.2 equivalents TSTU and 2 equivalents TEA. Formation of compound 50 (the NHS ester) was confirmed by LCMS of butylamide product. 1 equivalent of compound 18 (i.e., a cleavable linker) was added to reaction mixture to form compound 51 which was purified by reverse phase HPLC eluting with acetonitrile and 50 mM TEAB. Product fractions were dried down, desalted with MeOH, and compound 51 was confirmed by LCMS: calculated and observed m/3z for product+1×TEA counterion=1260.

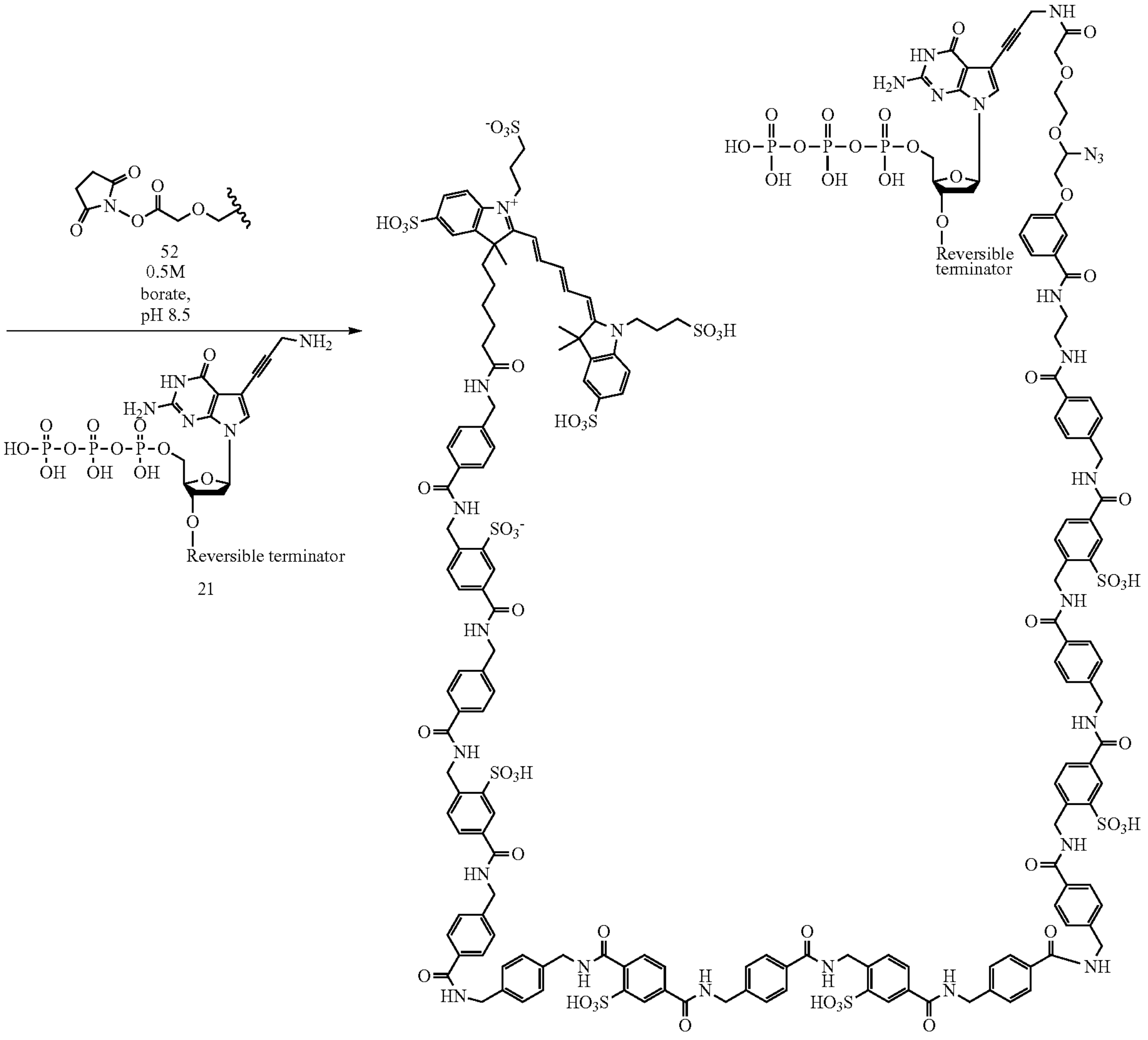

52

21

53

Scheme 28: Synthesis of compound 53. Compound 51 was dissolved in minimal volume anhydrous DMF and treated with 1.2 equivalents TSTU and 2 equivalents TEA. Formation of compound 52 (the NHS ester) was confirmed by LCMS of butylamide product. 1 equivalent of compound 21 (dGTP modified nucleotide) was added to reaction mixture to form compound 53 which was purified by reverse phase HPLC eluting with acetonitrile and 50 mM TEAB. Product fractions were dried down, desalted with MeOH, and compound 53 was confirmed by LCMS.

Example 3. Alternative Protocols to Produce Modified Nucleotides Containing Rigid Spacers

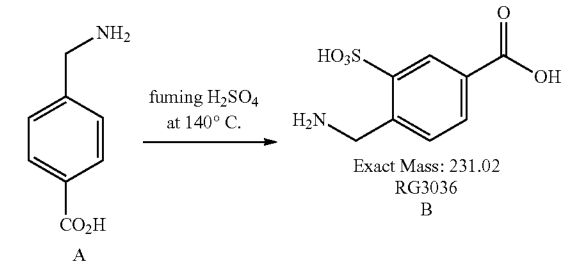

Scheme 29: Synthesis of compound B. Compound A was dissolved in 20% fuming sulfuric acid at 140° C. for 5 hours. Mixture was poured over 400 ml of ice, and resultant milky slush was vacuum filtered. Crude compound B was dissolved in TEA and $H_2O$ in a ratio of 50 mg:50 µl:90 µl compound B:TEA:$H_2O$. Formation of compound B was confirmed by LCMS (calculated=observed m/z), and reaction was purified by reverse phase HPLC eluting with 50 mM TEAB isocratic. Product fractions were dried down, desalted with MeOH, and dried by vacuum pump. Compound B was characterized by $^1H$ and $^{13}C$ NMR: $^1H$ NMR (500 MHz, $D_2O$) δ 8.37 (s, 1H), 8.03 (d, J=7.8 Hz, 1H), 7.63 (d, J=7.9 Hz, 1H), 4.55 (s, 2H), 3.19 (q, J=7.3 Hz, 6H), 1.27 (t, J=7.3 Hz, 9H). $^{13}C$ NMR (125 MHz, $D_2O$) δ 173.50, 142.17, 138.12, 132.41, 132.14, 131.74, 127.76, 46.74, 41.12, 8.28.

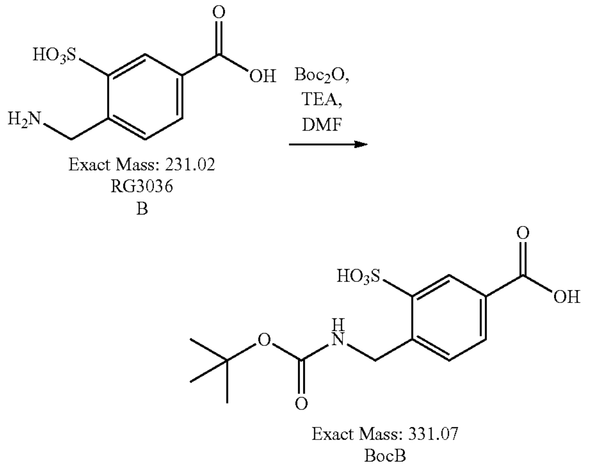

Scheme 30: Synthesis of compound BocB. Compound B was treated with $Boc_2O$ and TEA in DMF to yield compound BocB. Formation of compound BocB was confirmed by LCMS (calculated=observed m/z), and reaction was purified by reverse phase HPLC eluting with acetonitrile and 50 mM TEAB. Product fractions were dried down, desalted with MeOH, and dried by vacuum pump.

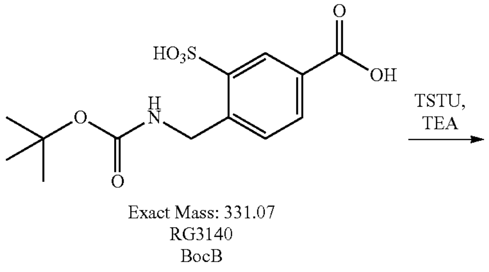

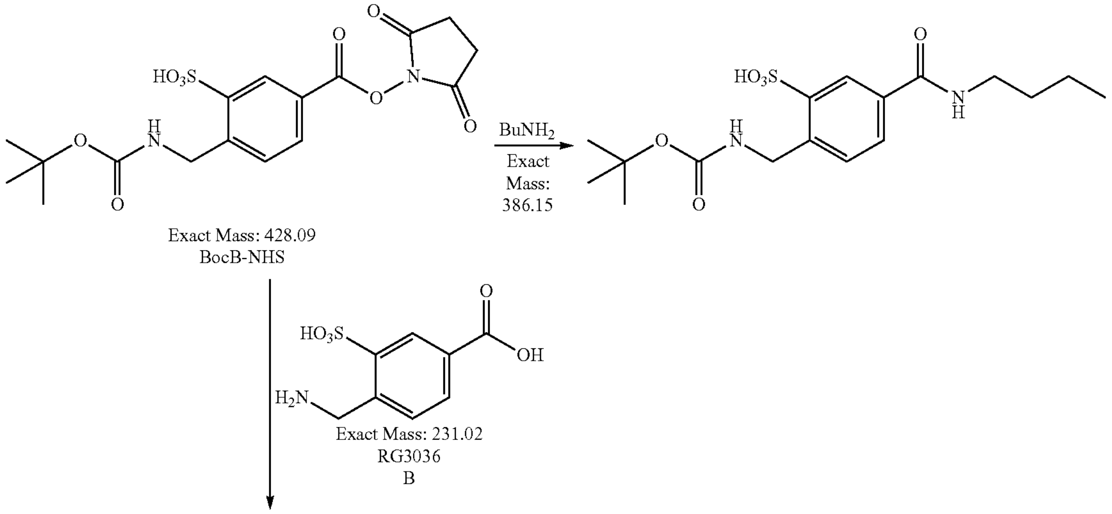

-continued

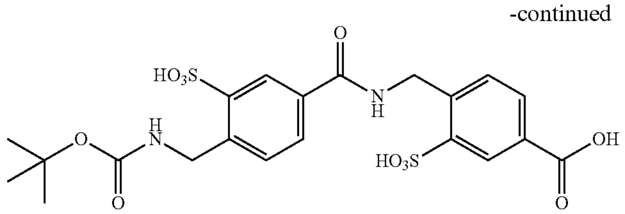

Exact Mass: 544.08

BocB2

Scheme 31. Synthesis of compound BocB2. Compound BocB was dissolved in minimal volume anhydrous DMF and treated with 1.2 equivalents TSTU and 2 equivalents TEA. Formation of NHS was confirmed by LCMS of butylamide product (expected=observed m/z). 1 equivalent of compound B was added to reaction mixture to form compound BocB2. Formation of compound BocB2 was confirmed by LCMS (calculated=observed m/z), and reaction was purified by reverse phase HPLC eluting with acetonitrile and 50 mM TEAB. Product fractions were dried down, desalted with MeOH, and dried by vacuum pump.

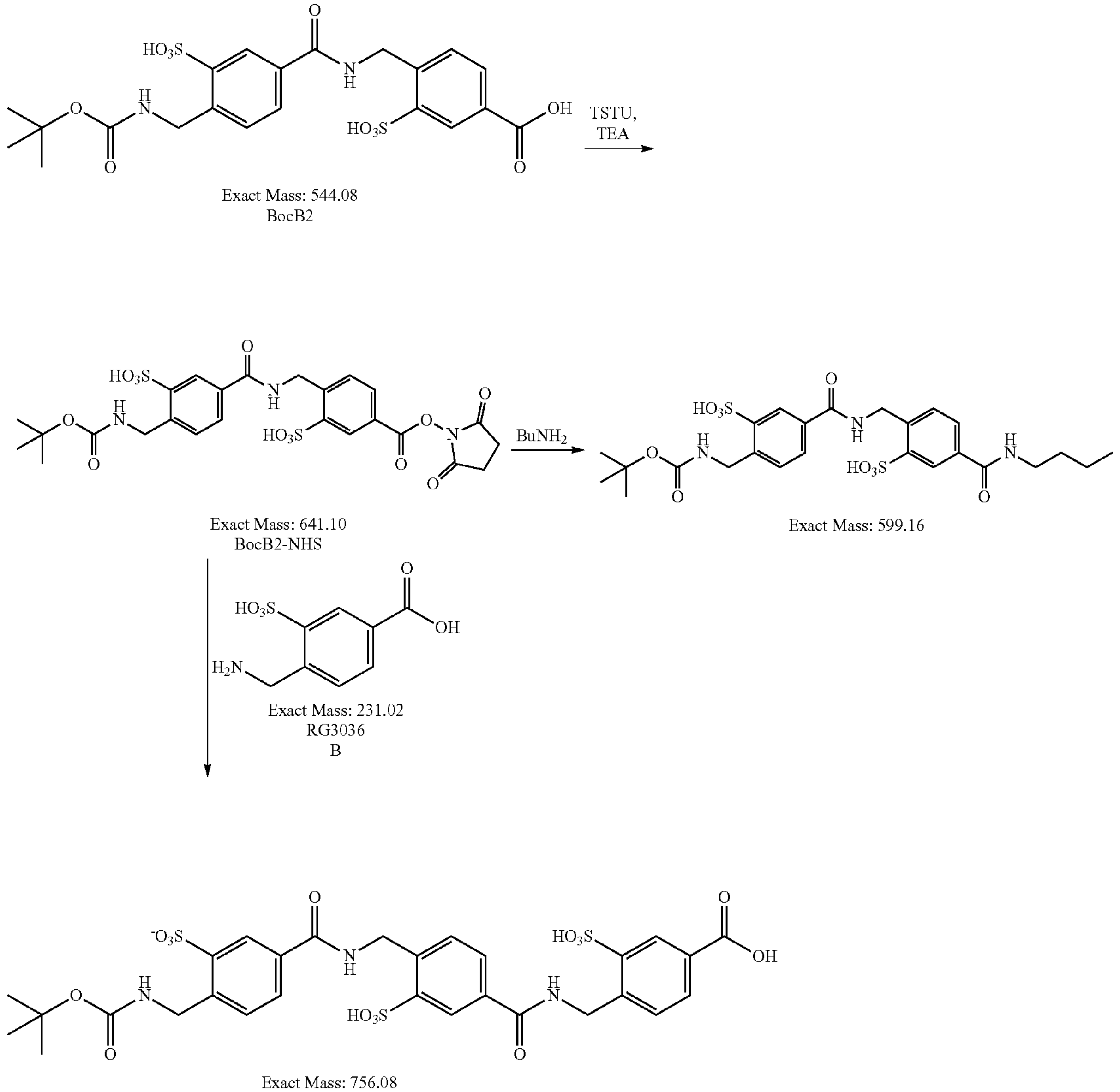

Exact Mass: 544.08

BocB2

Exact Mass: 641.10

BocB2-NHS

Exact Mass: 599.16

Exact Mass: 231.02

RG3036

B

Exact Mass: 756.08

BocB3

Scheme 32: Synthesis of compound BocB3. Compound BocB2 was dissolved in minimal volume anhydrous DMF and treated with 1.2 equivalents TSTU and 2 equivalents TEA. Formation of NHS was confirmed by LCMS of butylamide product (expected=observed m/z). 1 equivalent of compound B was added to reaction mixture to form compound BocB3. Formation of compound BocB3 was confirmed by LCMS (calculated=observed m/z), and reaction was purified by reverse phase HPLC eluting with acetonitrile and 50 mM TEAB. Product fractions were dried down, desalted with MeOH, and dried by vacuum pump.

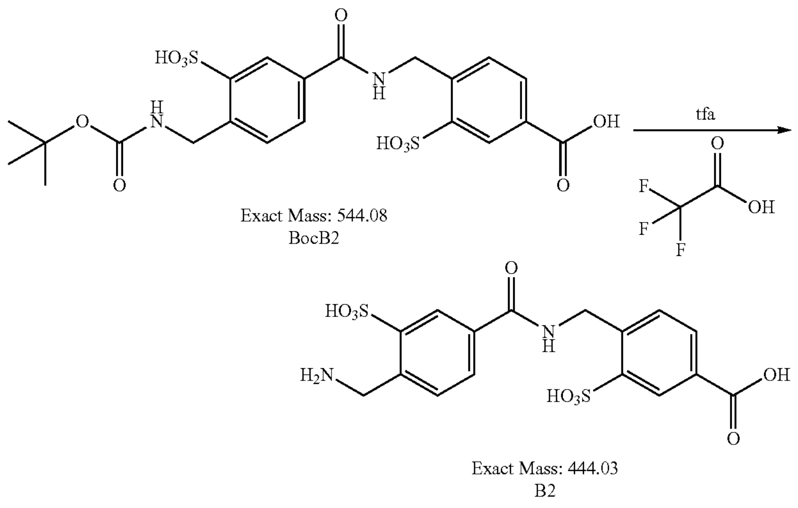

Scheme 33: Synthesis of compound B2. Compound BocB2 was dissolved in TFA for 15-30 minutes. Formation of compound B2 was confirmed by LCMS (calculated=observed m/z), and reaction was purified by reverse phase HPLC eluting with acetonitrile and 50 mM TEAB. Product fractions were dried down, desalted with MeOH, and dried by vacuum pump. Compound B2 was characterized by $^{1}H$ and $^{13}C$ NMR: $^{1}H$ NMR (500 MHz, $D_2O$) δ 8.48 (d, J=1.8 Hz, 1H), 8.35 (d, J=1.9 Hz, 1H), 8.09 (dd, J=8.1, 1.8 Hz, 1H), 8.01 (dd, J=7.9, 1.9 Hz, 1H), 7.71 (d, J=8.0 Hz, 1H), 7.62 (d, J=8.1 Hz, 1H), 5.06 (s, 2H), 4.57 (s, 2H). $^{13}C$ NMR (125 MHz, $D_2O$) δ 169.04, 168.57, 143.21, 141.35, 140.80, 134.83, 133.18, 132.94, 132.58, 130.49, 129.21, 128.90, 128.43, 126.37, 41.27, 41.02.

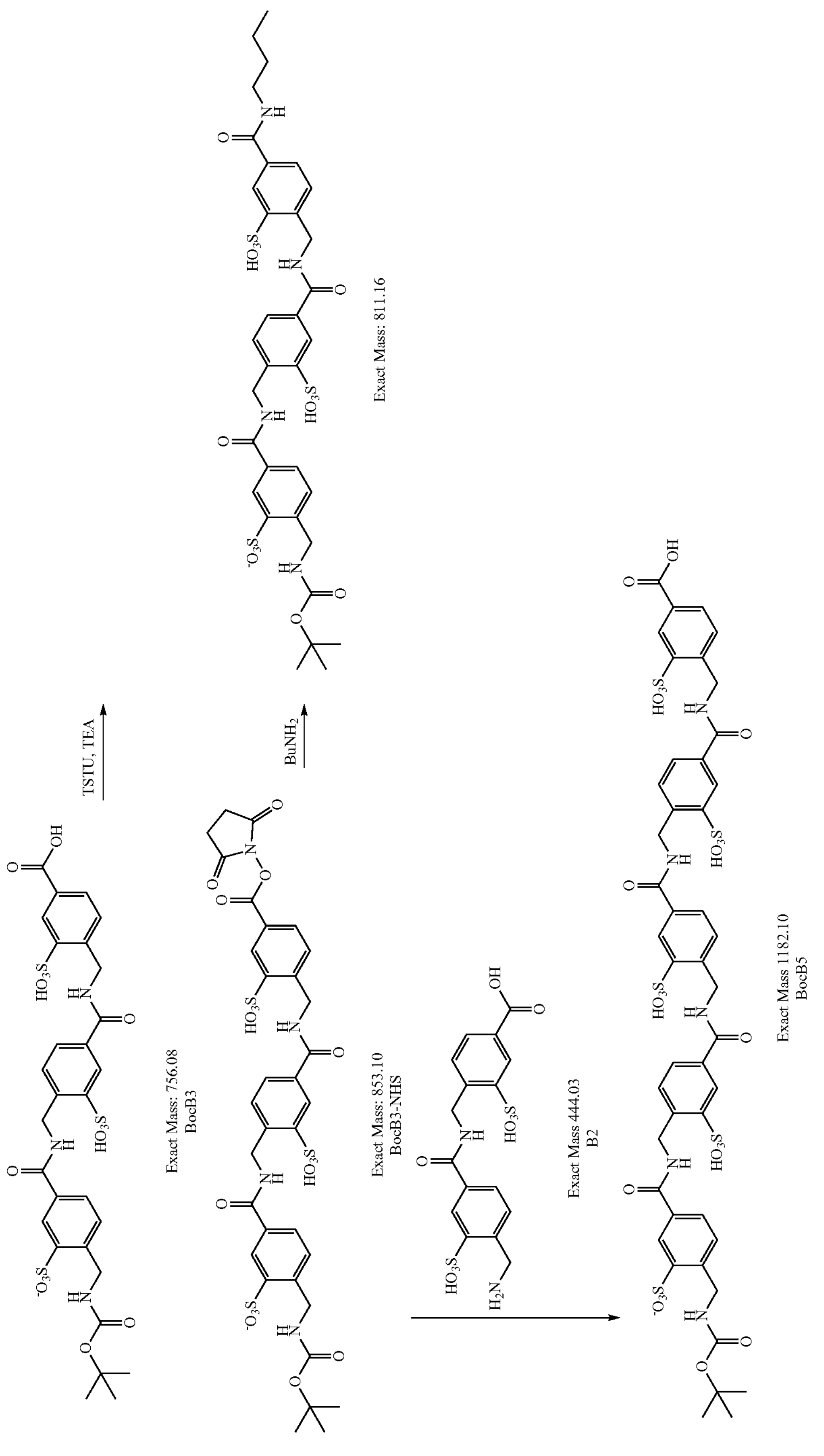
TSTU, TEA
$BuNH_2$
Exact Mass: 756.08
BocB3
Exact Mass: 853.10
BocB3-NHS
Exact Mass: 811.16
Exact Mass 444.03
B2
Exact Mass 1182.10
BocB5

Scheme 34: Synthesis of compound BocB5. Compound BocB3 was dissolved in minimal volume anhydrous DMF and treated with 1.2 equivalents TSTU and 2 equivalents TEA. Formation of NHS was confirmed by LCMS of butylamide product (expected=observed m/z). 1 equivalent of compound B2 was added to reaction mixture to form compound BocB5. Formation of compound BocB5 was confirmed by LCMS (calculated=observed m/z), and reaction was purified by reverse phase HPLC eluting with acetonitrile and 50 mM TEAB. Product fractions were dried down, desalted with MeOH, and dried by vacuum pump.

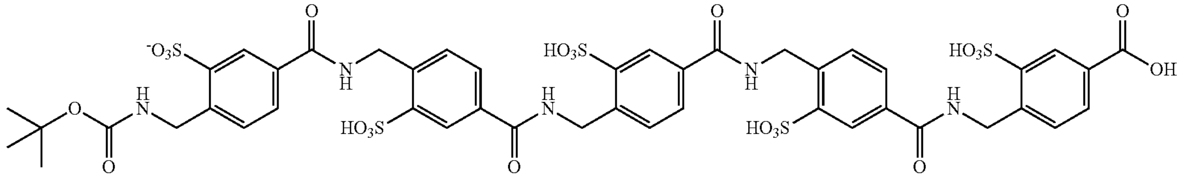

Exact Mass: 1182.10
BocB5

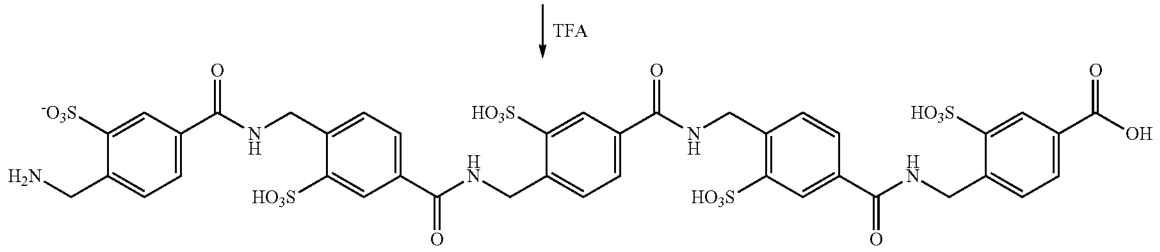

Exact Mass: 1082.05
B5

Scheme 35: Synthesis of compound B5. Compound BocB5 was dissolved in TFA for 15-30 minutes. Formation of compound B5 was confirmed by LCMS (calculated=observed m/z), and reaction was purified first by ion exchange eluting with 1M TEAB, then by reverse phase HPLC eluting with acetonitrile and 50 mM TEAB. Product fractions were dried down, desalted with MeOH, and dried by vacuum pump. Compound B5 was characterized by $^1H$ and 13C NMR: $^1H$ NMR (500 MHz, $D_2O$) δ 8.37 (s, 12H), 8.02 (d, J=7.9 Hz, 3H), 7.97 (d, J=7.9 Hz, 11H), 7.71 (d, J=8.0 Hz, 3H), 7.66 (d, J=8.1 Hz, 8H), 7.58 (d, J=8.0 Hz, 3H), 5.07 (s, 6H), 5.07 (s, 10H), 5.04 (s, 6H), 4.55 (s, 5H), 3.11 (q, J=7.3 Hz, 87H), 1.20 (t, J=7.3 Hz, 128H). $^{13}C$ NMR (125 MHz, $D_2O$) δ 176.31, 171.65, 171.50, 171.40, 145.33, 143.71, 143.06, 141.92, 141.78, 140.42, 138.46, 137.23, 136.48, 135.24, 135.20, 134.42, 133.10, 132.70, 132.65, 131.58, 131.24, 130.23, 128.87, 128.72, 49.21, 43.72, 43.62, 40.56, 10.77.

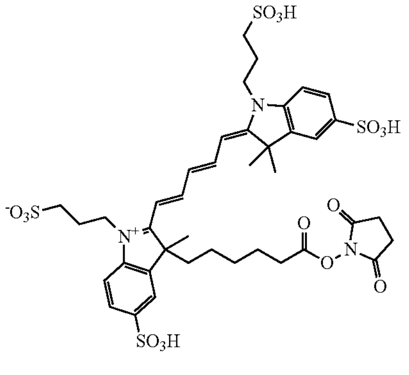

Exact Mass: 955.20
AF647 NHS

+

Exact Mass: 1082.05

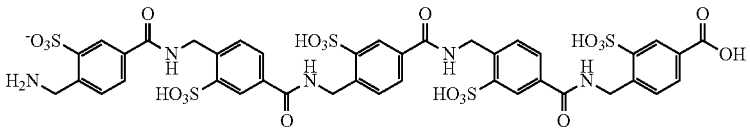

B5

DMF, TEA

-continued

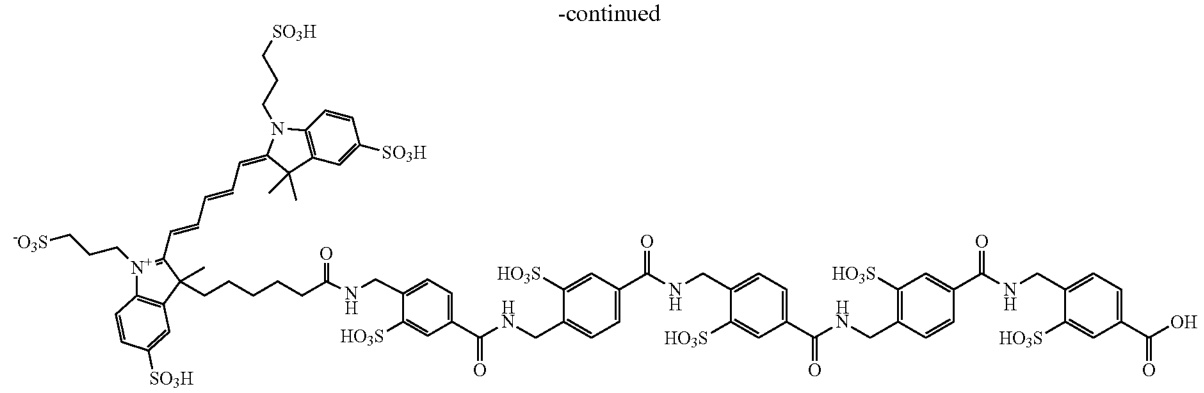

Exact Mass: 1923.23
AF647-B5

Scheme 36: Synthesis of compound AF647-B5. Compound AF647-NHS (a detectable label with $\lambda_{max}\approx 647$) was dissolved in minimal volume of anhydrous DMF, to which was added 1 equivalent compound B5 and 5 equivalents TEA. Formation of compound AF647-B5 was confirmed by LCMS (calculated=observed m/2z), and the reaction was purified by reverse phase HPLC eluting with acetonitrile and 50 mM TEAB. Product fractions were dried down, desalted with MeOH, and dried by vacuum pump.

Synthesis of remaining dye-B5 compounds. An analogous synthesis method was used for all four dye-labels. Compound AF647 (detectable label with $\lambda_{max}$~647 nm) was substituted for another dye with $\lambda_{max}$
.

Example 4. Controlled Synthesis of Dye-Spacers: 1-4Mer Examples

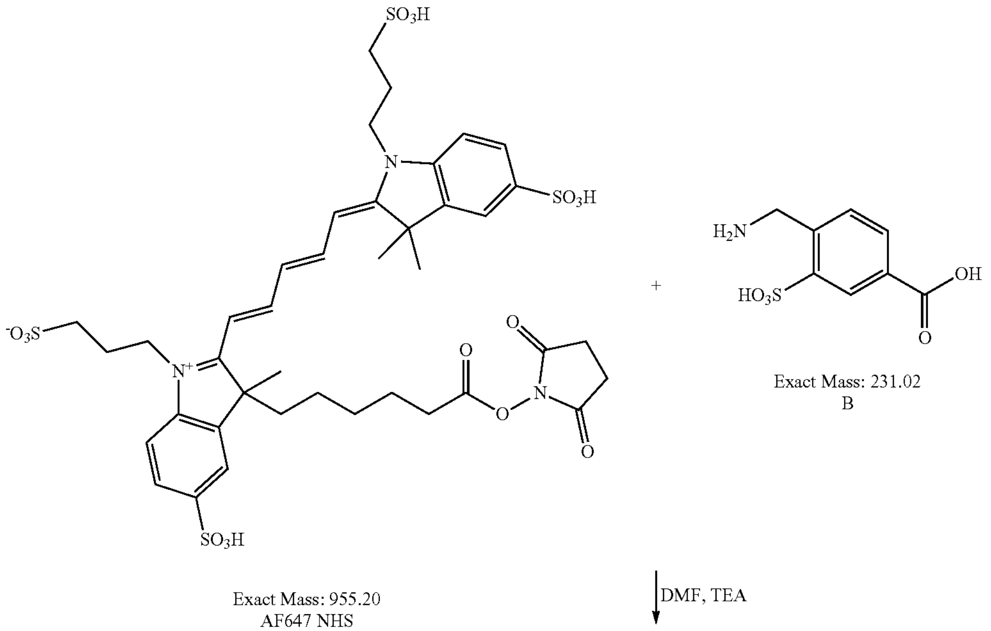

-continued

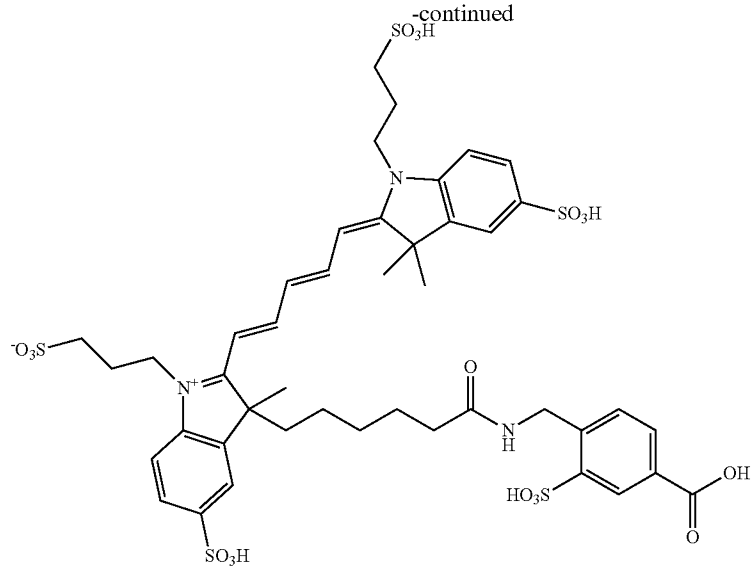

Exact Mass: 1071.19
AF647-B1

Scheme 37: Synthesis of compound AF647-B1. Compound AF647-NHS (a detectable label with $\lambda_{max}$≈647) was dissolved in minimal volume of anhydrous DMF, to which was added 1 equivalent compound B1 and 5 equivalents TEA. Formation of compound AF647-B1 was confirmed by LCMS (calculated=observed m/2z), and the reaction was purified by reverse phase HPLC eluting with acetonitrile and 50 mM TEAB. Product fractions were dried down, desalted with MeOH, and dried by vacuum pump.

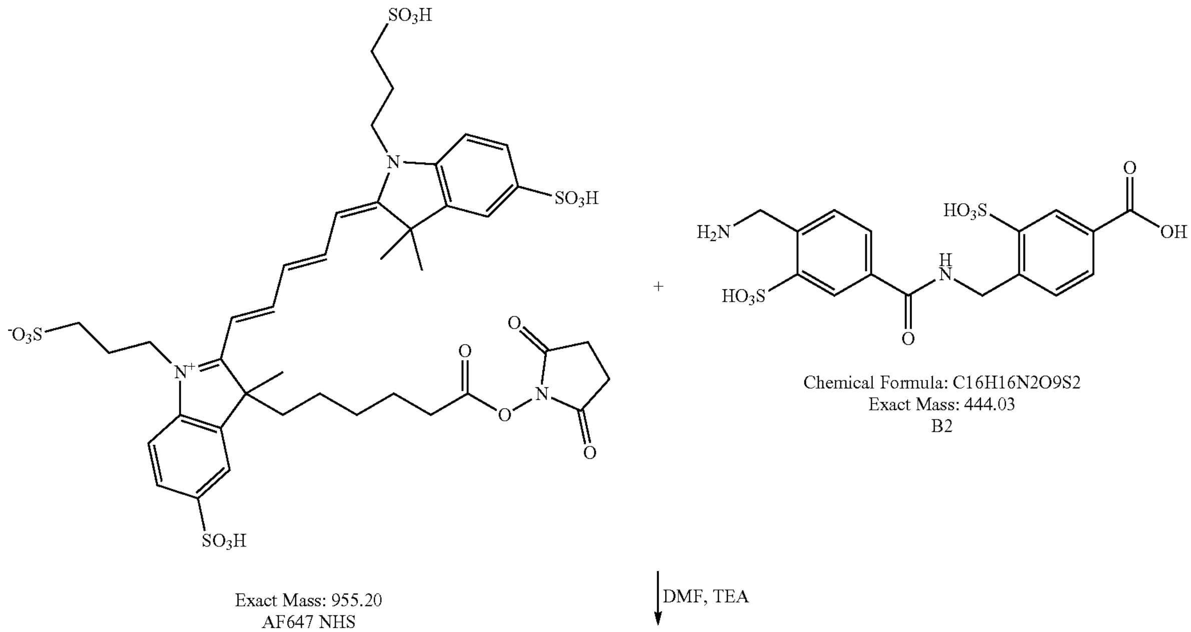

Exact Mass: 955.20
AF647 NHS

Chemical Formula: C16H16N2O9S2
Exact Mass: 444.03
B2

-continued

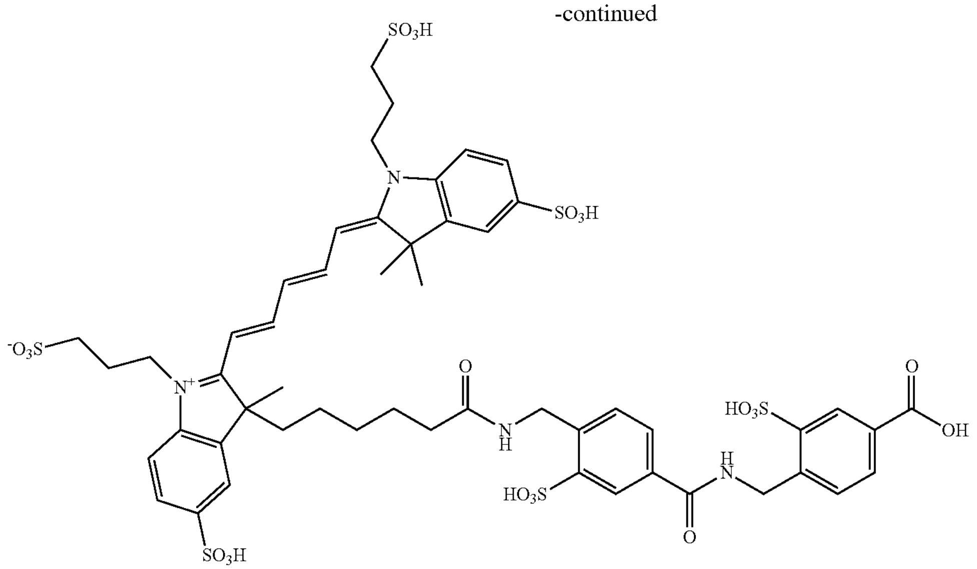

Exact Mass: 1284.20
AF647-B2

Scheme 38: Synthesis of compound AF647-B2. Compound AF647-NHS (a detectable label with $\lambda_{max}$≈647) was dissolved in minimal volume of anhydrous DMF, to which was added 1 equivalent compound B2 and 5 equivalents TEA. Formation of compound AF647-B2 was confirmed by LCMS (calculated=observed m/2z), and the reaction was purified by reverse phase HPLC eluting with acetonitrile and 50 mM TEAB. Product fractions were dried down, desalted with MeOH, and dried by vacuum pump.

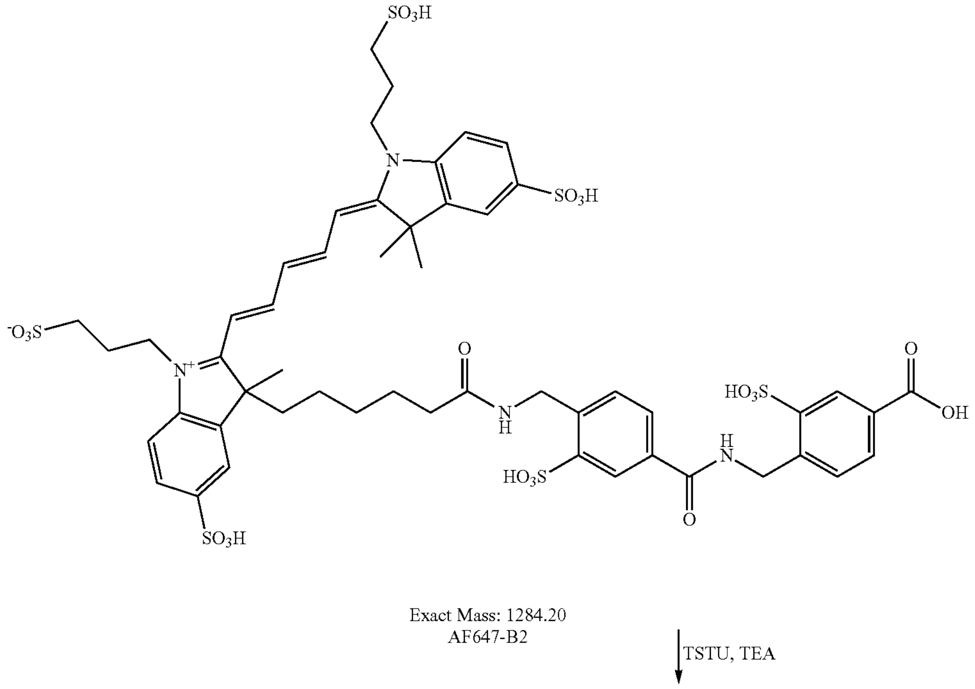

Exact Mass: 1284.20
AF647-B2

-continued
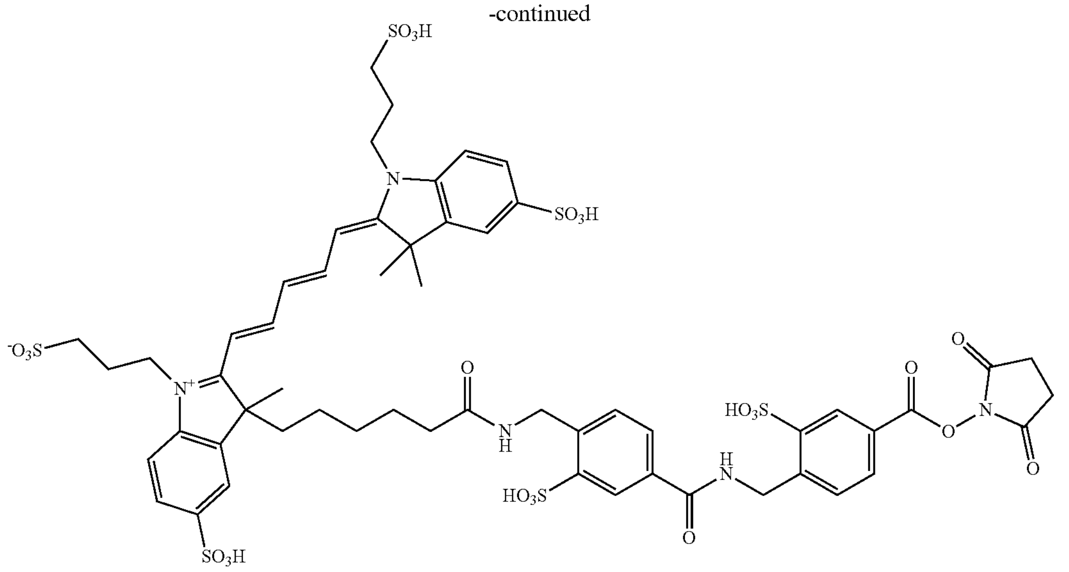
Exact Mass: 1381.22
AF647-B2-NHS
Scheme 39: Synthesis of compound AF647-B2-NHS. Compound AF647-B2 was dissolved in minimal volume anhydrous DMF and treated with 1.2 equivalents TSTU and 2 equivalents TEA. Formation of NHS was confirmed by LCMS of butylamide product (expected=observed m/2z).
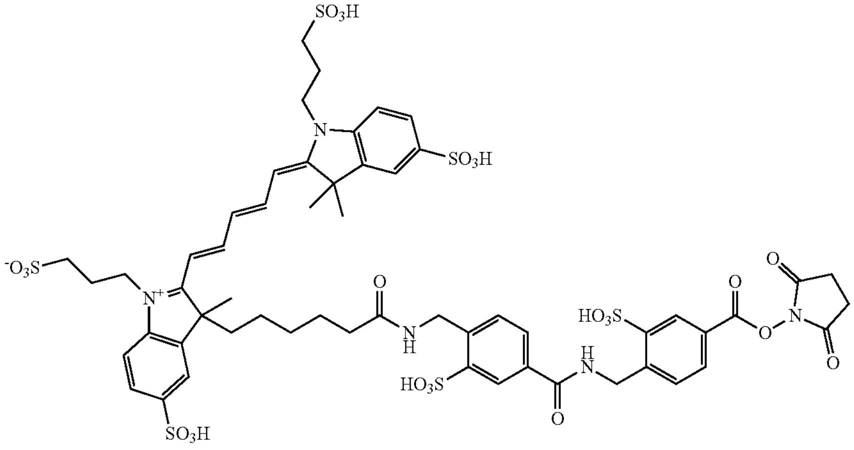
Exact Mass: 1381.22
AF647-B2-NHS
+
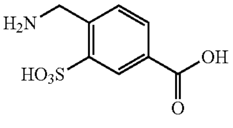
Exact Mass: 231.02
B

-continued

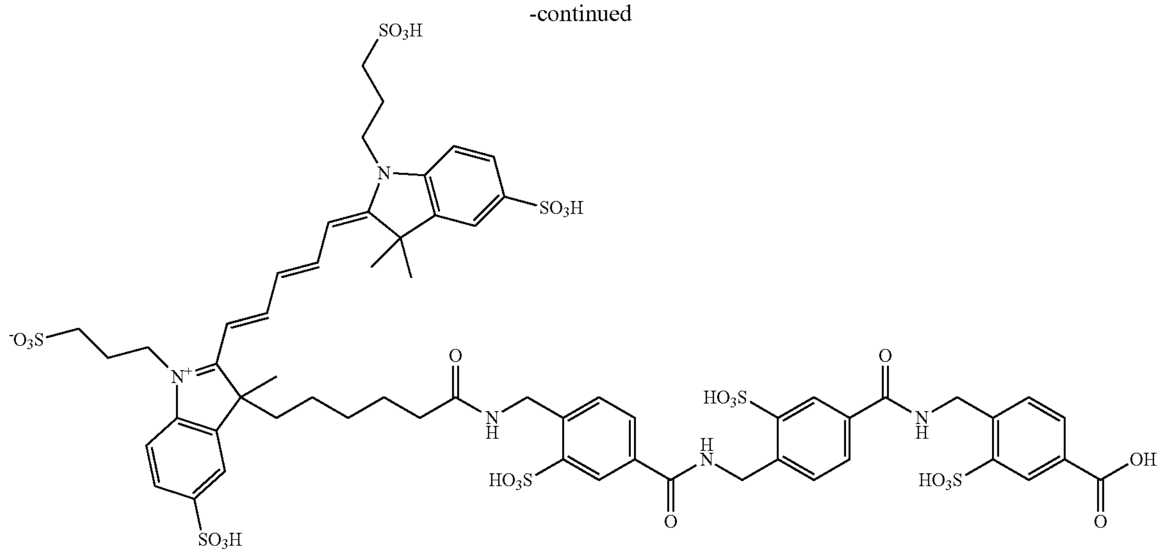

Exact Mass: 1497.21
AF647-B3

Scheme 40: Synthesis of compound AF647-B3. To AF647-B2-NHS reaction mixture, 1 equivalent of compound B was added. Formation of compound BocB3 was confirmed by LCMS (calculated=observed m/2z), and reaction was purified by reverse phase HPLC eluting with acetonitrile and 50 mM TEAB. Product fractions were dried down, desalted with MeOH, and dried by vacuum pump.

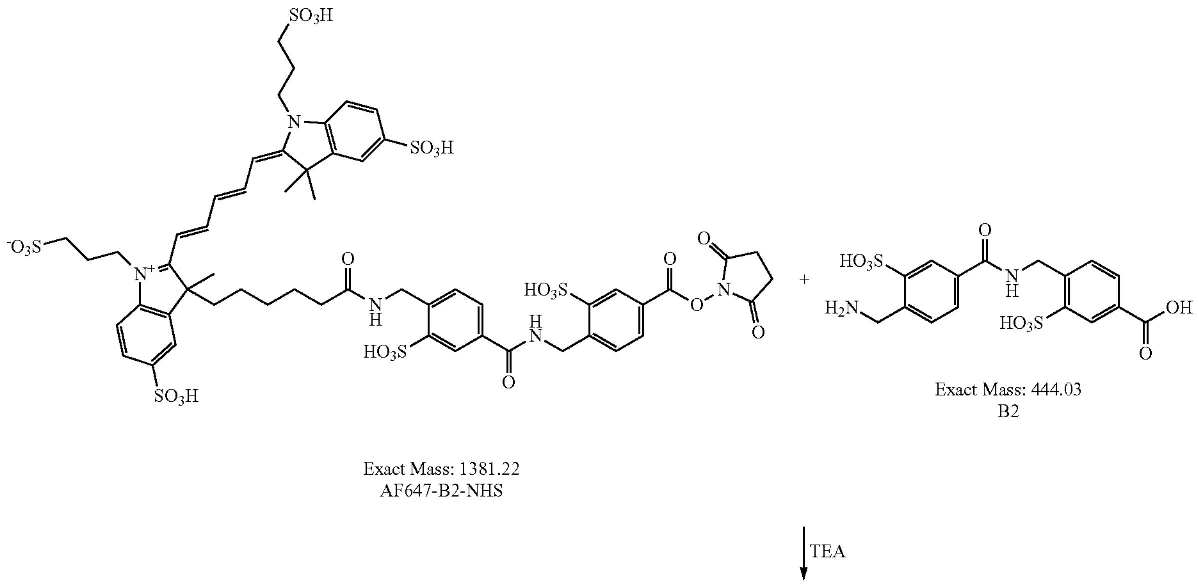

Exact Mass: 1381.22
AF647-B2-NHS

Exact Mass: 444.03
B2

-continued

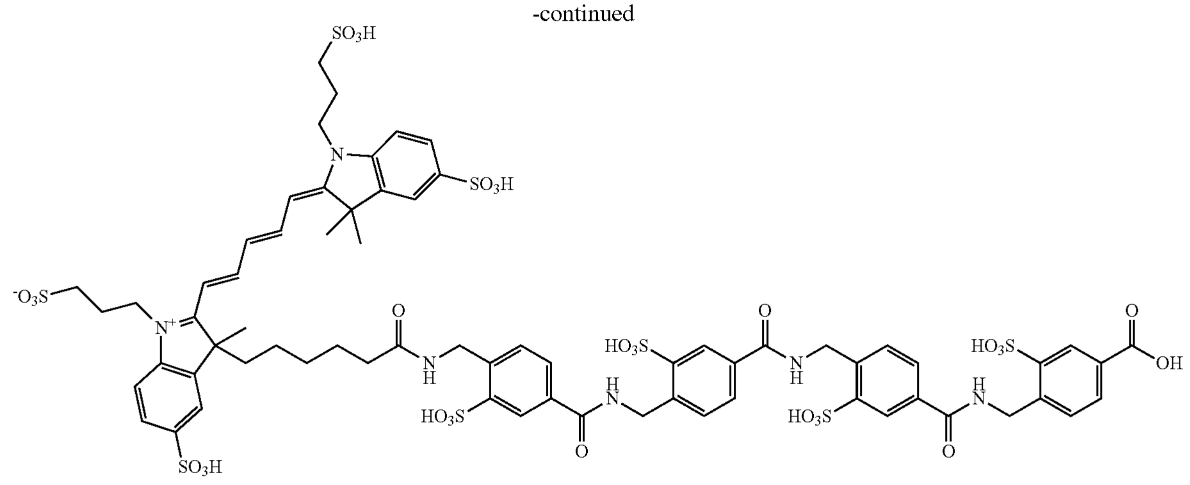

Exact Mass: 1710.22
AF647-B4

Scheme 41: Synthesis of compound AF647-B4. To AF6-(7-B2-NHS reaction mixture, 1 equivalent of compound B2 was added. Formation of compound BocB4 was confirmed by LCMS (calculated=observed m/2z), and reaction was purified by reverse phase HPLC eluting with acetonitrile and 50 mM TEAB. Product fractions were dried down, desalted with MeOH, and dried by vacuum pump.

Example 5. Assessing Linear Nature of the Rigid Spacer

Known methods in the art to quantify rigidity, or degree of linearity may be used. For example, Time-Resolved Energy Transfer experiments are able to provide distance distributions for a linker connecting a donor-acceptor pair. For a given donor-acceptor pair, the efficiency of energy transfer decreases as $r^{-6}$, where r is the distance between the donor and the acceptor dyes. The extent of the energy transfer directly corresponds to the distance between the donor and the acceptor. The use of resonance energy transfer has been used to quantify flexible and rigid poly peptides by providing distance distributions separating a donor and acceptor pair (see for example Haas et al PNAS USA 72:1807-1811 (1975); and Lakowicz et al. Proc SPIE 1204: 192-205 (1990). The FRET efficiency may then be converted to persistence length by comparing the FRET efficiency with calculated FRET efficiency based on models such as the worm-like chain model, or other known methods in the art.

For the rigid spacers of the present disclosure, the vector connecting the attachment points of the spacer monomer has restricted degrees of freedom and cannot move freely in all dimensions. In embodiments, the rigid spacers maintain the dye within a ligand cone angle, which is defined as the angle formed with the nucleobase at the vertex and the outermost edge of the van der Waals spheres of the dye atoms at the perimeter of the cone. The rigid spacers are laterally rigid (i.e., spacers which do not substantially bend or flex and do not allow substantial rotation either along their length or at their attachments points). The rigid spacers increase the persistence length ($l_P$) of the overall covalent linkage. Experimental and theoretical data suggests polyphenylene linkers have surprisingly large persistence length values, lp=9 nm (Forero-Martinez, N. C., Baumeier, B., & Kremer, K. (2019). Backbone Chemical Composition and Monomer Sequence Effects on Phenylene Polymer Persistence Lengths. Macromolecules, 52(14), 5307-5316), and extract a monomer persistence length of 0.86 nm/phenylene. The persistence length of the rigid spacer may be tuned by incorporating elements which do not have restricted degrees of freedom (e.g., glycine), as exemplified by linkers containing the polypeptide sequence GSSGSS (SEQ ID NO:2), GSSSSS (SEQ ID NO:3), and SSSSSS (SEQ ID NO:4), which have an lp of 4.5, 4.8, and 6.2 Å, respectively (van Rosmalen et al *Biochemistry* 2017 56 (50), 6565-6574 (2017)).

Figure 8A:
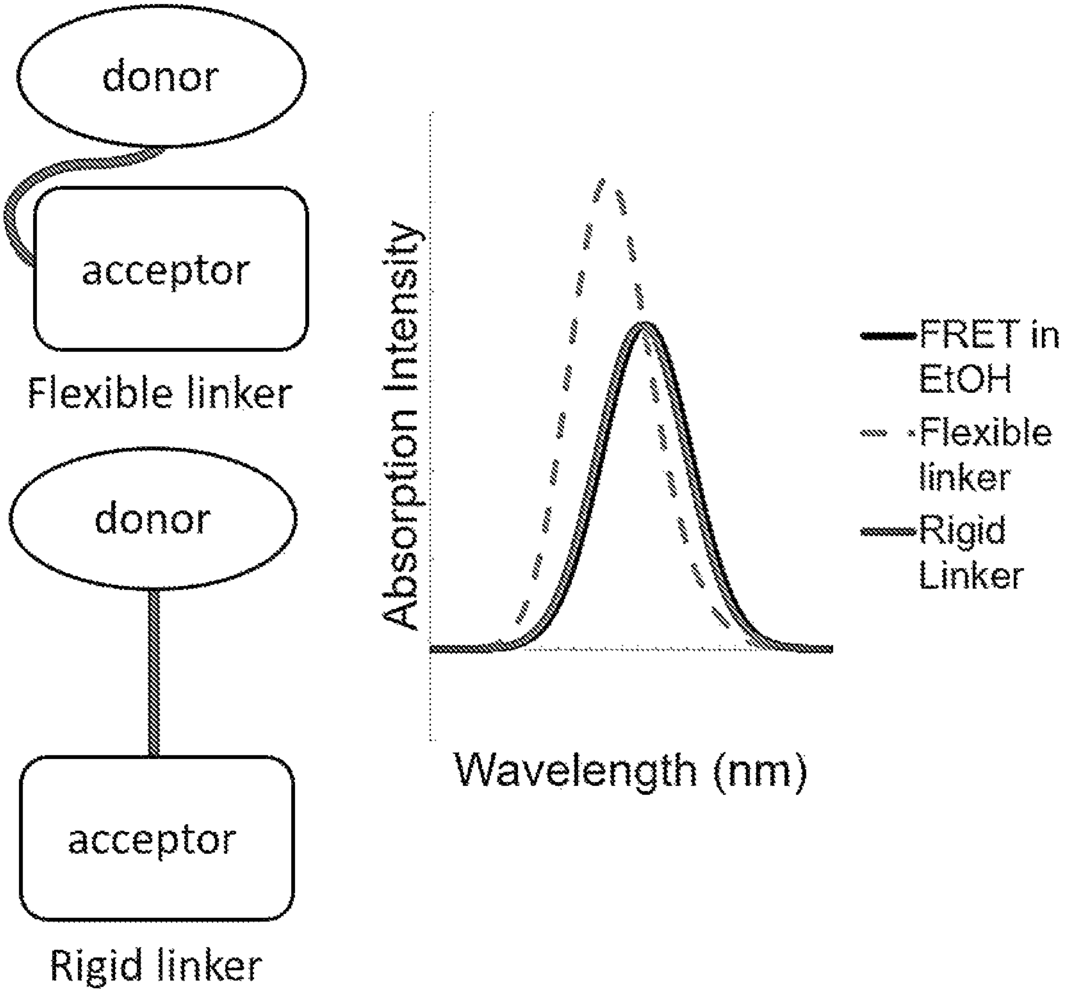
FIGS. 8A-8C. An illustration describing the rigidity test described herein. Briefly, in an organic solvent, (e.g., ethanol) the donor and acceptor moieties are solvated by the organic molecules and prevented from aggregating. The absorbance spectra of such an idealized FRET pair is illustrated in FIG. 8A (solid black line). If the linker is too flexible it permits the donor and acceptor moieties to come into contact, stack, or aggregate, which modifies the absorbance spectra, as depicted as the dashed line in FIG. 8A. Ideally, a rigid linker (i.e., a linker described herein containing rigid spacers) limits the contact between the FRET pair and will have an absorbance spectra similar to the FRET pair in EtOH. The absorbance spectra of compounds A-B2-Lys-D (FIG. 8B) and A-B5-Lys-D (FIG. 8C) was measured by a spectrophotometer in organic (EtOH) and aqueous ($H_2O$) solvents.

A simple method for quantifying the rigidity of a nucleotide containing a rigid spacer, is to measure the absorbance spectra of a FRET pair (i.e., a donor dye and acceptor dye) separated by a rigid spacer. In this sense, the efficiency of Fluorescence Resonance Energy Transfer (FRET) between a donor and an acceptor molecule attached to opposite ends of a linker containing a rigid spacer is used as a proxy for the nucleobase covalently linked to a detectable label. This rigidity test is similar to methods used to determine the optimum labeling density in DNA origami structures which seek minimize dye-dye interactions (Schroder et al. *Nano Lett.* 2019, 19, 2, 1275-1281). Briefly, in an organic solvent, (e.g., ethanol) the donor and acceptor moieties are solvated by the organic molecules and prevented from aggregating. The specta of such an idealized FRET pair is illustrated in FIG. 8A (solid black line). In water, the donor and acceptor moieties come into contact, stack, or aggregate in water and thus their absorbance spectra is altered. Similarly, if the linker is too flexible, it permits the donor and acceptor moieties to come into contact, stack, or aggregate, modifying the absorbance spectra as depicted as the dashed line in FIG. 8A. Ideally, a rigid linker (i.e., a linker described herein containing rigid spacers) limits the contact between the FRET pair and will have an absorbance spectra similar to the FRET pair in EtOH. Further, a FRET ratio may be calculated. A FRET ratio is calculated by dividing the peak intensity of the acceptor fluorescence by that of the donor fluorescence.

Figure 8B:
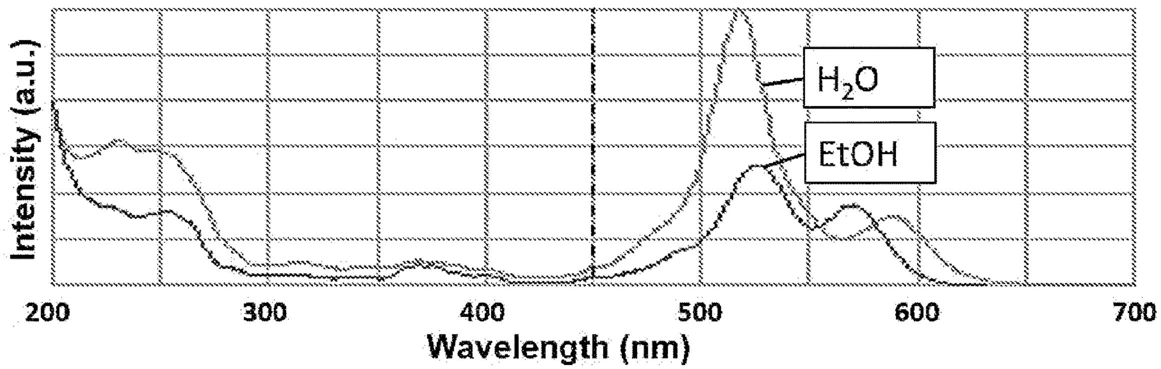
Figure 8C:
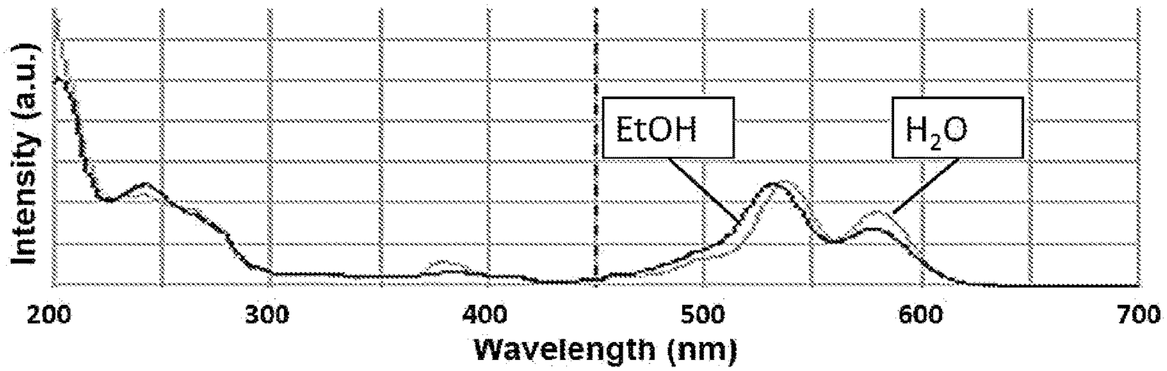
Figure 9:
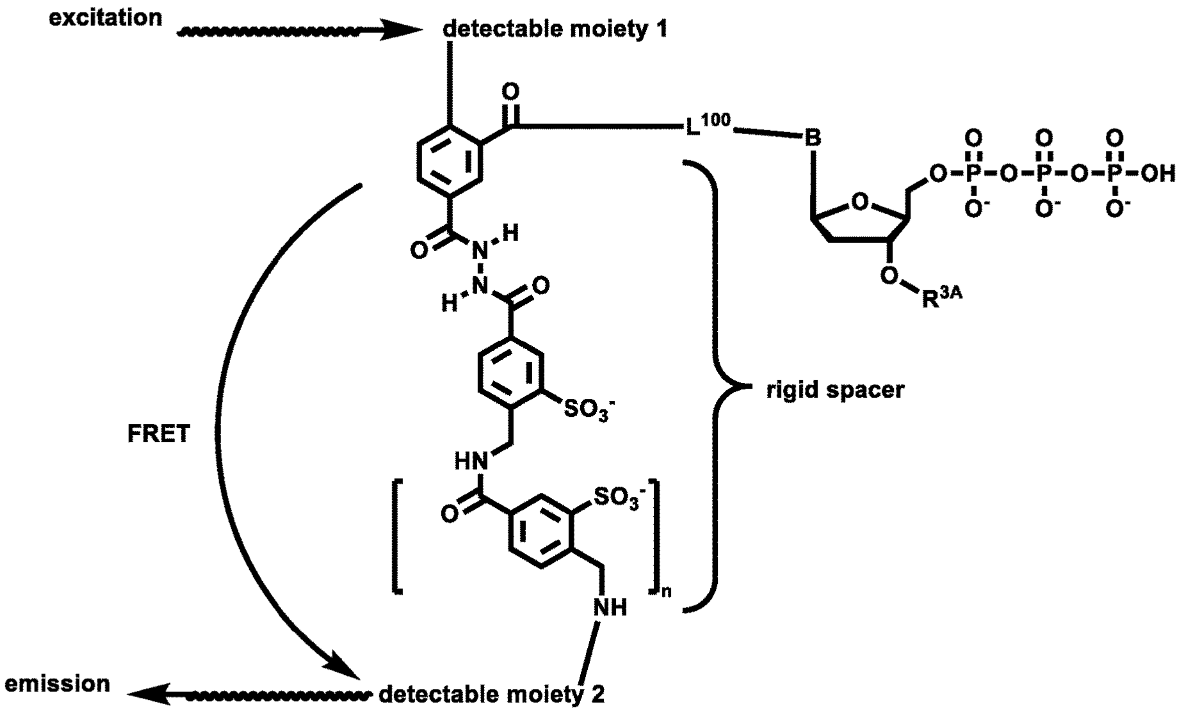
FIG. 9. Illustration of a nucleotide that contains two detectable labels (e.g., a FRET pair). Depicted in the figure, a first detectable moiety is excited with an excitation wavelength and non-radiatively transfers the energy to a second detectable moiety, wherein the rigid spacer separates the first and second detectable labels.

To test the rigidity of the linkers, an acceptor (A) and a donor (D) are separated by 2 rigid monomers (A-B2-Lys-D)

or 5 rigid spacer monomers (A-B5-Lys-D). The spectra of compound A-B5-Lys-D (FIG. 8B) and A-B5-Lys-D (FIG. 8C) was measured by a spectrophotometer in organic (EtOH) versus aqueous ($H_2O$) solvents. As observed from the absorbance specta, the 5mer (B5) prevents dye stacking/aggregation better than the 2mer (B2) because of the increased separation of the chromophores, D and A. It may be inferred that a 5mer (B5) is capable of maintaining the detectable label away from the nucleobase.

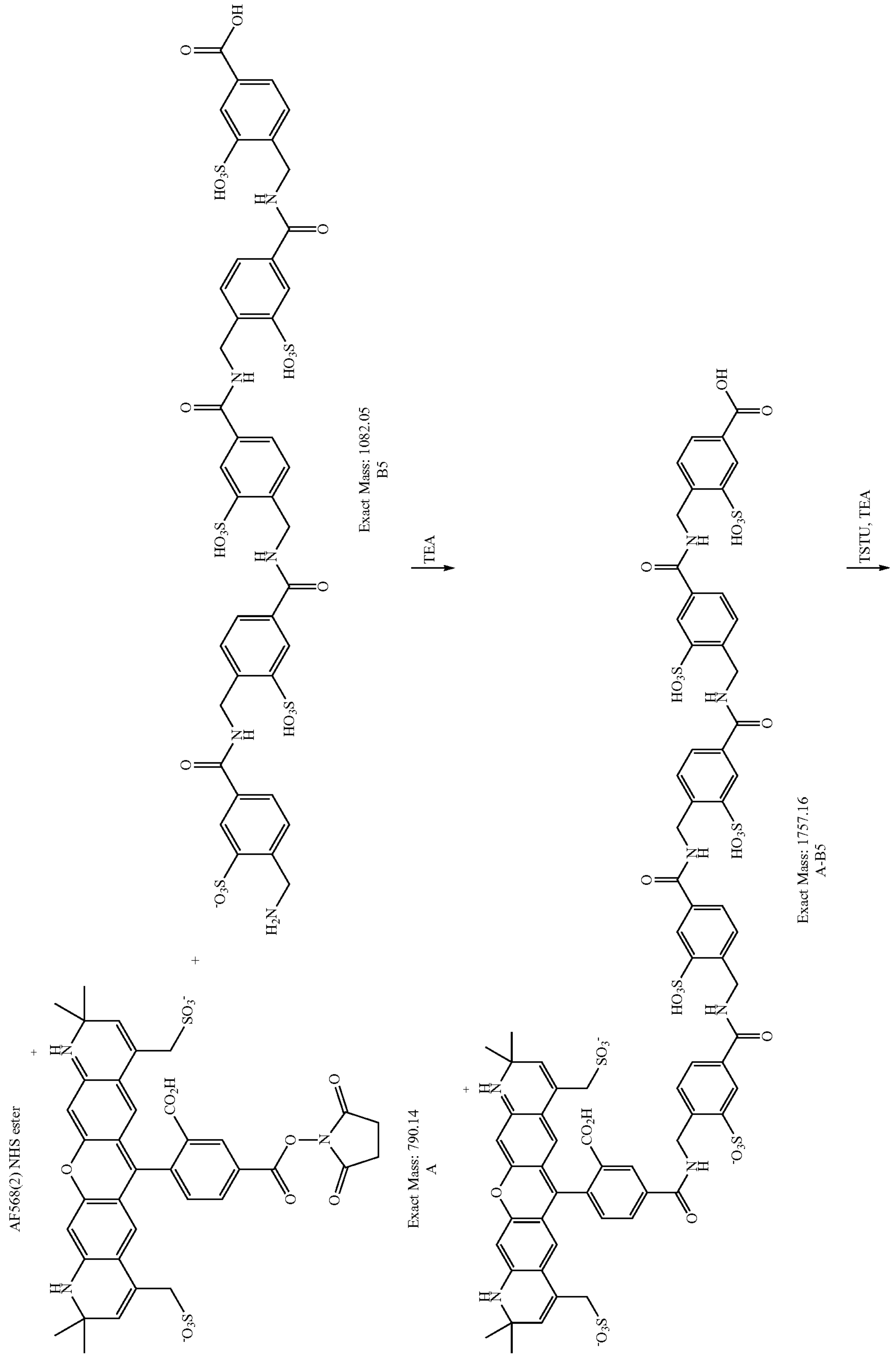
AF568(2) NHS ester
Exact Mass: 790.14
A
Exact Mass: 1082.05
B5
TEA
Exact Mass: 1757.16
A-B5
TSTU, TEA -continued
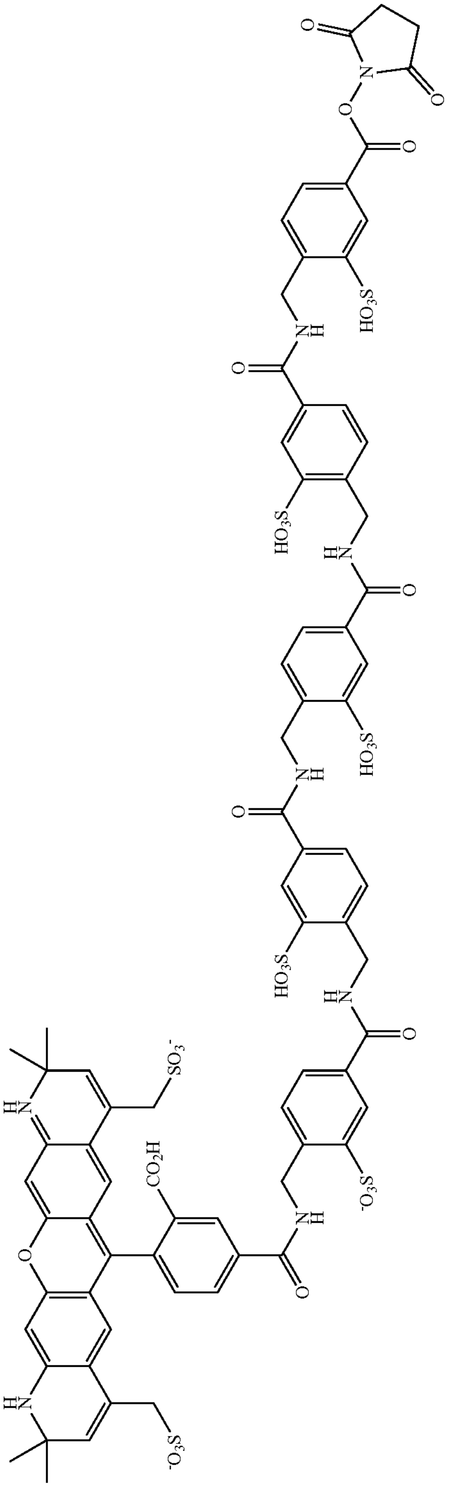
Exact Mass: 1854.18
A-B5-NHS Scheme 42: Synthesis of compound A-B5-NHS. Compound A (acceptor dye) was coupled to compound B5 (5-mer rigid linker) with TEA in DMF to yield compound A-B5, which was purified by reverse phase HPLC eluting with acetonitrile and 50 mM TEAB. Product fractions were dried down, desalted with MeOH, and dried by vacuum pump. Dry compound A-B5 was activated with TSTU in DMF. Formation of compounds A-B5 and A-B5-NHS was confirmed by LCMS of A-B5 and A-B5-butylamide, respectively (expected=observed m/2z). The compound A-B2-NHS is synthesized in an analogous manner, except a B2 (2-mer rigid linker) compound is added in the first step.

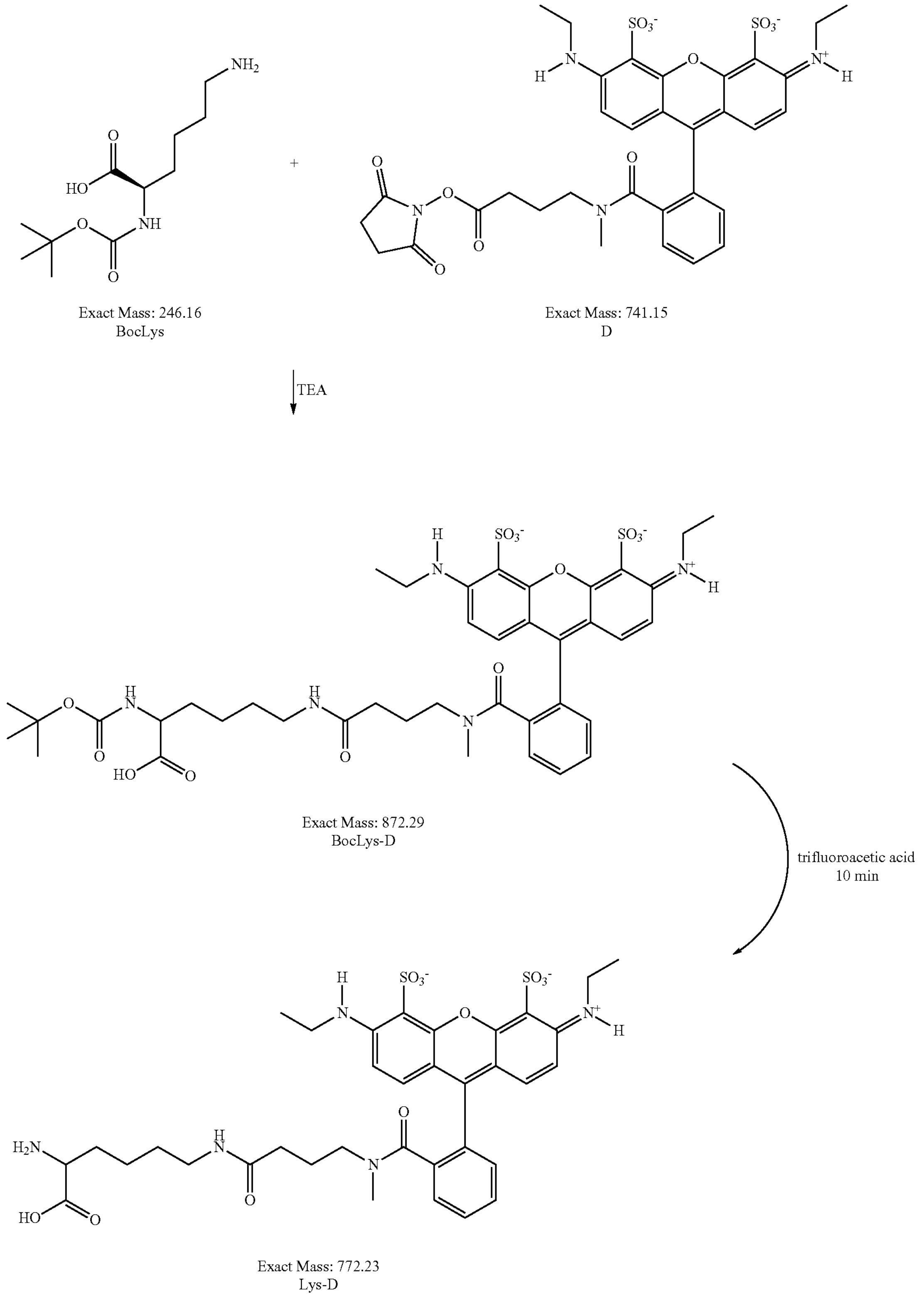

Scheme 43: Synthesis of compound Lys_D. Compound D (donor dye) was coupled to compound BocLys (commercially available) with TEA in DMF to yield compound BocLys-D, which was purified by reverse phase HPLC eluting with acetonitrile and 50 mM TEAB. Product fractions were dried down, desalted with MeOH, and dried by vacuum pump. Dry compound BocLys-D was deprotected with TFA to yield compound Lys-D, which was purified by reverse phase HPLC eluting with acetonitrile and 50 mM TEAB, dried, and desalted with MeOH. Formation of compounds BocLys-D and Lys-D was confirmed by LCMS (expected=observed m/z).

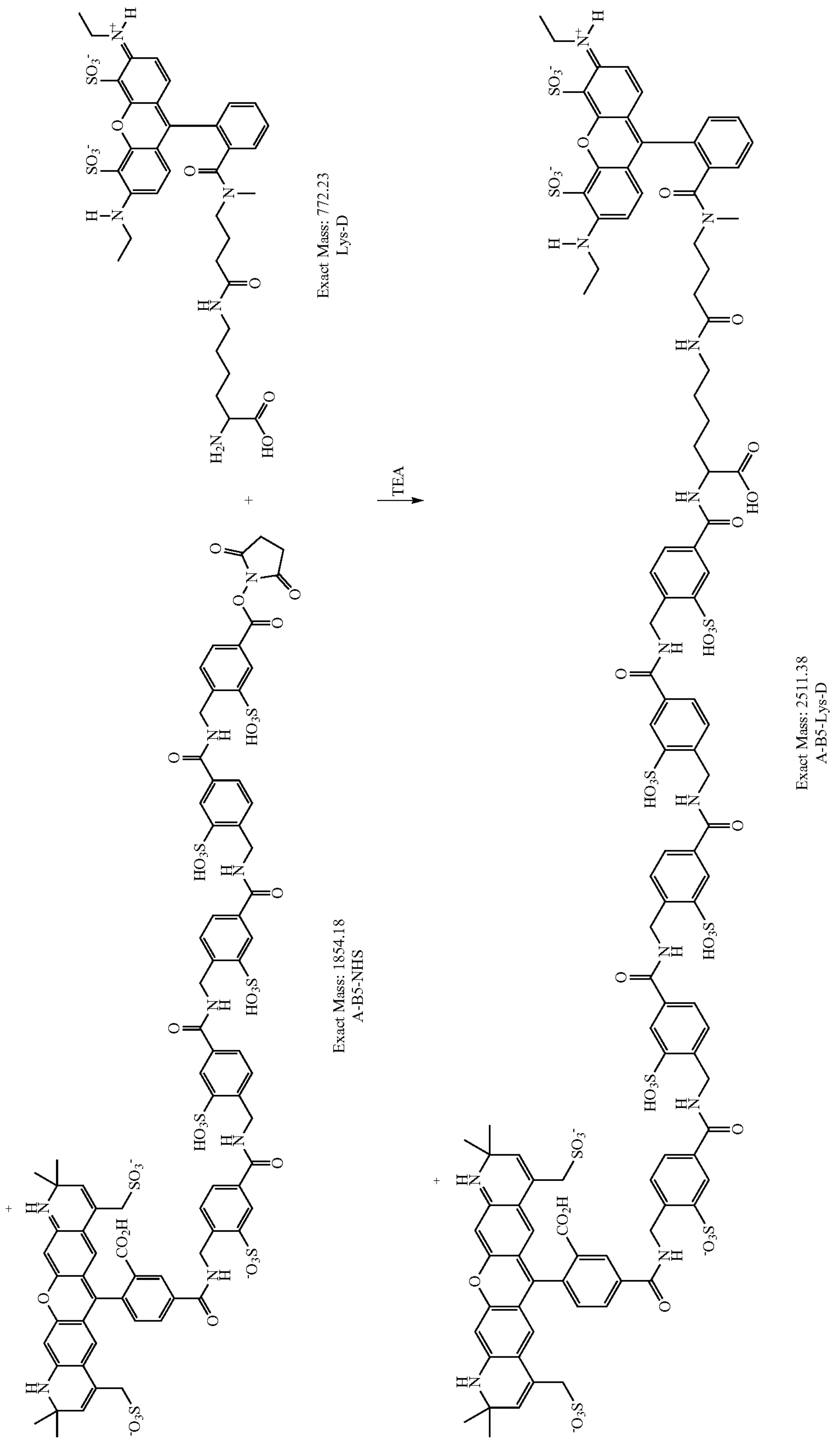
Exact Mass: 772.23
Lys-D
Exact Mass: 1854.18
A-B5-NHS
TEA
Exact Mass: 2511.38
A-B5-Lys-D Scheme 44. Synthesis of compound A-B5-Lys-D. Compound A-B5-NHS was couple to compound Lys-D with TEA in DMF to yield compound A-B5-Lys-D (FRET dye), which was purified by reverse phase HPLC eluting with acetonitrile and 50 mM TEAB. Formation of compound A-B5-Lys-D was confirmed by LCMS (expected=observed m/2z). Product fractions were dried down and desalted with MeOH.

Example 6. Photoswitchable Sequencing

Presented herein is a super-resolution microscopy technique for use in sequencing which utilizes modified nucleotides containing a dye and a photoswitchable moiety (e.g., a photoswitchable quencher or photoswitchable fluorophore). Photoswitchable moieties are compounds that can be switched from a dark to emissive state useful in improving spatial resolution (e.g., as described in Vaughan et al., FEBS Letters 588 (2014) 3603-3612). Photoswitchable moieties switch reversibly between states with distinct absorption spectra upon illumination by light of suitable wavelength and intensity, for example see Schemes 45 and 46. The photogenerated species typically revert back to the starting species by either thermal means or additional illumination.

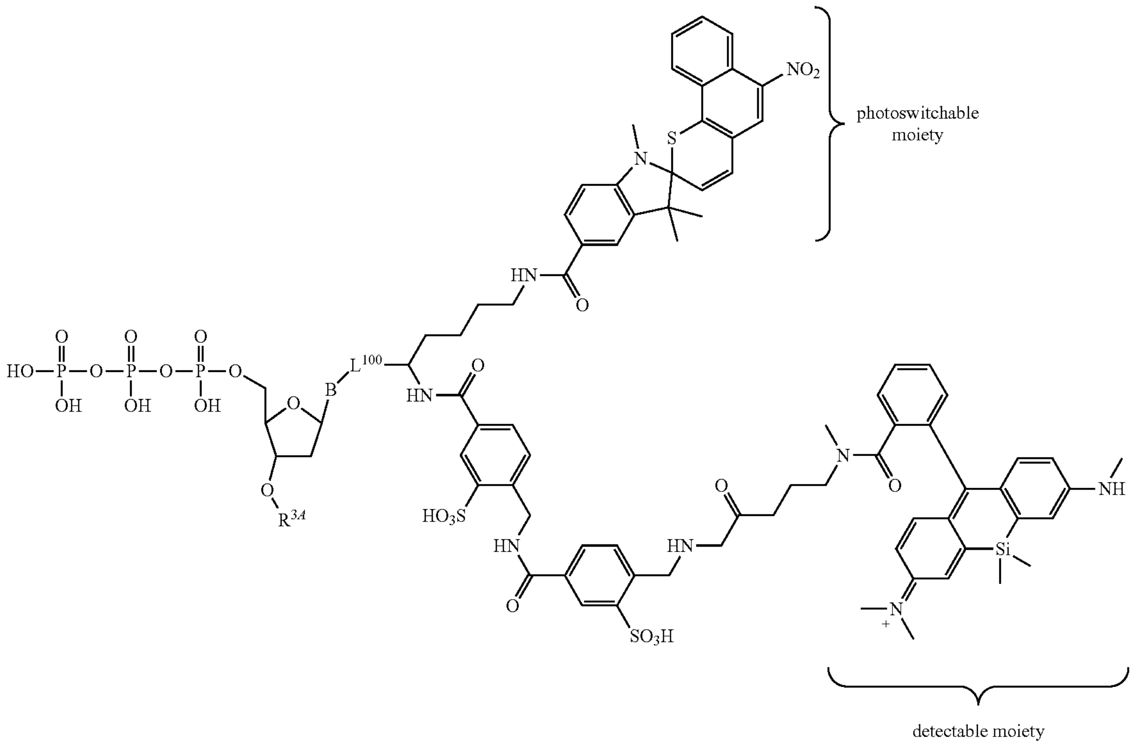

Scheme 45. Photoswitchable mechanism: Fluorescent nucleotide.

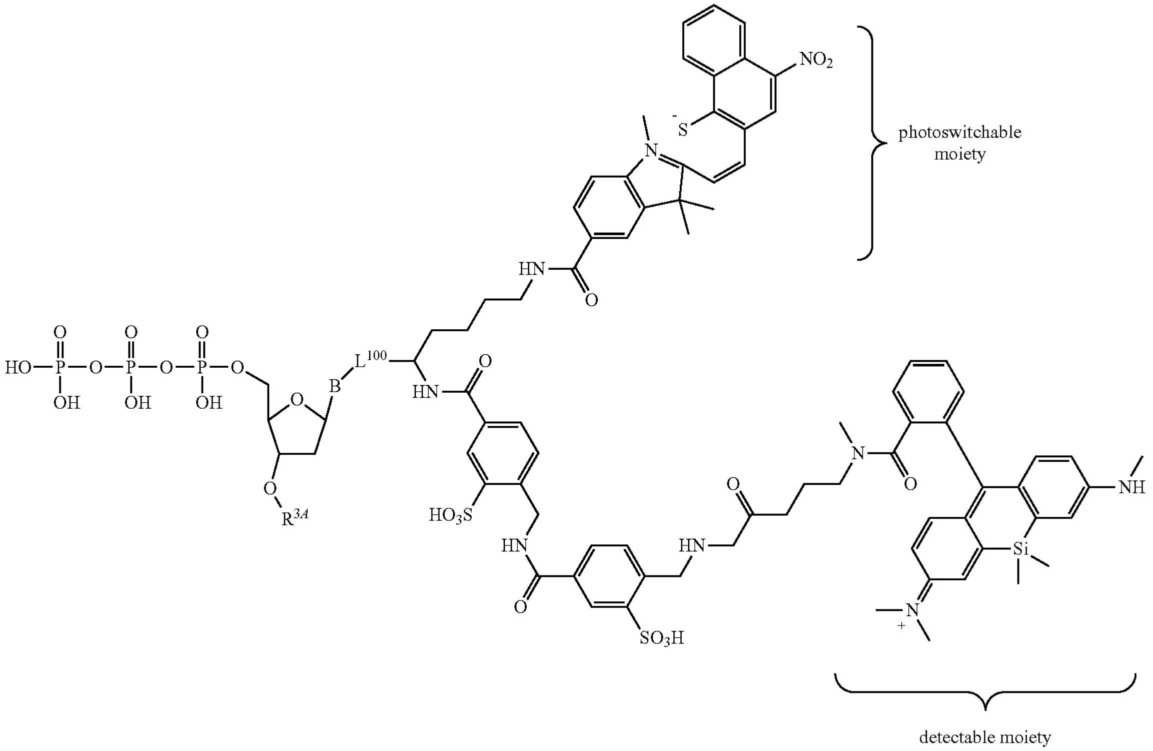

Scheme 46. Photoswitchable mechanism: Non-fluorescent nucleotide. Upon exposure to blue light (e.g., an illumination source emitting radiation at 405 nm), the photoswitchable moiety reversibly isomerizes, opens the ring, to quench the fluorescence from the detectable moiety. The photoswitchable moiety can revert back to the structure depicted in Scheme 45 upon exposure to an appropriate excitation energy (e.g., about 630 nm) or can thermally relax.

Single-molecule localization microscopy (SMLM) bypasses the lateral resolution limit by the separation of fluorescence emission of fluorophores closer than the diffraction limit in time and their accurate localization. For this purpose, photoactivatable or photoswitchable fluorophores are used, thus enabling the reconstruction of high-resolution images. Two concepts that rely on photoswitching or photoactivation are direct stochastic optical reconstruction microscopy (dSTORM) and photoactivated localization microscopy (PALM). dSTORM relies on switching fluorophores between a dark and a bright state to enable temporal separation of nearby fluorophores (see for example, Heilemann M. et al. Angew. Chem. Int. Ed. 2008, 47, 6172-76). Conventional synthetic fluorophores (i.e. commercially available, for example as antibody conjugates) operate as photoswitches in the presence of reducing buffers. The dSTORM method exploits the fact that most fluorophores are prone to reduction through suitable reagents that have a matching redox potential, and by that transit into a long-lived, non-fluorescent radical or other reduced state. One drawback of dSTORM is that is requires defined chemical buffers for imaging, as well as substantial laser power to ensure effective transition of the photoswitchable fluorophores into a dark state. In contrast to dSTORM, PALM was originally conceived with intrinsically photomodulatable fluorescent proteins, without the need of chemical buffers (Betzig E. et al. Science 2006, 313(5793): 1642-45). PALM has the advantage that stoichiometric labeling through co-expression of fluorescent proteins is accessible. The drawback is their lower quantum yield compared to organic dyes, which leads to a lower localization accuracy. Common fluorescent proteins for PALM imaging are mEos, PAmCherry, Dronpa and others.

Both dSTORM and PALM have been used primarily for subcellular localization of organelles, such as microtubules, live-cell imaging and tracking of exogenously-expressed proteins, and in studying the intracellular organization of cells. In the field of in situ spatial transcriptomics, one constraint is that the resolving power becomes limited when the RNA transcript (or protein) density is too high in each voxel (optically resolved volume of a sample). For example, an imaging system with a 0.8 NA objective, the maximum resolving power is 0.5 μm×0.5 μm×1.33 μm. Recent measurements determined that typical RNA transcript density in a cell is about 100 RNA transcripts/$m^3$. Using the imaging system with an 0.8 NA objective results in an about 30 RNA molecules (or proteins) detected in a voxel. Given this limitation, there is a need for higher resolution techniques that can increase the number of transcripts that can be accurately detected, especially when targeting a region with a dense population of nucleic acids. Disclosed herein are solutions to these and other problems in the art.

The compounds and nucleotides described herein provide a method of super-resolution sequencing which utilizes a nucleotide mixture wherein some of the nucleotides contain a dye and a photoswitchable quencher such that the fluorescence can be extinguished at a defined time. By enabling precise control over the fluorescence of a subset of nucleotides, regions of three-dimensional tissue space can be resolved to a higher degree than conventional methods, increasing the available detection space for overlapping nucleic acids. The photoswitchable quencher nucleotides disclosed herein are also amenable for use in standard sequencing workflows and with typical fluorescent microscopy equipment.

In addition to enhanced spatial resolution, an additional advantage of employing photoswitchable sequencing includes a reduction in cleavage reagent. In typical SBS sequencing, one or more labeled nucleotides and a DNA polymerase are flowed into/through a flow cell that houses an array of clusters. Primer extension of a complementary nucleotide (i.e., a nucleotide complementary to the template within the cluster) causes a labeled nucleotide (e.g., a compound as described herein) to be incorporated can then be detected. A cleavage reagent (e.g., a reducing agent) is delivered to the flow cell (before, during, or after detection occurs) for each cycle. Using photoswitchable moieties makes it possible to suppress the fluorescence of a detectable moiety, effectively suppressing the fluorescence following detection by exciting the photoswitchable moiety with an appropriate wavelength (e.g., 405 nm).

EMBODIMENTS

Embodiment P1. A compound having the formula:

(I)

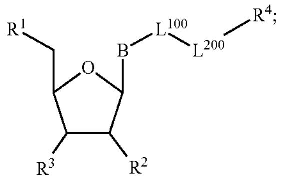

wherein B is a divalent nucleobase; $L^{100}$ is a polymerase-compatible cleavable linker; $L^{200}$ is a rigid spacer; $R^1$ is independently a polyphosphate moiety, monophosphate moiety, 5'-nucleoside protecting group, nucleic acid moiety, hydrogen, or —OH; $R^2$ is independently hydrogen, a —O-polymerase-compatible cleavable moiety, a polymerase-compatible cleavable moiety, or —OH; $R^3$ is independently an —O-polymerase-compatible cleavable moiety, a polymerase-compatible cleavable moiety, hydrogen, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^4$ is an anchor moiety or a detectable moiety.

Embodiment P2. The compound of embodiment P1, wherein $L^{200}$ is a divalent polymer, divalent double-stranded nucleic acid, or divalent polypeptide.

Embodiment P3. The compound of embodiment P2, wherein the divalent polypeptide is divalent polyproline.

Embodiment P4. The compound of embodiment P2, wherein the divalent polypeptide comprises the amino acid sequences $(EAAAK)_{n1}$ (SEQ ID NO:1), $(EP)_{n2}$ (SEQ ID NO:5), $(KP)_{n3}$ (SEQ ID NO:6), $(AP)_{n4}$ (SEQ ID NO:7), or $(TPR)_{n5}$ (SEQ ID NO:8), wherein n1, n2, n3, n4, and n5 are each independently an integer from 2 to 20.

Embodiment P5. The compound of embodiment P2, wherein the divalent polypeptide comprises the amino acid sequences $(EAAAK)_{n1}$ (SEQ ID NO:1), $(EP)_{n2}$ (SEQ ID NO:5), $(KP)_{n3}$ (SEQ ID NO:6), wherein n1, n2, and n3 are each independently an integer from 2 to 6.

Embodiment P6. The compound of embodiment P1, wherein $L^{200}$ has the formula:

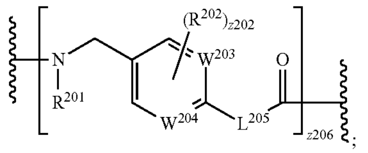

$R^{201}$ is independently hydrogen, $—CCl_3$, $—CBr_3$, $—CF_3$, $—Cl_3$, $—CHCl_2$, $—CHBr_2$, $—CHF_2$, $—CHI_2$, $—CH_2Cl$, $—CH_2Br$, $—CH_2F$, $—CH_2I$, —CN, —OH, —COOH, $—CONH_2$, $—OCCl_3$, $—OCF_3$, $—OCBr_3$, $—OCl_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, or substituted or unsubstituted heteroalkyl; $R^{202}$ is independently halogen, $—CCl_3$, $—CBr_3$, $—CF_3$, $—Cl_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCl_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, $—PO_3H$, $—PO_4H$, $—SO_2Cl$, substituted or unsubstituted alkyl, substituted or unsubstituted heteroalkyl, or $L^{202}$-$R^{202A}$; $L^{202}$ is independently a covalent linker; $R^{202A}$ is independently a detectable moiety, anchor moiety, triplet quencher moiety, or protein moiety;

z202 is independently an integer from 0 to 2; $R^{201}$ and $R^{202}$ may optionally be joined to form a substituted or unsubstituted heterocycloalkyl; $W^{203}$ and $W^{204}$ are independently CH, N, or $C(R^{202})$; $L^{205}$ is independently a bond or $—CH_2NH—$; and z206 is an integer from 1 to 100.

Embodiment P7. The compound of embodiment P6, wherein z206 is an integer from 1 to 20.

Embodiment P8. The compound of embodiment P6, wherein z206 is an integer from 2 to 10.

Embodiment P9. The compound of embodiment P6, wherein z206 is an integer from 5 to 8.

Embodiment P10. The compound of embodiment P6, wherein $L^{200}$ has the formula:

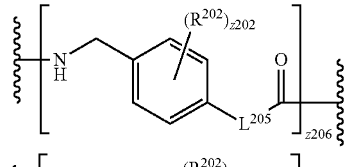

,

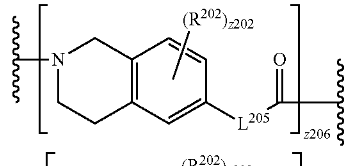

,

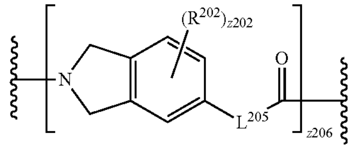

,

-continued
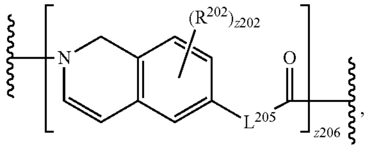
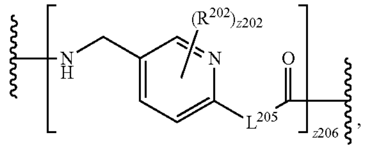
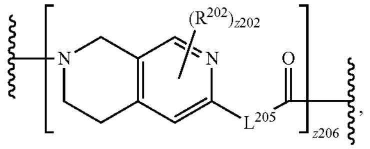
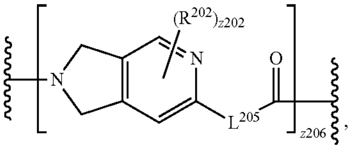
or
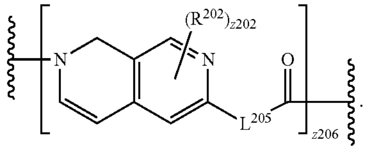
Embodiment P11. The compound of embodiment P6, wherein $L^{200}$ has the formula:
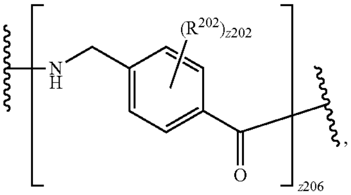
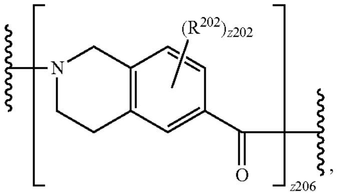
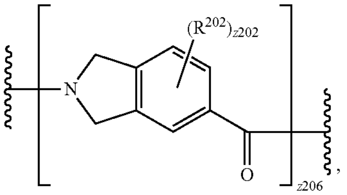
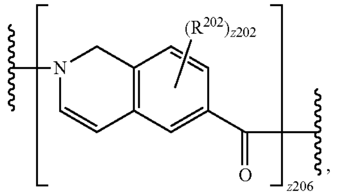
-continued
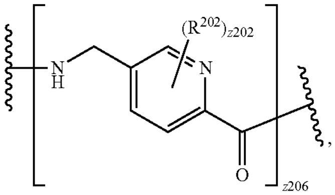
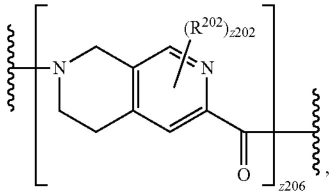
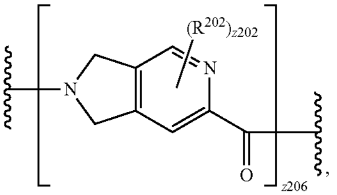
or
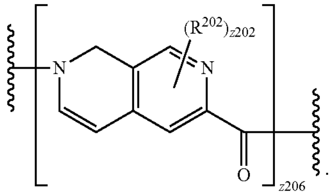
Embodiment P12. The compound of embodiment P6, wherein $L^{200}$ has the formula:
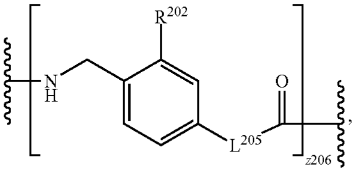
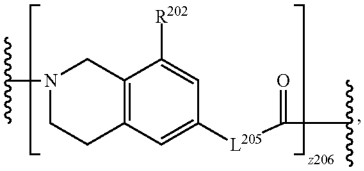
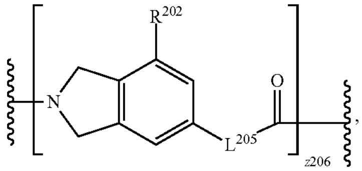
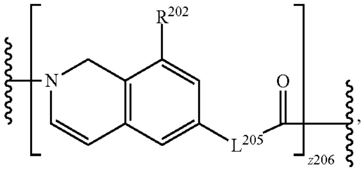

-continued
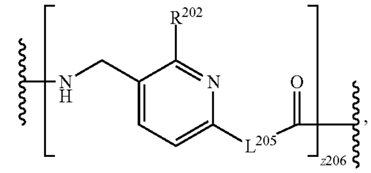
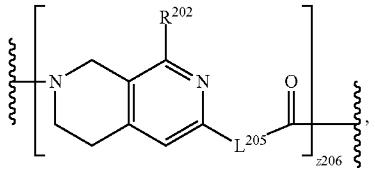
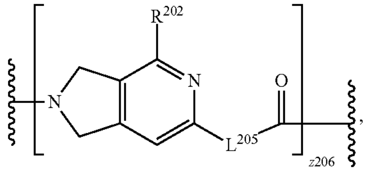
or
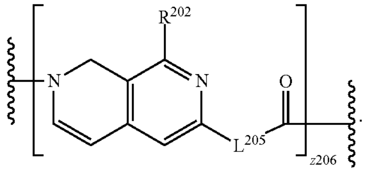
Embodiment P13. The compound of embodiment P6, wherein $L^{200}$ has the formula:
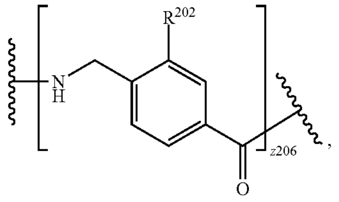
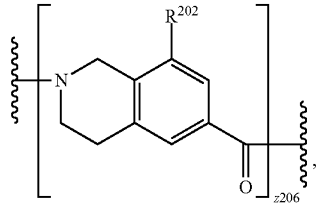
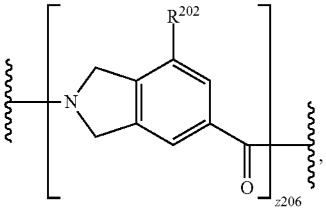
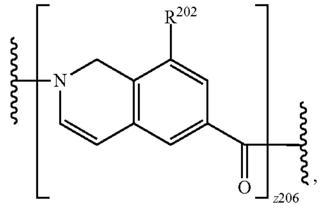
-continued
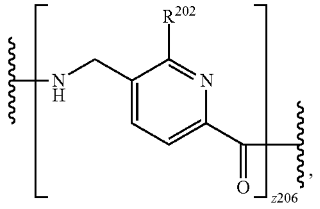
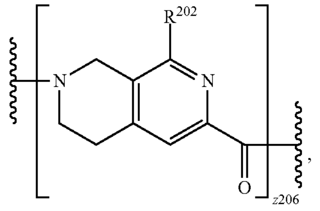
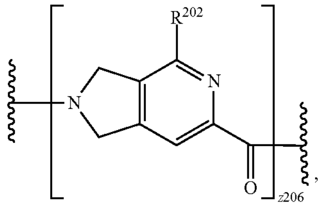
or
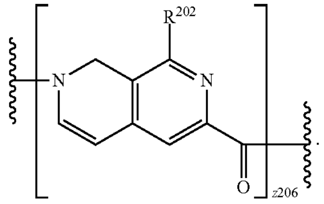
Embodiment P14. The compound of embodiment P6, wherein $L^{200}$ has the formula:
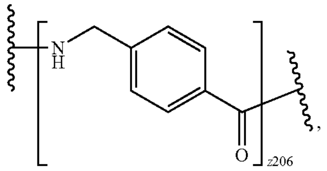
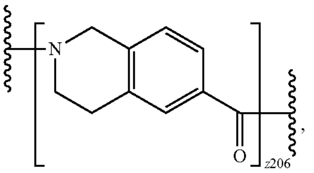
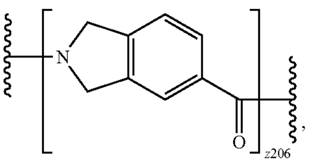
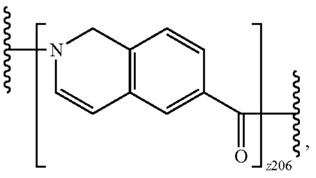

-continued

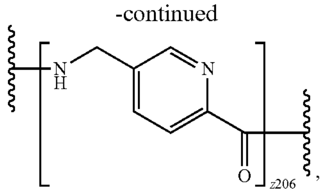

,

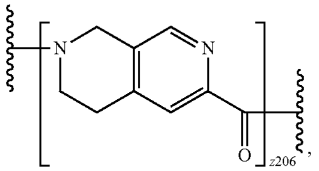

,

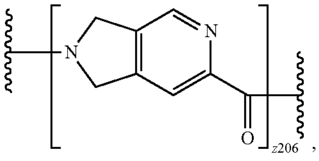

, or

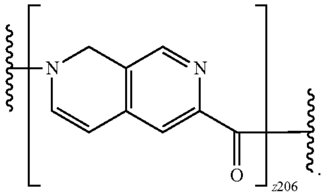

.

Embodiment P15. The compound of embodiment P6, wherein $L^{200}$ has the formula:

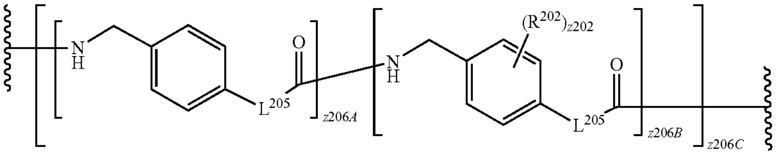

;

wherein z206A is an integer from 1 to 50; z206B is an integer from 1 to 50; and z206C is an integer from 1 to 50.

Embodiment P16. The compound of embodiment P15, wherein z206A is an integer from 1 to 10; z206B is an integer from 1 to 10; and z206C is an integer from 1 to 5.

Embodiment P17. The compound of embodiment P6, wherein $L^{200}$ has the formula:

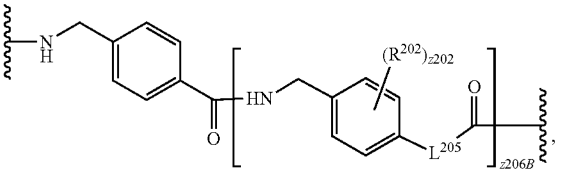

, wherein z206B wherein z206B is an integer from 1 to 20.

Embodiment P18. The compound of embodiment P6, wherein $L^{200}$ has the formula:

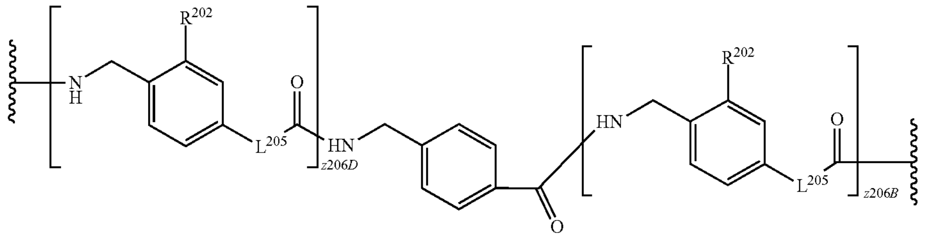

wherein z206B is an integer from 1 to 50 and z206D is an integer from 1 to 50.

Embodiment P19. The compound of embodiment P18, wherein z206B and z206D are each independently an integer from 1 to 10.

Embodiment P20. The compound of embodiment P6, wherein $L^{200}$ has the formula:

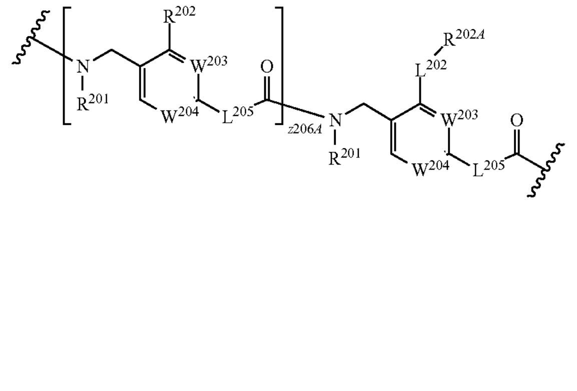

or

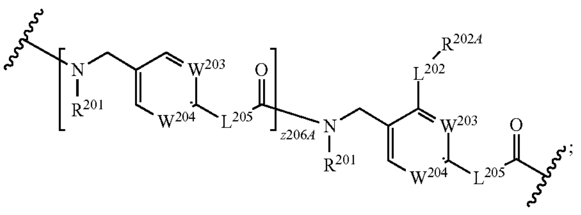

wherein z206A is an integer from 1 to 50.

Embodiment P21. The compound of embodiment P6, wherein $L^{200}$ has the formula:

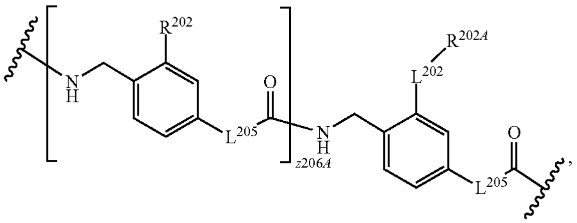

and z206A is an integer from 1 to 10.

Embodiment P22. The compound of embodiment P6, wherein $L^{200}$ has the formula:

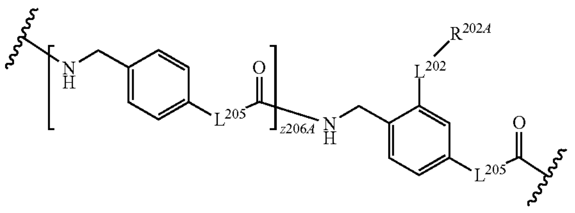

and z206A is an integer from 1 to 10.

Embodiment P23. The compound of embodiment P20 or P21, wherein $R^4$ and $R^{202A}$ are independently detectable moieties.

Embodiment P24. The compound of embodiment P20 or P21, wherein $R^4$ and $R^{202A}$ are a FRET pair of detectable moieties.

Embodiment P25. The compound of embodiment P20 or P21, wherein $R^4$ is a detectable moiety and $R^{202A}$ is a triplet state quencher.

Embodiment P26. The compound of embodiment P25, wherein the triplet state quencher is a monovalent ascorbic acid, monovalent cyclooctatetraene (COT), monovalent nitrobenzyl alcohol, monovalent methyl viologen, monovalent Trolox, or monovalent Trolox-quinone.

Embodiment P27. The compound of any one of Embodiments P6 to P13, or P15 to P26, wherein $R^{202}$ is independently $-SO_3H$, $-SO_4H$, $-SO_2NH_2$, $-PO_3H$, $-PO_4H$, or $-SO_2Cl$.

Embodiment P28. The compound of any one of embodiments P6 to P13, or P15 to P26, wherein $R^{202}$ is independently $-SO_3H$.

Embodiment P29. The compound of one of embodiments P1 to P28, wherein $R^3$ is an —O-polymerase-compatible cleavable moiety.

Embodiment P30. The compound of one of embodiments P1 to P29, wherein the polymerase-compatible cleavable moiety is independently -(substituted or unsubstituted alkylene)-SS-(unsubstituted alkyl).

Embodiment P31. The compound of one of embodiments P1 to P29, wherein the

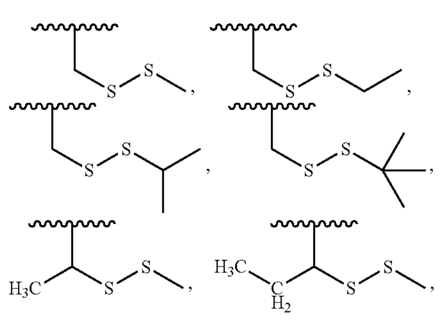

-continued
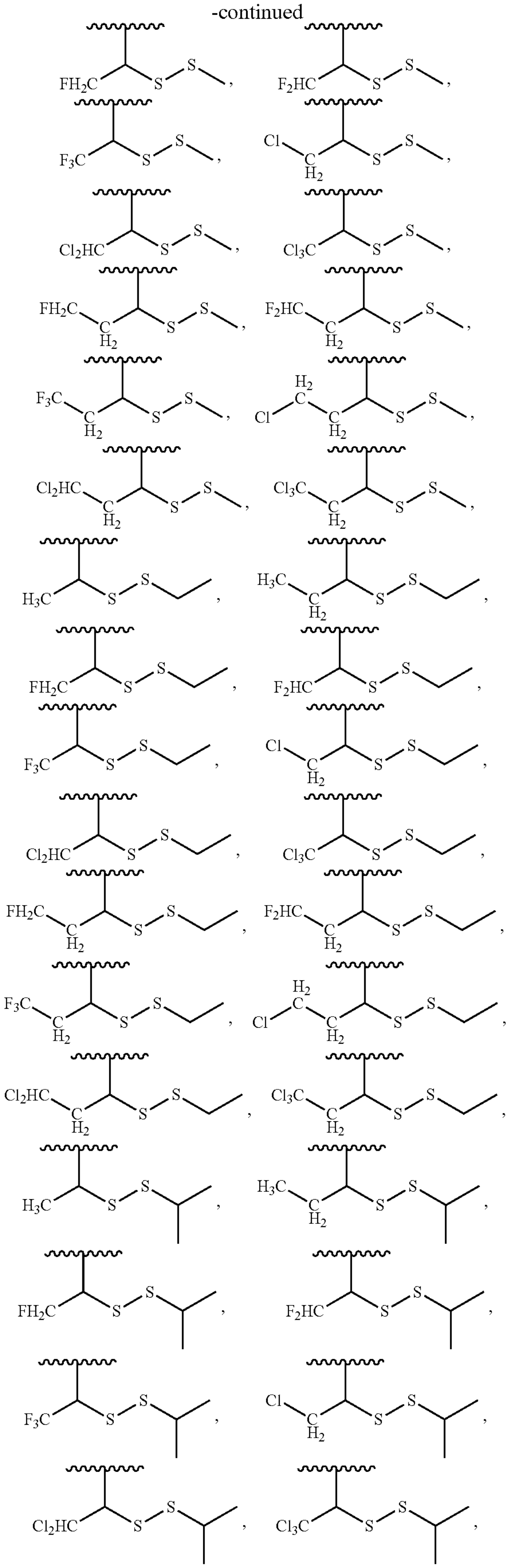
-continued
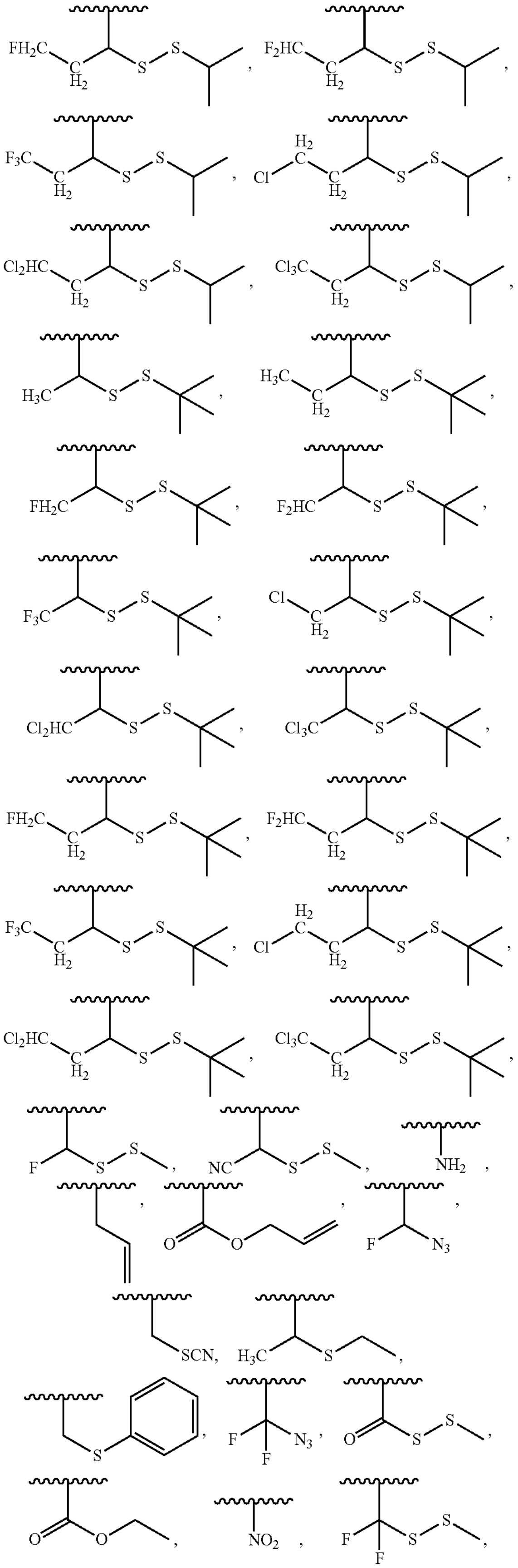

-continued

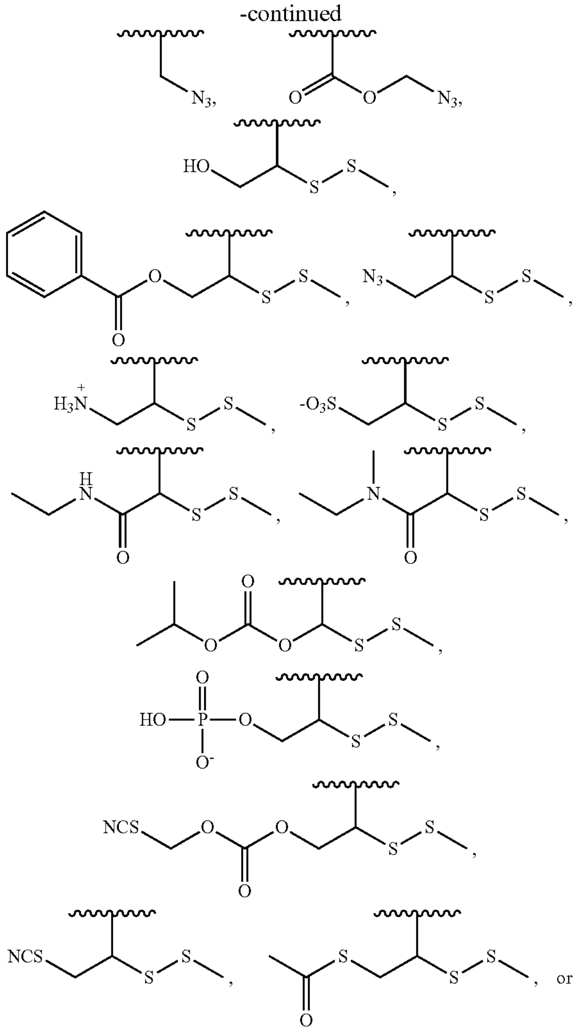

or

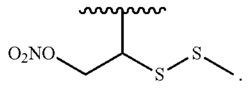

Embodiment P32. The compound of one of embodiments P1 to P29, wherein the polymerase-compatible cleavable moiety is independently:

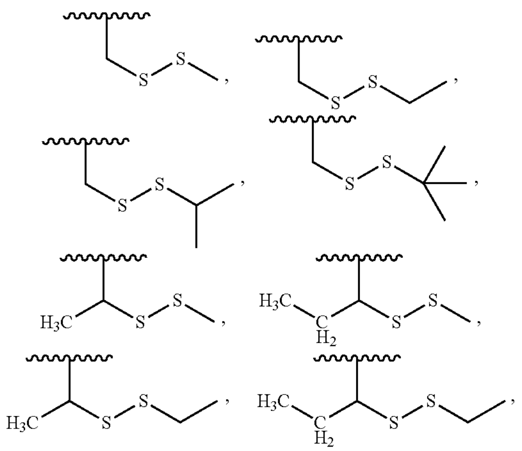

-continued

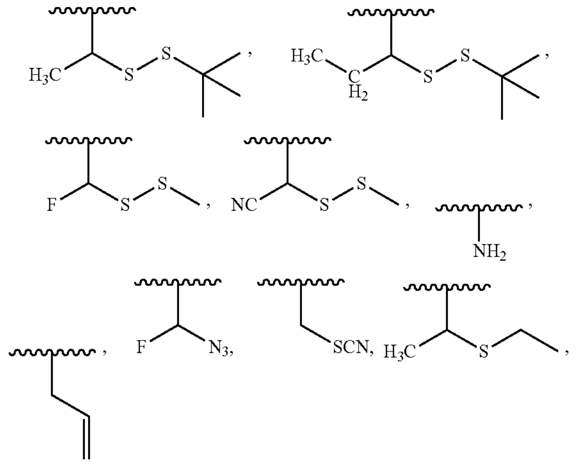

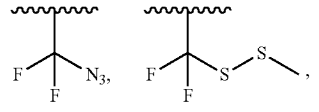

or

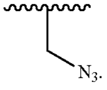

Embodiment P33. The compound of one of embodiments P1 to P32, wherein $R^2$ is hydrogen or —OH.

Embodiment P34. The compound of one of embodiments P1 to P32, wherein $R^2$ is hydrogen.

Embodiment P35. The compound of one of embodiments P1 to P34, having the formula:

(Ia)

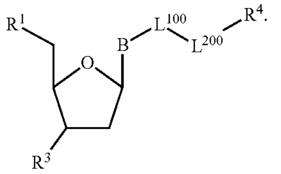

Embodiment P36. The compound of one of embodiments P1 to P35, wherein B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

Embodiment P37. The compound of one of embodiments P1 to P35, wherein B is

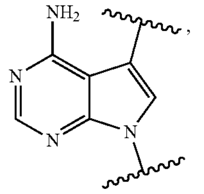

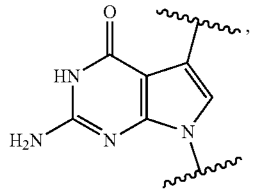

-continued

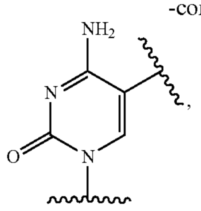

, or

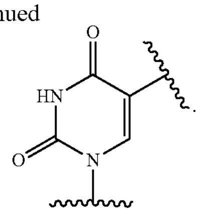

.

Embodiment P38. The compound of one of embodiments P1 to P37, wherein $L^{100}$ is $-L^{101}-L^{102}-L^{103}-L^{104}-L^{105}-$; and $L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, —SS—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, wherein at least one of $L^{101}$, $L^{102}$, $L^{103}$, $L^{104}$, and $L^{105}$ is not a bond.

Embodiment P39. The compound of embodiment P38, wherein $L^{100}$ is $-L^{101}$-O—CH(—$SR^{100}$)-$L^{103}$-$L^{104}$-$L^{105}$-, -$L^{101}$-O—C($CH_3$)(—$SR^{100}$)-$L^{103}$-$L^{104}$-$L^{105}$-, -$L^{101}$-O—CH ($N_3L^{103}$-$L^{104}$-$L^{105}$-, or -$L^{101}$-SS-$L^{103}$-$L^{104}$-$L^{105}$-; $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^{100}$ is —$SR^{102}$ or —CN; and $R^{102}$ is unsubstituted $C_1$-$C_4$ alkyl.

Embodiment P40. The compound of embodiment P38, wherein $L^{100}$ is -$L^{101}$-O—CH(—$SR^{100}$)-$L^{103}$-$L^{104}$-$L^{105}$-, -$L^{101}$-O—C($CH_3$)(—$SR^{100}$)-$L^{103}$-$L^{104}$-$L^{105}$-, -$L^{101}$-O—CH ($N_3$)-$L^{103}$-$L^{104}$-$L^{105}$- or -$L^{101}$-SS-$L^{103}$-$L^{104}$-$L^{105}$-; $L^{101}$ is independently a substituted or unsubstituted $C_1$-$C_4$ alkylene or substituted or unsubstituted 8 to 20 membered heteroalkylene; $L^{103}$ is independently a bond or substituted or unsubstituted 2 to 10 membered heteroalkylene; $L^{104}$ is independently a bond, substituted or unsubstituted 4 to 18 membered heteroalkylene, or substituted or unsubstituted phenylene; $L^{105}$ is independently bond or substituted or unsubstituted 4 to 18 membered heteroalkylene; $R^{100}$ is —$SR^{102}$ or —CN; and $R^{102}$ is unsubstituted $C_1$-$C_4$ alkyl.

Embodiment P41. The compound of embodiment P38, wherein $L^{100}$ is -$L^{101}$-O—CH(—$SR^{100}$)-$L^{103}$-$L^{104}$-$L^{105}$-, -$L^{101}$-O—C($CH_3$)(—$SR^{100}$)-$L^{103}$-$L^{104}$-$L^{105}$-, or -$L^{101}$-O—CH($N_3$)—$CH_2$—O-$L^{104}$-$L^{105}$-; $L^{101}$, $L^{103}$, and $L^{105}$ are independently a bond, —NH—, —O—, —C(O)—, —C(O) NH—, —NHC(O)—, —NHC(O)NH—, —C(O)O—, —OC (O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^{104}$ is unsubstituted phenylene; $R^{100}$ is —$SR^{102}$ or —CN; and $R^{102}$ is unsubstituted $C_1$-$C_4$ alkyl.

Embodiment P42. The compound of embodiment P39, wherein $L^{100}$ is

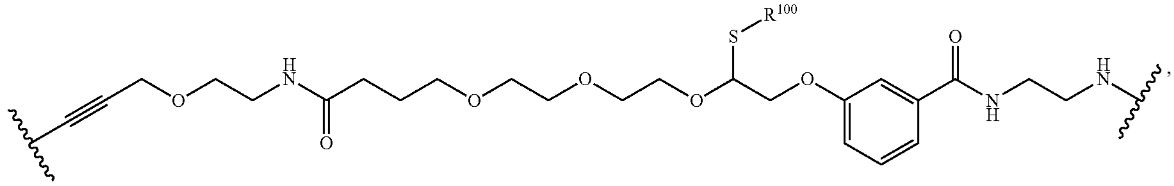

,

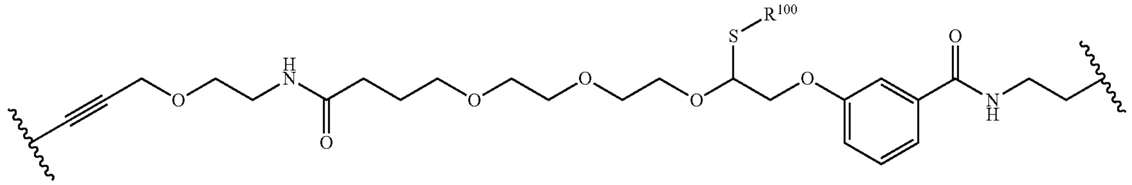

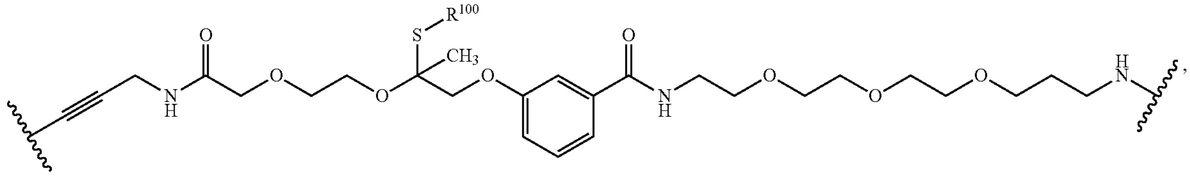

,

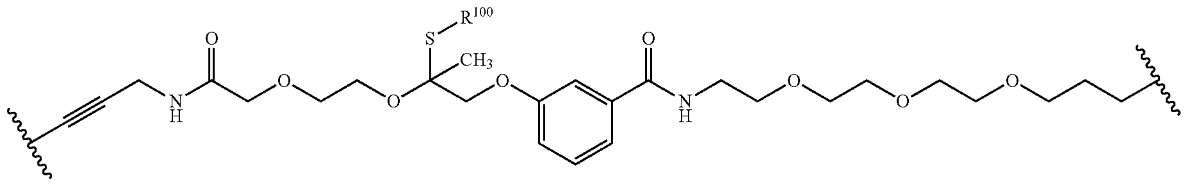

-continued
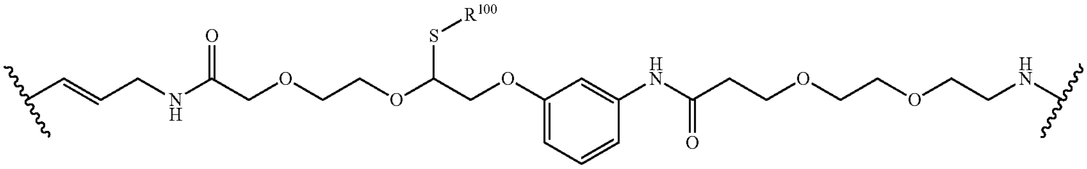,
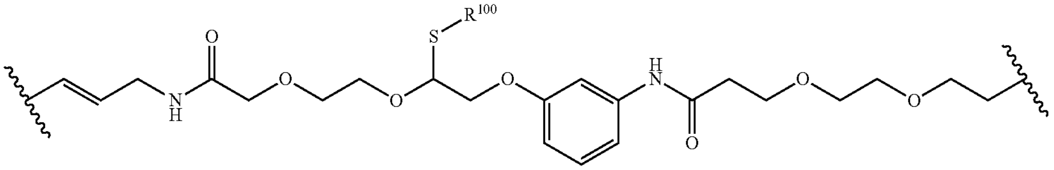
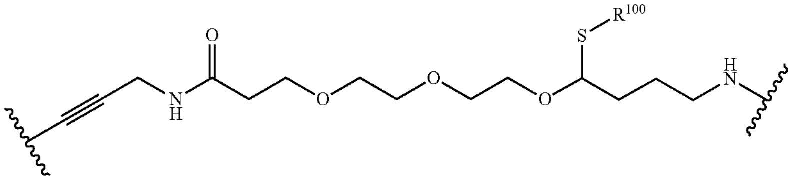,
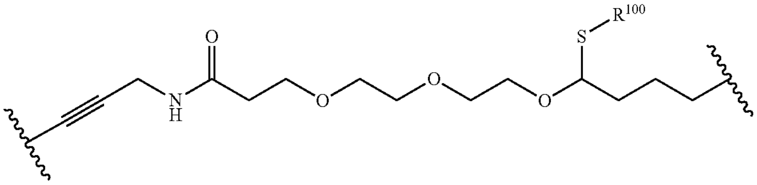,
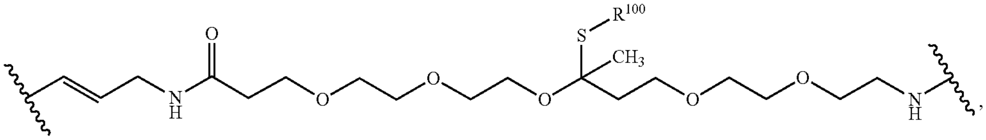,
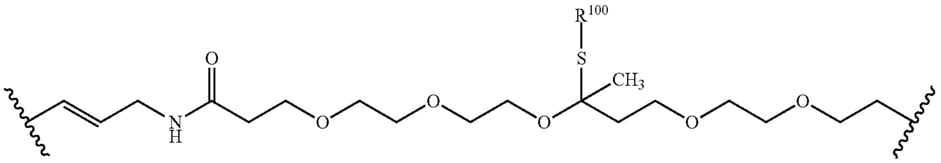,
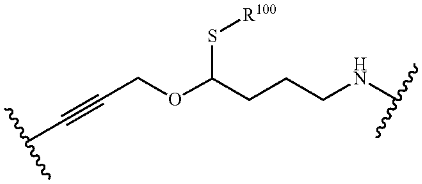, 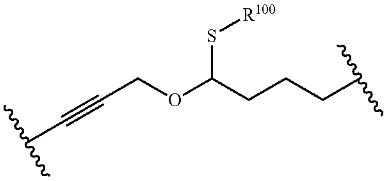,
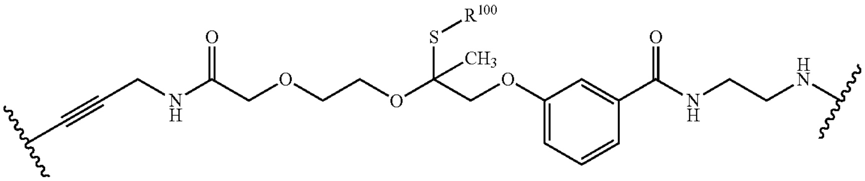,
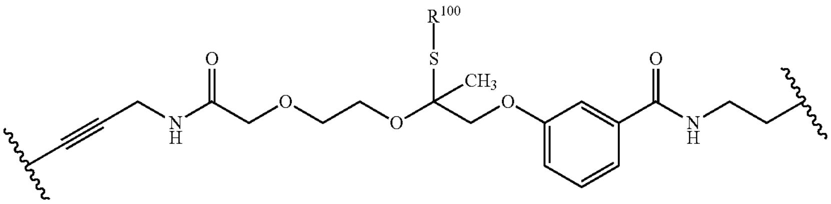, -continued
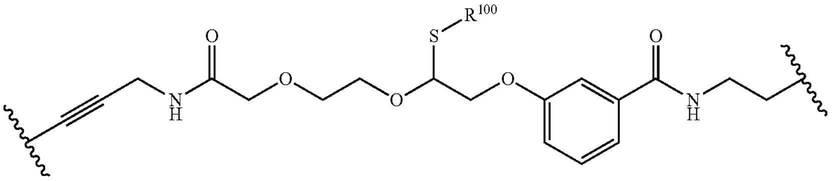
, or
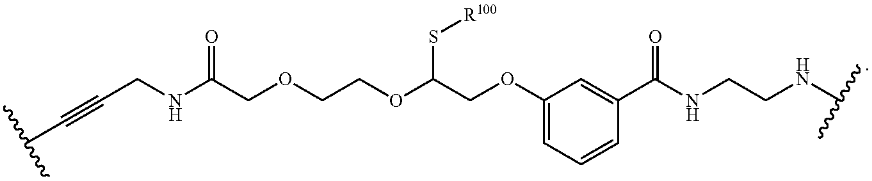
.
Embodiment P43. The compound of embodiment P42, wherein $R^{100}$ is S—$R^{102}$
Embodiment P44. The compound of embodiment P38, wherein $L^{100}$ is
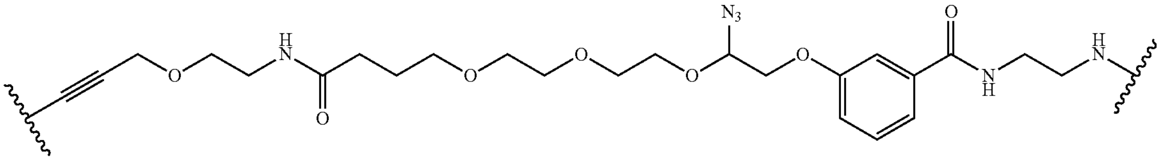
,
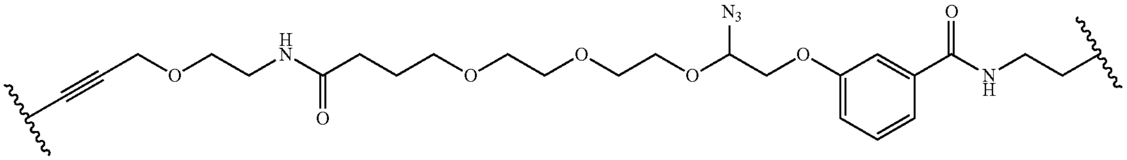
,
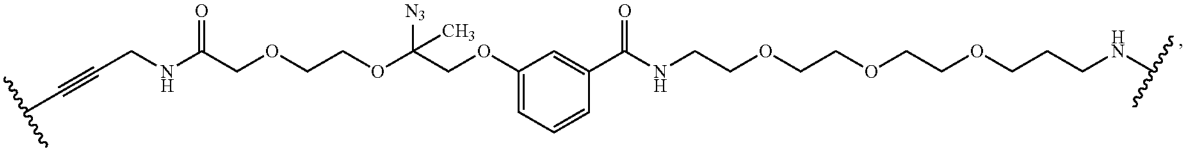
,
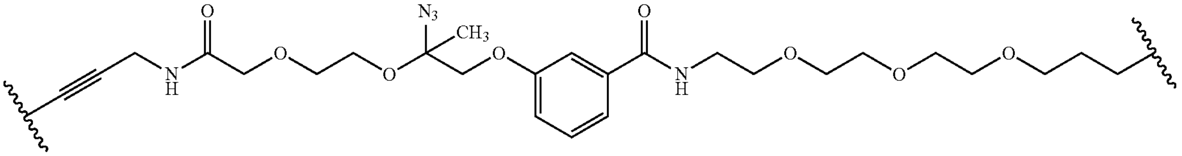
,
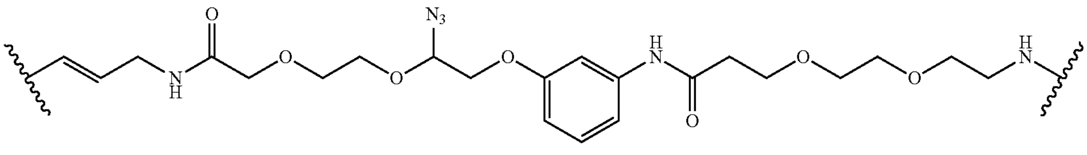
,
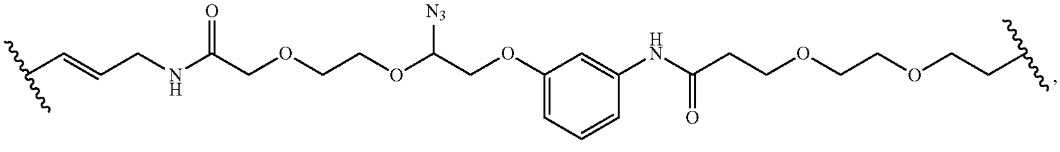
,
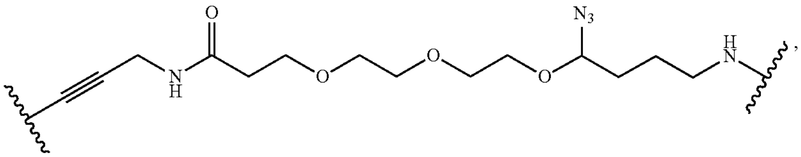
, -continued
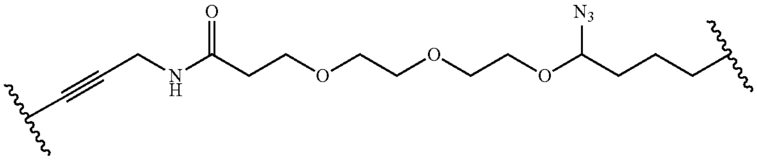
,
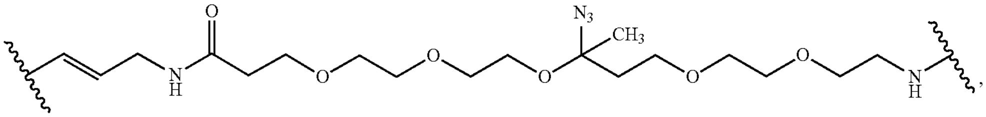
,
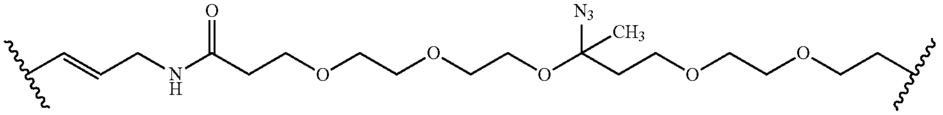
,
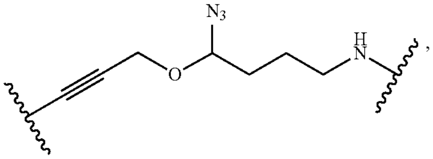
,
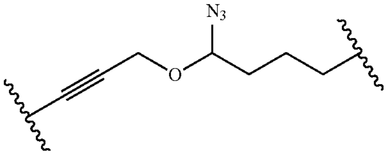
,
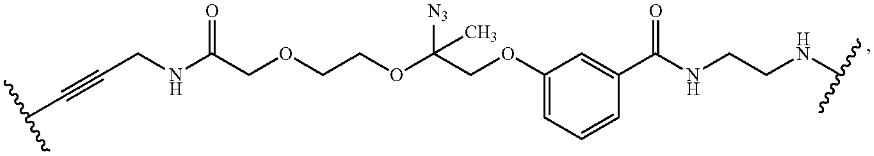
,
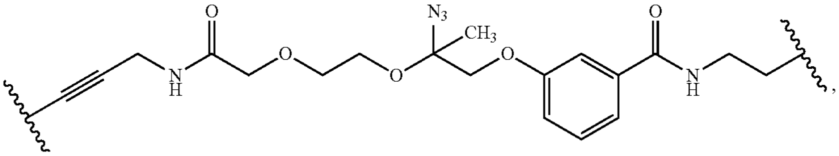
,
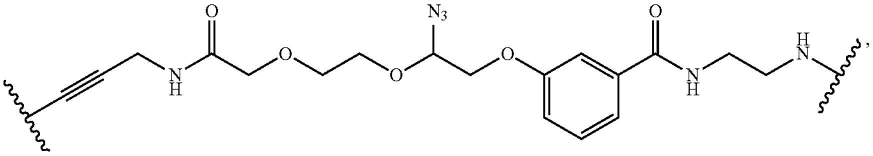
,
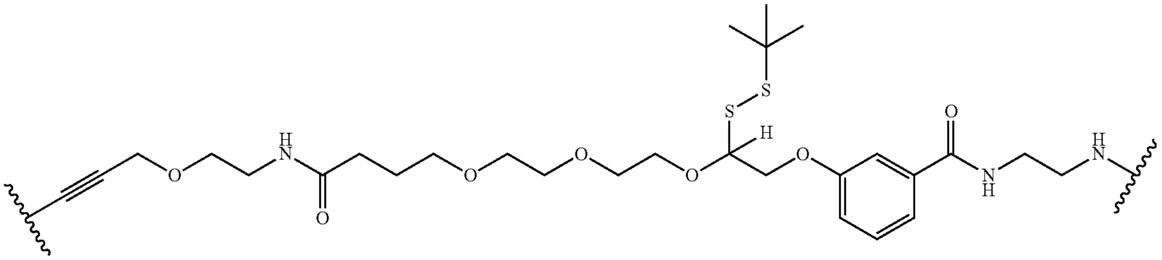
,
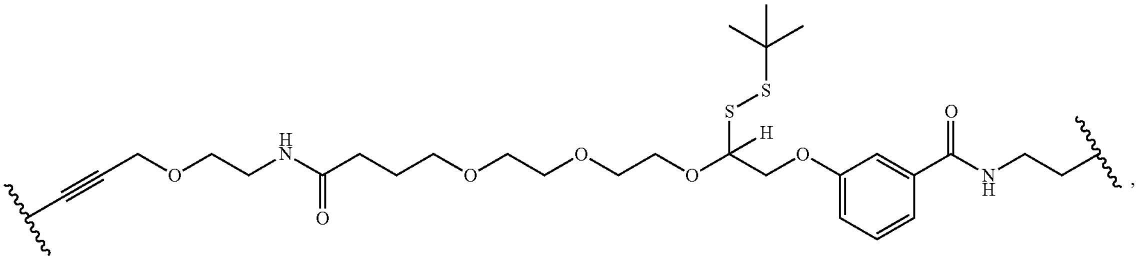
, -continued
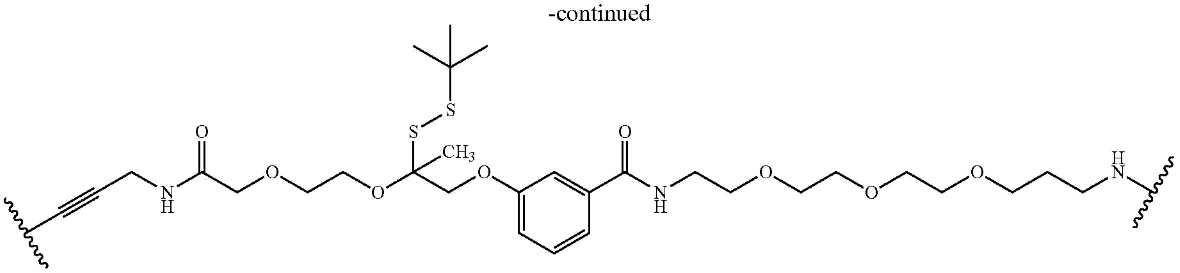,
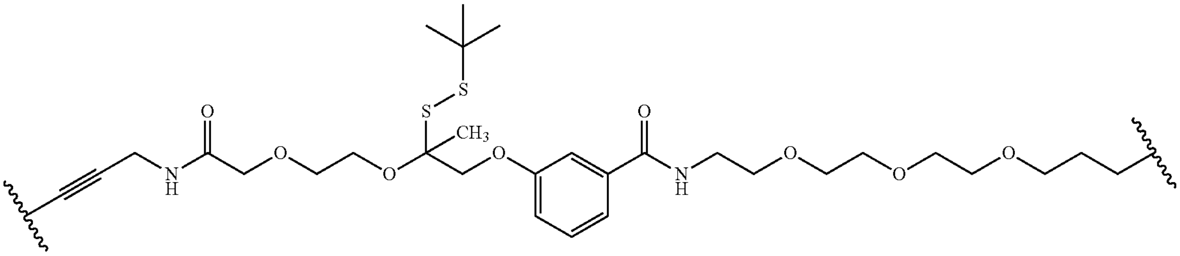,
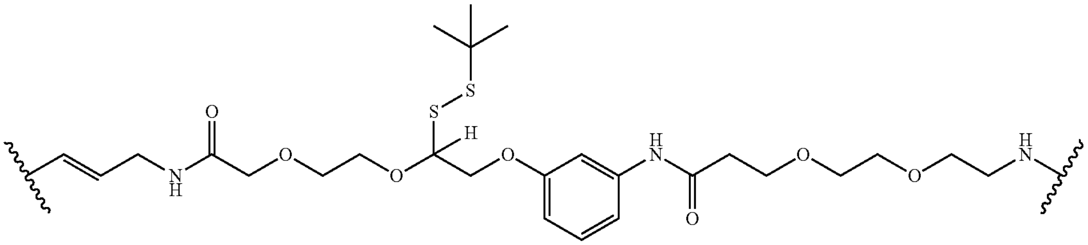,
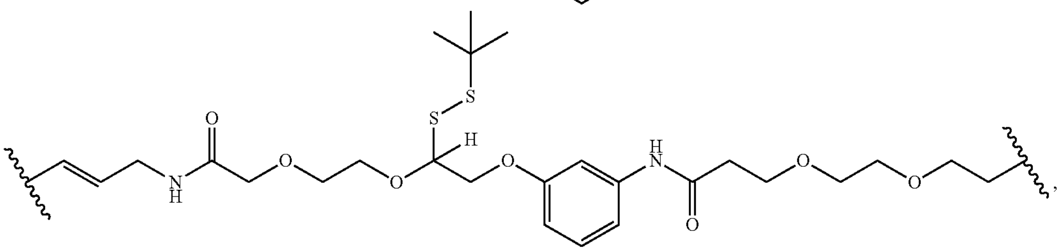,
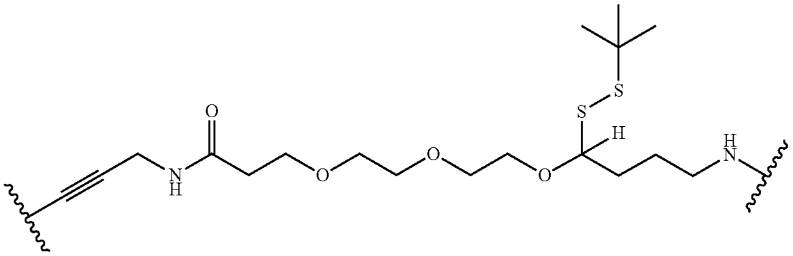,
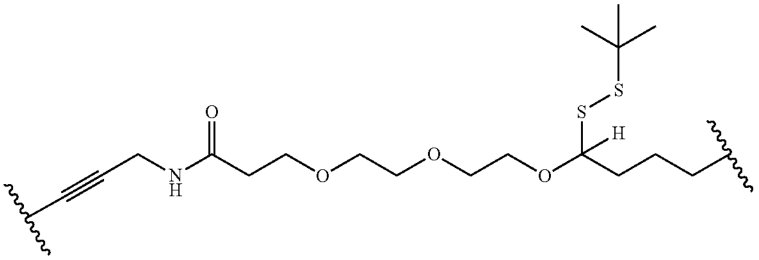,
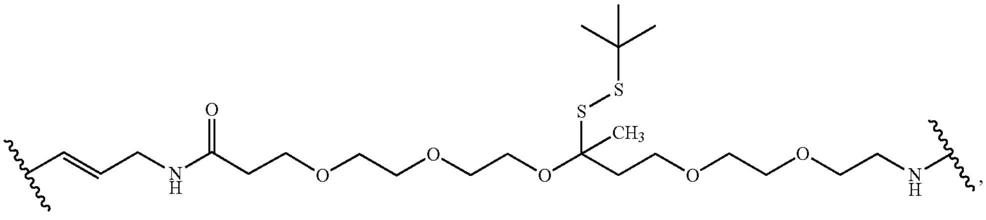, -continued
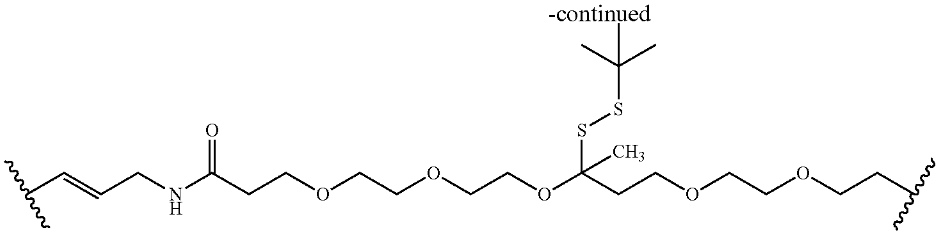
,
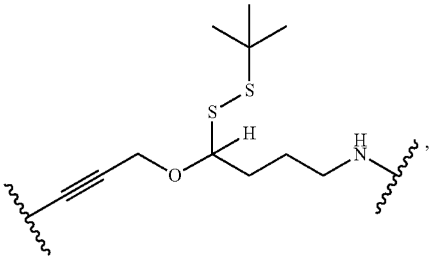
,
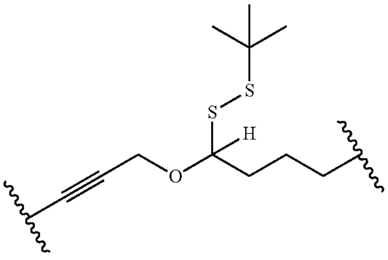
,
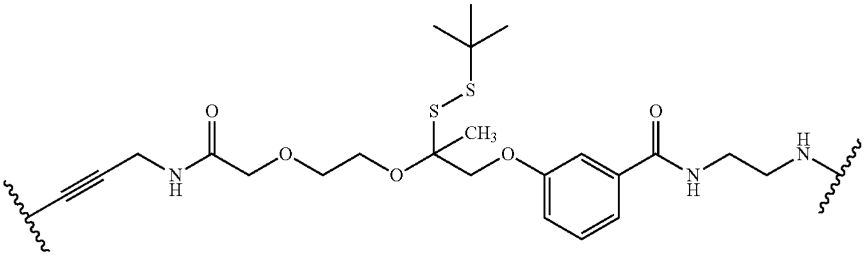
,
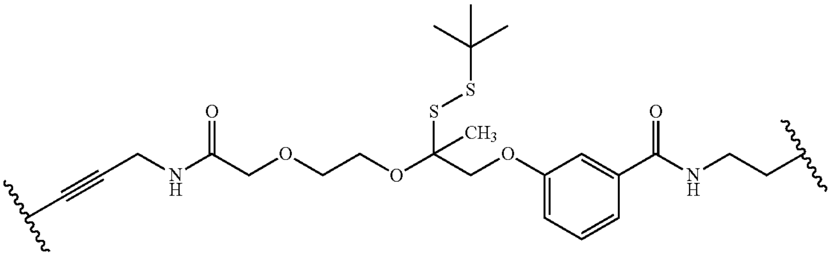
,
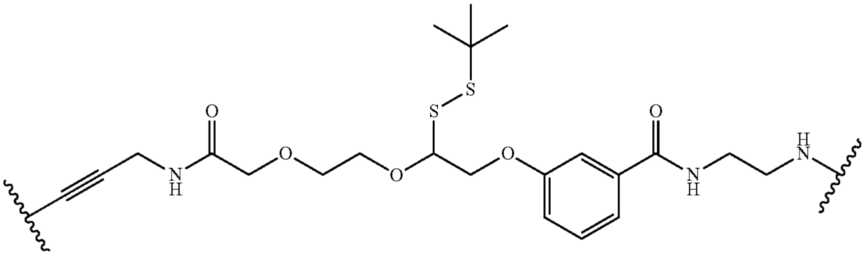
,
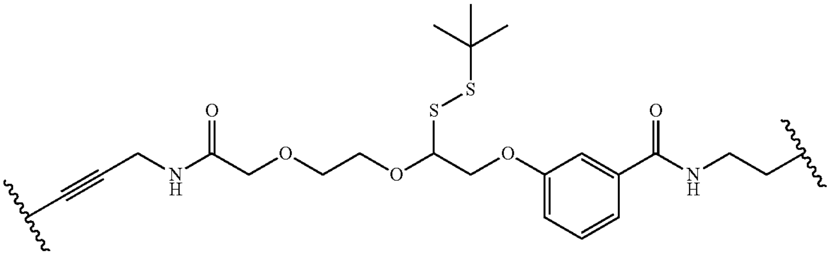
,
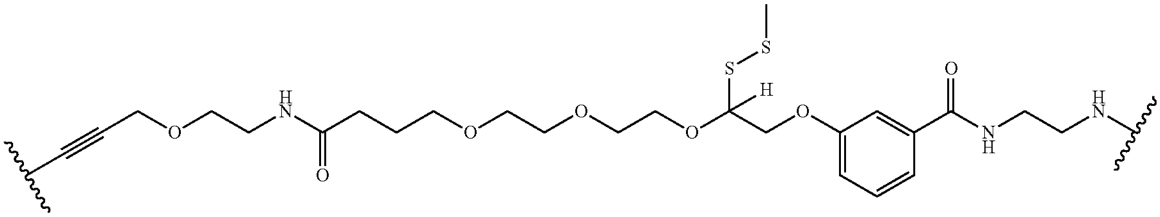
, -continued
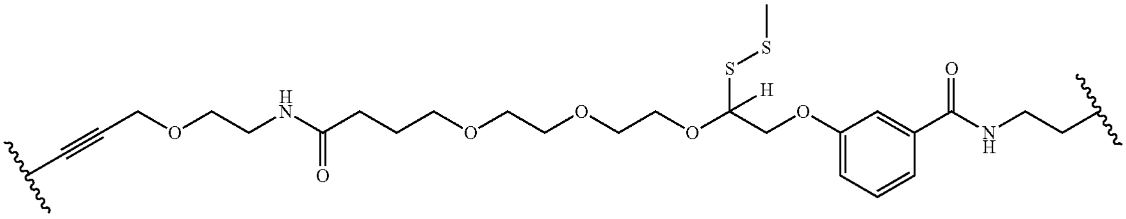
,
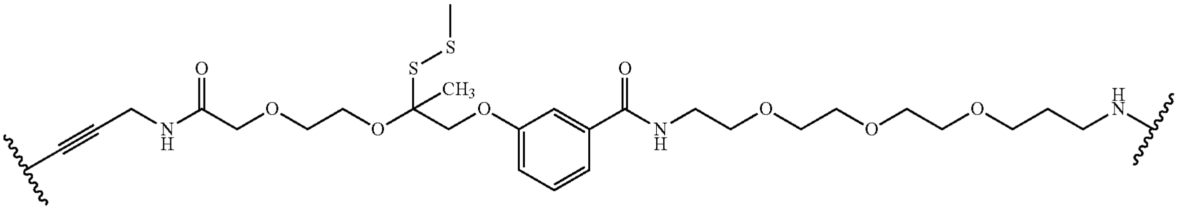
,
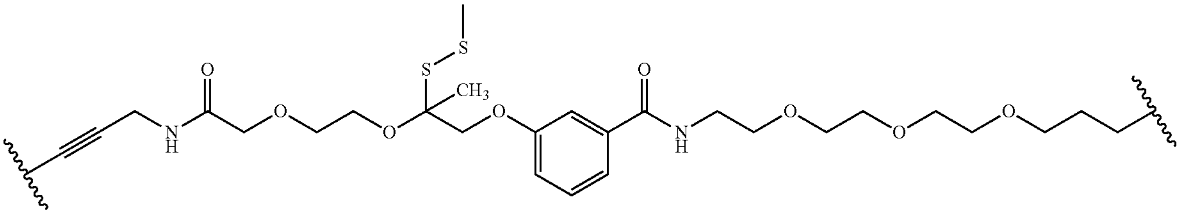
,
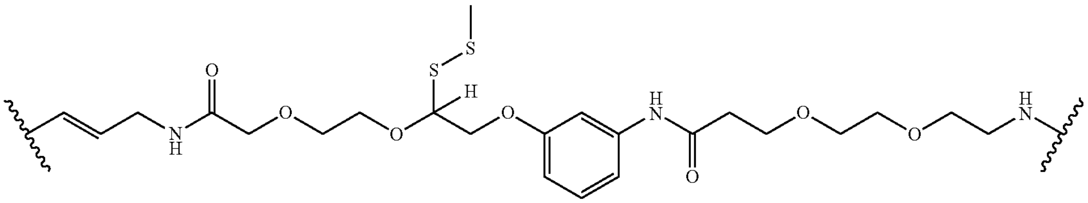
,
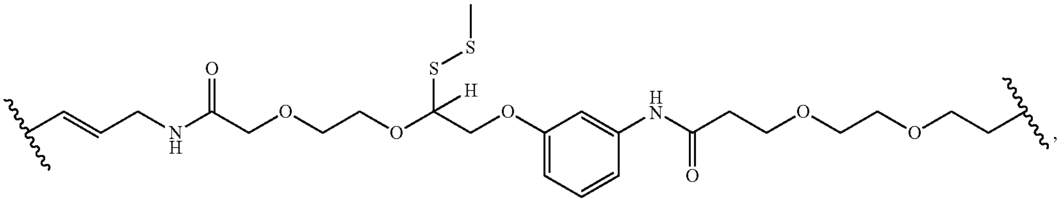
,
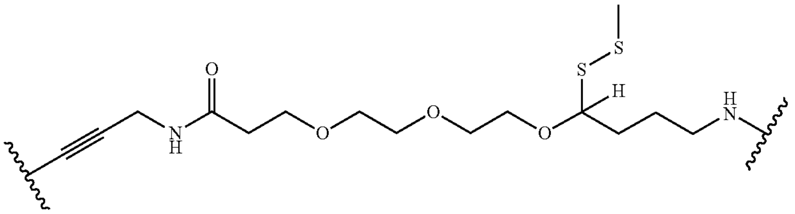
,
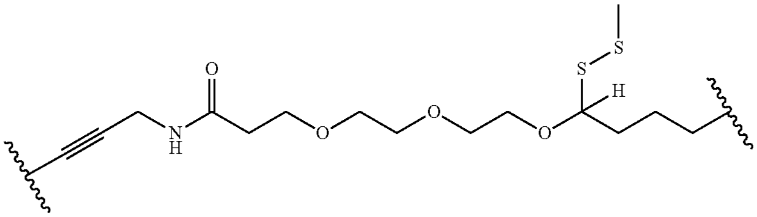
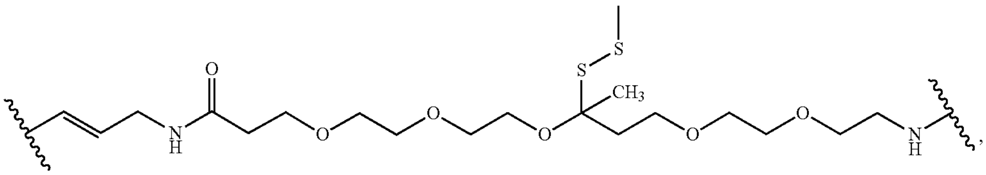
, -continued
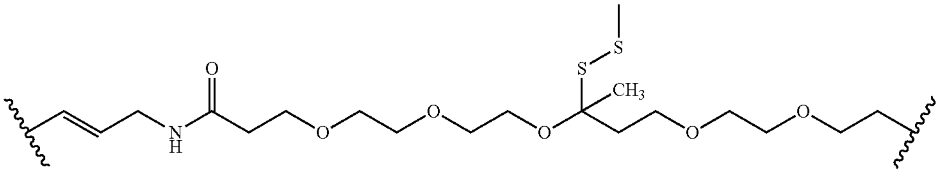,
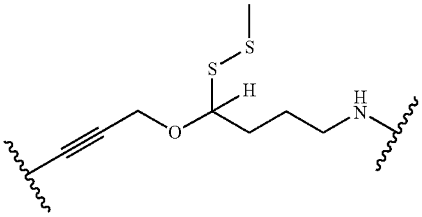,
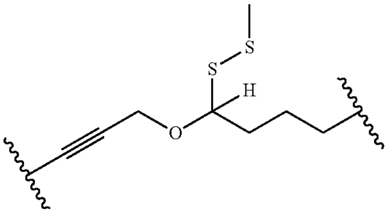,
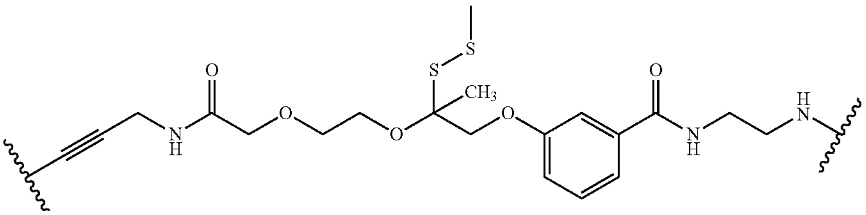,
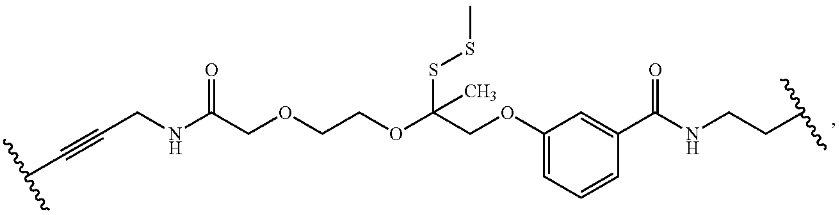,
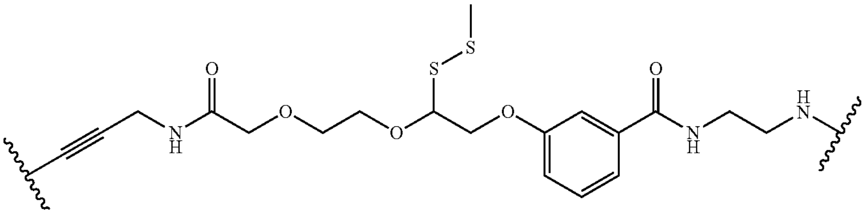,
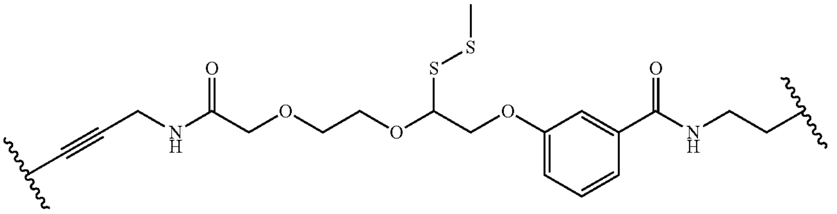
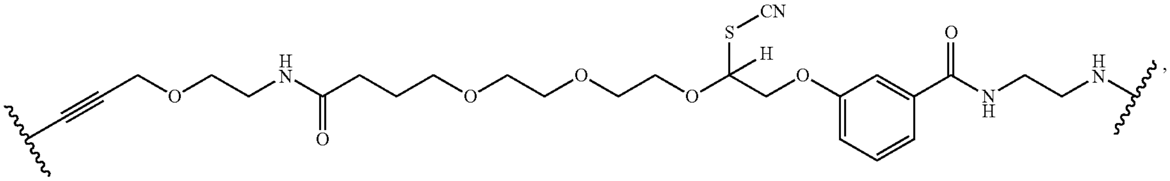,
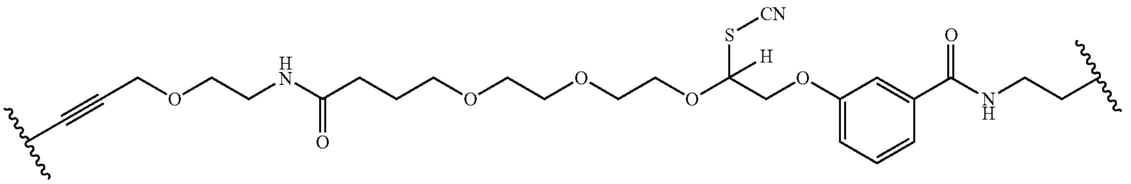, -continued
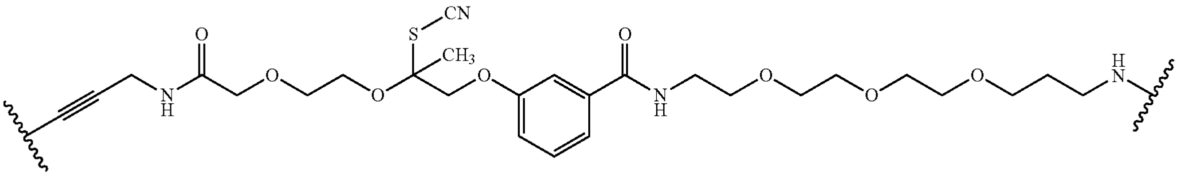
,
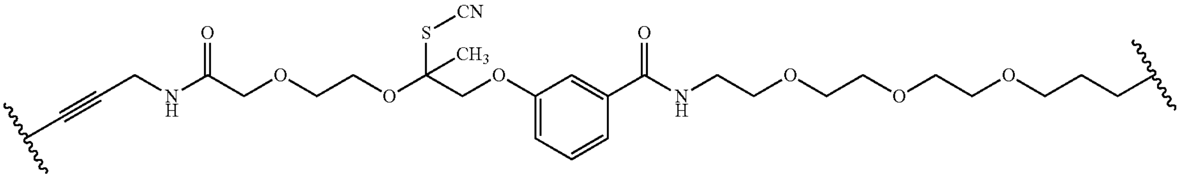
,
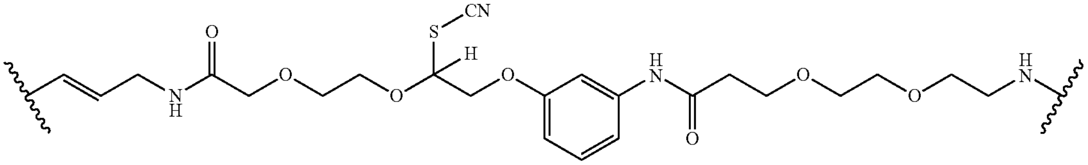
,
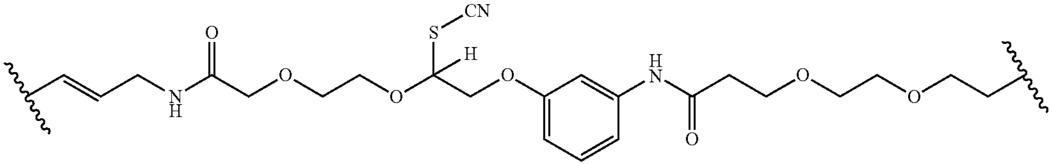
,
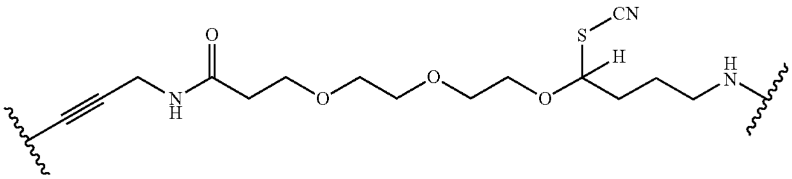
,
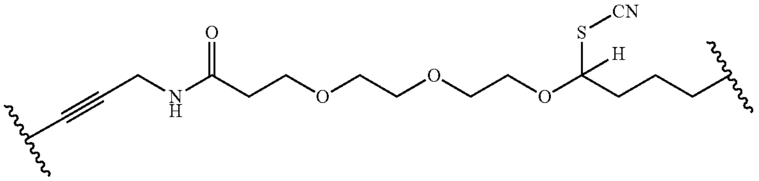
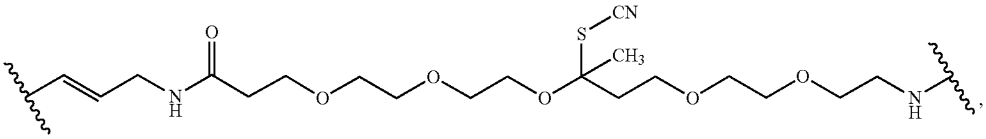
,
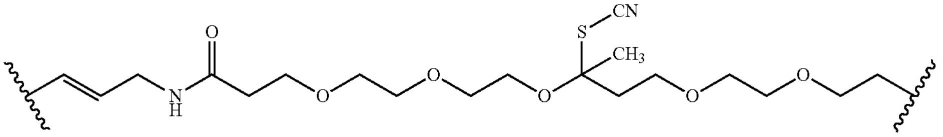
,
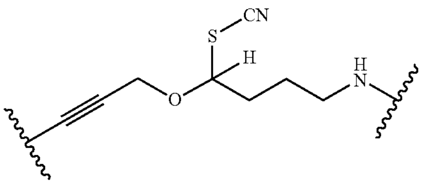
,
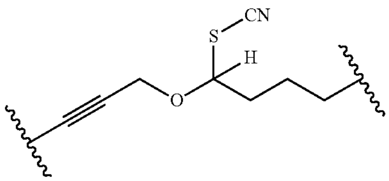
,
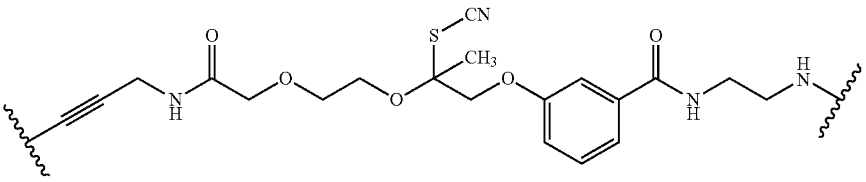
, -continued
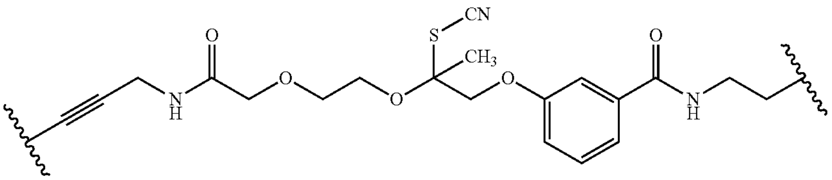
,
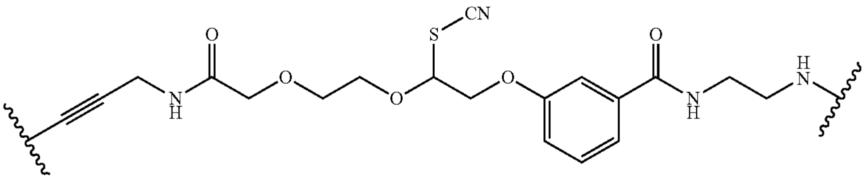
,
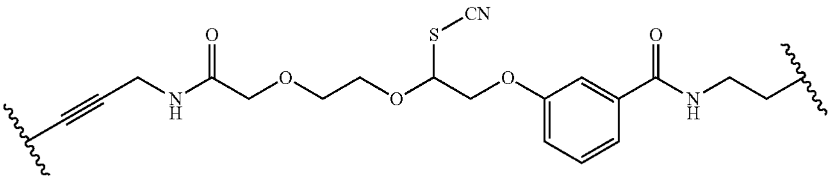
,
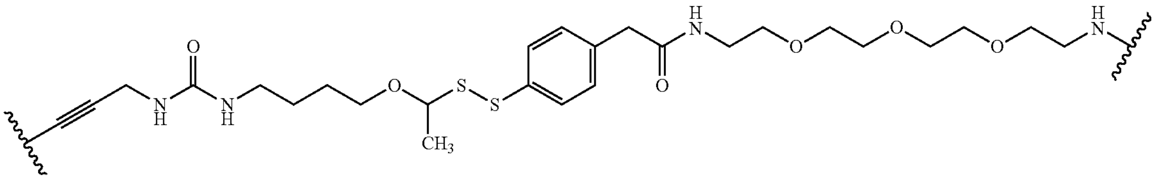
,
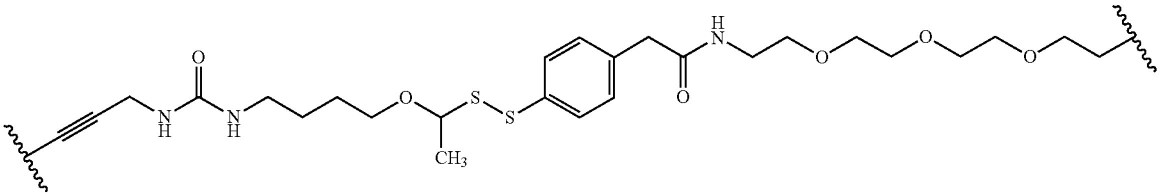
,
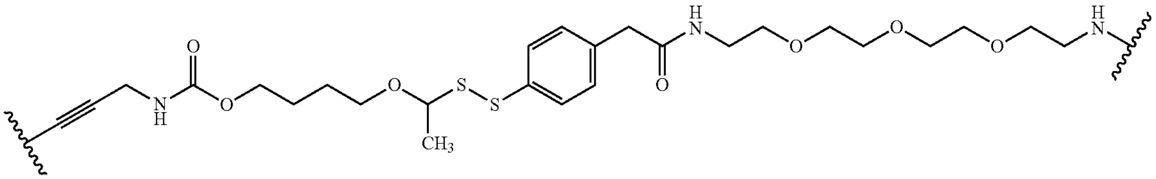
,
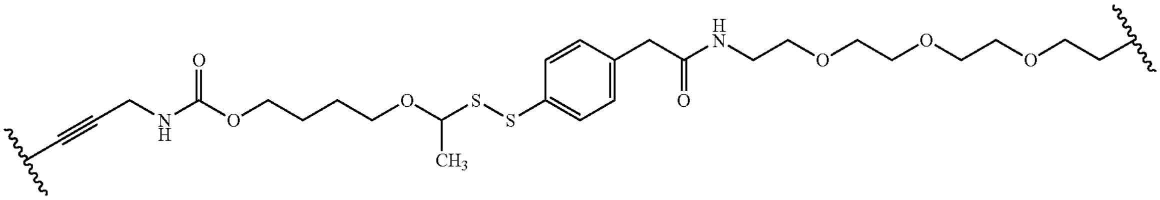
,
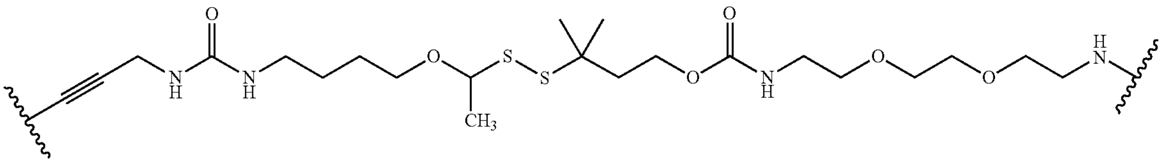
,
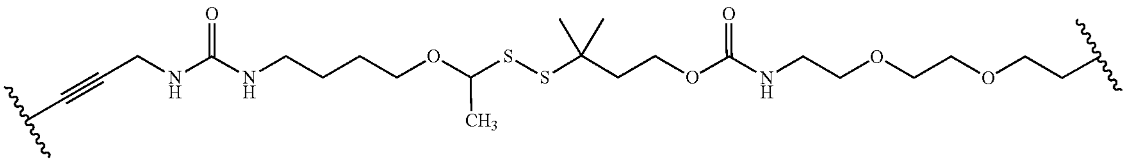
, -continued
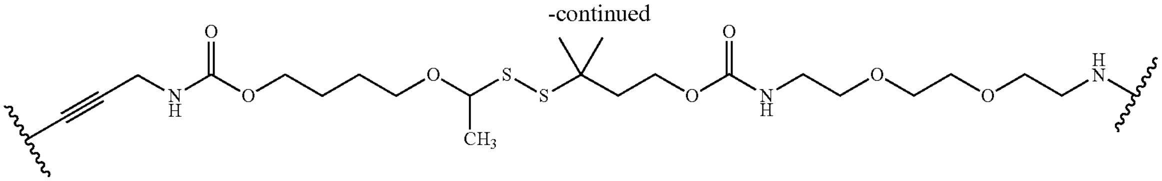
,
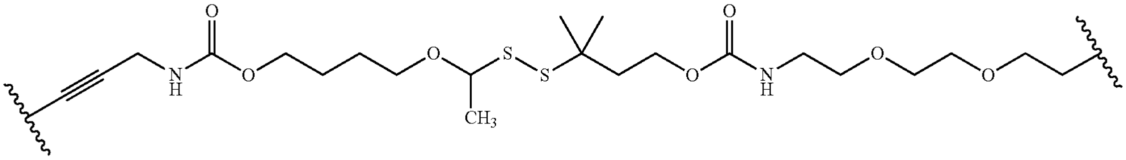
,
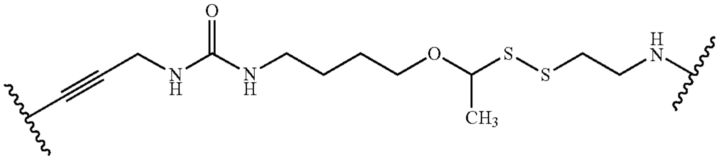
,
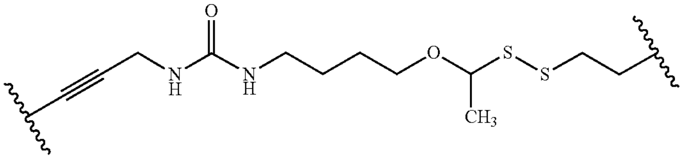
,
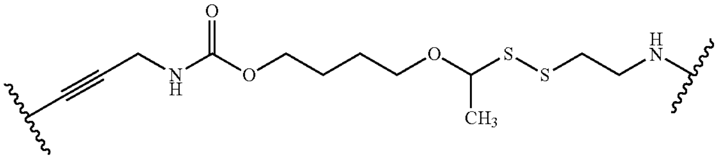
,
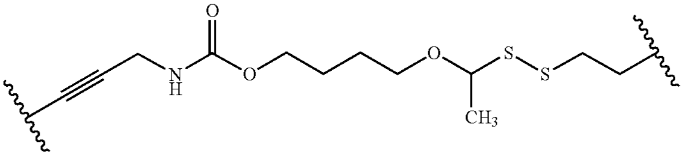
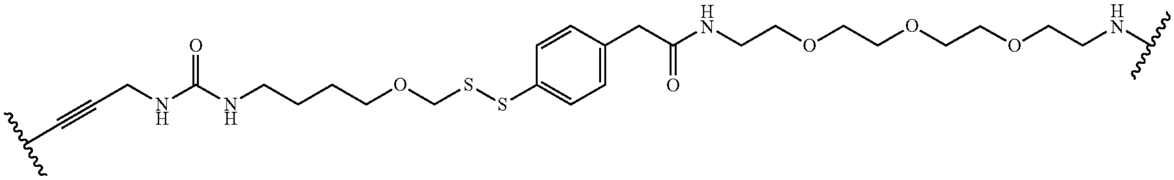
,
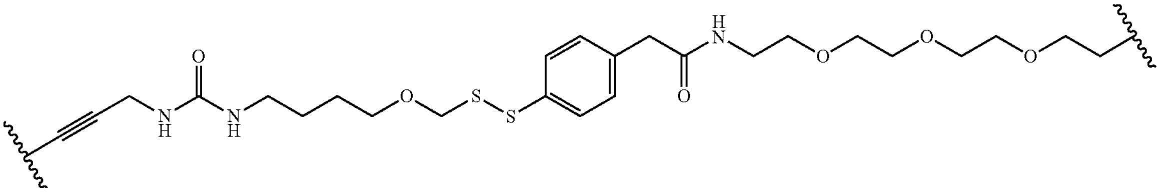
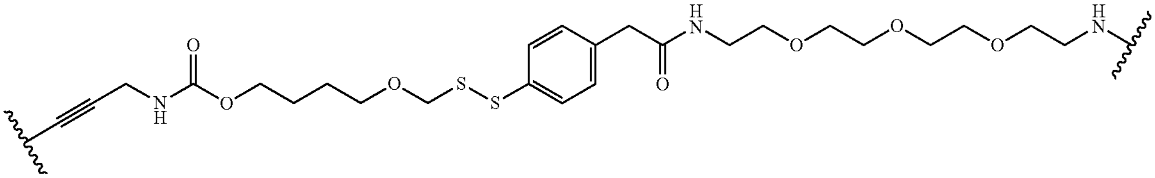
,
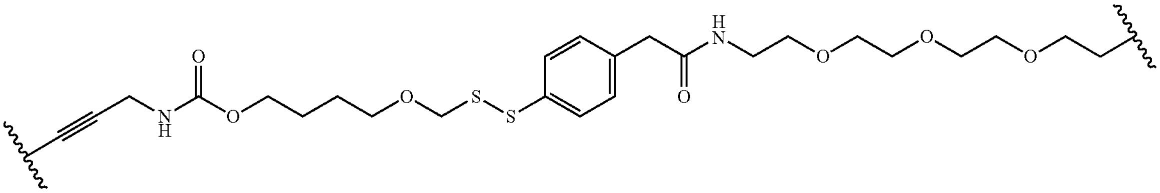
, -continued
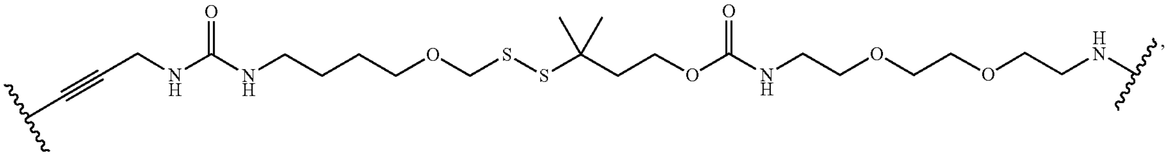,
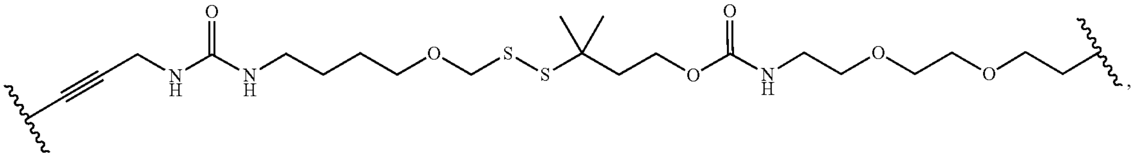,
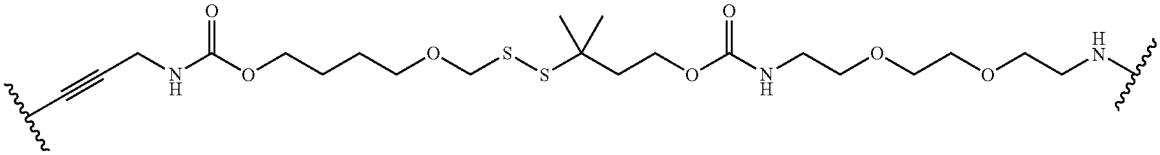,
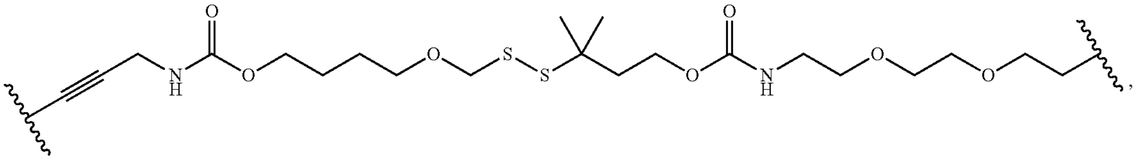,
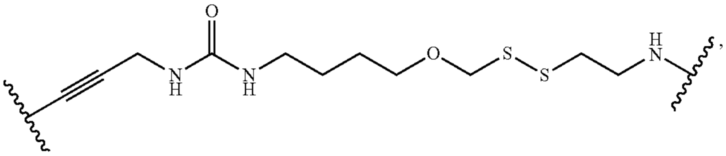,
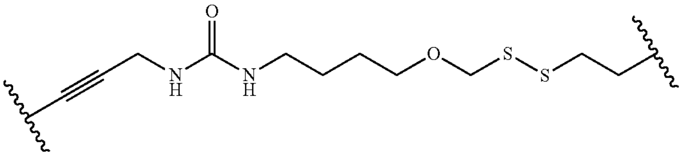,
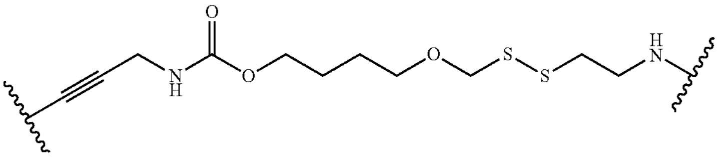,
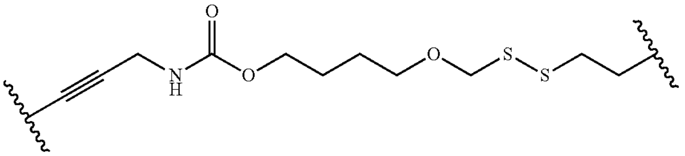,
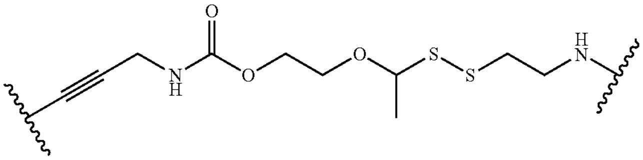,
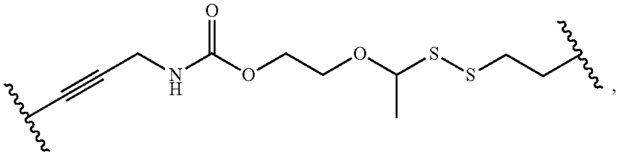, -continued
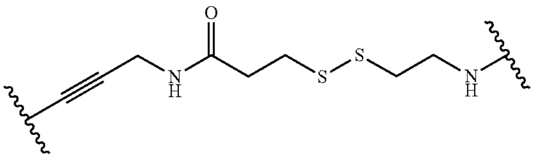,
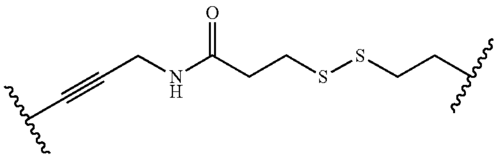,
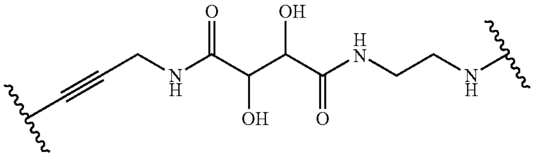,
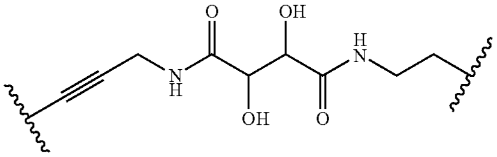,
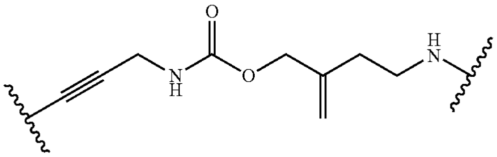,
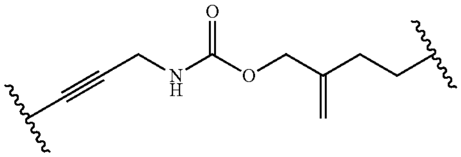,
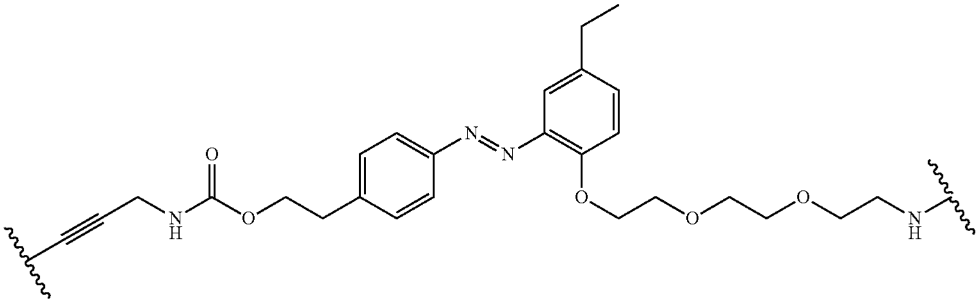,
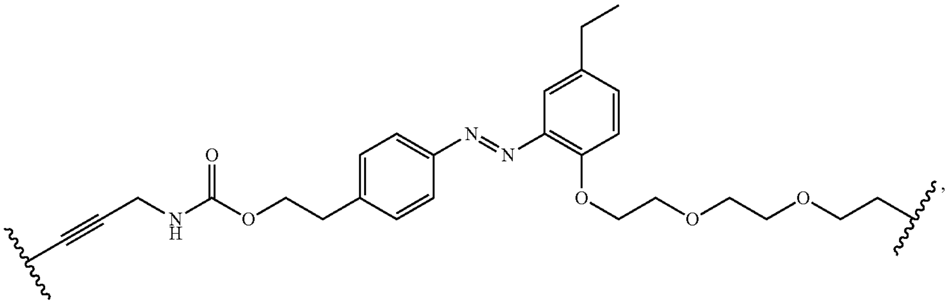,
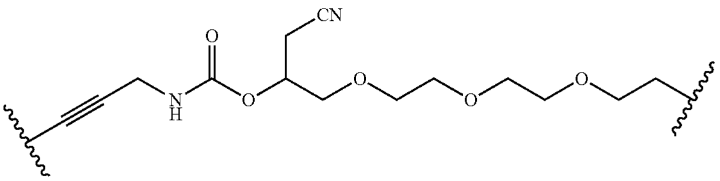, or
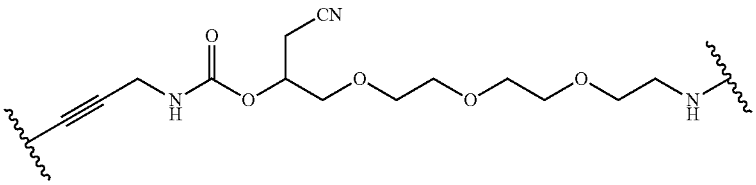.

Embodiment P45. The compound of embodiment P38, wherein $L^{100}$ is

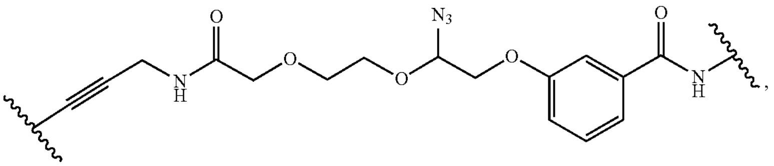
,

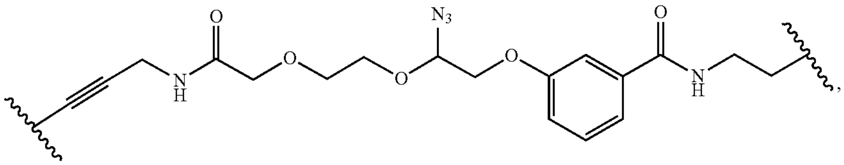
,

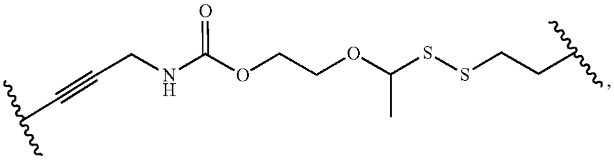
, or

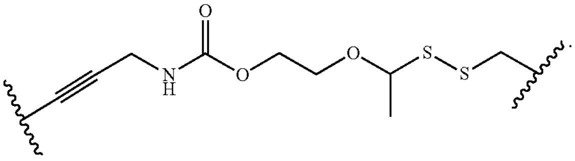
.

Embodiment P46. The compound of one of embodiments P1 to P45, wherein $R^1$ is independently a monophosphate moiety, polyphosphate or a nucleic acid moiety.

Embodiment P47. The compound of embodiment P1 to P21 or P27 to P45, wherein $R^4$ is a detectable moiety.

Embodiment P48. The compound of embodiment P1 to P21 or P27 to P45, wherein $R^4$ is a fluorescent dye moiety.

Embodiment P49. The compound of embodiment P1 to P21 or P27 to P45, wherein $R^4$ is independently an anchor moiety.

Embodiment P50. The compound of embodiment P49, wherein the anchor moiety is biotin, azide, transcyclooctene (TCO), or phenyl boric acid (PBA).

Embodiment P51. A composition comprising a first compound of one of embodiments P49 to P50 and a second compound having the formula: $R^5$-$L^5$-$R^6$; wherein $R^5$ is a complementary anchor moiety to the $R^4$ anchor moiety of the first compound; $L^5$ is a covalent linker; and $R^6$ is detectable moiety.

Embodiment P52. The composition of embodiment P51, wherein $R^5$ is a streptavidin moiety.

Embodiment P53. The composition of one of embodiments P51 to P52, further comprising a photodamage mitigating agent.

Embodiment P54. The composition of embodiment P53, wherein the photodamage mitigating agent is sodium pyruvate, N,N'-dimethylthiourea, mannitol, DMSO, carboxy-PTIO, 6-hydroxy-2,5,7,8-tetramethylchroman-2-carboxylic acid, alpha-tocopherol, 2-phenyl-1,2,benzisoselenazol-3 (2H)-one, uric acid, sodium azide, or manganese(III)-tetrakis(4-benzoic acid) porphyrin, 4,5-dihydroxybenzene-1,3-disulfonate.

Embodiment P55. The composition of embodiment P53, wherein the photodamage mitigating agent is 3-carboxy-proxyl, N-propyl gallate, ascorbic acid, methyl viologen, Trolox, or Trolox-quinone.

Embodiment P56. A method for sequencing a nucleic acid, comprising: (i) incorporating in series with a nucleic acid polymerase, within a reaction vessel, one of four different compounds into a primer to create an extension strand, wherein said primer is hybridized to said nucleic acid and wherein each of the four different compounds comprises a unique detectable moiety or a unique anchor moiety; (ii) if the compound of step (i) above comprises a unique anchor moiety, further adding to said reaction vessel a complementary anchor compound comprising a complementary anchor moiety to said unique anchor moiety bonded to a unique detectable moiety; and (iii) detecting the unique detectable moiety of each incorporated compound or incorporated compound-complementary anchor compound complex, so as to thereby identify each incorporated compound in said extension strand, thereby sequencing the nucleic acid; wherein each of said four different compounds is independently a compound of one of embodiments P1 to P50.

Embodiment P57. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of one of embodiments P1 to P50.

Embodiment P58. The method of one of embodiments P56 to P57, further comprising adding to said reaction vessel a photodamage mitigating agent.

Embodiment P59. The method of embodiment P58, wherein the photodamage mitigating agent is sodium pyruvate, N,N'-dimethylthiourea, mannitol, DMSO, carboxy-PTIO, 6-hydroxy-2,5,7,8-tetramethylchroman-2-carboxylic acid, alpha-tocopherol, 2-phenyl-1,2,benzisoselenazol-3 (2H)-one, uric acid, sodium azide, or manganese(III)-tetrakis(4-benzoic acid) porphyrin, 4,5-dihydroxybenzene-1,3-disulfonate.

Embodiment P60. The method of one of embodiments P56 to P57, wherein said complementary anchor compound is a composition of one of embodiments P51 to P54.

Embodiment P61. A nucleic acid polymerase complex comprising a nucleic acid polymerase, wherein said nucleic acid polymerase is bound to a compound of one of embodiments P1 to P50.

Embodiment P62. A method for increasing the accuracy of a sequencing reaction, the method comprising (i) incorporating in series with a nucleic acid polymerase, within a reaction vessel, one of four different compounds into a primer to create an extension strand, wherein said primer is hybridized to said nucleic acid and wherein each of the four different compounds comprises a unique detectable moiety or a unique anchor moiety; (ii) if the compound of step (i) above comprises a unique anchor moiety, further adding to said reaction vessel a complementary anchor compound comprising a complementary anchor moiety to said unique anchor moiety bonded to a unique detectable moiety; and (iii) detecting the unique detectable moiety of each incorporated compound or incorporated compound-complementary anchor compound complex, so as to thereby identify each incorporated compound in said extension strand, thereby sequencing the nucleic acid; wherein each of said four different compounds is independently a compound of one of embodiments P1 to P50.

Embodiment P63. A method of modulating the fluorescent intensity ratio of at least two different fluorescently-labeled compounds, the method comprising (i) providing a reaction mixture comprising two different fluorescently-labeled compounds, wherein each of two different compounds is independently a compound of one of embodiments P1 to P50; (ii) measuring the fluorescence intensity of the two different fluorescently-labeled compounds under excitation illumination to determine the first fluorescent intensity ratio; (iii) modulating the functional distance of the rigid spacer of at least one of the two different fluorescently-labeled compounds; and (iv) measuring the fluorescence intensity of the two different fluorescently-labeled compounds under excitation illumination to determine the second fluorescent intensity ratio, thereby modulating the fluorescent intensity ratio of at least two different fluorescently-labeled compounds.

Embodiment P64. A method of reducing photodamage to a biological component in a sequencing reaction, the method comprising (i) incorporating in series with a nucleic acid polymerase, within a reaction vessel, one of four different compounds into a primer to create an extension strand, wherein said primer is hybridized to said nucleic acid and wherein each of the four different compounds comprises a unique detectable moiety or a unique anchor moiety; (ii) if the compound of step (i) above comprises a unique anchor moiety, further adding to said reaction vessel a complementary anchor compound comprising a complementary anchor moiety to said unique anchor moiety bonded to a unique detectable moiety; (iii) detecting the unique detectable moiety of each incorporated compound or incorporated compound-complementary anchor compound complex, so as to thereby identify each incorporated compound in said extension strand, thereby sequencing the nucleic acid; and (iv) wherein each of said four different compounds is independently a compound of one of embodiments P1 to P50.

Embodiment P65. The method of embodiment P64, wherein the biological component comprise a nucleotide, DNA, or RNA.

Embodiment P66. The method of embodiment P64, wherein the biological component is an enzyme.

Embodiment P67. The method of embodiment P66, wherein the enzyme is a polymerase, nuclease, or ligase enzyme.

Embodiment P68. The method of embodiment P67, wherein the enzyme is a DNA polymerase.

Additional Embodiments

Embodiment 1. A compound having the formula:

(I)

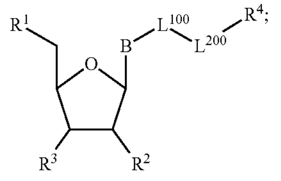

wherein B is a divalent nucleobase; $L^{100}$ is a polymerase-compatible cleavable linker; $R^1$ is a polyphosphate moiety, monophosphate moiety, 5'-O-nucleoside protecting group, nucleic acid moiety, hydrogen, or —OH; $R^2$ is hydrogen, a polymerase-compatible cleavable moiety, or —OH; $R^3$ is an —O-polymerase-compatible cleavable moiety, a polymerase-compatible cleavable moiety, hydrogen, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is an anchor moiety or a detectable moiety; $L^{200}$ has the formula:

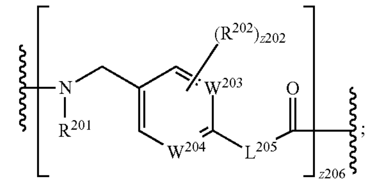

$R^{201}$ is independently hydrogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, —CN, —OH, —COOH, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, or substituted or unsubstituted heteroalkyl; $R^{202}$ is independently $-SO_3H$, $-SO_4H$, $-SO_2NH_2$, $-PO_3H$, $-PO_4H$, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, —CN, —OH, $-NH_2$, —COOH, $-CONH_2$, $-NO_2$, —SH, $-NHNH_2$, $-ONH_2$, —NHC(O)NHNH$_2$, —NHC(O)NH$_2$, $-NHSO_2H$, —NHC(O)H, —NHC(O)OH, —NHOH, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, $-SO_2Cl$, substituted or unsubstituted alkyl, substituted or unsubstituted heteroalkyl, or $L^{202}$-$R^{202A}$; $L^{202}$ is independently a covalent linker; $R^{202A}$ is independently a detectable moiety, anchor moiety, triplet quencher moiety, or protein moiety; z202 is independently an integer from 0 to 2; $R^{201}$ and $R^{202}$ may optionally be joined to form a substituted or unsubstituted heterocycloalkyl; $W^{203}$ and $W^{204}$ are independently CH, N, or $C(R^{202})$; $L^{205}$ is independently a bond or $—CH_2NH—$; and z206 is an integer from 1 to 100.

Embodiment 2. A compound having the formula:

(I)

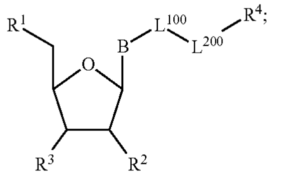

wherein B is a divalent nucleobase; $L^{100}$ is a polymerase-compatible cleavable linker; $R^1$ is a polyphosphate moiety, monophosphate moiety, 5'-O-nucleoside protecting group, nucleic acid moiety, hydrogen, or —OH; $R^2$ is hydrogen, a polymerase-compatible cleavable moiety, or —OH; $R^3$ is an —O-polymerase-compatible cleavable moiety, a polymerase-compatible cleavable moiety, hydrogen, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is an anchor moiety or a detectable moiety; and $L^{200}$ is a divalent polymer, divalent double-stranded nucleic acid, or divalent polypeptide.

Embodiment 3. The compound of Embodiment 2, wherein the divalent polypeptide is divalent polyproline.

Embodiment 4. The compound of Embodiment 2, wherein the divalent polypeptide comprises the amino acid sequences $(EAAAK)_{n1}$ (SEQ ID NO:1), $(EP)_{n2}$ (SEQ ID NO:5), $(KP)_{n3}$ (SEQ ID NO:6), $(AP)_{n4}$ (SEQ ID NO:7), or $(TPR)_{n5}$ (SEQ ID NO:8), wherein n1, n2, n3, n4, and n5 are each independently an integer from 2 to 20.

Embodiment 5. The compound of Embodiment 2, wherein the divalent polypeptide comprises the amino acid sequences $(EAAAK)_{n1}$ (SEQ ID NO:1), $(EP)_{n2}$ (SEQ ID NO:5), $(KP)_{n3}$ (SEQ ID NO:6), wherein n1, n2, and n3 are each independently an integer from 2 to 6.

Embodiment 6. The compound of Embodiment 1, wherein $L^{200}$ has the formula:

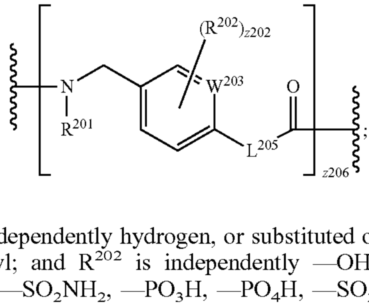

$R^{201}$ is independently hydrogen, or substituted or unsubstituted alkyl; and $R^{202}$ is independently —OH, $—SO_3H$, $—SO_4H$, $—SO_2NH_2$, $—PO_3H$, $—PO_4H$, $—SO_2Cl$, substituted or unsubstituted alkyl, substituted or unsubstituted heteroalkyl, or $L^{202}$-$R^{202A}$.

Embodiment 7. The compound of Embodiment 6, wherein z206 is an integer from 1 to 20.

Embodiment 8. The compound of Embodiment 6, wherein z206 is an integer from 2 to 10.

Embodiment 9. The compound of Embodiment 6, wherein z206 is an integer from 5 to 8.

Embodiment 10. The compound of Embodiment 6, wherein $L^{200}$ has the formula:

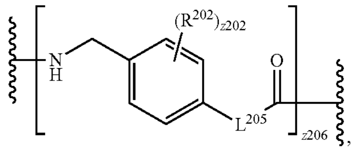,

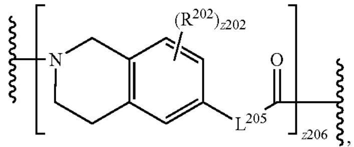,

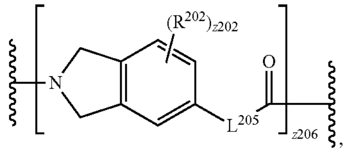,

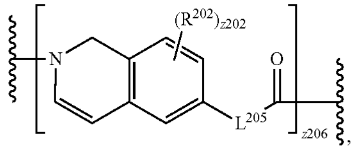,

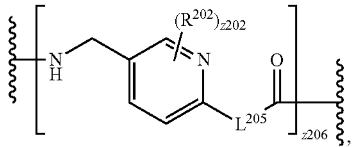,

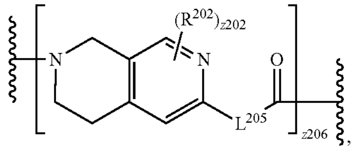,

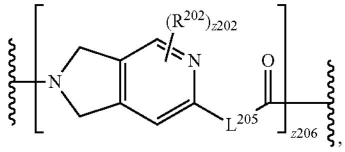, or

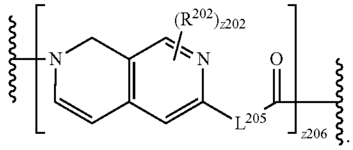.

Embodiment 11. The compound of Embodiment 6, wherein $L^{200}$ has the formula:

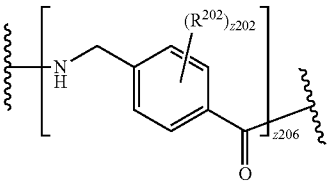,

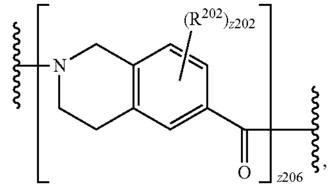,

-continued
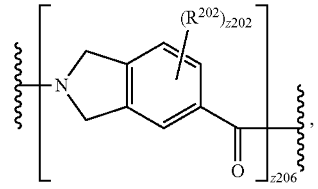
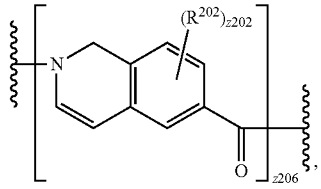
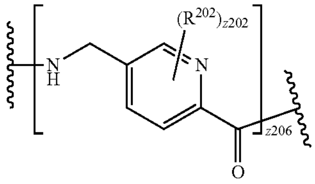
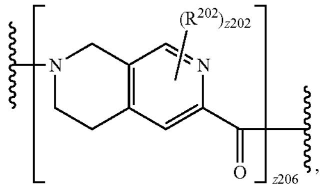
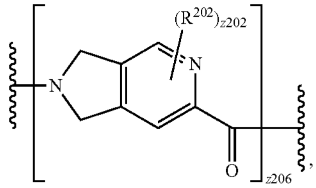
or
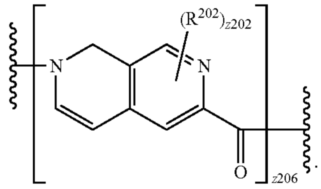
Embodiment 12. The compound of Embodiment 6, wherein $L^{200}$ has the formula:
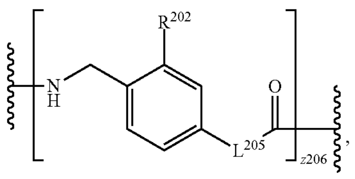
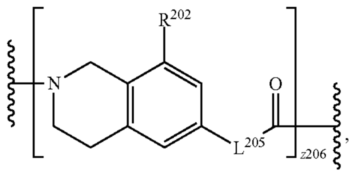
-continued
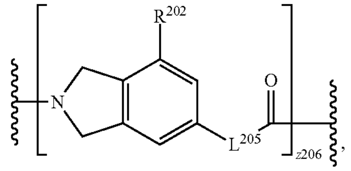
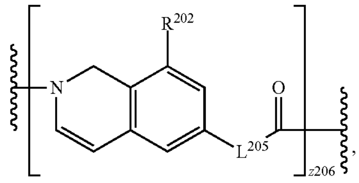
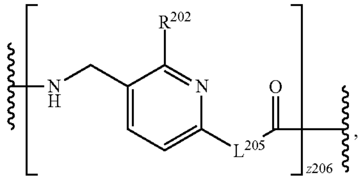
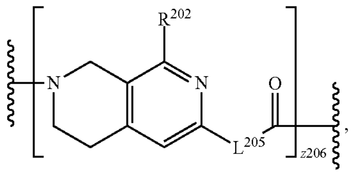
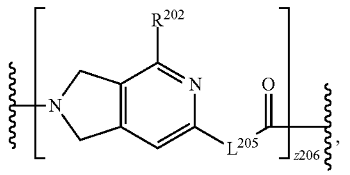
or
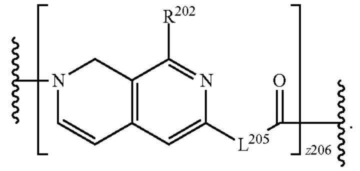
Embodiment 13. The compound of Embodiment 6, wherein $L^{200}$ has the formula:
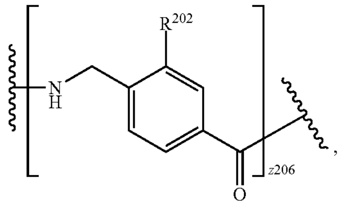
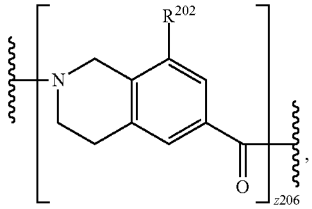

-continued
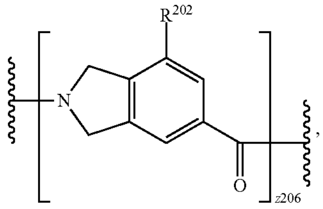
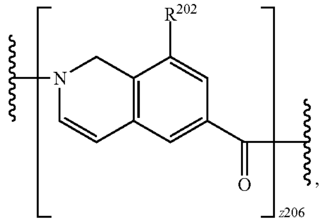
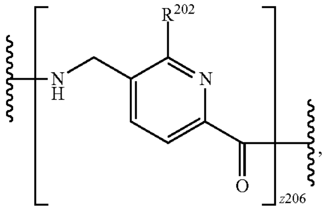
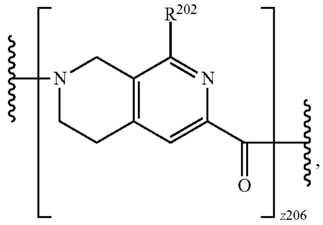
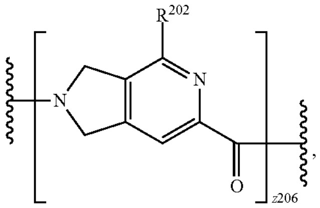
or
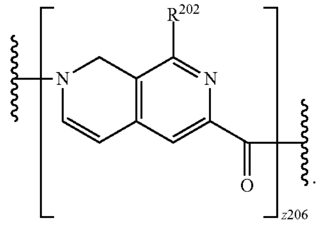
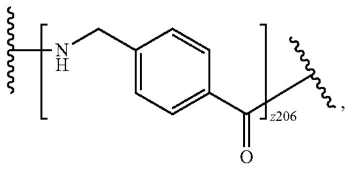
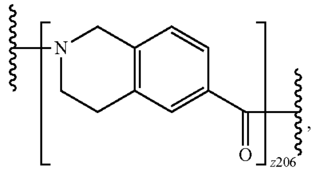
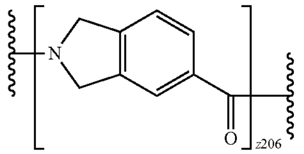
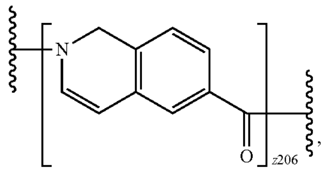
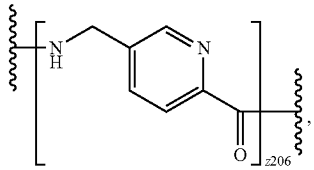
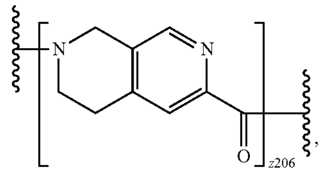
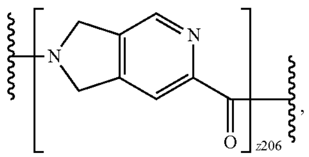
or
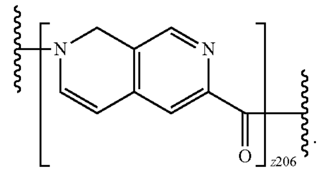
Embodiment 14. The compound of Embodiment 6, wherein $L^{200}$ has the formula:
Embodiment 15. The compound of Embodiment 6, wherein $L^{200}$ has the formula:
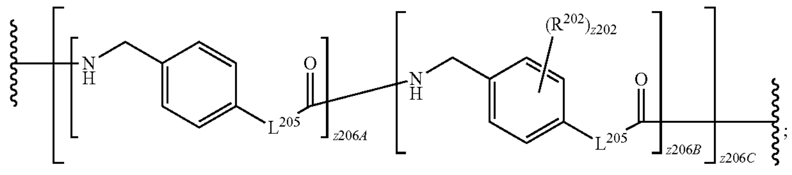

wherein z206A is an integer from 1 to 50; z206B is an integer from 1 to 50; and z206C is an integer from 1 to 50.

Embodiment 16. The compound of Embodiment 15, wherein z206A is an integer from 1 to 10; z206B is an integer from 1 to 10; and z206C is an integer from 1 to 5.

Embodiment 17. The compound of Embodiment 6, wherein $L^{200}$ has the formula:

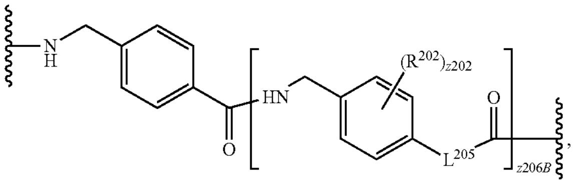

wherein z206B is an integer from 1 to 20.

Embodiment 18. The compound of Embodiment 6, wherein $L^{200}$ has the formula:

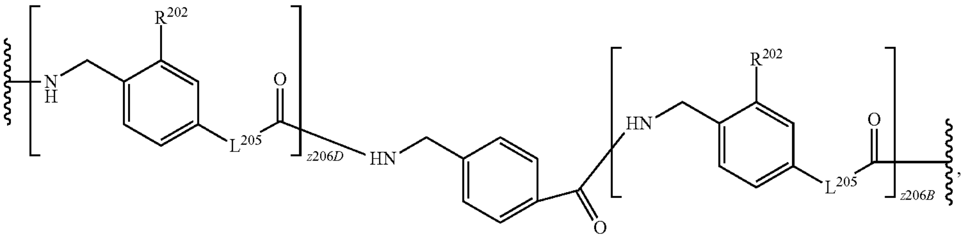

wherein z206B is an integer from 1 to 50 and z206D is an integer from 1 to 50.

Embodiment 19. The compound of Embodiment 18, wherein z206B and z206D are each independently an integer from 1 to 10.

Embodiment 20. The compound of Embodiment 6, wherein $L^{200}$ has the formula:

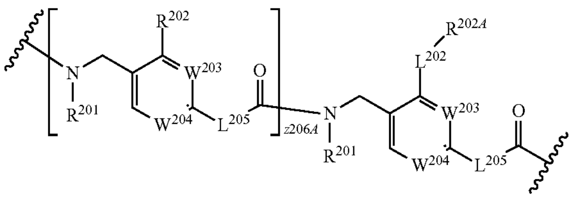

or

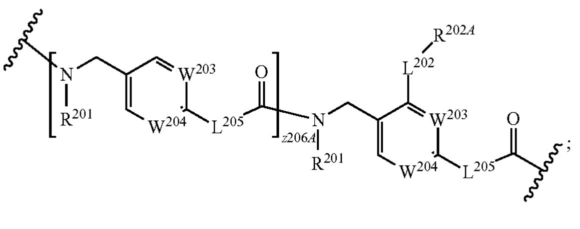

wherein z206A is an integer from 1 to 50.

Embodiment 21. The compound of Embodiment 6, wherein $L^{200}$ has the formula:

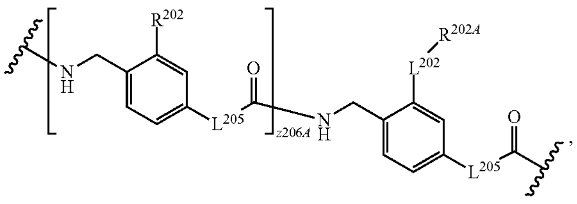

and z206A is an integer from 1 to 10.

Embodiment 22. The compound of Embodiment 6, wherein $L^{200}$ has the formula:

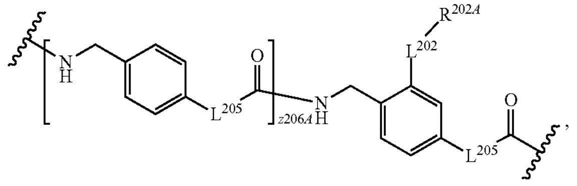

and z206A is an integer from 1 to 10.

Embodiment 23. The compound of Embodiments 20 or 21, wherein $R^4$ and $R^{202A}$ are independently a detectable moiety.

Embodiment 24. The compound of Embodiments 20 or 21, wherein $R^4$ and $R^{202A}$ are a FRET pair of detectable moieties.

Embodiment 25. The compound of Embodiments 20 or 21, wherein $R^4$ is a detectable moiety and $R^{202A}$ is a triplet state quencher.

Embodiment 26. The compound of Embodiment 25, wherein the triplet state quencher is a monovalent ascorbic acid, monovalent cyclooctatetraene (COT), monovalent nitrobenzyl alcohol, monovalent methyl viologen, monovalent Trolox, or monovalent Trolox-quinone.

Embodiment 27. The compound of any one of Embodiments 6 to 13, or 15 to 26, wherein $R^{202}$ is independently $—SO_3H$, $—SO_4H$, $—SO_2NH_2$, $—PO_3H$, $—PO_4H$, or $—SO_2Cl$.

Embodiment 28. The compound of any one of Embodiments 6 to 13, or 15 to 26, wherein $R^{202}$ is independently $—SO_3H$.

Embodiment 29. The compound of one of Embodiments 1 to 28, wherein $R^3$ is an —O-polymerase-compatible cleavable moiety.

Embodiment 30. The compound of any one of Embodiments 1 to 29, wherein the polymerase-compatible cleavable moiety is independently -(substituted or unsubstituted alkylene)-SS-(unsubstituted alkyl).
Embodiment 31. The compound of any one of Embodiments 1 to 29, wherein the polymerase-compatible cleavable moiety is independently:
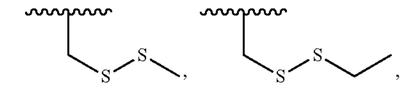
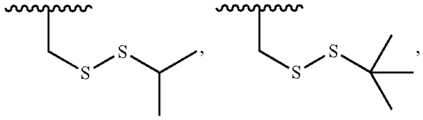
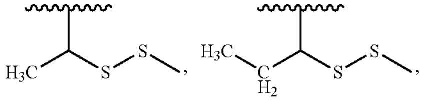
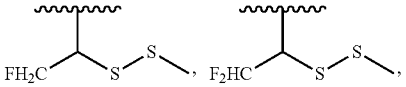
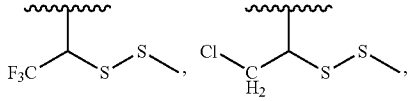
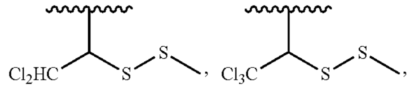
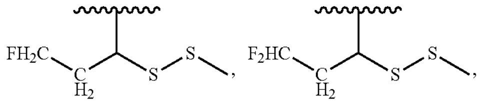
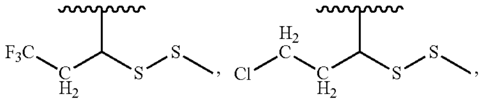
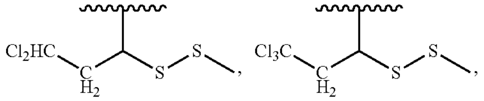
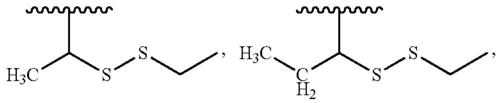
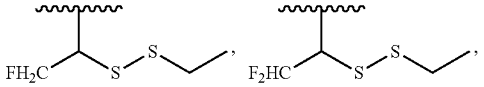
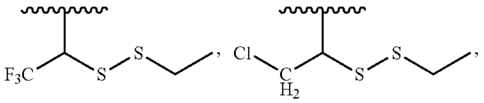
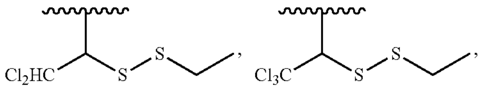
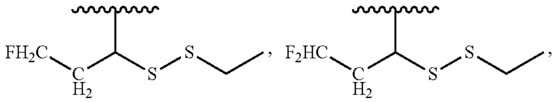
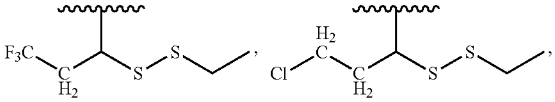
-continued
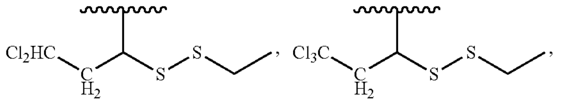
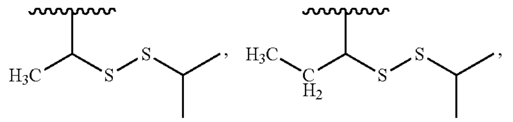
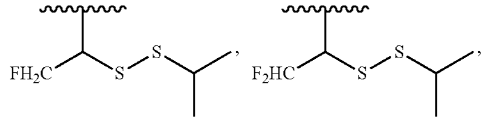
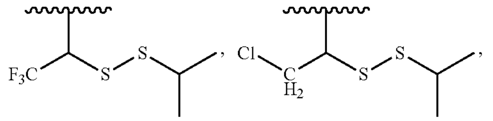
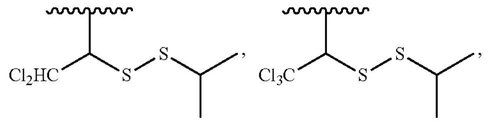
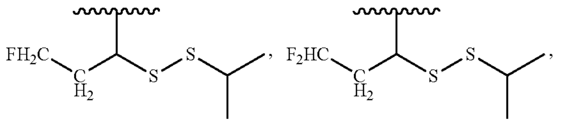
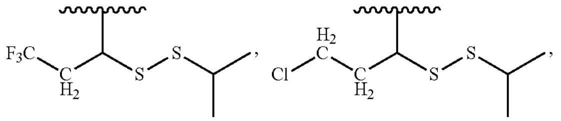
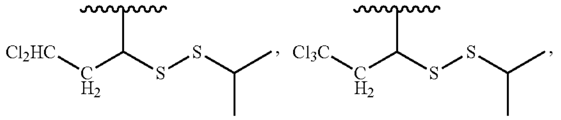
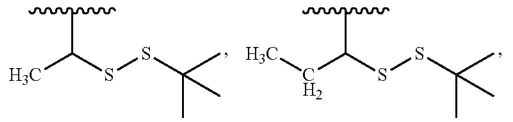
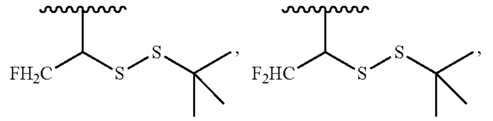
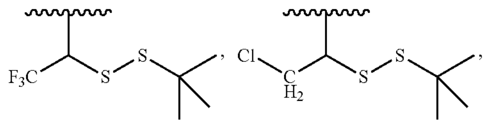
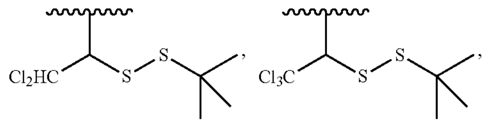
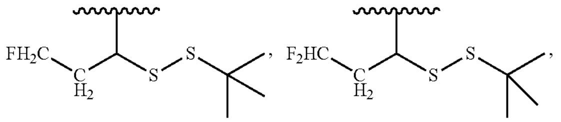
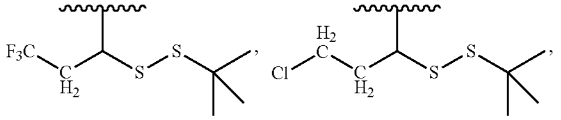

-continued

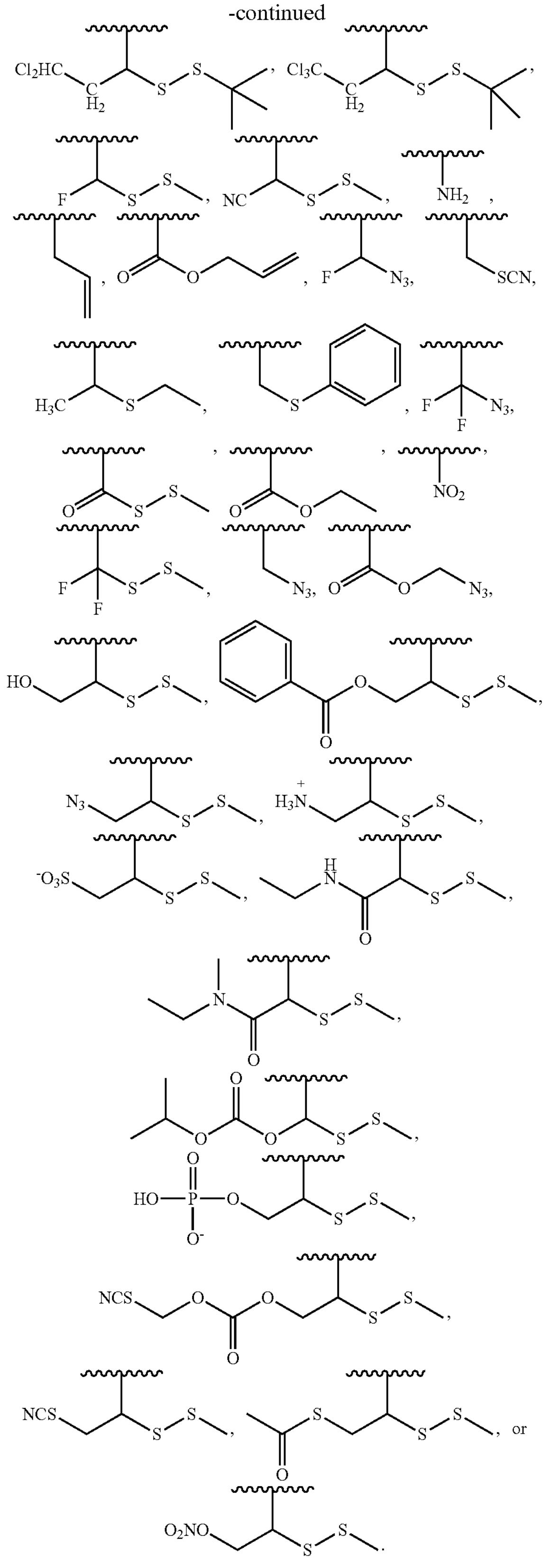

Embodiment 32. The compound of one of Embodiments 1 to 29 wherein the polymerase-compatible cleavable moiety is independently:

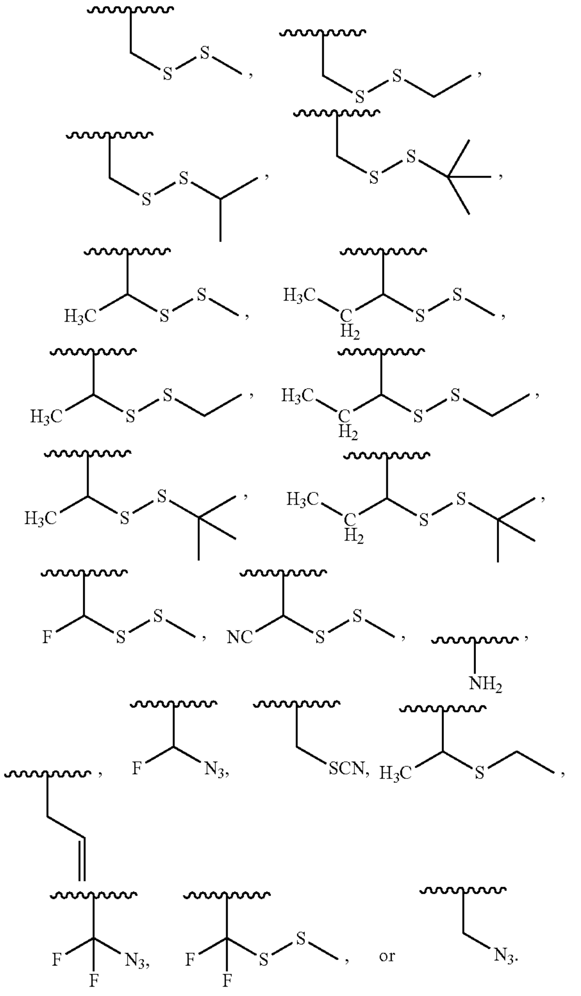

Embodiment 33. The compound of one of Embodiments 1 to 32, wherein $R^2$ is hydrogen or —OH.

Embodiment 34. The compound of one of Embodiments 1 to 32, wherein $R^2$ is hydrogen.

Embodiment 35. The compound of one of Embodiments 1 to 34, having the formula:

(Ia)

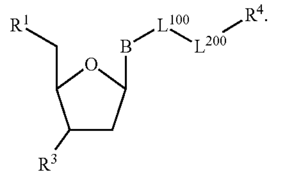

Embodiment 36. The compound of one of Embodiments 1 to 35, wherein B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

Embodiment 37. The compound of one of Embodiments 1 to 35, wherein B is

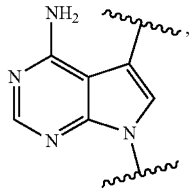,
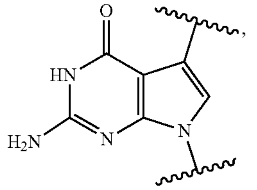,
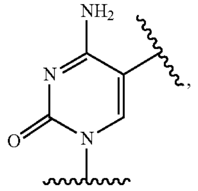, or
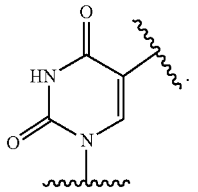.

Embodiment 38. The compound of one of Embodiments 1 to 37, wherein $L^{100}$ is a polymerase-compatible cleavable linker comprising:

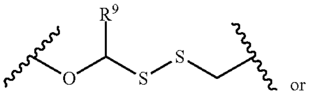 or

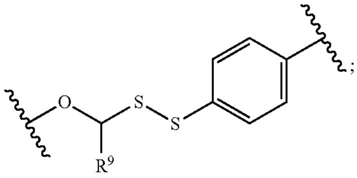;

wherein $R^9$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 39. The compound of one of Embodiments 1 to 37, wherein $L^{100}$ is a polymerase-compatible cleavable linker comprising

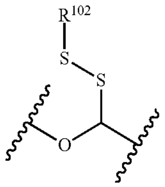 or 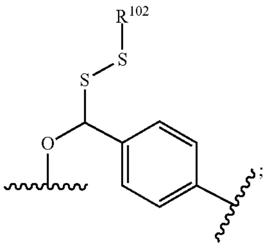;

wherein $R^{102}$ is unsubstituted $C_1$-$C_4$ alkyl.

Embodiment 40. The compound of one of Embodiments 1 to 37, wherein $L^{100}$ is $-L^{101}-L^{102}-L^{103}-L^{104}-L^{105}-$; and $L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, —SS—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{101}$, $L^{102}$, $L^{103}$, $L^{104}$, and $L^{105}$ is not a bond.

Embodiment 41. The compound of Embodiment 40, wherein $L^{100}$ is $-L^{101}$-O—CH(—$SR^{100}$)-$L^{103}$-$L^{104}$-$L^{105}$-, $-L^{101}$-O—C($CH_3$)(—$SR^{100}$)-$L^{103}$-$L^{104}$-$L^{105}$-, $-L^{101}$-O—CH($N_3$)-$L^{103}$-$L^{104}$-$L^{105}$-, or $-L^{101}$-SS-$L^{103}$-$L^{104}$-$L^{105}$-; $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^{100}$ is —$SR^{102}$ or —CN; and $R^{102}$ is unsubstituted $C_1$-$C_4$ alkyl.

Embodiment 42. The compound of Embodiment 40, wherein $L^{100}$ is $-L^{101}$-O—CH(—$SR^{100}$)-$L^{103}$-$L^{104}$-$L^{105}$-, $-L^{101}$-O—C($CH_3$)(—$SR^{100}$)-$L^{103}$-$L^{104}$-$L^{105}$-, $-L^{101}$-O—CH($N_3$)-$L^{103}$-$L^{104}$-$L^{105}$- or $-L^{101}$-SS-$L^{103}$-$L^{104}$-$L^{105}$-; $L^{101}$ is independently a substituted or unsubstituted $C_1$-$C_4$ alkylene or substituted or unsubstituted 8 to 20 membered heteroalkylene; $L^{103}$ is independently a bond or substituted or unsubstituted 2 to 10 membered heteroalkylene; $L^{104}$ is independently a bond, substituted or unsubstituted 4 to 18 membered heteroalkylene, or substituted or unsubstituted phenylene; $L^{105}$ is independently bond or substituted or unsubstituted 4 to 18 membered heteroalkylene; $R^{100}$ is —$SR^{102}$ or —CN; and $R^{102}$ is unsubstituted $C_1$-$C_4$ alkyl.

Embodiment 43. The compound of Embodiment 40, wherein $L^{100}$ is $-L^{101}$-O—CH(—$SR^{100}$)-$L^{103}$-$L^{104}$-$L^{105}$-, $-L^{101}$-O—C($CH_3$)(—$SR^{100}$)-$L^{103}$-$L^{104}$-$L^{105}$-, or $-L^{101}$-O—CH($N_3$)—$CH_2$—O-$L^{104}$-$L^{105}$-; $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^{104}$ is unsubstituted phenylene; $R^{100}$ is —$SR^{102}$ or —CN; and $R^{102}$ is unsubstituted $C_1$-$C_4$ alkyl.

Embodiment 44. The compound of Embodiment 40, wherein $L^{100}$ is

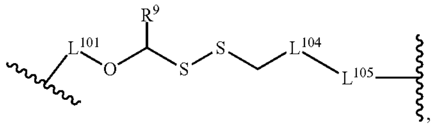,

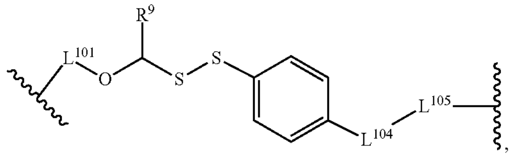,

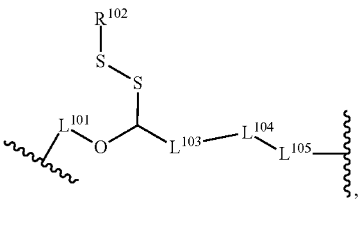, or

-continued
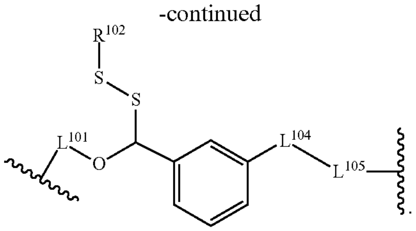
Embodiment 45. The compound of Embodiment 40, wherein $L^{100}$ is
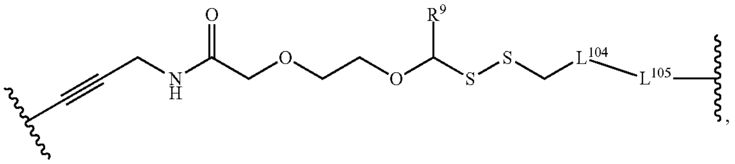
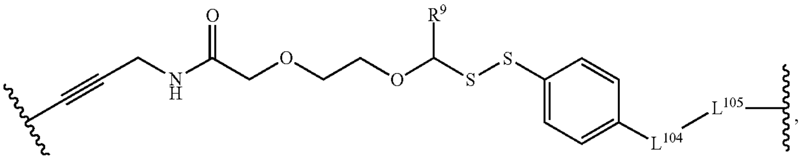
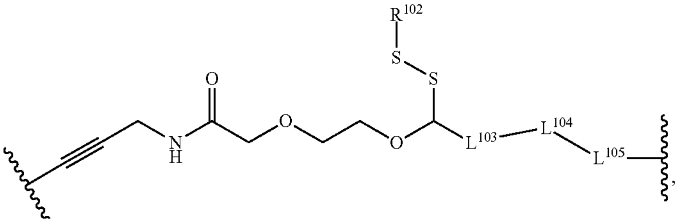
or
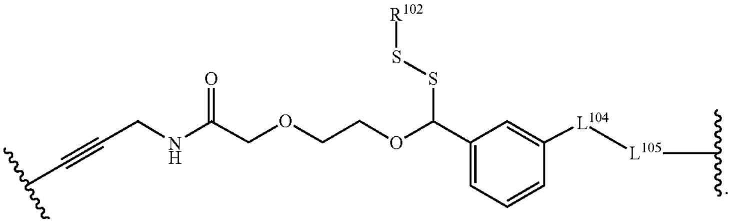
Embodiment 46. The compound of Embodiment 41, wherein $L^{100}$ is
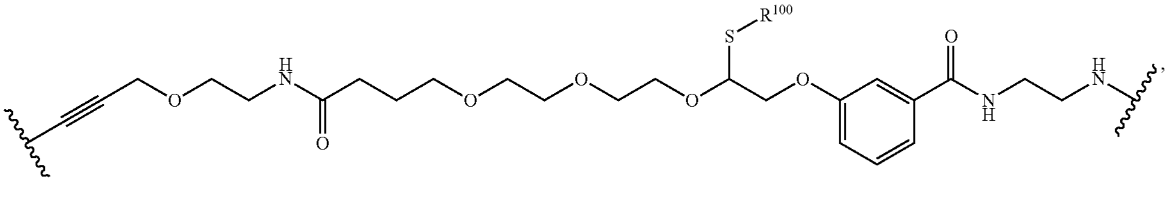
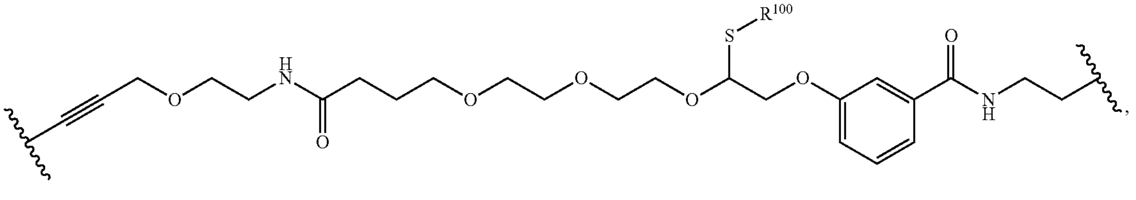

-continued
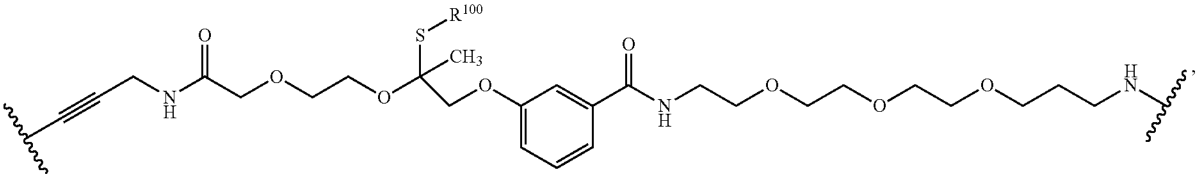
,
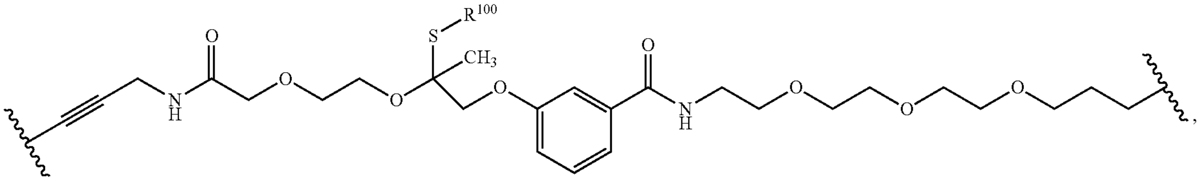
,
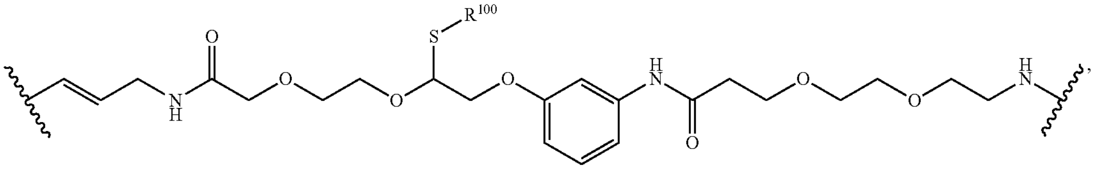
,
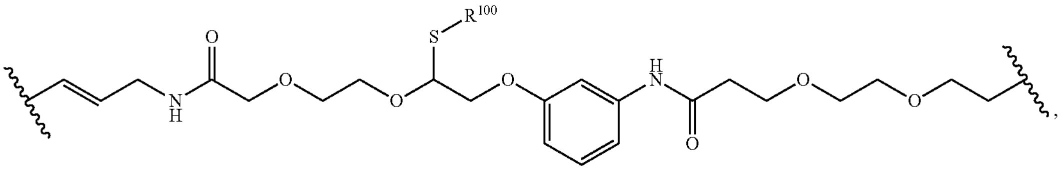
,
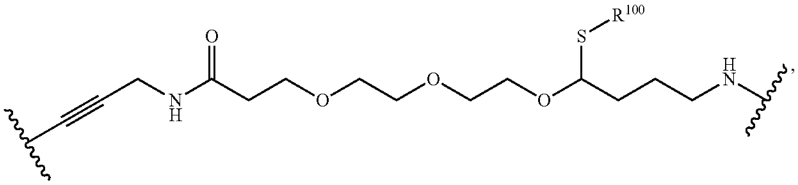
,
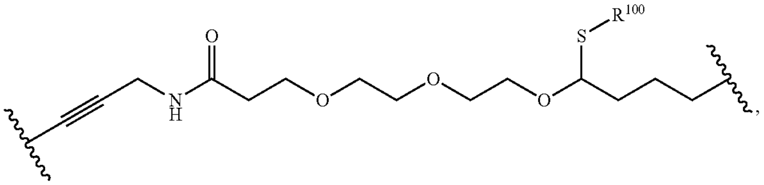
,
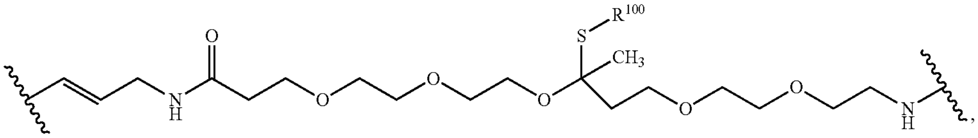
,
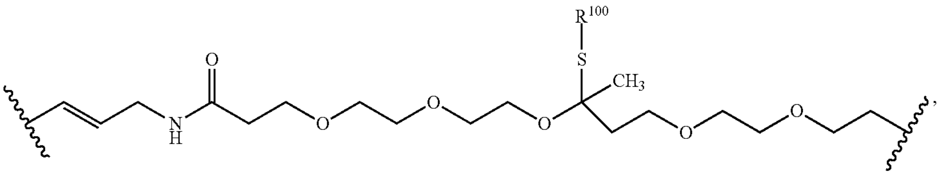
,
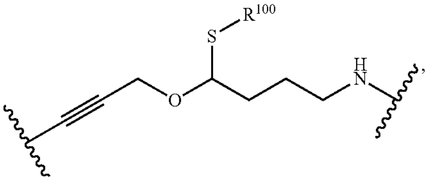
,
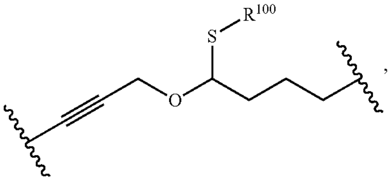
, -continued
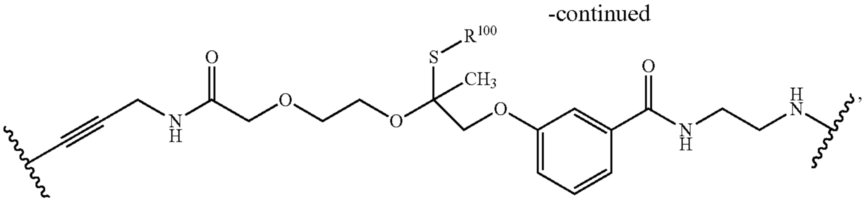
,
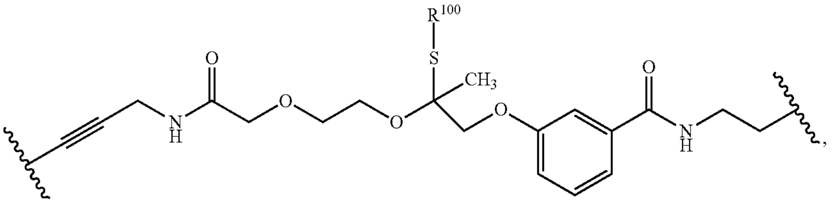
,
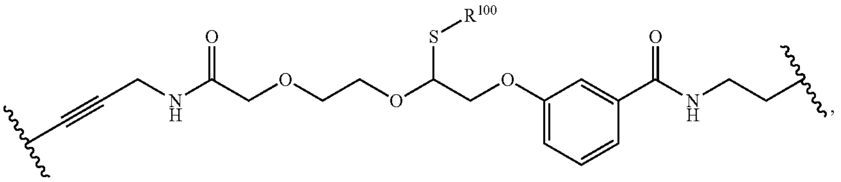
, or
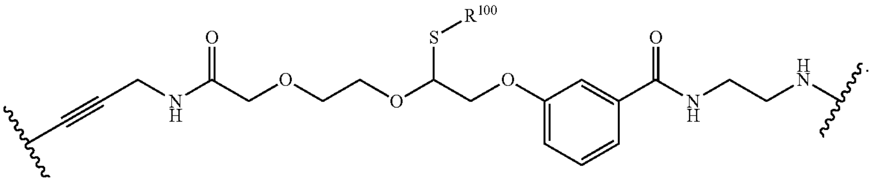
.
Embodiment 47. The compound of Embodiment 46, wherein $R^{100}$ is S—$R^{102}$.
Embodiment 48. The compound of Embodiment 40, wherein $L^{100}$ is
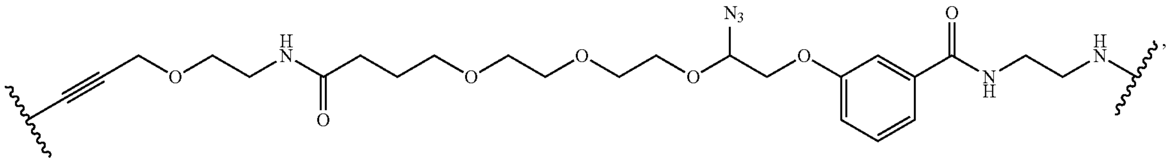
,
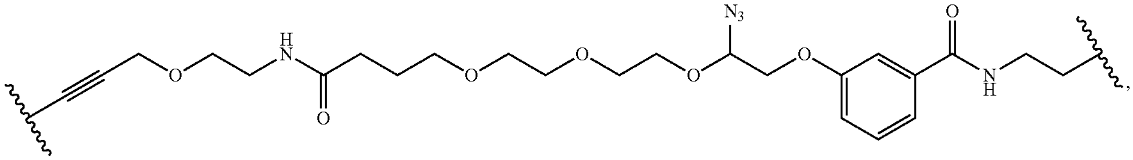
,
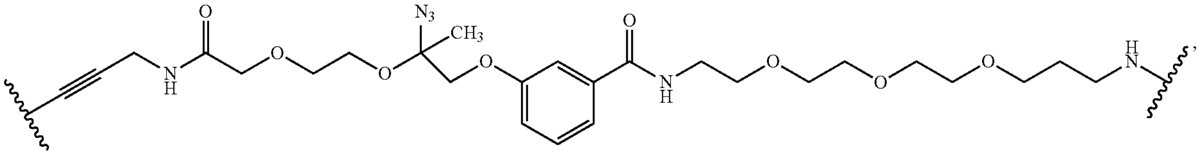
,
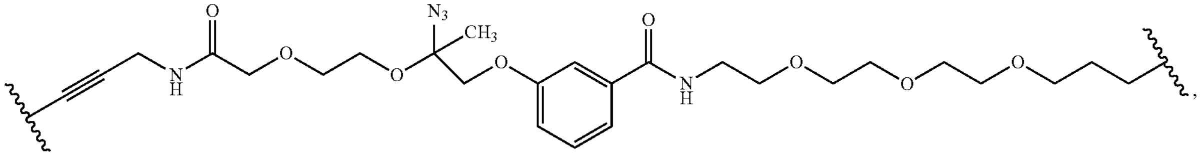
,
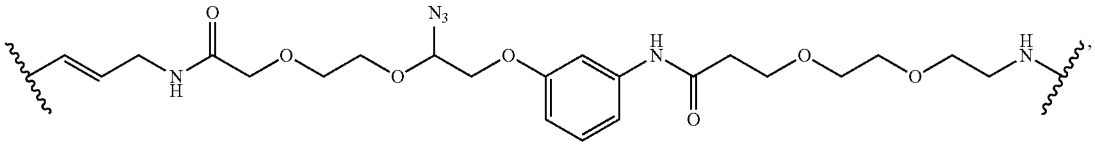
, -continued
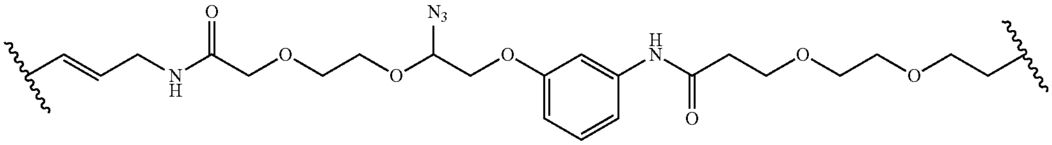
,
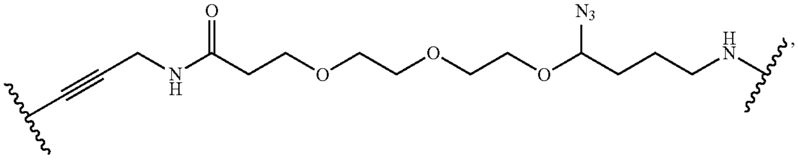
,
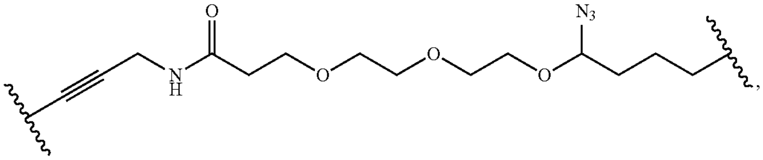
,
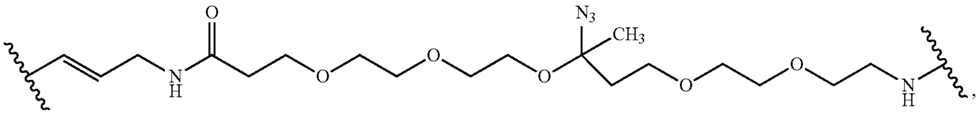
,
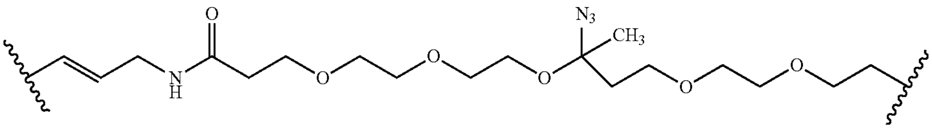
,
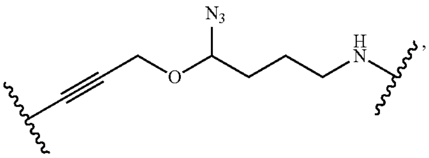
,
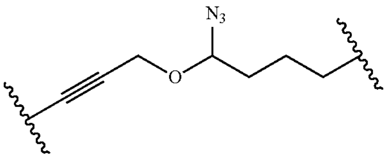
,
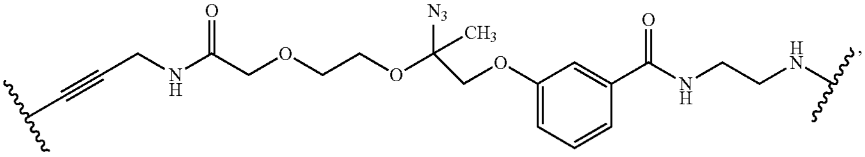
,
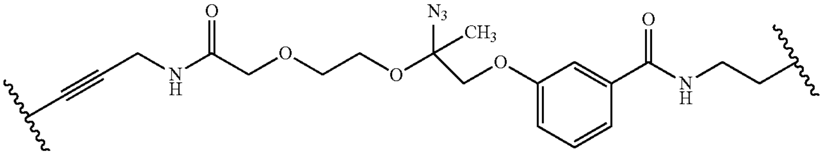
,
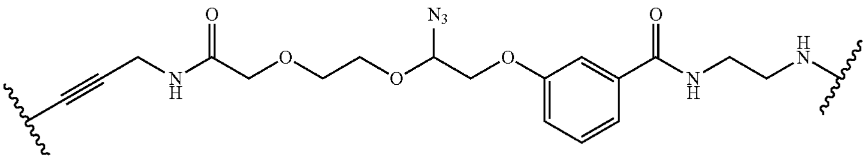
,
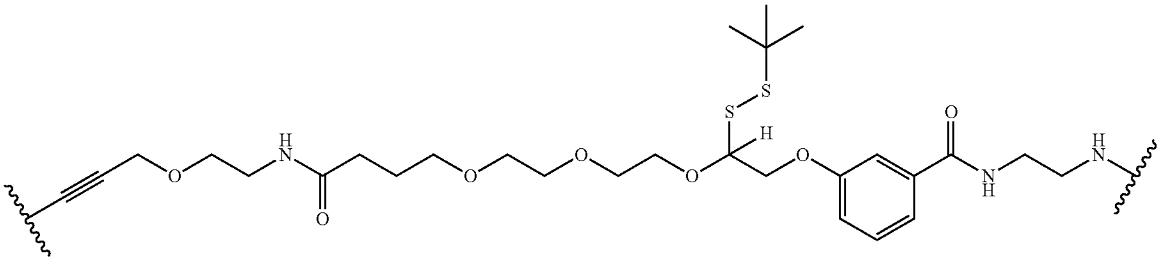

-continued
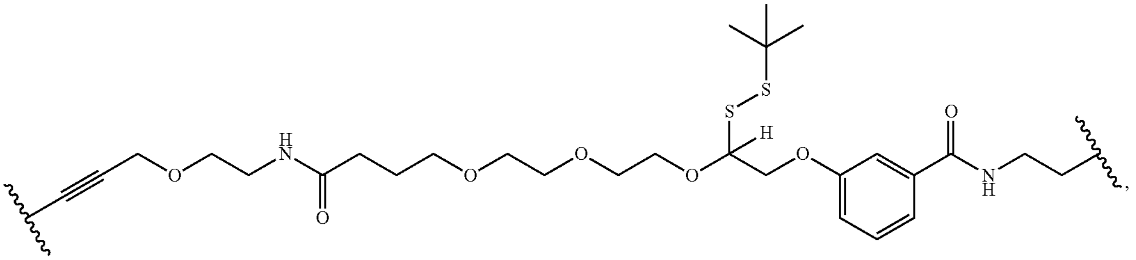
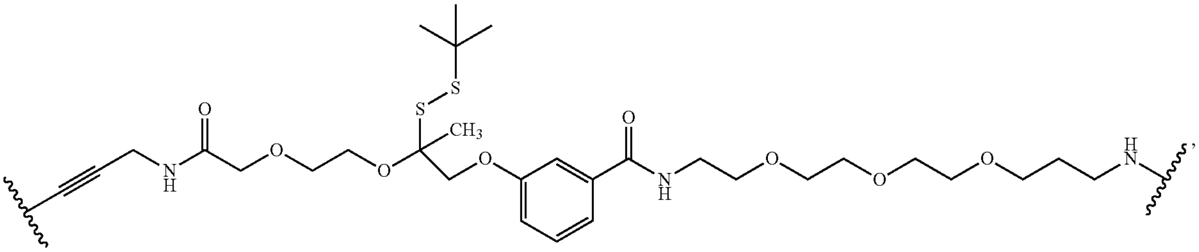
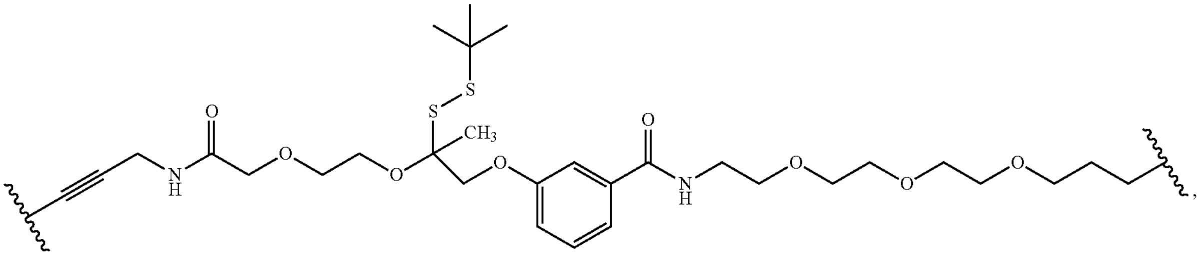
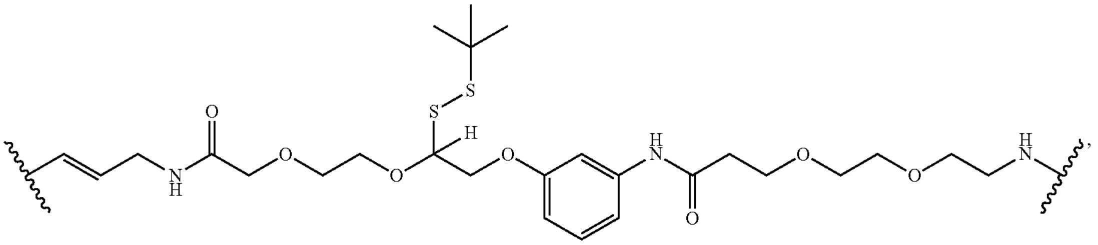
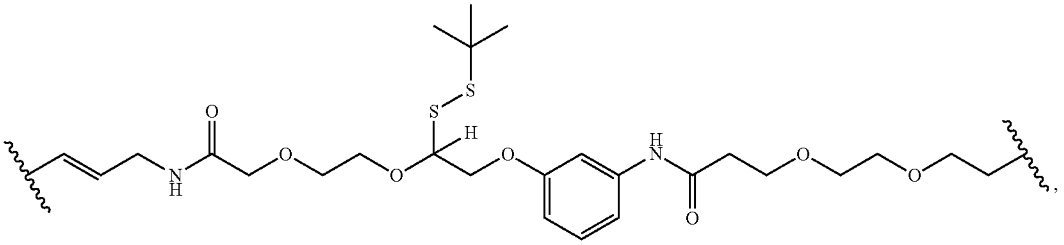
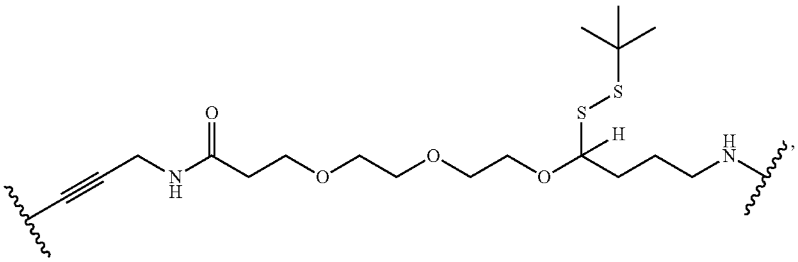

-continued
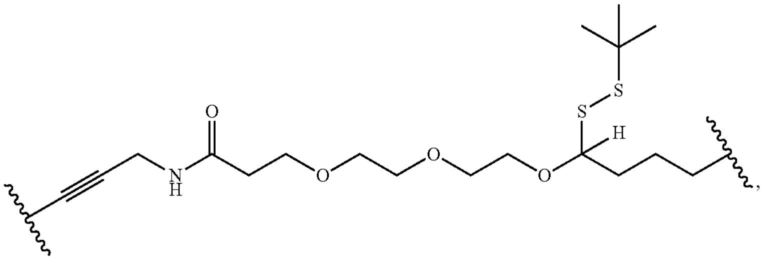
,
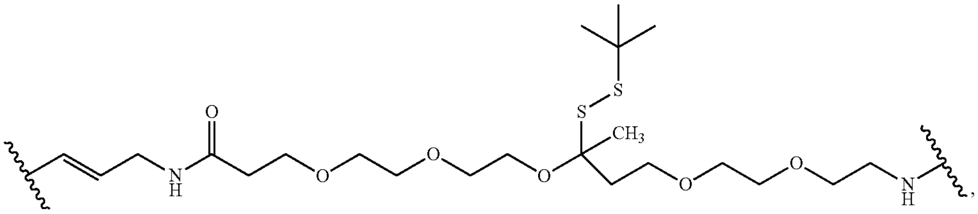
,
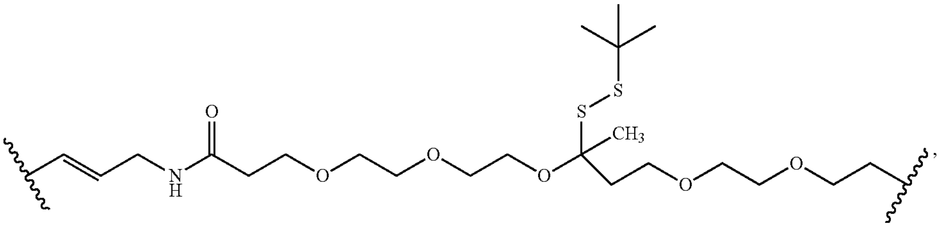
,
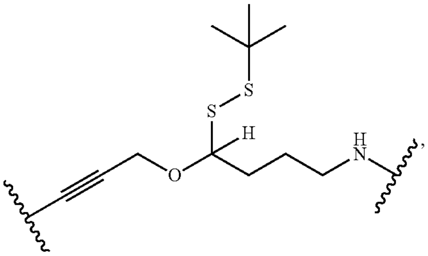
,
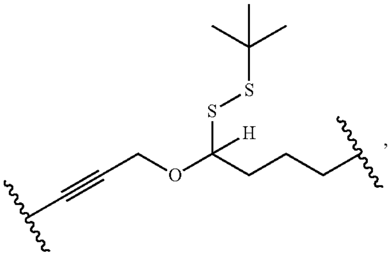
,
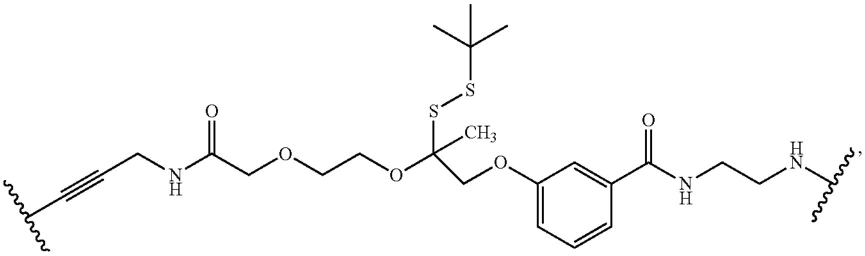
,
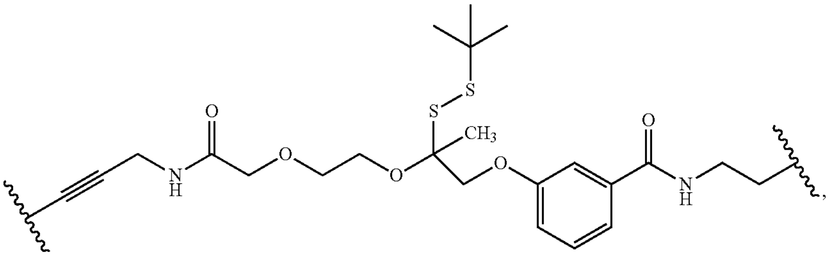
, -continued
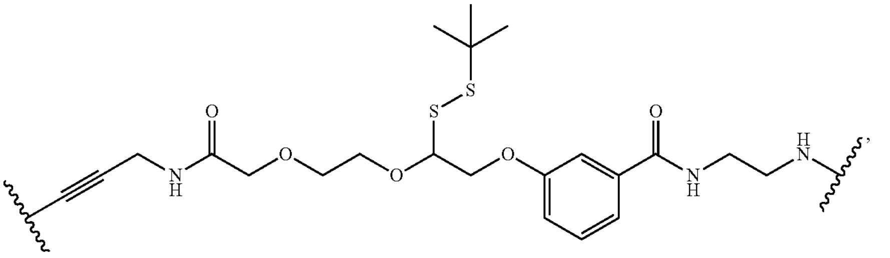
,
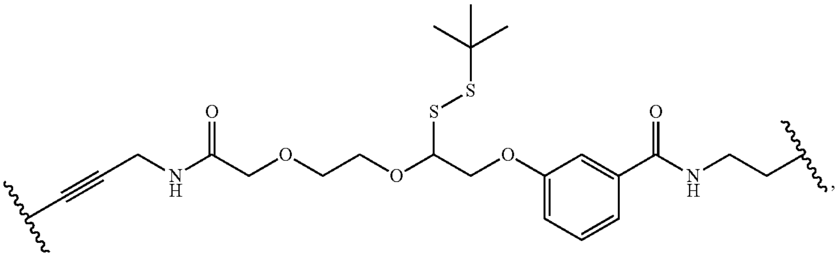
,
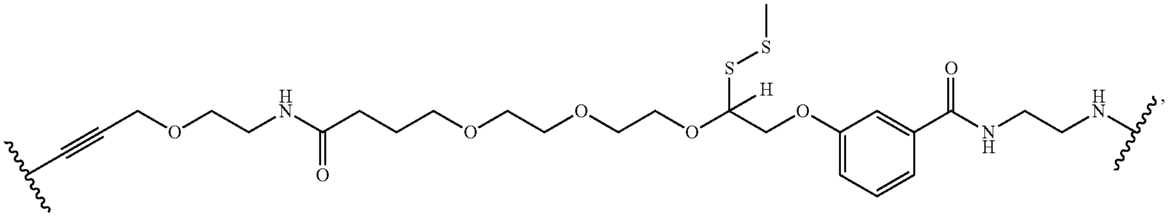
,
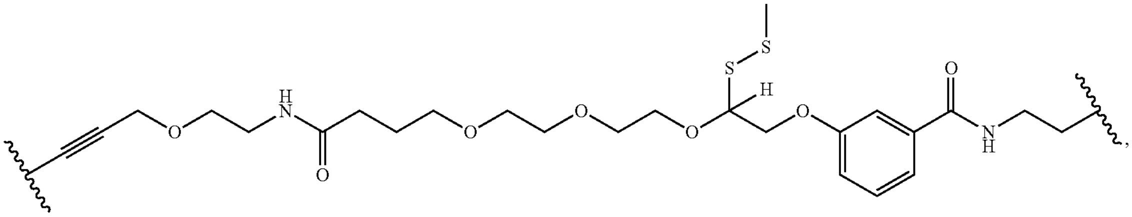
,
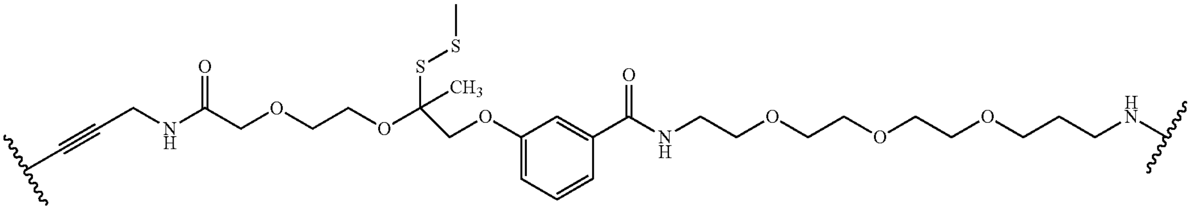
,
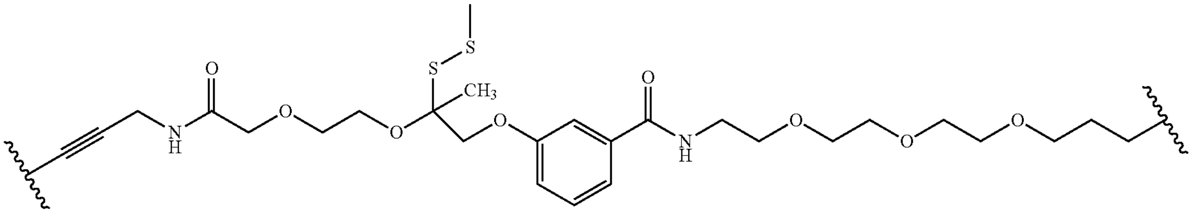
,
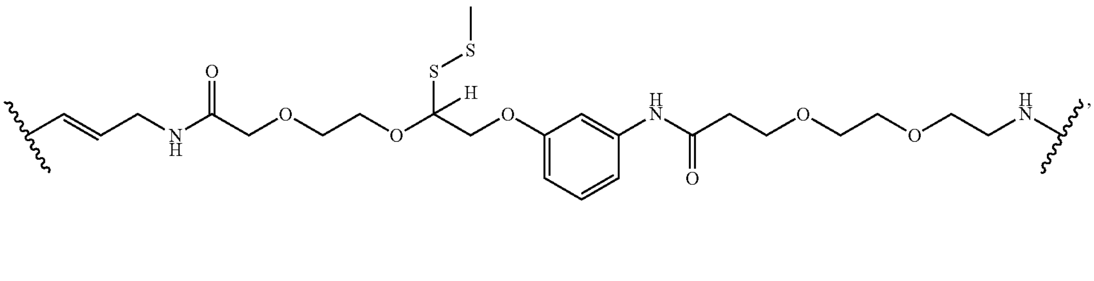
, -continued
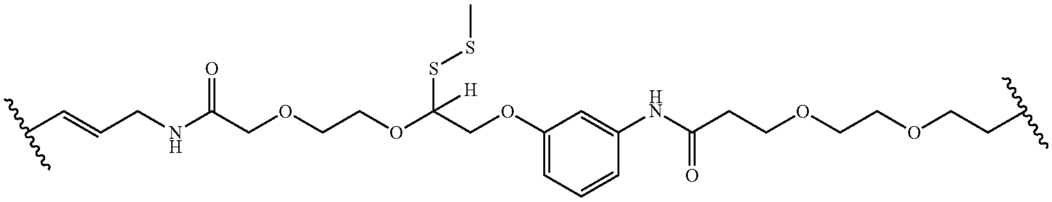
,
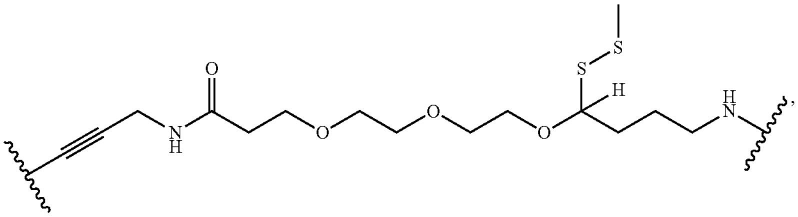
,
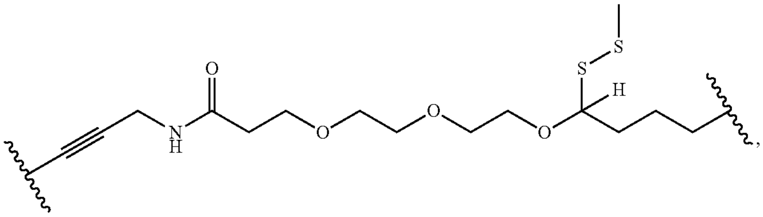
,
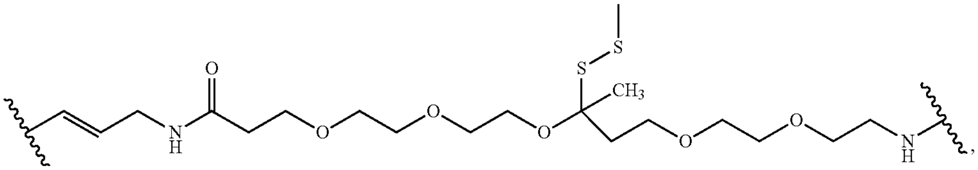
,
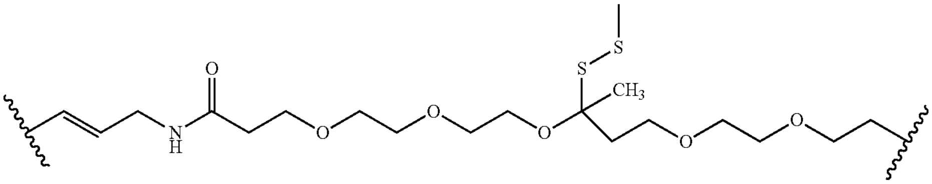
,
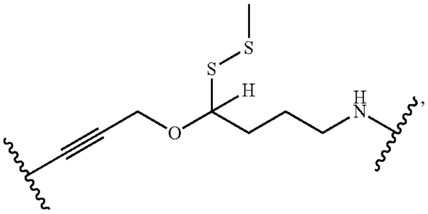
,
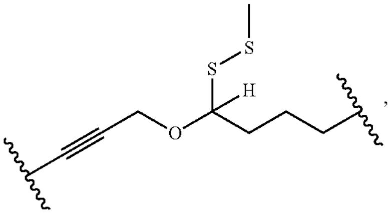
,
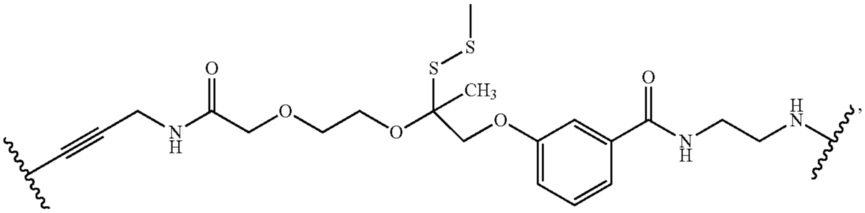
,
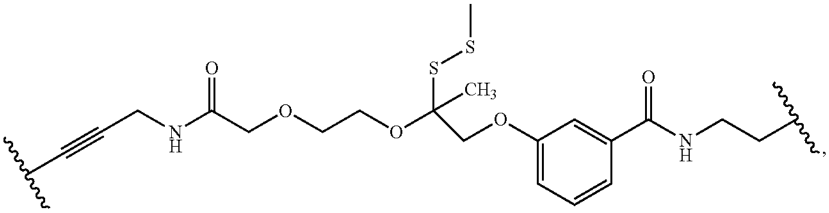
, -continued
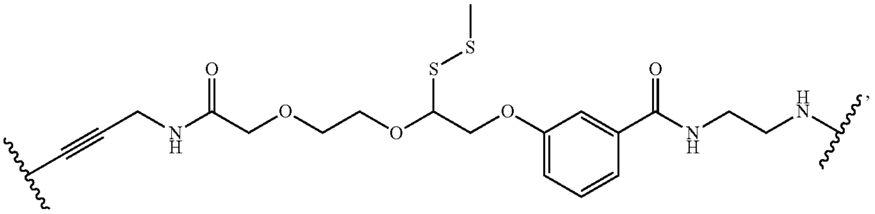
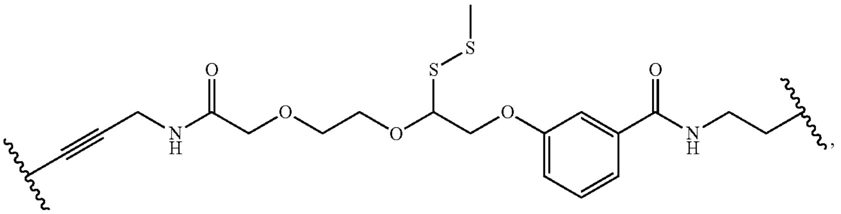
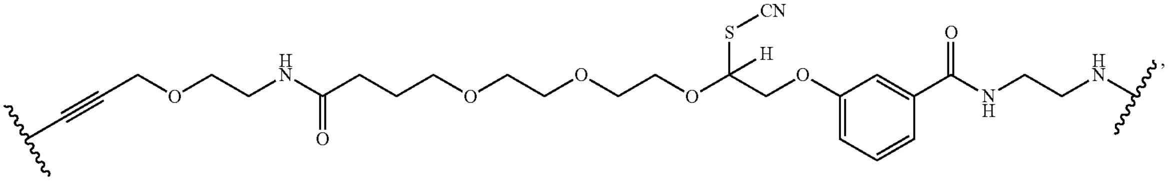
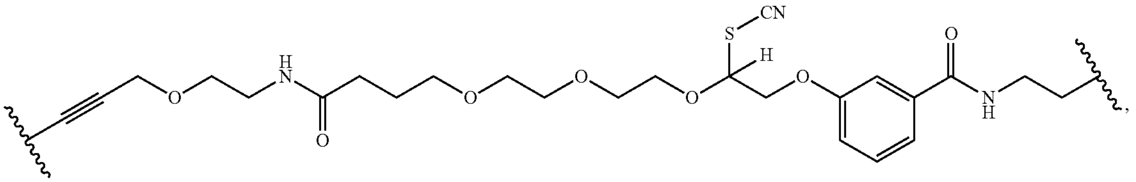
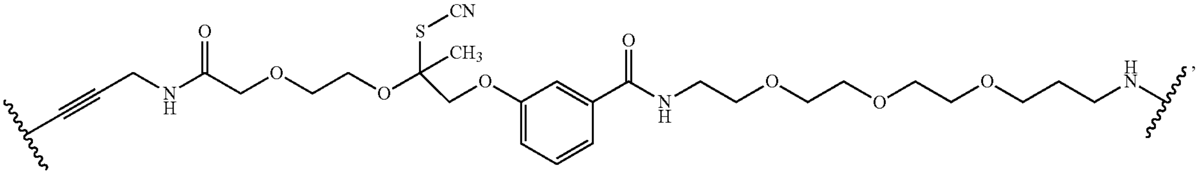
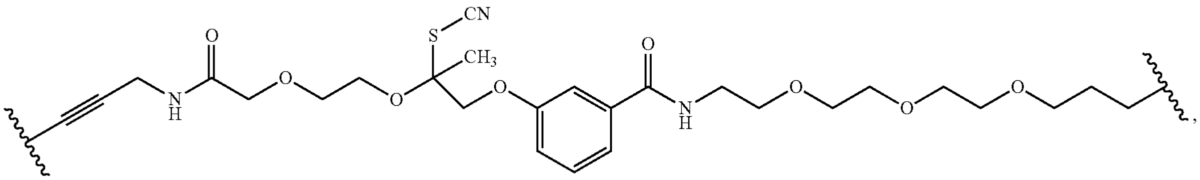
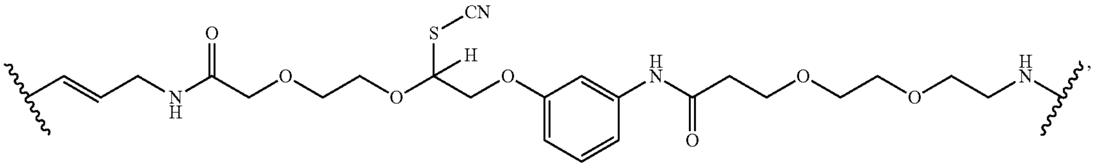
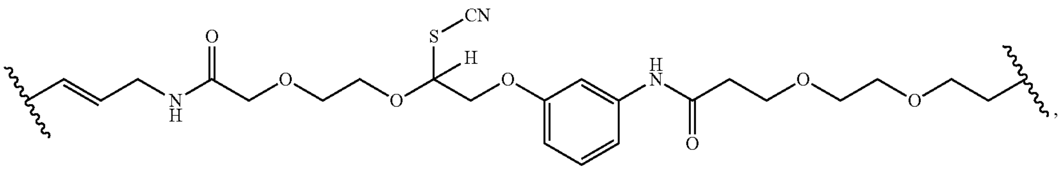
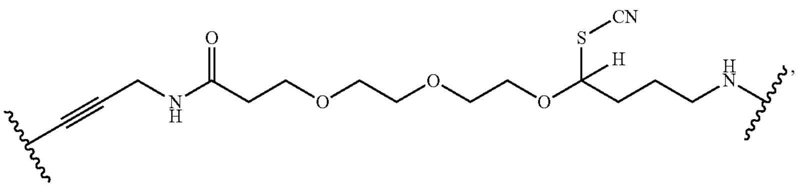

-continued
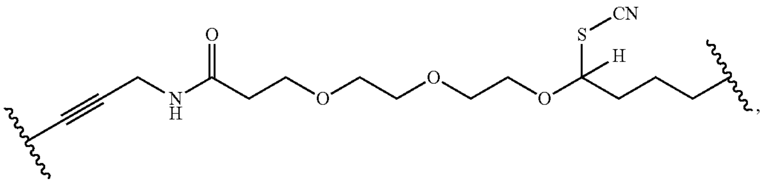
,
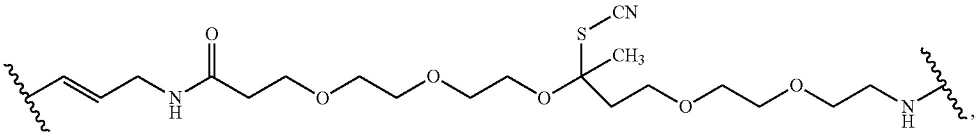
,
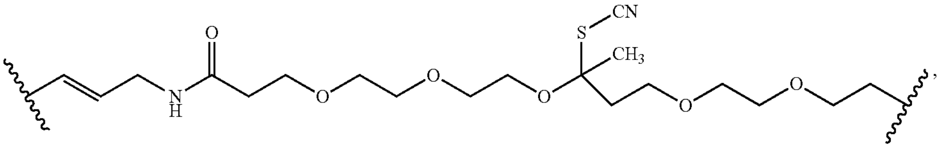
,
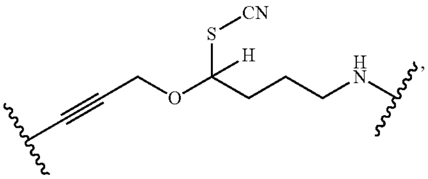
,
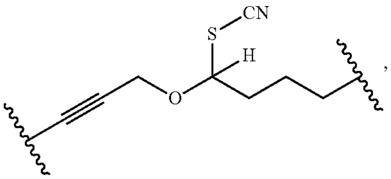
,
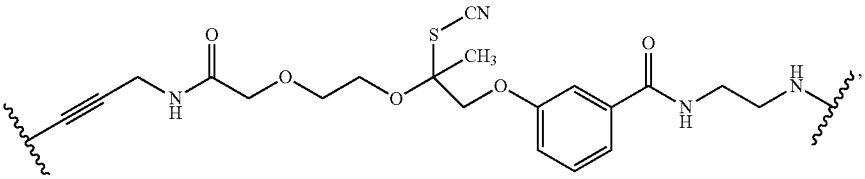
,
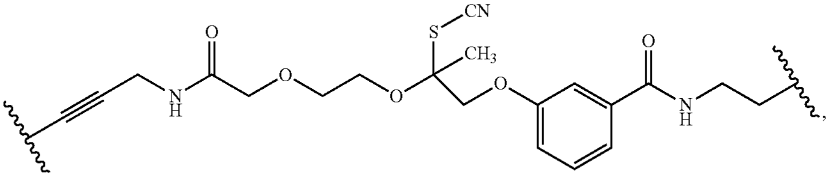
,
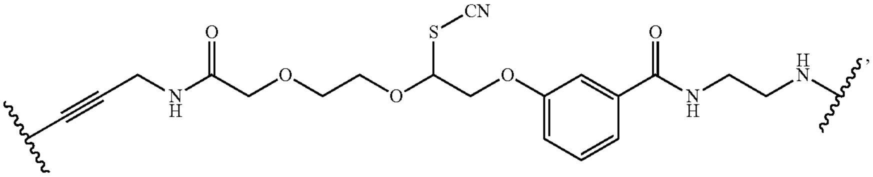
,
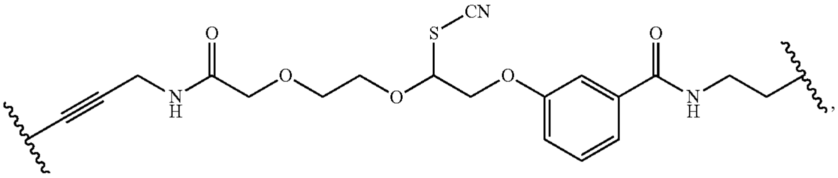
,
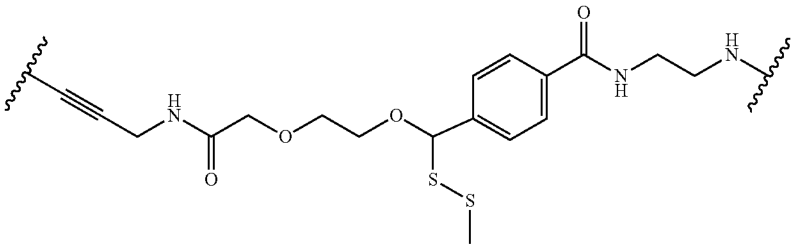
, -continued
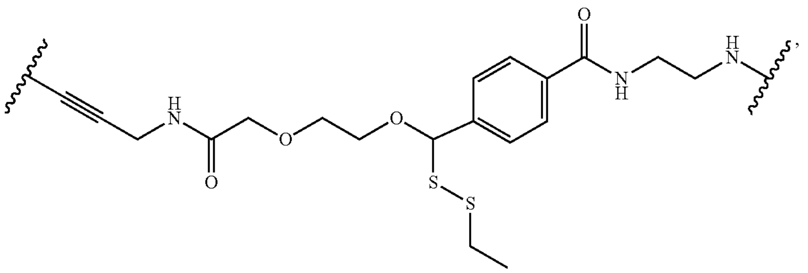
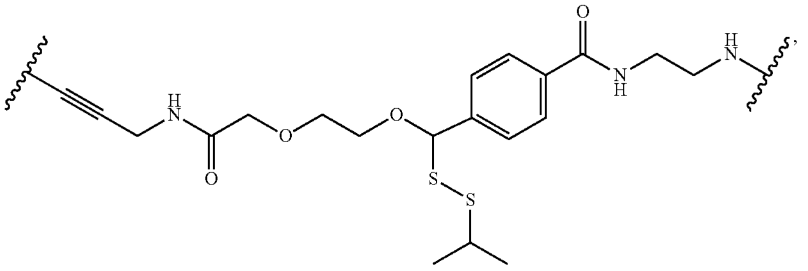
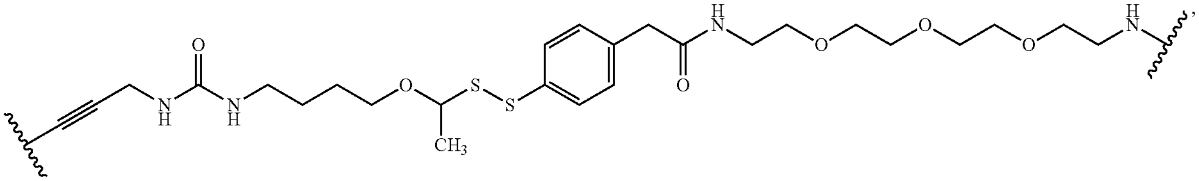
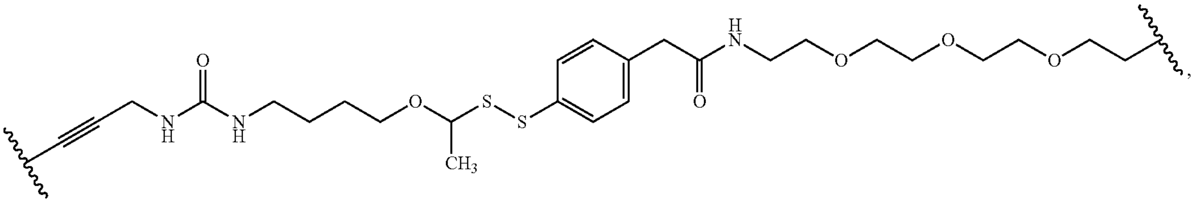
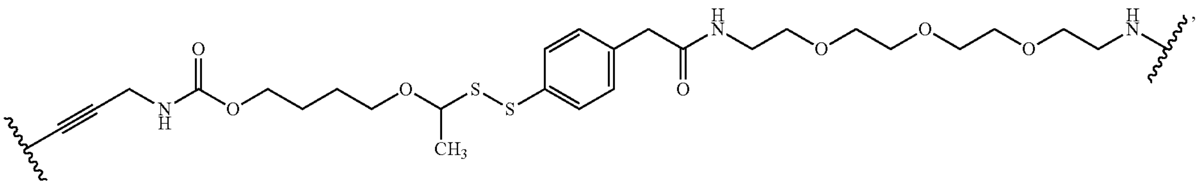
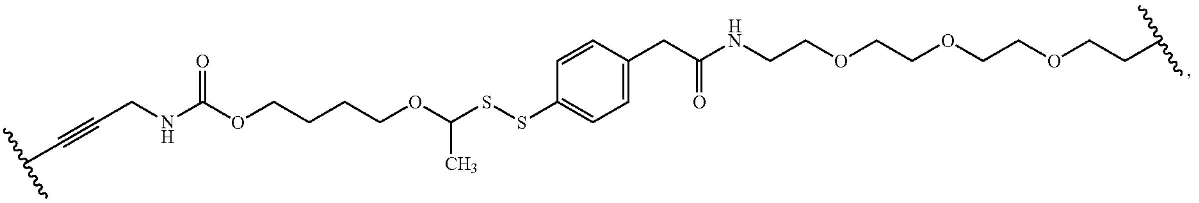
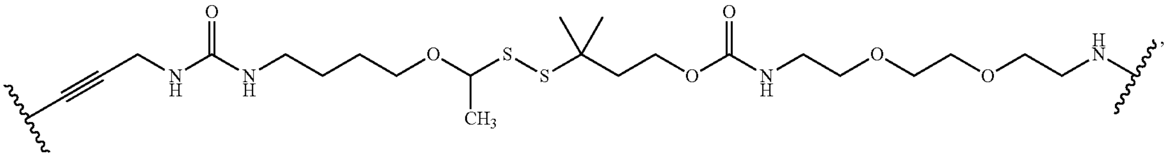
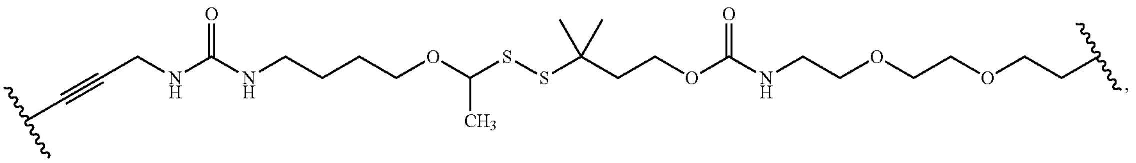

-continued
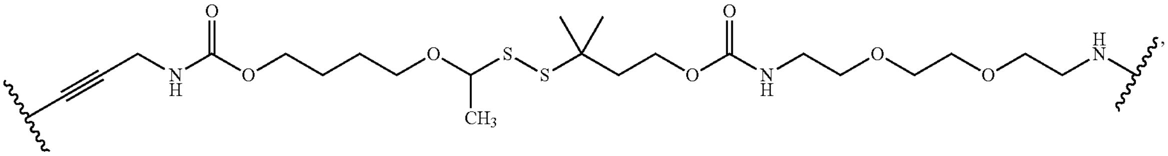,
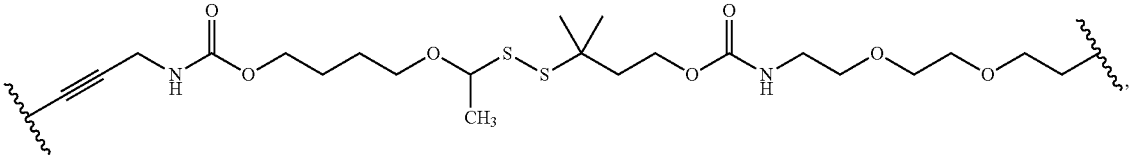,
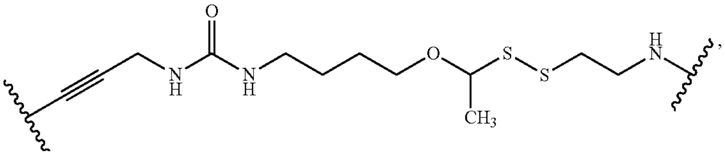,
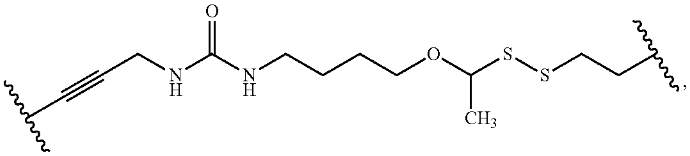,
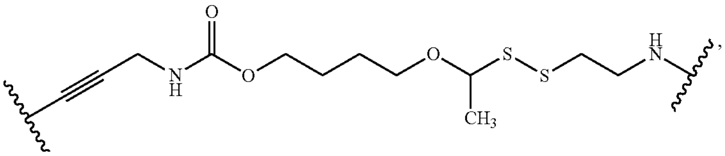,
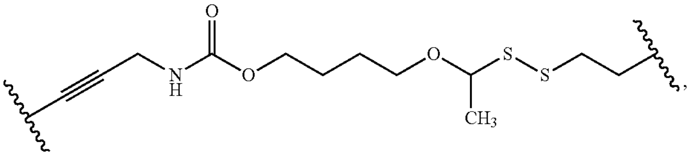,
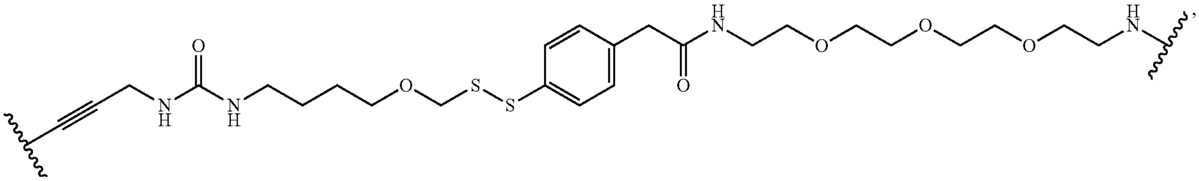,
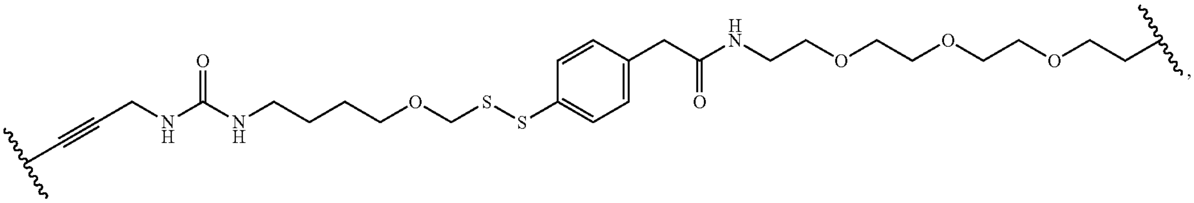,
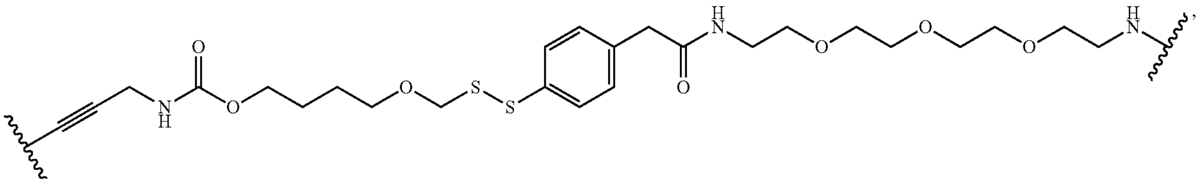, -continued
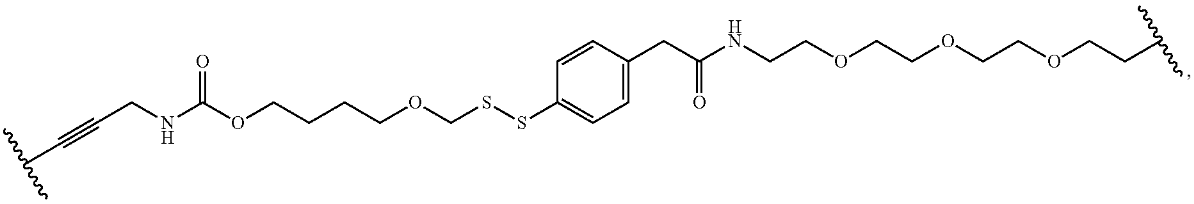,
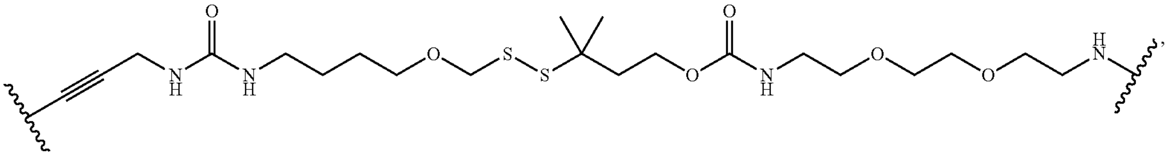,
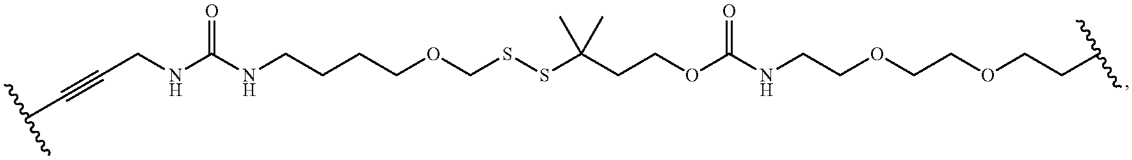,
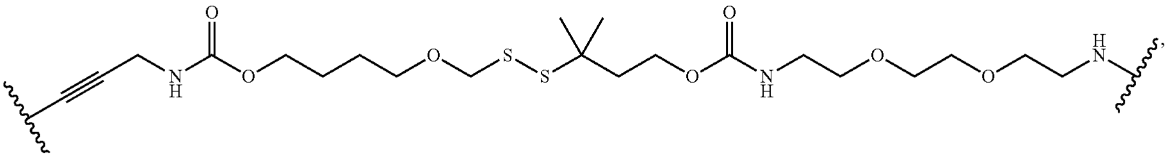,
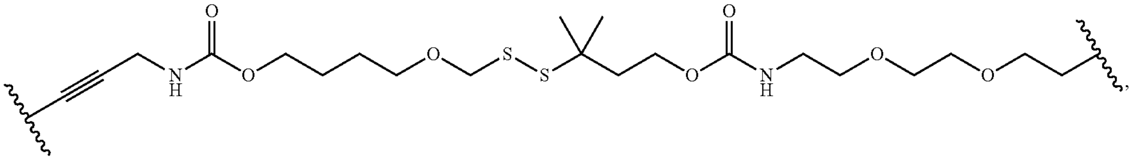,
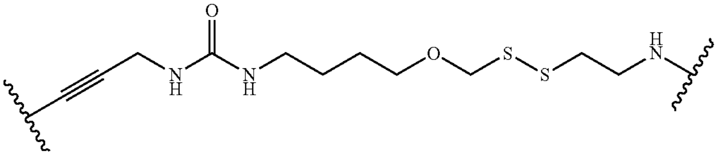,
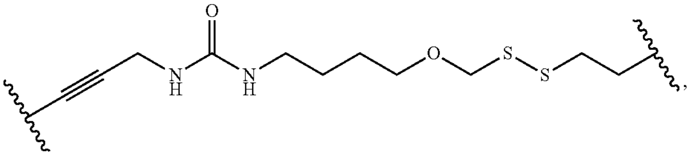,
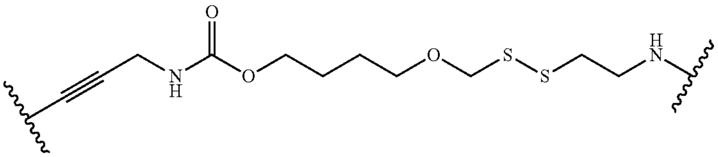,
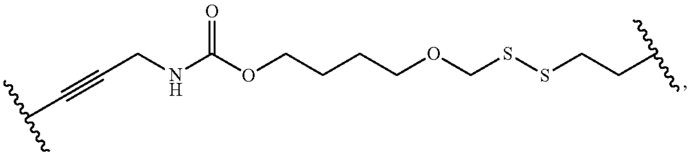,
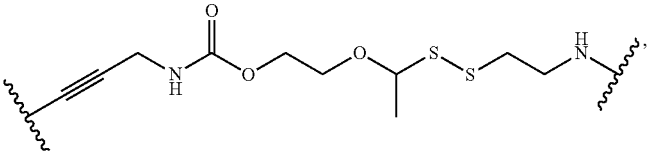, -continued
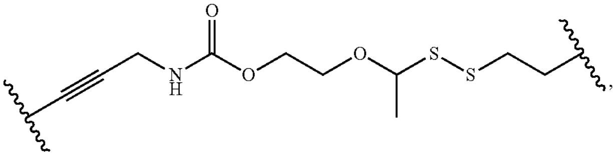,
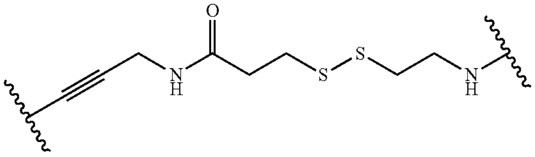,
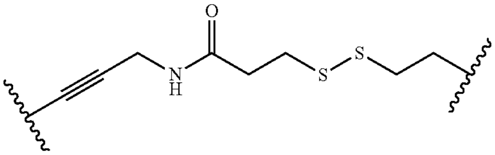,
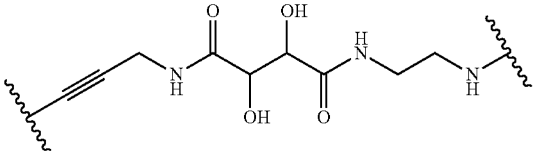,
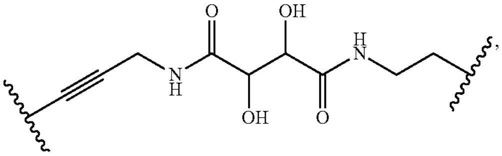,
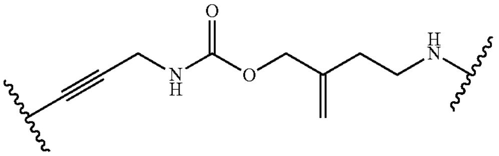,
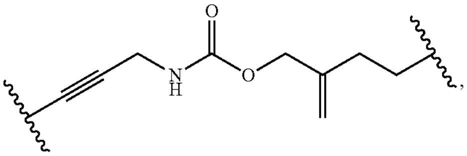,
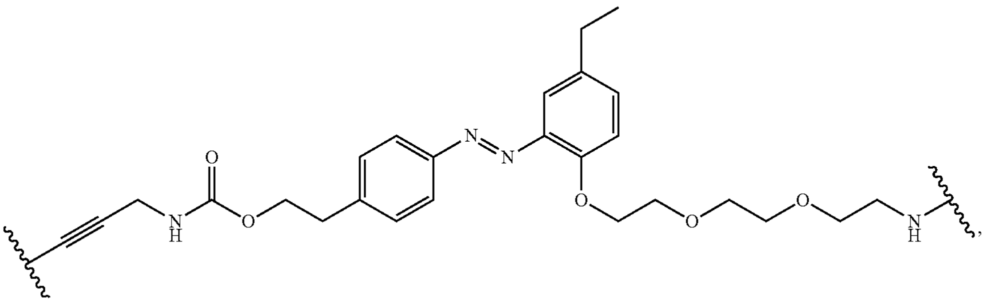,
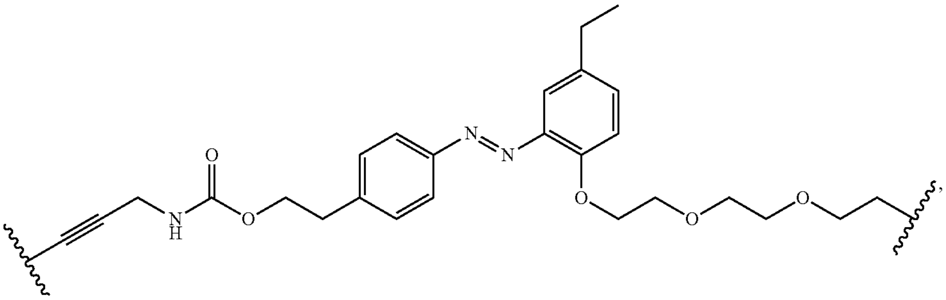,
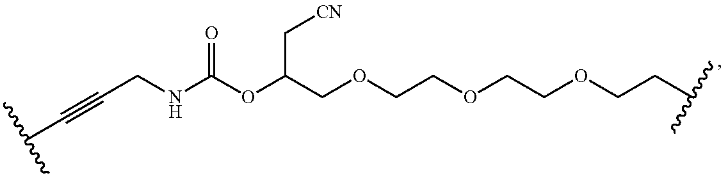,
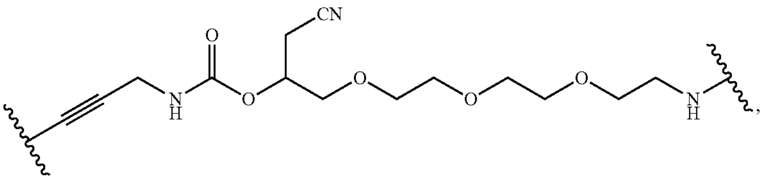, -continued
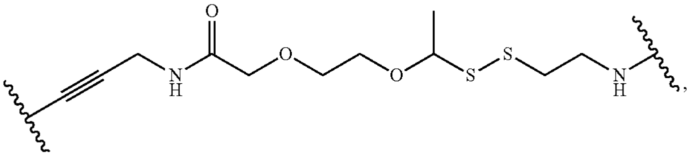
,
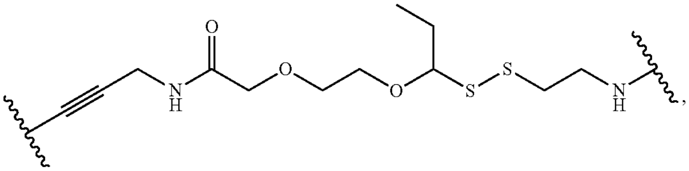
,
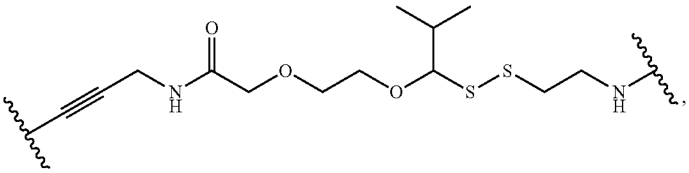
,
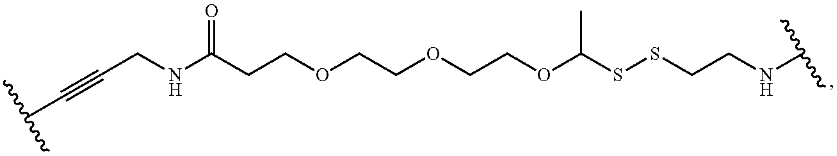
,
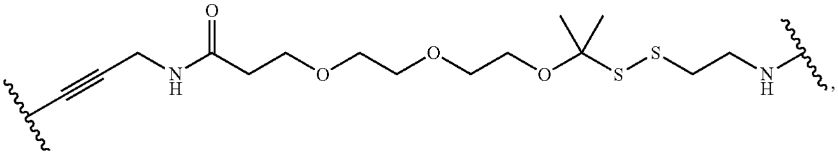
,
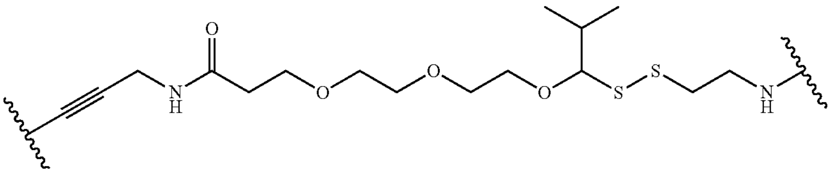
,
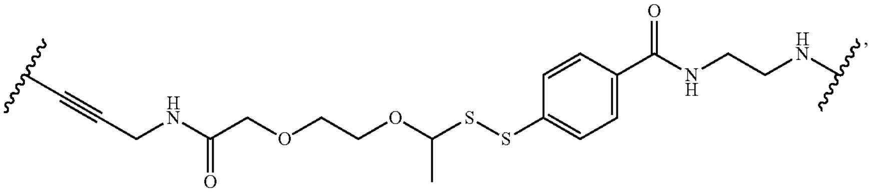
,
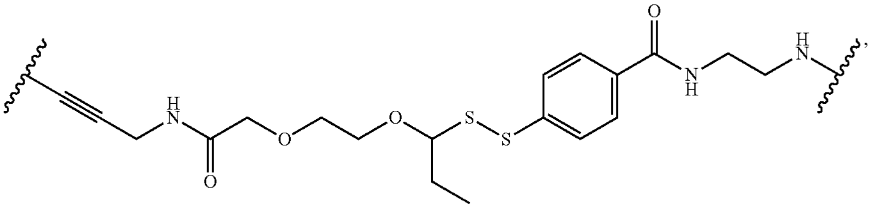
, or
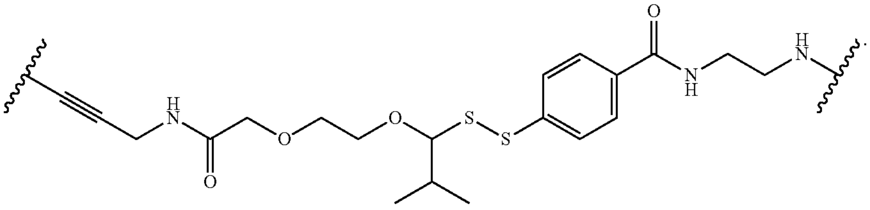
.

Embodiment 49. The compound of Embodiment 40, wherein $L^{100}$ is

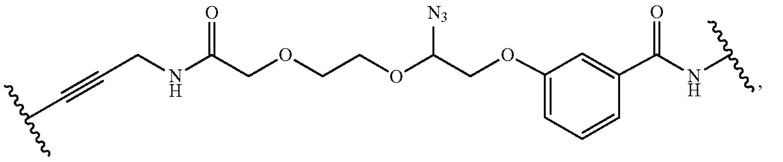

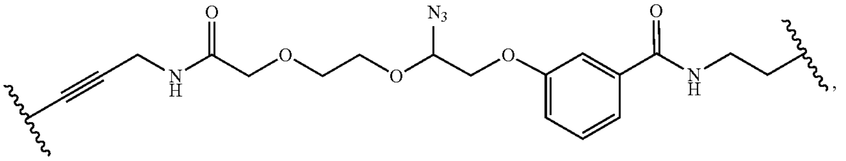

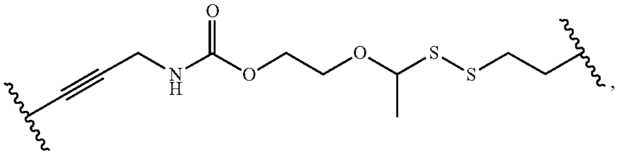

or

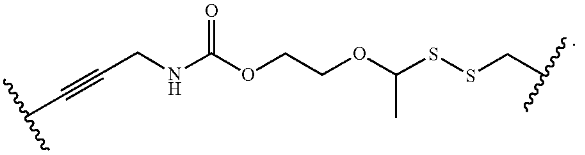

Embodiment 50. The compound of one of Embodiments 1 to 49, wherein $R^1$ is a monophosphate moiety, polyphosphate, or a nucleic acid moiety.

Embodiment 51. The compound of one of Embodiments 1 to 21 or 27 to 49, wherein $R^4$ is a detectable moiety.

Embodiment 52. The compound of one of Embodiments 1 to 21 or 27 to 49, wherein $R^4$ is a fluorescent dye moiety.

Embodiment 53. The compound of one of Embodiments 1 to 21 or 27 to 49, wherein $R^4$ is an anchor moiety.

Embodiment 54. The compound of Embodiment 53, wherein the anchor moiety is biotin, azide, transcyclooctene (TCO), or phenyl boric acid (PBA).

Embodiment 55. A composition comprising a first compound of one of Embodiments 53 to 54 and a second compound having the formula: $R^5$-$L^5$-$R^6$; wherein $R^5$ is a complementary anchor moiety to the $R^4$ anchor moiety of the first compound; $L^5$ is a covalent linker; and $R^6$ is detectable moiety.

Embodiment 56. The composition of Embodiment 55, wherein $R^5$ is a streptavidin moiety.

Embodiment 57. The composition of one of Embodiments 55 to 56, further comprising a photodamage mitigating agent.

Embodiment 58. The composition of Embodiment 57, wherein the photodamage mitigating agent is sodium pyruvate, N,N'-dimethylthiourea, mannitol, DMSO, carboxy-PTIO, 6-hydroxy-2,5,7,8-tetramethylchroman-2-carboxylic acid, alpha-tocopherol, 2-phenyl-1,2,benzisoselenazol-3 (2H)-one, uric acid, sodium azide, or manganese(III)-tetrakis(4-benzoic acid) porphyrin, 4,5-dihydroxybenzene-1,3-disulfonate.

Embodiment 59. The composition of Embodiment 57, wherein the photodamage mitigating agent is 3-carboxy-proxyl, N-propyl gallate, ascorbic acid, methyl viologen, Trolox, or Trolox-quinone.

Embodiment 60. A method for sequencing a nucleic acid, comprising: (i) incorporating in series with a nucleic acid polymerase, within a reaction vessel, one of four different compounds into a primer to create an extension strand, wherein said primer is hybridized to said nucleic acid and wherein each of the four different compounds comprises a unique detectable moiety or a unique anchor moiety; (ii) if the compound of step (i) above comprises a unique anchor moiety, further adding to said reaction vessel a complementary anchor compound comprising a complementary anchor moiety to said unique anchor moiety bonded to a unique detectable moiety; and (iii) detecting the unique detectable moiety of each incorporated compound or incorporated compound-complementary anchor compound complex, so as to thereby identify each incorporated compound in said extension strand, thereby sequencing the nucleic acid; wherein each of said four different compounds is independently a compound of one of Embodiments 1 to 54.

Embodiment 61. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of one of Embodiments 1 to 54.

Embodiment 62. The method of one of Embodiments 60 to 61, further comprising adding to said reaction vessel a photodamage mitigating agent.

Embodiment 63. The method of Embodiment 62, wherein the photodamage mitigating agent is sodium pyruvate, N,N'-dimethylthiourea, mannitol, DMSO, carboxy-PTIO, 6-hydroxy-2,5,7,8-tetramethylchroman-2-carboxylic acid, alpha-tocopherol, 2-phenyl-1,2,benzisoselenazol-3(2H)-one, uric acid, sodium azide, or manganese(III)-tetrakis(4-benzoic acid) porphyrin, 4,5-dihydroxybenzene-1,3-disulfonate.

Embodiment 64. The method of one of Embodiments 60 to 61, wherein said complementary anchor compound is a composition of one of Embodiments 55 to 58.

Embodiment 65. A nucleic acid polymerase complex comprising a nucleic acid polymerase, wherein said nucleic acid polymerase is bound to a compound of one of Embodiments 1 to 54.

Embodiment 66. A method for increasing the accuracy of a sequencing reaction, the method comprising: (i) incorporating in series with a nucleic acid polymerase, within a reaction vessel, one of four different compounds into a primer to create an extension strand, wherein said primer is hybridized to said nucleic acid and wherein each of the four different compounds comprises a unique detectable moiety or a unique anchor moiety; (ii) if the compound of step (i) above comprises a unique anchor moiety, further adding to said reaction vessel a complementary anchor compound comprising a complementary anchor moiety to said unique anchor moiety bonded to a unique detectable moiety; and (iii) detecting the unique detectable moiety of each incorporated compound or incorporated compound-complementary anchor compound complex, so as to thereby identify each incorporated compound in said extension strand, thereby sequencing the nucleic acid; wherein each of said four different compounds is independently a compound of one of Embodiments 1 to 54.

Embodiment 67. A method of modulating the fluorescent intensity ratio of at least two different fluorescently-labeled compounds, the method comprising (i) providing a reaction mixture comprising two different fluorescently-labeled compounds, wherein each of two different compounds is independently a compound of one of Embodiments 1 to 54; (ii) measuring the fluorescence intensity of the two different fluorescently-labeled compounds under excitation illumination to determine the first fluorescent intensity ratio; (iii) modulating the functional distance of the rigid spacer of at least one of the two different fluorescently-labeled compounds; and (iv) measuring the fluorescence intensity of the two different fluorescently-labeled compounds under excitation illumination to determine the second fluorescent intensity ratio, thereby modulating the fluorescent intensity ratio of at least two different fluorescently-labeled compounds.

Embodiment 68. A method of reducing photodamage to a biological component in a sequencing reaction, the method comprising: (i) incorporating in series with a nucleic acid polymerase, within a reaction vessel, one of four different compounds into a primer to create an extension strand, wherein said primer is hybridized to said nucleic acid and wherein each of the four different compounds comprises a unique detectable moiety or a unique anchor moiety; (ii) if the compound of step (i) above comprises a unique anchor moiety, further adding to said reaction vessel a complementary anchor compound comprising a complementary anchor moiety to said unique anchor moiety bonded to a unique detectable moiety; and (iii) detecting the unique detectable moiety of each incorporated compound or incorporated compound-complementary anchor compound complex, so as to thereby identify each incorporated compound in said extension strand, thereby sequencing the nucleic acid; wherein each of said four different compounds is independently a compound of one of Embodiments 1 to 54.

Embodiment 69. The method of Embodiment 68, wherein the biological component comprises a nucleotide, DNA, or RNA.

Embodiment 70. The method of Embodiment 68, wherein the biological component is an enzyme.

Embodiment 71. The method of Embodiment 70, wherein the enzyme is a polymerase, nuclease, or ligase enzyme.

Embodiment 72. The method of Embodiment 71, wherein the enzyme is a DNA polymerase.

What is claimed is:

1. A compound having the formula:

(I)

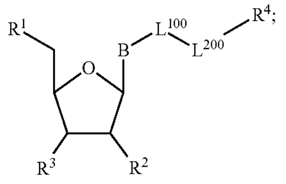

wherein

B is a divalent nucleobase;

$L^{100}$ is a polymerase-compatible cleavable linker;

$R^1$ is a polyphosphate moiety, monophosphate moiety, 5'-O-nucleoside protecting group, nucleic acid moiety, hydrogen, or —OH;

$R^2$ is hydrogen, a polymerase-compatible cleavable moiety, or —OH;

$R^3$ is an —O-polymerase-compatible cleavable moiety, a polymerase-compatible cleavable moiety, hydrogen, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is an anchor moiety or a detectable moiety;

$L^{200}$ has the formula:

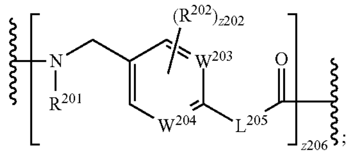

$R^{201}$ is independently hydrogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, —COOH, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, or substituted or unsubstituted heteroalkyl;

$R^{202}$ is independently $—SO_3H$, $—SO_4H$, $—SO_2NH_2$, $—PO_3H$, $—PO_4H$, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OC_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, $—SO_2Cl$, substituted or unsubstituted alkyl, substituted or unsubstituted heteroalkyl, or $L^{212}$-$R^{212A}$;

$L^{202}$ is independently a covalent linker;

$R^{202A}$ is independently a detectable moiety, anchor moiety, triplet state quencher moiety, or protein moiety;

z202 is independently an integer from 0 to 2;

$R^{201}$ and $R^{202}$ may optionally be joined to form a substituted or unsubstituted heterocycloalkyl;

$W^{203}$ and $W^{204}$ are independently CH, N, or $C(R^{202})$;

$L^{205}$ is independently a bond or $—CH_2NH—$; and z206 is an integer from 1 to 100;

wherein, when $R^4$ is a detectable moiety, then $R^{202}$ is $L^{202}$-$R^{202A}$, and $R^4$ and $R^{202A}$ are a FRET pair of detectable moieties.

2. A compound having the formula:

(I)

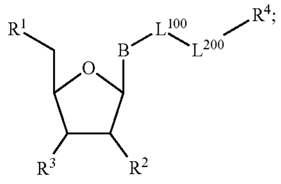

wherein

B is a divalent nucleobase;

$L^{100}$ is a polymerase-compatible cleavable linker;

$R^1$ is a polyphosphate moiety, monophosphate moiety, 5'-O-nucleoside protecting group, nucleic acid moiety, hydrogen, or —OH;

$R^2$ is hydrogen, a polymerase-compatible cleavable moiety, or —OH;

$R^3$ is an —O-polymerase-compatible cleavable moiety, a polymerase-compatible cleavable moiety, hydrogen, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is an anchor moiety or a detectable moiety; and $L^{200}$ is a divalent polymer, divalent double-stranded nucleic acid, or divalent polypeptide.

3. The compound of claim 2, wherein the divalent polypeptide comprises the amino acid sequences $(EAAAK)_{n1}$ (SEQ ID NO:1), $(EP)_{n2}$ (SEQ ID NO:5), $(KP)_{n3}$ (SEQ ID NO:6), $(AP)_{n4}$ (SEQ ID NO:7), or $(TPR)_{n5}$ (SEQ ID NO:8), wherein n1, n2, n3, n4, and n5 are each independently an integer from 2 to 20.

4. The compound of claim 1, wherein $L^{200}$ has the formula:

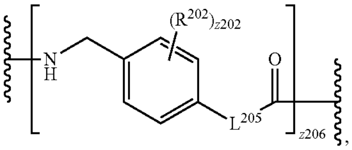

,

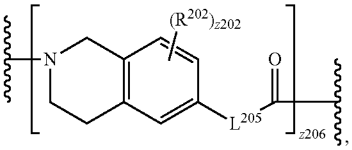

,

-continued

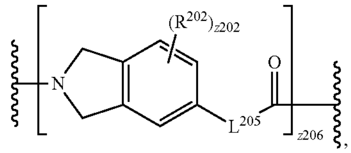

,

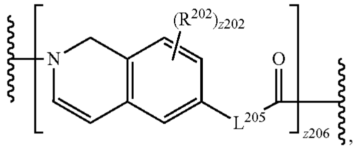

,

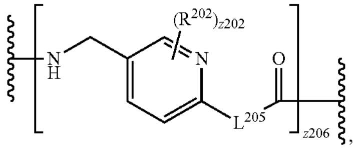

,

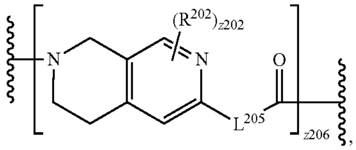

,

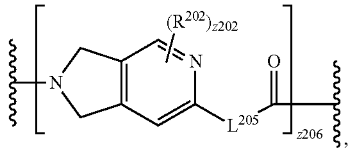

, or

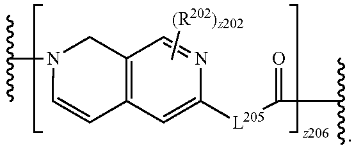

.

5. The compound of claim 1, wherein the triplet state quencher moiety is a monovalent ascorbic acid, monovalent cyclooctatetraene (COT), monovalent nitrobenzyl alcohol, monovalent methyl viologen, monovalent Trolox, or monovalent Trolox-quinone.

6. The compound of claim 1, wherein the polymerase-compatible cleavable moiety is independently -(substituted or unsubstituted alkylene)-SS-(unsubstituted alkyl).

7. The compound of claim 1, wherein the polymerase-compatible cleavable moiety is independently:

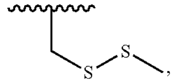

,

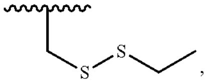

,

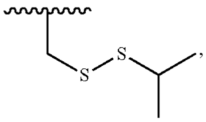

,

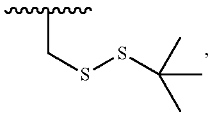

,

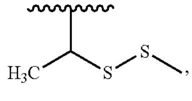

,

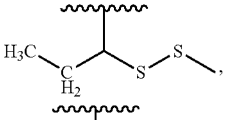

,

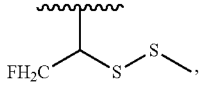

,

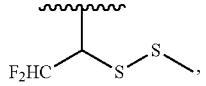

,

-continued
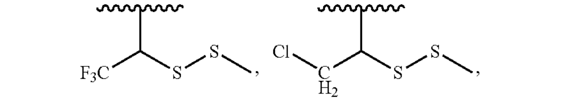
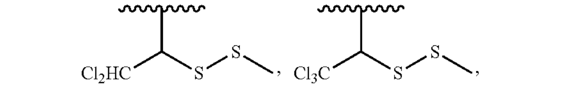
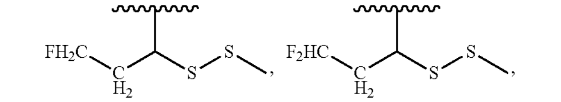
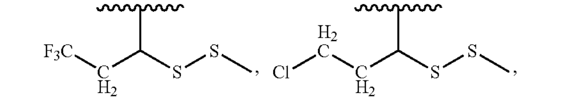
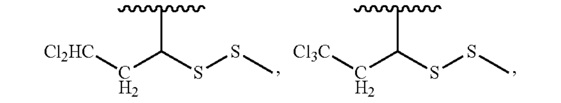
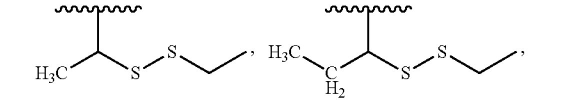
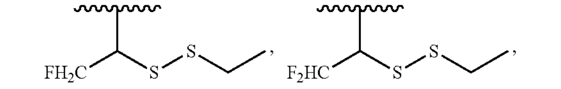
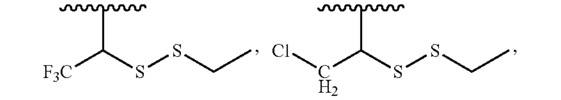
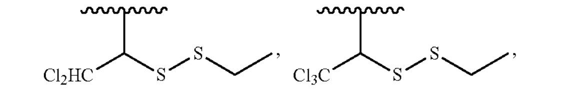
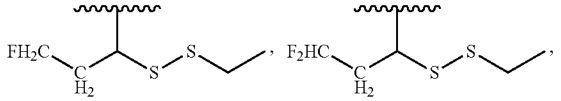
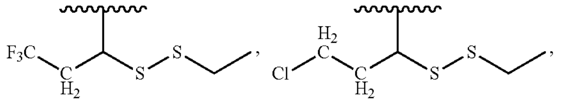
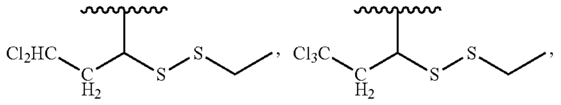
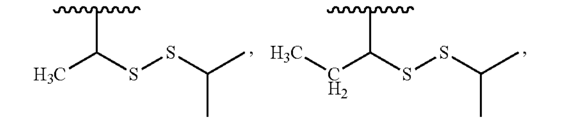
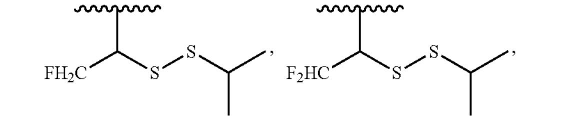
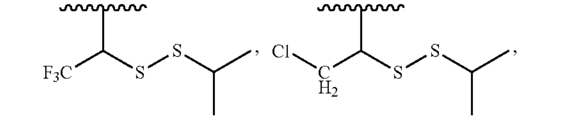
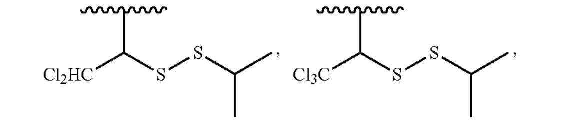
-continued
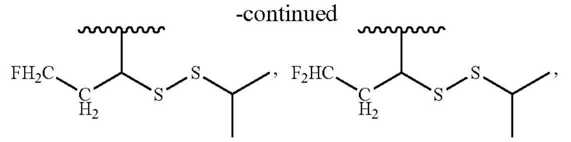
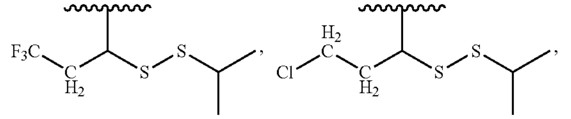
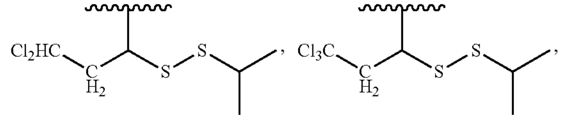
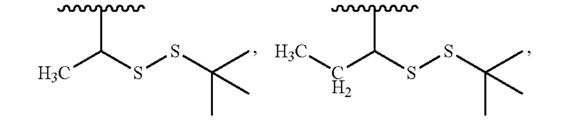
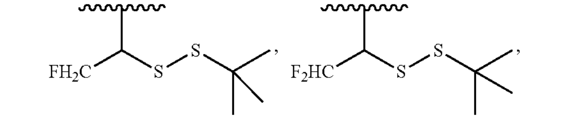
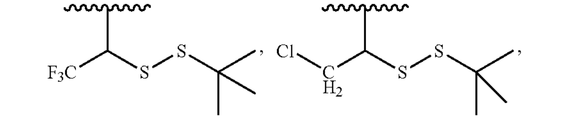
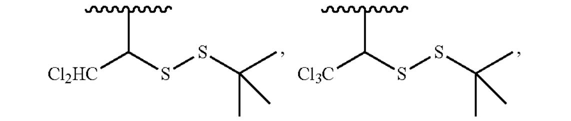
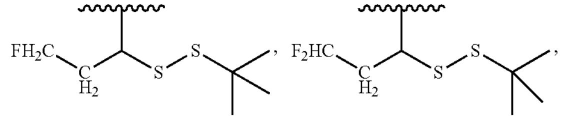
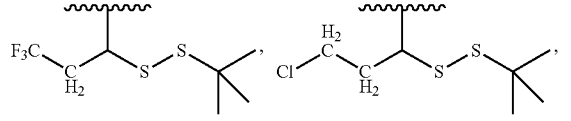
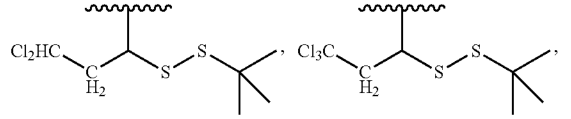
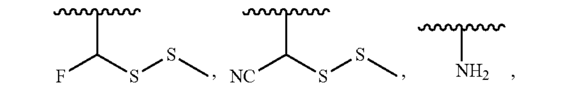
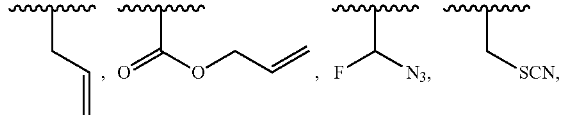
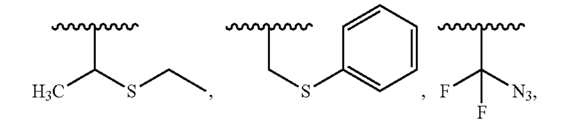
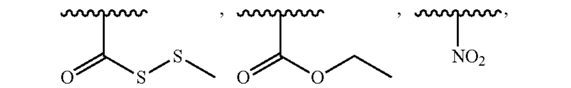
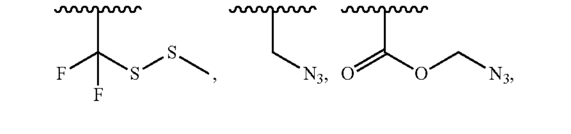

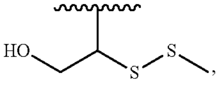, 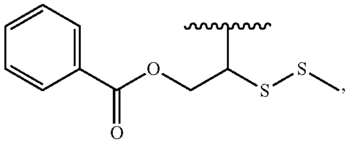,

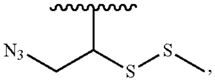, 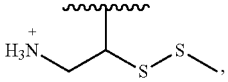,

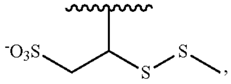, 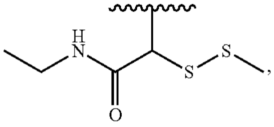,

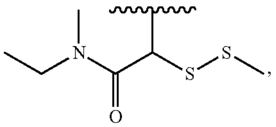,

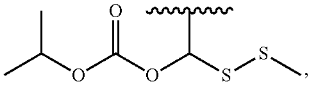,

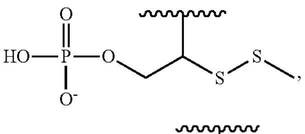,

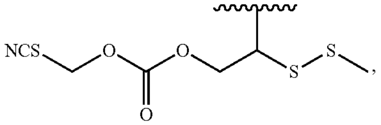,

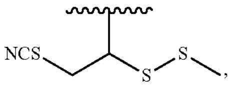, 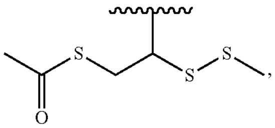, or

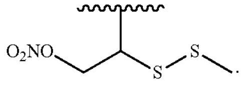.

8. The compound of claim 1, wherein B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

9. The compound of claim 1, wherein B is

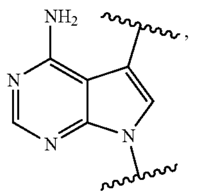, 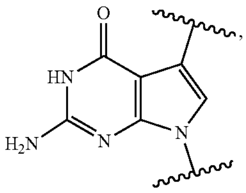,

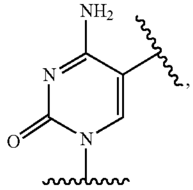, or 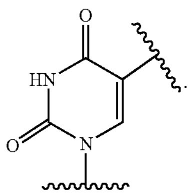.

10. The compound of claim 1, wherein $L^{100}$ is a polymerase-compatible cleavable linker comprising:

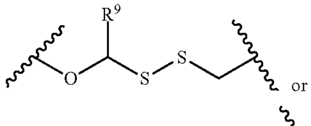 or

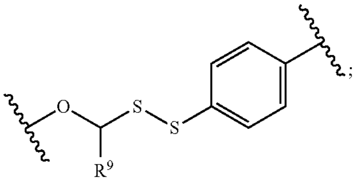;

wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

11. The compound of claim 1, wherein $L^{100}$ is a polymerase-compatible cleavable linker comprising

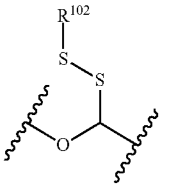 or 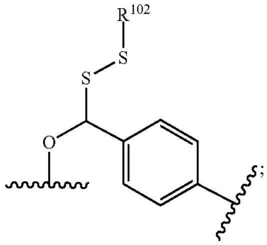;

wherein $R^{102}$ is unsubstituted $C_1$-$C_4$ alkyl.

12. The compound of claim 1, wherein $L^{100}$ is $-L^{101}-L^{102}-L^{103}-L^{104}-L^{105}-$; and $L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, —SS—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

wherein at least one of $L^{101}$, $L^{102}$, $L^{103}$, $L^{104}$, and $L^{105}$ is not a bond.

13. The compound of claim 12, wherein $L^{100}$ is $-L^{101}$-O—CH(—$SR^{100}$)-$L^{103}$-$L^{104}$-$L^{105}$-, $-L^{101}$-O—C($CH_3$)(—$SR^{100}$)-$L^{103}$-$L^{104}$-$L^{105}$-, $-L^{101}$-O—CH($N_3$)-$L^{103}$-$L^{104}$-$L^{105}$-, or $-L^{101}$-SS-$L^{103}$-$L^{104}$-$L^{105}$-;

$L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{100}$ is —$SR^{102}$ or —CN; and $R^{102}$ is unsubstituted $C_1$-$C_4$ alkyl.

14. The compound of claim 12, wherein $L^{100}$ is -$L^{101}$-O—CH(—$SR^{100}$)-$L^{103}$-$L^{104}$-$L^{105}$-, -$L^{101}$-O—C($CH_3$)(—$SR^{100}$)-$L^{103}$-$L^{104}$-$L^{105}$-, -$L^{101}$-O—CH($N_3$)-$L^{103}$-$L^{104}$-$L^{105}$-, or -$L^{101}$-SS-$L^{103}$-$L^{104}$-$L^{105}$-;

$L^{101}$ is a substituted or unsubstituted $C_1$-$C_4$ alkylene or substituted or unsubstituted 8 to 20 membered heteroalkylene;

$L^{103}$ is a bond or substituted or unsubstituted 2 to 10 membered heteroalkylene;

$L^{104}$ is a bond, substituted or unsubstituted 4 to 18 membered heteroalkylene, or substituted or unsubstituted phenylene;

$L^{105}$ is a bond or substituted or unsubstituted 4 to 18 membered heteroalkylene;

$R^{100}$ is —$SR^{102}$ or —CN; and $R^{102}$ is unsubstituted $C_1$-$C_4$ alkyl.

15. The compound of claim 12, wherein $L^{100}$ is

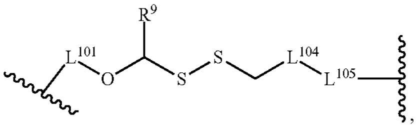

,

-continued

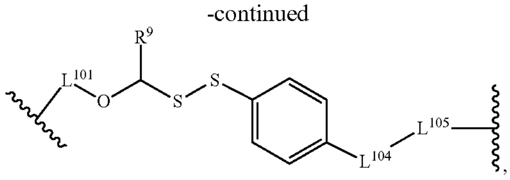

,

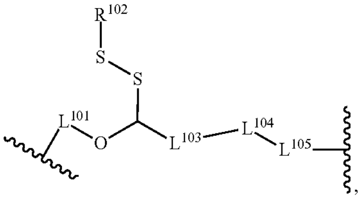

, or

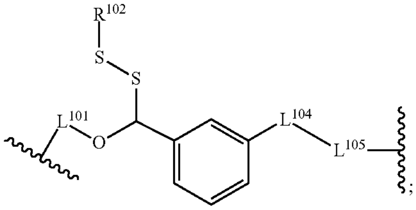

;

wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{102}$ is unsubstituted $C_1$-$C_4$ alkyl.

16. The compound of claim 12, wherein $L^{100}$ is

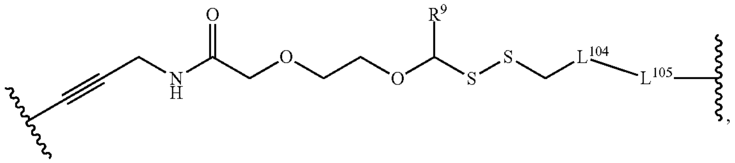

,

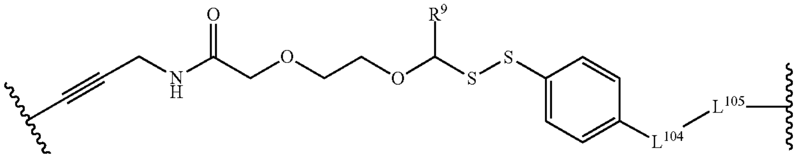

,

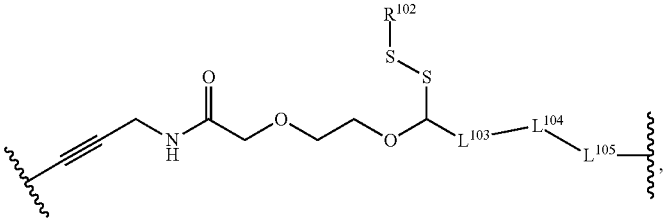

, or

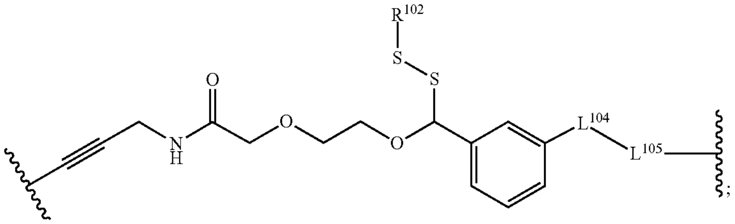

;

wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{102}$ is unsubstituted $C_1$-$C_4$ alkyl.

17. The compound of claim 12, wherein $L^{100}$ is

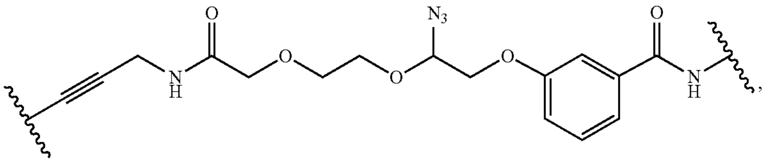

,

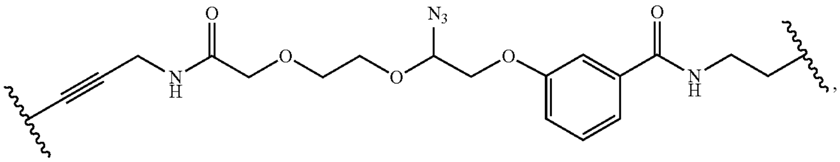

,

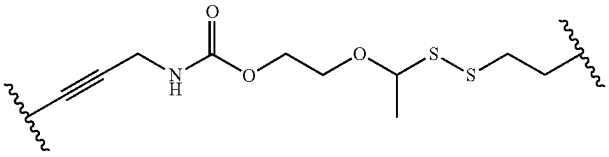

, or

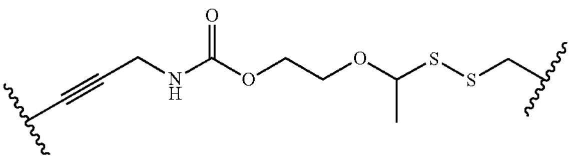

.

18. The compound of claim 1, wherein $R^4$ is an anchor moiety.

19. The compound of claim 18, wherein the anchor moiety is biotin, azide, transcyclooctene (TCO), or phenyl boric acid (PBA).

20. A method for sequencing a nucleic acid, comprising:

(i) incorporating in series with a nucleic acid polymerase, within a reaction vessel, one of four different compounds into a primer to create an extension strand, wherein said primer is hybridized to said nucleic acid and wherein each of the four different compounds comprises a unique detectable moiety or a unique anchor moiety;

(ii) if the compound of step (i) above comprises a unique anchor moiety, further adding to said reaction vessel a complementary anchor compound comprising a complementary anchor moiety to said unique anchor moiety bonded to a unique detectable moiety; and (iii) detecting the unique detectable moiety of each incorporated compound or incorporated compound-complementary anchor compound complex, so as to thereby identify each incorporated compound in said extension strand, thereby sequencing the nucleic acid;

wherein each of said four different compounds is independently a compound of claim 1.

21. The method of claim 20, further comprising adding to said reaction vessel a photodamage mitigating agent.

* * * * *